US 7,365,205 B2

(12) United States Patent
Ohta et al.

(10) Patent No.: US 7,365,205 B2
(45) Date of Patent: Apr. 29, 2008

(54) DIAMINE DERIVATIVES

(75) Inventors: Toshiharu Ohta, Tokyo (JP); Satoshi Komoriya, Tokyo (JP); Toshiharu Yoshino, Tokyo (JP); Masatoshi Nagamochi, Tokyo (JP); Makoto Ono, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 504 days.

(21) Appl. No.: 10/481,262

(22) PCT Filed: Mar. 20, 2002

(86) PCT No.: PCT/JP02/02683

§ 371 (c)(1),
(2), (4) Date: Jul. 14, 2004

(87) PCT Pub. No.: WO03/000657

PCT Pub. Date: Jan. 3, 2003

(65) Prior Publication Data
US 2005/0119486 A1  Jun. 2, 2005

(30) Foreign Application Priority Data
Jun. 20, 2001 (JP) ............ 2001-187105
Aug. 9, 2001 (JP) ............ 2001-243046
Oct. 9, 2001 (JP) ............ 2001-311808
Dec. 28, 2001 (JP) ............ 2001-398708

(51) Int. Cl.
C07D 405/00 (2006.01)
(52) U.S. Cl. .................................. 546/256
(58) Field of Classification Search ............ 546/256
See application file for complete search history.

(56) References Cited

U.S. PATENT DOCUMENTS

| 5,525,042 | A | 6/1996 | Batten |
| 5,668,159 | A | 9/1997 | Jin et al. |
| 5,707,994 | A | 1/1998 | Ikeda et al. |
| 5,811,441 | A | 9/1998 | Olson et al. |
| 5,849,736 | A | 12/1998 | Wityak et al. |
| 5,852,045 | A | 12/1998 | Askew et al. |
| 6,054,065 | A | 4/2000 | Uang et al. |
| 6,300,330 | B1 | 10/2001 | Stocker et al. |
| 6,359,134 | B1 | 3/2002 | Tawada et al. |
| 6,525,042 | B1 | 2/2003 | Kobayashi et al. |
| 6,747,023 | B1 | 6/2004 | Kobayashi et al. |
| 2005/0119486 | A1 | 6/2005 | Ohta et al. |

FOREIGN PATENT DOCUMENTS

| EP | 602 306 | 6/1994 |
| EP | 937 711 | 8/1999 |
| EP | 937 723 | 8/1999 |
| EP | 947 510 | 10/1999 |
| EP | 1 405 852 | 4/2004 |
| EP | 1 415 992 | 5/2004 |
| JP | 2000-86659 | 3/2000 |
| JP | 2000-302765 | 10/2000 |
| JP | 2001-11071 | 1/2001 |
| WO | 86/7257 | 12/1986 |
| WO | 92/4017 | 3/1992 |
| WO | 94/20062 | 9/1994 |
| WO | 94/21599 | 9/1994 |
| WO | 96/10022 | 4/1996 |
| WO | 96/31501 | 10/1996 |
| WO | 96/40100 | 12/1996 |
| WO | 97/06802 | 2/1997 |
| WO | 97/10853 | 3/1997 |
| WO | 97/29104 | 8/1997 |
| WO | 97/38984 | 10/1997 |

(Continued)

OTHER PUBLICATIONS

U.S. Appl. No. 10/481,629, filed Dec. 22, 2003, Ohta et al.
U.S. Appl. No. 10/481,262, filed Dec. 19, 2003, Ohta et al.
U.S. Appl. No. 10/240,725, filed Jul. 30, 2003, Yoshino et al.
U.S. Appl. No. 10/773,344, filed Feb. 9, 2004, Ohta et al.
J. Chromatogr., A. (1996), 724 (1 and 2), pp. 79-90 RN=176957-04-3 etc.
Jan J. Sixma, et al., Thrombosis Research, vol. 68, No. 6, pp. 507-513 1992.

(Continued)

Primary Examiner—D. Margaret Seaman
Assistant Examiner—Nizal S. Chandrakumar
(74) Attorney, Agent, or Firm—Oblon, Spivak, McClelland, Maier & Neustadt, P.C.

(57) ABSTRACT

A compound represented by the general formula (1):

$$Q^1\text{-}Q^2\text{-}T^0\text{-}N(R^1)\text{-}Q^3\text{-}N(R^2)\text{-}T^1\text{-}Q^4 \quad (1)$$

wherein $R^1$ and $R^2$ are hydrogen atoms or the like; $Q^1$ is a saturated or unsaturated, 5- or 6-membered cyclic hydrocarbon group which may be substituted, or the like; $Q^2$ is a single bond or the like; $Q^3$ is a group

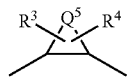

in which $Q^5$ is an alkylene group having 1 to 8 carbon atoms, or the like; and $T^0$ and $T^1$ are carbonyl groups or the like; a salt thereof, a solvate thereof, or an N-oxide thereof.

The compound is useful as an agent for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood drawing.

6 Claims, No Drawings

FOREIGN PATENT DOCUMENTS

| | | |
|---|---|---|
| WO | 98/06705 | 2/1998 |
| WO | 98/21188 | 5/1998 |
| WO | 98/35956 | 8/1998 |
| WO | 98/45262 | 10/1998 |
| WO | 98/54164 | 12/1998 |
| WO | 98/57952 | 12/1998 |
| WO | 99/00121 | 1/1999 |
| WO | 99/00126 | 1/1999 |
| WO | 99/00127 | 1/1999 |
| WO | 99/06371 | 2/1999 |
| WO | 99/09027 | 2/1999 |
| WO | 99/20606 | 4/1999 |
| WO | 99/32225 | 7/1999 |
| WO | 99/51614 | 10/1999 |
| WO | 99/54308 | 10/1999 |
| WO | 99/57099 | 11/1999 |
| WO | 99/57112 | 11/1999 |
| WO | 99/57113 | 11/1999 |
| WO | 00/00498 | 1/2000 |
| WO | 00/06570 | 2/2000 |
| WO | 00/09480 | 2/2000 |
| WO | 00/39092 | 7/2000 |
| WO | 00/39111 | 7/2000 |
| WO | 00/39117 | 7/2000 |
| WO | 00/47573 | 8/2000 |
| WO | 00/59913 | 10/2000 |
| WO | 00/64902 | 11/2000 |
| WO | 00/71516 | 11/2000 |
| WO | 00/76942 | 12/2000 |
| WO | 00/76971 | 12/2000 |
| WO | 00/78749 | 12/2000 |
| WO | 01/7440 | 2/2001 |
| WO | 01/17990 | 3/2001 |
| WO | 01/19795 | 3/2001 |
| WO | 01/19798 | 3/2001 |
| WO | 01/74774 | 4/2001 |
| WO | 01/38309 | 5/2001 |
| WO | 01/64642 | 9/2001 |
| WO | 01/64643 | 9/2001 |
| WO | 02/02519 | 1/2002 |
| WO | 02/26712 | 1/2002 |
| WO | 02/26720 | 4/2002 |
| WO | 02/26734 | 4/2002 |
| WO | 02/42270 | 5/2002 |
| WO | 02/060859 | 8/2002 |
| WO | 02/079145 | 10/2002 |
| WO | 02/102380 | 12/2002 |
| WO | 03/026652 | 4/2003 |
| WO | 03/045912 | 6/2003 |
| WO | 03/048081 | 6/2003 |
| WO | 03/048158 | 6/2003 |
| WO | 03/099276 | 12/2003 |

OTHER PUBLICATIONS

Jerome M. Teitel, et al., Journal of Clinical Investigation, vol. 71, pp. 1383-1391 1983.
Susan Eiödi, et al., Thrombosis Research, vol. 15, No. 5/6 pp. 617-629 1979.
SCIENCE, vol. 248, pp. 593-596.
MEBIO, vol. 14, No. 8, pp. 92-97, With Partial English Translation.
Elka Nutt, et al., The Journal of Biological Chemistry, vol. 263, No. 21, pp. 10162-10167 1988.
U.S. Appl. No. 10/539,995, filed Jun. 22, 2005, Nakamoto et al.
U.S. Appl. No. 10/540,259, filed Jun. 23, 2005, Ohta et al.
U.S. Appl. No. 11/217,837, filed Sep. 2, 2005, Yoshino et al.
218th ACS National Meeting, 0-8412-3685-2, American Chemical Society, MEDI 199, Aug. 22-26, 1999 (abstract only).
219th ACS National Meeting, 0-2412-3731-X, American Chemical Society, MEDI 187 Mar. 26-30, 2000 (abstract only).
220th ACS National Meeting, 0-8412-3749-2, American Chemical Society, MEDI 289, MEDI 328 Aug. 20-24, 2000 (abstract only).
221st ACS National Meeting, 0-8412-3788-3, American Chemical Society, MEDI 128 Apr. 1-5, 2001 (with poster).
226th ACS National Meeting, 10-*8412-3889-8, American Chemical Society, MEDI 79, Sep. 7-11, 2003 (with poster).
Scott M. Sheehan, et al., Bioorganic & Medicinal Chemistry Letters, vol. 13, pp. 2255-2259, 2003.
David K. Herron, et al, Journal of Medicinal Chemistry, vol. 43, No. 5, pp. 859-872, 2000.
Ying K. Yee, et al., Journal of Medicinal Chemistry, vol. 43, No. 5, pp. 873-882, 2000.
C. Wu, et al., Bioorganic & Medicinal Chemistry, vol. 5, No. 10, pp. 1925-1934, 1997.
You-Ling Chou, et al., Bioorganic & Medicinal Chemistry Letters, vol. 13, pp. 507-511, 2003.
March Adler, et al., Biochemistry, vol. 41, No. 52, pp. 15514-15523, 2002.
John J. Masters, et al., Journal of Medicinal Chemistry, vol. 43, No. 11, pp. 2087-2092, 2000.
Michael R. Wiley, et al., Journal of Medicinal Chemistry, vol. 43, No. 5, pp. 883-899, 2000.
Tetrahedron, (1997), 53(26), pp. 8739-8750.

DIAMINE DERIVATIVES

TECHNICAL FIELD

The present invention relates to novel compounds which inhibit activated blood coagulation factor X (hereinafter abbreviated as "FXa") to exhibit a potent anticoagulant effect and can be orally administered, and anticoagulants or agents for preventing and/or treating thrombosis or embolism, which comprise such a novel compound as an active ingredient.

BACKGROUND ART

In unstable angina, cerebral infarction, cerebral embolism, myocardial infarction, pulmonary infarction, pulmonary embolism, Buerger's disease, deep venous thrombosis, disseminated intravascular coagulation syndrome, thrombus formation after valve replacement, reocclusion after angioplasty and thrombus formation during extracorporeal circulation, hypercoagulable state is a pivotal factor. Therefore, there is a demand for development of excellent anticoagulants which have good dose responsiveness, long duration, low risk of hemorrhage and little side effects and fast onset of sufficient effects even by oral administration (Thrombosis Research, Vol. 68, pp. 507-512, 1992).

Based on the research of anticoagulants worked through various mechanism of action, it is suggested that FXa inhibitors are promising anticoagulants. A blood coagulation system comprises a series of reactions that a great amount of thrombin is produced through an amplification process by multi-stage enzyme reactions to form insoluble fibrin. In an endogenous system, activated factor IX activates into factor X on a phospholipid membrane in the presence of activated factor VIII and calcium ions after multi-stage reactions subsequent to activation of a contact factor. In an exogenous system, activated factor VII activates factor X in the presence of a tissue factor. More specifically, the activation of the factor X into FXa in the coagulation system is a crucial reaction in the formation of thrombin. The activated factor X (FXa) limitedly decomposes prothrombin to produce thrombin in the both systems. Since the produced thrombin activates coagulation factors in the upper stream, the formation of thrombin is more amplified. As described above, since the coagulation system in the upper stream of FXa is divided into the endogenous system and the exogenous system, production of FXa cannot be sufficiently inhibited by inhibiting enzymes in the coagulation system in the upper stream of FXa, leading to production of thrombin. Since the coagulation system comprises self-amplification reactions, inhibition of the coagulation system can be more efficiently achieved by inhibiting FXa in the upper stream of thrombin than the inhibition of thrombin (Thrombosis Research, Vol. 15, pp. 617-629, 1979).

An another excellent point of FXa inhibitors is a great difference between an effective dose in a thrombosis model and a dose elongating bleeding time in an experimental hemorrhagic model. From this experimental result, FXa inhibitors are considered to be anticoagulants having low risk of hemorrhage.

Various compounds have been reported as FXa inhibitors. It is known that antithrombin III and antithrombin III dependent pentasaccharides can generally not inhibit prothrombinase complexes which play a practical role in the thrombus formation in a living body (Thrombosis Research, Vol. 68, pp. 507-512, 1992; Journal of Clinical Investigation, Vol. 71, pp. 1383-1391, 1983; Mebio, Vol. 14, the August number, pp. 92-97). In addition, they do not exhibit effectiveness by oral administration. Tick anticoagulant peptide (TAP) (Science, Vol. 248, pp. 593-596, 1990) and antistasin (AST) (Journal of Biological Chemistry, Vol. 263, pp. 10162-10167, 1988) isolated from mites or leeches, which are bloodsuckers, also inhibit Fxa and exhibit anti-thrombotic effects against venous thrombosis and arterial thrombosis. However, these compounds are high-molecular weight peptides and unavailable in oral administration. As described above, development of antithrombin III independent low-molecular weight FXa inhibitors which directly inhibit coagulation factors has been conducted.

It is therefore an object of the present invention to provide a novel compound which has a potent FXa-inhibiting effect and exhibits an anti-thrombotic effect quickly, sufficiently and persistently by oral administration.

DISCLOSURE OF THE INVENTION

The present inventors have investigated synthesis and pharmacological effects of novel FXa inhibitors. As a result, diamine derivatives, salts thereof, and solvates and N-oxides thereof, which exhibit potent FXa-inhibiting effect and anticoagulant effect, have been found. It has also been found that these compounds promptly, persistently and potently inhibit FXa and exhibit potent anticoagulant effect and anti-thrombotic effect by oral administration, and are hence useful as prophylactics and remedies for various diseases based on thromboembolism, thus leading to completion of the present invention.

This invention provides a compound represented by the general formula (1):

$$Q^1\text{-}Q^2\text{-}T^0\text{-}N(R^1)\text{-}Q^3\text{-}N(R^2)\text{-}T^1\text{-}Q^4 \qquad (1)$$

wherein $R^1$ and $R^2$, independently of each other, represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic fused hydrocarbon group which may be substituted, or a saturated or unsaturated, bicyclic or tricyclic fused heterocyclic group which may be substituted;

$Q^2$ represents a single bond, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic fused hydrocarbon group which may be substituted, or a saturated or unsaturated, divalent bicyclic or tricyclic fused heterocyclic group which may be substituted;

$Q^3$ represents the following group:

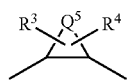

in which $Q^5$ means an alkylene group having 1 to 8 carbon atoms, an alkenylene group having 2 to 8 carbon atoms, or a group $-(CH_2)_m-CH_2\text{-}A\text{-}CH_2-(CH_2)_n-$, in which m and n are independently of each other 0 or an integer of 1-3, and A means an oxygen atom, nitrogen atom, sulfur atom, —SO—, —SO$_2$—, —NH—, —O—NH—, —NH—NH—, —S—NH—, —SO—NH— or —SO$_2$—NH—, and R$^3$ and R$^4$ are substituents on carbon atom(s), nitrogen atom(s) or a sulfur atoms of a ring comprising Q$^5$ and are independently of each other a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s) or alkylsulfonylacyl group, or R$^3$ and R$^4$, together with each other, denote an alkylene group having 1 to 5 carbon atoms, alkenylene group having 2 to 5 carbon atoms, alkylenedioxy group having 1 to 5 carbon atoms or carbonyldioxy group;

Q$^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic fused hydrocarbon group which may be substituted, or a saturated or unsaturated, bicyclic or tricyclic fused heterocyclic group which may be substituted;

T$^0$ represents a carbonyl or thiocarbonyl group; and

T$^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')—, in which R' means a hydrogen atom, hydroxyl group, alkyl group or alkoxy group, group —C(=O)-A$^1$-N(R")—, in which A$^1$ means an alkylene group having 1 to 5 carbon atoms, which may be substituted, and R" means a hydrogen atom, hydroxyl group, alkyl group or alkoxy group, group —C(=O)—NH—, group —C(=S)—NH—, group —C(=O)—NH—NH—, group —C(=O)-A$^2$-C(=O)—, in which A$^2$ means a single bond or alkylene group having 1 to 5 carbon atoms, group —C(=O)-A$^3$-C(=O)—NH—, in which A$^3$ means an alkylene group having 1 to 5 carbon atoms, group —C(=O)—C(=NOR$^a$)—N(R$^b$)—, group —C(=S)—C(=NOR$^a$)—N(R$^b$)—, in which R$^a$ means a hydrogen atom, alkyl group or alkanoyl group, and R$^b$ means a hydrogen atom, hydroxyl group, alkyl group or alkoxy group, group —C(=O)—N=N—, group —C(=S)—N=N—, or thiocarbonyl group;

a salt thereof, a solvate thereof, or an N-oxide thereof.

This invention also provides a medicine, an activated blood coagulation factor X inhibitor, an anticoagulant, an agent for preventing and/or treating thrombosis or embolism and an agent for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood gathering, which each comprises the compound represented by the general formula (1), the salt thereof, the solvate thereof, or N-oxide thereof.

This invention further provides an intermediate useful for preparing the compound represented by the general formula (1).

This invention still further provides use of the compound represented by the general formula (1), the salt thereof, the solvate thereof, or N-oxide thereof for preparation of a medicine.

This invention yet still further provides a method for treating thrombosis or embolism, which comprises administering an effective amount of the compound represented by the general formula (1), the salt thereof, the solvate thereof, or N-oxide thereof.

BEST MODE FOR CARRYING OUT THE INVENTION

Substituents in the diamine derivatives according to the present invention represented by the general formula (1) will hereinafter be described.

<On Group Q$^4$>

The group Q$^4$ means an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic fused hydrocarbon group which may be substituted, or a saturated or unsaturated, bicyclic or tricyclic fused heterocyclic group which may be substituted.

In the group Q$^4$, the aryl group may include aryl groups having 6 to 14 carbon atoms, for example, phenyl, naphthyl, anthryl and phenanthryl groups. The arylalkenyl group means a group formed by an aryl group having 6 to 14 carbon atoms and an alkenylene group having 2 to 6 carbon atoms, and examples thereof may include a styryl group. The arylalkynyl group means a group formed by an aryl group having 6 to 14 carbon atoms and an alkynylene group having 2 to 6 carbon atoms, and examples thereof may include a phenylethynyl group.

The heteroaryl group means a monovalent aromatic group having at least one hetero atom selected from oxygen, sulfur and nitrogen atoms, and examples thereof may include 5- or 6-membered heteroaryl groups, for example, pyridyl, pyridazinyl, furyl, thienyl, pyrrolyl, thiazolyl, oxazolyl, pyrimidinyl and tetrazolyl groups. The heteroarylalkenyl group means a group formed by the above-described heteroaryl group and an alkenylene group having 2 to 6 carbon atoms, and examples thereof may include thienylethenyl and pyridylethenyl groups.

The saturated or unsaturated, bicyclic or tricyclic fused hydrocarbon group means a monovalent group derived from a saturated or unsaturated, bicyclic or tricyclic fused hydrocarbon. The saturated or unsaturated, bicyclic or tricyclic fused hydrocarbon denotes a bicyclic or tricyclic fused hydrocarbon formed by fusing 2 or 3 saturated or unsaturated, 5- or 6-membered cyclic hydrocarbons which are the same or different from each other. In this case, examples of the saturated or unsaturated, 5- or 6-membered cyclic hydrocarbons may include cyclopentane, cyclopentene, cyclohexane, cyclohexene, cyclohexadiene and benzene. Specific examples of the saturated or unsaturated, bicyclic or tricyclic fused hydrocarbon group may include indenyl, indanyl, tetrahydronaphthyl and naphthyl groups. Incidentally, the position of the saturated or unsaturated, bicyclic or tricyclic fused hydrocarbon group bonded to $T^1$ in the general formula (1) is not particularly limited.

The saturated or unsaturated, bicyclic or tricyclic fused heterocyclic group means a monovalent group derived from a saturated or unsaturated, bicyclic or tricyclic fused heterocyclic ring. The saturated or unsaturated, bicyclic or tricyclic fused heterocyclic ring denotes the following heterocyclic ring ①, ② or ③:

①: a bicyclic or tricyclic fused heterocyclic ring formed by fusing 2 or 3 saturated or unsaturated, 5- to 7-membered heterocyclic rings which are the same or different from each other;

②: a bicyclic or tricyclic fused heterocyclic ring formed by fusing a saturated or unsaturated, 5- to 7-membered heterocyclic ring with 1 or 2 saturated or unsaturated, 5- or 6-membered cyclic hydrocarbons; or ③: a tricyclic fused heterocyclic ring formed by fusing 2 saturated or unsaturated, 5- to 7-membered heterocyclic rings with a saturated or unsaturated, 5- or 6-membered cyclic hydrocarbon.

The position of the saturated or unsaturated, bicyclic or tricyclic fused heterocyclic group bonded to $T^1$ in the general formula (1) is not particularly limited.

The saturated or unsaturated, 5- to 7-membered heterocyclic ring denotes a heterocyclic ring having at least one hetero atom selected from oxygen, sulfur and nitrogen atoms, and specific examples thereof may include furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, thiadiazole, oxadiazine, azepine, diazepine, triazepine, thiazepine and oxazepine. The saturated or unsaturated, 5- or 6-membered cyclic hydrocarbon denotes the same saturated or unsaturated, 5- or 6-membered cyclic hydrocarbon as shown in the description of the saturated or unsaturated, bicyclic or tricyclic fused hydrocarbon group. Specific examples of the saturated or unsaturated, bicyclic or tricyclic fused heterocyclic group may include benzofuryl, isobenzofuryl, benzothienyl, indolyl, indolinyl, isoindolyl, isoindolinyl, indazolyl, quinolyl, dihydroquinolyl, 4-oxodihydroquinolyl (dihydroquinolin-4-on), tetrahydroquinolyl, isoquinolyl, tetrahydroisoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalinyl, tetrahydroquinoxalinyl, cinnolinyl, tetrahydrocinnolinyl, indolizinyl, tetrahydroindolizinyl, benzothiazolyl, tetrahydrobenzothiazolyl, benzoxazolyl, benzoisothiazolyl, benzoisoxazolyl, benzimidazolyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolinyl, dihydropyridoquinazolinyl, pyridopyrimidinyl, tetrahydropyridopyrimidinyl, pyranothiazolyl, dihydropyranothiazolyl, furopyridyl, tetrahydrofuropyridyl, oxazolopyridyl, tetrahydrooxazolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, thienopyrrolyl, thiazolopyrimidinyl, 4-oxotetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazopyridyl, pyrazinopyridazinyl, benzoisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepinyl, benzoazepinyl, tetrahydrobenzoazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, 4,5,6,7-tetrahydro-5,6-tetramethylenethiazolopyridazinyl and 5,6-trimethylene-4,5,6,7-tetrahydrothiazolopyridazinyl groups.

No particular limitation is imposed on the fusing form of the fused heterocyclic group. For example, the naphthyridinyl group may be any of 1,5-, 1,6-, 1,7-, 1,8-, 2,6- and 2,7-naphthyridinyl groups, the thienopyridyl group may be any of thieno[2,3-b]pyridyl, thieno[2,3-c]pyridyl, thieno[3,2-b]pyridyl, thieno[3,2-c]pyridyl, thieno[3,4-b]pyridyl and thieno[3,4-c]pyridyl groups, the thienopyrrolyl group may be any of thieno[2,3-b]pyrrolyl and thieno[2,3-b]pyrrolyl groups, the thiazolopyridyl group may be any of thiazolo[4,5-b]pyridyl, thiazolo[4,5-c]pyridyl, thiazolo[5,4-b]pyridyl, thiazolo[5,4-c]pyridyl, thiazolo[3,4-a]pyridyl and thiazolo[3,2-a]pyridyl groups, the thiazolopyridazinyl group may be any of thiazolo-[4,5-c]pyridazinyl, thiazolo[4,5-d]pyridazinyl, thiazolo[5,4-c]pyridazinyl and thiazolo[3,2-b]-pyridazinyl groups, the pyrrolopyridyl may be any of pyrrolo[2,3-b]pyridyl, pyrrolo[2,3-c]pyridyl, pyrrolo[3,2-b]pyridyl, pyrrolo[3,2-c]pyridyl, pyrrolo[3,4-b]pyridyl and pyrrolo[3,4-c]pyridyl group, the pyridopyrimidinyl group may be any of pyrido[2,3-d]pyrimidinyl, pyrido[3,2-d]pyrimidinyl, pyrido[3,4-d]pyrimidinyl, pyrido[4,3-d]pyrimidinyl, pyrido[1,2-c]pyrimidinyl and pyrido[1,2-a]pyrimidinyl groups, the pyranothiazolyl group may be any of pyrano[2,3-d]thiazolyl, pyrano[4,3-d]thiazolyl, pyrano[3,4-d]thiazolyl and pyrano[3,2-d]thiazolyl groups, the furopyridyl group may be any of furo[2,3-b]pyridyl, furo[2,3-c]pyridyl, furo[3,2-b]pyridyl, furo[3,2-c]-pyridyl, furo[3,4-b]pyridyl and furo[3,4-c]pyridyl groups, the oxazolopyridyl group may be any of oxazolo[4,5-b]pyridyl, oxazolo[4,5-c]pyridyl, oxazolo[5,4-b]pyridyl, oxazolo[5,4-c]pyridyl, oxazolo[3,4-a]pyridyl and oxazolo[3,2-a]pyridyl groups, the oxazolopyridazinyl group may be any of oxazolo[4,5-c]pyridazinyl, oxazolo[4,5-d]-pyridazinyl, oxazolo[5,4-c]pyridazinyl and oxazolo[3,4-b]-pyridazinyl groups, the pyrrolothiazolyl group may be any of pyrrolo[2,1-b]thiazolyl, pyrrolo[1,2-c]thiazolyl, pyrrolo[2,3-d]thiazolyl, pyrrolo[3,2-d]thiazolyl and pyrrolo[3,4-d]thiazolyl groups, the pyrrolooxazolyl group may be any of pyrrolo[2,1-b]oxazolyl, pyrrolo[1,2-c]-oxazolyl, pyrrolo[2,3-d]oxazolyl, pyrrolo[3,2-d]oxazolyl and pyrrolo[3,4-d]oxazolyl groups, the benzoazepinyl group may be any of 1H-1-benzoazepinyl, 1H-2-benzoazepinyl and 1H-3-benzoazepinyl groups, or may be a dihydro-oxo derivative type benzoazepinyl group such as 4,5-dihydro-1-oxo-1H-2-benzoazepinyl group, the benzodiazepinyl group may be any of 1H-1,3-benzodiazepinyl, 1H-1,4-benzodiazepinyl and 1H-1,5-benzodiazepinyl groups, or may be a dihydro-oxo derivative type benzodiazepinyl group such as 4,5-dihydro-4-oxo-1H-1,3-benzodiazepinyl group, the benzotriazepinyl group may be any of 1H-1,3,4-benzotriazepinyl and 1H-1,3,5-benzotriazepinyl groups, or may be a dihydro-oxo derivative type benzotriazepinyl group such as 4,5-dihydro-5-oxo-1H-1,3,4-benzotriazepinyl group, and the thienoazepinyl group may be any of thieno[2,3-b]azepinyl, thieno[2,3-c]azepinyl, thieno[2,3-d]azepinyl, thieno[3,2-c]azepinyl and thieno[3,2-b]-azepinyl groups, or may be a dihydro-oxo derivative type thienoazepinyl group such as 5,6,7,8-tetrahydro-4-oxo-4H-thieno[3,2-c]azepinyl group. Thienodiazepinyl and thienotriazepinyl groups may also be any fusing forms, or may be those of the dihydro-oxo derivative type. The benzothiazepinyl group may be any of 1H-1-benzothiazepinyl, 1H-2-benzothiazepinyl and 1H-3-benzothiazepinyl groups, or may be a dihydro-oxo derivative type benzothiazepinyl group such as 4,5-dihydro-1-oxo-1H-2-benzothiazepinyl group, and the benzoxazepinyl group may be any of 1H-1-benzoxazepinyl, 1H-2-benzoxazepinyl and 1H-3-benzoxazepinyl groups, or may be a dihydro-oxo derivative type benzoxazepinyl group such as 4,5-dihydro-1-oxo-1H-2-benzoxazepinyl group. Other fusing forms than these may be allowed.

The above-described aryl groups, heteroaryl groups, arylalkenyl group, heteroarylalkenyl groups, saturated or unsaturated, bicyclic or tricyclic fused hydrocarbon groups and saturated or unsaturated, bicyclic or tricyclic fused heterocyclic groups may each have 1 to 3 substituents. Examples of the substituents may include a hydroxyl group, halogen atoms such as fluorine atom, chlorine atom, bromine atom and iodine atom, halogenoalkyl groups having 1 to 6 carbon atoms substituted by 1 to 3 halogen atoms, an amino group, a cyano group, aminoalkyl groups, a nitro group, hydroxyalkyl groups (for example, hydroxymethyl group, 2-hydroxyethyl group, etc.), alkoxyalkyl groups (for example, methoxymethyl group, 2-methoxyethyl group, etc.), a carboxyl group, carboxyalkyl groups (for example, carboxymethyl group, 2-carboxyethyl group, etc.), alkoxycarbonylalkyl groups (for example, methoxycarbonylmethyl group, ethoxycarbonylmethyl group, etc.), acyl groups (for example, alkanoyl groups such as formyl group, acetyl group and propionyl group), an amidino group, a hydroxyamidino group, linear, branched or cyclic alkyl groups having 1 to 6 carbon atoms (for example, methyl group, ethyl group, etc.), linear, branched or cyclic alkoxy groups having 1 to 6 carbon atom (for example, methoxy group, ethoxy group, etc.), amidino groups substituted by an alkoxycarbonyl group having 2 to 7 carbon atoms (for example, methoxycarbonylamidino group, ethoxycarbonylamidino group, etc.), linear, branched or cyclic alkenyl groups having 2 to 6 carbon atoms (for example, vinyl group, allyl group, etc.), linear or branched alkynyl groups having 2 to 6 carbon atoms (for example, ethynyl group, propynyl group, etc.), linear, branched or cyclic alkoxycarbonyl groups having 2 to 6 carbon atoms (for example, methoxycarbonyl group, ethoxycarbonyl group, etc.), a carbamoyl group, mono- or di-alkylcarbamoyl groups substituted by a linear, branched or cyclic alkyl groups having 1 to 6 carbon atoms on the nitrogen atom(s), mono- or di-alkylamino groups substituted by 1 or 2 linear, branched or cyclic alkyl groups having 1 to 6 carbon atoms (for example, ethylamino, dimethylamino and methylethylamino groups), and 5- or 6-membered nitrogen-containing heterocyclic groups (for example, pyrrolidino group, piperidino group, piperazino group, morpholino group, etc.).

As the group $Q^4$, are preferred the following 12 groups (a) to (l) among the above-described groups. Namely,

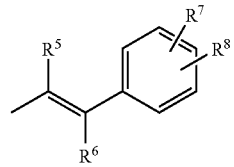

(a)

wherein $R^5$ and $R^6$, independently of each other, represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group, and $R^7$ and $R^8$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

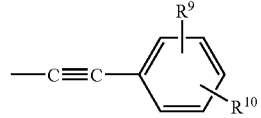

(b)

wherein $R^9$ and $R^{10}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

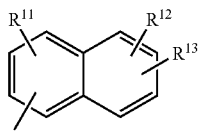
(c)

wherein $R^{11}$, $R^{12}$ and $R^{13}$, independently of one another, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

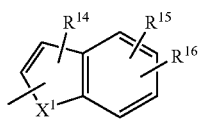
(d)

wherein $X^1$ represents $CH_2$, CH, NH, NOH, N, O or S, and $R^{14}$, $R^{15}$ and $R^{16}$, independently of one another, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

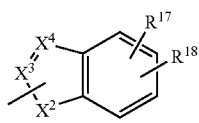
(e)

wherein $X^2$ represents NH, N, O or S, $X^3$ represents N, C or CH, $X^4$ represents N, C or CH, and $R^{17}$ and $R^{18}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, excluding the cases where $X^3$ and $X^4$ are combinations of C and CH, and are both C or CH;

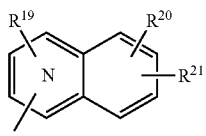
(f)

wherein N indicates that 1 or 2 carbon atoms of the ring substituted by $R^{19}$ have been substituted by a nitrogen atom, and $R^{19}$, $R^{20}$ and $R^{21}$, independently of one another, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

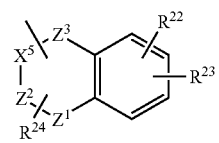
(g)

wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, $R^{22}$ and $R^{23}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, and $R^{24}$ represents a hydrogen atom or alkyl group;

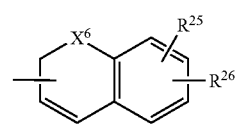
(h)

wherein $X^6$ represents O or S, and $R^{25}$ and $R^{26}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

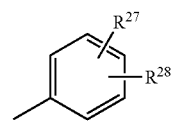
(i)

wherein $R^{27}$ and $R^{28}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

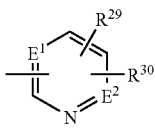

(j)

wherein $E^1$ and $E^2$, independently of each other, represent N or CH, and $R^{29}$ and $R^{30}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

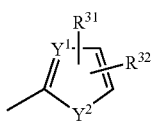

(k)

wherein $Y^1$ represents CH or N, $Y^2$ represents —N($R^{33}$)—, in which $R^{33}$ means a hydrogen atom or alkyl group having 1 to 6 carbon atoms, O or S, and $R^{31}$ and $R^{32}$, independently of each other, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group; and

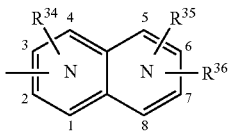

(l)

wherein numerals 1 to 8 indicate positions, each N indicates that any one of carbon atoms of positions 1 to 4 and any one of carbon atoms of positions 5 to 8 has been substituted by a nitrogen atom, and $R^{34}$, $R^{35}$ and $R^{36}$, independently of one another, represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group.

These groups will hereinafter be described.

In the description of $R^5$ to $R^{36}$, the halogen atom is a fluorine, chlorine, bromine or iodine atom, the alkyl group is a linear, branched or cyclic alkyl group having 1 to 6 carbon atoms, the alkenyl group is a linear, branched or cyclic alkenyl groups having 2 to 6 carbon atoms, the alkynyl group is a linear or branched alkynyl groups having 2 to 6 carbon atoms, the hydroxyalkyl group means the above-described $C_1$-$C_6$ alkyl group substituted by a hydroxyl group, the alkoxy group is a linear, branched or cyclic alkoxy group having 1 to 6 carbon atoms, the alkoxyalkyl group means the above-described $C_1$-$C_6$ alkyl group substituted by the above-described $C_1$-$C_6$ alkoxy group, the carboxyalkyl group means the above-described $C_1$-$C_6$ alkyl group substituted by a carboxyl group, the acyl group is an alkanoyl group (including formyl) having 1 to 6 carbon atom, an aroyl group such as a benzoyl or naphthoyl group, or an arylalkanoyl group with the above-described $C_6$-$C_{14}$ aryl group substituted on the above-described $C_1$-$C_6$ alkanoyl group, the N-alkylcarbamoyl group means a carbamoyl group with the above-described $C_1$-$C_6$ alkyl group substituted on the nitrogen atom, the N,N-dialkylcarbamoyl group means a carbamoyl group with two of the above-described $C_1$-$C_6$ alkyl groups substituted on the nitrogen atom, the alkoxycarbonyl group is a group composed of the above-described $C_1$-$C_6$ alkoxy group and a carbonyl group, the alkoxycarbonylalkyl group means the above-described $C_1$-$C_6$ alkyl group substituted by the above-described $C_1$-$C_6$ alkoxycarbonyl group, and the halogenoalkyl group means the above-described $C_1$-$C_6$ alkyl group substituted by 1 to 3 halogen atoms. Incidentally, in the above description, no particular limitation is imposed on the substituting position.

In the following group:

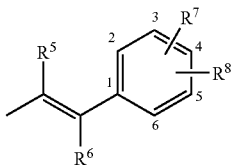

(a)

wherein $R^5$, $R^6$, $R^7$ and $R^8$ have the same meanings as defined above, and numerals 1 to 6 indicate positions, $R^5$ and $R^6$, independently of each other, are preferably a hydrogen atom, cyano group, halogen atom, alkyl group, alkenyl group, alkynyl group or halogenoalkyl group. $R^5$ and $R^6$ are more preferably hydrogen atoms or alkyl groups. In the case of the alkyl group, a methyl group is preferred. It is preferable that one of $R^7$ and $R^8$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned chlorostyryl, fluorostyryl, bromostyryl and ethynylstyryl groups. The position substituted by the halogen atom, alkyl group or alkynyl group is particularly preferably a 4-position in the above formula though it should not be particularly limited. As specific preferable examples thereof, may be mentioned 4-chlorostyryl, 4-fluorostyryl, 4-bromostyryl and 4-ethynylstyryl groups.

In the following group:

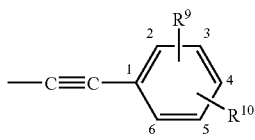

(b)

wherein $R^9$ and $R^{10}$ have the same meanings as defined above, and numerals 1 to 6 indicate positions, $R^9$ and $R^{10}$, independently of each other, are preferably a hydrogen atom, halogen atom, alkyl group or alkynyl group. It is further preferable that $R^9$ is a hydrogen atom, and $R^{10}$ is a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned chlorophenylethynyl, fluorophenylethynyl, bromophenylethynyl and ethynylphenylethynyl groups. The position substituted by the halogen atom, alkyl group or alkynyl group is particularly preferably a 4-position in the above formula though it should not be particularly limited. As specific preferable examples thereof, may be mentioned 4-chlorophenylethynyl, 4-fluorophenylethynyl, 4-bromophenylethynyl and 4-ethynylphenylethynyl groups.

In the following group:

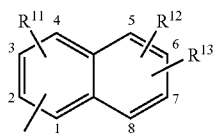

(c)

wherein $R^{11}$, $R^{12}$ and $R^{13}$ have the same meanings as defined above, and numerals 1 to 8 indicate positions, $R^{11}$, $R^{12}$ and $R^{13}$ are, independently of one another, preferably a hydrogen atom, cyano group, halogen atom, alkyl group, alkenyl group, alkynyl group or halogenoalkyl group. $R^{11}$ is preferably a hydrogen atom, alkyl group, halogen atom or hydroxyl group, with a hydrogen atom particularly preferred. It is preferable that one of $R^{12}$ and $R^{13}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. In the naphthyl group, a 2-naphthyl group is preferred to a 1-naphthyl group. In the case of the 2-naphthyl group, a position substituted by a halogen atom, alkyl group or alkynyl group is preferably a 6- or 7-position in the above formula though it should not be particularly limited, with a 6-position being most preferred. These naphthyl groups are preferbly substituted by a chlorine, fluorine or bromine atom, an alkynyl group, or the like, with a group having a substituents such as a chlorine, fluorine or bromine atom, an alkynyl group, or the like at the above-described position in the above formula being particularly preferred. As specific preferable examples thereof, may be mentioned 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl and 7-ethynyl-2-naphthyl groups.

In the following group:

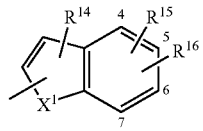

(d)

wherein $X^1$, $R^{14}$, $R^{15}$ and $R^{16}$ have the same meanings as defined above, and numerals 4 to 7 indicate positions, $X^1$ is preferably NH, NOH, N, O or S, with NH, O or S being particularly preferred. $R^{14}$ is preferably a hydrogen atom, halogen atom, acyl group, N-alkylcarbamoyl group, N,N-dialkylcarbamoyl group or alkyl group, and $R^{15}$ and $R^{16}$ are, independently of each other, preferably a hydrogen atom, cyano group, halogen atom, alkyl group, alkenyl group, alkynyl group or halogenoalkyl group. It is preferable that one of $R^{15}$ and $R^{16}$ is a hydrogen or a halogen atom, preferably fluorine atom or chlorine atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 4-, 5- or 6-position in the above formula though it should be not particularly limited. As specific preferable examples of the group represented by the above formula, may be mentioned 5-chloroindolyl, 5-fluoroindolyl, 5-bromoindolyl, 5-ethynylindolyl, 5-methylindolyl, 5-chloro-4-fluoroindolyl, 5-chloro-3-fluoroindolyl, 5-fluoro-3-chloroindolyl, 5-ethynyl-3-fluoroindolyl, 5-chloro-3-(N,N-dimethylcarbamoyl) indolyl, 5-fluoro-3-(N,N-dimethylcarbamoyl)indolyl, 5-chloro-3-formylindolyl, 5-fluoro-3-formylindolyl, 6-chloroindolyl, 6-fluoroindolyl, 6-bromoindolyl, 6-ethynylindolyl, 6-methylindolyl, 5-chlorobenzothienyl, 5-fluorobenzothienyl, 5-bromobenzothienyl, 5-ethynylbenzothienyl, 5-methylbenzothienyl, 5-chloro-4-fluorobenzothienyl, 6-chlorobenzothienyl, 6-fluorobenzothienyl, 6-bromobenzothienyl, 6-ethynylbenzothienyl, 6-methylbenzothienyl, 5-chlorobenzofuryl, 5-fluorobenzofuryl, 5-bromobenzofuryl, 5-ethynylbenzofuryl, 5-methylbenzofuryl, 5-chloro-4-fluorobenzofuryl, 6-chlorobenzofuryl, 6-fluorobenzofuryl, 6-bromobenzofuryl, 6-ethynylbenzofuryl and 6-methylbenzofuryl groups. The position of the above-described substituent group bonded to $T^1$ is not particularly limited, but is preferably a 2-position or 3-position in the formula (d). Specifically, more preferred are 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N- dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 6-chloroindol-2-yl, 6-fluoroindol-2-yl, 6-bromoindol-2-yl, 6-ethynylindol-2-yl, 6-methylindol-2-yl, 5-chloroindol-3-yl, 5-fluoroindol-3-yl, 5-bromoindol-3-yl, 5-ethynylindol-3-yl, 5-methylindol-3-yl, 5-chloro-4-fluoroindol-3-yl, 6-chloroindol-3-yl, 6-fluoroindol-3-yl, 6-bromoindol-3-yl, 6-ethynylindol-3-yl, 6-methylindol-3-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzothiophen-3-yl, 5-fluorobenzothiophen-3-yl, 5-bromobenzothiophen-3-yl, 5-ethynylbenzothiophen-3-yl, 5-methylbenzothiophen-3-yl, 5-chloro-4-fluorobenzothiophen-3-yl, 6-chlorobenzothiophen-3-yl, 6-fluorobenzothiophen-3-yl, 6-bromobenzothiophen-3-yl, 6-ethynylbenzothiophen-3-yl, 6-methylbenzothiophen-3-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzofuran-3-yl, 5-fluorobenzofuran-3-yl, 5-bromobenzofuran-3-yl, 5-ethynylbenzofuran-3-yl, 5-methylbenzofuran-3-yl, 5-chloro-4-fluorobenzofuran-3-yl, 6-chlorobenzofuran-3-yl, 6-fluorobenzofuran-3-yl, 6-bromobenzofuran-3-yl, 6-ethynylbenzofuran-3-yl and 6-methylbenzofuran-3-yl groups, with 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methyindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl and 6-methylbenzofuran-2-yl groups being particularly preferred.

In the following group:

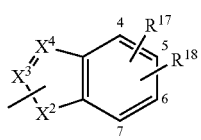

(e)

wherein $X^2$, $X^3$, $X^4$, $R^{17}$ and $R^{18}$ have the same meanings as defined above, and numerals 4 to 7 indicate positions, $X^2$ is preferably NH, O or S, any one of $X^3$ and $X^4$ is preferably CH or C, particularly preferably C. $R^{17}$ and $R^{18}$ are, independently of each other, preferably a hydrogen atom, cyano group, halogen atom, alkyl group, alkenyl group, alkynyl group or halogenoalkyl group. It is preferable that one of $R^{17}$ and $R^{18}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 5- or 6-position in the above formula though it should not be particularly limited. As specific preferable examples of the group represented by the above formula, may be mentioned 5-chloroindazolyl, 5-fluoroindazolyl, 5-bromoindazolyl, 5-ethynylindazolyl, 6-chloroindazolyl, 6-fluoroindazolyl, 6-bromoindazolyl, 6-ethynylindazolyl, 5-chlorobenzimidazolyl, 5-fluorobenzimidazolyl, 5-bromobenzimidazolyl, 5-ethynylbenzimidazolyl, 6-chlorobenzimidazolyl, 6-fluorobenzimidazolyl, 6-bromobenzimidazolyl, 6-ethynylbenzimidazolyl, 5-chlorobenzothiazolyl, 5-fluorobenzothiazolyl, 5-bromobenzothiazolyl, 5-ethynylbenzothiazolyl, 6-chlorobenzothiazolyl, 6-fluorobenzothiazolyl, 6-bromobenzothiazolyl, 6-ethynylbenzothiazolyl, 5-chlorobenzoxazolyl, 5-fluorobenzoxazolyl, 5-bromobenzoxazolyl, 5-ethynylbenzoxazolyl, 6-chlorobenzoxazolyl, 6-fluorobenzoxazolyl, 6-bromobenzoxazolyl, 6-ethynylbenzoxazolyl, 5-chlorobenzoisothiazolyl, 5-fluorobenzoisothiazolyl, 5-bromobenzoisothiazolyl, 5-ethynylbenzoisothiazolyl, 6-chlorobenzoisothiazolyl, 6-fluorobenzoisothiazolyl, 6-bromobenzoisothiazolyl, 6-ethynylbenzoisothiazolyl, 5-chlorobenzoisoxazolyl, 5-fluorobenzoisoxazolyl, 5-bromobenzoisoxazolyl, 5-ethynylbenzoisoxazolyl, 6-chlorobenzoisoxazolyl, 6-fluorobenzoisoxazolyl, 6-bromobenzoisoxazolyl and 6-ethynylbenzoisoxazolyl groups. The position of the above-described substituent group bonded to $T^1$ is not particularly limited. More preferred are 5-chloroindazol-3-yl, 5-fluoroindazol-3-yl, 5-bromoindazol-3-yl, 5-ethynylindazol-3-yl, 6-chloroindazol-3-yl, 6-fluoroindazol-3-yl, 6-bromoindazol-3-yl, 6-ethynylindazol-3-yl, 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, 6-ethynylbenzoxazol-2-yl, 5-chlorobenzoisothiazol-3-yl, 5-fluorobenzoisothiazol-3-yl, 5-bromobenzoisothiazol-3-yl, 5-ethynylbenzoisothiazol-3-yl, 6-chlorobenzoisothiazol-3-yl, 6-fluorobenzoisothiazol-3-yl, 6-bromobenzoisothiazol-3-yl, 6-ethynylbenzoisothiazol-3-yl, 5-chlorobenzoisoxazol-3-yl, 5-fluorobenzoisoxazol-3-yl, 5-bromobenzoisoxazol-3-yl, 5-ethynylbenzoisoxazol-3-yl, 6-chlorobenzoisoxazol-3-yl, 6-fluorobenzoisoxazol-3-yl, 6-bromobenzoisoxazol-3-yl and 6-ethynylbenzoisoxazol-3-yl groups, with 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazole-2-yl, 5-bromobenzothiazol-2-yl, 5-ethynylbenzothiazole-2-yl, 6-chlorobenzothiazol-2-yl, 6-fluorobenzothiazole-2-yl, 6-bromobenzothiazol-2-yl, 6-ethynylbenzothiazole-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl and 6-ethynylbenzoxazol-2-yl groups being particularly preferred. Among these, 5-chlorobenzimidazol-2-yl, 5-fluorobenzimidazol-2-yl, 5-bromobenzimidazol-2-yl and 5-ethynylbenzimidazol-2-yl are further preferred.

In the following group:

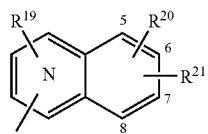

(f)

wherein N indicates that 1 or 2 carbon atoms of the ring substituted by $R^{19}$ have been substituted by a nitrogen atom, $R^{19}$, $R^{20}$ and $R^{21}$ have the same meanings as defined above, and numerals 5 to 8 indicate positions, $R^{19}$, $R^{20}$ and $R^{21}$ are, independently of each other, preferably a hydrogen atom, cyano group, halogen atom, alkyl group, alkenyl group, alkynyl group or halogenoalkyl group. $R^{19}$ is particularly preferably a hydrogen atom. It is preferable that one of $R^{20}$ and $R^{21}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should not be particularly limited. As specific preferable examples thereof, may be mentioned quinolinyl, isoquinolinyl and cinnolinyl groups. More preferred are 6-chloroquinolinyl, 6-fluoroquinolinyl, 6-bromoquinolinyl, 6-ethynylquinolinyl, 6-chloroisoquinolinyl, 6-fluoroisoquinolinyl, 6-bromoisoquinolinyl, 6-ethynylisoquinolinyl, 7-chlorocinnolinyl, 7-fluorocinnolinyl, 7-bromocinnolinyl and 7-ethynylcinnolinyl groups, with 6-chloroquinolin-2-yl, 6-fluoroquinolin-2-yl, 6-bromoquinolin-2-yl, 6-ethynylquinolin-2-yl, 6-chloroquinolin-3-yl, 6-fluoroquinolin-3-yl, 6-bromoquinolin-3-yl, 6-ethynylquinolin-3-yl, 7-chloroquinolin-2-yl, 7-fluoroquinolin-2-yl, 7-bromoquinolin-2-yl, 7-ethynylquinolin-2-yl, 7-chloroquinolin-3-yl, 7-fluoroquinolin-3-yl, 7-bromoquinolin-3-yl, 7-ethynylquinolin-3-yl, 6-chloroisoquinolin-3-yl, 6-fluoroisoquinolin-3-yl, 6-bromoisoquinolin-3-yl, 6-ethynylisoquinolin-3-yl, 7-chloroisoquin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl and 7-ethynylcinnolin-3-yl groups being particularly preferred. Among these, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl and 7-ethynylcinnolin-3-yl groups are further preferred.

In the following group:

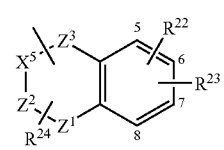

(g)

wherein numerals 5 to 8 indicate positions, $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, and $R^{22}$, $R^{23}$ and $R^{24}$ have the same meanings as defined above, numerals 5 to 8 indicate positions, $R^{22}$ and $R^{23}$ are, independently of each other, a hydrogen atom, cyano group, halogen atom, alkyl group, alkenyl group, alkynyl group or halogenoalkyl group. It is preferable that one of $R^{22}$ and $R^{23}$ is a hydrogen, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should be not particularly limited. $R^{24}$ is preferably a hydrogen atom or alkyl group, and a methyl group is preferred as the alkyl group. As $R^{24}$, is particularly preferred a hydrogen atom. As specific preferable examples of the group represented by the above formula, may be mentioned 4-oxodihydroquinolinyl, tetrahydroquinolinyl, dihydroquinazolin-4-one-2-yl, 4-oxotetrahydrocinnolinyl, 4-oxobenzopyranyl, 4-oxobenzothiadiazinyl, 1,1-dioxy-4-oxo-benzothiadiazinyl and benzoxadiazinyl groups. As specific preferable examples thereof, may be mentioned 6-chloro-4-oxodihydroquinolinyl, 6-fluoro-4-oxodihydroquinolinyl, 6-bromo-4-oxodihydroquinolinyl, 6-ethynyl-4-oxodihydroquinolinyl, 7-chloro-4-oxodihydroquinolinyl, 7-fluoro-4-oxodihydroquinolinyl, 7-bromo-4-oxodihydroquinolinyl, 7-ethynyl-4-oxodihydroquinolinyl, 6-chloro-4-oxo-1,4-dihydroquinazolinyl, 6-fluoro-4-oxo-1,4-dihydroquinazolinyl, 6-bromo-4-oxo-1,4-dihydroquinazolinyl, 6-ethynyl-4-oxo-1,4-dihydroquinazolinyl, 7-chloro-4-oxo-1,4-dihydroquinazolinyl, 7-fluoro-4-oxo-1,4-dihydroquinazolinyl, 7-ethynyl-4-oxo-1,4-dihydroquinazolinyl, 6-chloro-1,2,3,4-tetrahydroquinolinyl, 6-fluoro-1,2,3,4-tetrahydro-quinolinyl, 6-bromo-1,2,3,4-tetrahydroquinolinyl, 6-ethynyl-1,2,3,4-tetrahydroquinolinyl, 7-chloro-1,2,3,4-tetrahydroquinolinyl, 7-fluoro-1,2,3,4-tetrahydroquinolinyl, 7-bromo-1,2,3,4-tetrahydroquinolinyl, 7-ethynyl-1,2,3,4-tetrahydroquinolinyl, 6-chloro-1,2,3,4-tetrahydro-4-oxocinnolinyl, 6-fluoro-1,2,3,4-tetrahydro-4-oxocinnolinyl, 6-bromo-1,2,3,4-tetrahydro-4-oxocinnolinyl, 6-ethynyl-1,2,3,4-tetrahydro-4-oxocinnolinyl, 7-chloro-1,2,3,4-tetrahydro-4-oxocinnolinyl, 7-fluoro-1,2,3,4-tetrahydro-4-oxocinnolinyl, 7-bromo-1,2,3,4-tetrahydro-4-oxocinnolinyl, 7-ethynyl-1,2,3,4-tetrahydro-4-oxocinnolinyl, 6-chloro- 4H-4-oxobenzopyranyl, 6-fluoro-4H-4-oxobenzopyranyl, 6-bromo-4H-4-oxobenzopyranyl, 6-ethynyl-4H-4-oxobenzopyranyl, 7-chloro-4H-4-oxobenzopyranyl, 7-fluoro-4H-4-oxobenzopyranyl, 7-bromo-4H-4-oxobenzopyranyl, 7-ethynyl-4H-4-oxobenzopyranyl, 6-chloro-1,1-dioxy-2H-1,2,4-benzothiadiazinyl, 6-fluoro-1,1-dioxy-2H-1,2,4-benzothiadiazinyl, 6-bromo-1,1-dioxy-2H-1,2,4-benzothiadiazinyl, 6-ethynyl-1,1-dioxy-2H-1,2,4-benzothiadiazinyl, 7-chloro-1,1-dioxy-2H-1,2,4-benzothiadiazinyl, 7-fluoro-1,1-dioxy-2H-1,2,4-benzothiadiazinyl, 7-bromo-1,1-dioxy-2H-1,2,4-benzothiadiazinyl, 7-ethynyl-1,1-dioxy-2H-1,2,4-benzothiadiazinyl, 6-chloro-2H-1,2,4-benzoxadiazinyl, 6-fluoro-2H-1,2,4-benzoxadiazinyl, 6-bromo-2H-1,2,4-benzoxadiazinyl, 6-ethynyl-2H-1,2,4-benzoxadiazinyl, 7-chloro-2H-1,2,4-benzoxadiazinyl, 7-fluoro-2H-1,2,4-benzoxadiazinyl, 7-bromo-2H-1,2,4-benzoxadiazinyl and 7-ethynyl-2H-1,2,4-benzoxadiazinyl groups; with 6-chloro-1,4-dihydroquinolin-4-one-2-yl, 6-fluoro-1,4-dihydroquinolin-4-one-2-yl, 6-bromo-1,4-dihydroquinolin-4-one-2-yl, 6-ethynyl-1,4-dihydroquinolin-4-one-2-yl, 7-chloro-1,4-dihydroquinolin-4-one-2-yl, 7-fluoro-1,4-dihydroquinolin-4-one-2-yl, 7-bromo-1,4-dihydroquinolin-4-one-2-yl, 7-ethynyl-1,4-dihydroquinolin-4-one-2-yl, 6-chloro-1,4-dihydroquinazolin-4-one-2-yl, 6-fluoro-1,4-dihydroquinazolin-4-one-2-yl, 6-bromo-1,4-dihydroquinazolin-4-one-2-yl, 6-ethynyl-1,4-dihydroquinazolin-4-one-2-yl, 7-chloro-1,4-dihydroquinazolin-4-one-2-yl, 7-fluoro-1,4-dihydroquinazolin-4-one-2-yl, 7-bromo-1,4-dihydroquinazolin-4-one-2-yl, 7-ethynyl-1,4-dihydroquinazolin-4-one-2-yl, 6-chloro-1,2,3,4-tetrahydroquinolin-2-yl, 6-fluoro-1,2,3,4-tetrahydroquinolin-2-yl, 6-bromo-1,2,3,4-tetrahydroquinolin-2-yl, 6-ethynyl-1,2,3,4-tetrahydroquinolin-2-yl, 6-chloro-1,2,3,4-tetrahydro-4-oxocinnolin-2-yl, 6-fluoro-1,2,3,4-tetrahydro-4-oxocinnolin-2-yl, 6-bromo-1,2,3,4-tetrahydro-4-oxocinnolin-2-yl, 6-ethynyl-1,2,3,4-tetrahydro-4-oxocinnolin-2-yl, 7-chloro-1,2,3,4-tetrahydro-4-oxocinnolin-2-yl, 7-fluoro-1,2,3,4-tetrahydro-4-oxocinnolin-2-yl, 7-bromo-1,2,3,4-tetrahydro-4-oxocinnolin-2-yl, 7-ethynyl-1,2,3,4-tetrahydro-4-oxocinnolin-2-yl, 6-chloro-4H-4-oxobenzopyran-2-yl, 6-fluoro-4H-4-oxobenzopyran-2-yl, 6-bromo-4H-4-oxobenzopyran-2-yl, 6-ethynyl-4H-4-oxobenzopyran-2-yl, 7-chloro-4H-4-oxobenzopyran-2-yl, 7-fluoro-4H-4-oxobenzopyran-2-yl, 7-bromo-4H-4-oxobenzopyran-2-yl, 7-ethynyl-4H-4-oxobenzopyran-2-yl, 6-chloro-1,1-dioxy-2H-1,2,4-benzothiadiazin-3-yl, 6-fluoro-1,1-dioxy-2H-1,2,4-benzothiadiazin-3-yl, 6-bromo-1,1-dioxy-2H-1,2,4-benzothiadiazin-3-yl, 6-ethynyl-1,1-dioxy-2H-1,2,4-benzothiadiazin-3-yl, 7-chloro-1,1-dioxy-2H-1,2,4-benzothiadiazin-3-yl, 7-fluoro-1,1-dioxy-2H-1,2,4-benzothiadiazin-3-yl, 7-bromo-1,1-dioxy-2H-1,2,4-benzothiadiazin-3-yl, 7-ethynyl-1,1-dioxy-2H-1,2,4-benzothiadiazin-3-yl, 6-chloro-2H-1,2,4-benzoxadiazin-3-yl, 6-fluoro-2H-1,2,4-benzoxadiazin-3-yl, 6-bromo-2H-1,2,4-benzoxadiazin-3-yl, 6-ethynyl-2H-1,2,4-benzoxadiazin-3-yl, 7-chloro-2H-1,2,4-benzoxadiazin-3-yl, 7-fluoro-2H-1,2,4-benzoxadiazin-3-yl, 7-bromo-2H-1,2,4-benzoxadiazin-3-yl and 7-ethynyl-2H-1,2,4-benzoxadiazin-3-yl groups being preferred. Among these, 6-chloro-1,4-dihydroquinolin-4-one-2-yl, 6-fluoro-1,4-dihydroquinolin-4-one-2-yl, 6-bromo-1,4-dihydroquinolin-4-one-2-yl, 6-ethynyl-1,4-dihydroquinolin-4-one-2-yl, 6-chloro-1,4-dihydroquinazolin-4-one-2-yl, 6-fluoro-1,4-dihydroquinazolin-4-one-2-yl, 6-bromo-1,4-dihydroquinazolin-4-one-2-yl and 6-ethynyl-1,4-dihydroquinazolin-4-one-2-yl are particularly preferred.

In the following group:

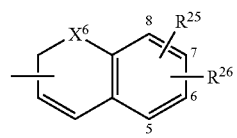

(h)

wherein $X^6$ represents O or S, $R^{25}$ and $R^{26}$ have the same meanings as defined above, and numerals 5 to 8 indicate positions, $X^6$ is preferably O, and $R^{25}$ and $R^{26}$ are, independently of each other, preferably a hydrogen atom, cyano group, halogen atom, alkyl group, alkenyl group, alkynyl group or halogenoalkyl group. It is preferable that one of $R^{25}$ and $R^{26}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should be not particularly limited. As specific preferable examples thereof, may be mentioned 6-chloro-2H-chromen-3-yl, 6-fluoro-2H-chromen-3-yl, 6-bromo-2H-chromen-3-yl, 6-ethynyl-2H-chromen-3-yl, 7-chloro-2H-chromen-3-yl, 7-fluoro-2H-chromen-3-yl, 7-bromo-2H-chromen-3-yl and 7-ethynyl-2H-chromen-3-yl groups, with 7-chloro-2H-chromen-3-yl, 7-fluoro-2H-chromen-3-yl, 7-bromo-2H-chromen-3-yl and 7-ethynyl-2H-chromen-3-yl groups being particularly preferred.

In the following group:

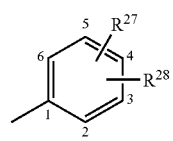

(i)

wherein $R^{27}$ and $R^{28}$ have the same meanings as defined above, and numerals 1 to 6 indicate positions, it is preferable that one of $R^{27}$ and $R^{28}$ is a hydrogen atom or halogen atom, and the other is a hydrogen atom, cyano group, nitro group, amino group, halogen atom, alkyl group, alkenyl group, alkynyl group, halogenoalkyl group or N,N-dialkylcarbamoyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned, chlorophenyl, fluorophenyl, bromophenyl, ethynylphenyl and chlorofluorophenyl groups. The position substituted by the halogen atom, alkyl group or alkynyl group in these groups is particularly preferably a 3- or 4-position in the above formula in the case of one substituent or a combination of a 4-position and a 2- or 3-position in the above formula in the case of two substituents though it should be not particularly limited. As specific preferable examples thereof, may be mentioned, 4-chlorophenyl, 4-fluorophenyl, 4-bromophenyl, 4-ethynylphenyl, 3-chlorophenyl, 3-fluorophenyl, 3-bromophenyl, 3-ethynylphenyl, 3-chloro-4-fluorophenyl, 4-chloro-3-fluorophenyl, 4-chloro-2-fluorophenyl, 2-chloro-4-fluorophenyl, 4-bromo-2-fluorophenyl, 2-bromo-4-fluorophenyl, 2,4-dichlorophenyl, 2,4-difluorophenyl, 2,4-dibromophenyl, 4-chloro-3-methylphenyl, 4-fluoro-3-methylphenyl, 4-bromo-3-methylphenyl, 4-chloro-2-methylphenyl, 4-fluoro-2-methylphenyl, 4-bromo-2-methylphenyl, 3,4-dichlorophenyl, 3,4-difluorophenyl and 3,4-dibromophenyl.

In the following group:

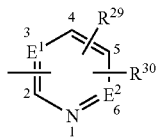

(j)

wherein $E^1$, $E^2$, $R^{29}$ and $R^{30}$ have the same meanings as defined above, and numerals 1 to 6 indicate positions, it is preferable that one of $R^{29}$ and $R^{30}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned pyridyl, pyrimidyl and pyridazinyl groups. The position substituted by the halogen atom, alkyl group or alkynyl group in these groups is particularly preferably a 4- or 5-position in the above formula in the case where its bonding to the group $T^1$ is at a 2-position in the above formula though it should be not particularly limited. As specific preferable examples thereof, may be mentioned 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 5-chloro-2-pyrimidyl, 5-fluoro-2-pyrmidyl, 5-bromo-2-pyrimidyl, 5-ethynyl-2-pyrimidyl, 4-chloro-3-pyridazinyl, 4-fluoro-3-pyridazinyl, 4-bromo-3-pyridazinyl, 4-ethynyl-3-pyridazinyl, 6-chloro-3-pyridazinyl, 6-fluoro-3-pyridazinyl, 6-bromo-3-pyridazinyl and 6-ethynyl-3-pyridazinyl groups. Particularly preferred are 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 6-chloro-3-pyridazinyl, 6-fluoro-3-pyridazinyl, 6-bromo-3-pyridazinyl and 6-ethynyl-3-pyridazinyl groups. Among these, 2-pyridyl, 3-pyridyl, 4-pyridyl, 5-chloro-2-pyridyl, 5-fluoro-2-pyridyl, 5-bromo-2-pyridyl, 5-ethynyl-2-pyridyl, 5-chloro-4-fluoro-2-pyridyl, 4-chloro-5-fluoro-2-pyridyl, 4-chloro-3-pyridazinyl, 4-fluoro-3-pyridazinyl, 4-bromo-3-pyridazinyl and 4-ethynyl-3-pyridazinyl groups are further preferred.

In the following group:

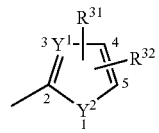

(k)

wherein $Y^1$, $Y^2$, $R^{31}$ and $R^{32}$ have the same meanings as defined above, and numerals 1 to 5 indicate positions, it is preferable that one of $R^{31}$ and $R^{32}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned thienyl, pyrrolyl, furyl, oxazolyl and thiazolyl groups. The position substituted by the halogen atom, alkyl group or alkynyl group in these groups is particularly preferably a 4- or 5-position in the above formula though it should be not particularly limited. As specific preferable examples thereof, may be mentioned 4-chloro-2-thienyl, 4-fluoro-2-thienyl, 4-bromo-2-thienyl, 4-ethynyl-2-thienyl, 4-chloro-2-pyrrolyl, 4-fluoro-2-pyrrolyl, 4-bromo-2-pyrrolyl, 4-ethynyl-2-pyrrolyl, 4-chloro-2-furyl, 4-fluoro-2-furyl, 4-bromo-2-furyl, 4-ethynyl-2-furyl, 5-chloro-2-thienyl, 5-fluoro-2-thienyl, 5-bromo-2-thienyl, 5-ethynyl-2-thienyl, 5-chloro-2-thiazolyl, 5-fluoro-2-thiazolyl, 5-bromo-2-thiazolyl, 5-ethynyl-2-thiazolyl, 5-chloro-2-oxazolyl, 5-fluoro-2-oxazolyl, 5-bromo-2-oxazolyl and 5-ethynyl-2-oxazolyl groups. Paticularly preferred are 5-chloro-2-thiazolyl, 5-fluoro-2-thiazolyl, 5-bromo-2-thiazolyl and 5-ethynyl-2-thiazolyl groups.

In the following group:

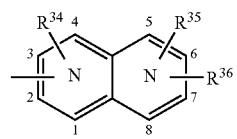

(l)

wherein numerals 1 to 8 indicate positions, each N indicates that any one of 4 carbon atoms at positions 1 to 4 and any one of 4 carbon atoms at positions 5 to 8 have been substituted by a nitrogen atom, and $R^{34}$ to $R^{36}$ have the same meanings as defined above, the position of each nitrogen atom may be in any positional relation, and $R^{34}$ is preferably a hydrogen atom or halogen atom. It is preferable that one of $R^{35}$ and $R^{36}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is not be particularly limited. As preferable examples of specific groups represented by the above formula, may be mentioned 6-chloro-1,5-naphthyridin-2-yl, 6-fluoro-1,5-naphthyridin-2-yl, 6-bromo-1,5-naphthyridin-2-yl, 6-ethynyl-1,5-naphthyridin-2-yl, 7-chloro-1,5-naphthyridin-2-yl, 7-fluoro-1,5-naphthyridin-2-yl, 7-bromo-1,5-naphthyridin-2-yl, 7-ethynyl-1,5-naphthyridin-2-yl, 6-chloro-1,5-naphthyridin-3-yl, 6-fluoro-1,5-naphthyridin-3-yl, 6-bromo-1,5-naphthyridin-3-yl, 6-ethynyl-1,5-naphthyridin-3-yl, 7-chloro-1,5-naphthyridin-3-yl, 7-fluoro-1,5-naphthyridin-3-yl, 7-bromo-1,5-naphthyridin-3-yl, 7-ethynyl-1,5-naphthyridin-3-yl, 6-chloro-1,7-naphthyridin-2-yl, 6-fluoro-1,7-naphthyridin-2-yl, 6-bromo-1,7-naphthyridin-2-yl, 6-ethynyl-1,7-naphthyridin-2-yl, 6-chloro-1,7-naphthyridin-3-yl, 6-fluoro-1,7-naphthyridin-3-yl, 6-bromo-1,7-naphthyridin-3-yl, 6-ethynyl-1,7-naphthyridin-3-yl, 6-chloro-1,8-naphthyridin-2-yl, 6-fluoro-1,8-naphthyridin-2-yl, 6-bromo-1,8-naphthyridin-2-yl, 6-ethynyl-1,8-naphthyridin-2-yl, 7-chloro-1,8-naphthyridin-2-yl, 7-fluoro-1,8-naphthyridin-2-yl, 7-bromo-1,8-naphthyridin-2-yl, 7-ethynyl-1,8-naphthyridin-2-yl, 6-chloro-1,8-naphthyridin-3-yl, 6-fluoro-1,8-naphthyridin-3-yl, 6-bromo-1,8-naphthyridin-3-yl, 6-ethynyl-1,8-naphthyridin-3-yl, 7-chloro-1,8-naphthyridin-3-yl, 7-fluoro-1,8-naphthyridin-3-yl, 7-bromo-1,8-naphthyridin-3-yl, 7-ethynyl-1,8-naphthyridin-3-yl, 6-chloro-2,5-naphthyridin-3-yl, 6-fluoro-2,5-naphthyridin-3-yl, 6-bromo-2,5-naphthyridin-3-yl, 6-ethynyl-2,5-naphthyridin-3-yl, 7-chloro-2,5-naphthyridin-3-yl, 7-fluoro-2,5-naphthyridin-3-yl, 7-bromo-2,5-naphthyridin-3-yl, 7-ethynyl-2,5-naphthyridin-3-yl, 7-chloro-2,6-naphthyridin-3-yl, 7-fluoro-2,6-naphthyridin-3-yl, 7-bromo-2,6-naphthyridin-3-yl, 7-ethynyl-2,6-naphthyridin-3-yl, 6-chloro-2,8-naphthyridin-3-yl, 6-fluoro-2,8-naphthyridin-3-yl, 6-bromo-2,8-naphthyridin-3-yl, 6-ethynyl-2,8-naphthyridin-3-yl, 7-chloro-2,8-naphthyridin-3-yl, 7-fluoro-2,8-naphthyridin-3-yl, 7-bromo-2,8-naphthyridin-3-yl and 7-ethynyl-2,8-naphthyridin-3-yl groups. Particularly preferable example thereof include 7-chloro-2,5-naphthyridin-3-yl, 7-fluoro-2,5-naphthyridin-3-yl, 7-bromo-2,5-naphthyridin-3-yl, 7-ethynyl-2,5-naphthyridin-3-yl.

In addition to the above-mentioned 12 groups (a) to (l), a thienopyrrolyl group which may be substituted is preferred. This group may have 1 to 3 substituents, and examples of the substituents include a hydroxyl group, a nitro group, an amino group, a cyano group, halogen atoms, alkyl groups, alkenyl groups, alkynyl groups, halagenoalkyl groups, hydroxyalkyl groups, alkoxy groups, alkoxyalkyl groups, a carboxyl group, carboxyalkyl groups, acyl groups, a carbamoyl group, N-alkylcarbamoyl groups, N,N-dialkylcarbamoyl groups, alkoxycarbonyl groups, an amidino group and alkoxycarbonylalkyl groups. Among these, a cyano group, halogen atoms, alkyl groups, alkenyl groups alkynyl groups and halogenoalkyl groups are preferred. As specific preferable examples thereof, may be mentioned 2-chlorothieno[2,3-b]pyrrol-5-yl, 2-fluorothieno[2,3-b]-pyrrol-5-yl, 2-bromothieno[2,3-b]pyrrol-5-yl, and 2-ethynylthieno[2,3-b]pyrrol-5-yl groups.

<On Group $Q^1$>

In the present invention, $Q^1$ means a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic fused hydrocarbon group which may be substituted, or a saturated or unsaturated, bicyclic or tricyclic fused heterocyclic group which may be substituted.

As examples of the saturated or unsaturated, 5- or 6-membered cyclic hydrocarbon group, may be mentioned cyclopentyl, cyclopentenyl, cyclohexyl, cyclohexenyl and phenyl groups. Cyclopentyl, cyclohexyl and phenyl groups are preferred, with a phenyl group being particularly preferred.

The saturated or unsaturated, 5- to 7-membered heterocyclic group means a monovalent heterocyclic group having at least one hetero atom selected from oxygen, sulfur and nitrogen atoms, and examples thereof may include furyl, pyrrolyl, thienyl, pyrazolyl, imidazolyl, pyrazolinyl, oxazolyl, oxazolinyl, thiazolyl, thiazolinyl, thiadiazolyl, furazanyl, pyranyl, pyridyl, pyrimidyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl, triazinyl, azepinyl, diazepinyl and triazepinyl groups. Thienyl, pyrazolyl, imidazolyl, oxazolyl, thiazolyl, thiadiazolyl, furazanyl, pyridyl, pyrimidyl, pyridazinyl, pyrrolidinyl, piperazinyl, piperidinyl, morpholinyl, thiadiazinyl and triazolyl groups are preferred, with thienyl, thiazolyl, pyrazolyl, imidazolyl, pyridyl, pyrimidyl, pyridazinyl, pyrrolidinyl, piperazinyl and piperidinyl groups being particularly preferred. Of these heterocyclic groups, the nitrogen-containing heterocyclic groups may be in the form of an N-oxide.

The saturated or unsaturated, bicyclic or tricyclic fused hydrocarbon group means the same saturated or unsaturated, bicyclic or tricyclic fused hydrocarbon group as described in the description of $Q^4$ in the general formula (1). As specific examples thereof, may be mentioned indenyl, indanyl, naphthyl, tetrahydronaphthyl, anthryl and phenanthryl groups, with indenyl, indanyl, naphthyl and tetrahydronaphthyl groups being preferred.

The saturated or unsaturated, bicyclic or tricyclic fused heterocyclic group means the same saturated or unsaturated, bicyclic or tricyclic fused heterocyclic group as described in the description of $Q^4$ in the general formula (1). As specific examples thereof, may be mentioned benzofuryl, isobenzofuryl, benzothienyl, indolyl, indolinyl, isoindolyl, isoindolinyl, indazolyl, quinolyl, dihydroquinolyl, 4-oxodihydroquinolyl(dihydroquinon-4-on), tetrahydroquinolyl, isoquinolyl, tetrahydroisoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalyl, tetrahydroquinoxalyl, cinnolinyl, tetrahydrocinnolinyl, indolizinyl, tetrahydroindolizinyl, benzothiazolyl, tetrahydrobenzothiazolyl, benzoxazolyl, benzoisothiazolyl, benzoisoxazolyl, benzimidazoyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolyl, dihydropyridoquinazolyl, pyridopyrimidinyl, tetrahydropyridopyrimidinyl, pyranothiazolyl, dihydropyranothiazolyl, furopyridyl, tetrahydrofuropyridyl, oxazolopyridyl, tetrahydrooxazolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, thienopyrrolyl, thiazolopyrimidinyl, dihydrothiazolopyrimidinyl, 4-oxotetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazopyridyl, pyrazinopyridazinyl, benzisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepinyl, benzoazepinyl, tetrahydrobenzoazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, 4,5,6,7-tetrahydro-5,6-tetramethylenethiazolopyridazinyl and 5,6-trimethylene-4,5,6,7-tetrahydrothiazolopyridazinyl groups. Preferred are benzothiazolyl, tetrahydrobenzothiazolyl, thienopyridyl, tetrahydrothienopyridyl, thienopyrrolyl, thiazolopyridyl, tetrahydrothiazolopyridyl, thiazolopyridazinyl, tetrahydrothiazolopyridazinyl, pyrrolopyrimidinyl, dihydropyrrolopyrimidinyl, pyranothiazolyl, dihydropyranothiazolyl, furopyridyl, tetrahydrofuropyridyl, oxazolopyridyl, tetrahydrooxazolopyridyl, pyrrolopyridyl, dihydropyrrolopyridyl, tetrahydropyrrolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, thiazolopyrimidinyl, dihydrothiazolopyrimidinyl, benzoazepinyl, tetrahydrobenzoazepinyl, thiazoloazepinyl, tetrahydrothiazoloazepinyl, thienoazepinyl, tetrahydrothienoazepinyl, 4,5,6,7-tetrahydro-5,6-tetramethylenethiazolopyridazinyl and 5,6-trimethylene-4,5,6,7-tetrahydrothiazolopyridazinyl groups, with tetrahydrobenzothiazolyl, tetrahydrothienopyridyl, tetrahydrothiazolopyridyl, tetrahydrothiazolopyridazinyl, dihydropyrrolopyrimidinyl, dihydropyranothiazolyl, tetrahydrooxazolopyridyl, dihydropyrrolothiazolyl, 4,5,6,7-tetrahydro-5,6-tetramethylenethiazolopyridazinyl and 5,6-trimethylene-4,5,6,7-tetrahydrothiazolopyridazinyl groups being particularly preferred.

No particular limitation is imposed on the fusing form of the fused heterocyclic groups. For example, thienopyridine may be any of thieno[2,3-b]pyridine, thieno[2,3-c]pyridine, thieno[3,2-b]pyridine, thieno-[3,2-c]pyridine, thieno[3,4-b]pyridine and thieno[3,4-c]pyridine, with thieno[2,3-c]pyridine and thieno[3,2-c]-pyridine being preferred. Thienopyrrolyl may be any of thieno[2,3-b]pyrrolyl and thieno[3,2-b]-pyrrolyl. Thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, with thiazolo[4,5-c]pyridine and thiazolo[5,4-c]pyridine being preferred. Thiazolopyridazine may be any of thiazolo-[4,5-c]pyridazine, thiazolo[4,5-d]pyridazine, thiazolo[5,4-c]pyridazine and thiazolo[3,2-b]pyridazine, with thiazolo[4,5-d]pyridazine being preferred. Pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, with pyrrolo[2,3-c]pyridine and pyrrolo[3,2-c]pyridine being preferred. Pyrrolopyrimidine may be any of pyrrolo[3,4-d]pyrimidine, pyrrolo[3,2-d]pyrimidine and pyrrolo[2,3-d]pyrimidine, with pyrrolo[3,4-d]pyrimidine being preferred. Pyridopyrimidine may be any of pyrido[2,3-d]pyrimidine, pyrido[3,2-d]pyrimidine, pyrido[3,4-d]pyrimidine, pyrido[4,3-d]pyrimidine, pyrido[1,2-c]pyrimidine and pyrido[1,2-a]pyrimidine, with pyrido[3,4-d]pyrimidine and pyrido[4,3-d]pyrimidine being preferred. Pyranothiazole may be any of pyrano[2,3-d]thiazole, pyrano[4,3-d]thiazole, pyrano[3,4-d]thiazole and pyrano[3,2-d]thiazole, with pyrano[4,3-d]thiazole and pyrano[3,4-d]thiazole being preferred. Furopyridine may be any of furo[2,3-b]pyridine, furo[2,3-c]pyridine, furo[3,2-b]pyridine, furo[3,2-c]pyridine, furo[3,4-b]pyridine and furo[3,4-c]pyridine, with furo[2,3-c]pyridine and furo[3,2-c]pyridine being preferred. Oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, with oxazolo[4,5-c]pyridine and oxazolo[5,4-c]pyridine being preferred. Oxazolopyridazine may be any of oxazolo[4,5-c]pyridazine, oxazolo[4,5-d]pyridazine, oxazolo[5,4-c]pyridazine and oxazolo[3,4-b]pyridazine, with oxazolo[4,5-d]pyridazine being preferred. Pyrrolothiazole may be any of pyrrolo[2,1-b]thiazole, pyrrolo[1,2-c]thiazole, pyrrolo[2,3-d]thiazole, pyrrolo[3,2-d]thiazole and pyrrolo[3,4-d]thiazole, with pyrrolo[3,4-d]thiazole being preferred. Pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole, with pyrrolo[3,4-d]oxazole being preferred. Benzoazepine may be any of 1H-1-benzoazepine, 1H-2-benzoazepine and 1H-3-benzoazepine, with 1H-3-benzoazepine being preferred. Thiazolo[4,5-c]azepine may be any of 4H-thiazolo[4,5-c]azepine, 4H-thiazolo[4,5-d]azepine and 4H-thiazolo[5,4-c]azepine, with 4H-thiazolo[4,5-d]azepine being preferred. Thieno[2,3-c]azepine may be any of 4H-thieno[2,3-d]azepine and 4H-thieno[3,2-c]azepine, with 4H-thieno[2,3-d]azepine being preferred.

Of these heterocyclic groups, the nitrogen-containing heterocyclic groups may be in the form of an N-oxide. Incidentally, the position of the above substituent group bonded to $Q^2$ is not particularly limited.

The above-described saturated or unsaturated, 5- or 6-membered cyclic hydrocarbon groups, saturated or unsaturated, 5- to 7-membered heterocyclic groups, saturated or unsaturated, bicyclic or tricyclic fused hydrocarbon groups and saturated or unsaturated, bicyclic or tricyclic fused heterocyclic groups may each have 1 to 3 substituents. Examples of the substituents may include a hydroxyl group; halogen atoms of fluorine atom, chlorine atom, bromine atom and iodine atom; halogenomethyl groups having 1 to 3 halogen atoms; an amino group; a cyano group; an amidino group; a hydroxyamidino group; linear, branched or cyclic alkyl groups having 1 to 6 carbon atoms (hereinafter referred to as $C_1$-$C_6$ alkyl groups which mean linear, branched and cyclic alkyl groups; for example, linear or branched $C_1$-$C_6$ alkyl groups such as methyl group, ethyl group, isopropyl group and tert-butyl group; $C_3$-$C_6$ cycloalkyl groups such as cyclopropyl group, cyclobutyl group, cyclopentyl group and 1-methylcyclopropyl group; and $C_3$-$C_6$ cycloalkyl-$C_1$-$C_6$ alkyl groups such as cyclopropylmethyl group); hydroxy-$C_1$-$C_6$ alkyl groups (such as hydroxyethyl and 1,1-dimethyl-2-hydroxyethyl groups); $C_1$-$C_6$ alkoxy groups (for example, methoxy group, ethoxy group and the like); $C_1$-$C_6$ alkoxy-$C_1$-$C_6$ alkyl groups; a carboxyl group; $C_2$-$C_6$ carboxyalkyl groups (for example, carboxymethyl group and the like); $C_2$-$C_6$ alkoxycarbonyl-$C_1$-$C_6$ alkyl groups (for example, methoxycarbonylmethyl group, tert-butoxycarbonylmethyl group and the like); amidino groups substituted by a $C_2$-$C_6$ alkoxycarbonyl group; $C_2$-$C_6$ alkenyl groups (for example, vinyl group, allyl group and the like); $C_2$-$C_6$ alkynyl groups (for example, ethynyl group, propynyl group and the like); $C_2$-$C_6$ alkoxycarbonyl groups (for example, methoxycarbonyl group, ethoxycarbonyl group, tert-butoxycarbonyl group and the like); amino $C_1$-$C_6$ alkyl groups (for example, aminomethyl group, aminoethyl group and the like); $C_1$-$C_6$ alkylamino-$C_1$-$C_6$ alkyl groups (for example, N-methylaminomethyl group, N-ethylaminomethyl group and the like); di($C_1$-$C_6$ alkyl)amino-$C_1$-$C_6$ alkyl groups (for example, N,N-dimethylaminomethyl group, N,N-diethylaminomethyl group, N-ethyl-N- methylaminoethyl group and the like); $C_2$-$C_6$ alkoxycarbonylamino-$C_1$-$C_6$ alkyl groups (for example, methoxycarbonylaminoethyl group, tert-butoxycarbonylaminoethyl group and the like); $C_1$-$C_6$ alkanoyl groups (for example, formyl group, acetyl group, methylpropionyl group, cyclopentanecarbonyl group and the like); $C_1$-$C_6$ alkanoylamino-$C_1$-$C_6$ alkyl groups (for example, acetylaminomethyl group and the like); $C_1$-$C_6$ alkylsulfonyl groups (for example, methanesulfonyl group and the like); $C_1$-$C_6$ alkylsulfonylamino-$C_1$-$C_6$ alkyl groups (for example, methanesulfonylaminomethyl group and the like); a carbamoyl group; $C_1$-$C_6$ alkylcarbamoyl groups (for example, methylcarbamoyl group, ethylcarbamoyl group, isopropylcarbamoyl group, tert-butylcarbamoyl group and the like); N,N-di($C_1$-$C_6$ alkyl)carbamoyl groups (for example, dimethylcarbamoyl group, diethylcarbamoyl group, methylethylcarbamoyl group and the like); $C_1$-$C_6$ alkylamino groups (for example, N-methylamino group, N-ethylamino group and the like); di($C_1$-$C_6$ alkyl)amino groups (for example, N,N-dimethylamino group, N,N-diethylamino group, N-ethyl-N-methylamino group and the like); 5- or 6-membered heterocyclic groups containing one of nitrogen, oxygen and sulfur or the same or different two atoms thereof (for example, pyrrolidinyl group, piperidinyl group, piperazinyl group, morpholinyl group, pyridyl group, pyrimidinyl group, tetrahydropyranyl group and the like); the above 5- or 6-membered heterocyclic-$C_1$-$C_4$ alkyl groups (for example, morpholinomethyl group and the like); and the above 5- or 6-membered heterocyclic-amino-$C_1$-$C_4$ alkyl groups (for example, N-(oxazol-2-yl)aminomethyl group and the like).

As specific examples of $Q^1$, may be mentioned bicyclic heterocyclic groups such as 5-methyl-4,5,6,7-tetrahydrothiazolo[5,4-c]pyridin-2-yl, 4,5,6,7-tetrahydrothiazolo[5,4-c]pyridin-2-yl, 5-cyclopropyl-4,5,6,7-tetrahydrothiazolo[5,4-c]pyridin-2-yl, 5-carboxymethyl-4,5,6,7-tetrahydrothiazolo[5,4-c]pyridin-2-yl, 5-butyl-4,5,6,7-tetrahydrothiazolo[5,4-c]pyridin-2-yl, 5-(4-pyridyl)-4,5,6,7-tetrahydrothiazolo[5,4-c]-pyridin-2-yl, 5-methyl-4,5,6,7-tetrahydrothiazolo[4,5-c]pyridin-2-yl, 6-methyl-4,5,6,7-tetrahydrothieno[2,3-c]pyridin-2-yl, 5-methyl-4,5,6,7-tetrahydrooxazolo[5,4-c]pyridin-2-yl, 5-methyl-4,6-dihydro-5H-pyrrolo[3,4-d]thiazol-2-yl, 5,7-dihydro-6-methylpyrrolo[3,4-d]pyrimidin-2-yl, 5,6-dimethyl-4,5,6,7-tetrahydrothiazolo[4,5-d]pyridazin-2-yl, 5,6-dimethyl-4,5,6,7-tetrahydrooxazolo[4,5-d]pyridazin-2-yl, 5-dimethylamino-4,5,6,7-tetrahydrobenzo[d]thiazol-2-yl, S-(4-pyridyl)-4,5,6,7-tetrahydrothiazolo[5,4-c]pyridin-2-yl and 6,7-dihydro-4H-pyrano[4,3-d]thiazol-2-yl groups; and 5- or 6-membered heterocyclic groups such as pyridyl groups such as 4-pyridyl and 2-pyridyl; dihydrooxazolyl groups such as 4,5-dihydrooxazol-2-yl; 4-[N-(4,5-dihydrooxazol-2-yl)-N-methylaminomethyl]thiophen-2-yl, 4-[N-(4,5-dihydrooxazol-2-yl)-N-methylaminomethyl]-3-chlorothiophen-2-yl, 5-(N-methylaminomethyl)thiazol-2-yl, 5-(N-methylaminomethyl)thiophen-2-yl, 5-(N,N-dimethylaminomethyl)thiazol-2-yl, 5-(N,N-dimethylaminomethyl)thiophen-2-yl and 5-(N,N-dimethylaminomethyl)pyridin-2-yl groups. Incidentally, $Q^1$ is not limited by these examples at all.

<On Group $Q^2$>

The group $Q^2$ means a single bond, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic fused hydrocarbon group which may be substituted, or a saturated or unsaturated, divalent bicyclic or tricyclic fused heterocyclic group which may be substituted.

In the group $Q^2$, the saturated or unsaturated, 5- or 6-membered divalent cyclic hydrocarbon group means a divalent group derived from the saturated or unsaturated, 5- or 6-membered cyclic hydrocarbon described in the description of $Q^4$ in the general formula (1). As specific examples thereof, may be mentioned cyclohexylene, cyclohexenylene and phenylene groups, with cyclohexylene and phenylene groups being preferred.

The saturated or unsaturated, 5- to 7-membered divalent heterocyclic group means a divalent group derived from the saturated or unsaturated, 5- to 7-membered heterocyclic ring described in the description of $Q^4$ in the general formula (1). As specific examples thereof, may be mentioned divalent groups derived from furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, azepien, diazepine and triazepine. Among these, preferable examples thereof include divalent groups derived from pyrazole, imidazole, oxazole, thiazole, thiadiazole, furazane, pyridine, pyrimidine, pyridazine, pyrrolidine, piperazine, piperidine, triazole, triazine, azepien, diazepine and triazepine.

The saturated or unsaturated, divalent bicyclic or tricyclic fused hydrocarbon means a divalent group derived from the saturated or unsaturated, bicyclic or tricyclic fused hydrocarbon group described in the description of $Q^4$ in the general formula (1). As specific examples thereof, may be mentioned divalent groups derived from indene, indane, naphthalene, tetrahydronaphthalene, anthracene, phenanthrene and the like. As preferable examples thereof, may be mentioned divalent groups derived from indane and naphthalene.

The saturated or unsaturated, divalent bicyclic or tricyclic fused heterocyclic group means a divalent group derived from the saturated or unsaturated, bicyclic or tricyclic fused heterocyclic ring described in the description of $Q^4$ in the general formula (1). As specific examples thereof, may be mentioned divalent groups derived from benzofuran, benzothiophene, indole, isoindole, indazole, quinoline, tetrahydroquinoline, isoquinoline, tetrahydroisoquinoline, quinazoline, dihydroquinazoline, tetrahydroquinazoline, quinoxaline, tetrahydroquinoxaline, cinnoline, tetrahydrocinnoline, indolizine, tetrahydroindolizine, benzothiazole, tetrahydrobenzothiazole, naphthyridine, tetrahydronaphthyridine, thienopyridine, tetrahydrothienopyridine, thiazolopyridine, tetrahydrothiazolopyridine, thiazolopyridazine, tetrahydrothiazolopyridazine, pyrrolopyridine, dihydropyrrolopyridine, tetrahydropyrrolopyridine, pyrrolopyrimidine, dihydropyrrolopyrimidine, dihydropyridoquinazoline, pyranothiazole, dihydropyranothiazole, furopyridine, tetrahydrofuropyridine, oxazolopyridine, tetrahydrooxazolopyridine, oxazolopyridazine, tetrahydrooxazolopyridazine, pyrrolothiazole, dihydropyrrolothiazole, pyrrolooxazole, dihydropyrrolooxazole and benzoazepine. As preferable examples thereof, may be mentioned divalent groups derived from benzofuran, benzothiophene, indole, indazole, quinoline, isoquinoline, tetrahydroisoquinoline, benzothiazole, naphthyridine, thienopyridine, thiazolopyridine, tetrahydrothiazolopyridine, thiazolopyridazine, pyrrolopyridine, tetrahydropyrrolopyridine, pyridopyrimidine, pyranothiazole, dihydropyranothiazole, furopyridine, oxazolopyridine, oxazolopyridazine, pyrrolothiazole, dihydropyrrolothiazole, pyrrolooxazole and dihydropyrrolooxaazole. No particular limitation is imposed on the fusing form of the fused heterocyclic group. For example, naphthyridine may be any of 1,5-, 1,6-, 1,7-, 1,8-, 2,6- and 2,7-naphthyridine, thienopyridine may be any of thieno[2,3-b]pyridine, thieno[2,3-c]pyridine, thieno[3,2-b]pyridine, thieno[3,2-c]pyridine, thieno-[3,4-b]pyridine and thieno[3,4-c]pyridine, thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, thiazolopyridazine may be any of thiazolo[4,5-c]pyridazine, thiazolo[4,5-d]pyridazine, thiazolo[5,4-c]pyridazine and thiazolo[3,2-b]pyridazine, pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, pyrrolopyrimidine may be any of pyrrolo[3,4-d]pyrimidine, pyrrolo[3,2-d]pyrimidine and pyrrolo[2,3-d]pyrimidine, pyridopyrimidine may be any of pyrido[2,3-d]pyrimidine, pyrido[3,2-d]pyrimidine and pyrido[3,4-d]pyrimidine, pyranothiazole may be any of pyrano[2,3-d]thiazole, pyrano[4,3-d]thiazole, pyrano[3,4-d]thiazole and pyrano[3,2-d]thiazole, furopyridine may be any of furo[2,3-b]pyridine, furo[2,3-c]pyridine, furo[3,2-b]pyridine, furo[3,2-c]pyridine, furo[3,4-b]-pyridine and furo[3,4-c]pyridine, oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, oxazolopyridazine may be any of oxazolo[4,5-c]pyridazine, oxazolo[4,5-d]pyridazine, oxazolo[5,4-c]pyridazine and oxazolo[3,4-b]pyridazine, pyrrolothiazole may be any of pyrrolo[2,1-b]thiazole, pyrrolo[1,2-c]thiazole, pyrrolo[3,2-d]thiazole and pyrrolo[3,4-d]thiazole, and pyrrolooxazole may be any of pyrrolo[2,1-b]oxazole, pyrrolo[1,2-c]oxazole, pyrrolo[2,3-d]oxazole, pyrrolo-[3,2-d]oxazole and pyrrolo[3,4-d]oxazole. Other fusing forms than these may be allowed.

The above-described saturated or unsaturated, 5- or 6-membered divalent cyclic hydrocarbon groups, saturated or unsaturated, 5- to 7-membered divalent heterocyclic groups, saturated or unsaturated, divalent bicyclic or tricyclic fused hydrocarbon groups and saturated or unsaturated, divalent bicyclic or tricyclic fused heterocyclic groups may each have 1 to 3 substituents. Examples of the substituents may include a hydroxyl group, halogen atoms of a fluorine, chlorine, bromine and iodine atoms, halogenoalkyl groups having 1 to 3 halogen atoms, an amino group, a cyano group, aminoalkyl groups, an amidino group, a hydroxyamidino group, linear, branched or cyclic alkyl groups having 1 to 6 carbon atoms (for example, methyl group, ethyl group, etc.), linear, branched or cyclic alkoxy groups having 1 to 6 carbon atoms (for example, methoxy group, ethoxy group, etc.), an amidino group substituted by a linear, branched or cyclic alkoxycarbonyl groups having 2 to 7 carbon atoms (for example, methoxycarbonylamidino group, ethoxycarbonylamidino group, etc.), linear, branched or cyclic alkenyl groups having 2 to 6 carbon atoms (for example, vinyl group, allyl group, etc.), linear or branched alkynyl groups having 2 to 6 carbon atoms (for example, ethynyl group, propynyl group, etc.), linear, branched or cyclic alkoxycarbonyl group having 2 to 6 carbon atoms (for example, methoxycarbonyl group, ethoxycarbonyl group, etc.), and a carbamoyl group.

Preferable groups in $Q^2$ described above are a single bond, saturated or unsaturated, 5- or 6-membered divalent cyclic hydrocarbon groups which may be substituted, saturated or unsaturated, 5- to 7-membered divalent heterocyclic groups which may be substituted, and saturated or unsaturated, divalent bicyclic or tricyclic fused heterocyclic groups which may be substituted. In particular, a single bond, saturated or unsaturated, divalent 5- or 6-membered cyclic hydrocarbon groups, saturated or unsaturated, 5- to 7-membered divalent heterocyclic groups are preferred.

When $Q^1$ is a saturated or unsaturated, bicyclic or tricyclic fused hydrocarbon group which may be substituted, or a saturated or unsaturated, bicyclic or tricyclic fused heterocyclic group which may be substituted, the group $Q^2$ is preferably a single bond. The case where $Q^2$ is a single bond in the above-described combination means that the general formula (1):

$$Q^1\text{-}Q^2\text{-}T^0\text{-}N(R^1)\text{-}Q^3\text{-}N(R^2)\text{-}T^1\text{-}Q^4 \qquad (1)$$

wherein $R^1$, $R^2$, $Q^1$, $Q^2$, $Q^3$, $Q^4$, $T^0$ and $T^1$ have the same meanings as defined above, comes to the following general formula (1'):

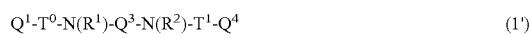

$$Q^1\text{-}T^0\text{-}N(R^1)\text{-}Q^3\text{-}N(R^2)\text{-}T^1\text{-}Q^4 \qquad (1')$$

wherein $Q^1$ represents the above bicyclic or tricyclic fused hydrocarbon group or bicyclic or tricyclic fused heterocyclic group, and $R^1$, $R^2$, $Q^3$, $Q^4$, $T^0$ and $T^1$ have the same meanings as defined above.

Specifically, are preferred those in which the group $Q^1$ is a thienopyridyl group which may be substituted; a tetrahydrothienopyridyl group which may be substituted; a thiazolopyridyl group which may be substituted; a tetrahydrothiazolopyridyl group which may be substituted; a thiazolopyridazinyl group which may be substituted; a tetrahydrothiazolopyridazinyl group which may be substituted; a pyranothiazolyl group which may be substituted; a dihydropyranothiazolyl group which may be substituted; a furopyridyl group which may be substituted; a tetrahydrofuropyridyl group which may be substituted; an oxazolopyridyl group which may be substituted; a tetrahydrooxazolopyridyl group which may be substituted; a pyrrolopyridyl group which may be substituted; a dihydropyrrolopyridyl group which may be substituted; a tetrahydropyrrolopyridyl group which may be substituted; a pyrrolopyrimidinyl group which may be substituted; a dihydropyrrolopyrimidinyl group which may be substituted; an oxazolopyridazinyl group which may be substituted; a tetrahydrooxazolopyridazinyl group which may be substituted; a pyrrolothiazolyl group which may be substituted; a dihydropyrrolothiazolyl group which may be substituted; a pyrrolooxazolyl group which may be substituted; a dihydropyrrolooxazolyl group which may be substituted; a benzothiazolyl group which may be substituted; a tetrahydrobenzothiazolyl group which may be substituted; a thiazolopyrimidinyl which may be substituted; a dihydrothiazolepyrimidinyl which may be substituted; a benzoazepinyl which may be substituted; a tetrahydrobenzoazepinyl which may be substituted; a thiazoloazepinyl which may be substituted; a tetrahydrothiazoloazepinyl which may be substituted; a thienoazepinyl which may be substituted; a tetrahydrothienoazepinyl which may be substituted; a 4,5,6,7-tetrahydro-5,6-tetramethylenethiazolopyridazinyl group which may be substituted; or a 5,6-trimethylene-4,5,6,7-tetrahydrothiazolopyridazinyl group which may be substituted, and $Q^2$ is a single bond.

When $Q^1$ is a saturated or unsaturated, 5- or 6-membered cyclic hydrocarbon group which may be substituted, or a saturated or unsaturated, 5- to 7-membered heterocyclic group which may be substituted, the group $Q^2$ is preferably a saturated or unsaturated, 5- or 6-membered divalent cyclic hydrocarbon group which may be substituted, or a saturated or unsaturated, 5- to 7-membered divalent heterocyclic group which may be substituted. As preferable example of the group $Q^1$-$Q^2$, may be mentioned 4-(4-pyridyl)phenyl, 4-(2-pyridyl)phenyl, 5-(4-pyridyl)thiazolyl, 1-(4-pyridyl)piperidyl, 4-(4-pyridyl)piperidyl, 4-hydroxy-1-(4-pyridyl)piperidin-4-yl, biphenylyl, 4-(2-aminosulfonylphenyl)phenyl, 4-(2-amidinophenyl)phenyl, 4-(2-methylsulfonylphenyl)phenyl, 4-(2-aminomethylphenyl)phenyl, 4-(2-carbamoylphenyl)phenyl, 4-(2-imidazolyl)phenyl, 4-(1-methyl-2-imidazolyl)phenyl, 4-(2,3,4,5-tetrahydropyrimidin-2-yl)phenyl, 4-(1-methyl-2,3,4,5-tetrahydropyrimidin-2-yl)phenyl, 4-(5-tetrazolyl)phenyl, 1-(4-pyridyl)piperidin-4-yl, 3-(4-piperidyl)isoxazolin-5-yl, 3-(4-amidinophenyl)isoxazolin-5-yl, 3-(4-piperidyl)isoxazolidin-5-yl, 3-(4-amidinophenyl)isoxazolidin-5-yl, 2-(4-piperidyl)-1,3,4-thiadiazol-5-yl, 2-(4-aminophenyl)-1,3,4-oxadiazol-5-yl, 4-(4-piperidyl)piperidin-1-yl, 4-(4-piperidyl)piperazin-1-yl, 4-(4-piperazinyl)piperazin-1-yl, 1-(4-pyrimidinyl)piperidin-1-yl, 1-(2-methylpyrimidin-4-yl)piperidin-4-yl, 1-(4-pyrimidinyl)pyrrolidin-3-yl, 1-(4-methylpyrimidin-6-yl)piperazin-4-yl, 1-(2-methylpyrimidin-4-yl)pyrrolidin-4-yl, 1-(6-chloropyrimidin-4-yl)piperidin-4-yl, 5-(4-chlorophenyl)thiophen-2-yl, 2-(4-chlorophenyl)thiazol-4-yl, 3-(4-chlorophenyl)-1H-pyrrol-2-yl, 4-(4-pyrimidinyl)phenyl and 4-(4-imidazolyl)phenyl groups.

<On Group $Q^3$>

The group $Q^3$ represents the following group:

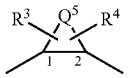

wherein $Q^5$ means an alkylene group having 1 to 8 carbon atoms, an alkenylene group having 2 to 8 carbon atoms, or a group —(CH$_2$)$_m$—CH$_2$-A-CH$_2$—(CH$_2$)$_n$—, in which m and n are independently of each other 0 or an integer of 1-3, and A means an oxygen atom, nitrogen atom, sulfur atom, —SO—, —SO$_2$—, —NH—, —O—NH—, —NH—NH—, —S—NH—, —SO—NH— or —SO$_2$—NH—, numerals 1 and 2 indicate positions, and $R^3$ and $R^4$ are substituents on carbon atom(s), nitrogen atom(s) or sulfur atom(s) of a ring comprising $Q^5$ and are independently of each other a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s) or alkylsulfonylacyl group, or $R^3$ and $R^4$, together with each other, denote an alkylene group having 1 to 5 carbon atoms, alkenylene group having 2 to 5 carbon atoms, alkylenedioxy group having 1 to 5 carbon atoms or carbonyldioxy group.

The following group will be described in detail.

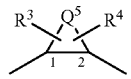

wherein $Q^5$, $R^3$ and $R^4$ have the same meanings as defined above, and numerals 1 and 2 indicate positions.

A portion of the cyclic structure having the group $Q^5$ is a 3- to 10-membered divalent cyclic hydrocarbon group which may have a double bond, or a 5- to 12-membered divalent heterocyclic group containing 1 or 2 hetero atoms, preferably a 3- to 8-membered divalent cyclic hydrocarbon group or a 5- to 8-membered divalent heterocyclic group, more preferably a 5- to 7-membered divalent cyclic hydrocarbon group or a 5- to 7-membered divalent heterocyclic group. Among others, a group in which $Q^5$ is an alkylene group having 3 to 6 carbon atoms or a group —(CH$_2$)$_m$—CH$_2$-A-CH$_2$—(CH$_2$)$_n$—, in which m and n are independently of each other 0 or 1, and A has the same meaning as defined above, is preferred. In particular, a group in which $Q^5$ is an alkylene group having 4 carbon atoms is preferred.

This cyclic hydrocarbon group or heterocyclic group may have both cis and trans structures in the relation between position 1 and position 2. However, the trans-form is preferred in the case of the 5-membered ring, while both cis-form and trans-form are preferred in the 6- or 7-membered ring.

The substituents $R^3$ and $R^4$ will now be described in detail. The halogen atom means a fluorine, chlorine, bromine or iodine atom. Examples of the alkyl group include linear, branched or cyclic $C_1$-$C_6$ alkyl groups (for example, methyl group, cyclopropyl group, isobutyl group and the like). Examples of the halogenoalkyl group include the 1 to 3 halogen-substituted alkyl groups (for example, chloromethyl group, 1-bromoethyl group, trifluoromethyl group and the like). Examples of the cyanoalkyl group include the $C_1$-$C_6$ alkyl groups substituted with a cyano group (for example, cyanomethyl group, 1-cyanoethyl group and the like). Examples of the alkenyl group include linear or branched alkenyl groups having 2 to 6 carbon atoms and a double bond (for example, vinyl group, allyl group and the like). Examples of the alkynyl group include linear or branched alkynyl groups having 2 to 6 carbon atoms and a triple bond (for example, ethynyl group, propynyl group and the like). Examples of the acyl group include $C_1$-$C_6$ alkanoyl groups (for example, formyl group, acetyl group and the like), $C_7$-$C_{15}$ aroyl groups such as a benzoyl group and a naphthoyl group, and arylalkanoyl groups that are the $C_1$-$C_6$ alkanoyl groups substituted with a $C_6$-$C_{14}$ aryl group (for example, phenacetyl group and the like). Examples of the acylalkyl group include the $C_1$-$C_6$ alkyl groups substituted with the acyl group (for example, acethylmethyl group and the like) Examples of the alkoxy group include linear, branched or cyclic $C_1$-$C_6$ alkoxy groups (for example, methoxy group, cyclopropoxy group, an isopropoxy group and the like). Examples of the alkoxyalkyl group include the $C_1$-$C_6$ alkyl groups substituted with the $C_1$-$C_6$ alkoxy group (for example, methoxymethyl group, ethoxymethyl group and the like). Examples of the hydroxyalkyl group include the $C_1$-$C_6$ alkyl groups substituted with a hydroxyl group (for example, hydroxymethyl group, 1-hydroxyethyl group and the like). Examples of the carboxyalkyl group include the $C_1$-$C_6$ alkyl groups substituted with a carboxyl group (for example, carboxymethyl group, 1-carboxyethyl group and the like). Examples of the alkoxycarbonyl group include groups composed of the $C_1$-$C_6$ alkoxy group and a carbonyl group (for example, methoxycarbonyl group, ethoxycarbonyl group and the like) Examples of the alkoxycarbonylalkyl group include the $C_1$-$C_6$ alkyl groups substituted with the $C_1$-$C_6$ alkoxycarbonyl group (for example, methoxycarbonylethyl group, ethoxycarbonylethyl group and the like). Examples of the carbamoylalkyl group include the $C_1$-$C_6$ alkyl groups substituted a carbamoyl group (for example, carbamoylmethyl group, carbamoylethyl group and the like).

Examples of the heteroaryl group include the same heteroaryl groups as described in the description of $Q^4$ in the general formula (1). Examples of the heteroarylalkyl group include the $C_1$-$C_6$ alkyl groups substituted with the heteroaryl group (for example, thienylmethyl group, pyridylethyl group and the like). Examples of the aryl group include aryl groups having 6 to 14 carbon atoms, such as phenyl group and naphthyl group. The aryl groups may have 1 to 3 substituents selected from the $C_1$-$C_6$ alkyl groups, the $C_1$-$C_6$ alkanoyl groups, a hydroxyl group, a nitro group, a cyano group, halogen atoms, the $C_2$-$C_6$ alkenyl groups, the $C_2$-$C_6$ alkynyl groups, the $C_1$-$C_6$ halogenoalkyl groups, the $C_1$-$C_6$ alkoxy groups, a carboxy group, a carbamoyl group, the $C_1$-$C_6$ alkoxycarbonyl groups and the like. Examples of the aralkyl group include the $C_1$-$C_6$ alkyl groups substituted with the $C_6$-$C_{14}$ aryl groups (for example, benzyl group, phenethyl group and the like). Incidentally, in the above description, no particular limitation is imposed on the substituting position. Examples of the acylamino group which may be substituted include the amino groups substituted with the $C_1$-$C_6$ acyl group (for example, formylamino group, acetylamino group and the like) and besides acyl groups having 1 to several substituents selected from halogen atoms, a hydroxyl group, $C_1$-$C_6$ alkoxy groups, a amino group, N-$C_1$-$C_6$ alkylamino groups, N,N-di-$C_1$-$C_6$ alkylamino groups, a carboxyl group, $C_2$-$C_6$ alkoxycarbonyl groups and the like (for example, 2-methoxyacetylamino group, 3-aminopropionylamino group and the like). Examples of the acylaminoalkyl group include the $C_1$-$C_6$ alkyl groups substituted with the $C_1$-$C_6$ acylamino group (for example, formylaminomethyl group, acetylaminomethyl group and the like). Examples of the aminoalkyl group include the $C_1$-$C_6$ alkyl groups substituted with an amino group (for example, aminomethyl group, 1-aminoethyl group and the like). Examples of the N-alkylaminoalkyl group include the amino-$C_1$-$C_6$ alkyl groups substituted with the $C_1$-$C_6$ alkyl group on the nitrogen atom (for example, N-methylaminomethyl group, N-methylaminoethyl group and the like). Examples of N,N-dialkylaminoalkyl group include the amino-$C_1$-$C_6$ alkyl groups respectively substituted with two $C_1$-$C_6$ alkyl groups on the nitrogen atom (for example, N,N-dimethylaminomethyl group, N-ethyl-N-methylaminoethyl group and the like). Examples of the N-alkenylcarbamoyl group include carbamoyl groups substituted with a linear or branched $C_2$-$C_6$ alkenyl group (for example, allylcarbamoyl group and the like). Examples of the N-alkenylcarbamoylalkyl group include the $C_1$-$C_6$ alkyl groups substituted with the N-$C_2$-$C_6$ alkenylcarbamoyl group (for example, allylcarbamoylethyl group and the like). Examples of the N-alkenyl-N-alkylcarbamoyl group include the N-$C_2$-$C_6$ alkenylcarbamoyl groups substituted with a linear or branched $C_1$-$C_6$ alkyl group on the nitrogen atom (for example, N-allyl-N-methylcarbamoyl group and the like). Examples of the N-alkenyl-N-alkylcarbamoylalkyl group include the N-$C_2$-$C_6$ alkenylcarbamoylalkyl groups substituted with a linear or branched $C_1$-$C_6$ alkyl group on the nitrogen atom (for example, N-allyl-N-methylcarbamoylmethyl group and the like). Example of the N-alkoxycarbamoyl group include carbamoyl groups substituted with a linear or branched $C_1$-$C_6$ alkoxy group (for example, methoxycarbamoyl group and the like). Examples of the N-alkoxycarbamoylalkyl group include linear or branched $C_1$-$C_6$ alkyl groups substituted with the N-$C_1$-$C_6$ alkoxycarbamoyl group (for example, methoxycarbamoylmethyl group and the like). Examples of the N-alkyl-N-alkoxycarbamoyl group include carbamoyl groups substituted with linear or branched $C_1$-$C_6$ alkoxy group and $C_1$-$C_6$ alkyl group (for example, N-ethyl-N-methoxycarbamoyl group and the like). Examples of the N-alkyl-N-alkoxycarbamoylalkyl group include linear or branched $C_1$-$C_6$ alkyl groups substituted with the N-$C_1$-$C_6$ alkyl-N-$C_1$-$C_6$ alkoxycarbamoyl group (for example, N-ethyl-N-methoxycarbamoylmethyl group and the like). Examples of the carbazoyl group which may be substituted by 1 to 3 alkyl groups include a carbazoyl group, and besides carbazoyl groups substituted with 1 to 3 linear or branched $C_1$-$C_6$ alkyl groups (for example, 1-methylcarbazoyl group, 1,2-dimethylcarbazoyl group and the like). Examples of the alkylsulfonyl group include linear, branched or cyclic $C_1$-$C_6$ alkylsulfonyl groups (for example, methanesulfonyl group and the like). Examples of the alkylsulfonylalkyl group include linear or branched $C_1$-$C_6$ alkyl groups substituted with the $C_1$-$C_6$ alkylsulfonyl group (for example, methanesulfonylmethyl group and the like). Examples of the alkoxyimino group include $C_1$-$C_6$ alkoxyimino groups (for example, methoxyimino group, ethoxyimino group and the like). Examples of the alkoxycarbonylalkylamino group include amino groups substituted with the $C_1$-$C_6$ alkoxycarbonylalkyl group (for example, methoxycarbonylmethylamino group, ethoxycarbonylpropylamino group and the like). Examples of the carboxyalkylamino group include amino groups substituted with the carboxy-$C_1$-$C_6$ alkyl group (for example, carboxymethylamino group, carboxyethylamino group and the like). Examples of the alkoxycarbonylamino group include amino groups substituted with the $C_1$-$C_6$ alkoxycarbonyl group (for example, methoxycarbonylamino group, tert-butoxycarbonylamino group and the like). Examples of the alkoxycarbonylaminoalkyl group include the alkyl groups substituted with the $C_1$-$C_6$ alkoxycarbonylamino group (for example, methoxycarbonylaminomethyl group, tert-butoxycarbonylaminoethyl group and the like). The N-alkylcarbamoyl group which may have a substituent on the alkyl group means a carbamoyl group substituted with a linear, branched or cyclic $C_1$-$C_6$ alkyl group which may be substituted with a hydroxyl group, amino group, N-$C_1$-$C_6$ alkylamino group, amidino group, halogen atom, carboxyl group, cyano group, carbamoyl group, $C_1$-$C_6$ alkoxy group, $C_1$-$C_6$ alkanoyl group, $C_1$-$C_6$ alkanoylamino group, $C_1$-$C_6$ alkylsulfonylamino group or the like, and examples thereof include N-methylcarbamoyl group, N-ethylcarbamoyl group, N-isopropylcarbamoyl group, N-cyclopropylcarbamoyl group, N-(2-hydroxyethyl)carbamoyl group, N-(2-fluoroethyl)carbamoyl group, N-(2-cyanoethyl)carbamoyl group, N-(2-methoxyethyl)carbamoyl group, N-carboxymethylcarbamoyl group, N-(2-aminoethyl)carbamoyl group, N-(2-amidinoethyl)carbamoyl group and the like. Examples of the N,N-dialkylcarbamoyl group which may have a substituent on the alkyl(s) group means a carbamoyl group substituted with 2 linear, branched or cyclic $C_1$-$C_6$ alkyl groups which may be substituted with a hydroxyl group, amino group, N-$C_1$-$C_6$ alkylamino group, amidino group, halogen atom, carboxyl group, cyano group, carbamoyl group, $C_1$-$C_6$ alkoxy group, $C_1$-$C_6$ alkanoyl group, $C_1$-$C_6$ alkanoylamino group, $C_1$-$C_6$ alkylsulfonylamino group or the like, and examples thereof include N,N-dimethylcarbamoyl group, N,N-diethylcarbamoyl group, N-ethyl-N-methylcarbamoyl group, N-isopropyl-N-methylcarbamoyl group, N-(2-hydroxyethyl)-N-methylcarbamoyl group, N,N-bis(2-hydroxyethyl)carbamoyl group, N,N-bis(2-fluoroethyl)carbamoyl group, N-(2-cyanoethyl)-N-methylcarbamoyl group, N-(2-methoxyethyl)-N-methylcarbamoyl group, N-carboxymethyl-N-methylcarbamoyl group, N,N-bis(2-aminoethyl)carbamoyl group and the like. Examples of the N-alkylcarbamoylalkyl group which may have a substituent on the alkyl group(s) include linear or branched $C_1$-$C_6$ alkyl groups substituted with the N-alkylcarbamoyl group which may have a substituent on the $C_1$-$C_6$ alkyl group (for example, N-methylcarbamoylmethyl group, N-(2-hydroxyethyl)carbamoylmethyl group and the like). Examples of the N,N-dialkylcarbamoylalkyl group which may have a substituent on the alkyl group(s) include linear or branched $C_1$-$C_6$ alkyl groups substituted with the N,N-dialkylcarbamoyl group which may have a substituent on the $C_1$-$C_6$ alkyl group(s) (for example, N,N-dimethylcarbamoylmethyl group, N-(2-hydroxyethyl)-N-methylcarbamoylmethyl group and the like). The 3- to 6-membered heterocyclic carbonyl group which may be substituted is a group composed of a saturated or unsaturated heterocyclic ring and a carbonyl group. The heterocyclic ring means a 3- to 6-membered heterocyclic ring which may containing 1 to 3 hetero atoms (nitrogen atom, oxygen atom, sulfur atom, etc.). The heterocyclic ring may have a substituent such as a hydroxy group, halogen atom, amino group, $C_1$-$C_6$ alkyl group or the like. As specific examples thereof, may be mentioned an aziridinylcarbonyl group, azetidinylcarbonyl group, 3-hydroxyazetidinylcarbonyl group, 3-methoxyazetidinylcarbonyl group, pyrrolidinylcarbonyl group, 3-hydroxypyrrolidinylcarbonyl group, 3-fluoropyrrolidinylcarbonyl group, piperidinylcarbonyl group, piperazinylcarbonyl group, morpholinylcarbonyl group, tetrahydropyranylcarbonyl group, pyridylcarbonyl group, furoyl group and thiophenecarbonyl group. Examples of the 3- to 6-membered heterocyclic carbonylalkyl group which may be substituted include the $C_1$-$C_6$ alkyl groups substituted with the 3- to 6-membered heterocyclic carbonyl group which may be substituted (for example, azetidinylcarbonylmethyl group, pyrrolidinylcarbonylethyl group and the like). Examples of the 3- to 6-membered heterocyclic carbonyloxyalkyl group which may be substituted include the $C_1$-$C_6$ alkyl groups substituted with the 3- to 6-membered heterocyclic carbonyloxy group which is composed of the 3- to 6-membered heterocyclic carbonyl group and an oxygen atom (for example, piperidinylcarbonyloxyethyl group, morpholinylcarbonyloxymethyl group and the like).

Examples of the carbamoyloxyalkyl group include the $C_1$-$C_6$ alkyl groups substituted with a carbamoyloxy group which is composed of a carbamoyl group and an oxygen atom (for example, carbamoyloxymethyl group, carbamoyloxyethyl group and the like). Examples of the N-alkylcarbamoyloxyalkyl group include the $C_1$-$C_6$ alkyl groups substituted with the N-alkylcarbamoyloxy group which is composed of the N-alkylcarbamoyl group, which may have a substituent on the $C_1$-$C_6$ alkyl group, and an oxygen atom (for example, N-methylcarbamoyloxymethyl group, N-methylcarbamoyloxyethyl group and the like). Examples of the N,N-dialkylcarbamoyloxyalkyl group include the $C_1$-$C_6$ alkyl groups substituted with the N,N-dialkylcarbamoyloxy group which is composed of the N,N-dialkylcarbamoyl group, which may have a substituent on the alkyl group(s), and an oxygen atom (for example, N,N-dimethylcarbamoyloxymethyl group, N-ethyl-N-methylcarbamoyloxyethyl group and the like) Examples of the alkylsulfonylamino group include amino groups substituted with an alkylsulfonyl group having the $C_1$-$C_6$ alkyl group (for example, methylsulfonylamino group, isopropylsulfonylamino group and the like). Examples of the arylsulfonylamino group include amino groups substituted with an arylsulfonyl group having the aryl group (for example, phenylsulfonylamino group, naphthylsulfonylamino group and the like). Examples of the alkylsulfonylaminoalkyl group include the $C_1$-$C_6$ alkyl groups substituted with the $C_1$-$C_6$ alkylsulfonylamino group (for example, methylsulfonylaminomethyl group, methylsulfonylaminoethyl group and the like). Examples of the arylsulfonylaminoalkyl group include the $C_1$-$C_6$ alkyl groups substituted with the arylsulfonylamino group (for example, phenylsulfonylaminomethyl group, naphthylsulfonylaminoethyl group and the like). Examples of the alkylsulfonylaminocarbonyl group include groups composed of the $C_1$-$C_6$ alkylsulfonylamino group and a carbonyl group (for example, methylsulfonylaminocarbonyl group, isopropylsulfonylaminocarbonyl group and the like). Examples of the arylsulfonylaminocarbonyl group include groups composed of the arylsulfonylamino group and a carbonyl group (for example, phenylsulfonylaminocarbonyl group, naphthylsulfonylaminocarbonyl group and the like). Examples of the alkylsulfonylaminocarbonylalkyl group include the $C_1$-$C_6$ alkyl groups substituted with the $C_1$-$C_6$ alkylsulfonylaminocarbonyl group (for example, methylsulfonylaminocarbonylmethyl group, isopropylsulfonylaminocarbonylmethyl group and the like). Examples of the arylsulfonylaminocarbonylalkyl group include the $C_1$-$C_6$ alkyl groups substituted with the arylsulfonylaminocarbonyl group (for example, phenylsulfonylaminocarbonylmethyl group, naphthylsulfonylaminocarbonylmethyl group and the like). The acyloxy group means a group composed of acyl group and an oxygen atom (for example, formyloxy group, acetyloxy group and the like). Examples of the acyloxyalkyl group include the $C_1$-$C_6$ alkyl groups substituted with the acyloxy group (for example, formyloxymethyl group, acetyloxymethyl group and the like). Examples of the aralkyloxy group include the $C_1$-$C_6$ alkoxy groups substituted with the aryl group (for example, benzyloxy group, naphthylmethoxy group and the like). Examples of the carboxyalkyloxy group include the alkoxy groups substituted with a carboxyl group (for example, carboxymethoxy group, carboxyethoxy group and the like).

Examples of the arylsulfonyl group include $C_6$-$C_{14}$ arylsulfonyl groups (for example, phenylsulfonyl group, naphthylsulfonyl group and the like). Examples of the alkoxycarbonylalkylsulfonyl group include groups composed of the $C_1$-$C_6$ alkoxycarbonylalkyl group and a sulfonyl group (for example, methoxycarbonylethylsulfonyl group, ethoxycarbonylethylsulfonyl group and the like). Examples of the carboxyalkylsulfonyl group include groups composed of the carboxyalkyl group and a sulfonyl group (for example, carboxymethylsulfonyl group, carboxyethylsulfonyl group and the like). Examples of the alkoxycarbonylacyl group include groups composed of the alkoxycarbonylalkyl group and a carbonyl group (for example, methoxycarbonylmethylcarbonyl group, ethoxycarbonylmethylcarbonyl group and the like). Examples of the alkoxyalkyloxycarbonyl group include the alkoxycarbonyl groups substituted with the the $C_1$-$C_6$ alkoxy group (for examples, methoxymethyloxycarbonyl group, methoxyethyloxycarbonyl group and the like). Examples of the hydroxyacyl group include the acyl groups (including $C_1$-$C_6$ alkanoyl and aroyl) substituted with a hydroxyl group (for example, glycoloyl group, lactoyl group, benziloyl group and the like). Examples of the alkoxyacyl group include the acyl groups substituted with the $C_1$-$C_6$ alkoxy group (for example, methoxyacetyl group, ethoxyacetyl group and the like). Examples of the halogenoacyl group include groups composed of the halogenoalkyl group and a carbonyl group (for example, chloromethylcarbonyl group, trifluoromethylcarbonyl group and the like). Examples of the carboxyacyl group include the acyl groups sucstituted with a carboxyl group (for example, carboxyacetyl group, 2-carboxypropionyl group and the like). Examples of the aminoacyl group include the acyl groups (including $C_1$-$C_6$ alkanoyl and aroyl) substituted with an amino group (for example, aminomethylcarbonyl group, 1-aminoethylcarbonyl group and the like). Examples of the acyloxyacyl group include groups composed of the acyloxyalkyl and a carbonyl group (for example, formyloxymethylcarbonyl group, acetyloxymethylcarbonyl group and the like). Examples of the acyloxyalkylsulfonyl group include groups composed of the acyloxyalkyl and a sulfonyl group (for example, formyloxymethylsulfonyl group, acetyloxymethylsulfonyl group and the like). Examples of the hydroxyalkylsulfonyl group include groups composed of the $C_1$-$C_6$ hydroxyalkyl group and a sulfonyl group (for example, hydroxymethylsulfonyl group, 1-hydroxyethylsulfonyl group and the like). Examples of the alkoxyalkylsulfonyl group include the groups composed of $C_1$-$C_6$ alkoxyalkyl group and a sulfonyl group (for example, methoxymethylsulfonyl group, ethoxyethylsulfonyl group and the like). Examples of the 3- to 6-membered heterocyclic sulfonyl group which may be substituted include groups composed of the 3- to 6-membered heterocyclic group which may be substituted and a sulfonyl group (for example, aziridinylsulfonyl group, azetidinylsulfonyl group, pyrrolidinylsulfonyl group, piperidylsulfonyl group, piperazinylsulfonyl group, morpholinylsulfonyl group, tetrahydropyranylsulfonyl group and the like). Examples of the N-alkylaminoacyl group include the aminoacyl groups substituted with the $C_1$-$C_6$ alkyl group on the nitrogen atom (for example, N-methylaminoacetyl group, N-ethylaminoacetyl group and the like). Examples of the N,N-dialkylaminoacyl group include the aminoacyl groups substituted with the two $C_1$-$C_6$ alkyl groups on the nitrogen atoms (for example, N,N-dimethylaminoacetyl group, N-ethyl-N-methylaminoacetyl group and the like). Examples of the N,N-dialkylcarbamoylacyl group which may have a substituent on the alkyl group(s) include the acyl groups substituted with the N,N-dialkylcarbamoyl group which may have a substituent on the $C_1$-$C_6$ alkyl group(s) (for example, N,N-dimethylcarbamoylacetyl group, N,N-diethylcarbamoylacyl group, N-ethyl-N-methylcarbamoylacetyl group and the like). Examples of the N,N-dialkylcarbamoylalkylsulfonyl group which may have a substituent on the alkyl group(s) include groups composed of the N,N-dialkylcarbamoyl group which may have a substituent on the $C_1$-$C_6$ alkyl group(s) and a sulfonyl group (for example, N,N-dimethylcarbamoylmethylsulfonyl group, N-(2-hydroxyethyl)-N-methylcarbamoylmethyl-sulfonyl group and the like). Examples of the alkylsulfonylacyl group include the acyl groups substituted with the alkylsulfonyl group having the $C_1$-$C_6$ alkyl group (for example, methylsulfonylacetyl group, isopropylsulfonylacetyl group and the like).

The alkylene group means a linear or branched alkylene group having 1 to 5 carbon atoms, and examples thereof include methylene group, ethylene group, propylene group and the like. The alkenylene group is an alkenylene group having 2 to 5 carbon atoms and a double bond, and examples thereof include vinylene group, propenylene group and the like. Examples of the alkylenedioxy group include those having 1 to 5 carbon atoms, such as methylenedioxy group, ethylenedioxy group and propylenedioxy group. The carbonyldioxy group is a group represented by —O—C(=O)—O—. Incidentally, no particular limitation is imposed on the substituting position in the above description.

Among these substituents represented by $R^3$ and $R^4$, the hydrogen atom, hydroxyl group, alkyl group, alkenyl group, alkynyl group, halogen atom, halogenoalkyl group, amino group, hydroxyimino group, alkoxyimino group, aminoalkyl group, N-alkylaminoalkyl group, N,N-dialkylaminoalkyl group, acyl group, acylalkyl group, acylamino group which may be substituted, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered heterocyclic carbonyl group which may be substituted, 3- to 6-membered heterocyclic carbonyloxyalkyl group which may be substituted, carbamoylalkyl group, carbamoyloxyalkyl group, N-alkylcarbamoyloxyalkyl group, N,N-dialkylcarbamoyloxyalkyl group, N-alkylcarbamoylalkyl group which may have a substituent on the alkyl group(s), N,N-dialkylcarbamoylalkyl group which may have a substituent on the alkyl group(s), alkylsulfonylamino group, alkylsulfonylaminoalkyl group, oxo group, acyloxy group, acyloxyalkyl group, arylsulfonyl group, alkoxycarbonylalkylsulfonyl group, carboxyalkylsulfonyl group, alkoxycarbonylacyl group, carboxyacyl group, alkoxyalkyloxycarbonyl group, halogenoacyl group, N,N-dialkylaminoacyl group, acyloxyacyl group, hydroxyacyl group, alkoxyacyl group, alkoxyalkylsulfonyl group, N,N-dialkylcarbamoylacyl group, N,N-dialkylcarbamoylalkylsulfonyl group, alkylsulfonylacyl group and the like are preferred. The alkylene group, alkenylene group, alkylenedioxy group carbonyldioxy group and the like which are formed by $R^3$ and $R^4$ together with each other are also preferred.

It is preferred that $R^3$ be a hydrogen atom, and $R^4$ be one of the substituents mentioned above as preferable groups. In this case, examples of a group more preferred as $R^4$ include the hydrogen atom, hydroxyl group, alkyl group, halogen atom, hydroxyimino group, N-alkylaminoalkyl group, N,N-dialkylaminoalkyl group, acyl group, acylamino group which may be substituted, acylaminoalkyl group, alkoxy group, alkoxyalkyl group, hydroxyalkyl group, carboxyl group, alkoxycarbonyl group, alkoxycarbonylalkyl group, alkoxycarbonylamino group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkyl-N-alkoxycarbamoylalkyl group, carbazoyl group which may be substituted by 1 to 3 alkyl groups, alkylsulfonyl group, alkylsulfonylalkyl group, 3- to 6-membered heterocyclic carbonyl group which may be substituted, 3- to 6-membered heterocyclic carbonyloxyalkyl group which may be substituted, carbamoylalkyl group, N,N-dialkylcarbamoyloxyalkyl group, N-alkylcarbamoylalkyl group which may have a substituent on the alkyl group(s), N,N-dialkylcarbamoylalkyl group which may have a substituent on the alkyl group(s), alkylsulfonylamino group, alkylsulfonylaminoalkyl group, acyloxy group, arylsulfonyl group, alkoxycarbonylalkylsulfonyl group, carboxyalkylsulfonyl group, alkoxycarbonylacyl group, carboxyacyl group, alkoxyalkyloxycarbonyl group, halogenoacyl group, N,N-dialkylaminoacyl group, acyloxyacyl group, hydroxyacyl group, alkoxyacyl group, alkoxyalkylsulfonyl group, N,N-dialkylcarbamoylacyl group, N,N-dialkylcarbamoylalkylsulfonyl group, alkylsulfonylacyl group and the like.

Of these, as examples of $R^4$, are particularly preferred the hydrogen atom, hydroxyl group, alkyl group, N,N-dialkylaminoalkyl group, acylamino group which may be substituted, acylaminoalkyl group, alkoxy group, alkoxyalkyl group, hydroxyalkyl group, alkoxycarbonyl group, alkoxycarbonylamino group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkyl-N-alkoxycarbamoyl group, carbazoyl group which may be substituted by 1 to 3 alkyl groups, alkylsulfonyl group, alkylsulfonylalkyl group, 3- to 6-membered heterocyclic carbonyl group which may be substituted, N,N-dialkylcarbamoyloxyalkyl group, N-alkylcarbamoylalkyl group which may have a substituent on the alkyl group(s), N,N-dialkylcarbamoylalkyl group which may have a substituent on the alkyl group(s), alkylsulfonylamino group, alkylsulfonylaminoalkyl group, acyloxy group, acyl group, alkoxyalkyloxycarbonyl group, halogenoacyl group, N,N-dialkylaminoacyl group, hydroxyacyl group, alkoxyacyl group and the like.

As specific preferable examples of $R^3$ and $R^4$, may be mentioned a hydrogen atom, hydroxyl group, methyl group, ethyl group, isopropyl group, N,N-dimethylaminomethyl group, N,N-dimethylaminoethyl group, N,N-diethylaminomethyl group, acetylamino group, methoxyacetylamino group, acetylaminomethyl group, acetylaminoethyl group, methoxy group, ethoxy group, methoxymethyl group, methoxyethyl group, hydroxymethyl group, 2-hydroxyethyl group, 1-hydroxy-1-methylethyl group, methoxycarbonyl group, ethoxycarbonyl group, methoxycarbonylamino group, ethoxycarbonylamino group, N-allylcarbamoyl group, N-allylcarbamoylmethyl group, N-allyl-N-methylcarbamoyl group, N-allyl-N-methylcarbamoylmethyl group, N-methoxy-N-methylcarbamoyl group, N,N-dimethylcarbazoyl group, N,N,N'-trimethylcarbazoyl group, methanesulfonyl group, methanesulfonylmethyl group, ethanesulfonylmethyl group, N-methylcarbamoyl group, N-ethylcarbamoyl group, N-propylcarbamoyl group, N-isopropylcarbamoyl group, N-tert-butylcarbamoyl group, N-cyclopropylcarbamoyl group, N-cyclopropylmethylcarbamoyl group, N-(1-ethoxycarbonylcyclopropyl)carbamoyl group, N-(2-hydroxyethyl)carbamoyl group, N-(2-fluoroethyl)carbamoyl group, N-(2-methoxyethyl)carbamoyl group, N-(carboxymethyl)-carbamoyl group, N-(2-aminoethyl)carbamoyl group, N-(2-amidinoethyl)carbamoyl group, N,N-dimethylcarbamoyl group, N,N-diethylcarbamoyl group, N-ethyl-N-methylcarbamoyl group, N-isopropyl-N-methylcarbamoyl group, N-methyl-N-propylcarbamoyl group, N-(2-hydroxyethyl)-N-methylcarbamoyl group, N-(2-fluoroethyl)-N-methylcarbamoyl group, N,N-bis(2-hydroxyethyl)carbamoyl group, N,N-bis(2-fluoroethyl)carbamoyl group, N-(2-methoxyethyl)-N-methylcarbamoyl group, N-carboxymethyl-N-methylcarbamoyl group, N,N-bis(2-aminoethyl)carbamoyl group, azetidinocarbonyl group, 3-methoxyazetidinocarbonyl group, 3-hydroxyazetidinocarbonyl group, pyrrolidinocarbonyl group, 3-hydroxypyrrolidinocarbonyl group, 3-fluoropyrrolidinocarbonyl group, 3,4-dimethoxypyrrolidinocarbonyl group, piperidinocarbonyl group, piperazinocarbonyl group, morpholinocarbonyl group, (tetrahydropyran-4-yl)carbonyl group, benzoyl group, pyridylcarbonyl group, N-methylcarbamoylmethyl group, N-methylcarbamoylethyl group, N-ethylcarbamoylmethyl group, N-(2-fluoroethyl)carbamoylmethyl group, N-(2-methoxyethyl)carbamoylmethyl group, N,N-dimethylcarbamoylmethyl group, N,N-dimethylcarbamoylethyl group, N-(2-fluoroethyl)-N-methylcarbamoylmethyl group, N-(2-methoxyethyl)-N-methylcarbamoylmethyl group, N,N-dimethylcarbamoyloxymethyl group, 2-(N-ethyl-N-methylcarbamoyloxy)ethyl group, methylsulfonylamino group, ethylsulfonylamino group, methylsulfonylaminomethyl group, methylsulfonylaminoethyl group, acetyl group, propionyl group, isobutyryl group, 2-methoxyethoxycarbonyl group, trifluoroacetyl group, N,N-dimethylaminoacetyl group, N-ethyl-N-methylaminoacetyl group, hydroxyacetyl group, 1,1-dimethyl-2-hydroxyethylcarbonyl group, methoxyacetyl group, 1,1-dimethyl-2-methoxyethylcarbonyl group and the like.

As described above, it is preferred that $R^3$ be a hydrogen atom, and $R^4$ be one of these specified substituents, preferably, an N,N-dialkylcarbamoyl group which may have a substituent on the alkyl group(s), particularly preferably, an N,N-dimethylcarbamoyl group. However, $R^3$ and $R^4$ are not limited to these specific substituents at all.

<On Group T⁰>

The group T⁰ represents a carbonyl group or thiocarbonyl group, with the carbonyl group being preferred.

<On Group T¹>

The group T¹ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')—, in which R' means a hydrogen atom, hydroxyl group, alkyl group or alkoxy group, group —C(=O)-A¹-N(R")—, in which A¹ means an alkylene group having 1 to 5 carbon atoms, which may be substituted, and R" means a hydrogen atom, hydroxyl group, alkyl group or alkoxy group, group —C(=O)—NH—, group —C(=S)—NH—, group —C(=O)—NH—NH—, group —C(=O)-A²-C(=O)—, in which A² means a single bond or alkylene group having 1 to 5 carbon atoms, group —C(=O)-A³-C(=O)—NH—, in which A³ means an alkylene group having 1 to 5 carbon atoms, group —C(=O)—C(=NOR^a)—N(R^b)—, group —C(=S)—C(=NOR^a)—N(R^b)—, in which R^a means a hydrogen atom, alkyl group or alkanoyl group, and R^b means a hydrogen atom, hydroxyl group, alkyl group or alkoxy group, group —C(=O)—N=N—, group —C(=S)—N=N—, or thiocarbonyl group.

In the above group, the alkylene group having 1 to 5 carbon atoms in A¹, A² and A³ means a linear, branched or cyclic alkylene group having 1 to 5 carbon atoms, and examples thereof include methylene, ethylene, propylene, cyclopropylene, 1,3-cyclopentylene groups and the like. The alkyl group in R', R", R^a and R^b means a linear, branched or cyclic alkyl group having 1 to 6 carbon atoms, and examples thereof include methyl, ethyl groups and the like. The alkoxy group means a linear, branched or cyclic alkoxy group having 1 to 6 carbon atoms, and examples thereof include methoxy, ethoxy groups and the like.

In R^a, the alkanoyl group means a group composed of a linear, branched or cyclic alkyl group having 1 to 6 carbon atoms and a carbonyl group, and examples thereof include acetyl, propionyl groups and the like.

As T¹, is preferred a carbonyl group, group —C(=O)—C(=O)—N(R')—, group —C(=S)—C(=O)—N(R')—, group —C(=O)—C(=S)—N(R')—, group —C(=S)—C(=S)—N(R')— and group —C(=O)—CH₂—N(R")—, with a carbonyl group, group —C(=O)—C(=O)—N(R')—, group —C(=S)—C(=O)—N(R')—, group —C(=O)—C(=S)—N(R')— and group —C(=S)—C(=S)—N(R')— being particularly preferred.

<On Group R¹ and Group R²>

R¹ and R² are, independently of each other, a hydrogen atom, hydroxyl group, alkyl group or alkoxy group, preferably a hydrogen atom or alkyl group, more preferably a hydrogen atom.

In R¹ and R², the alkyl group means a linear, branched or cyclic alkyl group having 1 to 6 carbon atoms, and examples thereof include methyl, ethyl groups and the like. The alkoxy group means a linear, branched or cyclic alkoxy group having 1 to 6 carbon atoms, and examples thereof include methoxy, ethoxy groups and the like. R¹ and R² are preferably, independently of each other, a hydrogen atom or alkyl group, more preferably both hydrogen atoms.

When T¹ is a carbonyl or sulfonyl group, and Q⁵ in the group Q³ is an alkylene group having 1 to 8 carbon atoms or an alkenylene group having 2 to 8 carbon atoms, Q⁴ is preferably a group (b), (f), (g), (h), (i), (j), (k) and (l) of the above-described 12 groups, with the provise that N in the group (f) indicates that 2 carbon atoms of the ring substituted by R¹⁹ have been substituted by a nitrogen atom.

When T¹ is a carbonyl or sulfonyl group, and Q⁵ in the group Q³ is an alkylene group having 1 to 8 carbon atoms or an alkenylene group having 2 to 8 carbon atoms, the substituent on the group Q⁵ is preferably an N-alkylcarbamoyl or N,N-dialkylcarbamoyl group.

When T¹ is a group —C(=O)—C(=O)—N(R')—, group —C(=S)—C(=O)—N(R')—, group —C(=O)—C(=S)—N(R')— or group —C(=S)—C(=S)—N(R')—, and Q⁵ in the group Q³ is an alkylene group having 1 to 8 carbon atoms or an alkenylene group having 2 to 8 carbon atoms, Q⁴ is preferably a group (i), (j) or (k) of the above-described 12 groups.

When T¹ is a group —C(=O)—C(=O)—N(R')—, group —C(=S)—C(=O)—N(R')—, group —C(=O)—C(=S)—N(R')— or group —C(=S)—C(=S)—N(R')—, and Q⁵ in the group Q³ is an alkylene group having 1 to 8 carbon atoms or an alkenylene group having 2 to 8 carbon atoms, the substituent on the group Q⁵ is preferably an N-alkylcarbamoyl or N,N-dialkylcarbamoyl group.

A feature of the compounds of the present invention represented by the general formula (1), the salts thereof, the solvates thereof, or the N-oxides thereof resides in a combination of the group T¹ and the group Q³. The combination is roughly divided into the following 2 cases (I) and (II):

(I) A case where T¹ is a carbonyl, sulfonyl or thiocarbonyl group, and Q³ is the following group:

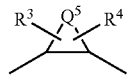

wherein Q⁵ means a group —(CH₂)$_m$—CH₂-A-CH₂-(CH₂)$_n$—, in which m and n are independently of each other 0 or an integer of 1-3, and A means an oxygen atom, nitrogen atom, sulfur atom, —SO—, —SO₂—, —NH—, —O—NH—, —NH—NH—, —S—NH—, —SO—NH— or —SO₂—NH—; and (II) a case where T¹ is a group —C(=O)—C(=O)—N(R')—, group —C(=S)—C(=O)—N(R')—, group —C(=O)—C(=S)—N(R')— or group —C(=S)—C(=S)—N(R')—, in which R' means a hydrogen atom, hydroxyl group, alkyl group or alkoxy group, group —C(=O)-A¹-N(R")—, in which A¹ means an alkylene group having 1 to 5 carbon atoms, which may be substituted, and R" means a hydrogen atom, hydroxyl group, alkyl group or alkoxy group, group —C(=O)—NH—, group —C(=S)—NH—, group —C(=O)—NH—NH—, group —C(=O)-A²-C(=O)—, in which A² means a single bond or alkylene group having 1 to 5 carbon atoms, group —C(=O)-A³-C(=O)—NH—, in which A³ means an alkylene group having 1 to 5 carbon atoms or thiocarbonyl group, and Q³ is the following group:

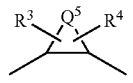

wherein Q⁵ means an alkylene group having 1 to 8 carbon atoms, an alkenylene group having 2 to 8 carbon atoms or a group —(CH₂)$_m$—CH₂-A-CH₂—(CH₂)$_n$—, in which m and n are independently of each other 0 or an integer of 1-3, and A means an oxygen atom, nitrogen atom, sulfur atom, —SO—, —SO$_2$—, —NH—, —O—NH—, —NH—NH—, —S—NH—, —SO—NH— or —SO$_2$—NH—.

In the cases (I) and (II), the following (i) and (ii) are mentioned as preferred examples, respectively.

(i) An example where the group $R^1$ and the group $R^2$ are, independently of each other, a hydrogen atom or alkyl group, the group $Q^1$ is a saturated or unsaturated, bicyclic or tricyclic fused hydrocarbon group which may be substituted, or a saturated or unsaturated, bicyclic or tricyclic fused heterocyclic group which may be substituted, the group $Q^2$ is a single bond, the group $Q^5$ in the group $Q^3$ is a group —(CH$_2$)$_m$—CH$_2$-A-CH$_2$—(CH$_2$)$_n$—, in which m and n are independently of each other 0 or 1, and A has the same meaning as defined above, the group $Q^4$ is selected from 9 groups (a) to (h) and (l) of the above-described 12 groups, the group $T^0$ is a carbonyl group or thiocarbonyl group, and the group $T^1$ is a carbonyl group or sulfonyl group; and (ii) An example where in the generaly formula (1), the groups $R^1$ and $R^2$ are, independently of each other, a hydrogen atom or alkyl group, the group $Q^1$ is a saturated or unsaturated, bicyclic or tricyclic fused hydrocarbon group which may be substituted, or a saturated or unsaturated, bicyclic or tricyclic fused heterocyclic group which may be substituted, the group $Q^2$ is a single bond, the group $Q^5$ in the group $Q^3$ is an alkylene group having 3 to 6 carbon atoms or a group —(CH$_2$)$_m$—CH$_2$-A-CH$_2$—(CH$_2$)$_n$—, in which m and n are independently of each other 0 or 1, and A has the same meaning as defined above, the group $Q^4$ is selected from 3 groups (i), (j) and (k) of the above-described 12 groups, the group $T^0$ is a carbonyl group or thiocarbonyl group, and the group $T^1$ is a group —C(=O)—C(=O)—N(R')—, group —C(=S)—C(=O)—N(R')—, group —C(=O)—C(=S)—N(R')— or group —C(=S)—C(=S)—N(R')—.

Stereoisomers or optical isomers derived from an asymmetric carbon atom may be present in the compounds of the present invention represented by the general formula (1). However, these stereoisomers, optical isomers and mixtures thereof are all included in the present invention.

No particular limitation is imposed on salts of the compounds of the present invention represented by the general formula (1) so far as they are pharmaceutically acceptable salts. However, specific examples thereof include mineral acid salts such as hydrochlorides, hydrobromides, hydriodides, phosphates, nitrates and sulfates; benzoates; organic sulfonates such as methanesulfonates, 2-hydroxyethanesulfonates and p-toluenesulfonates; and organic carboxylates such as acetates, propanoates, oxalates, malonates, succinates, glutarates, adipates, tartrates, maleates, malates and mandelates. In the case where the compounds represented by the general formula (1) have an acidic group, they may be salts of alkali metal ions or alkaline earth metal ions. No particular limitation is imposed on the solvates thereof so far as they are pharmaceutically acceptable solvates. As specific examples thereof, however, may be mentioned hydrates and solvates with ethanol. When a nitrogen atom is present in the general formula (1), such a compound may be converted to an N-oxide thereof.

As the compounds according to the present invention, are preferred the compounds described in the following Examples and salts thereof as well as the following compounds and salts thereof.

1) 3-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)[1,6]naphthyridine-7-carboxamide;

2) 7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-fluorocinnoline-3-carboxamide;

3) 7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4a,8a-dihydro-4H-1,2,4-benzoxadiazine-3-carboxamide;

4) N-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-6-fluoro-4-oxo-1,4-dihydroquinoline-2-carboxamide;

5) 7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-5-oxo-4,5-dihydro-1H-1,3,4-benzotriazepine-2-carboxamide;

6) 6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-3,4-dihydro-2(1H)-cinnolinecarboxamide;

7) 6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-1,2,3,4-tetrahydroquinoline-2-carboxamide;

8) N-{(1R,2S,5S)-2-{[3-(3-chlorophenyl)-2-propinoyl]amino}-5-[(dimethylamino)carbonyl]cyclohexyl}-5-methyl-4,5,6,7-tetrahydrothiazolo[5,4-c]pyridin-2-carboxamide;

9) N-{(1R,2S,5S)-2-[(4-chlorobenzoyl)amino]-5-[(dimethylamino)carbonyl]cyclohexyl}-5-methyl-4,5,6,7-tetrahydrothiazolo[5,4-c]pyridin-2-carboxamide;

10) N-{(1R,2S,5S)-2-{[(5-chloroindol-2-yl)carbonyl]amino}-5-[(dimethylamino)carbonyl]cyclohexyl}-6-methyl-5,6,7,8-tetrahydro-4H-thiazolo[4,5-d]azepin-2-carboxamide;

11) 5-Chloro-N-[(1S,2R,4S)-4-[(dimethylamino)carbonyl]-2-({[5-(3-pyrrolidinyloxy)thiazol-2-yl]carbonyl}amino)cyclohexyl]indole-2-carboxamide;

12) $N^1$-(4-Chlorophenyl)-$N^2$-((1S,2R)-2-{[(5-methyl-4,5,6,7-tetrahydrothiazolo[5,4-c]pyridin-2-yl)carbonyl]amino}-cyclohexyl)ethanediamide;

13) $N^1$-(5-Chloropyridin-2-yl)-$N^2$-((1S,2R)-2-{[(5-methyl-4,5,6,7-tetrahydrothiazolo[5,4-c]pyridin-2-yl)carbonyl]amino}cyclohexyl)ethanediamide;

14) $N^1$-(5-Chloropyridin-2-yl)-$N^2$-((1S,2R)-2-{[(5-methyl-5,6-dihydro-4H-pyrrolo[3,4-d]thiazol-2-yl)carbonyl]amino}-cyclohexyl)ethanediamide;

15) $N^1$-(4-Chlorophenyl)-$N^2$-((1S,2R)-2-{[(5-methyl-5,6-dihydro-4H-pyrrolo[3,4-d]thiazol-2-yl)carbonyl]amino}-cyclohexyl)ethanediamide;

16) $N^1$-(5-Chloropyridin-2-yl)-$N^2$-((1R,2R)-2-{[(5-methyl-5,6-dihydro-4H-pyrrolo[3,4-d]thiazol-2-yl)carbonyl]amino}-cyclopentyl)ethanediamide;

17) $N^1$-(4-Chlorophenyl)-$N^2$-((1R,2R)-2-{[(5-methyl-5,6-dihydro-4H-pyrrolo[3,4-d]thiazol-2-yl)carbonyl]amino}-cyclopentyl)ethanediamide;

18) $N^1$-(4-Chlorophenyl)-$N^2$-((1R,2R)-2-{[(S-methyl-4,5,6,7-tetrahydrothiazolo[5,4-c]pyridin-2-yl)carbonyl]amino}-cycloheptyl)ethanediamide;

19) $N^1$-(5-Chloropyridin-2-yl)-$N^2$-((1R,2R)-2-{[(5-methyl-4,5,6,7-tetrahydrothiazolo[5,4-c]pyridin-2-yl)carbonyl]amino}cycloheptyl)ethanediamide;

20) $N^1$-(5-Chloropyridin-2-yl)-$N^2$-((1R,2R)-2-{[(5-methyl-5,6-dihydro-4H-pyrrolo[3,4-d]thiazol-2-yl)carbonyl]amino}cycloheptyl)ethanediamide;

21) $N^1$-(4-Chlorophenyl)-$N^2$-((1R,2R)-2-{[(5-methyl-5,6-dihydro-4H-pyrrolo[3,4-d]thiazol-2-yl)carbonyl]amino}cycloheptyl)ethanediamide;

22) $N^1$-(5-Chloro-6-methylpyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

23) $N^1$-(5-Chloro-3-methylpyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]-amino)cyclohexyl)ethanediamide;

24) $N^1$-(5-Chloro-4-methylpyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

25) $N^1$-(4-Chloro-3-hydroxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

26) $N^1$-(4-Chloro-2-hydroxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

27) $N^1$-[4-Chloro-2-(fluoromethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

28) $N^1$-[4-Chloro-2-(methoxymethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

29) N-{(1R,2S,5S)-2-({[[1-(4-Chloroanilino)cyclopropyl]carbonyl}amino)-5-[(dimethylamino)carbonyl]cyclohexyl}-5-methyl-4,5,6,7-tetrahydrothiazolo[5,4-c]pyridin-2-carboxamide;

30) $N^1$-(5-Chloropyridin-2-yl)-$N^2$-((1R,2R,4R)-4-(hydroxymethyl)-2-{[(5-methyl-4,5,6,7-tetrahydrothiazolo[5,4-c]pyridin-2-yl)carbonyl]amino}cyclopentyl)ethanediamide;

31) $N^1$-(5-Chloropyridin-2-yl)-$N^2$-((1R,2R,4S)-4-(hydroxymethyl)-2-{[(5-methyl-4,5,6,7-tetrahydrothiazolo[5,4-c]pyridin-2-yl)carbonyl]amino}cyclopentyl)ethanediamide;

32) $N^1$-((3R,4S)-1-Acetyl-3-{[(5-methyl-4,5,6,7-tetrahydrothiazolo[5,4-c]pyridin-2-yl)carbonyl]amino}-piperidin-4-yl)-$N^2$-(5-chloropyridin-2-yl)ethanediamide;

33) $N^1$-(5-Chloropyridin-2-yl)-$N^2$-((3R,4S)-1-(methylsulfonyl)-3-{[(5-methyl-4,5,6,7-tetrahydrothiazolo-[5,4-c]pyridin-2-yl)carbonyl]amino}piperidin-4-yl)ethanediamide;

34) $N^1$-{(1S,2R,4S)-2-{[(3-Chlorobenzothiophen-2-yl)carbonyl]amino}-4-[(dimethylamino)carbonyl]cyclohexyl}-$N^2$-(5-chloropyridin-2-yl)ethanediamide;

35) $N^1$-(5-Chloropyridin-2-yl)-$N^2$-((1S,2R,4S)-4-[(dimethylamino)carbothioyl]-2-{[(5-methyl-4,5,6,7-tetrahydrothiazolo[5,4-c]pyridin-2-yl)carbonyl]amino}-cyclohexyl)ethanediamide;

36) $N^1$-(5-Chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbothioyl]amino}-cyclohexyl)ethanediamide;

37) $N^1$-(5-Chloropyridin-2-yl)-$N^2$-((3R,4S)-1-(2-methoxyethanethioyl)-3-{[(5-methyl-4,5,6,7-tetrahydrothiazolo[5,4-c]pyridin-2-yl)carbonyl]amino}piperidin-4-yl)ethanediamide;

38) $N^1$-(5-Chloropyridin-2-yl)-$N^2$-((3R,4S)-1-(2-methoxyacetyl)-3-{[(5-methyl-4,5,6,7-tetrahydrothiazolo-[5,4-c]pyridin-2-yl)carbothioyl]amino}piperidin-4-yl)ethanediamide;

39) N-[(3R,4S)-4-({2-[(5-Chloropyridin-2-yl)amino]-2-oxoethanethioyl}amino)-1-(2-methoxyacetyl)piperidin-3-yl]-5-methyl-4,5,6,7-tetrahydrothiazolo[5,4-c]pyridine-2-carboxamide;

40) N-[(3R,4S)-4-({2-[(5-Chloropyridin-2-yl)amino]-2-thioxoacetyl}amino)-1-(2-methoxyacetyl)piperidin-3-yl]-5-methyl-4,5,6,7-tetrahydrothiazolo[5,4-c]pyridine-2-carboxamide;

41) $N^1$-(4-Chlorophenyl)-$N^2$-((3R,4S)-1-(2-methoxyethanethioyl)-3-{[(5-methyl-4,5,6,7-tetrahydrothiazolo[5,4-c]-pyridin-2-yl)carbonyl]amino}piperidin-4-yl)ethanediamide;

42) $N^1$-(4-Chlorophenyl)-$N^2$-((3R,4S)-1-(2-methoxyacetyl)-3-{[(5-methyl-4,5,6,7-tetrahydrothiazolo[5,4-c]pyridin-2-yl)carbothioyl]amino}piperidin-4-yl)ethanediamide;

43) N-[(3R,4S)-4-{[2-[(4-Chloroanilino)-2-oxoethanethioyl]amino}-1-(2-methoxyacetyl)piperidin-3-yl]-5-methyl-4,5,6,7-tetrahydrothiazolo[5,4-c]pyridine-2-carboxamide;

44) N-[(3R,4S)-4-({2-[(4-Chlorophenyl)amino]-2-thioxoacetyl}amino)-1-(2-methoxyacetyl)piperidin-3-yl]-5-methyl-4,5,6,7-tetrahydrothiazolo[5,4-c]pyridine-2-carboxamide;

45) $N^1$-((1S,2R,4S)-4-(1-azetidinylcarbonyl)-2-{[(5-methyl-4,5,6,7-tetrahydrothiazolo[5,4-c]pyridin-2-yl)carbonyl]-amino)cyclohexyl)-$N^2$-(5-chloropyridin-2-yl)ethanediamide;

46) $N^1$-(5-Chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1-pyrrolidinylcarbonyl)cyclohexyl]ethanediamide;

47) $N^1$-(5-Chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1-piperidinylcarbonyl)cyclohexyl]ethanediamide;

48) $N^1$-(5-Chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(4-morpholinylcarbonyl)cyclohexyl]ethanediamide;

49) $N^1$-(5-Chloropyridin-2-yl)-$N^2$-((1S,2R,4S)-4-[(methylamino)carbonyl]-2-{[(5-methyl-4,5,6,7-tetrahydrothiazolo[5,4-c]pyridin-2-yl)carbonyl]amino}-cyclohexyl)ethanediamide;

50) $N^1$-{(1R,2S,5S)-2-({2-[(6-Chloropyridazin-3-yl)amino]-2-oxoethanethioyl}amino)-5-[(dimethylamino)carbonyl]cyclohexyl}-5-methyl-4,5,6,7-tetrahydrothiazolo-[5,4-c]pyridine-2-carboxamide;

51) $N^1$-(4-Bromophenyl)-$N^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide;

52) $N^1$-(5-Chloropyridin-2-yl)-$N^2$-((3R,4S)-1-(2-methoxyacetyl)-3-{[4-(pyridin-4-yl)benzoyl]amino}-piperidin-4-yl)ethanediamide;

53) $N^1$-(5-Chloropyridin-2-yl)-$N^2$-[(3R,4S)-1-(2-methoxyacetyl)-3-({[2-(pyridin-4-yl)pyrimidin-5-yl]carbonyl}amino)piperidin-4-yl]ethanediamide;

54) $N^1$-(5-Chloropyridin-2-yl)-$N^2$-[(1S,2R,4S)-4-[(dimethylamino)carbonyl]-2-({[2-(pyridin-4-yl)pyrimidin-5-yl]carbonyl]amino)cyclohexyl]ethanediamide;

55) N-{(1R,2S,5S)-2-{[2-(4-Chloroanilino)-2-oxoethane(methoxy)imidoyl]amino}-5-[(dimethylamino)carbonyl]cyclohexyl}-5-methyl-4,5,6,7-tetrahydrothiazolo-[5,4-c]pyridine-2-carboxamide;
56) N-{(1R,2S,5S)-2-{[2-(4-Chloroanilino)-2-(methoxyimino)acetyl]amino}-5-[(dimethylamino)carbonyl]cyclohexyl}-5-methyl-4,5,6,7-tetrahydrothiazolo-[5,4-c]pyridine-2-carboxamide;
57) $N^1$-(5-Chloropyridin-2-yl)-$N^2$-((1S,2R,4S)-4-[(dimethylamino)carbonyl]-2-{[(4,4,5-trimethyl-5,6-dihydro-4H-pyrrolo[3,4-d]thiazol-2-yl)carbonyl]amino}cyclohexyl)ethanediamide;
58) $N^1$-(5-Chloropyridin-2-yl)-$N^2$-((1S,2R,4S)-4-[(dimethylamino)carbonyl]-2-{[(4,4-ethylene-5-methyl-5,6-dihydro-4H-pyrrolo[3,4-d]thiazol-2-yl)carbonyl]amino}cyclohexyl)ethanediamide;
59) N-{(1R,2S,5S)-2-({[(E)-2-(4-Chlorophenyl)ethenyl]sulfonyl}amino)-5-[(dimethylamino)carbonyl]cyclohexyl}-5-methyl-4,5,6,7-tetrahydrothiazolo[5,4-c]pyridine-2-carboxamide;
60) N-{(1R,2S,5S)-2-{[(4-Chlorobenzyl)sulfonyl]amino}-5-[(dimethylamino)carbonyl]cyclohexyl}-5-methyl-4,5,6,7-tetrahydrothiazolo[5,4-c]pyridine-2-carboxamide;
61) N-{(1R,2S,5S)-2-[(2-{[(4-Chlorophenyl)sulfonyl]amino}acetyl)amino]-5-[(dimethylamino)carbonyl]cyclohexyl}-5-methyl-4,5,6,7-tetrahydrothiazolo[5,4-c]-pyridine-2-carboxamide.

The preparation process of the diamine derivatives (1) according to the present invention will hereinafter be described.

[Preparation Process 1]

A compound represented by the general formula (1), a salt thereof, a solvate thereof, or an N-oxide thereof can be prepared in accordance with, for example, the following process:

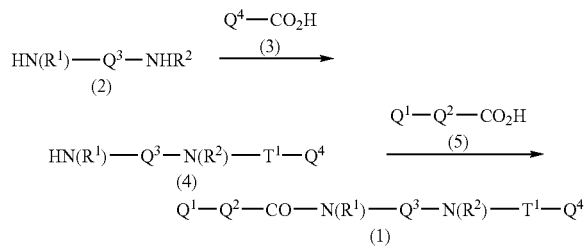

wherein $Q^1$, $Q^2$, $Q^3$, $Q^4$, $R^1$ and $R^2$ have the same meanings as defined above, and $T^1$ represents a carbonyl group.

A mixed acid anhydride, acid halide, activated ester or the like, which is derived from carboxylic acid (3), may react with diamine (2), giving compound (4). The resultant compound (4) may react with carboxylic acid (5) under the same conditions, giving compound (1) according to the present invention. In the above reaction steps, reagents and conditions, which are generally used in peptide synthesis, may be applied. The mixed acid anhydride can be prepared by, for example, reaction of a chloroformate such as ethyl chloroformate or isobutyl chloroformate with carboxylic acid (3) in the presence of a base. The acid halide can be prepared by treating carboxylic acid (3) with an acid halide such as thionyl chloride or oxalyl chloride. The activated ester includes various kinds of esters. Such an ester can be prepared by, for example, reaction of a phenol such as p-nitrophenol, N-hydroxybenzotriazol, or N-hydroxysccinimide with carboxylic acid (3) using a condensing agent such as N,N'-dicyclohexylcarbodiimide or 1-ethyl-3-(3-dimethylaminopropyl)carbodiimide hydrochloride. The activated ester can also be prepared by reaction of carboxylic acid (3) with pentafluorophenyl trifluoroacetate or the like, reaction of carboxylic acid (3) with 1-benzotriazolyloxytripyrrolidinophosphonium hexafluorophosphite, reaction of carboxylic acid (3) with diethyl cyanophosphonate (Shioiri method), reaction of carboxylic acid (3) with triphenylphosphine and 2,2'-dipyridyl disulfide (Mukaiyama method) or the like. The thus-obtained mixed acid anhydride, acid halide or activated ester of carboxylic acid (3) may react with diamine (2) at −78° C. to 150° C. in the presence of a proper base in an inert solvent, giving compound (4). Thus-obtained compound (4) may react with a mixed acid anhydride, acid halide or activated ester of carboxylic acid (5) under the same conditions, giving compound (1) according to the present invention. The reagents and reaction conditions in the reaction of compound (4) with carboxylic acid (5) are the same as those in the reaction of diamine (2) with carboxylic acid (3).

As specific examples of the base used in each of the above mentioned step, may be carbonates of alkali metals or alkaline earth metals, such as sodium carbonate and potassium carbonate, alkali metal alkoxides such as sodium ethoxide and potassium butoxide, alkali metal hydroxides such as sodium hydroxide and potassium hydroxide, and hydrides of alkali metals or alkaline earth metals, such as sodium hydride and potassium hydride; organic metal bases exemplified by alkyllithium such as n-butyllithium, and dialkylaminolithium such as lithium diisopropylamide; organic metal bases exemplified by bis(silyl)amine, such as lithiumbis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent used in this reaction include alkyl halide type solvents such as dichloromethane, chloroform and carbon tetrachloride, etheric solvents such as tetrahydrofuran, 1,2-dimethoxyethane and dioxane, aromatic solvents such as benzene and toluene, and amide solvents such as N,N-dimethylformamide, N,N-dimethylacetamide and N-methylpyrrolidin-2-one. In addition to these solvent, a sulfoxide solvent such as dimethyl sulfoxide or sulfolane, a ketone solvent such as acetone or methyl ethyl ketone, or the like may be used in some cases.

[Preparation Process 2]

Compound (1) according to the present invention can also be prepared in accordance with the following process:

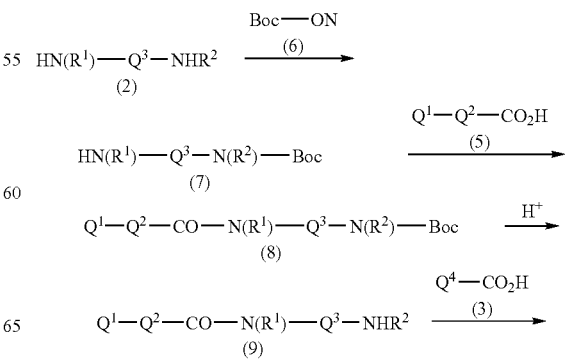

-continued

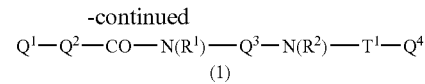

wherein $Q^1$, $Q^2$, $Q^3$, $Q^4$, $R^1$ and $R^2$ have the same meanings as defined above, $T^1$ represents a carbonyl group, Boc represents a tert-butoxycarbonyl group, and Boc-ON represents a 2-(tert-butoxycarbonyloxyimino)-2-phenylacetonitrile.

As described above, diamine (2) is treated with Boc-ON (6) to prepare compound (7) in which one of 2 amino groups has been protected with tert-butoxycarbonyl group. The resultant compound (7) reacts with carboxylic acid (5) and affords compound (8). Compound (8) is successively treated with an acid to give compound (9). Compound (9) then reacts with the carboxylic acid (3), giving compound (1) according to the present invention. Compound (7) can be prepared by a reaction at −10° C. to 40° C. in the presence of triethylamine in a solvent such as dichloromethane. Reaction of compound (7) with the mixed acid anhydride, acid halide or activated ester of the carboxylic acid (5) is carried out using the same reagents and reaction conditions as those described in Preparation Process 1, whereby compound (8) can be prepared. The resultant compound (8) is treated with trifluoroacetic acid or the like at −20° C. to 70° C., whereby amine (9) can be prepared. In the reaction of the resultant amine (9) with carboxylic acid (3), the same reagents and conditions as those described in Preparation Process 1 may be used.

By the way, the tert-butoxycarbonyl group of compound (7) may be replaced by other amino-protecting groups. In this case, reagent (6) is also changed to other reagents, and reaction conditions and the like according to the reagents must be used. As examples of other protecting groups for amino groups, may be mentioned alkanoyl groups such as an acetyl group, alkoxycarbonyl groups such as methoxycarbonyl and ethoxycarbonyl groups, arylmethoxycarbonyl groups such as benzyloxycarbonyl, p-methoxybenzyloxycarbonyl and p- or o-nitrobenzyloxycarbonyl groups, arylmethyl groups such as benzyl and triphenylmethyl groups, aroyl groups such as a benzoyl group, and arylsulfonyl groups such as 2,4-dinitrobenzenesulfonyl and o-nitrobenzenesulfonyl groups. These protecting groups may be chosen for use according to the nature and the like of the compound of which amino group is to be protected. Upon leaving such a protecting group, reagents and conditions may be employed according to the protecting group.

[Preparation Process 3]

Compound (1) according to the present invention can be prepared by reacting diamine (2) with sulfonyl halide (10) and then condensing the reaction product with carboxylic acid (5).

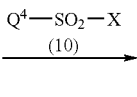

-continued

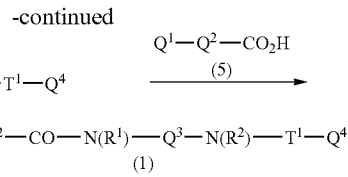

wherein $Q^1$, $Q^2$, $Q^3$, $Q^4$, $R^1$ and $R^2$ have the same meanings as defined above, $T^1$ represents a sulfonyl group, and X represents a halogen atom.

Diamine (2) reacts with sulfonyl halide (10) at −10° C. to 30° C. in the presence of a base such as triethylamine in an inert solvent, giving compound (4). The inert solvent and base may be suitably chosen for use from those described in Preparation Process 1. The resultant compound (4) is condensed with carboxylic acid (5) using the reagents and conditions described in Preparation Process 1, whereby compound (1) according to the present invention can be prepared. Sulfonyl halide (10) may be synthesized in a proper base in accordance with the publicly known process (WO96/10022, WO00/09480) or a process according to it.

[Preparation Process 4]

Compound (1) according to the present invention can also be prepared in accordance with the following process:

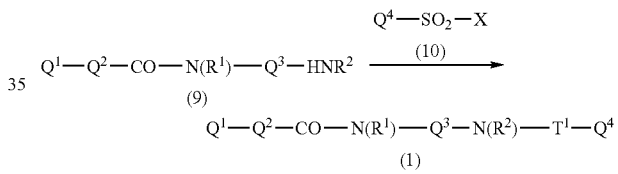

wherein $Q^1$, $Q^2$, $Q^3$, $Q^4$, $R^1$, $R^2$ and X have the same meanings as defined above, and $T^1$ represents a sulfonyl group.

More specifically, amine (9) may react with sulfonyl halide (10) at −10° C. to 30° C. in the presence of a base in an inert solvent, giving compound (1). The inert solvent and base may be suitably chosen for use from those described in Preparation Process 1.

[Preparation Process 5]

In the compounds (1) according to the present invention, geometrical isomers of trans-form and cis-form in the relation between position 1 and position 2 are present when $Q^3$ is the following group:

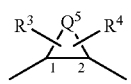

wherein $R^3$, $R^4$ and $Q^5$ have the same meanings as defined above, and numerals 1 and 2 indicate positions.

The preparation processes of such compounds (1) having the trans-form and the cis-form will hereinafter be described.

<Preparation Process of Trans-Form>

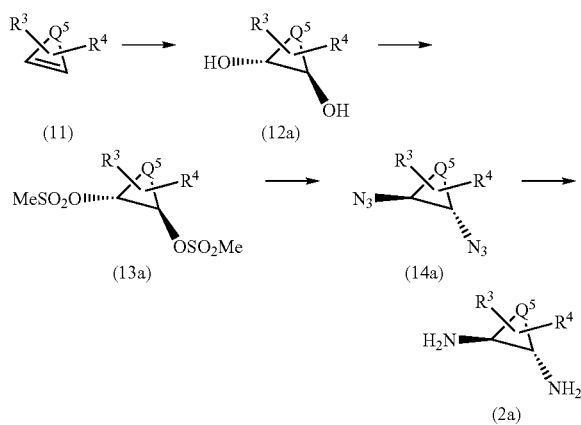

wherein $Q^5$, $R^3$ and $R^4$ have the same meanings as defined above.

As an example of preparation of trans-diol (12a) from cyclic alkene (11), conversion from, for example, cyclohexene to trans-cyclohexanediol (Organic Synthesis, 1995, Vol. III, p. 217) is known. As an example of preparation of trans-diamine (2a) from trans-diol (12a), conversion from trans-cyclopentanediol to trans-cyclopentanediamine (WO98/30574) is reported. Trans-diamine (2a) can be prepared from te cyclic alkene (11) according to these reports.

Trans-diamine (2a) prepared in accordance with the above-described process can be converted into trans-compound (1) by any of the above-described Preparation Processes 1 to 4.

<Preparation Process of Cis-Form>

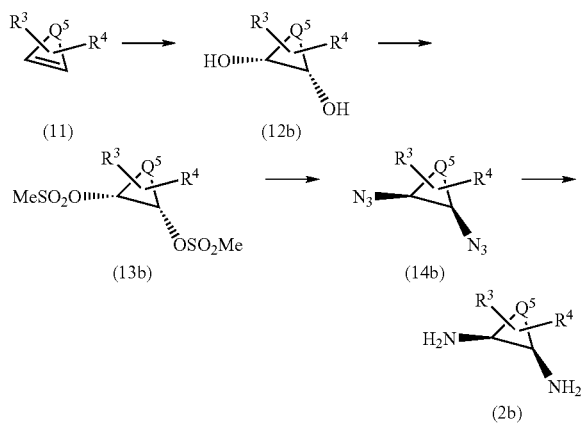

wherein $Q^5$, $R^3$ and $R^4$ have the same meanings as defined above, and numerals.

As an example of preparation of cis-diol (12b) from cyclic alkene (11), conversion from cyclohexene to cis-cyclohexanediol (J. Org. Chem., 1998, Vol. 63, p. 6094) and the like is known. As an example of preparation of cis-diamine (2b) from cis-diol (12a), conversion from cis-cyclopentanediol to cis-cyclopentanediamine (WO98/30574) and the like is reported. Cis-diamine (2b) can be prepared from cyclic alkene (11) according to these reports.

Cis-diamine (2b) prepared in accordance with the above-described process can be converted into the cis-compound (1) by any of the above-described Preparation Processes 1 to 4.

[Preparation Process 6]

As described above, either cis-form or trans-form generated in $Q^3$ may be present in the compounds (1) according to the present invention, and so geometrical isomers are present. Further, optical isomers may be present in the respective geometrical isomers. The preparation process of an optically active substance will hereinafter be described.

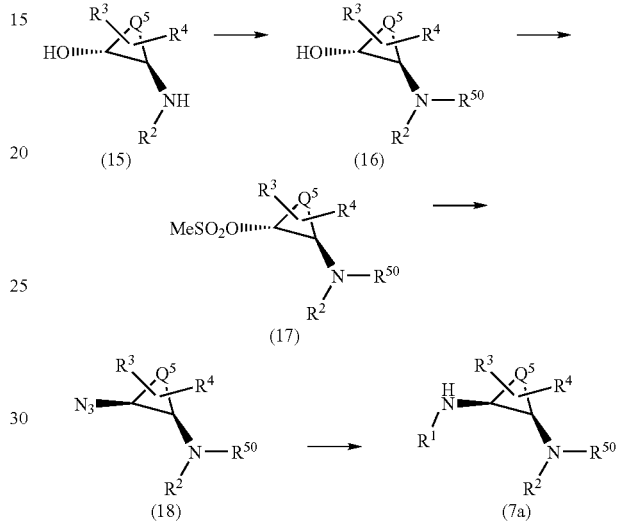

wherein $Q^5$, $R^1$, $R^2$, $R^3$ and $R^4$ have the same meanings as defined above, and $R^{50}$ represents a protecting group for amino group.

With respect to the preparation process of optically active aminoalcohol derivative (15) of 1,2-trans-form, for example, the preparation process of optically active 1,2-trans-2-aminocyclopentanol from cyclopentene oxide or the preparation process of optically active 1,2-trans-2-aminocyclohexanol from cyclohexene oxide is known (Tetrahedron: Asymmetry, 1996, Vol. 7, p. 843; J. Org. Chem., 1985, Vol. 50, p. 4154; J. Med. Chem., 1998, Vol. 41, p. 38). When the amino group of optically active aminoalcohol derivative (15) prepared by such an already known process or by applying such a process reacts with a proper protecting reagent, compound (16) can be produced. As a protecting group corresponding to $R^{50}$ in compound (16), is preferred, among the ordinary acyl type protecting groups, an alkoxycarbonyl group such as methoxycarbonyl, ethoxycarbonyl, tert-butoxycarbonyl group and the like, an arylmethoxycarbonyl group such as benzyloxycarbonyl, p-methoxybenzyloxycarbonyl, p- or o-nitrobenzyloxy-carbonyl group and the like, or an arylsulfonyl group such as 2,4-dinitrobenzenesulfonyl, o-nitrobenzenesulfonyl group and the like. When the amino group is protected with, for example, a tert-butoxycarbonyl group, aminoalcohol derivative (15) may react with di-tert-butyl dicarbonate at −78° C. to 50° C. in an inert solvent, giving compound (16). The inert solvent may be suitably chosen for use from those described in Preparation Process 1.

Compound (16) may react with methanesulfonyl chloride at −78° C. to 50° C. in the presence of a base in an inert solvent, giving compound (17). The inert solvent may be suitably chosen for use from those described in Preparation Process 1. As the base, is preferred an organic base such as pyridine, 2,6-lutidine, collidine, 4-dimethylaminopyridine, triethylamine, N-methylmorpholine, diisopropylethylamine and diazabicyclo[5.4.0]undec-7-ene (DBU) and the like.

Compound (17) may react with sodium azide at −10° C. to 150° C. in a proper solvent, giving compound (18). As the solvent, an amide solvent such as N,N-dimethylformamide, N,N-dimethylacetamide or N-methylpyrrolidin-2-one, an alcoholic solvent such as methanol or ethanol, an etheric solvent such as tetrahydrofuran, 1,2-dimethoxyethane or dioxane, benzenoid solvent such as toluene, a carbon halogenide such as dichloromethane, chloroform or carbon tetrachloride, acetone, dimethyl sulfoxide, or a mixed solvent of such a solvent with water is suitable.

As a process for converting azide derivative (18) into compound (7a), there are many processes such as a process of conducting hydrogenation with a palladium catalyst, Raney nickel catalyst or platinum catalyst, a reaction using a reducing agent such as lithium aluminum hydride, sodium borohydride or zinc borohydride, a reaction using zinc in the presence of nickel chloride or cobalt chloride, a reaction using triphenylphosphine and the like. Suitable reaction conditions may be selected according to the nature of the compound. For example, azide derivative (18) is hydrogenated at a temperature of −10° C. to 70° C. using 1 to 20% palladium carbon as a catalyst in a proper solvent, whereby compound (7a) can be prepared. The hydrogen pressure may be raised higher than atmospheric pressure. As the solvent, an alcoholic solvent such as methanol or ethanol, an etheric solvent such as tetrahydrofuran, 1,2-dimethoxyethane or dioxane, an amide solvent such as N,N-dimethylformamide, N,N-dimethylacetamide or N-methylpyrrolidin-2-one, an ester solvent such as ethyl acetate, acetic acid, hydrochloric acid, water, a mixed solvent thereof and the like is suitable.

Optically active amine (7a) prepared in accordance with the above-described process can be converted to optically active compound (1) in accordance with the above-described Preparation Process 2. Antipode (1) of optically active substance (1) obtained from optically active amine (7a) may also be prepared in accordance with a similar process.

Optically active compound (1) may be prepared by separating racemic compound (1) through a column composed of an optically active carrier. It is also possible to separate intermediate (2), (4), (7), (8) or (9) for preparing racemic compound (1) through a column composed of an optically active carrier to isolate optically active intermediate (2), (4), (7), (8) or (9), and then prepare optically active compound (1) in accordance with any of Preparation Processes 1 to 4. As a process for isolating optically active compound (1), optically active intermediate (2), (4), (7), (8) or (9), a process of fractionally crystallizing a salt with an optically active carboxylic acid, or a process of fractionally crystallizing a salt with an optically active base on the contrary may be used.

[Preparation Process 7]

Among the compounds (1) according to the present invention, a preparation process of compound (1c) containing heteroatom(s) in the group $Q^3$ will hereinafter be described in detail.

A compound represented by the general formula (1c), a salt thereof, a solvate thereof, or an N-oxide thereof can be prepared in accordance with, for example, the following process:

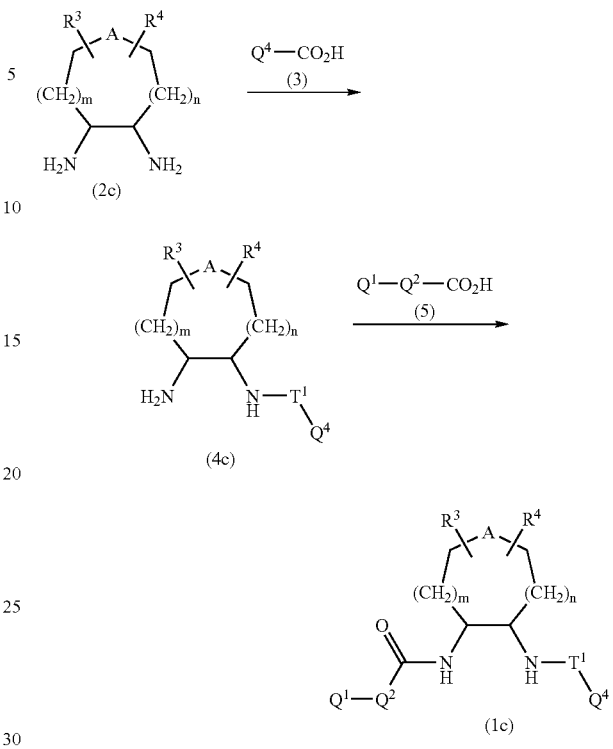

wherein $Q^1$, $Q^2$, $Q^3$, $Q^4$, $R^3$, $R^4$, A, m and n have the same meanings as defined above, and $T^1$ represents a carbonyl group.

A mixed acid anhydride, acid halide, activated ester or the like, which is derived from carboxylic acid (3), may react with compound (2c), giving compound (4c). The resultant compound (4c) may react with carboxylic acid (5) under the same conditions, giving compound (1c) according to the present invention.

In the above reaction steps, reagents and conditions, which are generally used in peptide synthesis, may be applied. The mixed acid anhydride can be prepared by, for example, reaction of a chloroformate such as ethyl chloroformate or isobutyl chloroformate with carboxylic acid (3) in the presence of a base. The acid halide can be prepared by treating carboxylic acid (3) with an acid halide such as thionyl chloride or oxalyl chloride. The activated ester includes various kinds of esters. Such an ester can be prepared by, for example, reaction of a phenol such as p-nitrophenol, N-hydroxybenzotriazol, or N-hydroxysccinimide with carboxylic acid (3) using a condensing agent such as N,N'-dicyclohexylcarbodiimide (DCC) or 1-ethyl-3-(3-dimethylaminopropyl)carbodiimide hydrochloride. The activated ester can also be prepared by reaction of carboxylic acid (3) with pentafluorophenyl trifluoroacetate or the like, reaction of carboxylic acid (3) with 1-benzotriazolyloxytripyrrolidinophosphonium hexafluorophosphite, reaction of carboxylic acid (3) with diethyl cyanophosphonate (Shioiri method), reaction of carboxylic acid (3) with triphenylphosphine and 2,2'-dipyridyl disulfide (Mukaiyama method) or the like. The thus-obtained mixed acid anhydride, acid halide or activated ester of carboxylic acid (3) may react with compound (2c) at a temperature under cooling to a temperature under heating in the presence of a proper base in an inert solvent, giving compound (4c). Thus-obtained compound (4c) may react with a mixed acid anhydride, acid halide or activated ester of carboxylic acid (5) under the same conditions, giving compound (1c) according to the present invention. The reagents and reaction conditions in the reaction of compound (4C) with carboxylic acid (5) are the same as those in the reaction of diamine (2c) with carboxylic acid (3).

As specific examples of the base used in each of the above step, may be mentioned carbonates of alkali metals or alkaline earth metals, such as sodium carbonate and potassium carbonate, alkali metal alkoxides such as sodium ethoxide and potassium butoxide, alkali metal hydroxides such as sodium hydroxide and potassium hydroxide, and hydrides of alkali metals, such as sodium hydride and potassium hydride; organic metal bases exemplified by alkyllithium such as n-butyllithium, and organic metal bases exemplified by dialkylaminolithium such as lithium diisopropylamide; organic metal bases of bis(silyl)amine, such as lithium-bis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU) or the like.

Examples of the inert solvent used in this reaction include alkyl halide type solvents such as methylene chloride and chloroform, etheric solvents such as tetrahydrofuran and 1,4-dioxane, aromatic solvents such as benzene and toluene, and amide solvents such as N,N-dimethylformamide. In addition to these solvent, a sulfoxide solvent such as dimethyl sulfoxide, a ketone solvent such as acetone, or the like may be used in some cases.

In the above-described preparation steps, processes such as attaching and leaving of a protecting group, and conversion of a functional group can be suitably applied, thereby preparing compound (1c).

As the protecting group for amino group, it is only necessary to use a protecting group, which is generally used as a protecting group for amino group in syntheses of organic compounds, particularly, peptide synthesis. As examples thereof, may be mentioned alkoxycarbonyl groups such as tert-butoxycarbonyl, methoxycarbonyl and ethoxycarbonyl groups, arylmethoxycarbonyl groups such as benzyloxycarbonyl, p-methoxybenzyloxycarbonyl and p- or o-nitrobenzyloxycarbonyl group, arylmethyl groups such as benzyl, 4-methoxybenzyl and triphenylmethyl groups, alkanoyl groups such as formyl and acetyl groups, aroyl groups such as a benzoyl group, and arylsulfonyl groups such as 2,4-dinitrobenzenesulfonyl and o-nitrobenzenesulfonyl groups.

As the protecting group for hydroxyl group, it is only necessary to use a protecting group for hydroxyl group, which is generally used in syntheses of organic compounds. As examples thereof, may be mentioned alkoxymethyl groups such as a methoxymethyl group, arylmethyl groups such as benzyl, 4-methoxybenzyl, triphenylmethyl groups, alkanoyl groups such as an acetyl group, aroyl groups such as a benzoyl group, and a tert-butyldiphenylsilyloxy group. A carboxyl group can be protected as an ester with an alkyl group such as a methyl group, ethyl group, tert-butyl group or an arylmethyl group such as a benzyl group. The attaching and leaving of the protecting group may be conducted in accordance with a method known per se in the art.

Compound (1c) according to the present invention can be converted into various derivatives by converting its functional group. For example, a compound in which A is a nitrogen atom having no substituent can be converted into an amide compound by acylation using a mixed acid anhydride, acid halide, activated ester or the like in accordance with ordinary organic chemical methods, a sulfonamide compound by reaction with a sulfonyl halide, an N-alkyl compound by reaction with an alkyl halide, an N-aryl compound by reaction with an aryl halide or a carbamate compound by reaction with an isocyanate. Incidentally, the compound in which A is a nitrogen atom having no substituent can be prepared by, for example, treating compound (1c) prepared from diamine (2c), in which A has been protected with tert-butoxycarbonyl group, in accordance with Preparation Process 7 with an acid.

The compounds according to the present invention thus prepared can be isolated and purified by publicly known methods, for example, extraction, precipitation, fractional chromatography, fractional crystallization, recrystallization, etc. The compounds according to the present invention can be converted into desired salts in accordance with ordinary salt-forming reactions.

Optical isomers derived from an asymmetric carbon atom are present in the compounds of the present invention. Such an optically active isomer can be prepared by the process of preparing from optically active diamine (2c), and besides, a process of forming an optically active amine or acid and a salt from racemic compound (1c) and fractionally crystallizing it, a process of separating it by column chromatography using an optically active carrier.

Compound (1c), in which $T^1$ is a sulfonyl group, can be prepared by changing carboxylic acid (3) to sulfonyl halide (10) in the reaction of compound (2c) with carboxylic acid (3).

[Preparation Process 8]

Compound (1c) according to the present invention can also be prepared in accordance with the following process:

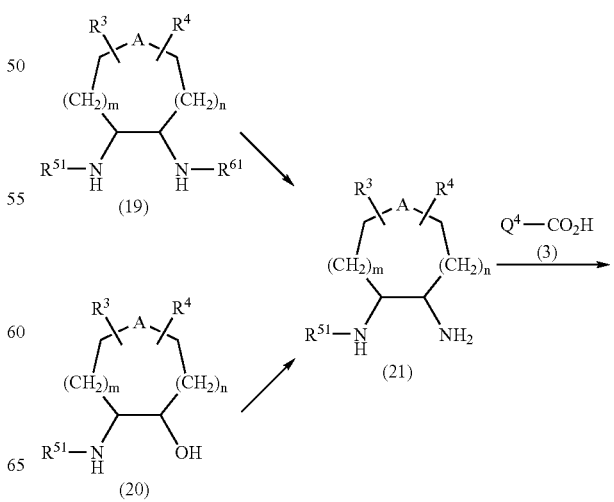

-continued

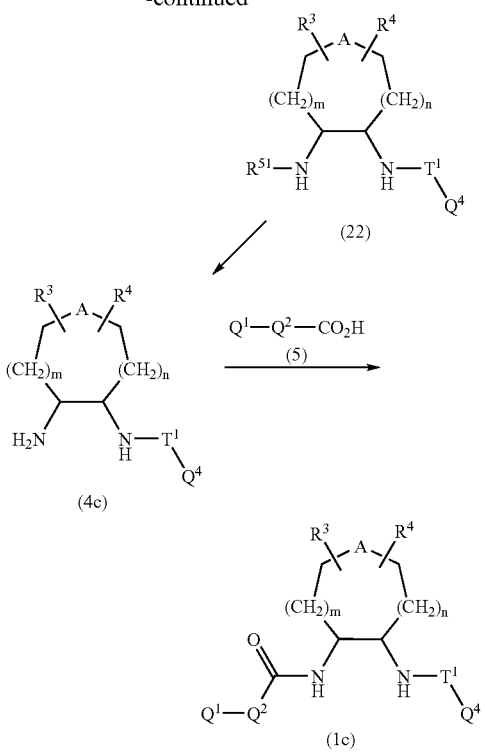

wherein $Q^1$, $Q^2$, $Q^4$, $R^3$, $R^4$, A, m and n have the same meanings as defined above, $T^1$ represents a carbonyl group, and $R^{51}$ and $R^{61}$ represent protecting groups for amino group.

Compound (21) can be prepared by removing the protecting group $R^{61}$ of compound (19) obtained by protecting the amino groups of compound (2c). No particular limitation is imposed on the protecting groups for amino acid illustrated as $R^{51}$ and $R^{61}$ so far as they are groups generally used in protection of the amino group. However, as typical examples thereof, may be mentioned the protecting groups for amino group described in Preparation Process 7. In this case, $R^{51}$ and $R^{61}$ are required to be protecting groups capable of leaving by different methods or conditions from each other. As typical examples thereof, m a y be mentioned a combination that $R^{51}$ is a tert-butoxycarbonyl group, and $R^{61}$ is a benzyloxycarbonyl group. These protecting groups may be chosen for use according to the nature and the like of the compound of which amino groups are to be protected. Upon leaving such a protecting group, reagents and conditions may be employed according to the protecting group.

Compound (21) can also be prepared by converting the hydroxyl group in aminoalcohol derivative (20) into an amino group. As an example of the preparation of aminoalcohol derivative (20), is known conversion of methionine into 3-hydroxy-4-aminothiopyrane-1,1-dioxide (Tetrahedron Lett., Vol. 37, p. 7457, 1996) or the like.

As a process for converting the hydroxyl group in aminoalcohol derivative (20) into an amino group, may be mentioned a process in which aminoalcohol derivative (20) may react with methanesulfonyl chloride, p-toluenesulfonyl chloride, trifluoromethanesulfonic anhydride or the like, the resultant product may then react with ammonia, a primary arylalkylamine such as benzylamine, p-methoxybenzylamine or 2,4-dimethoxybenzylamine, a secondary arylalkylamine such as dibenzylamine, or a hydroxylamine such as N-benzylhydroxylamine or N,O-dibenzylhydroxylamine, and benzyl group or the like is then removed as needed, thereby preparing diamine (21). Aminoalcohol derivative (20) can also be converted into diamine (21) by reacting it with phthalimide or succinimide in accordance with the reaction with triphenylphosphine and ethyl azodicarboxylate (Mukaiyama method) or the like, and then treating the reaction product with hydrazine, N-methylhydrazine or the like. When A in the formula is $SO_2$, and n is 0, diamine (21) can be prepared by adding ammonia, a primary arylalkylamine such as ammonia, benzylamine, p-methoxybenzylamine or 2,4-dimethoxybenzylamine, a secondary arylalkylamine such as dibenzylamine, or a hydroxylamine such as N-benzylhydroxylamine or N,O-dibenzylhydroxylamine to an α,β-unsaturated cyclic sulfone formed by reacting aminoalcohol derivative (20) with methanesulfonyl chloride, p-toluenesulfonyl chloride, trifluoromethanesulfonic anhydride or the like and then treating the reaction product with a proper base or directly reacting aminoalcohol derivative (20) with triphenylphosphine and ethyl azodicarboxylate, and removing the benzyl group or the like as needed.

The resultant diamine (21) may react with carboxylic acid (3), giving compound (22). The protecting group $R^{51}$ is successively removed, giving compound (4c). Compound (4c) may react with carboxylic acid (5), giving compound (1c) according to the present invention. The reagents and reaction conditions in the reaction of compound (21) with carboxylic acid (3) and the reaction of compound (4C) with carboxylic acid (5) may be the same as those described in Preparation Process 7.

Similarly, compound (1c) in which $T^1$ is a sulfonyl group can be prepared by changing carboxylic acid (3) to sulfonyl halide (10) in the reaction of compound (21) with carboxylic acid (3).

[Preparation Process 9]

A typical preparation process of intermediate (2c) for preparation described in Preparation Process 7 will be described.

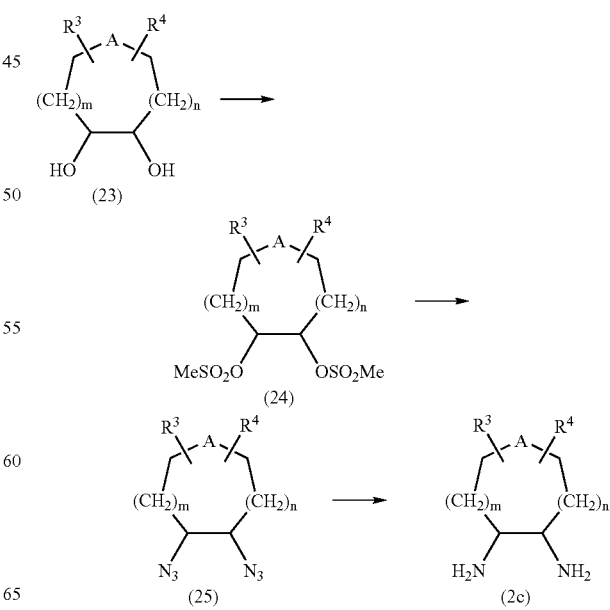

wherein $R^3$, $R^4$, A, m and n have the same meanings as defined above.

As preparation processes of diol derivative (23), are known, for example, conversion of 1,2,3,6-tetrahydropyridine into 1-benzyloxycarbonyl-3,4-cis-dihydroxypyrrolidine (Japanese Patent Application Laid-Open No. 138264/1995), conversion of L-tartaric acid into (R,R)-tetrahydrofurandiol or (R,R)-N-benzylpyrrolidinediol (Tetrahedron: Asymmetry, Vol. 8, p. 1861, 1997) and the like. Diol derivative (23) can be prepared by using such an already known process or applying such a process and removing a protecting group or converting a functional group as needed.

Diol derivative (23) may react with methanesulfonyl chloride at a temperature under cooling to room temperature in the presence of a base in an inert solvent, giving compound (24). The inert solvent may be suitably chosen for use from those described in Preparation Process 7. However, particularly preferred are alkyl halide type solvents such as methylene chloride and chloroform, and etheric solvents such as tetrahydrofuran and 1,4-dioxane. As the base, is preferred an organic base such as pyridine, 2,6-lutidine, 4-dimethylaminopyridine, triethylamine, N-methylmorpholine, diisopropylethylamine or diazabicyclo-[5.4.0]undec-7-ene (DBU).

Compound (24) may react with sodium azide at a temperature under cooling to a temperature under heating in a proper solvent, giving azide derivative (25). As the solvent, an amide solvent such as N,N-dimethylformamide, N-methylpyrrolidin-2-one, an alcoholic solvent such as methanol or ethanol, an etheric solvent such as tetrahydrofuran or 1,4-dioxane, aromatic solvent such as benzene or toluene, a carbon halogenide such as methylene chloride or chloroform, dimethyl sulfoxide, acetone, or the like is suitable. Such a solvent may be a mixed solvent with water.

As a process for converting azide derivative (25) into compound (2c), there are many processes such as a process of conducting hydrogenation with a palladium catalyst, Raney nickel catalyst or platinum catalyst, a reaction using a reducing agent such as lithium aluminum hydride or sodium borohydride, a reaction using zinc in the presence of nickel chloride or cobalt chloride, and a reaction using triphenylphosphine ot the like. Suitable reagents and reaction conditions may be selected according to the nature of the compound. The hydrogen pressure may be raised higher than atmospheric pressure. As the solvent, an alcoholic solvent such as methanol or ethanol, an etheric solvent such as tetrahydrofuran or 1,4-dioxane, an amide solvent such as N,N-dimethylformamide or N-methylpyrrolidin-2-one, an ester solvent such as ethyl acetate, acetic acid, hydrochloric acid, water, a mixed solvent thereof or the like is suitable. Compound (1c) according to the present invention can be derived from diamine derivative (2c) prepared in accordance with the above-described process in accordance with Preparation Process 7.

When diol derivative (23) is trans-3,4-dihydroxytetrahydrofuran or trans-1-substituted 3,4-dihydroxypyrrolidine and the like, optically active substances are present. These optically active diol derivatives (23) can be converted into optically active diamine derivatives (2c), and further into optically active compounds (1c) according to the present invention in accordance with Preparation Process 7.

[Preparation Process 10]

A typical preparation process of optically active compounds (30), (31) and (32) included in compound (19) described in Preparation Process 8 will be described. Incidentally, the position of an asymmetric carbon atom shown in the following preparation scheme is indicated by way of example.

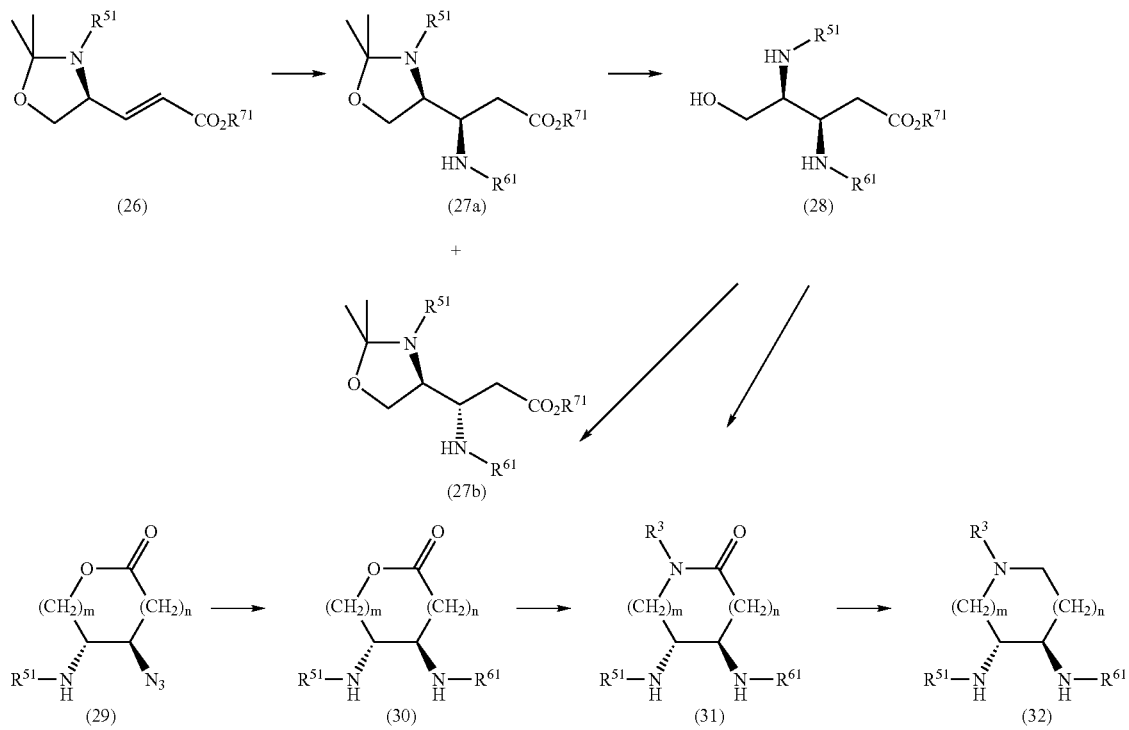

wherein m, n, $R^3$, $R^{51}$ and $R^{61}$ have the same meanings as defined above, and $R^{71}$ represents a protecting group for carboxyl group.

Optically active α,β-unsaturated ester derivative (26) can be prepared in accordance with the process described in literature (J. Org. Chem., Vol. 61, p. 581, 1996; J. Org. Chem., Vol. 57, p. 6279, 1992, etc.) or by applying such a process. Optically active α,β-unsaturated ester derivative (26) may react with an amine at a temperature under cooling, or under heating in a proper solvent, giving diastereomers (27a) and (27b). The amine may be suitably chosen for use from those described in Preparation Process 8. The solvent is desirably an organic solvent unreactive to a substrate, product or reagent, particularly, an alcoholic solvent such as methanol or ethanol, or an etheric solvent such as tetrahydrofuran, 1,2-dimethoxyethane, 1,4-dioxane and the like. Diastereomers (27a) and (27b) can also be prepared by reaction of α,β-unsaturated ester derivative (26) with an organometallic base such as lithium N-benzyl(trimethylsilyl)amide and the like by applying the process described in literature (J. Org. Chem., Vol. 63, p. 7263, 1998). The diastereomers may be separated to use, for example, diastereomer (27a) in the next reaction.

Compound (27a) is treated with an acid at a temperature under cooling, or under heating in a proper solvent, giving compound (28). Examples of the acid used include hydrochloric acid, sulfuric acid, Lewis acids such as boron trifluoride, trifluoroacetic acid, p-toluenesulfonic acid or the like. As the solvent, is used water or an alcoholic solvent such as methanol or ethanol. Such a solvent may be a mixed solvent with water. In this reaction, the protecting group $R^{61}$ may be left in some cases. In such a case, such a compound is required to react with a proper protecting reagent for amino group as needed.

Compound (28) may be treated with an acid at a temperature under cooling, or under heating in a proper solvent, giving optically active compound (30). The acid used may be suitably chosen for use from the acids mentioned above, with a Lewis acid such as boron trifluoride, or p-toluenesulfonic acid or the like being particularly preferred. As the solvent used in the reaction, is used an etheric solvent such as 1,4-dioxane or tetrahydrofuran, or an aromatic solvents such as benzene or toluene. Compound (30) can also be prepared from azide derivative (29). As examples of the preparation of optically active azide derivative (29), are known conversion of L-asparagic acid into (R,R)-(3S,4S)-3-amino-4-azide-5-oxotetrahydrofuran (Can. J. Chem., Vol. 71, p. 1047, 1993) and the like. Optically active azide derivative (29) can be prepared by using such an already known process or applying such a process and removing a protecting group or converting a functional group as needed. The azide in azide derivative (29) may be reduced into an amino group, and the resultant product may react with a proper protecting reagent for amino group, giving compound (30). The reagents and reaction conditions used in the reduction of azide (29) may be the same as those described in the process of converting azide derivative (25) into compound (2c).

The hydroxyl group portion of compound (28) may be converted into an amino group and then treated with a base, giving compound (31). The conversion of the hydroxyl group in compound (28) into the amino group can be performed in accordance with, for example, Preparation Process 8. Compound (31) can also be prepared by treating alcohol derivative (28) with an oxidizing agent and then reductively aminating the resultant aldehyde derivative. Specific preferable examples of the oxidizing agent used in the above reaction include pyridinium chlorochromate (PCC), pyridinium dichromate (PDC), sulfur trioxide pyridine complexes or the like. Example of the amine include primary alkylamines such as ammonia, methylamine and ethylamine, and primary arylalkylamine such as benzylamine, p-methoxybenzylamine and 2,4-dimethoxybenzylamine. As the reducing process, there are a process of conducting hydrogenation with a palladium catalyst, Raney nickel catalyst or platinum catalyst, a reaction using a reducing agent such as sodium borohydride, sodium triacetoxyborohydride or sodium cyanoborohydride, and suitable reagents and reaction conditions may be selected according to the nature of the compound or the like. The base used in the above process may be suitably chosen for use from those described in Preparation Process 7. Compound (31) can also be prepared by using compound (30) and an amine in accordance with the process described in literature (Tetrahedron Lett., Vol. 41, p. 1141, 2000; Heterocycles, Vol. 53, p. 173, 2000) or by applying such a process. Examples of the amine used include primary alkylamines such as ammonia, methylamine and ethylamine, and primary arylalkylamine such as benzylamine and p-methoxybenzyl-amine.

Compound (31) may be treated with a reducing agent at a temperature under cooling to a temperature under heating in a solvent, giving compound (32). Examples of the reducing agent include borane-tetrahydrofuran complexes, borane-methyl sulfide complexes, lithium aluminum hydride. However, suitable reagents and reaction conditions may be selected according to the nature of the compound or the like. The solvent is desirably an organic solvent unreactive to a substrate, product, reagent or the like, particularly, an etheric solvent such as tetrahydrofuran or 1,4-dioxane.

Optically active substances (1c) of the compounds according to the present invention can be derived from the compounds (30), (31) and (32) prepared by the processes described above.

In the above-described preparation scheme, one of optically active substances has been described by way of example. However, other optically active substances different in conformation from each other may also be prepared in accordance with similar preparation schemes by respectively using starting materials different in conformation from each other.

[Preparation Process 11]

Compound (1) in which $T^1$ is a group —CO—CO—N(R')—, in which R' has the same meaning as defined above, can be prepared in accordance with the following scheme:

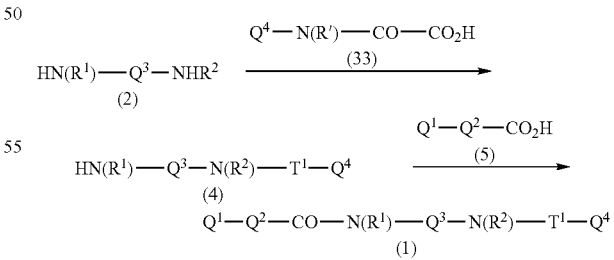

wherein $Q^1$, $Q^2$, $Q^3$, $Q^4$, $R^1$, $R^2$ and R' have the same meanings as defined above, and $T^1$ represents a group —CO—CO—N(R')—, in which R' has the same meaning as defined above.

An acid halide, activated ester or the like, which is derived from carboxylic acid (33), may react with diamine (2), giving compound (4). The resultant compound (4) may react with carboxylic acid (5) under the same conditions, giving compound (1) according to the present invention. In the above reaction steps, reagents and conditions, which are generally used in peptide synthesis, may be applied. The acid halide can be prepared by treating carboxylic acid (33) with an acid halide such as thionyl chloride or oxalyl chloride. The activated ester includes various kinds of esters. Such an ester can be prepared by, for example, reaction of a phenol such as p-nitrophenol, N-hydroxybenzotriazol, or N-hydroxysccinimide with carboxylic acid (33) using a condensing agent such as N,N'-dicyclohexylcarbodiimide or 1-ethyl-3-(3-dimethylaminopropyl)carbodiimide hydrochloride. The activated ester can also be prepared by reaction of carboxylic acid (33) with pentafluorophenyl trifluoroacetate or the like, reaction of carboxylic acid (33) with 1-benzotriazolyloxytripyrrolidinophosphonium hexafluorophosphite, reaction of carboxylic acid (33) with diethyl cyanophosphonate (Shioiri method), reaction of carboxylic acid (33) with triphenylphosphine and 2,2'-dipyridyl disulfide (Mukaiyama method) or the like. The thus-obtained mixed acid anhydride, acid halide or activated ester of carboxylic acid (33) may react with diamine (2) at −78° C. to 150° C. in the presence of a proper base in an inert solvent, giving compound (4). Thus-obtained compound (4) may react with a mixed acid anhydride, acid halide or activated ester of carboxylic acid (5) under the same conditions, giving compound (1) according to the present invention. The reagents and reaction conditions in the reaction of compound (4) with carboxylic acid (5) are the same as those in the reaction of diamine (2) with carboxylic acid (33). The bases and solvents used in the above respective steps may be suitably chosen from those described in Preparation Process 1.

When compound (1) in which $Q^3$ is the following group:

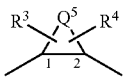

wherein $R^3$, $R^4$ and $Q^5$ have the same meanings as defined above, and numerals 1 and 2 indicate positions, and the relation between position 1 and position 2 is a trans-form or cis-form, is prepared, it is only necessary to use diamine (2a) or (2b) described in Preparation Process 5.

When compound (1) in which a heteroatom such as a nitrogen atom, oxygen atom or sulfured atom is contained in $Q^5$ is prepared, it is only necessary to change carboxylic acid (3) to carboxylic acid (33) in the reaction of compound (2c) with carboxylic acid (3) as described in Preparation Process 7. Namely, compound (1) in which a heteroatom is contained in $Q^5$ in the following reaction scheme, i.e., compound (1c) can be prepared.

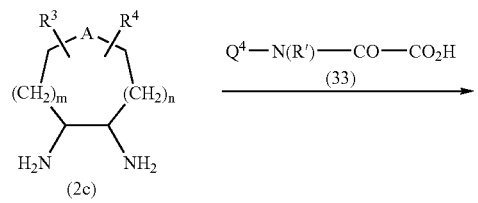

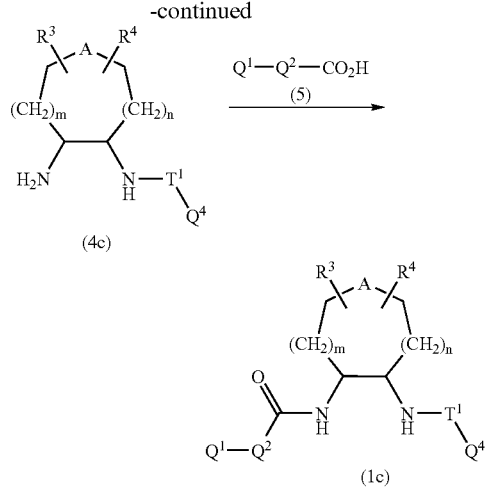

wherein $Q^1$, $Q^2$, $Q^4$, $R^3$, $R^4$, R', A, m and n have the same meanings as defined above, and $T^1$ represents a group —CO—CO—N(R')—, in which R' has the same meaning as defined above.

[Preparation Process 12]

Compound (1) in which $T^1$ is a group —CO—CO—N (R')—, in which R' has the same meaning as defined above, can also be prepared in accordance with the following scheme:

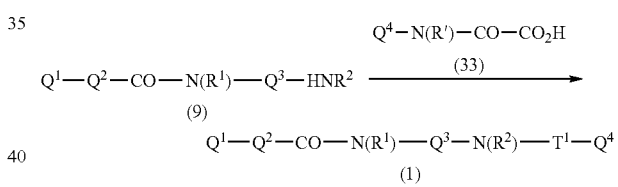

wherein $Q^1$, $Q^2$, $Q^3$, $Q^4$, $R^1$, $R^2$ and R' have the same meanings as defined above, and $T^1$ represents a group —CO—CO—N(R')—, in which R' has the same meaning as defined above.

In the reaction of amine (9) with carboxylic acid (33), the same reagents and conditions as those described in Preparation Process 1 may be used.

Amine (9) used herein can also be prepared in accordance with the following scheme shown as a preparation scheme of amine (41) in addition of the scheme described in Preparation Process 2.

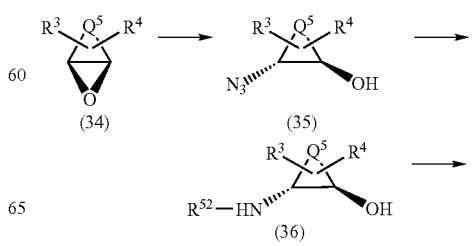

-continued

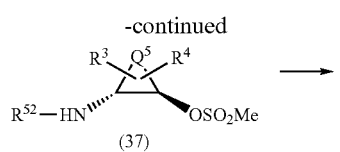
(37)

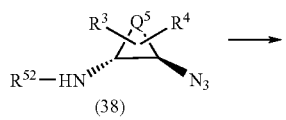
(38)

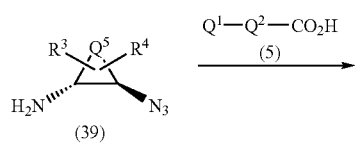
(39)

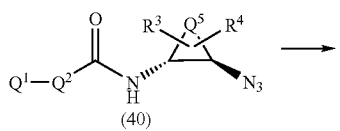
(40)

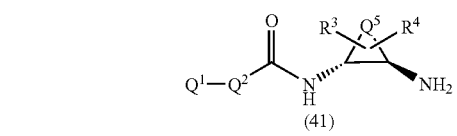
(41)

wherein $R^3$, $R^4$, $Q^1$, $Q^2$ and $Q^5$ have the same meanings as defined above, and $R^{52}$ represents a protecting group for amino group.

Compound (34) in the above preparation scheme can be prepared by treating a cycloalkene with perbenzoic acid or a derivative thereof and the like in a solvent such as methylene chloride to epoxidate it. Ordinary conditions for epoxidation of an alkene may be applied to the conditions of this reaction. Compound (34) can also be prepared in accordance with the process described in J. Org. Chem., Vol. 61, pp. 8687-8691 (1996) or a process corresponding thereto.

Compound (34) may react with sodium azide or the like in accordance with a method known per se in the art, giving azide (35). Azide (35) may be catalytically reduced, and the amino group of the resultant compound may be protected, giving compound (36). As examples of the protecting group for amino group in this reaction, may be mentioned those described in Preparation Process 2. Compound (36) may be converted into azide (38) in a similar manner to the process described Preparation Process 5, and the protecting group for the amino group thereof may be left, giving compound (39). Compound (39) may react with carboxylic acid (5), giving compound (40).

The compound (40) may then be catalytically reduced, giving compound (41).

[Preparation Process 13]

Compound (1) in which $T^1$ is a group —CO—CO—N(R')—, in which R' has the same meaning as defined above, can also be prepared by changing the reaction of compound (9) with carboxylic acid (3) in the scheme described in Preparation Process 2 to a reaction of compound (9) with compound (33).

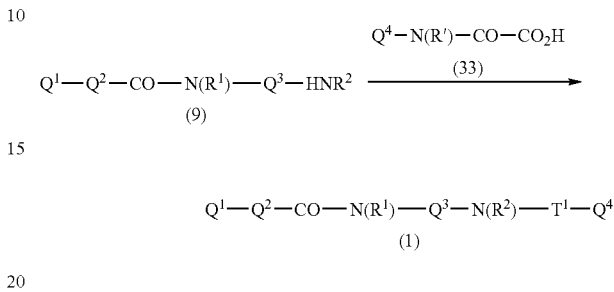

wherein $Q^1$, $Q^2$, $Q^3$, $Q^4$, $R^1$, $R^2$ and R' have the same meanings as defined above, and $T^1$ represents a group —CO—CO—N(R'), in which R' has the same meaning as defined above.

As the reaction conditions, may be applied those described in Preparation Process 2.

When compound (1) in which $Q^3$ is the following group:

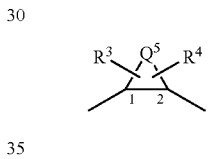

wherein $R^3$, $R^4$ and $Q^5$ have the same meanings as defined above, and numerals 1 and 2 indicate positions, and a heteroatom such as a nitrogen atom, oxygen atom or sulfured atom is contained in $Q^5$ is prepared, it is only necessary to change carboxylic acid (3) to carboxylic acid (33) in the reaction of compound (21) with carboxylic acid (3) as described in Preparation Process 8. Namely, compound (1) in which a heteroatom is contained in $Q^5$ in the following reaction scheme, i.e., compound (1c) can be prepared.

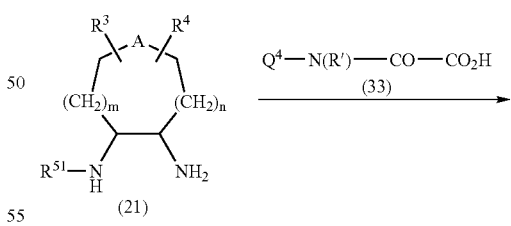
(21)

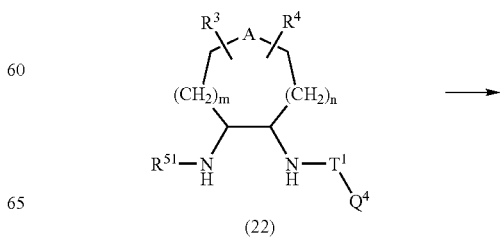
(22)

-continued

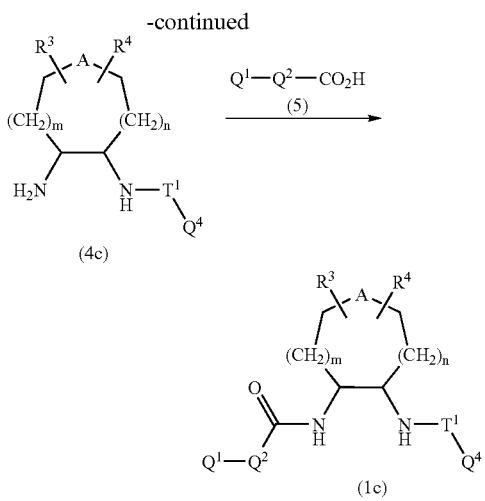

(4c)

(1c)

wherein $Q^1$, $Q^2$, $Q^4$, $R^3$, $R^4$, $R'$, A, m and n have the same meanings as defined above, and $T^1$ represents a group —CO—CO—N(R')—, in which R' has the same meaning as defined above, and $R^{51}$ represents a protecting group for amino group.

[Preparation Process 14]

Compound (1) in which $T^1$ is a group —CO-$A^1$-N(R")—, in which R" represents a hydrogen atom, hydroxyl group, alkyl group or alkoxy group, and $A^1$ represents an alkylene group having 1 to 5 carbon atoms, which may be substituted, can be prepared by reaction of compound (9) described in Preparation Process 2 with $Q^4$-N(R")-$A^1$-$CO_2H$ (42) at –55° C. to 50° C. using a condensing agent in an inert solvent. As examples of the condensing agent, may be mentioned N,N'-dicyclohexylcarbodiimide, 1-ethyl-3-(3-dimethylaminopropyl)carbodiimide hydrochloride or the like. As examples of the inert solvent, may be mentioned alkyl halide type solvents such as methylene chloride, chloroform and carbon tetrachloride, etheric solvents such as tetrahydrofuran, 1,2-dimethoxyethane and dioxane, aromatic solvents such as benzene and toluene, and amide solvents such as N,N-dimethylformamide.

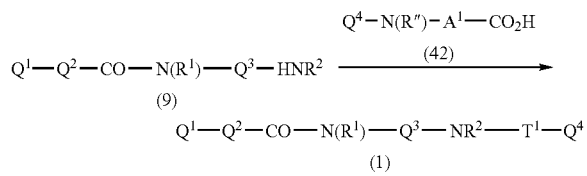

wherein $Q^1$, $Q^2$, $Q^3$, $Q^4$, $R^1$, $R^2$ and R" have the same meanings as defined above, and $T^1$ represents a group —CO-$A^1$-N(R")—, in which R" represents a hydrogen atom, hydroxyl group, alkyl group or alkoxy group, and $A^1$ represents an alkylene group having 1 to 5 carbon atoms, which may be substituted.

Compound (42) described in the preparation process described above can be prepared by, for example, reacting an arylamine such as 4-chloroaniline with an ester of a bromoalkanoic acid at 40 to 120° C. in the presence of a base such as potassium carbonate in a solvent such as acetonitrile or N,N-dimethylformamide and then hydrolyzing the ester with an alkali such as lithium hydroxide, potassium hydroxide or sodium hydroxide. Compound (42) may be used in reaction in the form of a salt such as a potassium salt as it is.

[Preparation Process 15]

Compound (1) in which $T^1$ is a group —C(=O)—NH— or a group —C(=S)—NH—, can be prepared by reaction of compound (9) described in Preparation Process 2 with isocyanate ($Q^4$-N=C=O) or isothiocyanate ($Q^4$-N=C=S) at –20° C. to 50° C. in an inert solvent. A typical examples of the iner solvent is described in Preparation Process 14. When isocyanate or isothiocyanate is not commercialized, isocyanate or isothiocyanate can be synthesized using ordinary methods.

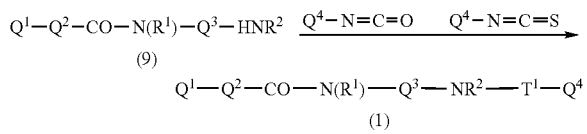

wherein $Q^1$, $Q^2$, $Q^3$, $Q^4$, $R^1$ and $R^2$ have the same meanings as defined above, and $T^1$ represents a group —C(=O)—NH— or group —C(=S)—NH—.

[Preparation Process 16]

Compound (1) in which $T^1$ is a group —CO—NH—NH— can be prepared by reaction of compound (9) described in Preparation Process 2 with $Q^4$-NH—NH—$CO_2$Ph (43) at room temperature to 150° C. in an inert solvent in the presence of a base if necessary. As typical examples of the inert solvent, may be mentioned acetonitrile and N,N-dimethylformamide, and besides those described in Preparation Process 14. As examples of the base, may be mentioned pyridine, 2,6-lutidine, collidine, 4-dimethylaminopyridine, triethylamine, N-methylmorpholine, diisopropylethylamine and diazabicyclo[5.4.0]undec-7-ene (DBU).

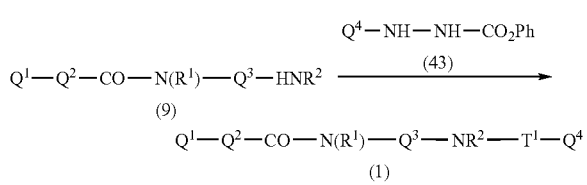

wherein $Q^1$, $Q^2$, $Q^3$, $Q^4$, $R^1$ and $R^2$ have the same meanings as defined above, $T^1$ represents a group —CO—NH—NH— and ph represents phenyl group.

Compound (43) described in the preparation process described above can be prepared by, for example, reacting an arylhydrazine such as 4-chlorophenylhydrazine with diphenyl carbonate at room temperature to 120° C. in a solvent such as acetonitrile, N,N-dimethylformamide, methylene chloride, chloroform, tetrahydrofuran, 1,2-dimethoxyethane, dioxane, benzene or toluene.

[Preparation Process 17]

Compound (1) in which $T^1$ is a group —CO-$A^2$-CO—, in which $A^2$ represents a single bond or alkylene group having 1 to 5 carbon atoms can be prepared by reaction of compound (9) described in Preparation Process 2 with $Q^4$-CO-$A^2$-$CO_2H$ (44) at –50° C. to 50° C. using a condensing agent in an inert solvent. As examples of the condensing agent, may be mentioned N,N'-dicyclohexylcarbodiimide, 1-ethyl-3-(3-dimethylaminopropyl)carbodiimide hydrochloride or the like. As examples of the solvent, may be mentioned those described in Preparation Process 16 or the like.

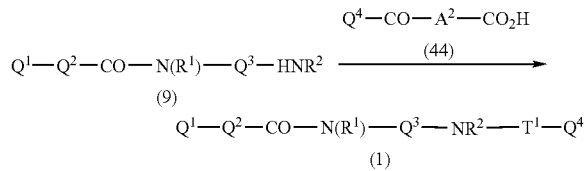

wherein $Q^1$, $Q^2$, $Q^3$, $Q^4$, $R^1$ and $R^2$ have the same meanings as defined above, and $T^1$ represents a group —CO-$A^2$-CO—, in which $A^2$ represents a single bond or alkylene group having 1 to 5 carbon atoms.

When $A^2$ is a single bond, compound (44) described in the preparation process described above can be prepared by, for example, hydrolyzing a compound (for example, $Q^4$-CO—$CO_2Et$) prepared by the Friedel-Crafts reaction of an aromatic hydrocarbon such as chlorobenzene or an aromatic heterocyclic compound such as thiophene with a chloroxoacetate (for example, ClCO—$CO_2Et$) using an alkali such as lithium hydroxide, potassium hydroxide or sodium hydroxide.

When $A^2$ is a methylene group, compound (44) can be prepared by, for example, hydrolyzing a ketoester derivative (for example, $Q^4$-CO—$CH_2$—$CO_2Et$) obtained by reaction of an arylcarbonyl chloride such as 4-chlorobenzoyl chloride or a heteroarylcarbonyl chloride such as thiophenecarbonyl chloride with potassium malonic monoester monocarboxylate in the presence of magnesium chloride and triethylamine with an alkali such as lithium hydroxide, potassium hydroxide or sodium hydroxide. The ketoester derivative may be used in the above reaction with compound (9) in the form of a carboxylic acid obtained by hydrolysis after conversion of its carbonyl group into ethyleneketal. When $A^2$ is an alkylene group having at least 2 carbon atoms, compound (44) can be prepared by, for example, hydrolyzing a ketoester derivative (for example, $Q^4$-CO-$A^2$-$CO_2Et$) obtained by the Friedel-Crafts reaction of an aromatic hydrocarbon such as benzene or an aromatic heterocyclic compound such as thiophene with an alkylenedicarboxylic monoester monochloride using an alkali such as lithium hydroxide, potassium hydroxide or sodium hydroxide.

[Preparation Process 18]

Compound (1) in which $T^1$ is a group —CO-$A^3$-CO—NH—, in which $A^3$ represents an alkylene group having 1 to 5 carbon atoms can be prepared by reaction of compound (9) described in Preparation Process 2 with $Q^4$-NH—CO-$A^3$-$CO_2H$ (45) at −50 to 50° C. using a condensing agent in an inert solvent. As examples of the condensing agent, may be mentioned N,N'-dicyclohexylcarbodiimide, 1-ethyl-3-(3-dimethylaminopropyl)carbodiimide hydrochloride and the like. Examples of the inert solvent include alkyl halide type solvents such as methylene chloride, chloroform, carbon tetrachloride, etheric solvents such as tetrahydrofuran, 1,2-dimethoxyethane and dioxane, aromatic solvents such as benzene and toluene, and amide solvents such as N,N-dimethylformamide.

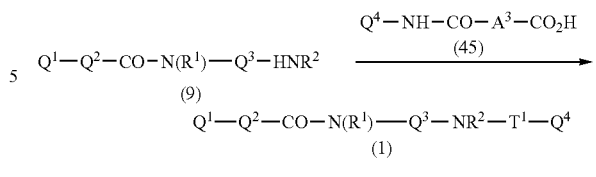

wherein $Q^1$, $Q^2$, $Q^3$, $Q^4$, $R^1$ and $R^2$ have the same meanings as defined above, and $T^1$ represents a group —CO-$A^3$-CO—, in which $A^3$ represents an alkylene group having 1 to 5 carbon atoms.

Compound (45) can be prepared by hydrolyzing a compound (for example, $Q^4$-NH—CO-$A^3$-$CO_2Et$) obtained by reaction of an arylamine such as 4-chloroaniline or a heteroarylamine such as aminopyridine corresponding to $Q^4$-$NH_2$ with potassium alkylenedicarboxylic monoester monocarboxylate at −50 to 50° C. using a condensing agent in an inert solvent with an alkali such as lithium hydroxide, potassium hydroxide or sodium hydroxide.

[Preparation Process 19]

Compound (1) in which $T^1$ is a group —CS—CO—N(R')—, in which R' has the same meaning as defined above can be prepared in accordance with the following scheme:

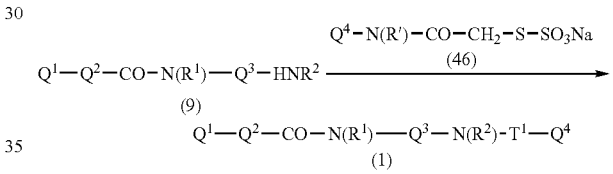

wherein $Q^1$, $Q^2$, $Q^3$, $Q^4$, $R^1$, $R^2$ and R' have the same meanings as defined above, and $T^1$ represents a group —CS—CO—N(R')—, in which R' has the same meaning as defined above.

More specifically, sodium thiosulfate (46) and compound (9) may be dissolved or dispersed in a solvent and heated, giving compound (1) according to the present invention. The reaction temperature is preferably 80 to 200° C., particularly preferably about 150° C. As the solvent used in this reaction, may be mentioned water, alcohols such as methanol and ethanol, basic solvents such as pyridine and N-methylmorpholine, alkyl halide type solvents such as methylene chloride, chloroform, etheric solvents such as tetrahydrofuran, 1,2-dimethoxyethane and dioxane, and amide solvents such as N,N-dimethylformamide. These solvents may be suitably mixed for use. As examples of mixed solvents, may be mentioned a mixed solvent of methanol and methylene chloride or the like. In this reaction, the solvent is not necessarily refluxed. For example, when the mixed solvent of methanol and methylene chloride is used, a reaction solution (or a reaction mixture) is heated at an external temperature of 150° C. to distill off the solvent, and the residue is then heated at the same temperature.

[Preparation Process 20]

Compound (1) in which $T^1$ is a group —CO—CS—N(R')—, in which R' has the same meaning as defined above can be prepared in accordance with the following scheme:

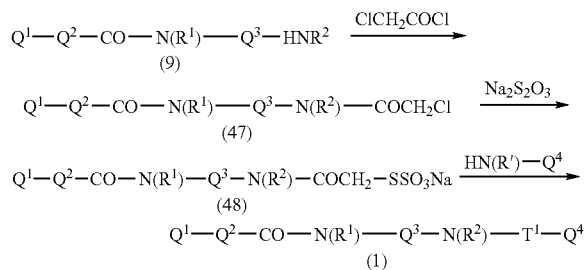

wherein $Q^1$, $Q^2$, $Q^3$, $Q^4$, $R^1$, $R^2$ and R' have the same meanings as defined above, and $T^1$ represents a group —CO—CS—N(R')—, in which R' has the same meaning as defined above.

More specifically, compound (9) may react with chloroacetyl chloride in the presence of a base, giving compound (47). Compound (47) may be heated together with sodium thiosulfate in a solvent, giving sodium thiosulfate derivative (48). The thus-obtained sodium thiosulfate derivative (48) may be heated with an amine, i.e., HN(R')-$Q^4$, giving compound (1) according to the present invention.

As conditions, solvent and the like for preparing compound (47) from compound (9), may be applied those commonly used in reaction of an amine with acid chloride. In order to prepare compound (48) from compound (47), it is only necessary to heat compound (47) together with sodium thiosulfate under reflux for about 1 hour in a solvent such as ethanol. When compound (47) is a salt with hydrochloric acid or the like, the reaction may be performed in the presence of a base such as sodium hydrogencarbonate. The preparation conditions of compound (48) are not limited to those described herein, and the temperature and the kinds of the solvent and base may be suitably changed. The conditions for the reaction of compound (48) with HN(R')-$Q^4$ are the same as those described in Preparation Process 19.

[Preparation Process 21]

Compound (1) in which $T^0$ is a thiocarbonyl group (—CS—) can be prepared in accordance with the following scheme:

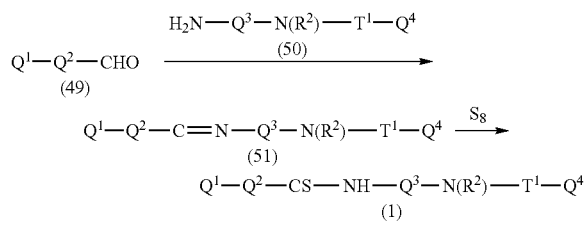

wherein $Q^1$, $Q^2$, $Q^3$, $Q^4$ and $R^2$ have the same meanings as defined above, and $T^1$ represents a group —SO$_2$—, —CO—, —CO—NH—, —CS—NH—, —CO—NH—NH—, —CO—CO—N(R'), in which R' has the same meaning as defined above, —CO—CS—N(R'), in which R' has the same meaning as defined above, —CS—CO—N(R')—, in which R' has the same meaning as defined above, —CS—CS—N(R')—, in which R' has the same meaning as defined above, —CO-$A^1$-N(R")—, in which $A^1$ and R" have the same meanings as defined above, —CO-$A^2$-CO—, in which $A^2$ has the same meaning as defined above, —CO-$A^3$-CO—NH—, in which $A^3$ has the same meanings as defined above, or —CO-$A^3$-CO—, in which $A^3$ has the same meaning as defined above.

More specifically, compound (49) may be subjected to dehydration reaction with amine (50) in the presence of an acid catalyst such as p-toluenesulfonic acid, giving compound (51). Compound (51) may be heated together with sulfur powder in a solvent such as a mixed solvent of methanol/methylene chloride, giving compound (1) according to the present invention. As conditions for preparing compound (51) from compound (49) and amine (50), may be applied those commonly used in preparation of a Schiff base. Specifically, heating under reflux may be conducted in the presence of an acid catalyst in benzene or toluene under conditions that water is removed from the reaction system by, for example, using a Dean-Stark trap. Molecular sieve may also be used in removing water from the reaction system.

The important intermediates described in Preparation Process 1 to 21 of the compounds (1) according to the present invention will hereinafter be described.

1) The compounds described in Preparation Process 1, 3 and 11 and represented by the following general formula (4):

$$HN(R^1)\text{-}Q^3\text{-}N(R^2)\text{-}T^1\text{-}Q^4 \qquad (4)$$

wherein $R^1$, $R^2$, $Q^3$ and $Q^4$ have the same meanings as defined above, and $T^1$ represents a carbonyl group, sulfonyl group or group —CO—CO—N(R'), in which R' has the same meaning as defined above, are important as intermediates for preparing compounds (1) according to the present invention.

Among the above-described intermediates, are preferred compounds in which $T^1$ is a group —C(=O)—C(=O)—N(R'), in which R' means a hydrogen atom, hydroxyl group, alkyl group or alkoxy group, and compounds in which $T^1$ in the above formula is a carbonyl group, and $Q^3$ is the following group:

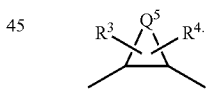

in which $R^3$ and $R^4$ have the same meanings as defined above, and $Q^5$ means a group —(CH$_2$)$_m$—CH$_2$-A-CH$_2$—(CH$_2$)$_n$—, in which m and n are independently of each other 0 or an integer of 1-3, and A means an oxygen atom, nitrogen atom, sulfur atom, —SO—, —SO$_2$—, —NH—, —O—NH—, —NH—NH—, —S—NH—, —SO—NH— or —SO$_2$—NH—.

2) The compounds described in Preparation Process 2, 4 and 12 and represented by the following general formula (9):

$$Q^1\text{-}Q^2\text{-}C(=O)\text{-}N(R^1)\text{-}Q^3\text{-}NHR^2 \qquad (9)$$

wherein $R^1$, $R^2$, $Q^1$, $Q^2$ and $Q^3$ have the same meanings as defined above, are important as intermediates for preparing compounds (1) according to the present invention.

Among the above-described intermediates, are preferred compounds in which $Q^3$ is the following group:

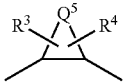

in which $R^3$ and $R^4$ have the same meanings as defined above, and $Q^5$ means a group —$(CH_2)_m$—$CH_2$-A-$CH_2$—$(CH_2)_n$—, in which m and n are independently of each other 0 or an integer of 1-3, and A means an oxygen atom, nitrogen atom, sulfur atom, —SO—, —$SO_2$—, —NH—, —O—NH—, —NH—NH—, —S—NH—, —SO—NH— or —$SO_2$—NH—.

3) The following compounds (4C) described in Preparation Process 7, 11 and 13 are important as intermediates for preparing compounds (1) according to the present invention.

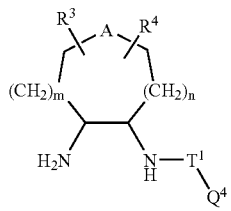

(4c)

wherein $Q^4$, $R^3$, $R^4$, A, m and n have the same meanings as defined above, and $T^1$ represents a carbonyl group, sulfonyl group or group —CO—CO—N(R'), in which R' has the same meaning as defined above.

Among the above-described intermediates, are preferred compounds in which $T^1$ in the above formula is a group —CO—CO—N(R'), in which R' has the same meaning as defined above, and compounds in which $T^1$ is a carbonyl group, and A is an oxygen atom, nitrogen atom, sulfur atom, —SO—, —$SO_2$—, —NH—, —O—NH—, —NH—NH—, —S—NH—, —SO—NH— or —$SO_2$—NH—.

4) The following compounds (22) described in Preparation Process 8 and 13 are important as intermediates for preparing compounds (1) according to the present invention.

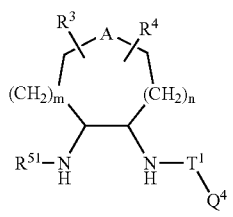

(22)

wherein $Q^4$, $R^3$, $R^4$, A, m and n have the same meanings as defined above, $T^1$ represents a carbonyl group, sulfonyl group or group —CO—CO—N(R'), in which R' has the same meaning as defined above, and $R^{51}$ represents a protecting group for amino group.

Among the above-described intermediates, are preferred compounds in which $T^1$ in the above formula is a group —CO—CO—N(R'), in which R' has the same meaning as defined above, and compounds in which $T^1$ is a carbonyl group, and A is an oxygen atom, nitrogen atom, sulfur atom, —SO—, —$SO_2$—, —NH—, —O—NH—, —NH—NH—, —S—NH—, —SO—NH— or —$SO_2$—NH—.

5) The following optically active compounds (7a) described in Preparation Process 6 are important as intermediates for preparing compounds (1) according to the present invention.

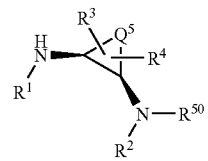

(7a)

wherein $Q^5$, $R^1$, $R^2$, $R^3$ and $R^4$ have the same meanings as defined above, and $R^{50}$ represents a protecting group for amino group.

Among the above-described intermediates, are preferred compounds in which $Q^5$ in the above formula is a group —$(CH_2)_m$—$CH_2$-A-$CH_2$—$(CH_2)_n$—, in which m and n are independently of each other 0 or an integer of 1-3, and A means an oxygen atom, nitrogen atom, sulfur atom, —SO—, —$SO_2$—, —NH—, —O—NH—, —NH—NH—, —S—NH—, —SO—NH— or —$SO_2$—NH—.

6) The following compounds (21) described in Preparation Process 8 are important as intermediates for preparing compounds (1) according to the present invention.

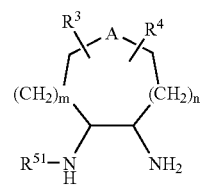

(21)

wherein $R^3$, $R^4$, A, m and n have the same meanings as defined above, and $R^{51}$ represents a protecting group for amino group.

Among the above-described intermediates, are preferred compounds in which A in the above formula is an oxygen atom, nitrogen atom, sulfur atom, —SO—, —$SO_2$—, —NH—, —O—NH—, —NH—NH—, —S—NH—, —SO—NH— or —$SO_2$—NH—.

7) The following compounds described in Preparation Process 10 are important as intermediates for preparing compounds (1) according to the present invention. More specifically, the following optically active trans-form compounds (30), (31) and (32):

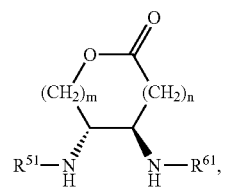

(30)

(31)
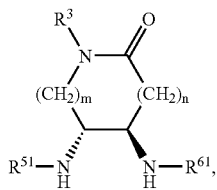

(32)
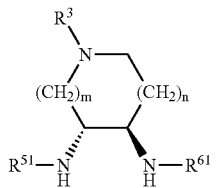

wherein $R^3$, m and n have the same meanings as defined above, and $R^{51}$ and $R^{61}$ represent protecting groups for amino group, enantiomers (30a), (31a) and (32a) of the above compounds prepared in a similar manner:

(30a)
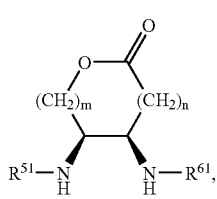

(31a)

(32a)

wherein $R^3$, m and n have the same meanings as defined above, and $R^{51}$ and $R^{61}$ represent protecting groups for amino group, cis-form compounds (30b), (31b) and (32b):

(30b)

(31b)
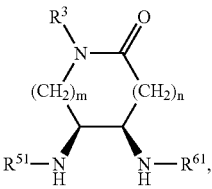

(32b)
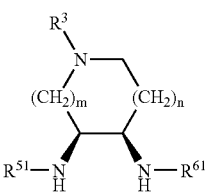

wherein $R^3$, m and n have the same meanings as defined above, and $R^{51}$ and $R^{61}$ represent protecting groups for amino group, and enantiomers (30c), (31c) and (32c) thereof:

(30c)
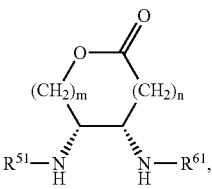

(31c)
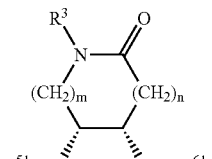

(32c)
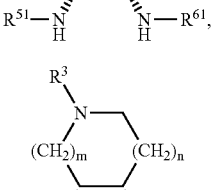

wherein $R^3$, m and n have the same meanings as defined above, and $R^{51}$ and $R^{61}$ represent protecting groups for amino group, are important as intermediates for preparing compounds (1) according to the present invention.

The cyclic diamine derivatives according to the present invention exhibit strong inhibitory effects on activated blood coagulation factor X and are thus useful for medicines for mammal including human, anticoagulants factor X, agents for preventing and/or treating thrombosis or embolism, agents for preventing and/or treating thrombtic diseases, and agents for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after valve or joint replacement, thrombus formation and reocclusion after angioplasty, systemic inflammatory reaction syndrome (SIRS), multiple organ disease syndrome (MODS), thrombus formation during extracorporeal circulation, or blood clotting upon blood gathering.

When a compound according to the present invention is used as a medicine for human body, the dose is within a range of 1 mg to 1 g, preferably 10 to 300 mg, per day for an adult. The dose for animal varies according to the object (treatment or prevention) of the administration, the kind and size of an animal to be treated, the kind of a contagium, and the condition of a disease attacked. However, it is generally within a range of 0.1 to 200 mg, preferably 0.5 to 100 mg, per kg of weight a day. Meanwhile, the administration may be once per day, or may be divided into 2 to 4 times per day. The dose per day may exceed the above range if necessary.

Medicinal compositions comprising the compound according to the present invention can be prepared by selecting a suitable preparation form according to an administration method in accordance with a preparation method for the preparation form used. As examples of the preparation forms of the medicinal compositions comprising the compound according to the present invention as a main component, may be mentioned tablets, tablets, powder, granules, capsules, solutions, syrups, elixirs, oil or aqueous suspensions or the like for oral preparations.

In the case of an injection, a stabilizer, a preservative and a dissolution aid may be used in a preparation. A solution which may contain these auxiliaries in some cases may also be provided as a solid form for preparing upon use by containing the solution into a container and then drying the solution by lyophilization or the like. A dose or doses of the injection may also be contained into a container.

As example of preparation forms for external application, may be mentions solutions, suspensions, emulsions, ointments, gel, creams, lotions, sprays, plasters or the like.

A solid preparation may contain pharmaceutically acceptable additives in addition to the compound according to the present invention. For example, fillers, extenders, binders, disintegrators, dissolution accelerators, wetting agents, etc. may be suitably selected and mixed, giving a preparation.

As example of preparation forms of a liquid preparation, may be mentioned solutions, suspensions, emulsions and the like. They may contain a suspending agent, emulsifier and/or the like in some cases.

EXAMPLES

However, the present invention is not limited to these examples.

Referential Example 1 tert-Butyl pyridin-4-ylcarbamate

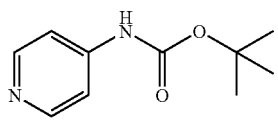

4-Aminopyridine (10 g) was dissolved in tetrahydrofuran (500 ml), di-tert-butyl dicarbonate (25.5 g) was added to the solution, and the mixture was stirred at room temperature for 10 minutes. The resultant reaction mixture was concentrated under reduced pressure, and deposited solids were washed with hexane to obtain the title compound (16.9 g).

$^1$H-NMR (CDCl$_3$) δ: 1.53 (9H, s), 6.86 (1H, br.s), 7.30 (2H, dd, J=1.5, 4.9 Hz), 8.44 (2H, dd, J=1.5, 4.9 Hz). MS (FAB) m/z: 195 (M+H)$^+$.

Referential Example 2 tert-Butyl 3-sulfanylpyridin-4-ylcarbamate

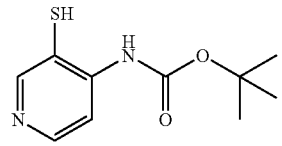

The compound (61.6 g) obtained in Referential Example 1 was dissolved in tetrahydrofuran (2,000 ml), and the solution was stirred at −78° C. for 10 minutes. A hexane solution (1.59 mol/l, 500 ml) of n-butyllithium was added dropwise to the solution, and the mixture was stirred for 10 minutes and then for 2 hours with ice cooling. After the reaction mixture was cooled to −78° C., sulfur powder (12.2 g) was added, and the resultant mixture was warmed to room temperature and stirred for 1 hour. Water (1,000 ml) was added to the reaction mixture to separate a water layer. After 3N hydrochloric acid was added to the water layer to adjust the pH of the water layer to 3 to 4, methylene chloride was added to separate an organic layer. The organic layer was dried over anhydrous sodium sulfate, and the solvent was distilled off under reduced pressure. The residue was purified by column chromatography on silica gel (methylene chloride:methanol=50:1) to obtain the title compound (33.2 g).

$^1$H-NMR (DMSO-d$_6$) δ: 1.52 (9H, s), 7.89 (1H, d, J=6.4 Hz), 7.99 (1H, d, J=6.4 Hz), 8.20 (1H, s), 9.91 (1H, br.s). MS (FAB) m/z: 227 (M+H)$^+$.

Referential Example 3

Thiazolo[5,4-c]pyridine

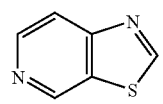

The compound (33.2 g) obtained in Referential Example 2 was dissolved in formic acid (250 ml), and the solution was heated under reflux for 3 days. The reaction mixture was concentrated under reduced pressure, and a 5N aqueous solution (100 ml) of potassium hydroxide and diethyl ether were added to the residue to separate an organic layer. The organic layer was dried over anhydrous sodium sulfate, and the solvent was then distilled off under reduced pressure. The residue was purified by column chromatography on silica gel (methylene chloride:methanol=25:1) to obtain the title compound (9.03 g).

$^1$H-NMR (CDCl$_3$) δ: 8.05 (1H, d, J=5.4 Hz), 8.70 (1H, d, J=5.4 Hz), 9.23 (1H, s), 9.34 (1H, s). MS (FAB) m/z: 137 (M+H)$^+$.

Referential Example 4

5-Methyl-4,5,6,7-tetrahydrothiazolo[5,4-c]pyridine

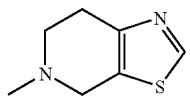

The compound (1.61 g) obtained in Referential Example 3 was dissolved in N,N-dimethylformamide (50 ml), and to the solution methyl iodide (1.50 ml) was added, the resultant mixture was stirred at 80° C. for 4 hours. The reaction mixture was concentrated under reduced pressure, and the residue was dissolved in methanol (100 ml), sodium borohydride (1.53 g) was added, and the resultant mixture was stirred at room temperature for 1 hour. The reaction mixture was concentrated under reduced pressure, and a saturated aqueous solution of potassium carbonate and diethyl ether were added to the residue to separate an organic layer. The organic layer was dried over anhydrous sodium sulfate, and the solvent was distilled off under reduced pressure. The residue was purified by column chromatography on silica gel (methylene chloride:methanol=25:1) to obtain the title compound (1.28 g).

$^1$H-NMR (CDCl$_3$) δ: 2.52 (3H, s), 2.83 (2H, t, J=5.9 Hz), 2.98 (2H, t, J=5.9 Hz), 3.70 (2H, s), 8.63 (1H, s). MS (FAB) m/z: 155 (M+H)$^+$.

Referential Example 5

Lithium 5-methyl-4,5,6,7-tetrahydrothiazolo[5,4-c]-pyridine-2-carboxylate

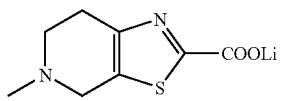

The compound (6.43 g) obtained in Referential Example 4 was dissolved in absolute tetrahydrofuran (200 ml), to the soltion n-butyllithium (1.47N hexane solution, 34.0 ml) was added dropwise at −78° C., and the resultant mixture was stirred for 40 minutes. After carbon dioxide gas was blown into the reaction mixture at −78° C. for 1 hour, the reaction mixture was warmed to room temperature and then concentrated under reduced pressure to obtain the title compound (9.42 g).

$^1$H-NMR (DMSO-d$_6$) δ: 2.37 (3H, s), 2.64-2.77 (4H, m), 3.54 (2H, s). MS (FAB) m/z: 199 (M+H)$^+$.

Referential Example 6 tert-Butyl 2-amino-6,7-dihydrothiazolo[5,4-c]pyridine-5[4H]-carboxylate

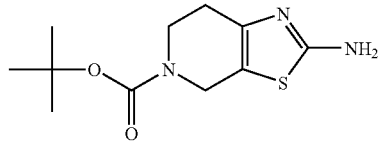

1-tert-Butoxycarbonyl-4-piperidone (40.0 g) was dissolved in cyclohexane (80 ml), and to the solution p-toluenesulfonic acid monohydrate (191 mg) and pyrrolidine (17.6 ml) were added. The mixture was heated under reflux for 2 hours while removing water using a Dean-Stark trap. After the reaction mixture was concentrated under reduced pressure, the residue was dissolved in methanol (60 ml), and sulfur powder (6.42 g) was added. A methanol solution (10 ml) of cyanamide (8.44 g) was slowly added dropwise to the solution with ice cooling, and the mixture was stirred at room temperature for 5 hours. Precipitated solid materials were collected by filtration to obtain the title compound (31.0 g).

$^1$H-NMR (DMSO-d$_6$) δ: 1.41 (9H, s), 2.44 (2H, t, J=5.6 Hz), 3.57 (2H, t, J=5.6 Hz), 4.29 (2H, s), 6.79 (2H, s). MS (EI) m/z: 255 (M$^+$).

Referential Example 7 tert-Butyl 2-bromo-6,7-dihydrothiazolo[5,4-c]pyridine-5[4H]-carboxylate

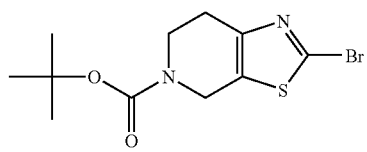

Copper(II) bromide (1.05 g) was suspended in N,N-dimethylformamide (20 ml), and tert-butyl nitrite (0.696 ml) and the compound (1.00 g) obtained in Referential Example 6 were added with ice cooling, the reaction mixture was heated and stirred at 40° C. for 30 minutes. The reaction mixture was concentrated under reduced pressure, and the residue was purified by column chromatography on silica gel (ethyl acetate:hexane=1:5) to obtain the title compound (568 mg).

$^1$H-NMR (CDCl$_3$) δ: 1.48 (9H, s), 2.85 (2H, br.s), 3.72 (2H, br.s), 4.56 (2H, br.s). MS (FAB) m/z: 319 (M+H)$^+$.

Referential Example 8

2-Bromo-4,5,6,7-tetrahydrothiazolo[5,4-c]pyridine Trifluoroacetate

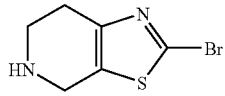

The compound (890 mg) obtained in Referential Example 7 was dissolved in methylene chloride (2 ml), and to the solution trifluoroacetic acid (15 ml) was added, and the mixture was stirred at room temperature for 30 seconds. The reaction mixture was concentrated under reduced pressure, and diethyl ether was added to the residue. Precipitated solid materials were collected by filtration to obtain the title compound (867 mg).

$^1$H-NMR (DMSO-$d_6$) δ: 2.98 (2H, t, J=6.1 Hz), 3.45 (2H, t, J=6.1 Hz), 4.35 (2H, s), 9.53 (2H, br.s). MS (FAB) m/z: 219 (M+H)$^+$.

Referential Example 9

2-Bromo-5-methyl-4,5,6,7-tetrahydrothiazolo[5,4-c]-pyridine

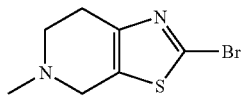

The compound (422 mg) obtained in Referential Example 8 was suspended in methylene chloride (10 ml), and triethylamine (0.356 ml) was added to make a solution. Acetic acid (0.216 ml), an aqueous solution (35% solution, 0.202 ml) of formaldehyde and sodium triacetoxyborohydride (428 mg) were successively added to the solution, and the resultant mixture was stirred at room temperature for 1 hour. A saturated aqueous solution (100 ml) of sodium hydrogencarbonate, methylene chloride (100 ml) and a 3N aqueous solution (3 ml) of sodium hydroxide were added to the reaction mixture to conduct liquid separation. After an organic layer was dried over anhydrous sodium sulfate, the solvent was distilled off under reduced pressure. The residue was purified by column chromatography on silica gel (methylene chloride:methanol=100:3) to obtain the title compound (286 mg).

$^1$H-NMR (CDCl$_3$) δ: 2.49 (3H, s), 2.79 (2H, t, J=5.7 Hz), 2.85-2.93 (2H, m), 3.58 (2H, t, J=1.8 Hz). MS (FAB) m/z: 233 (M+H)$^+$.

Referential Example 10

Lithium 5-methyl-4,5,6,7-tetrahydrothiazolo[5,4-c]-pyridine-2-carboxylate

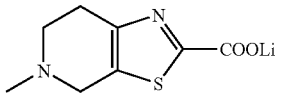

The compound (531 mg) obtained in Referential Example 9 was dissolved in absolute diethyl ether (20 ml), n-butyl-lithium (1.54N hexane solution, 1.63 ml) was added dropwise at −78° C., and the mixture was stirred for 30 minutes with ice cooling. After passing carbon dioxide into the reaction mixture at −78° C. for 10 minutes, the mixture was warmed to room temperature. The reaction mixture was concentrated under reduced pressure to obtain the title compound (523 mg).

$^1$H-NMR (DMSO-$d_6$) δ: 2.37 (3H, s), 2.64-2.85 (4H, m), 3.54 (2H, s).

Referential Example 11

Ethyl 2-[(E)-2-phenylethenyl]oxazole-4-carboxylate

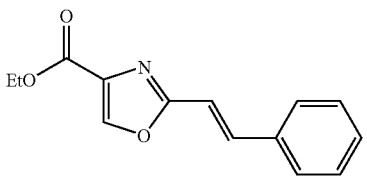

Synthesis was conducted in accordance with the report (J. Org. Chem., 1996, Vol. 61, p. 6496) by Panek et al. Sodium hydrogencarbonate (22.8 g) and ethyl bromopyruvate (10.5 ml) were added to a solution of cinnamamide (10.0 g) in tetrahydrofuran (250 ml) at room temperature, and the mixture was heated under reflux for 48 hours. The reaction mixture was allowed to cool to room temperature, filtered through Celite and then concentrated under reduced pressure to obtain residue. Trifluoroacetic anhydride (30 ml) was added to a solution of this residue in tetrahydrofuran (30 ml) at 0° C., and the mixture was gradually warmed to room temperature. After the mixture was stirred for 63 hours, a saturated aqueous solution (500 ml) of sodium hydrogencarbonate and ethyl acetate (150 ml) were added to the reaction mixture, and a water layer was separated. The water layer was extracted with ethyl acetate (150 ml). The organic layers were combined, washed with saturated aqueous solution of sodium chloride (150 ml), dried over anhydrous sodium sulfate and then concentrated under reduced pressure. The residue was purified by column chromatography on silica gel (hexane:ethyl acetate=5:1→3:1) to obtain the title compound (10.9 g).

$^1$H-NMR (CDCl$_3$) δ: 1.41 (3H, t, J=7.0 Hz), 4.42 (2H, q, J=7.0 Hz), 6.96 (1H, d, J=16.6 Hz), 7.30-7.40 (3H, m), 7.53 (2H, d, J=6.8 Hz), 7.63 (1H, d, J=16.6 Hz), 8.20 (1H, s).

Referential Example 12

2-[(E)-2-phenylethenyl]oxazole-4-carbaldehyde

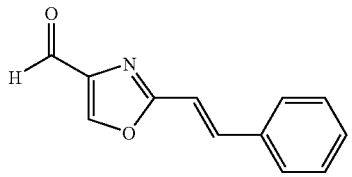

Diisobutylaluminum hydride (1.0N hexane solution, 66 ml) was added dropwise to a solution of the compound (8.57 g) obtained in Referential Example 11 in methylene chloride (80 ml) at −78° C. After 15 minutes, methanol (11 ml) was added dropwise, and the mixture was warmed to room temperature over 1 hour. The reaction mixture was filtered through Celite, and the resultant pasty substance was dissolved in ethyl acetate (200 ml) and a saturated aqueous solution (200 ml) of ammonium chloride was added, and a water layer was separated. The water layer was then extracted with methylene chloride (2×100 ml). The resultant organic layers were collected and washed with a saturated aqueous solution (100 ml) of sodium hydrogencarbonate and saturated aqueous solution of sodium chloride (100 ml), combined with the filtrate obtained by the filtration through Celite and then dried over anhydrous sodium sulfate, and the solvent was distilled off under reduced pressure. The residue was purified by column chromatography on silica gel (methylene chloride:ethyl acetate=5:1→methylene chloride:methanol=10:1) to obtain the title compound (5.86 g).

$^1$H-NMR (CDCl$_3$) δ: 6.96 (1H, d, J=16.6 Hz), 7.35-7.45 (3H, m), 7.56 (2H, d, J=6.4 Hz), 7.67 (1H, d, J=16.6 Hz), 8.26 (1H, s), 9.98 (1H, s). MS (FAB) m/z: 200 (M+H)$^+$.

Referential Example 13

2-[(E)-2-Phenylethenyl]-4-vinyloxazole

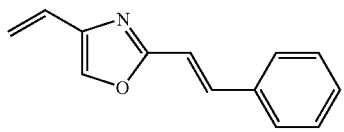

n-Butyllithium (1.54N hexane solution, 14.2 ml) was added dropwise to a solution of methyltriphenylphosphonium bromide (8.16 g) in tetrahydrofuran (80 ml) at 0° C., and the mixture was stirred at room temperature for 30 minutes. The reaction mixture was cooled again to 0° C., a solution of the compound (3.64 g) obtained in Referential Example 12 in tetrahydrofuran (20 ml) was added, and the mixture was warmed to room temperature. After stirring for 2 hours, water (200 ml) and ethyl acetate (100 ml) were added and a water layer was separated. The water layer was extracted with ethyl acetate (50 ml). After the organic layers were combined, washed with saturated aqueous solution of sodium chloride (100 ml) and dried over anhydrous sodium sulfate, the solvent was distilled off under reduced pressure. The residue was purified by column chromatography on silica gel (hexane:ethyl acetate=4:1→3:1) to obtain the title compound (2.84 g).

$^1$H-NMR (CDCl$_3$) δ: 5.33 (1H, dd, J=1.5, 10.7 Hz), 5.98 (1H, dd, J=1.5, 17.6 Hz), 6.56 (1H, dd, J=10.7, 17.6 Hz), 6.95 (1H, d, J=16.6 Hz), 7.31-7.42 (3H, m), 7.49-7.56 (4H, m). MS (FAB) m/z: 198 (M+H)$^+$.

Referential Example 14

2-{2-[(E)-2-Phenylethenyl]oxazol-4-yl}-1-ethanol

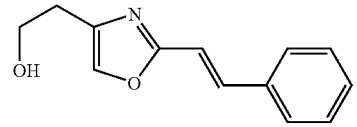

9-Borabicyclo[3.3.1]nonane (0.5N tetrahydrofuran solution, 158 ml) was added to a solution of the compound (13.0 g) obtained in Referential Example 13 in tetrahydrofuran (500 ml), and the mixture was stirred at room temperature for 15 hours. Water (10 ml), a 3N aqueous solution (80 ml) of sodium hydroxide and aqueous hydrogen peroxide (80 ml) were successively added dropwise to the reaction mixture at 0° C., and the mixture was stirred at room temperature for 6 hours. After water (600 ml) and ethyl acetate (200 ml) were added to the resultant reaction mixture to separate a water layer, the water layer was extracted with ethyl acetate (200 ml). After the organic layers were collected, washed with saturated aqueous solution of sodium chloride (200 ml) and dried over anhydrous sodium sulfate, the solvent was distilled off under reduced pressure. The residue was purified by column chromatography on silica gel (hexane:ethyl acetate=2:1→ethyl acetate alone) to obtain the title compound (14.1 g).

$^1$H-NMR (CDCl$_3$) δ: 2.69 (1H, br.s), 2.80 (2H, t, J=5.6 Hz), 3.90-3.97 (2H, m), 6.91 (1H, d, J=16.6 Hz), 7.30-7.42 (4H, m), 7.43-7.56 (3H, m). MS (FAB) m/z: 216 (M+H)$^+$.

Referential Example 15

2-(2-{2-[(E)-2-Phenylethenyl]oxazol-4-yl}ethyl)-1H-isoindol-1,3(2H)-dione

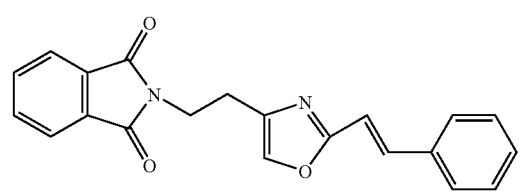

Phthalimide (200 mg), triphenylphosphine (357 mg) and diethyl azodicarboxylate (0.214 ml) were added to a solution of the compound (292 mg) obtained in Referential Example 14 in tetrahydrofuran (15 ml) at room temperature, and the mixture was stirred for 4 hours. The solvent of the reaction mixture was distilled off under reduced pressure. The residue was purified by column chromatography on silica gel (hexane:ethyl acetate=3:1) to obtain the title compound (447 mg).

$^1$H-NMR (CDCl$_3$) δ: 2.98 (2H, t, J=7.2 Hz), 4.03 (2H, t, J=7.2 Hz), 6.88 (1H, d, J=16.6 Hz), 7.28-7.45 (5H, m), 7.48 (2H, d, J=7.3 Hz), 7.71 (2H, dd, J=2.9, 5.4 Hz), 7.84 (2H, dd, J=2.9, 5.4 Hz). MS (FAB) m/z: 345 (M+H)$^+$.

Referential Example 16 tert-Buthyl 2-{2-[(E)-2-phenylethenyl]oxazol-4-yl}ethylcarbamate

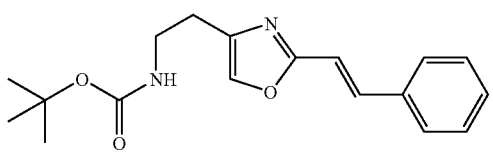

After hydrazine monohydrate (1.50 ml) was added to a solution of the compound (6.40 g) obtained in Referential Example 15 in ethanol (150 ml) at room temperature, and the mixture was stirred for 1 hour, hydrazine monohydrate (0.500 ml) was added again at room temperature, and the mixture was stirred for 2 hours. Methylene chloride (150 ml), a saturated aqueous solution (150 ml) of sodium hydrogencarbonate and di-tert-butyl dicarbonate (13.4 g) were added to the reaction mixture at room temperature. After stirring for 30 minutes, a water layer was separated and extracted with methylene chloride (50 ml). The resultant organic layers were combined and dried over anhydrous sodium sulfate, and the solvent was then distilled off under reduced pressure. The residue was purified by column chromatography on silica gel (hexane:ethyl acetate=2:1→1:1) to obtain the title compound (5.06 g).

$^1$H-NMR (CDCl$_3$) δ: 1.45 (9H, s), 2.75 (2H, t, J=6.6 Hz), 3.46 (2H, dt, J=5.9, 6.6 Hz), 4.92 (1H, br.s), 6.91 (1H, d, J=16.6 Hz), 7.29-7.45 (4H, m), 7.48 (1H, d, J=16.6 Hz), 7.52 (2H, d, J=7.3 Hz). MS (FAB) m/z: 315 (M+H)$^+$, 259 (M-isobutene+H)$^+$, 315 (M-Boc+H)$^+$.

Referential Example 17 tert-Buthyl 2-[(E)-2-phenylethenyl]-6,7-dihydrooxazolo-[5,4-c]pyridine-5(4H)-carboxylate

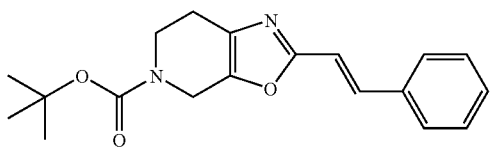

Paraformaldehyde (54.5 mg) and p-toluenesulfonic acid (7.2 mg) were added to a solution of the compound (190 mg) obtained in Referential Example 16 in toluene (15 ml) at room temperature. After heating under reflux for 1 hour, the reaction mixture was allowed to cool, and ethyl acetate (15 ml) and a saturated aqueous solution (15 ml) of sodium hydrogencarbonate were added to the reaction mixture to separate a water layer. After the water layer was extracted with ethyl acetate (10 ml), the resultant organic layers were combined and dried over anhydrous sodium sulfate, and the solvent was distilled off under reduced pressure. The residue was purified by column chromatography on silica gel (hexane:ethyl acetate=3:1→2:1) to obtain the title compound (153 mg).

$^1$H-NMR (CDCl$_3$) δ: 1.50 (9H, s), 2.67 (2H, br.s), 3.73 (2H, br.s), 4.55 (2H, s), 6.90 (1H, d, J=16.1 Hz), 7.29-7.42 (3H, m), 7.46 (1H, d, J=16.1 Hz), 7.52 (2H, d, J=7.3 Hz). MS (FAB) m/z: 327 (M+H)$^+$, 271 (M-isobutene+H)$^+$, 227 (M-Boc+H)$^+$.

Referential Example 18 tert-Butyl 2-formyl-6,7-dihydrooxazolo[5,4-c]pyridine-5(4H)-carboxylate

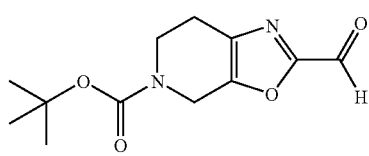

Acetone (8.0 ml), water (4.0 ml), N-methylmorpholine N-oxide (577 mg) and a 0.039 M aqueous solution (3.20 ml) of osmium tetroxide were added to a solution of the compound (803 mg) obtained in Referential Example 17 in tetrahydrofuran (16 ml) at room temperature, and the mixture was stirred overnight. Ethyl acetate (50 ml) and a 10% aqueous solution (50 ml) of sodium thiosulfate were added to the reaction mixture to separate a water layer. The water layer was then extracted with ethyl acetate (30 ml). After the resultant organic layers were combined and dried over anhydrous sodium sulfate, the solvent was distilled off under reduced pressure. Methanol (8.0 ml), water (8.0 ml) and sodium metaperiodate (790 mg) were added to a solution of the residue in tetrahydrofuran (16 ml). After stirring for 3 hours, ethyl acetate (30 ml) and water (50 ml) were added to the reaction mixture to separate a water layer. The water layer was extracted with ethyl acetate (20 ml). After the resultant organic layers were combined, washed with a saturated solution (50 ml) of sodium hydrogencarbonate and dried over anhydrous sodium sulfate, the solvent was distilled off under reduced pressure. The residue was purified by column chromatography on silica gel (hexane:ethyl acetate=4:1→2:1) to obtain the title compound (234 mg). Since this aldehyde was unstable, it was immediately used in the next reaction.

$^1$H-NMR (CDCl$_3$) δ: 1.49 (9H, s), 2.77 (2H, br.s), 3.77 (2H, br.s), 4.62 (2H, s), 9.70 (1H, s).

Referential Example 19

5-(tert-Butyl) 2-methyl 6,7-dihydrooxazolo[5,4-c]pyridine-2,5(4H)-dicarboxylate

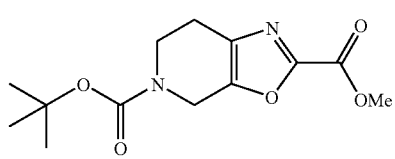

Sodium cyanide (220 mg) and manganese dioxide (780 mg) were added to a solution of the compound (225 mg) obtained in Referential Example 18 in methanol (9.0 ml) at room temperature. After stirring for 30 minutes, the reaction mixture was filtered through Celite with ethyl acetate. The filtrate was washed with water (50 ml) and saturated aqueous solution of sodium chloride (50 ml) and dried over anhydrous sodium sulfate. The solvent was then distilled off under reduced pressure, and the residue was purified by column chromatography on silica gel (hexane:ethyl acetate=3:2→1:1) to obtain the title compound (120 mg).

$^1$H-NMR (CDCl$_3$) δ: 1.49 (9H, s), 2.73 (2H, br.s), 3.74 (2H, br.s), 4.01 (3H, s), 4.59 (2H, s). MS (FAB) m/z: 283 (M+H)$^+$.

Referential Example 20

Methyl 5-methyl-4,5,6,7-tetrahydrooxazolo[5,4-c]pyridine-2-carboxylate

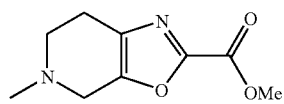

Trifluoroacetic acid (15 ml) was added to a solution of the compound (500 mg) obtained in Referential Example 19 in methylene chloride (15 ml) at room temperature, and the mixture was stirred for 10 minutes. The reaction mixture was concentrated under reduced pressure, and methylene chloride (20 ml), triethylamine (0.495 ml), acetic acid (205 ml), formalin (0.230 ml) and sodium triacetoxyborohydride (570 mg) were added to the resultant residue at room temperature. After stirring for 15 minutes, methylene chloride (20 ml) and a saturated aqueous solution (50 ml) of sodium hydrogencarbonate were added to separate an organic layer. The water layer was extracted with methylene chloride (3×20 ml). After the resultant organic layers were combined and dried over anhydrous sodium sulfate, the solvent was distilled off under reduced pressure. The residue was purified by column chromatography on silica gel (chloroform:methanol=20:1→10:1) to obtain the title compound (257 mg).

$^1$H-NMR (CDCl$_3$) δ: 2.52 (3H, s), 2.72-2.78 (2H, m), 2.78-2.83 (2H, m), 3.61 (2H, t, J=1.7 Hz), 4.00 (3H, s). MS (FAB) m/z: 197 (M+H)$^+$, 165 (M-OCH$_3$)$^+$.

Referential Example 21

Lithium 5-methyl-4,5,6,7-tetrahydrooxazolo[5,4-c]-pyridine-2-carboxylate

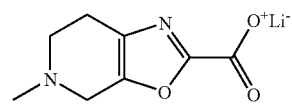

Water (6.0 ml) and lithium hydroxide (99.7 mg) were added to a solution of (800 mg) obtained in Referential Example 20 in tetrahydrofuran (24 ml) at room temperature, and the mixture was stirred for 10 minutes. The reaction mixture was concentrated under reduced pressure to obtain the title compound (825 mg).

$^1$H-NMR (DMSO-d$_6$) δ: 2.37 (3H, s), 2.47 (2H, t, J=5.6 Hz), 2.64 (2H, t, J=5.6 Hz), 3.43 (2H, s).

Referential Example 22

Methyl 5-chloro-6-fluoroindole-2-carboxylate

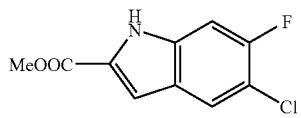

A mixture of methyl 3-chloro-4-fluoro-α-azidocinnamate (Japanese Patent Application Laid-Open No. 149723/1995) (1.85 g) and xylene (140 ml) was heated under reflux for 1 hour, and the solvent was then distilled off. The residue was purified by column chromatography on silica gel (methylene chloride) to obtain the title compound (491 mg).

$^1$H-NMR (CDCl$_3$) δ: 3.95 (3H, s), 7.13-7.15 (1H, m), 7.20 (1H, dd, J=9.3, 0.49 Hz), 7.71 (1H, d, J=7.3 Hz), 8.93 (1H, br.s). MS (FAB) m/z: 227 M$^+$.

Referential Example 23

5-Chloro-6-fluoroindole-2-carboxylic Acid

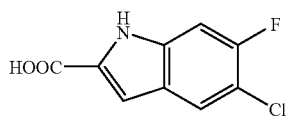

The compound (461 mg) obtained in Referential Example 22 was dissolved in a mixed solvent of tetrahydrofuran (15 ml), methanol (10 ml) and water (10 ml), lithium hydroxide (283 mg) was added at room temperature, and the mixture was stirred for 4 hours. The solvent was distilled off under reduced pressure, and 1N hydrochloric acid was added to the residue to weakly acidify it. The resultant powder was collected by filtration and dried to obtain the title compound (422 mg).

$^1$H-NMR (CDCl$_3$) δ: 7.08-7.10 (1H, m), 7.34 (1H, d, J=9.5 Hz), 7.88 (1H, d, J=7.6 Hz), 12.04 (1H, s), 13.16 (1H, s). MS (FAB) m/z: 213 (M$^+$).

Referential Example 24

5-(Pyridin-4-yl)-4,5,6,7-tetrahydrothiazolo[5,4-c]-pyridine

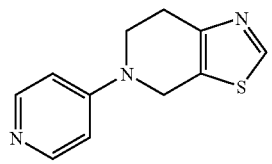

1) Diphosphorus pentasulfide (500 g) was suspended in formamide (3,000 ml) with ice cooling, and the suspension was stirred overnight. Water and diethyl ether were added to the reaction mixture, and an organic layer was separated and dried over anhydrous magnesium sulfate, and the solvent was distilled off to obtain an oil. After the oil was dissolved in n-butanol (350 ml), and ethyl 3-chloro-4-oxo-1-piperidinecarboxylate (150 g) synthesized according to the process described in literature (Tetrahedron, 1983, Vol. 39, p. 3767) was added to the solution, the resultant mixture was stirred at 100° C. for 2.5 hours. The reaction mixture was filtered through Celite. The filtrate was washed with a saturated aqueous solution of sodium hydrogencarbonate and saturated aqueous solution of sodium chloride, and then dried over anhydrous sodium sulfate. The solvent was distilled off under reduced pressure, and the residue was purified by column chromatography on silica gel (methylene chloride→ethyl acetate:hexane=1:2) to obtain ethyl 6,7-dihydrothiazolo[5,4-c]pyridine-5(4H)-carboxylate (79.0 g).

$^1$H-NMR (CDCl$_3$) δ: 1.30 (3H, t, J=7.3 Hz), 2.96 (2H, br.s), 3.82 (2H, br.s), 4.19 (2H, +, J=7.3 Hz), 4.73 (2H, br.s), 8.68 (1H, s). MS (FAB) m/z: 213 (M+H)$^+$.

2) A 3.5N aqueous solution (250 ml) of sodium hydroxide was added to the reaction product (33.5 g) obtained above, and the mixture was heated under reflux overnight. After the reaction mixture was cooled to room temperature, di-tert-butyl dicarbonate (103 g) was added with ice cooling, and the mixture was stirred overnight at room temperature. After 3N hydrochloric acid was added to the reaction mixture to adjust the pH thereof to 1 to 2, methylene chloride was added. After separation of an organic layer, the organic layer was washed successively with an aqueous solution of sodium hydrogencarbonate and saturated aqueous solution of sodium chloride and then dried over anhydrous sodium sulfate. After the organic layer was concentrated under reduced pressure, the resultant residue was purified by column chromatography on silica gel (ethyl acetate:hexane=1:2) to obtain tert-butyl 6,7-dihydrothiazolo[5,4-c]pyridine-5(4H)-carboxylate (21.1 g).

$^1$H-NMR (CDCl$_3$) δ: 1.49 (9H, s), 2.94 (2H, br.s), 3.76 (2H, br.s), 4.68 (2H, s), 8.67 (1H, s). MS (FAB) m/z: 241 (M+H)$^+$.

3) Trifluoroacetic acid (25 ml) was added to a solution of the compound (5.00 g) obtained in the step 2) in methylene chloride (25 ml) at room temperature. After stirring for 10 minutes, the reaction mixture was concentrated under reduced pressure, and 4-bromopyridine (5.20 g), N,N-dimethylformamide (30 ml) and triethylamine (15.5 ml) were added to the residue at room temperature, and the mixture was stirred at 150° C. for 2 days and then allowed to cool to room temperature. Colorless precipitates were separated by filtration, and the filtrate was concentrated under reduced pressure. Thereafter, methylene chloride (50 ml) and a saturated aqueous solution (100 ml) of sodium hydrogencarbonate were added, and the resultant water layer was saturated with sodium chloride. After separation of an organic layer, the resultant water layer was extracted with methylene chloride (5×30 ml). After the resultant organic layers were combined and dried over anhydrous sodium sulfate, the solvent was distilled off under reduced pressure. The residue was purified by column chromatography on silica gel (methylene chloride:methanol=20:1→8:1) to obtain the title compound (2.97 g).

$^1$H-NMR (CDCl$_3$) δ: 3.07 (2H, t, J=5.9 Hz), 3.81 (2H, t, J=5.9 Hz), 4.61 (2H, s), 6.74 (2H, t, J=6.5 Hz), 8.30 (2H, t, J=6.5 Hz), 8.70 (1H, s). MS (ESI) m/z: 218 (M+H)$^+$.

Referential Example 25

2-Chloro-6,7-dihydro-4H-pyrano[4,3-d]thiazole

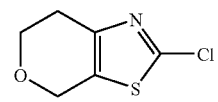

1) Tetrahydro-4H-pyran-4-one (5.0 g) was dissolved in cyclohexane (20 ml), pyrrolidine (4.35 ml) and p-toluenesulfonic acid monohydrate (48 mg) were added, and the mixture was heated under reflux for 70 minutes while removing water by a Dean-Stark trap. The reaction mixture was cooled to room temperature, and a supernatant was taken out and concentrated under reduced pressure. The residue was dissolved in methanol (15 ml), and sulfur powder (1.60 g) was added with ice cooling. After 15 minutes, a methanol solution (10 ml) of cyanamide (2.10 g) was added dropwise over 20 minutes, and the mixture was stirred for 3 days. The solvent was distilled off under reduced pressure, and the residue was purified by column chromatography on silica gel (methylene chloride:methanol=20:1→10:1→4:1) to obtain 6,7-dihydro-4H-pyrano[4,3-d]thiazol-2-ylamine (3.97 g).

$^1$H-NMR (CDCl$_3$) δ: 2.66-2.70 (2H, m), 3.97 (2H, t, J=5.6 Hz), 4.63 (2H, s), 4.94 (2H, br.s). MS (FAB) m/z: 157 (M+H)$^+$.

2) Copper(II) chloride (4.10 g) was dissolved in acetonitrile (50 ml), and tert-butyl nitrite (3.93 g) was added in one portion with ice cooling. After 10 minutes, the compound obtained in the above-described reaction (3.97 g) was added over about 1 hour, and the reaction mixture was stirred at room temperature for 1 hour. The reaction mixture was heated to 65° C. and continuously stirred for 2 hours. After silica gel (20 g) was added to the reaction mixture, the solvent was distilled off under reduced pressure, and the residue was purified by column chromatography on silica gel (hexane:ethyl acetate=3:1) to obtain the title compound (1.78 g).

$^1$H-NMR (CDCl$_3$) δ: 2.85-2.89 (2H, m), 4.02 (2H, t, J=5.6 Hz), 4.73 (2H, s). MS (FAB) m/z: 175 (M+H)$^+$.

Referential Example 26

Lithium 6,7-dihydro-4H-pyrano[4,3-d]thiazol-2-carboxylate

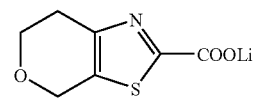

1) The compound (1.78 g) obtained in Referential Example 25 was dissolved in methanol (30 ml), and to the solution 10% palladium on carbon (300 mg) and sodium acetate (830 mg) were added. The mixture was stirred for 5 days in a hydrogen stream of 5 atm. After the catalyst was separated by filtration, the solvent was concentrated, and the residue was subjected to column chromatography on silica gel (hexane:ethyl acetate=2:1) to obtain 6,7-dihydro-4H-pyrano[4,3-d]thiazole (1.14 g).

$^1$H-NMR (CDCl$_3$) δ: 2.97-3.01 (2H, m), 4.04 (2H, t, J=5.6 Hz), 4.87 (2H, s), 8.69 (1H, s). MS (FAB) m/z: 142 (M+H)$^+$.

2) After the product (1.14 g) obtained above was dissolved in diethyl ether (30 ml) and cooled to −78° C., 1.6 M butyllithium (6.6 ml) was added, and the mixture was stirred. After 20 minutes, bubbling was conducted with carbon dioxide for 15 minutes. The reaction mixture was warmed to room temperature and concentrated under reduced pressure to obtain the title compound (1.65 g).

$^1$H-NMR (DMSO-d$_6$) δ: 2.83 (2H, t, J=5.6 Hz), 3.92 (2H, t, J=5.6 Hz), 4.73 (2H, s).

Referential Example 27

Thiazolo[4,5-c]pyridine

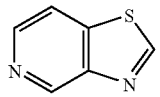

3-(tert-Butoxycarbonylamino)-4-mercaptopyridine (Japanese Patent Application Laid-Open No. 321691/1992) (9.20 g) was dissolved in formic acid (60 ml) and heated under reflux for 4 hours. The reaction mixture was concentrated under reduced pressure, and a 5N aqueous solution (100 ml) of potassium hydroxide and diethyl ether were added to the residue to conduct liquid separation. The resultant organic layer was dried over anhydrous sodium sulfate, and the solvent was distilled off under reduced pressure. Diethyl ether was added to the residue, and solids deposited were collected by filtration to obtain the title compound (3.97 g).

$^1$H-NMR (CDCl$_3$) δ: 7.93 (1H, d, J=5.4 Hz), 8.60 (1H, d, J=5.4 Hz), 9.07 (1H, s), 9.46 (1H, s).

Referential Example 28

5-Methyl-4,5,6,7-tetrahydrothiazolo[4,5-c]pyridine

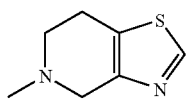

The title compound was obtained from the compound obtained in Referential Example 27 in a similar manner to Referential Example 4.

$^1$H-NMR (CDCl$_3$) δ: 2.52 (3H, s), 2.77 (2H, t, J=5.4 Hz), 2.92-3.00 (2H, m), 3.69 (2H, t, J=2.0 Hz), 8.61 (1H, s). MS (FAB) m/z: 155 (M+H)$^+$.

Referential Example 29

Lithium 5-methyl-4,5,6,7-tetrahydrothiazolo[4,5-c]-pyridine-2-carboxylate

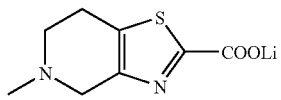

The title compound was obtained from the compound obtained in Referential Example 28 in a similar manner to Referential Example 5.

$^1$H-NMR (DMSO-d$_6$) δ: 2.38 (3H, s), 2.64 (2H, br.s), 2.80 (2H, br.s), 3.44 (2H, br.s).

Referential Example 30

2-Chloro-N,N-dimethyl-4,5,6,7-tetrahydrobenzothiazole-6-amine

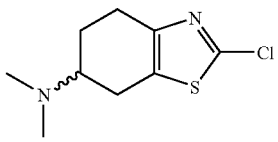

2-Chloro-4,7-dihydro-1,3-benzothiazol-6(5H)-one (Helv. Cim. Acta., 1994, Vol. 77, p. 1256) (2.0 g) was dissolved in methanol (100 ml), and ammonium acetate (8.2 g) and sodium cyanoborohydride (4.0 g) were added to heat the mixture under reflux for 20 hours. Hydrochloric acid was added to the reaction mixture to decompose excessive sodium cyanoborohydride before the solvent was distilled off under reduced pressure. The residue was alkalified with a 1N solution of sodium hydroxide and then extracted with methylene chloride. The resultant organic layer was dried over anhydrous magnesium sulfate, and the solvent was distilled off under reduced pressure to obtain a pale yellow oil. This oil was dissolved in methanol (50 ml), and an aqueous solution (4.29 g) of formaldehyde and sodium cyanoborohydride (3.49 g) were added to stir the mixture at room temperature for 12 hours. The solvent was distilled off under reduced pressure, and methylene chloride was added to the residue, the organic layer was washed with a saturated aqueous solution of sodium hydrogencarbonate and dried over anhydrous magnesium sulfate. The solvent was distilled off under reduced pressure, and the residue was purified by column chromatography on silica gel (methylene chloride:methanol=10:1) to obtain the title compound (740 mg).

$^1$H-NMR (CDCl$_3$) δ: 1.71-1.78 (1H, m), 2.10-2.19 (1H, m), 2.35 (6H, s), 2.66-2.94 (5H, m). MS (FAB) m/z: 217 (M+H)$^+$.

Referential Example 31

Lithium 6-(dimethylamino)-4,5,6,7-tetrahydrobenzothiazole-2-carboxylate

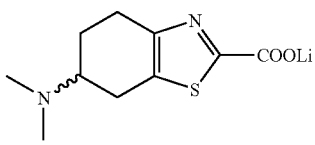

After the compound (750 mg) obtained in Referential Example 30 was dissolved in diethyl ether (15 ml), and the solution was cooled to −78° C., 1.5N t-butyllithium (3.5 ml) was added, the mixture was stirred for 20 minutes, and carbon dioxide was then bubbled for about 15 minutes. The reaction mixture was warmed to room temperature and concentrated under reduced pressure to obtain the title compound.

$^1$H-NMR (DMSO-d$_6$) δ: 1.75-1.78 (1H, m), 1.98-2.07 (1H, m), 2.50 (6H, s), 2.64-2.88 (5H, m).

Referential Example 32 tert-Butyl 2-amino-4,6-dihydro-5H-pyrrolo[3,4-d]thiazole-5-carboxylate

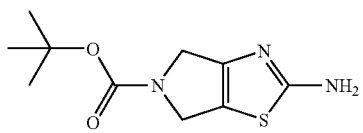

1-tert-Butoxycarbonyl-3-pyrrolidone (1.58 g) was dissolved in cyclohexane (10 ml), p-toluenesulfonic acid monohydrate (8.12 mg) and pyrrolidine (607 mg) were added, and the mixture was heated under reflux for 1.5 hours while dewatering with a Dean-Stark trap. After a supernatant was taken out and concentrated under reduced pressure, the residue was dissolved in methanol (5 ml), and sulfur powder (274 mg) was added. The mixture was stirred for 15 minutes under ice cooling. A methanol solution (2 ml) of cyanamide (377 mg) was slowly added dropwise to the reaction mixture, and the mixture was stirred overnight at room temperature. The mixture was additionally heated under reflux for 2 hours, the reaction mixture was concentrated, and methylene chloride and a saturated aqueous solution of sodium hydrogen carbonate were added. The resultant organic layer was dried over anhydrous sodium sulfate. The solvent was distilled off under reduced pressure, and the residue was purified by column chromatography on silica gel (methanol:methylene chloride=1:39) to obtain the title compound (248 mg).

$^1$H-NMR (CDCl$_3$) δ: 1.50 (9H, s), 4.34-4.37 (1H, m), 4.40-4.45 (1H, m), 4.49-4.55 (2H, m), 4.99 (2H, m).

Referential Example 33 tert-Butyl 2-bromo-4,6-dihydro-5H-pyrrolo[3,4-d]thiazole-5-carboxylate

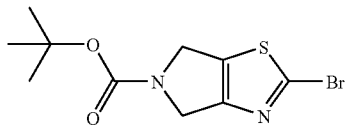

Copper(II) bromide (445 mg) was suspended in N,N-dimethylformamide, and tert-butyl nitrite (256 mg) was added dropwise at room temperature. After an N,N-dimethylformamide solution (1 ml) of the compound (400 mg) obtained in Referential Example 32 was added under ice cooling, the reaction mixture was heated and stirred at 60° C. for 1.5 hours. Diethyl ether and saturated aqueous solution of sodium chloride were added to the reaction mixture, and the resultant organic layer was dried over anhydrous magnesium sulfate and concentrated under reduced pressure. The residue was purified by column chromatography on silica gel (ethyl acetate:hexane=1:4) to obtain the title compound (174 mg).

$^1$H-NMR (CDCl$_3$) δ: 1.51 (9H, s), 4.52-4.55 (1H, m), 4.57-4.67 (3H, m). MS (FAB) m/z: 305 (M+H)$^+$.

Referential Example 34

Lithium(5-tert-butoxycarbonyl)-4,5,6,7-tetrahydrothiazolo[5,4-c]pyridine-2-carboxylate

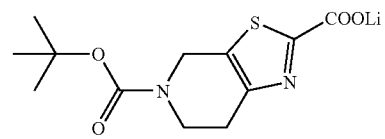

The title compound was obtained from the compound obtained in Referential Example 7 in a similar manner to Referential Example 10.

$^1$H-NMR (DMSO-d$_6$) δ: 1.42 (9H, s), 2.69-2.77 (2H, m), 3.60-3.68 (2H, m), 4.51-4.58 (2H, m).

Referential Example 35

Methyl 2-bromo-4-(2-methoxy-2-oxoethyl)thiazole-5-carboxylate

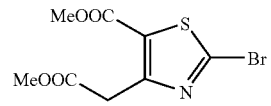

Copper(II) chloride (26.8 g) was added to a solution of tert-butyl nitrite (15.5 g) in acetonitrile (500 ml) at a time under ice cooling. A solution of methyl 2-amino-5-methoxycarbonylthiazole-4-acetate (Yakugaku Zasshi, 1966, Vol. 86, p. 300) (23.0 g) in acetonitrile (500 ml) was added dropwise to the reaction mixture over 45 minutes, and the resulting mixture was stirred for 1 hour under ice cooling and for 30 minutes at room temperature. The solvent was concentrated, and 10% hydrochloric acid and diethyl ether were added to the residue to separate an organic layer. The organic layer was dried over anhydrous magnesium sulfate. The solvent was distilled off under reduced pressure, and the residue was purified by column chromatography on silica gel (ethyl acetate:hexane=1:4) to obtain the title compound (25.9 g).

$^1$H-NMR (CDCl$_3$) δ: 3.73 (3H, s), 3.87 (3H, s), 4.21 (2H, s).

Referential Example 36

2-[5-(hydroxymethyl)thiazol-4-yl]-1-ethanol

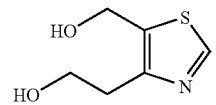

A solution of the compound (23.4 g) obtained in Referential Example 35 in tetrahydrofuran (500 ml) was added dropwise over 1 hour to a suspension of lithium aluminum hydride (9.03 g) in tetrahydrofuran (500 ml) under ice cooling. After stirring for additional 1 hour under ice cooling, water (9 ml), a 35% aqueous solution (9 ml) of sodium hydroxide and water (27 ml) were successively added, and the mixture was stirred at room temperature for 1 hour. After anhydrous magnesium sulfate was added to the reaction mixture, and the resultant mixture was stirred, insoluble matter was removed by filtration with Celite, and the filtrate was concentrated. The residue was purified by column chromatography on silica gel (methanol:methylene chloride=7:93) to obtain the title compound (8.64 g).

$^1$H-NMR (CDCl$_3$) δ: 3.01 (2H, t, J=5.5 Hz), 3.30 (1H, br.s), 3.57 (1H, br.s), 3.90 (2H, br.s), 4.75 (2H, br.s), 8.66 (1H, s). MS (ESI) m/z: 160 (M+H)$^+$.

Referential Example 37

2-(5-{[(Methylsulfonyl)oxy]methyl}thiazol-4-yl)ethyl Methanesulfonate

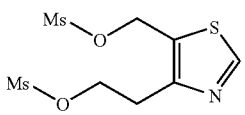

A methylene chloride solution of methanesulfonyl chloride (12.6 ml) was added dropwise to a solution of the compound (8.64 g) obtained in Referential Example 36 and triethylamine (45.4 ml) dissolved in methylene chloride (500 ml) over 20 minutes at −78° C. After stirring the reaction mixture for 15 minutes at −78° C. and 1 hour at 0° C., water was added to separate an organic layer. The organic layer was dried over anhydrous sodium sulfate. The solvent was distilled off under reduced pressure to obtain the title compound (13.4 g).

$^1$H-NMR (CDCl$_3$) δ: 2.93 (3H, s), 3.03 (3H, s), 3.28 (2H, t, J=6.3 Hz), 4.61 (2H, t, J=6.3 Hz), 5.44 (2H, s), 8.84 (1H, s).

Referential Example 38

5-(1-Methylcyclopropyl)-4,5,6,7-tetrahydrothiazolo-[5,4-c]pyridine

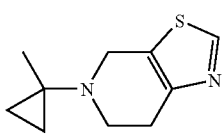

1-Methylcyclopropylamine hydrochloride (J. Org. Chem., 1989, Vol. 54, p. 1815) (1.89 g) was added to methylene chloride (20 ml) containing the compound obtained in Referential Example 37 (4.46 g) under ice cooling, and the mixture was stirred overnight at room temperature. 1-Methylcyclopropylamine hydrochloride (1.89 g) was additionally added, and the mixture was stirred for 20 hours at room temperature and 5 hours under refluxing. Methylene chloride and water were added to the reaction mixture to separate an organic layer. The organic layer was dried over anhydrous sodium sulfate. The solvent was distilled off under reduced pressure, and the residue was purified by column chromatography on silica gel (methanol:methylene chloride=1:49) to obtain the title compound (944 mg).

$^1$H-NMR (CDCl$_3$) δ: 0.40-0.50 (2H, m), 0.68-0.73 (2H, m), 1.16 (3H, s), 2.88-2.94 (2H, m), 3.03 (2H, t, J=5.7 Hz), 3.89 (2H, br.s), 8.60 (1H, s). MS (ESI) m/z: 195 (M+H)$^+$.

Referential Example 39

Lithium 5-(1-methylcyclopropyl)-4,5,6,7-tetrahydrothiazolo[5,4-c]pyridine-2-carboxylate

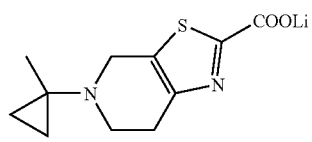

The title compound was obtained from the compound obtained in Referential Example 38 in a similar manner to Referential Example 5.

$^1$H-NMR (DMSO-d$_6$) δ: 0.39 (2H, br.s), 0.56 (2H, br.s), 1.10 (3H, br.s), 2.66 (2H, br.s), 2.89 (2H, br.s), 3.75 (2H, br.s).

Referential Example 40

2-[6,7-Dihydrothiazolo[5,4-c]pyridin-5(4H)-yl]-2-methyl-1-propanol

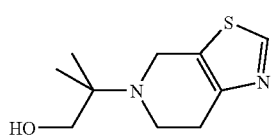

The title compound was obtained from the compound obtained in Referential Example 37 and 2-amino-2-methyl-1-propanol in a similar manner to Referential Example 38.

$^1$H-NMR (CDCl$_3$) δ: 1.15 (6H, s), 2.91 (4H, s), 3.45 (2H, s), 3.87 (2H, s), 8.63 (1H, s).

Referential Example 41

5-(2-{[tert-Butyl(diphenyl)silyl]oxy}-1,1-dimethylethyl)-4,5,6,7-tetrahydrothiazolo[5,4-c]pyridine

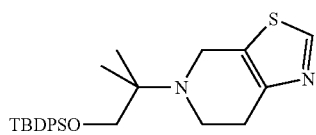

tert-Butylchlorodiphenylsilane (1.93 g) and imidazole (994 mg) were added to a solution of the compound obtained in Referential Example 40 (1.24 g) in N,N-dimethylformamide (5 ml) at room temperature, and the mixture was stirred overnight. Water and diethyl ether were added to the reaction mixture to separate an organic layer. The organic layer was dried over anhydrous magnesium sulfate. The solvent was distilled off under reduced pressure, and the residue was purified by column chromatography on silica gel (hexane:ethyl acetate=1:2) to obtain the title compound (2.46 g).

¹H-NMR (CDCl₃) δ: 1.07 (9H, s), 1.15 (6H, s), 2.83-2.90 (2H, m), 2.93-3.00 (2H, m), 3.63 (2H, s), 3.97 (2H, s), 7.35-7.48 (6H, m), 7.63-7.70 (4H, m), 8.58 (1H, s). MS (ESI) m/z: 451 (M+H)⁺.

Referential Example 42

Lithium 5-(2-{[tert-butyl(diphenyl)silyl]oxy}-1,1-dimethylethyl)-4,5,6,7-tetrahydrothiazolo[5,4-c]pyridine-2-carboxylate

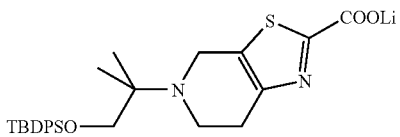

The title compound was obtained from the compound obtained in Referential Example 41 in a similar manner to Referential Example 5.

¹H-NMR (DMSO-d₆) δ: 1.01 (9H, s), 1.11 (6H, s), 2.55-2.65 (2H, m), 2.80-2.90 (2H, m), 3.57 (2H, s), 3.80 (2H, br.s), 7.40-7.52 (6H, m), 7.60-7.65 (4H, m).

Referential Example 43

4,7,8,10-Tetrahydro-6H-pyrazolo[1,2-a]thiazolo[4,5-d]-pyridazine

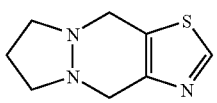

1) 4,5-Dimethylthiazole (5.00 g), N-bromosuccinimide (15.7 g) and α,α'-azobisisobutyronitrile (362 mg) were dissolved in ethylene dichloride (500 ml) at room temperature, and the solution was heated under reflux for 1 hour. The solvent was distilled off, and the residue was purified by column chromatography on silica gel (hexane:diethyl ether=1:4) to obtain 4,5-bis(bromomethyl)thiazole (5.24 g).

¹H-NMR (CDCl₃) δ: 4.64 (2H, s), 4.74 (2H, s), 8.75 (1H, s).

2) 4,5-Bis(bromomethyl)thiazole (1.37 g) and 1,2-trimethylenehydrazine hydrochloride (WO9532965) (732 mg) were suspended in ethanol (15 ml) under ice cooling, and triethylamine (2.82 ml) was added dropwise over 5 minutes. After stirring the mixture at room temperature for 2 hours, the solvent was distilled off, and methylene chloride (50 ml) and a saturated aqueous solution of sodium hydrogencarbonate were added to the residue to separate an organic layer. The organic layer was dried over anhydrous sodium sulfate. The solvent was distilled off under reduced pressure, and the residue was purified by column chromatography on silica gel (methanol:methylene chloride=3:47) to obtain the title compound (358 mg).

¹H-NMR (CDCl₃) δ: 2.10-2.25 (2H, m), 3.01 (4H, br.s), 3.95 (2H, s), 3.99 (2H, br.s), 8.64 (1H, s). MS (FAB) m/z: 182 (M+H)⁺.

Referential Example 44

Lithium 4,7,8,10-tetrahydro-6H-pyrazolo[1,2-a]thiazolo-[4,5-d]pyridazine-2-carboxylate

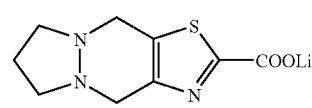

The title compound was obtained from the compound obtained in Referential Example 43 in a similar manner to Referential Example 5.

¹H-NMR (DMSO-d₆) δ: 1.90-2.10 (2H, m), 2.60-3.10 (4H, br.s), 3.65-4.00 (4H, m).

Referential Example 45

4,6,7,8,9,11-Hexahydropyridazino[1,2-a]thiazolo[4,5-d]-pyridazine

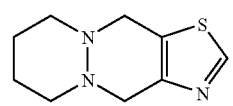

The title compound was obtained from 4,5-bis(bromomethyl)thiazole (2.20 g) obtained in 1) of Referential Example 43 and 1,2-tetramethylenehydrazine hydrochloride (U.S. Pat. No. 5,726,126) in a similar manner to Referential Example 43.

¹H-NMR (CDCl₃) δ: 1.77 (4H, br.s), 2.20-3.50 (4H, br), 3.92 (4H, br.s), 8.65 (1H, s). MS (FAB) m/z: 196 (M+H)⁺.

Referential Example 46

Lithium 4,6,7,8,9,11-hexahydropyridazino[1,2-a]thiazolo-[4,5-d]pyridazine-2-carboxylate

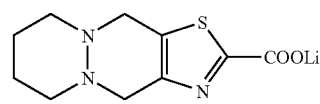

The title compound was obtained from the compound obtained in Referential Example 45 in a similar manner to Referential Example 5.

Referential Example 47 tert-Butyl 2-(methylsulfanyl)-5,7-dihydro-6H-pyr-rolo-[3,4-d]pyrimidine-6-carboxylate

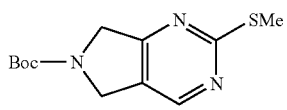

1-tert-Butoxycarbonyl-3-pyrrolidone (4.57 g) was added to N,N-dimethylformamide dimethyl acetal (30 ml) at room temperature, and the mixture was heated for 1 hour at 140° C. After allowing the reaction mixture to cool to room temperature, it was concentrated under reduced pressure. Hexane was added to the residue, and yellow powder deposited was collected by filtration. This powder was dissolved in ethanol (100 ml), and methylisothiourea sulfate (9.24 g) and sodium ethoxide (4.52 g) were added to the resultant solution at room temperature, and the mixture was heated under reflux for 24 hours. Saturated aqueous solution of sodium chloride and diethyl ether were added to the reaction mixture to separate an organic layer. The organic layer was dried over anhydrous sodium sulfate and concentrated under reduced pressure, and the residue was purified by column chromatography on silica gel (methanol:methylene chloride=1:99) to obtain the title compound (1.10 g).

$^1$H-NMR (CDCl$_3$) δ: 1.51 (9H, s), 2.57 (3H, m), 4.15-4.45 (4H, m), 8.39 (1/2H, s), 8.43 (1/2H, s). MS (FAB) m/z: 268 (M+H)$^+$.

Referential Example 48 tert-Butyl 2-(methylsulfonyl)-5,7-dihydro-6H-pyr-rolo-[3,4-d]pyrimidine-6-carboxylate

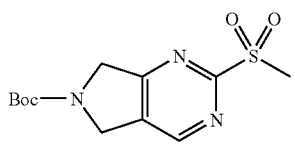

m-Chloroperbenzoic acid (1.99 g) was added to a methylene chloride solution (20 ml) of the compound (1.08 g) obtained in Referential Example 47 under ice cooling, and the mixture was stirred for 5 hours. A saturated aqueous solution of sodium sulfite, a saturated aqueous solution of sodium hydrogen carbonate and methylene chloride were added to separate an organic layer. The organic layer was then dried over anhydrous sodium sulfate. The solvent was distilled off under reduced pressure, hexane was added to the residue, and powder deposited was collected by filtration to obtain the title compound (1.09 g).

$^1$H-NMR (CDCl$_3$) δ: 1.53 (9H, s), 3.36 (3H, m), 4.77-4.90 (4H, m), 8.77 (1/2H, s), 8.81 (1/2H, s). MS (FAB) m/z: 300 (M+H)$^+$.

Referential Example 49 tert-Butyl 2-cyano-5,7-dihydro-6H-pyrrolo[3,4-d]-pyrimidine-6-carboxylate

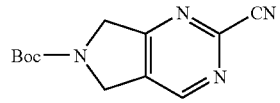

Tetrabutylammonium cyanide (1.04 g) was added to a solution of the compound (1.05 g) obtained in Referential Example 48 in methylene chloride (30 ml) at room temperature, and the mixture was stirred at room temperature for 1 hour. 1N sodium hydroxide was added to the reaction mixture to separate an organic layer, and the organic layer was dried over anhydrous sodium sulfate. The solvent was distilled off under reduced pressure, and the residue was purified by column chromatography on silica gel (methylene chloride:acetone=20:1) to obtain the title compound (776 mg).

$^1$H-NMR (CDCl$_3$) δ: 1.52 (9H, s), 4.70-4.85 (4H, m), 8.68-8.77 (1H, m). MS (FAB) m/z: 247 (M+H)$^+$.

Referential Example 50

6-tert-Butyl 2-methyl 5,7-dihydro-6H-pyrrolo[3,4-d]pyrimidine-2,6-dicarboxylate

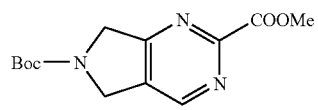

Concentrated hydrochloric acid (5 ml) was added to a solution of the compound (776 mg) obtained in Referential Example 49 in methanol (10 ml) at room temperature, and the mixture was stirred at 100° C. for 1 hour. After allowing to cool, the reaction mixture was concentrated under reduced pressure, and the residue was dissolve in methanol (10 ml). Triethylamine (2.20 ml) and di-tert-butyl dicarbonate (1.37 g) were added to the solution at room temperature and stirred for 1 hour. The reaction mixture was concentrated under reduced pressure, and methylene chloride and saturated aqueous solution of sodium chloride were added to the residue to separate an organic layer, and the organic layer was dried over anhydrous sodium sulfate. The solvent was distilled off under reduced pressure, and the residue was purified by column chromatography on silica gel (methanol:methylene chloride=3:97) to obtain the title compound (317 mg).

$^1$H-NMR (CDCl$_3$) δ: 1.53 (9H, s), 4.09 (3H, s), 4.75-4.85 (4H, m), 8.81 (1/2H, s), 8.85 (1/2H, s). MS (FAB) m/z: 280 (M+H)$^+$.

Referential Example 51

Lithium 5,6-dimethyl-4,5,6,7-tetrahydrothiazolo[4,5-d]-pyridazine-2-carboxylate

1) After 4,5-bis(bromomethyl)thiazole (600 mg) obtained in 1) of Referential Example 43 was dissolved in ethanol (20 ml), and 1,2-dimethylhydrazine hydrochloride (294 mg) was added under ice cooling, triethylamine (1.23 ml) was added at a time, and the mixture was stirred for 30 minutes at room temperature and 30 minutes at 50° C. The solvent was distilled off, and the residue was purified by column chromatography on silica gel (methanol:methylene chloride=1:19) to obtain 5,6-dimethyl-4,5,6,7-tetrahydrothiazolo[4,5-d]pyridazine (90 mg).

$^1$H-NMR (CDCl$_3$) δ: 2.43 (3H, s), 2.56 (3H, s), 3.92 (2H, s), 4.06 (2H, br.s), 8.68 (1H, s). MS (FAB) m/z: 170 (M+H)$^+$.

2) The title compound was obtained from 5,6-dimethyl-4,5,6,7-tetrahydrothiazolo[4,5-d]pyridazine in a similar manner to Referential Example 5.

$^1$H-NMR (DMSO-d$_6$) δ: 2.28 (3H, s), 2.39 (3H, s), 3.66 (2H, br.s), 3.88 (2H, br.s).

Referential Example 52

4-Nitrophenyl 5-chloroindole-2-carboxylate

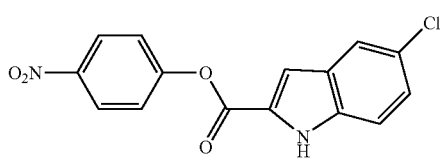

After 5-chloroindole-2-carboxylic acid (20 g) was suspended in methylene chloride (1500 ml), and N,N-dimethylformamide (2 ml) was added, thionyl chloride (11 ml) was added dropwise at room temperature. The reaction mixture was heated overnight under reflux and then concentrated under reduced pressure. The residue was dissolved in methylene chloride (1000 ml), and triethylamine (84.7 ml) and p-nitrophenol (14.2 g) were added to the mixture under ice cooling. After stirring for 1 hour at room temperature, the reaction mixture was concentrated under reduced pressure, and ethyl acetate and 0.2N hydrochloric acid were added to the residue to separate an organic layer. The organic layer was successively washed with a saturated aqueous solution of sodium hydrogencarbonate and saturated aqueous solution of sodium chloride and then dried over anhydrous sodium sulfate. The solvent was distilled off under reduced pressure to obtain the title compound (29.9 g).

$^1$H-NMR (CDCl$_3$) δ: 7.35 (1H, dd, J=9.0, 1.7 Hz), 7.39-7.42 (2H, m), 7.45 (2H, dd, J=7.3, 1.7 Hz), 7.73 (1H, d, J=1.0 Hz), 8.35 (2H, dd, J=7.3, 1.7 Hz), 9.09 (1H, br.s). MS (FD) m/z: 316 (M$^+$).

Referential Example 53

6-Chloro-2-quinolinecarbonitrile

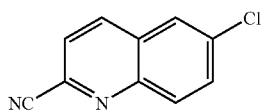

6-Chloroquinoline (2.50 g) was dissolved in methylene chloride (25 ml), and m-chloroperbenzoic acid (3.71 g) was added under ice cooling to stir the mixture at room temperature for 1 hour. After the reaction mixture was diluted with methylene chloride, the diluted mixture was washed with an aqueous solution of sodium thiosulfate and an aqueous solution of sodium hydroxide and dried over anhydrous sodium sulfate. The solvent was distilled off under reduced pressure, and the residue was dissolved in methylene chloride (40 ml), and trimethylsilyl cyanide (2.0 ml) and N,N-dimethylcarbamoyl chloride (1.50 ml) were added to heat the resultant mixture for 9 hours under reflux. After trimethylsilyl cyanide (1.0 ml) and N,N-dimethylcarbamoyl chloride (0.80 ml) were additionally added, and the mixture was heated for 16 hours under reflux, the reaction mixture was diluted with methylene chloride, and a 10% aqueous solution (40 ml) of potassium carbonate was added to stir the mixture for 30 minutes. After an organic layer was separated and dried over anhydrous sodium sulfate, the solvent was distilled off under reduced pressure. Methylene chloride was added to the residue, and crystals deposited were collected by filtration to obtain the title compound (1.77 g). Further, a mother liquor was purified by column chromatography on silica gel (methylene chloride) to obtain the title compound (0.80 g).

$^1$H-NMR (DMSO-d$_6$) δ: 7.94 (1H, dd, J=9.0, 2.2 Hz), 8.09 (1H, d, J=8.5 Hz), 8.15 (1H, d, J=9.0 Hz), 8.29 (1H, d, J=2.2 Hz), 8.63 (1H, d, J=8.5 Hz). MS (FAB) m/z: 189 (M+H)$^+$.

Referential Example 54

6-Chloro-2-quinolinecarboxylic Acid

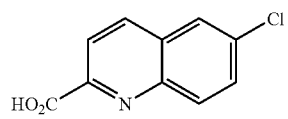

The compound (1.73 g) obtained in Referential Example 53 was dissolved in concentrated hydrochloric acid (40 ml), and the solution was heated for 19 hours under reflux. The reaction mixture was cooled to room temperature, and deposits were collected by filtration and then washed with water to obtain the title compound (1.81 g).

$^1$H-NMR (DMSO-d$_6$) δ: 7.87 (1H, dd, J=9.0, 2.4 Hz), 8.10-8.20 (2H, m), 8.24 (1H, d, J=2.2 Hz), 8.52 (1H, d, J=8.5 Hz). MS (FAB) m/z: 208 (M+H)$^+$.

Referential Example 55

Methyl 3-(4-chlorophenyl)-2-(formylamino)propionate

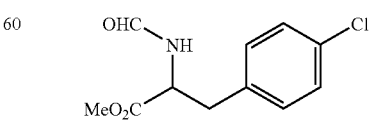

(±)-(4-Chlorophenyl)alanine methyl ester hydrochloride (2.00 g) was suspended in methylene chloride (20 ml), and 1-(3-dimethylaminopropyl)-3-ethylcarbodiimide hydrochloride (1.60 g), 1-hydroxybenzotriazole monohydrate (1.23 g), N-methylmorpholine (1.90 ml) and formic acid (0.30 ml) were added to stir the mixture for 15 minutes. After a process in which formic acid (0.30 ml) was additionally added to stir the mixture for 15 minutes was repeated 3 times, the reaction mixture was diluted with methylene chloride. After an ogranic layer was washed with water and then dried over anhydrous sodium sulfate, the solvent was distilled off under reduced pressure. The residue was purified by column chromatography on silica gel (methylene chloride:methanol=40:1) to obtain the title compound (1.21 g).

$^1$H-NMR (CDCl$_3$) δ: 3.10 (1H, dd, J=13.9, 5.6 Hz), 3.18 (1H, dd, J=13.9, 5.9 Hz), 3.75 (3H, s), 4.95 (1H, m), 6.07 (1H, br), 7.05 (2H, d, J=8.3 Hz), 7.27 (2H, d, J=8.3 Hz), 8.18 (1H, s). MS (FAB) m/z: 242 (M+H)$^+$.

Referential Example 56

Methyl 7-chloro-3-isoquinolinecarboxylate

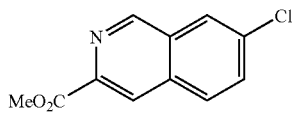

The compound (1.45 g) obtained in Referential Example 55 was dissolved in methylene chloride (40 ml), and oxalyl chloride (0.57 ml) was added dropwise. After the mixture was stirred at room temperature for 30 minutes, ferric chloride (1.17 g) was added at an ambient temperature of about −10° C. to stir the mixture at room temperature for 4 days. 1N Hydrochloric acid was added, and the resultant mixture was diluted with methylene chloride to separate an organic layer. The organic layer was dried over anhydrous sodium sulfate. The solvent was distilled off under reduced pressure, and the residue was dissolved in methanol (38 ml), and concentrated sulfuric acid (2 ml) was added to heat the mixture for 20 hours under reflux. An aqueous solution of sodium hydrogencarbonate was added to the reaction mixture, the resultant mixture was extracted with methylene chloride, and the extract was dried over anhydrous sodium sulfate. The solvent was distilled off under reduced pressure, and the residue was purified by column chromatography on silica gel (hexane:ethyl acetate=2:1→ethyl acetate) to obtain the title compound (0.25 g).

$^1$H-NMR (CDCl$_3$) δ: 4.07 (3H, s), 7.74 (1H, dd, J=8.8, 2.0 Hz), 7.94 (1H, d, J=8.8 Hz), 8.06 (1H, d, J=2.0 Hz), 8.59 (1H, s), 9.28 (1H, s).

Referential Example 57

7-Chloro-3-chloroisoquinolinecarboxylic Hydrochloride

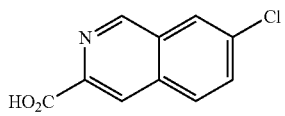

The compound (0.23 g) obtained in Referential Example 56 was dissolved in concentrated hydrochloric acid (10 ml) to heat the mixture for 18 hours under reflux. The temperature of the reaction mixture was dropped to room temperature, and deposits were collected by filtration and then washed with water to obtain the title compound (0.21 g).

$^1$H-NMR (DMSO-d$_6$) δ: 7.96 (1H, m), 8.29 (1H, d, J=8.5 Hz), 8.44 (1H, s), 8.72 (1H, s), 9.45 (1H, d, J=6.6 Hz). MS (FAB) m/z: 208 (M+H)$^+$.

Referential Example 58

(3R)-1-Benzyl-3-(tert-butyldiphenylsilyloxy)pyrrolidine

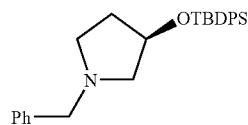

(3R)-1-Benzyl-3-hydroxypyrrolidine (500 μl) and imidazole (466 mg) were dissolved in N,N-dimethylformamide (15 ml), tert-butyldiphenylsilyl chloride (1.57 ml) was added under ice cooling., and the mixture was stirred at room temperature for 9 days. After the solvent was distilled off under reduced pressure, and methylene chloride and water were added to the residue to conduct liquid separation, the resultant organic layer was dried over anhydrous sodium sulfate, and the solvent was distilled off under reduced pressure. The residue was subjected to flash column chromatography on silica gel (hexane:ethyl acetate=3:1) to obtain the title compound (1.27 g).

$^1$H-NMR (CDCl$_3$) δ: 1.05 (9H, s), 1.70-1.85 (1H, m), 1.90-2.00 (1H, m), 2.45-2.65 (3H, m), 2.70-2.80 (1H, m), 3.50-3.70 (2H, m), 4.35-4.45 (1H, m), 7.20-7.45 (11H, m), 7.60-7.70 (4H, m). MS (ESI) m/z: 416 (M+H)$^+$.

Referential Example 59

N-[(1R*,2S*)-2-Aminocyclopropyl]-5-chloroindole-2-carboxamide

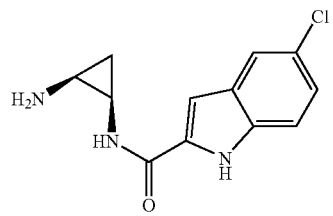

1-Hydroxybenzotriazole monohydrate (377 mg), 1-(3-dimethylaminopropyl)-3-ethylcarbodiimide hydrochloride (642 mg) and diisopropylethylamine (1.95 ml) were added to a solution of cis-1,2-cyclopropanediamine hydrochloride (J. Med. Chem., 1998, Vol. 41, pp. 4723-4732) (405 mg) and 5-chloroindole-2-carboxylic acid (546 mg) in N,N-dimethylformamide (10 ml) at room temperature, and the mixture was stirred for 50 hours. After the reaction mixture was concentrated under reduced pressure, methylene chloride (50 ml) and a saturated solution (200 ml) of sodium hydrogencarbonate were added to separate colorless solid deposited by filtration. The filtrate was extracted with methylene chloride. After the resultant organic layers were combined and dried over anhydrous sodium sulfate, the solvent was distilled off under reduced pressure to obtain residue. The residue was purified by flash column chromatography on silica gel (methylene chloride:methanol=100:7→10:1) to obtain the title compound (110 mg).

$^1$H-NMR (DMSO-$d_6$) δ: 0.44 (1H, dd, J=10.7, 4.4 Hz), 1.11 (1H, dd, J=14.0, 7.4 Hz), 2.63-2.70 (1H, m), 3.07-3.16 (1H, m), 6.77 (1H, s), 6.97 (1H, br.s), 7.23 (1H, dd, J=8.9, 1.8 Hz), 7.36 (1H, d, J=8.9 Hz), 7.60 (1H, s), 9.32 (1H, s). MS (FAB) m/z: 250 (M+H)$^+$.

Referential Example 60

N-[(1R*,2S*)-2-Aminocyclobutyl]-5-chloroindole-2-carboxamide

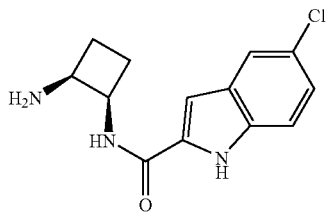

The title compound was obtained from cis-1,2-cyclobutanediamine hydrochloride (J. Am. Chem. Soc., 1942, Vol. 64, pp. 2696-2700) in a similar manner to Referential Example 59.

$^1$H-NMR (DMSO-$d_6$) δ: 1.55-2.20 (4H, m), 3.52-3.62 (1H, m), 4.35-4.50 (1H, m), 7.16 (1H, dd, J=8.7, 2.1 Hz), 7.19 (1H, s), 7.42 (1H, d, J=8.7 Hz), 7.70 (1H, d, J=2.1 Hz), 8.36 (1H, d, J=7.8 Hz), 11.77 (1H, br.s). MS (ESI) m/z: 264 (M+H)$^+$.

Referential Example 61 tert-Butyl (1R*,2R*)-2-aminocyclopentylcarbamate

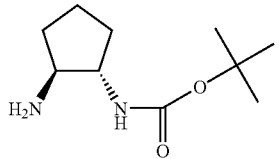

(±)-trans-1,2-Cyclopentanediamine (WO98/30574) (692 mg) was dissolved in methylene chloride (10 ml), to which triethylamine (1.1 ml) and 2-(tert-butoxycarbonyloxyimino)-2-phenylacetonitrile (493 mg) were added, and the mixture was stirred at 0° C. for 1 hour. Thereafter, 2-(tert-butoxycarbonyloxyimino)-2-phenylacetonitrile (493 mg) were additionally added, and the mixture was stirred at room temperature for 7 hours. Water was added to the reaction mixture to separate an organic layer. The organic layer was washed with saturated aqueous solution of sodium chloride and dried over anhydrous sodium sulfate. The residue was purified by flash column chromatography on silica gel (methylene chloride:methanol=9:1) to obtain the title compound (395 mg).

$^1$H-NMR (CDCl$_3$) δ: 1.25-1.40 (2H, m), 1.49 (9H, s), 1.59-1.77 (2H, m), 1.92-2.08 (1H, m), 2.10-2.17 (1H, m), 2.98 (1H, q, J=7.2 Hz), 3.48-3.53 (1H, m), 4.49 (1H, br.s). MS (ESI) m/z: 201 (M+H)$^+$.

Referential Example 62

N-[(1R*,2R*)-2-Aminocyclopentyl]-5-methyl-4,5,6,7-tetrahydrothiazolo[5,4-c]pyridine-2-carboxamide Hydrochloride

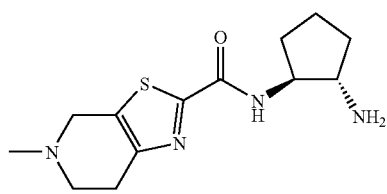

The compound (175 mg) obtained in Referential Example 61 was dissolved in N,N-dimethylformamide (3 ml), and to the solution lithium 5-methyl-4,5,6,7-tetrahydrothiazolo[5,4-c]pyridine-2-carboxylate (purity: 90%, 258 mg), 1-(3-dimethylaminopropyl)-3-ethylcarbodiimide hydrochloride (252 mg) and 1-hydroxybenzotriazole monohydrate (60 mg) were added. The mixture was stirred at room temperature for 2 days. The solvent was distilled off under reduced pressure using a pump, and methylene chloride and a saturated solution of sodium hydrogencarbonate were added to the residue to separate an organic layer. The resultant organic layer was washed with saturated aqueous solution of sodium chloride and dried over anhydrous sodium sulfate, and the solvent was distilled off under reduced pressure. The residue was purified by flash column chromatography on silica gel (methylene chloride:methanol=47:3). The resultant pale yellow oil was dissolved in a ethanol solution (5 ml) of hydrochloric acid, and the solution was stirred at room temperature for 1 hour. Ethyl acetate was then added, and the solvent was distilled off under reduced pressure. Ethyl acetate was added to the residue to collect precipitate formed by filtration, thereby obtaining the title compound (120 mg).

$^1$H-NMR (DMSO-$d_6$) δ: 1.63-1.73 (4H, m), 1.99-2.06 (2H, m), 2.91 (3H, s), 3.09-3.14 (1H, m), 3.25-3.70 (4H, m), 4.27-4.32 (1H, m), 4.42-4.46 (1H, m), 4.68-4.71 (1H, m), 8.20-8.23 (3H, m), 9.09 (1H, d, J=8.3 Hz), 11.82-12.01 (1H, m). MS (ESI) m/z: 281 (M+H)$^+$.

Referential Example 63

N-[(1R*,2R*)-2-Aminocyclopentyl]-5-chloro-1H-indol-2-carboxamide Hydrochloride

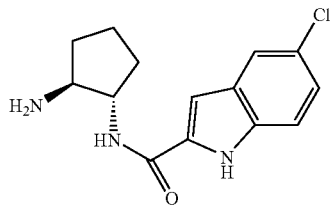

The compound (1.40 g) obtained in Referential Example 61 was dissolved in N,N-dimethylformamide (15 ml), and to the solution 5-chloroindole-2-carboxylic acid (1.64 g), 1-(3-dimethylaminopropyl)-3-ethylcarbodiimide hydrochloride (2.68 g) and 1-hydroxybenzotriazole monohydrate (473 mg) were added. The mixture was stirred at room temperature for 23 hours. The solvent was distilled off under reduced pressure, and methylene chloride and a saturated solution of sodium hydrogencarbonate were added to the residue to collect precipitates by filtration. The precipitates were washed with ethyl acetate, methylene chloride and methanol. On the other hand, the filtrate was separated to give an organic layer, which was taken out and dried over anhydrous sodium sulfate, and the solvent was then distilled off under reduced pressure. The residue was purified by flash column chromatography on silica gel (methylene chloride:methanol=19:1) to obtain a pale yellow solid. This pale yellow solid was combined with the precipitates obtained by the filtration and dissolved in methylene chloride (10 ml), and trifluoroacetic acid (10 ml) was added to stir the mixture at room temperature for 3 hours. The solvent was distilled off under reduced pressure, and methylene chloride and 1N aqueous solution of sodium hydroxide were added to the residue to collect precipitate by filtration. The organic layer of the filtrate was separated and dried over anhydrous sodium sulfate. The precipitates collected by the filtration were added to this solution, and a 4N dioxane solution (20 ml) of hydrochloric acid was further added. The solvent was distilled off under reduced pressure, and methylene chloride (10 ml) and a 4N dioxane solution (10 ml) of hydrochloric acid were added to the residue. The solvent was distilled off again under reduced pressure. Ethyl acetate was added to the residue to collect precipitates formed by filtration, thereby obtaining the title compound (1.83 g).

$^1$HNMR (DMSO-d$_6$) δ: 1.60-1.75 (4H, m), 2.05-2.10 (2H, m), 3.49 (1H, q, J=7.6 Hz), 4.27 (4H, quintet, J=7.6 Hz), 7.17 (1H, d, J=8.6 Hz), 7.19 (1H, s), 7.42 (1H, d, J=8.6 Hz), 7.70 (1H, s), 8.24 (3H, br.s), 8.85 (1H, d, J=7.3 Hz), 11.91 (1H, s). MS (ESI) m/z: 278 (M+H)$^+$.

Referential Example 64 tert-Butyl (1R*,2R*)-2-aminocyclohexylcarbamate

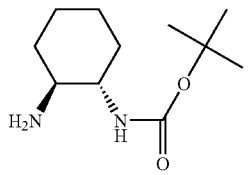

The title compound was obtained from (±)-trans-1,2-cyclohexanediamine in a similar manner to Referential Example 61.

m.p. 79-81. $^1$H-NMR (CDCl$_3$) δ: 1.05-1.34 (4H, m), 1.45 (9H, s), 1.68-1.75 (2H, m), 1.92-2.02 (2H, m), 2.32 (1H, dt, J=10.3, 3.9 Hz), 3.08-3.20 (1H, m), 4.50 (1H, br.s). MS (FAB) m/z: 215 (M+H)$^+$.

Referential Example 65

N-[(1R*,2R*)-2-Aminocyclohexyl]-5-methyl-4,5,6,7-tetrahydrothiazolo[5,4-c]pyridine-2-carboxamide trifluoroacetate(hydrochloride)

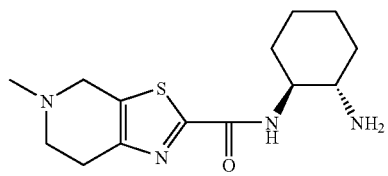

The title compound was obtained from the compound obtained in Referential Example 64 in a similar manner to Referential Example 62.

$^1$H-NMR (DMSO-d$_6$) δ: 1.10-1.80 (7H, m), 1.95-2.05 (1H, m), 2.97 (3H, s), 3.00-3.20 (3H, m), 3.63 (2H, br.s), 3.72-3.88 (1H, m), 4.61 (2H, br.s), 7.98 (3H, s), 8.89 (1H, d, J=9.2 Hz). MS (FAB) m/z: 295 (M+H)$^+$.

The hydrochloride was obtained in a similar manner.

Referential Example 66 tert-Butyl (1R*,2S*)-2-aminocyclohexylcarbamate

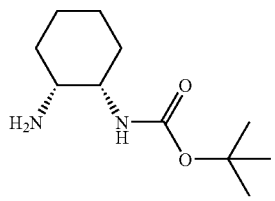

The title compound was obtained from cis-1,2-cyclohexanediamine in a similar manner to Referential Example 61.

$^1$H-NMR (CDCl$_3$) δ: 1.30-1.70 (17H, m), 2.98-3.05 (1H, m), 3.60 (1H, br.s), 4.98 (1H, br.s). MS (FAB) m/z: 215 (M+H)$^+$.

Referential Example 67

N-[(1R*,2S*)-2-Aminocyclohexyl]-5-methyl-4,5,6,7-tetrahydrothiazolo[5,4-c]pyridine-2-carboxamide hydrochloride(trifluoroacetate)

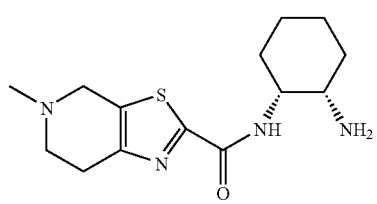

The title compound was obtained from the compound obtained in Referential Example 66 in a similar manner to Referential Example 62.

$^1$H NMR (DMSO-d$_6$) δ: 1.30-1.90 (8H, m), 2.92 (3H, s), 3.05-3.79 (5H, m), 4.23 (1H, br.s), 4.34-4.79 (2H, m), 8.01-8.34 (3H, m), 8.30-8.49 (1H, m), 11.90-12.30 (1H, m). MS (FAB) m/z: 295 (M+H)⁺.

The trifluoroacetate was obtained in a similar manner.

Referential Example 68 tert-Buthyl (1R*,2R*)-2-{[(5-chloroindol-2-yl)carbonyl]-amino}cyclohexylcarbamate

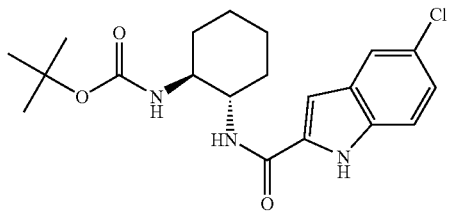

5-Chloroindole-2-carboxylic acid (2.88 g), 1-hydroxybenzotriazole monohydrate (2.08 g) and 1-(3-dimethylaminopropyl)-3-ethylcarbodiimide hydrochloride (2.95 g) were added to a solution of the compound (3.00 g) obtained in Referential Example 64 in N,N-dimethylformamide (10 ml) at room temperature. After stirring for 3 days, the reaction mixture was concentrated under reduced pressure, and methylene chloride (30 ml), a saturated aqueous solution of sodium hydrogencarbonate (150 ml) and water (150 ml) were added to the residue. After collecting colorless precipitate formed by filtration and the precipitate was dried to obtain the title compound (5.21 g).

¹H-NMR (DMSO-d₆) δ: 1.10-1.45 (4H, m), 1.21 (9H, s), 1.68 (2H, d, J=8.1 Hz), 1.86 (2H, t, J=16.2 Hz), 3.22-3.42 (1H, m), 3.69 (1H, br.s), 6.66 (1H, d, J=8.5 Hz), 7.02 (1H, s), 7.15 (1H, dd, J=8.5, 2.0 Hz), 7.41 (1H, d, J=8.5 Hz), 7.67 (1H, d, J=2.0 Hz), 8.15 (1H, d, J=8.1 Hz), 11.73 (1H, br.s). MS (ESI) m/z: 392 (M+H)⁺.

Referential Example 69

N-[(1R*,2R*)-2-Aminocyclohexyl]-5-chloroindole-2-carboxamide Hydrochloride

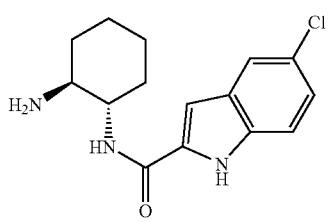

An ethanol solution (100 ml) of hydrochloric acid was added to a solution of the compound (5.18 g) obtained in Referential Example 68 in methylene chloride (100 ml) at room temperature. After stirring for 2 days, the reaction mixture was concentrated under reduced pressure, diethyl ether (300 ml) was added to the resultant residue, and colorless precipitate formed was collected by filtration and dried to obtain the title compound (4.30 g).

¹H-NMR (DMSO-d₆) δ: 1.20-1.36 (2H, m), 1.36-1.50 (2H, m), 1.60 (2H, br.s), 1.90 (1H, d, J=13.0 Hz), 2.07 (1H, d, J=13.7 Hz), 3.06 (1H, br.s), 3.83-3.96 (1H, m), 7.15-7.24 (2H, m), 7.45 (1H, d, J=8.6 Hz), 7.73 (1H, s), 8.00 (3H, br.s), 8.60 (1H, d, J=8.3 Hz), 11.86 (1H, s). MS (ESI) m/z: 292 (M+H)⁺.

Referential Example 70 tert-Buthyl (1R*,2S*)-2-{[(5-chloroindol-2-yl)carbonyl]-amino}cyclohexylcarbamate

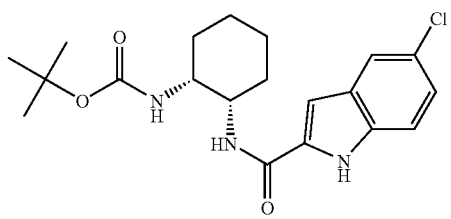

The title compound was obtained from the compound obtained in Referential Example 66 in a similar manner to Referential Example 68.

¹H-NMR (DMSO-d₆) δ: 1.20-1.45 (11H, m), 1.45-1.70 (4H, m), 1.70-1.85 (2H, m), 3.76 (1H, br.s), 4.08 (1H, br.s), 6.64 (1H, d, J=7.6 Hz), 7.12 (1H, s), 7.16 (1H, dd, J=8.8, 2.0 Hz), 7.43 (1H, d, J=8.8 Hz), 7.69 (1H, d, J=2.0 Hz), 7.85 (1H, d, J=6.9 Hz), 11.80 (1H, br.s). MS (ESI) m/z: 392 (M+H)⁺.

Referential Example 71

N-[(1R*,2S*)-2-Aminocyclohexyl]-5-chloroindole-2-carboxamide Hydrochloride

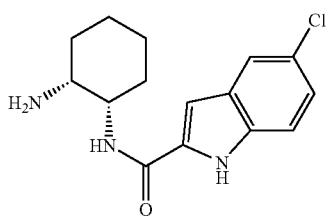

The title compound was obtained from the compound obtained in Referential Example 70 in a similar manner to Referential Example 69.

¹H-NMR (DMSO-d₆) δ: 1.30-1.50 (2H, m), 1.55-1.95 (6H, m), 3.41 (1H, br.s), 4.32 (1H, br.s), 7.19 (1H, dd, J=8.7, 2.0 Hz), 7.33 (1H, s), 7.45 (1H, d, J=8.7 Hz), 7.60-7.90 (4H, m), 8.17 (1H, d, J=7.1 Hz), 11.91 (1H, s). MS (FAB) m/z: 292 (M+H)⁺.

Referential Example 72

(1R*,2R*)-1,2-Cycloheptanediol

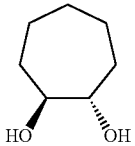

Cycloheptene (3.85 g) was added portionwise to 30% aqueous hydrogen peroxide (45 ml) and 88% formic acid (180 ml), and the mixture was stirred at 40 to 50° C. for 1 hour and then at room temperature for a night. The solvent was distilled off under reduced pressure, and a 35% aqueous solution of sodium hydroxide was added to the residue to alkalify it. After this residue was stirred at 40 to 50° C. for 10 minutes, ethyl acetate was added to conduct liquid separation. The resultant water layer was extracted 4 times with ethyl acetate. The resultant organic layers were collected and dried over anhydrous sodium sulfate, and the solvent was distilled off under reduced pressure to obtain the title compound (4.56 g).

$^1$H-NMR (CDCl$_3$) δ: 1.44-1.56 (6H, m), 1.63-1.70 (2H, m), 1.83-1.91 (2H, m), 2.91 (2H, br.s), 3.40-3.44 (2H, m). MS (FAB) m/z: 131 (M+H)$^+$.

Referential Example 73

(1R*,2R*)-1,2-Cycloheptanediamine Hydrochloride

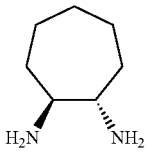

The compound (4.56 g) obtained in Referential Example 72 was dissolved in methylene chloride (35 ml), triethylamine (29 ml) was added, and the mixture was cooled to −78° C. Methanesulfonyl chloride (8.13 ml) was added dropwise thereto. Methylene chloride (10 ml) was slowly added, and the mixture was stirred for 20 minutes at the same temperature and then for 1.5 hours at 0° C. Water was added to the reaction mixture to conduct liquid separation, and the resultant organic layer was washed with a saturated aqueous solution of sodium hydrogencarbonate and dried over anhydrous sodium sulfate. The solvent was distilled off under reduced pressure to obtain an oil. This oil was dissolved in N,N-dimethylformamide (90 ml), sodium azide (13.65 g) was added, and the mixture was stirred at 65° C. for 18 hours. Ether and water was added to the reaction mixture to conduct liquid separation. The resultant ether layer was washed with a saturated aqueous solution of sodium hydrogencarbonate and saturated aqueous solution of sodium chloride and dried over anhydrous sodium sulfate. The solvent was distilled off under reduced pressure to obtain an oil.

This oil was dissolved in ethanol (70 ml), 10% palladium on carbon (containing 50% of water, 4 g) was added, and the mixture was stirred for 4 days in a hydrogen (3.5 atm) atmosphere. After separating the palladium on carbon by filtration, a 1N ethanol solution (70 ml) of hydrochloric acid was added to the filtrate, and the solvent was distilled off under reduced pressure. The residue was dissolved in methanol, ethyl acetate was added, and the solvent was distilled off under reduced pressure again. Precipitate formed was collected by filtration to obtain the title compound (3.57 g).

$^1$H-NMR (DMSO) δ: 1.44 (4H, br.s), 1.73-1.81 (6H, m), 3.43 (2H, br.s), 8.63 (6H, br.s). MS (ESI) m/z: 129 (M+H)$^+$.

Referential Example 74

N-[(1R*,2R*)-2-Aminocycloheptyl]-5-chloroindole-2-carboxamide

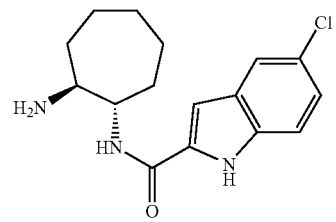

The title compound was obtained from the compound obtained in Referential Example 73 in a similar manner to Referential Example 59.

$^1$H-NMR (DMSO-d$_6$) δ: 1.49-1.52 (4H, m), 1.72-1.91 (6H, m), 4.04-4.10 (1H, m), 7.17-7.23 (2H, m), 7.44 (1H, d, J=8.8 Hz), 7.72 (1H, d, J=2.0 Hz), 7.96 (2H, br.s), 8.75 (1H, d, J=8.5 Hz), 11.89 (1H, br.s). MS (ESI) m/z: 306 (M+H)$^+$.

Referential Example 75

(1R*,2S*)-1,2-Cyclooctanediol

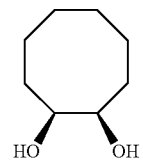

Cyclooctene (4.41 g) was dissolved in acetonitrile (45 ml) and water (15 ml), and to the solution N-methylmorpholine N-oxide (5.15 g) and microcapsulated osmium tetroxide (1 g, containing 10% osmium tetroxide) were added, and the mixture was stirred at 40 to 50° C. for 21 hours. Insoluble microcapsulated osmium tetroxide was removed by filtration, and washed with acetonitrile, and the filtrate was concentrated under reduced pressure. The residue was purified by flash column chromatography on silica gel (hexane:ethyl acetate=1:1) to obtain the title compound (4.97 g).

$^1$H-NMR (CDCl$_3$) δ: 1.48-1.58 (6H, m), 1.64-1.75 (4H, m), 1.86-1.96 (2H, m), 2.28 (2H, d, J=2.9 Hz), 3.90 (2H, d, J=8.3 Hz). MS (FAB) m/z: 145 (M+H)$^+$.

Referential Example 76

(1R*,2S*)-1,2-diazidocyclooctane

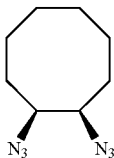

After cis-1,2-cyclooctanediol (4.82 g) was dissolved in methylene chloride (60 ml), and to the solution triethylamine (27.7 ml) was added, and the interior of a vessel was purged with argon, the mixture was cooled to −78° C., and methanesulfonyl chloride (7.7 ml, 100 mmol) was added dropwise thereto. The mixture was stirred for 1 hour at the same temperature and then for 1 hour at 0° C. Water was then added to the reaction mixture to conduct liquid separation, and the resultant organic layer was washed with water, 0.5N hydrochloric acid, water and a saturated aqueous solution of sodium hydrogencarbonate and dried over anhydrous sodium sulfate. The solvent was distilled off under reduced pressure, and the residue was dissolved in N,N-dimethylformamide (80 ml), sodium azide (13.0 g) was added, and the mixture was stirred at 65° C. for 19 hours. Ether and water was added to the reaction mixture to conduct liquid separation. The resultant ether layer was washed with a saturated aqueous solution of sodium hydrogencarbonate and saturated aqueous solution of sodium chloride and dried over anhydrous sodium sulfate. The solvent was distilled off under reduced pressure, and the residue was purified by flash column chromatography on silica gel (hexane:ethyl acetate=6:1) to obtain the title compound (4.85 g).

$^1$H-NMR (CDCl$_3$) δ: 1.49-1.64 (6H, m), 1.67-1.78 (2H, m), 1.81-1.97 (4H, m), 3.74-3.76 (2H, m).

Referential Example 77

(1R*,2S*)-1,2-Cyclooctanediamine Hydrochloride

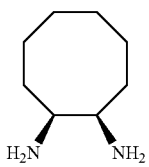

The compound (4.85 g) obtained in Referential Example 76 was dissolved in ethanol (55 ml), to the solution 10% palladium on carbon (containing 50% of water, 3.0 g) was added, and the mixture was stirred for 21 hours in a hydrogen (4.5 atm) atmosphere. After separating the catalyst by filtration, a 1N ethanol solution (50 ml) of hydrochloric acid was added to the filtrate, and the solvent was distilled off under reduced pressure. Ethyl acetate was added to the residue, and precipitate formed was collected by filtration to obtain the title compound (4.14 g).

$^1$H-NMR (DMSO) δ: 1.51 (6H, br.s), 1.69 (2H, br.s), 1.79-1.99 (4H, m), 3.68-3.70 (2H, m), 8.66 (6H, br.s). MS (ESI) m/z: 143 (M+H)$^+$.

Referential Example 78

N-[(1R*,2S*)-2-aminocyclooctyl]-5-chloroindole-2-carboxamide

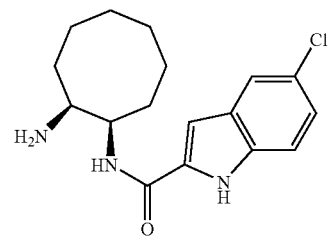

The title compound was obtained from the compound obtained in Referential Example 77 in a similar manner to Referential Example 59.

MS (ESI) m/z: 320 (M+H)$^+$.

Referential Example 79

(1R*,2R*)-4-Methoxy-1,2-cyclopentanediol
(Mixture of 4-Position Stereoisomers)

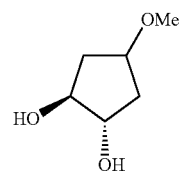

60% Sodium hydride (800 mg) was added portionwise to a solution of 3-cyclopentene-1-ol (1.68 g) and methyl iodide (1.25 ml) dissolved in tetrahydrofuran (20 ml) under ice cooling, and the mixture was stirred overnight at room temperature. Water and diethyl ether was added to the reaction mixture to separate an organic layer, the organic layer was dried over anhydrous magnesium sulfate, and the solvent was distilled off under reduced pressure with ice cooling to obtain crude 4-methoxy-1-cyclopentene.

88% Formic acid (90 ml) and 30% hydrogen peroxide (3.17 ml) were added to 4-methoxy-1-cyclopentene thus obtained, and the mixture was stirred overnight at room temperature. The reaction mixture was concentrated under reduced pressure, and a 35% aqueous solution of sodium hydroxide was added to the residue to alkalify the reaction mixture, followed by stirring at 50° C. for 10 minutes. The reaction mixture was cooled to room temperature and extracted with ethyl acetate to dry the organic layer over anhydrous magnesium sulfate. The solvent was distilled off, and the residue was purified by column chromatography on silica gel (methanol:methylene chloride=1:19) to obtain the title compound (1.21 g).

$^1$H-NMR (CDCl$_3$) δ: 1.65-1.85 (2H, m), 2.15-2.30 (2H, m), 3.28 (3H, s), 3.90-4.00 (2H, m), 4.26 (1H, br.s).

Referential Example 80

(1R*,2R*)-1,2-Diazido-4-methoxycyclopentane (Mixture of 4-Position Stereoisomers)

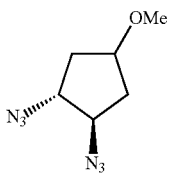

The compound (1.21 g) obtained in Referential Example 79 and triethylamine (7.66 ml) were dissolved in methylene chloride (20 ml), and methanesulfonyl chloride (2.13 ml) was added dropwise over 20 minutes at −78° C. After completion of drop addition, the mixture was warmed to 0° C. and stirred for 80 minutes to obtain crude (1R*,2R*)-1,2-bis(methanesulfonyloxy)-4-methoxycyclopentane. This product was dissolved in N,N-dimethylformamide (20 ml), and sodium azide (3.57 g) was added to heat and stir the mixture at 65° C. for 22 hours. Sodium azide (3.57 g) was additionally added to stir the mixture at 70° C. for 2 days. The reaction mixture was allowed to cool, and water and diethyl ether was added to separate an organic layer. The organic layer was dried over anhydrous magnesium sulfate. The solvent was distilled off, and the residue was purified by column chromatography on silica gel (hexane:ethyl acetate=2:1) to obtain the title compound (584 mg).

$^1$H-NMR (CDCl$_3$) δ: 1.65-1.80 (2H, m), 2.05-2.18 (1H, m), 2.25-2.40 (1H, m), 3.21 (3H, s), 3.55-3.65 (1H, m), 3.75-3.90 (2H, m).

Referential Example 81

(1R*,2R*)-4-Methoxy-1,2-cyclopentane Diamine Hydrochloride (Mixture of 4-Position Stereoisomers)

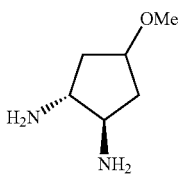

The compound (584 mg) obtained in Referential Example 80 was dissolved in ethanol, and 10% palladium on carbon (321 mg) was added to conduct hydrogenation at normal temperature and normal pressure for 2 days. After removing the catalyst by filtration, the reaction mixture was concentrated, and a 1N ethanol solution of hydrochloric acid and ethyl acetate were added to the residue. The mixture was concentrated to obtain the title compound (488 mg).

$^1$H-NMR (CDCl$_3$) δ: 1.72-1.83 (1H, m), 1.91-2.03 (1H, m), 2.07-2.18 (1H, m), 2.37-2.50 (1H, m), 3.19 (3H, s), 3.55-3.75 (2H, br), 3.85-3.95 (1H, m), 8.60-8.90 (6H, br). MS (ESI) m/z: 261 (2M+H)$^+$.

Referential Example 82

N-[(1R*,2R*)-2-Amino-4-methoxycyclopentyl]-5-chloroindole-2-carboxamide (Mixture of 4-Position Stereoisomers)

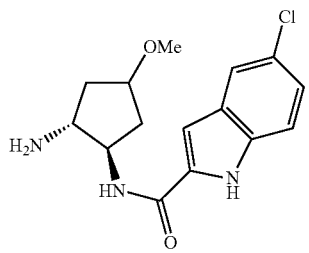

The compound (470 mg) obtained in Referential Example 81 was suspended in N,N-dimethylformamide (5 ml), and triethylamine (0.966 ml) and p-nitrophenyl 5-chloroindole-2-carboxylate (805 mg) was added. The mixture was stirred at room temperature for 4 days. After the solvent was distilled off under reduced pressure, and methylene chloride and a saturated aqueous solution of sodium hydrogencarbonate were added to conduct liquid separation, an organic layer was dried over anhydrous sodium sulfate. The solvent was distilled off under reduced pressure, and the residue was purified by column chromatography on silica gel (methanol:methylene chloride=1:9) to obtain the title compound (268 mg).

Referential Example 83

(1R*,2R*)-4-[(Benzyloxy)methyl]-1,2-cyclopentanediol (Mixture of 4-Position Stereoisomers)

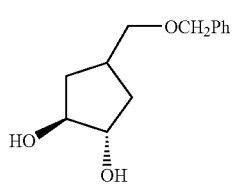

The title compound was obtained by benzylating 4-hydroxymethyl-1-cyclopentene (J. Heterocycl. Chem., 1989, Vol. 26, p. 451) with benzyl bromide and then reacting the product with formic acid-hydrogen peroxide in a similar manner to Referential Example 79.

$^1$H-NMR (CDCl$_3$) δ: 1.44-1.52 (1H, m), 1.77-1.85 (1H, m), 1.89-1.97 (1H, m), 2.25-2.35 (1H, m), 2.46-2.58 (1H, m), 3.40-3.50 (2H, m), 3.89 (1H, br.s), 4.08 (1H, br.s), 4.54 (2H, s), 7.27-7.39 (5H, m). MS (FAB) m/z: 223 (M+H)$^+$.

Referential Example 84

(1R*,2R*)-4-[(Benzyloxy)methyl]-1,2-cyclopentanediamine (Mixture of 4-Position Stereoisomers)

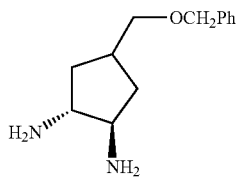

(1R*,2R*)-4-Benzyloxymethyl-1,2-diazidocyclopentane was obtained from the compound obtained in Referential Example 83 in a similar manner to Referential Example 80. The title compound was obtained in a similar manner to Referential Example 81 without purifying this product.

Referential Example 85

N-{(1R*,2R*)-2-Amino-4-[(benzyloxy)methyl]cyclopentyl}-5-chloroindole-2-carboxamide (Mixture of 4-Position Stereoisomers)

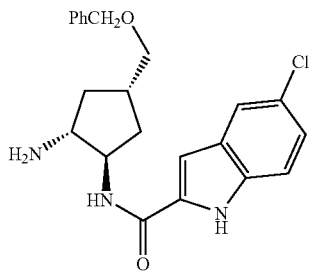

The title compound was obtained from the compound obtained in Referential Example 84 in a similar manner to Referential Example 59.

$^1$H-NMR (DMSO-$d_6$) δ: 1.07-1.15 (0.5H, m), 1.26-1.35 (0.5H, m), 1.47-1.55 (0.5H, m), 1.61-1.79 (1H, m), 1.83-1.92 (0.5H, m), 1.99-2.10 (0.5H, m), 2.12-2.20 (0.5H, m), 2.27-2.40 (1H, m), 3.10-3.20 (1H, m), 3.33-3.39 (2H, m), 3.81-3.92 (1H, m), 4.48 (2H, s), 7.13-7.20 (2H, m), 7.22-7.39 (5H, m), 7.43 (1H, d, J=8.5 Hz), 7.69 (1H, d, J=2.2 Hz), 8.34 (1H, t, J=7.1 Hz). MS (FAB) m/z: 398 (M+H)$^+$.

Referential Example 86

Ethyl (1R*,3R*,6S*)-7-oxabicyclo[4.1.0]heptane-3-carbooxylate

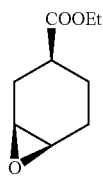

(1R*,4R*,5R*)-4-Iodo-6-oxabicyclo[3.2.1]octan-7-one (J. Org. Chem., 1996, Vol. 61, p. 8687) (14.3 g) was dissolved in ethanol (130 ml), a 2N aqueous solution (34.5 ml) of sodium hydroxide was added under ice cooling, and the mixture was then stirred at room temperature for 7 hours. After the solvent was distilled off under reduced pressure, and water was added to the residue to conduct extraction with methylene chloride, the extract was dried over anhydrous sodium sulfate. The solvent was distilled off under reduced pressure, and the residue was purified by column chromatography on silica gel (hexane:ethyl acetate=83:17) to obtain the title compound (6.54 g).

$^1$H-NMR (CDCl$_3$) δ: 1.25 (3H, t, J=7.1 Hz), 1.50-1.70 (2H, m), 1.71-1.82 (1H, m), 2.08-2.28 (4H, m), 3.16 (2H, s), 4.12 (2H, q, J=7.1 Hz).

Referential Example 87

Ethyl (1R*,3S*,4S*)-3-azido-4-hydroxycyclohexanecarboxylate

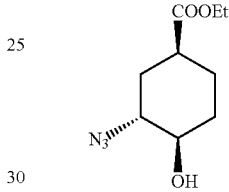

The compound (13.6 g) obtained in Referential Example 86 was dissolved in N,N-dimethylformamide (100 ml), ammonium chloride (6.45 g) and sodium azide (7.8 g) were successively added at room temperature, and the mixture was then stirred at 75° C. for 12 hours. The solvent was concentrated to about 1/3, and the residue was diluted with water and ethyl acetate to conduct stirring for 3 minutes. The resultant organic layer was washed with water and saturated aqueous solution of sodium chloride and dried over anhydrous magnesium sulfate. The solvent was distilled off under reduced pressure, and the residue was purified by column chromatography on silica gel (ethyl acetate:hexane=1:4) to obtain the title compound (15.8 g).

$^1$H-NMR (CDCl$_3$) δ: 1.28 (3H, t, J=7.1 Hz), 1.37-1.67 (2H, m) 1.86-1.95 (1H, m), 2.04-2.18 (2H, m), 2.32-2.43 (1H, m), 2.68-2.78 (1H, m), 3.40-3.60 (2H, m), 4.17 (2H, q, J=7.1 Hz).

Referential Example 88

Ethyl (1R*,3S*,4S*)-3-[(tert-butoxycarbonyl)amino]]-4-hydroxycyclohexanecarboxylate

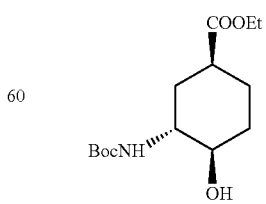

The compound (100 mg) obtained in Referential Example 87 and di-tert-butyl dicarbonate (133 mg) were dissolved in ethyl acetate (12 ml) and a catalytic amount of 10% palladium on carbon was added to stir the mixture at room temperature for 12 hours in a hydrogen atmosphere. After insoluble matter was removed by filtration, the solvent was distilled off under reduced pressure, and the residue was purified by column chromatography on silica gel (hexane:ethyl acetate=3:1) to obtain the title compound (145 mg).

$^1$H-NMR (CDCl$_3$) δ: 1.28 (3H, t, J=7.1 Hz), 1.45 (9H, s), 1.38-1.57 (2H, m), 1.86-1.95 (1H, m), 2.05-2.17 (1H, m), 2.29-2.39 (2H, m), 2.61-2.68 (1H, m), 3.25-3.66 (3H, m), 4.17 (2H, q, J=7.1 Hz), 4.53 (1H, br.s).

Referential Example 89

Ethyl (1R*,3S*,4R*)-4-azido-3-[(tert-butoxycarbonyl)amino]-cyclohexanecarboxylate and ethyl (1R*,3S*,4S*)-4-azido-3-[(tert-butoxycarbonyl)amino]cyclohexanecarboxylate

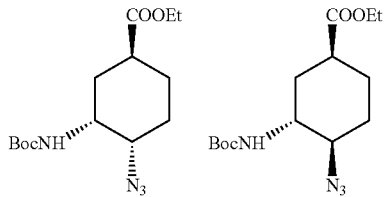

After the compound (16 g) obtained in Referential Example 88 and triethylamine (38 ml) were dissolved in methylene chloride (150 ml), and the solution was cooled to −78° C., methanesulfonyl chloride (13 ml) was added dropwise at the same temperature. After stirring for 15 minutes at the same temperature, the mixture was heated to 0° C. and stirred for 30 minutes and then 2 hours at room temperature. After 0.1N hydrochloric acid was added, and the mixture was diluted with methylene chloride, the resultant organic layer was separated, washed with a saturated aqueous solution of sodium hydrogencarbonate and saturated aqueous solution of sodium chloride and dried over anhydrous magnesium sulfate. The solvent was distilled off under reduced pressure to obtain crude ethyl (1R*,3S*,4S*)-3-[(tert-butoxycarbonyl)amino]-4-[(methanesulfonyl)oxy]cyclohexane-carboxylate.

The product obtained above was dissolved in N,N-dimethylformamide (100 ml), and sodium azide (18 g) was added at room temperature. The mixture was heated to 75° C. and stirred for 12 hours. The solvent was concentrated to about 1/3, and the residue was diluted with water and ethyl acetate to conduct stirring for 3 minutes. The resultant organic layer was separated, washed with saturated aqueous solution of sodium chloride and dried over anhydrous magnesium sulfate. The solvent was distilled off under reduced pressure, and the residue was purified by column chromatography on silica gel (ethyl acetate:hexane=1:4) to obtain the title compounds [(1R*,3S*,4R*)-form (6.74 g) and (1R*,3S*,4S*)-form (1.32 g)].

(1R*,3S*,4R*)-Form:

$^1$H-NMR (CDCl$_3$) δ: 1.26 (3H, t, J=7.1 Hz), 1.45 (9H, s), 1.38-2.33 (6H, m), 2.57-2.68 (1H, m), 3.77-4.20 (4H, m), 4.63 (1H, br.s).

(1R*,3S*,4S*)-Form:

$^1$H-NMR (CDCl$_3$) δ: 1.27 (3H, t, J=7.1 Hz), 1.46 (9H, s), 1.53-2.30 (6H, m), 2.50-2.65 (1H, m), 3.42-3.72 (2H, m), 4.15 (2H, q.J=7.1 Hz), 4.67 (1H, br.s).

Referential Example 90

Ethyl (1R*,3S*,4R*)-4-amino-3-[(tert-butoxycarbonyl)amino]cyclohexanecarboxylate

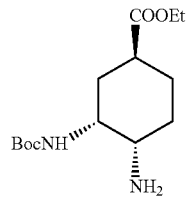

Ethyl (1R*,3S*,4R*)-4-azido-3-[(tert-butoxycarbonyl)amino]cyclohexanecarboxylate (5.4 g) obtained in Referential Example 89 was dissolved in a mixed solvent of ethanol (10 ml) and ethyl acetate (10 ml), and a catalytic amount of 10% palladium on carbon was added to stir the mixture at room temperature for 20 hours in a hydrogen atmosphere. After insoluble matter was removed by filtration, the solvent was distilled off under reduced pressure to obtain the title compound (4.7 g).

Referential Example 91

Ethyl (1R*,3S*,4R*)-3-[(tert-butoxycarbonyl)amino]-4-{[(5-chloroindol-2-yl)carbonyl]amino}cyclohexanecarboxylate

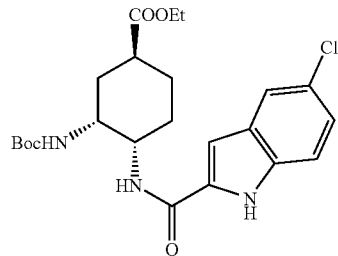

The compound (4.62 g) obtained in Referential Example 90 was dissolved in methylene chloride (50 ml), 5-chloroindole-2-carboxylic acid (3.63 g), 1-hydroxybenzotriazole monohydrate (2.43 g) and 1-(3-dimethylaminopropyl)-3-ethylcarbodiimide hydrochloride (3.45 g) were added at room temperature, and the mixture was stirred for 12 hours. After 0.1N hydrochloric acid was added, and the mixture was extracted with methylene chloride, the resultant organic layer was washed with a saturated aqueous solution of sodium hydrogencarbonate and saturated aqueous solution of sodium chloride and dried over anhydrous magnesium sulfate. The solvent was distilled off under reduced pressure, and the residue was purified by column chromatography on silica gel (ethyl acetate:hexane=2:3) to obtain the title compound (5.3 g).

$^1$H-NMR (CDCl$_3$) δ: 1.26 (3H, t, J=7.1 Hz), 1.43 (9H, s), 1.35-2.46 (7H, m), 3.91-4.02 (1H, m), 4.10-4.22 (2H, m), 4.79 (1H, br.s), 6.79 (1H, s), 7.18-7.40 (2H, m), 7.59 (1H, s), 8.00 (1H, br.s), 9.13 (1H, br.s).

Referential Example 92

Ethyl (1S,3S,6R)-7-oxabicyclo[4.1.0]heptane-3-carboxylate (1S,4S,5S)-4-Iodo-6-oxabicyclo[3.2.1]octan-7-one (J. Org. Chem., 1996, Vol. 61, p. 8687) (89.3 g) was suspended in ethanol (810 ml), a 2N aqueous solution (213 ml) of sodium hydroxide was added, and the mixture was then stirred at room temperature for 3 hours. After the solvent was distilled off under reduced pressure, and water was added to the residue to conduct extraction with methylene chloride, the extract was dried over anhydrous magnesium sulfate. The solvent was distilled off under reduced pressure, and the residue was purified by column chromatography on silica gel (hexane:ethyl acetate=17:3) to obtain the title compound (41.3 g).

$[\alpha]_D^{25}=-58°$ (C=1.0, chloroform).

Referential Example 93

Ethyl (1S,3R,4R)-3-azido-4-hydroxycyclohexanecarboxylate

The compound (41 g) obtained in Referential Example 92 was dissolved in N,N-dimethylformamide (300 ml), ammonium chloride (19.3 g) and sodium azide (23.5 g) were successively added at room temperature, and the mixture was then stirred at 76° C. for 13 hours. The reaction mixture was filtered, the filtrate was concentrated, the product previously captured by the filter was put in the residue, and water was added to dissolve the collected product. The solution was extracted with ethyl acetate. The resultant organic layer was washed with water and saturated aqueous solution of sodium chloride and then dried over anhydrous magnesium sulfate. The solvent was distilled off under reduced pressure to obtain the title compound (51.5 g).

$[\alpha]_D^{25}=+8°$ (C=1.0, chloroform).

Referential Example 94

Ethyl (1S,3R,4R)-3-[(tert-butoxycarbonyl)amino]-4-hydroxycyclohexanecarboxylate

The compound (51.2 g) obtained in Referential Example 93 and di-tert-butyl dicarbonate (68.1 g) were dissolved in ethyl acetate (1000 ml), 5% palladium on carbon (5.0 g) was added, and the mixture was stirred overnight at room temperature under a hydrogen pressure of 7 kg/cm². After insoluble matter was removed by filtration, the solvent was distilled off under reduced pressure, the residue was purified by column chromatography on silica gel (hexane:ethyl acetate=4:1→3:1), and hexane was added to solidify it to obtain the title compound (46.9 g).

$[\alpha]_D^{25}=+25°$ (C=1.0, chloroform).

Referential Example 95

Ethyl (1S,3R,4S)-4-azido-3-[(tert-butoxycarbonyl)amino]-cyclohexanecarboxylate and ethyl (1S,3R,4R)-4-azido-3-[(tert-butoxycarbonyl)amino]cyclohexanecarboxylate The compound (53.5 g) obtained in Referential Example 94 and triethylamine (130 ml) were dissolved in methylene chloride (500 ml), and methanesulfonyl chloride (42 ml) was added dropwise over 20 minutes under cooling at −10° C. to −15° C. After stirring for 20 minutes at the same temperature, the mixture was heated to room temperature over 2 hours. The reaction mixture was cooled to 0° C., 0.5N hydrochloric acid (800 ml) was added dropwise, and the mixture was extracted with methylene chloride. The resultant organic layer was washed with a saturated aqueous solution of sodium hydrogencarbonate and saturated aqueous solution of sodium chloride and dried over anhydrous magnesium sulfate. The solvent was distilled off under reduced pressure to obtain crude ethyl (1S,3R,4R)-3-[(tert-butoxycarbonyl)amino]-4-[(methylsulfonyl)oxy]cyclohexanecarboxylate.

The crude product obtained above was dissolved in N,N-dimethylformamide (335 ml), and sodium azide (60.5 g) was added to stir the mixture at 67° C. to 75° C. for 16 hours. The reaction mixture was filtered, the filtrate was concentrated to distill off 250 ml of the solvent, the product captured by the filter was put in the residue, and the collected product was dissolved in water and extracted with ethyl acetate. The resultant organic layer was washed with saturated aqueous solution of sodium chloride and dried over anhydrous magnesium sulfate. The solvent was distilled off under reduced pressure, and the residue was purified by column chromatography on silica gel (ethyl acetate:hexane=1:4) to obtain the title compounds [(1S,3R,4S)-form (18.4 g) and (1S,3R,4R)-form (3.3 g)].

(1S,3R,4S)-form: $[\alpha]_D^{25}=+62°$ (C=1.0, chloroform).
(1S,3R,4R)-form: $[\alpha]_D^{25}=-19°$ (C=1.0, chloroform).

Referential Example 96

Ethyl (1S,3R,4S)-4-Amino-3-[(tert-butoxycarbonyl)amino]cyclohexanecarboxylate

The compound (4.0 g) obtained in Referential Example 95 was dissolved in a mixed solvent of ethanol (150 ml) and ethyl acetate (150 ml), and 5% palladium on carbon (0.5 g) was added to stir the mixture at room temperature for 17 hours in a hydrogen atmosphere (5 kg/cm²). After insoluble matter was removed by filtration, the solvent was distilled off under reduced pressure to obtain the title compound (4.2 g).

Referential Example 97

Ethyl (1S,3R,4S)-3-[(tert-butoxycarbonyl)amino]-4-{[(5-chloroindol-2-yl)carbonyl]amino}cyclohexanecarboxylate

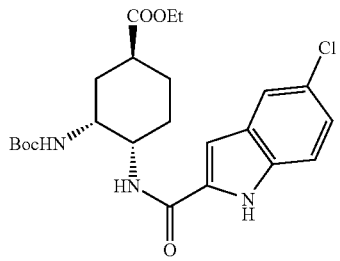

The compound (4.2 g) obtained in Referential Example 96 was dissolved in methylene chloride (50 ml), 5-chloroindole-2-carboxylic acid (3.33 g), 1-hydroxybenzotriazole monohydrate (2.52 g) and 1-(3-dimethylaminopropyl)-3-ethylcarbodiimide hydrochloride (3.15 g) were added at room temperature, and the mixture was stirred for 12 hours. After 0.1N hydrochloric acid was added to the reaction mixture, and the mixture was extracted with methylene chloride, the resultant organic layer was washed with a saturated aqueous solution of sodium hydrogencarbonate and saturated aqueous solution of sodium chloride and dried over anhydrous magnesium sulfate. The solvent was distilled off under reduced pressure, and the residue was purified by column chromatography on silica gel (ethyl acetate:hexane=1:1) to obtain the title compound (4.36 g).

$[\alpha]_D^{25}$=−27° (C=1.0, chloroform).

Referential Example 98

Ethyl (1R*,3S*,4R*)-3-[(tert-butoxycarbonyl) amino]-4-{[(5-methyl-4,5,6,7-tetrahydrothiazolo[5,4-c]pyridin-2-yl)carbonyl] amino}cyclohexanecarboxylate

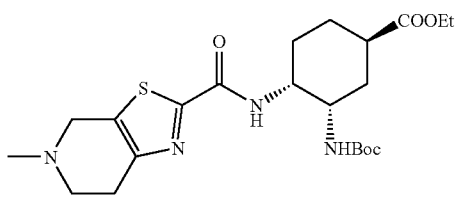

The title compound was obtained from the compound obtained in Referential Example 90 and the compound obtained in Referential Example 10 in a similar manner to Referential Example 91.

Referential Example 99

Benzyl 3-cyclohexene-1-carboxylate

(±)-3-Cyclohexene-1-carboxylic acid (50 g) was dissolved in N,N-dimethylformamide (550 ml), and triethylamine (170 ml) and benzyl bromide (61 ml) were added under ice cooling to stir the mixture at room temperature for 12 hours. Water was added, extraction was conducted with ethyl acetate, and the resultant organic layer was washed with saturated aqueous solution of sodium chloride and then dried over anhydrous magnesium sulfate. The solvent was distilled off under reduced pressure, and the residue was purified by column chromatography on silica gel (hexane:ethyl acetate=3:1) to obtain the title compound (70.8 g).

$^1$H-NMR (CDCl$_3$) δ: 1.66-1.76 (1H, m), 2.00-2.13 (3H, m), 2.27-2.29 (2H, m), 2.58-2.65 (1H, m), 5.13 (2H, s), 5.66 (2H, br.s), 7.29-7.38 (5H, m).

Referential Example 100

Benzyl (1R*,3S,6S*)-7-oxabicyclo[4.1.0]heptane-3-carboxylate

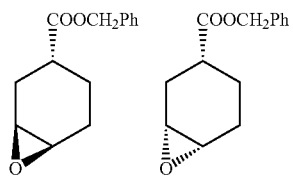

The compound (40 g) obtained in Referential Example 99 was dissolved in methylene chloride (500 ml), and m-chloroperbenzoic acid (86 g) was added under ice cooling to stir the mixture for 2 hours. After a 10% aqueous solution of sodium thiosulfate was added to conduct stirring for 20 minutes, an organic layer was separated, washed with a saturated aqueous solution of sodium hydrogencarbonate and saturated aqueous solution of sodium chloride and then dried over anhydrous magnesium sulfate. The solvent was distilled off under reduced pressure, and the residue was purified by column chromatography on silica gel (ethyl acetate:hexane=1:9) to obtain the title compound (23.4 g) and benzyl (1R*,3R*,6S*)-7-oxabicyclo[4.1.0]heptane-3-carboxylate (12.1 g).

$^1$H-NMR (CDCl$_3$) δ: 1.39-1.49 (1H, m), 1.75-1.82 (1H, m), 1.90-2.04 (3H, m), 2.30 (1H, dd, J=14.9, 4.9 Hz), 2.54-2.61 (1H, m), 3.12-3.14 (1H, m), 3.22-3.24 (1H, m), 5.12 (2H, s), 7.30-7.39 (5H, m). MS (FAB) m/z: 233 (M+H)$^+$.

Referential Example 101

Benzyl (1R*,3S*,4S*)-4-azido-3-hydroxycyclohexanecarboxylate

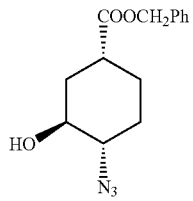

The compound (52.3 g) obtained in Referential Example 100 was dissolved in N,N-dimethylformamide (1000 ml), ammonium chloride (21.9 g) and sodium azide (18.1 g) were added, and the mixture was heated to 70° C. and stirred for 24 hours. The solvent was distilled off under reduced pressure, and water was added to conduct extraction with ethyl acetate. The resultant organic layer was washed with saturated aqueous solution of sodium chloride and dried over anhydrous magnesium sulfate. The solvent was distilled off under reduced pressure to obtain the title compound (61.8 g).

$^1$H-NMR (CDCl$_3$) δ: 1.51-1.66 (2H, m), 1.91-1.98 (1H, m) 2.07-2.10 (1H, m), 2.27-2.32 (1H, m), 2.51-2.52 (1H, m), 2.81-2.86 (1H, m), 3.30-3.36 (1H, m), 3.70-3.75 (1H, m), 5.13 (2H, s), 7.30-7.39 (5H, m).

Referential Example 102

Benzyl (1R*,3S*,4S*)-4-[(tert-butoxycarbonyl)amino]-3-hydoxycyclohexanecarboxylate

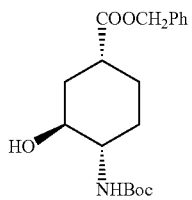

The compound (5.27 g) obtained in Referential Example 101 was dissolved in tetrahydrofuran (25 ml), and triphenylphosphine (5.53 g) and water (0.55 ml) were added to stir the mixture at room temperature for 20 hours. Di-tert-butyl dicarbonate (4.82 g) was added to the reaction mixture to continue stirring for additional 2 hours. The solvent was distilled off under reduced pressure, and the residue was purified by column chromatography on silica gel (hexane:ethyl acetate=2:1) to obtain the title compound (6.22 g).

$^1$H-NMR (CDCl$_3$) δ: 1.44 (9H, s), 1.59-1.66 (2H, m) 1.88-2.00 (2H, m), 2.29-2.32 (1H, m), 2.80-2.85 (1H, m), 3.02 (1H, br.s), 3.42 (1H, br.s), 3.59-3.65 (1H, m), 4.56 (1H, br.s), 5.12 (2H, q, J=12.5 Hz), 7.30-7.38 (5H, m). MS (FAB) m/z: 350 (M+H)$^+$.

Referential Example 103

Methyl (1R*,3S*,4S*)-4-[(tert-butoxycarbonyl)amino]-3-hydroxycyclohexanecarboxylate

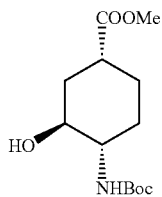

The compound (2.54 g) obtained in Referential Example 102 was dissolved in ethyl acetate (15 ml), and a catalytic amount of 10% palladium on charcoal was added to the solution. The mixture was stirred in a hydrogen stream at room temperature for 20 hours. After the catalyst was filtered off, the filtrate was concentrated under reduced pressure to give (1R*,3S*,4S*)-4-[(tert-butoxycarbonyl)amino]-3-hydroxycyclohexanecarboxylic acid as an colorless oil. The oil was dissolved in a mixture of methanol (8 ml) and toluene (15 ml), to which a 2N hexane solution (10 ml) of trimethylsilyldiazomethane was added under ice cooling, and the resulting mixture was stirred for 30 minutes at room temperature. After removal of the solvent under reduced pressure, the resulting residue was purified by column chromatography on silica gel (hexane:ethyl acetate=1:1) to obtain the title compound (1.82 g).

$^1$H-NMR (CDCl$_3$) δ: 1.44 (9H, s), 1.36-2.32 (7H, m), 2.74-2.82 (1H, m), 3.04 (1H, br.s), 3.33-3.47 (1H, m), 3.55-3.65 (1H, m), 3.68 (3H, s), 4.56 (1H, br.s). MS (FAB) m/z: 274 (M+H)$^+$.

Referential Example 104

Methyl (1R*,3R*,4S*)-3-azido-4-[(tert-butoxycarbonyl)amino]cyclohexanecarboxylate and methyl (1R*,3S*,4S*)-3-azido-4-[(tert-butoxycarbonyl)amino]cyclohexanecarboxylate

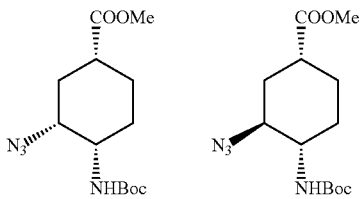

The compound (1.81 g) obtained in Referential Example 103 was dissolved in methylene chloride (36 ml), and triethylamine (4.6 ml) and methanesulfonyl chloride (1.63 ml) were added at −78° C. After 30 minutes, the mixture was heated to 0° C. and stirred for 30 minutes. 1N Hydrochloric acid was added, extraction was conducted with methylene chloride, and the resultant organic layer was washed with saturated aqueous solution of sodium chloride and dried over anhydrous magnesium sulfate. The solvent was distilled off under reduced pressure to obtain crude methyl (1R*,3S*,4S*)-4-[(tert-butoxycarbonyl)amino]-3-[(methylsulfonyl)oxy]-cyclohexanecarboxylate.

The crude product obtained above was dissolved in N,N-dimethylformamide (23 ml), sodium azide (1.29 g) was added, and the mixture was heated to 70° C. and stirred for 12 hours. Water was added to the reaction mixture, extraction was conducted with ethyl acetate, and the resultant organic layer was washed with saturated aqueous solution of sodium chloride and dried over anhydrous magnesium sulfate. The solvent was distilled off under reduced pressure, and the residue was purified by flash column chromatography on silica gel (ethyl acetate:hexane=3:17) to obtain methyl (1R*,3S*,4S*)-3-azido-4-[(tert-butoxycarbonyl)amino]-cyclohexanecarboxylate (85 mg) and methyl (1R*,3R*,4S*)-3-azido-4-[(tert-butoxycarbonyl)amino]cyclohexanecarboxylate (590 mg).

(1R*,3R*,4S*)-form: $^1$H-NMR (CDCl$_3$) δ: 1.45 (9H, s), 1.35-2.35 (7H, m), 2.45-2.55 (1H, m), 3.73 (3H, s), 3.67-3.84 (2H, m), 4.70 (1H, br.s). MS (FAB) m/z: 299 (M+H)$^+$.

(1R*,3S*,4S*)-form: $^1$H-NMR (CDCl$_3$) δ: 1.45 (9H, s), 1.56-2.25 (7H, m), 2.68-2.80 (1H, m), 3.70 (3H, s), 3.48-3.68 (2H, m), 4.56 (1H, br.s). MS (FAB) m/z: 299 (M+H)$^+$.

Referential Example 105

Methyl (1R*,3R*,4S*)-3-amino-4-[(tert-butoxycarbonyl)amino]cyclohexanecarboxylate

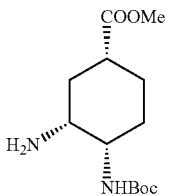

The (1R*,3R*,4S*)-compound (230 mg) obtained in Referential Example 104 was dissolved in ethyl acetate (8 ml), and a catalytic amount of 10% palladium on carbon was added to stir the mixture at room temperature for 20 hours in a hydrogen atmosphere. Insoluble matter was removed by filtration, and the filtrate was concentrated under reduced pressure to obtain the title compound (220 mg).

Referential Example 106

Methyl (1R*,3R*,4S*)-4-[(tert-butoxycarbonyl)amino-3-{[(5-methyl-4,5,6,7-tetrahydrothiazolo[5,4-c]pyridin-2-yl)carbonyl]amino}cyclohexanecarboxylate

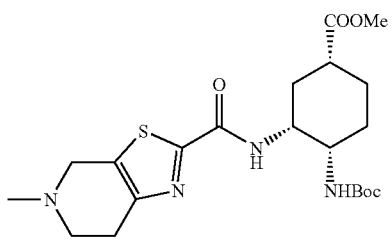

The title compound was obtained from the compound obtained in Referential Example 105 and the compound obtained in Referential Example 10 in a similar manner to Referential Example 91.

$^1$H-NMR (CDCl$_3$) δ: 1.46 (9H, s), 1.53-1.95 (5H, m), 2.17-2.24 (1H, m), 2.50 (3H, s), 2.50-2.53 (1H, m), 2.80-2.96 (4H, m), 3.67 (3H, s), 3.69-3.74 (1H, m), 4.10 (2H, br.s), 4.88 (1H, br.s). MS (FAB) m/z: 453 (M+H)$^+$.

Referential Example 107

Methyl (1R*,3R*,4S*)-4-[(tert-butoxycarbonyl)amino-3-{[(5-chloroindol-2-yl)carbonyl]amino}cyclohexanecarboxylate

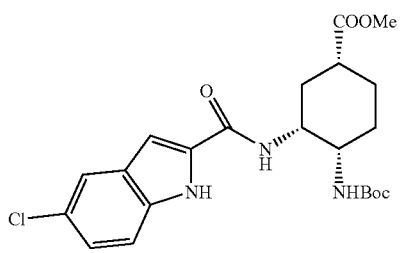

The title compound was obtained from the compound obtained in Referential Example 105 in a similar manner to Referential Example 91.

$^1$H-NMR (CDCl$_3$) δ: 1.33 (9H, s), 1.42-2.47 (6H, m) 2.78-2.88 (1H, m), 3.70 (3H, s), 3.86-4.15 (2H, m), 4.65-4.75 (1H, m), 6.86 (1H, br.s), 7.18-7.38 (2H, m), 7.57-7.61 (1H, m), 8.32 (1H, br.s). MS (ESI) m/z: 450 (M+H)$^+$.

Referential Example 108

Benzyl (1S,3R,6R)-7-oxabicyclo[4.1.0]heptane-3-carboxylate

1) Benzyl (1R)-3-cyclohexene-1-carboxylate was obtained from (1R)-3-cyclohexene-1-carboxylic acid (J. Am. Chem. Soc., 1978, Vol. 100, p. 5199) in a similar manner to Referential Example 99.

2) The title compound was obtained from the above-described product in a similar manner to Referential Example 100.

MS (FAB) m/z: 233 (M+H)$^+$.

Referential Example 109

Benzyl (1R,3S,4S)-4-[(tert-butoxycarbonyl)amino]-3-hydroxycyclohexanecarboxylate 1) Benzyl (1R,3S,4S)-4-azido-3-hydroxycyclohexanecarboxylate was obtained from the compound obtained in Referential Example 108 in a similar manner to Referential Example 101.

2) The title compound was obtained from the above-described product in a similar manner to Referential Example 102.

MS (FAB) m/z: 350 (M+H)$^+$.

Referential Example 110

Benzyl (1R,3R,4S)-3-azido-4-[(tert-butoxycarbonyl)amino]cyclohexanecarboxylate

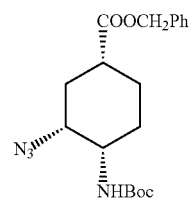

The title compound was obtained from the compound obtained in Referential Example 109 in a similar manner to Referential Example 104.

$^1$H-NMR (CDCl$_3$) δ: 1.45 (9H, s), 1.52-1.66 (2H, m), 1.83-2.01 (3H, m), 2.20-2.28 (1H, m), 2.51-2.54 (1H, m), 3.77 (2H, br.s), 4.70 (1H, br.s), 5.15 (2H, ABq, J=12.2 Hz), 7.33-7.38 (5H, m). MS (FAB) m/z: 375 (M+H)$^+$.

Referential Example 111

Methyl (1R,3R,4S)-3-azido-4-[(tert-butoxycarbonyl)amino]cyclohexanecarboxylate

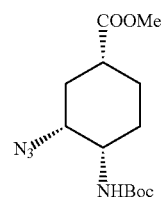

The compound (3.5 g) obtained in Referential Example 110 was dissolved in tetrahydrofuran (130 ml) and water (16 ml), and lithium hydroxide (291 mg) was added under ice cooling. After 10 minutes, the mixture was heated to room temperature to continue stirring. After 20 hours, the reaction was stopped, the solvent was distilled off under reduced pressure, and the resultant residue was subjected to column chromatography on silica gel (methanol:methylene chloride=1:20) to obtain (1R,3R,4S)-3-azido-4-[(tert-butoxycarbonyl)amino]cyclohexanecarboxylic acid (3.34 g) as a pale yellow oil. This product was dissolved in methanol (18 ml) and toluene (64 ml), a 2N hexane solution (6.1 ml) of trimethylsilyldiazomethane was added under ice cooling. After 10 minutes, the mixture was heated to room temperature and stirred for 2 hours. After the solvent was distilled off under reduced pressure, the residue was purified by column chromatography on silica gel (ethyl acetate:hexane=1:4) to obtain the title compound (3.35 g).

$^1$H-NMR (CDCl$_3$) δ: 1.45 (9H, s), 1.57-1.63 (2H, m), 1.82-1.85 (1H, m), 1.95-1.99 (2H, m), 2.20-2.28 (1H, m), 2.48-2.51 (1H, m), 3.73 (3H, s), 3.78 (2H, br.s), 4.70-4.72 (1H, m). MS (FAB) m/z: 299 (M+H)$^+$.

Referential Example 112

Methyl (1R,3R,4S)-4-[(tert-butoxycarbonyl)amino]-3-{[(5-methyl-4,5,6,7-tetrahydrothiazolo[5,4-c]pyridin-2-yl)carbonyl]amino}cyclohexanecarboxylate

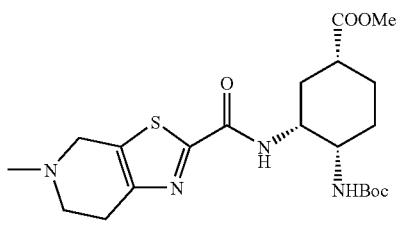

1) Methyl (1R,3R,4S)-3-amino-4-[(tert-butoxycarbonyl)amino]cyclohexanecarboxylate was obtained from the compound obtained in Referential Example 111 in a similar manner to Referential Example 105.

2) The title compound was obtained from the above-described product and the compound obtained in Referential Example 10 in a similar manner to Referential Example 106.

MS (FAB) m/z: 453 (M+H)$^+$.

Referential Example 113 tert-Buthyl (1R*,2S*,5S*)-5-aminocarbonyl-2-{[(5-chloroindol-2-yl)carbonyl]amino}cyclohexylcarbamate

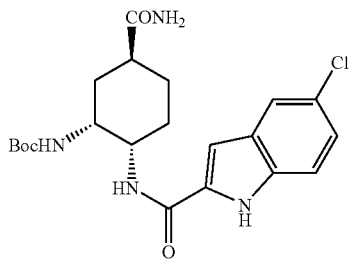

The compound (590 mg) obtained in Referential Example 91 was dissolved in a mixed solvent of ethanol (3 ml) and tetrahydrofuran (6 ml), a 1N aqueous solution (2.5 ml) of sodium hydroxide was added at room temperature, and the mixture was stirred for 12 hours. The solvent was distilled off to obtain sodium(1R*,3S*,4R*)-3-[(tert-butoxycarbonyl)amino]-4-{[(5-chloroindol-2-yl)carbonyl]amino}cyclohexanecarboxylate. This product was suspended in N,N-dimethylformamide (4 ml), di-tert-butyl dicarbonate (654 mg) and ammonium hydrogencarbonate (1 g) were added at room temperature, and the mixture was stirred for 18 hours. The solvent was distilled off under reduced pressure, and water was added to conduct extraction with chloroform. The resultant organic layer was washed with saturated aqueous solution of sodium chloride and dried over anhydrous magnesium sulfate. The solvent was distilled off under reduced pressure, and the residue was purified by column chromatography on silica gel (methylene chloride:methanol=47:3) to obtain the title compound (82 mg). MS (ESI) m/z: 435 (M+H)$^+$.

Referential Example 114

Benzyl (1R,6S)-6-{[(benzyloxy)carbonyl]amino}-3-cyclohexen-1-ylcarbamate

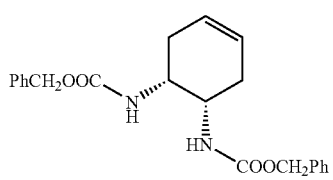

4-Cyclohexene-1,2-diamine hydrochloride (4.0 g) was dissolved in a mixed solvent of water (20 ml) and acetonitrile (20 ml), and benzyl chloroformate (7.66 ml) and potassium carbonate (14.9 g) were added, and the mixture was stirred at room temperature for 3 days. The reaction mixture was poured into water to conduct extraction with methylene chloride. The resultant organic layer was washed with saturated aqueous solution of sodium chloride, and dried over anhydrous sodium sulfate. The solvent was distilled off under reduced pressure, and the residue was purified by column chromatography on silica gel (methylene chloride) to obtain the title compound (8.22 g).

$^1$H-NMR (CDCl$_3$) δ: 2.03 (2H, m), 2.53 (2H, d, J=17.1 Hz), 3.77 (2H, m), 5.03 (2H, q, J=12.3 Hz), 5.09 (2H, q, J=12.3 Hz), 5.59 (2H, s), 7.32 (10H, m). MS (ESI) m/z: 381 (M+H)$^+$.

Referential Example 115

Benzyl (1R*,2S*)-2-{[(benzyloxy)carbonyl]amino}-5-hydroxycyclohexylcarbamate

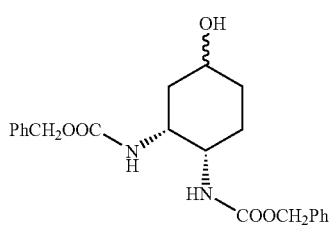

The compound (10 g) obtained in Referential Example 114 was dissolved in absolute tetrahydrofuran (70 ml), borane-dimethyl sulfide complex (7.4 ml) was added at 0° C., and the mixture was gradually heated to room temperature and stirred for 14 hours. Ice was added to the reaction mixture to decompose excessive borane, and a 1N aqueous solution (80 ml) of sodium hydroxide and 30% aqueous hydrogen peroxide (80 ml) were added to stir the mixture for 1 hour as it is. The reaction mixture was extracted with ethyl acetate, and the resultant organic layer was washed with saturated aqueous solution of sodium chloride and dried over anhydrous sodium sulfate. The solvent was distilled off under reduced pressure, and the residue was purified by column chromatography on silica gel (ethyl acetate:hexane=2:1) to obtain the title compound (9.2 g).

$^1$H-NMR (CDCl$_3$) δ: 1.98 (1H, m), 2.08 (1H, m), 2.30 (1H, m), 3.43 (2H, m), 3.73 (1H, m), 5.06 (6H, m), 7.32 (10H, s). MS (ESI) m/z: 399 (M+H)$^+$.

Referential Example 116

Benzyl (1R*,2S*)-2-{[(benzyloxy)carbonyl]amino}-5-oxocyclohexylcarbamate

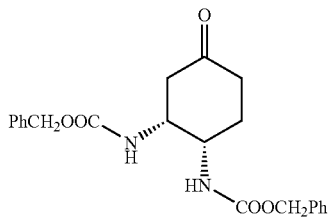

Dimethyl sulfoxide (8.2 ml) was added to a solution of oxalyl chloride (9.9 ml) in methylene chloride (90 ml) at −60° C., and a solution of the compound (9.2 g) obtained in Referential Example 115 in tetrahydrofuran (90 ml) was added to the mixture at a time. After 1 hour, the temperature of the mixture was raised to −40° C., and triethylamine (26 ml) was added at a time. The mixture was heated to room temperature as it is, and stirred for 3 hours. The reaction mixture was poured into water and extracted with methylene chloride. The resultant organic layer was washed with saturated aqueous solution of sodium chloride and then dried over anhydrous sodium sulfate. The solvent was distilled off under reduced pressure, and the residue was purified by column chromatography on silica gel (ethyl acetate:hexane=1:1) to obtain the title compound (8.0 g).

$^1$H-NMR (CDCl$_3$) δ: 2.27-2.43 (4H, m), 2.78 (1H, dd, J=14.4, 3.9 Hz), 3.86 (2H, m), 5.08 (4H, m), 5.22 (2H, m), 7.32 (10H, m). MS (ESI) m/z: 397 (M+H)$^+$.

Referential Example 117

Benzyl (1R*,2S*)-2-{[(benzyloxy)carbonyl]amino}-5,5-dimethoxycyclohexylcarbamate

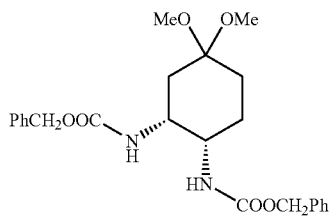

The compound (3.89 g) obtained in Referential Example 116 was dissolved in a mixed solvent of methanol (15 ml) and tetrahydrofuran (15 ml), 2,2-dimethoxypropane (10.7 ml) and p-toluenesulfonic acid (187 mg) were added, and the mixture was stirred at room temperature for 3 hours. The solvent was concentrated, and a saturated aqueous solution of sodium hydrogencarbonate was added to conduct extraction with ethyl acetate. After the resultant organic layer was washed with saturated aqueous solution of sodium chloride and dried over anhydrous sodium sulfate, the solvent was distilled off under reduced pressure, and the residue was purified by column chromatography on silica gel (ethyl acetate:hexane=1:2) to obtain the title compound (3.54 g).

$^1$H-NMR (CDCl$_3$) δ: 1.30-1.41 (4H, m), 1.93 (1H, m), 2.38 (1H, m), 3.19 (6H, s), 3.46 (1H, m), 3.59 (1H, m), 5.03 (2H, q, J=12.5 Hz), 5.09 (2H, q, J=12.5 Hz), 7.32 (10H, s).

Referential Example 118

N-[(1R*,2S*)-2-Amino-4,4-dimethoxycyclohexyl]-5-chloroindole-2-carboxamide and N-[(1R*,2S*)-2-amino-5,5-dimethoxycyclohexyl]-5-chloroindole-2-carboxamide

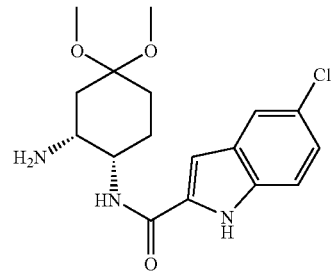

The compound (1.45 g) obtained in Referential Example 117 was dissolved in methanol (12 ml), and 10% palladium on carbon (290 mg) was added to stir the mixture at room temperature for 20 hours in a hydrogen atmosphere. 10% Palladium on carbon (290 mg) and methanol (10 ml) were additionally added to stir the mixture for 8 hours. The reaction mixture was filtered through Celite, and mother liquor was concentrated, and the residue was dissolved in N,N-dimethylformamide (10 ml). 5-Chloroindole-2-carboxylic acid (320 mg), 1-(3-dimethylaminopropyl)-3-ethylcarbodiimide hydrochloride (377 mg), 1-hydroxybenzotriazole monohydrate (301 mg) and N-methylmorpholine (360 ml) were added, and the mixture was stirred at room temperature for 14 hours. The reaction mixture was poured into an aqueous solution of sodium hydrogencarbonate and extracted with ethyl acetate. The resultant organic layer was washed with saturated aqueous solution of sodium chloride and then dried over anhydrous sodium sulfate, the solvent was distilled off under reduced pressure, and the residue was isolated and purified by preparative thin-layer chromatography on silica gel (methylene chloride:methanol=93:7) to obtain N-[(1R*,2S*)-2-amino-4,4-dimethoxycyclohexyl]-5-chloroindole-2-carboxamide (or N-[(1R*,2S*)-2-amino-5,5-dimethoxycyclohexyl]-5-chloroindole-2-carboxamide) (98 mg) and N-[(1R*,2S*)-2-amino-5,5-dimethoxycyclohexyl]-5-chloroindole-2-carboxamide (or N-[(1R*,2S*)-2-amino-4,4-dimethoxycyclohexyl]-5-chloroindole-2-carboxamide)(105 mg).

N-[(1R*,2S*)-2-Amino-4,4-dimethoxycyclohexyl]-5-chloroindole-2-carboxamide $^1$H-NMR (CDCl$_3$) δ: 1.45-1.50 (2H, m), 2.06-2.10 (2H, m), 2.34 (1H, d, J=13.1 Hz), 2.78 (1H, dt, J=2.9, 13.1 Hz), 3.18 (3H, s), 3.23 (3H, s), 3.75-3.77 (1H, m), 6.24 (1H, d, J=8.3 Hz), 6.79 (1H, s), 7.23 (1H, dd, J=8.8, 2.0 Hz), 7.35 (1H, d, J=8.8 Hz), 7.60 (1H, d, J=8.8 Hz), 9.53 (1H, br.s). MS (ESI) m/z: 352 (M+H)$^+$.

N-[(1R*,2S*)-2-Amino-5,5-dimethoxycyclohexyl]-5-chloroindole-2-carboxamide $^1$H-NMR (CDCl$_3$) δ: 1.83-1.87 (1H, m), 1.97-2.01 (1H, m), 2.39 (1H, br, J=13.2 Hz), 2.86-2.90 (1H, m), 3.22-3.28 (10H, m), 4.00-4.02 (1H, m), 6.77 (1H, s), 7.23 (1H, d, J=8.5 Hz), 7.37 (1H, d, J=8.5 Hz), 7.61 (1H, s), 9.49 (1H, br.s). MS (ESI) m/z: 352 (M+H)$^+$.

Referential Example 119

Benzyl (7R*,8S*)-7-{[(benzyloxy)carbonyl]amino}-1,4-dioxaspiro[4.5]dec-8-ylcarbamate

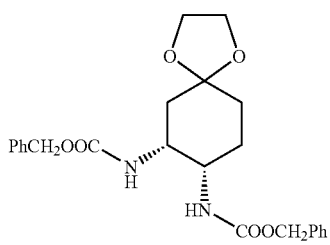

The compound (4.0 g) obtained in Referential Example 116 was dissolved in absolute tetrahydrofuran (30 ml), and ethylene glycol (5.6 ml) and p-toluenesulfonic acid (192 mg) were added to stir the mixture at room temperature for 17 hours. The reaction mixture was poured into a saturated aqueous solution of sodium hydrogencarbonate and extracted with ethyl acetate. The resultant organic layer was washed with saturated aqueous solution of sodium chloride and then dried over anhydrous sodium sulfate, the solvent was distilled off under reduced pressure, and the residue was purified by column chromatography on silica gel (ethyl acetate:hexane 1:1) to obtain the title compound (4.23 g).

$^1$H-NMR (CDCl$_3$) δ: 1.65-1.71 (4H, m), 2.00 (1H, m), 2.11 (1H, m), 3.49 (1H, m), 3.73 (1H, m), 3.93 (4H, s), 5.03 (2H, q, J=12.2 Hz), 5.08 (2H, q, J=12.2 Hz), 7.32 (10H, s). MS (ESI) m/z: 441 (M+H)$^+$.

Referential Example 120

N-[(7R*,8S*)-7-Amino-1,4-dioxaspiro[4.5]dec-8-yl]-5-chloroindole-2-carboxamide and N-((7R*,8S*)-8-amino-1,4-dioxaspiro[4.5]dec-7-yl]-5-chloroindole-2-carboxamide

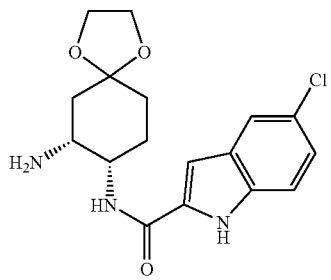

N-[(7R*,8S*)-7-Amino-1,4-dioxaspiro[4.5]dec-8-yl]-5-chloroindole-2-carboxamide (or N-[(7R*,8S*)-8-amino-1,4-dioxaspiro[4.5]dec-7-yl]-5-chloroindole-2-carboxamide) and N-[(7R*,8S*)-8-amino-1,4-dioxaspiro[4.5]dec-7-yl]-5-chloroindole-2-carboxamide (or N-[(7R*,8S*)-7-amino-1,4-dioxaspiro[4.5]dec-8-yl]-5-chloroindole-2-carboxamide) were obtained from the compound obtained in Referential Example 119 in a similar manner to Referential Example 118. N-[(7R*,8S*)-7-Amino-1,4-dioxaspiro[4.5]dec-8-yl]-5-chloroindole-2-carboxamide (or N-[(7R*,8S*)-8-amino-1,4-dioxaspiro[4.5]dec-7-yl]-5-chloroindole-2-carboxamide $^1$H-NMR (CDCl$_3$) δ: 1.68-1.81 (4H, m), 2.11 (2H, m), 2.87 (1H, td, J=3.9, 11.2 Hz), 3.77 (1H, m), 3.97 (4H, s), 6.27 (1H, d, J=7.6 Hz), 6.80 (1H, s), 7.24 (1H, d, J=9.0 Hz), 7.35 (1H, d, J=9.0 Hz), 7.61 (1H, s), 9.47 (br.s, 1H). MS (ESI) m/z: 350 (M+H)$^+$.

N-[(7R*,8S*)-8-Amino-1,4-dioxaspiro[4.5]dec-7-yl]-5-chloroindole-2-carboxamide (or N-[(7R*,8S*)-7-amino-1,4-dioxaspiro[4.5]dec-8-yl]-5-chloroindole-2-carboxamide)

$^1$H-NMR (CDCl$_3$) δ: 1.65 (2H, m), 1.88 (1H, m), 1.96 (1H, m), 2.31 (1H, dd, J=12.9, 3.2 Hz), 2.96 (1H, m), 3.98 (1H, m), 4.02 (4H, s), 4.12 (1H, m), 6.77 (1H, s), 7.06 (1H, br.s), 7.23 (1H, dd, J=8.8, 2.0 Hz), 7.37 (1H, d, J=8.8 Hz), 7.62 (1H, d, J=2.0 Hz), 9.49 (1H, br.s). MS (ESI) m/z: 350 (M+H)$^+$.

Referential Example 121 tert-Butyl (1R,6S)-6-[(tert-butoxycarbonyl)amino]-3-cyclohexene-1-ylcarbamate

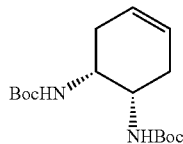

cis-4-Cyclohexene-1,2-diamine hydrochloride (4.0 g) was dissolved in a mixed solvent of water (40 ml) and acetonitrile (40 ml), and di-tert-butoxy carbonate (11.8 g) and triethylamine (12 ml) were added, and the mixture was stirred at room temperature for 4.5 hours. The reaction mixture was poured into water to conduct extraction with methylene chloride, and the resultant methylene chloride layer was washed with saturated aqueous solution of sodium chloride and then dried over anhydrous sodium sulfate. The solvent was distilled off under reduced pressure, and the residue was purified by column chromatography on silica gel (ethyl acetate:hexane=1:4) to obtain the title compound (6.12 g).

$^1$H-NMR (CDCl$_3$) δ: 1.44 (18H, s), 1.98 (2H, dd, J=9.3, 15.9 Hz), 2.48 (2H, br.d, J=15.9 Hz), 3.66 (2H, br.s), 4.88 (2H, br.s), 5.58 (2H, d, J=2.7 Hz).

Referential Example 122 tert-Butyl (1R*,2S*)-2-[(tert-butoxycarbonyl)amino]-5-hydroxycyclohexylcarbamate (Mixture of Stereoisomers)

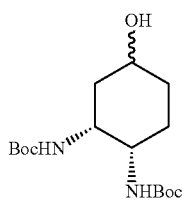

The compound (6.1 g) obtained in Referential Example 121 was dissolved in absolute tetrahydrofuran (40 ml), and borane-dimethyl sulfide complex (2.22 ml) was added under ice cooling. The mixture was stirred for 16 hours while gradually heating the mixture to room temperature as it is. Ice was added to the reaction mixture, and a 1N aqueous solution of sodium hydroxide and 30% aqueous hydrogen peroxide (50 ml) were added to stir the mixture at room temperature for 2 hours as it is. The reaction mixture was extracted with ethyl acetate, and the resultant organic layer was washed with saturated aqueous solution of sodium chloride and dried over anhydrous sodium sulfate. The solvent was distilled off under reduced pressure, and the residue was purified by column chromatography on silica gel (ethyl acetate:hexane=1:2→2:1) to obtain the title compound (6.1 g).

$^1$H-NMR (CDCl$_3$) δ: 1.42 (9H, s), 1.43 (9H, s), 1.83-1.67 (5H, m), 2.15 (1H, m), 2.22 (1H, s), 3.34 (1H, m), 3.78 (1H, m), 4.15 (1H, s), 4.98 (1H, q, J=9.0 Hz), 5.02 (1H, q, J=9.0 Hz). MS (ESI) m/z: 331 (M+H)$^+$.

Referential Example 123 tert-Butyl (1R*,2S*)-2-[(tert-butoxycarbonyl)amino]-5-oxocyclohexylcarbamate

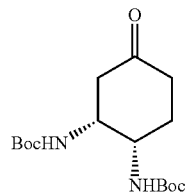

Oxalyl chloride (8.2 ml) and dimethyl sulfoxide (6.8 ml) were dissolved in methylene chloride (100 ml) at −60° C., and a solution of the compound (mixture of stereoisomers) (6.32 g) obtained in Referential Example 122 in tetrahydrofuran (80 ml) was added at a time, and the mixture was stirred for 1 hour. The temperature of the mixture was raised to −40° C., and triethylamine (21 ml) was added. The mixture was heated to room temperature. After 3 hours, the reaction mixture was poured into water and extracted with methylene chloride. The resultant organic layer was washed with saturated aqueous solution of sodium chloride and then dried over anhydrous sodium sulfate. The solvent was distilled off under reduced pressure, and the residue was purified by column chromatography on silica gel (ethyl acetate:hexane=1:1) to obtain the title compound (3.8 g).

$^1$H-NMR (CDCl$_3$) δ: 1.43 (9H, s), 1.44 (9H, s), 2.24-2.36 (3H, m), 2.39-2.44 (2H, m), 2.75 (1H, dd, J=14.6, 2.9 Hz), 3.66-3.81 (2H, m), 4.95-4.90 (1H, m), 4.97-5.03 (1H, m). MS (ESI) m/z: 329 (M+H)$^+$.

Referential Example 124 tert-Butyl (1R*,2S*)-2-[(tert-butoxycarbonyl)amino]-5-(methoxyimino)cyclohexylcarbamate

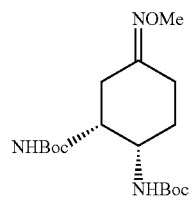

The compound (1.5 g) obtained in Referential Example 123 was dissolved in methanol (30 ml), and O-methylhydroxyamine hydrochloride (572 mg) and pyridine (737 ml) were added to stir the mixture at room temperature for 17 hours. After the reaction mixture was concentrated, water was added to conduct extraction with ethyl acetate. The resultant organic layer was washed with saturated aqueous solution of sodium chloride and then dried over anhydrous sodium sulfate. The solvent was distilled off under reduced pressure, and the residue was purified by column chromatography on silica gel (ethyl acetate:hexane=1:4) to obtain the title compound (1.52 g).

$^1$H-NMR (CDCl$_3$) δ: 1.44 (18H, s), 1.64 (1H, m), 2.16 (2H, m), 2.44 (1H, m), 3.45-3.63 (3H, m), 3.82 (3H, s), 4.93 (1H, m). MS (ESI) m/z: 358 (M+H)$^+$.

Referential Example 125 tert-Butyl (1R*,2S*)-2-[(tert-butoxycarbonyl)amino]-5-{[tert-butyl(diphenyl)silyl]oxy}cyclohexylcarbamate (Stereoisomer A)

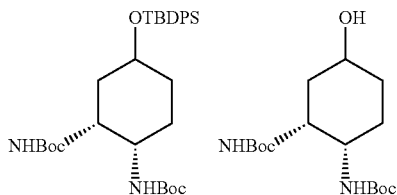

The title compound was obtained from the compound (mixture of stereoisomers) obtained in Referential Example 122 in a similar manner to Referential Example 58, and tert-butyl (1R*,2S*)-2-[(tert-butoxycarbonyl)amino]-5-hydroxycyclohexylcarbamate (Stereoisomer B) was recovered.

$^1$H-NMR (CDCl$_3$) δ: 1.03 (9H, s), 1.39 (9H, s), 1.40 (9H, s), 1.72 (1H, m), 1.86 (1H, m), 2.13 (1H, m), 3.24 (2H, m), 3.65 (1H, m), 4.83 (1H, m), 7.37 (10H, m).

Referential Example 126

Benzyl (1R*,2S*)-2-{[(benzyloxy)carbonyl]amino}-5-hydroxy-5-methylcyclohexylcarbamate

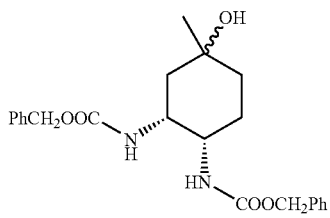

Anhydrous cerium chloride (6.4 g) was suspended in tetrahydrofuran (50 ml), and the suspension was cooled to −78° C. in an argon atmosphere. A methyllithium solution (1.14N diethyl ether solution, 22.5 ml) was added to the suspension, and the mixture was stirred at −78° C. for 30 minutes. A tetrahydrofuran solution (50 ml) of the compound (3.0 g) obtained in Referential Example 116 was added dropwise at −78° C., and the mixture was stirred for 30 minutes. The reaction mixture was poured into a 3% aqueous solution (100 ml) of acetic acid, and diethyl ether (50 ml) was added to stir the mixture at room temperature for 10 minutes. The reaction mixture was extracted with ethyl acetate, and the resultant organic layer was washed with a saturated aqueous solution of sodium hydrogencarbonate and saturated aqueous solution of sodium chloride and then dried over anhydrous sodium sulfate. The solvent was distilled off under reduced pressure, and the residue was purified twice by column chromatography on silica gel (methanol:chloroform=0:100-1:19) to obtain the title compound (Stereoisomer A) (780 mg) and the title compound (Stereoisomer B) (1.1 g).

Stereoisomer A:
$^1$H-NMR (CDCl$_3$) δ: 1.26 (3H, s), 1.27-2.08 (6H, m), 3.48 (1H, br.s), 3.59 (1H, br.s), 5.02-5.09 (5H, m), 5.33 (1H, br.s), 7.30-7.32 (10H, s). MS (FAB) m/z: 413 (M+H)$^+$.

Stereoisomer B:
$^1$H-NMR (CDCl$_3$) δ: 1.25 (3H, s), 1.29-2.07 (6H, m), 3.39 (1H, br.s), 3.82 (1H, br.s), 5.02-5.23 (6H, m), 7.30 (10H, s). MS (FAB) m/z: 413 (M+H)$^+$.

Referential Example 127

(3R*,4S*)-3,4-Diamino-1-methylcyclohexanol (Stereoisomer A)

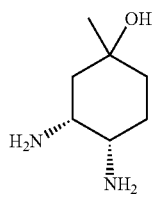

10% Palladium on carbon (350 mg) was suspended in a methanol solution (100 ml) of the compound (Stereoisomer A) (780 mg) obtained in Referential Example 126, and the suspension was stirred for 5 hours in a hydrogen atmosphere. The catalyst was removed by filtration, and the filtrate was concentrated under reduced pressure. After the residue was dissolved in methylene chloride (100 ml), and the solution was dried over anhydrous sodium sulfate, the solvent was distilled off to obtain the title compound (Stereoisomer A) (190 mg).

$^1$H-NMR (CDCl$_3$) δ: 1.22 (3H, s), 1.25-2.48 (11H, m), 2.62 (1H, br.s), 2.78 (1H, br.s).

Referential Example 128

Mixture of N-[(1R*,2S*)-2-Amino-4-hydroxy-4-methylcyclohexyl]-5-chloroindole-2-carboxamide (Stereoisomer A) and N-[(1R*,2S*)-2-amino-5-hydroxy-5-methylcyclohexyl]-5-chloroindole-2-carboxamide (Stereoisomer A)

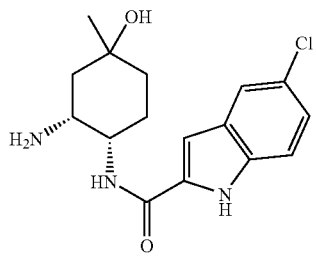

The title compound was obtained from the compound (Stereoisomer A) obtained in Referential Example 127 and 5-chloroindole-2-carboxylic acid in a similar manner to Referential Example 59.

$^1$H-NMR (CDCl$_3$) δ: 1.32 (3H, s), 1.34-2.29 (6H, m), 4.42-4.70 (4H, br), 7.13 (2H, s), 7.50 (2H, s), 8.00 (1H, s), 11.0 (1H, br).

Referential Example 129 tert-Butyl (1R*,2R*,5S*)-2-[(5-chloroindol-2-yl)carbonyl]-amino}-5-(hydroxymethyl)cyclohexylcarbamate

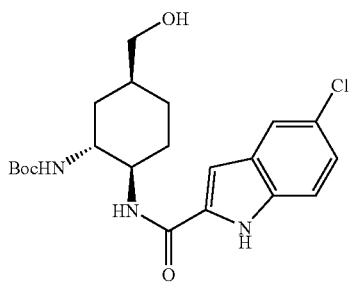

1) Ethyl (1R*,3S*,4S*)-3-[(tert-butoxycarbonyl)amino]-4-{[(5-chloroindol-2-yl)carbonyl]amino}-cyclohexanecarboxylate was obtained from the (1R*,3S*,4S*)-form obtained in Referential Example 89 in a similar manner to the process described in Referential Examples 90 and 91.

$^1$H-NMR (CDCl$_3$) δ: 1.22-1.72 (6H, m), 2.15-2.28 (2H, m), 2.41-2.49 (1H, m), 2.85 (1H, brs), 3.62-3.75 (1H, m), 3.78-3.92 (1H, m), 4.12-4.28 (2H, m), 4.56-4.63 (1H, m), 6.88 (1H, brs), 7.20 (1H, dd, J=8.8 and 2.0 Hz), 7.33 (1H, d, J=8.8 Hz), 7.52-7.57 (1H, m), 7.59 (1H, d, J=2.0 Hz), 9.24 (1H, s). MS (ESI) m/z: 464 (M+H)$^+$.

2) The product (735 mg) obtained above was dissolved in methylene chloride (10 ml), a 1N hexane solution (5 ml) of diisobutylalminium hydride was added at −78° C., and the mixture was stirred for 3 hours and then 30 minutes at 0° C. A saturated aqueous solution of ammonium chloride was added at −78° C., the mixture was extracted with methylene chloride, and the resultant organic layer was washed with a saturated aqueous solution of sodium bicarbonate and saturated aqueous solution of sodium chloride and then dried over anhydrous magnesium sulfate. The solvent was distilled off under reduced pressure, and the residue was purified by column chromatography on silica gel (methylene chloride:methanol=19:1) to obtain the title compound (480 mg).

$^1$H-NMR (CDCl$_3$) δ: 1.20-2.30 (7H, m), 3.60-3.86 (4H, m), 4.64 (1H, br.s), 6.87 (1H, s), 7.20-7.48 (3H, m), 9.15 (1H, br.s). MS (ESI) m/z: 422 (M+H)$^+$.

Referential Example 130

(1R*,3R*,6S*)-3-(Methoxymethyl)oxabicyclo[4.1.0]heptane

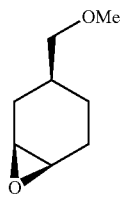

1) (1R*,4R*,5R*)-4-Iodo-6-oxabicyclo[3.2.1]octan-7-one (2.8 g) was dissolved in a mixed solvent of tetrahydrofuran (27 ml) and water (3 ml), concentrated hydrochloric acid (0.1 ml) was added, and the mixture was heated under reflux for 1 hour. The solvent was distilled off under reduced pressure to obtain (1R*,3R*,4R*)-3-hydroxy-4-iodocyclohexanecarboxylic acid (3.23 g) as a colorless solid.

2) The product (3.22 g) obtained by the reaction described above was dissolved in tetrahydrofuran (50 ml), borane-dimethyl sulfide complex (2 M tetrahydrofuran solution, 47 ml) was added under ice cooling, and the mixture was stirred at room temperature for 12 hours. The solvent was distilled off under reduced pressure, the residue was dissolved in isopropanol (10 ml), a 1N aqueous solution (12 ml) of sodium hydroxide was added, and the mixture was stirred for 12 hours. After the solvent was concentrated to about 1/5, the reaction mixture was diluted with water and methylene chloride to stir it for 10 minutes. An organic layer was separated, successively washed with a saturated aqueous solution of ammonium chloride and saturated aqueous solution of sodium chloride and dried over anhydrous magnesium sulfate. The solvent was distilled off under reduced pressure, and the residue was purified by column chromatography on silica gel (ethyl acetate:hexane=1:2) to obtain (1R*,3R*,6S*)-7-oxabicyclo[4.1.0]hept-3-ylmethanol (1.25 g) as a colorless oil.

3) The product (4.63 g) obtained by the reaction in 2) was dissolved in tetrahydrofuran (50 ml), potassium bis(trimethylsilyl)amide (0.5N toluene solution, 80 ml) was added to the solution at −78° C. After stirring at same temperature for 10 minutes, methyl iodide (2.93 ml) was added. After heating the mixture to 0° C., it was stirred for 1 hour, quenched with a saturated aqueous solution of ammonium chloride and then diluted with diethyl ether. An organic layer was separated, washed with saturated aqueous solution of sodium chloride and dried over anhydrous magnesium sulfate. The solvent was distilled off under reduced pressure, and the residue was purified by column chromatography on silica gel (ethyl acetate:hexane=1:4) to obtain the title compound (3.7 g).

$^1$H-NMR (CDCl$_3$) δ: 0.89-1.63 (5H, m), 1.80-2.05 (2H, m), 1.89-3.06 (4H, m), 3.16 (3H, s).

Referential Example 131

(1R*,2R*,4S*)-2-Azido-4-(methoxymethyl)cyclohexanol

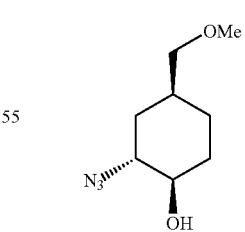

The title compound was obtained from the compound obtained in Referential Example 130 in a similar manner to Referential Example 87.

$^1$H-NMR (CDCl$_3$) δ: 1.45-1.70 (5H, m), 1.77-1.95 (2H, m), 1.98-2.08 (1H, m), 3.30 (2H, d, J=6.8 Hz), 3.35 (3H, s), 3.45-3.65 (2H, m).

Referential Example 132 tert-Butyl (1R*,2R*,5S*)-2-hydroxy-5-(methoxymethyl)cyclohexylcarbamate

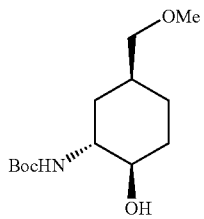

The title compound was obtained from the compound obtained in Referential Example 131 in a similar manner to Referential Example 88.

$^1$H-NMR (CDCl$_3$) δ: 1.35-2.01 (16H, m), 3.05 (1H, br.s), 3.32 (2H, d, J=7.1 Hz), 3.34 (3H, s), 3.44-3.62 (2H, m), 4.59 (1H, br.s).

Referential Example 133 tert-Butyl (1R*,2S*,5S*)-2-azido-5-(methoxymethyl)cyclohexylcarbamate

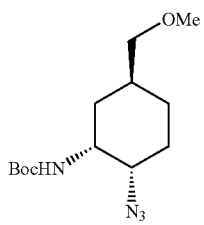

The title compound was obtained from the compound obtained in Referential Example 132 through the methansulfonate thereof in a similar manner to Referential Example 89.

$^1$H-NMR (CDCl$_3$) δ: 1.31-1.93 (16H, m), 3.27 (2H, d, J=6.4 Hz), 3.32 (3H, s), 3.57-3.70 (1H, m), 3.67 (1H, br.s), 3.95 (1H, br.s).

Referential Example 134 tert-Butyl (1R*,2S*,5S*)-2-amino-5-(methoxymethyl)cyclohexylcarbamate

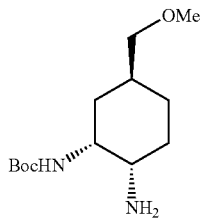

The title compound was obtained from the compound obtained in Referential Example 133 in a similar manner to Referential Example 90.

Referential Example 135 tert-Butyl (1R*,2S*,5S*)-2-{[(5-chloroindol-2-yl)carbonyl]-amino}-5-(methoxymethyl)cyclohexylcarbamate

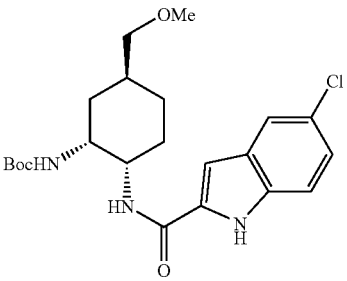

The title compound was obtained from the compound obtained in Referential Example 134 and 5-chloroindole-2-carboxylic acid in a similar manner to Referential Example 91.

$^1$H-NMR (CDCl$_3$) δ: 1.12-2.31 (16H, m), 3.14-3.30 (2H, m), 3.34 (3H, s), 3.92 (1H, br.s), 4.13 (1H, br.s), 4.88 (1H, br.s), 6.82 (1H, s), 7.21 (1H, br.d, J=8.8 Hz), 7.33 (1H, d, J=8.8 Hz), 7.60 (1H, s), 8.09 (1H, br.s), 9.42 (1H, br.s). MS (ESI) m/z: 436 (M+H)$^+$.

Referential Example 136 tert-Butyl (1R*,2S*,5S*)-2-{[(5-chloroindol-2-yl)carbonyl]-amino}-5-(hydroxymethyl)cyclohexylcarbamate

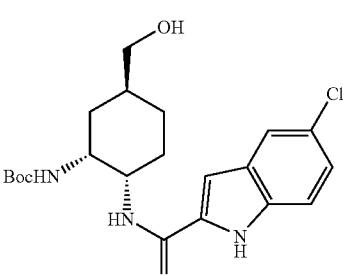

The title compound was obtained from the compound obtained in Referential Example 91 in a similar manner to Referential Example 129.

$^1$H-NMR (CDCl$_3$) δ: 0.78-2.30 (16H, m), 3.41-3.59 (3H, m), 3.86-3.95 (1H, m), 4.12-4.20 (1H, m), 4.82-4.91 (1H, m), 6.81 (1H, s), 7.17-7.40 (2H, m), 7.60 (1H, s), 8.03 (1H, br.s), 9.18 (1H, br.s). MS (ESI) m/z: 422 (M+H)$^+$.

Referential Example 137 tert-Butyl (1R*,2S*,5S*)-5-(azidomethyl)-2-{[(5-chloroindol-2-yl)carbonyl]amino}cyclohexylcarbamate

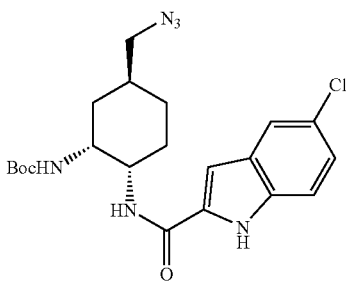

The title compound was obtained from the compound obtained in Referential Example 136 in a similar manner to Referential Example 80.

Referential Example 138 tert-Butyl 3-cyclohexen-1-ylcarbamate

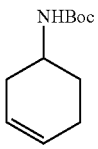

3-Cyclohexene-1-carboxylic acid (25.3 g) was dissolved in tert-butanol (250 ml), triethylamine (28 ml) and diphenylphosphorylazide (43.0 ml) were added, and the mixture was stirred for 1 hour at room temperature and 2 days at 90° C. The solvent was distilled off under reduced pressure, and the residue was purified by column chromatography on silica gel (methylene chloride) and then repurified by column chromatography on silica gel (hexane:ethyl acetate=20:1) to obtain the title compound (24.9 g).

$^1$H-NMR (CDCl$_3$) δ: 1.45 (9H, s), 1.45-1.60 (1H, m), 1.80-1.90 (2H, m), 2.05-2.20 (2H, m), 2.35-2.45 (1H, m), 3.78 (1H, br), 4.56 (1H, br), 5.55-5.65 (1H, m), 5.65-5.75 (1H, m).

Referential Example 139 tert-Butyl (3R*,4S*)-3,4-dihydroxycyclohexylcarbamate

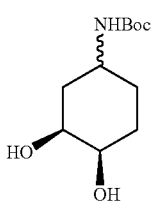

The compound (1.24 g) obtained in Referential Example 138 was dissolved in a mixed solvent of acetonitrile (15 ml) and water (5 ml), N-methylmorpholine N-oxide (0.90 g) and microcapsulated 10% osmium tetroxide (1 g) were added, and the mixture was stirred at about 80° C. for a day. After insoluble matter was removed by filtration, the filtrate was concentrated under reduced pressure. The thus-obtained residue was purified by column chromatography on silica gel (methylene chloride:methanol=20:1) to obtain the title compound (1.28 g).

$^1$H-NMR (CDCl$_3$) δ: 1.15-1.30 (1/2H, m), 1.35-2.00 (15H, m), 2.15-2.30 (3/2H, m), 2.40-2.60 (1H, m), 3.64 (1H, br), 3.75-3.90 (3/2H, m), 4.00 (1/2H, br). MS (FAB) m/z: 232 (M+H)$^+$.

Referential Example 140 tert-Butyl (3R*,4S*)-3,4-diazidocyclohexylcarbamate (Stereoisomer A and Stereoisomer B)

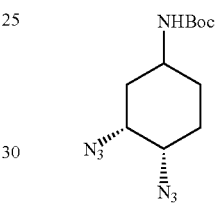

The title compounds (Stereoisomer A and Stereoisomer B) were obtained from the compound obtained in Referential Example 139 in a similar manner to Referential Example 80.

Stereoisomer A:

$^1$H-NMR (CDCl$_3$) δ: 1.45 (9H, s), 1.40-1.55 (1H, m), 1.55-1.80 (3H, m), 1.95-2.15 (2H, m), 3.53 (1H, m), 3.59 (1H, br), 3.80 (1H, m), 4.70 (1H, br).

Stereoisomer B:

$^1$H-NMR (CDCl$_3$) δ: 1.27 (1H, m), 1.44 (9H, s), 1.40-1.55 (1H, m), 1.80-2.00 (2H, m), 2.00-2.15 (1H, m), 2.21 (1H, m), 3.48 (1H, m), 3.77 (1H, br), 3.89 (1H, br), 4.34 (1H, br).

Referential Example 141

Ethyl (1S,3R,4S)-4-{((benzyloxy)carbonyl]amino}-3-[(tert-butoxycarbonyl)amino]cyclohexanecarboxylate

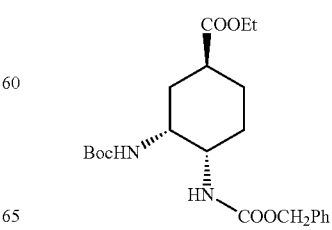

The compound (3.10 g) obtained in Referential Example 96 was dissolved in tetrahydrofuran (50 ml), and a saturated aqueous solution (50 ml) of sodium hydrogencarbonate was added. After benzyloxycarbonyl chloride (1.71 ml) was added dropwise to the reaction mixture under ice cooling, the mixture was stirred at room temperature for 4 days. Ethyl acetate (200 ml) and water (200 ml) were added to the reaction mixture to conduct liquid separation. After the resultant organic layer was dried over anhydrous sodium sulfate, the solvent was distilled off under reduced pressure. Solids deposited were collected by filtration to obtain the title compound (3.24 g).

$^1$H-NMR (CDCl$_3$) δ: 1.24 (3H, t, J=7.1 Hz), 1.29-1.44 (1H, m), 1.44 (9H, s), 1.51-1.64 (1H, m), 1.72-2.10 (4H, m), 2.27-2.43 (1H, m), 3.60-3.73 (1H, m), 4.00-4.18 (3H, m), 4.62 (1H, br.s), 5.01-5.13 (2H, m), 5.26 (1H, br.s), 7.27-7.38 (5H, m).

Referential Example 142

(1S,3R,4S)-4-{[(Benzyloxy)carbonyl]amino}-3-[(tert-butoxycarbonyl)amino]cyclohexanecarboxylic Acid

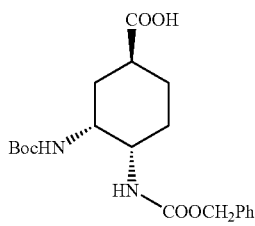

The compound (620 mg) obtained in Referential Example 141 was dissolved in tetrahydrofuran (20 ml), and an aqueous solution (10 ml) of lithium hydroxide monohydrate (93 mg) was added to stir the mixture at room temperature for 16 hours. After lithium hydroxide monohydrate (217 mg) was additionally added to the reaction mixture, and the mixture was stirred at room temperature for 2 hours, the reaction mixture was neutralized with 1N hydrochloric acid and extracted with methylene chloride. An organic layer was washed with saturated aqueous solution of sodium chloride and then dried over anhydrous sodium sulfate. The solvent was distilled off under reduced pressure to obtain the title compound (600 mg).

$^1$H-NMR (CDCl$_3$) δ: 1.22-2.20 (6H, m), 1.44 (9H, s), 2.45 (1H, br.s), 3.60-3.80 (1H, br), 4.09 (1H, br.s), 4.66 (1H, br.s), 5.00-5.20 (2H, m), 5.26 (1H, br.s), 7.20-7.40 (5H, m). MS (ESI) m/z: 393 (M+H)$^+$.

Referential Example 143

Benzyl (1S,2R,4S)-2-[(tert-butoxycarbonyl)amino]-4-[(dimethylamino)carbonyl]cyclohexylcarbamate

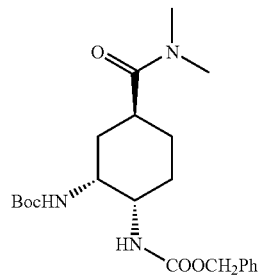

After the compound (600 mg) obtained in Referential Example 142 and dimethylamine hydrochloride (240 mg) were suspended in methylene chloride (50 ml), a proper amount of tetrahydrofuran was added to the suspension to prepare a solution. To this solution were added triethylamine (0.41 ml), 1-(3-dimethylaminopropyl)-3-ethylcarbodiimide hydrochloride (422 mg) and 1-hydroxybenzotriazole monohydrate (338 mg), and the mixture was stirred at room temperature for 1 hour. Dimethylamine hydrochloride (480 mg) and triethylamine (0.82 ml) were additionally added to the reaction mixture to stir the mixture at room temperature for additional 18 hours. The reaction mixture was poured into water to separate an organic layer. After the organic layer was washed with 1N hydrochloric acid and saturated aqueous solution of sodium chloride and dried over anhydrous sodium sulfate. The solvent was distilled off under reduced pressure, and the residue was purified by column chromatography on silica gel (methanol:methylene chloride=3:47→2:23) to obtain the title compound (620 mg).

$^1$H-NMR (CDCl$_3$) δ: 1.20-1.50 (2H, m), 1.44 (9H, s), 1.50-2.10 (4H, m), 2.60 (1H, br.t, J=11.6 Hz), 2.93 (3H, s), 3.02 (3H, s), 3.70 (1H, br.s), 4.14 (1H, br.s), 4.65 (1H, br.s), 5.00-5.30 (3H, m), 7.26-7.40 (5H, m). MS (ESI) m/z=420 (M+H)$^+$.

Referential Example 144 tert-Butyl (1R,2S,5S)-2-amino-5-[(dimethylamino)carbonyl]cyclohexylcarbamate

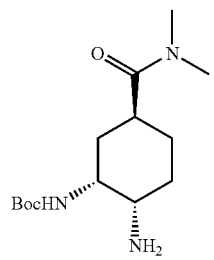

10% Palladium on carbon (57 g) was added to a solution of the compound (190 g) obtained in Referential Example 143 in methanol (8000 ml), and the mixture was stirred for 3 hours under a hydrogen pressure (7 atm). After the catalyst was removed by filtration, the filtrate was concentrated under reduced pressure. After toluene was added to the residue, and the mixture was concentrated under reduced pressure, hexane (2500 ml) was added to solidify a product. The product was collected by filtration and dried to obtain the title compound (121 g).

$^1$H-NMR (CDCl$_3$) δ: 1.20-1.77 (6H, m), 1.45 (9H, s), 2.20-2.35 (1H, br), 2.63-2.74 (1H, m), 2.92 (3H, s), 3.02 (3H, s), 3.02-3.11 (2H, m), 3.74-3.82 (1H, m), 4.88-5.00 (1H, br). MS (ESI) m/z: 286 (M+H)$^+$.

Referential Example 145 tert-Butyl (1R,2S,5S)-2-{[(6-chloroquinolin-2-yl)carbonyl]amino}-5-[(dimethylamino)carbonyl]cyclohexylcarbamate

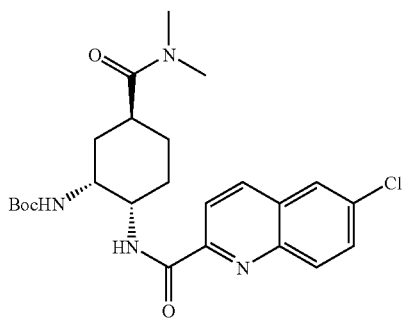

The title compound was obtained from the compound obtained in Referential Example 144 and the compound obtained in Referential Example 54 in a similar manner to Referential Example 91.

$^1$H-NMR (CDCl$_3$) δ: 1.41 (9H, br), 1.50-1.70 (1H, m), 1.75-1.95 (2H, m), 1.95-2.25 (3H, m), 2.65-2.80 (1H, m), 2.96 (3H, s), 3.07 (3H, s), 4.15-4.30 (1H, m), 4.30-4.40 (1H, m), 4.95 (1H, br), 7.66 (1H, d, J=8.8 Hz), 7.84 (1H, s), 8.00 (1H, d, J=8.8 Hz), 8.19 (1H, d, J=8.6 Hz), 8.30 (1H, d, J=8.6 Hz). MS (FAB) m/z: 475 (M+H)$^+$.

Referential Example 146 tert-Butyl (1R,2S,5S)-2-{[(7-chloroquinolin-3-yl)carbonyl]amino}-5-[(dimethylamino)carbonyl]cyclohexylcarbamate

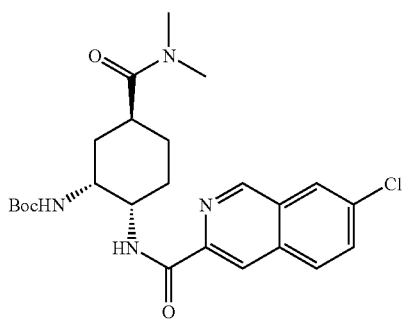

The title compound was obtained from the compound obtained in Referential Example 144 and the compound obtained in Referential Example 57 in a similar manner to Referential Example 91.

$^1$H-NMR (CDCl$_3$) δ: 1.30-1.65 (10H, br), 1.75-1.90 (2H, m), 1.90-2.25 (3H, m), 2.65-2.90 (1H, br), 2.96 (3H, s), 3.08 (3H, s), 4.20-4.30 (1H, m), 4.30-4.40 (1H, m), 4.93 (1H, br), 7.68 (1H, m), 7.90 (1H, br), 7.99 (1H, s), 8.35-8.70 (2H, m), 9.01 (1H, br). MS (FAB) m/z: 475 (M+H)$^+$.

Referential Example 147

2-Bromo-5-isopropyl-4,5,6,7-tetrahydrothiazolo[5,4-c]-pyridine

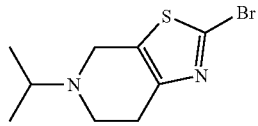

The title compound was obtained from the compound obtained in Referential Example 8 in a similar manner to Referential Example 9.

$^1$H-NMR (CDCl$_3$) δ: 1.13 (6H, d, J=6.5 Hz), 2.86 (4H, s), 2.89-3.00 (1H, m), 3.70 (2H, s).

Referential Example 148

Lithium 5-isopropyl-4,5,6,7-tetrahydrothiazolo[5,4-c]-pyridine-2-carboxylate

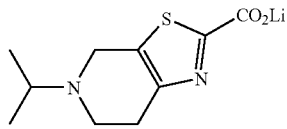

The title compound was obtained from the compound obtained in Referential Example 147 in a similar manner to Referential Example 10.

$^1$H-NMR (DMSO-d$_6$) δ: 1.05 (6H, d, J=6.4 Hz), 2.68-2.70 (2H, m), 2.75-2.77 (2H, m), 2.87-2.93 (1H, m), 3.66 (2H, s).

Referential Example 149

4-Nitrophenyl 5-methyl-4,5,6,7-tetrahydrothiazolo[5,4-c]-pyridine-2-carboxylate

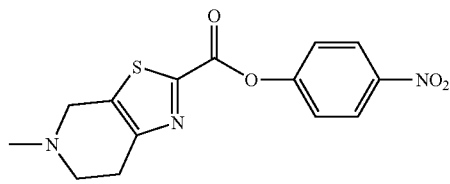

The title compound was obtained from the compound obtained in Referential Example 10 and p-nitrophenol in a similar manner to Referential Example 52.

$^1$H-NMR (CDCl$_3$) δ: 2.55 (3H, s), 2.88 (2H, t, J=5.7 Hz), 3.06-3.12 (2H, m), 3.80 (2H, s), 7.46 (2H, d, J=9.3 Hz), 8.32 (2H, d, J=9.3 Hz). MS (ESI) m/z: 320 (M+H$^+$).

Referential Example 150

Benzyl 3-oxocyclobutanecarboxylate

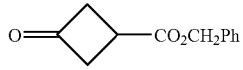

Triethylamine (2.0 ml) and benzyl bromide (1.2 ml) were added to a solution of 3-oxocyclobutanecarboxylic acid (J. Org. Chem., Vol. 53, pp. 3841-3843, 1981) (995 mg) in tetrahydrofuran (5.0 ml), and the mixture was stirred at room temperature for 2 hours. The reaction mixture was diluted with ethyl acetate, and washed successively with 1N hydrochloric acid, a saturated aqueous solution of sodium hydrogencarbonate and saturated saline and dried over anhydrous sodium sulfate. The solvent was then distilled off under reduced pressure, and the resultant residue was purified by column chromatography on silica gel (ethyl acetate:hexane=1:6) to obtain the title compound (886 mg).

$^1$H-NMR (CDCl$_3$) δ: 3.22-3.33 (3H, m), 3.37-3.48 (2H, m), 5.19 (2H, s), 7.31-7.42 (5H, m). MS (FAB) m/z: 205 (M+H$^+$).

Referential Example 151

Benzyl 3-hydroxycyclobutanecarboxylate

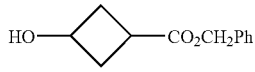

Sodium borohydride (76 mg) was added to a solution of the compound (781 mg) obtained in Referential Example 150 in a mixed solvent of tetrahydrofuran (10 ml) and methanol (0.5 ml) at 0° C., and the mixture was stirred at the same temperature for 30 minutes. The reaction mixture was diluted with ethyl acetate, and washed with a saturated aqueous solution of sodium hydrogencarbonate and saturated aqueous solution of sodium chloride in that order and dried over anhydrous sodium sulfate. The solvent was then distilled off under reduced pressure, and the resultant residue was purified by column chromatography on silica gel (ethyl acetate:hexane=1:2) to obtain the title compound (770 mg).

$^1$H-NMR (CDCl$_3$) δ: 2.13-2.27 (3H, m), 2.55-2.71 (3H, m), 4.14-4.23 (1H, m), 5.12 (2H, s), 7.28-7.39 (5H, m). MS (FAB) m/z: 207 (M+H$^+$).

Referential Example 152

3-Hydroxycyclobutanecarboxylic Acid

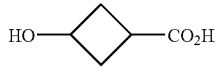

10% Palladium on carbon (108 mg) was added to a solution of the compound (706 mg) obtained in Referential Example 151 in ethanol (10 ml), and the mixture was stirred at room temperature for 2 hours in a hydrogen atmosphere. After the catalyst was removed by filtration through Celite, the filtrate was concentrated under reduced pressure to obtain the title compound (399 mg).

$^1$H-NMR (CD$_3$OD) δ: 2.00-2.21 (2H, m), 2.41-2.61 (3H, m), 4.01-4.13 (1H, m).

Referential Example 153

Benzyl 3-methoxycyclobutanecarboxylate

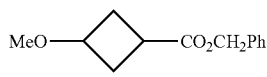

Methyl iodide (194 µl) and silver oxide (237 mg) were added to a solution of the compound (317 mg) obtained in Referential Example 151 in N,N-dimethylformamide (3.0 ml), and the mixture was stirred at 45° C. for 1 hour. Methyl iodide (194 µl) and silver oxide (226 mg) were additionally added to the reaction mixture, and the mixture was stirred at 45° C. for 16 hours. After the catalyst was removed by filtration, the filtrate was concentrated under reduced pressure, and the residue was purified by column chromatography on silica gel (ethyl acetate:hexane=1:10) to obtain the title compound (152 mg).

$^1$H-NMR (CDCl$_3$) δ: 2.14-2.24 (2H, m), 2.44-2.54 (2H, m), 2.59-2.72 (1H, m), 3.21 (3H, s), 3.73-3.81 (1H, m), 5.11 (2H, s), 7.22-7.39 (5H, m). MS (ESI) m/z: 221 (M+H$^+$).

Referential Example 154

3-Methoxycyclobutanecarboxylic Acid

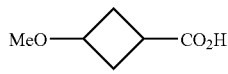

The title compound was obtained from the compound obtained in Referential Example 153 in a similar manner to Referential Example 152.

$^1$H-NMR (CDCl$_3$) δ: 2.17-2.27 (2H, m), 2.48-2.58 (2H, m), 2.62-2.73 (1H, m), 3.25 (3H, s), 3.76-3.86 (1H, m), 8.60-9.30 (1H, br).

Referential Example 155

Methyl 3-methoxy-2-(methoxymethyl)propionate

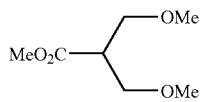

Sodium methoxide (1.21 g) was added to a solution of methyl 2-(bromomethyl)acrylate (1.0 ml) in methanol (10 ml), and the mixture was heated under reflux for 26 hours. After cooling, the reaction mixture was diluted with diethyl ether, and precipitate was collected by filtration and the filtrate was concentrated under reduced pressure. The resultant residue was purified by column chromatography on silica gel (ethyl acetate:hexane=1:4) to obtain the title compound (726 mg).

¹H-NMR (CDCl₃) δ: 2.90-2.96 (1H, m), 3.34 (6H, s), 3.57 (2H, dd, J=9.3, 5.9 Hz), 3.64 (2H, dd, J=9.3, 6.6 Hz), 3.73 (3H, s).
¹³C-NMR (CDCl₃) δ: 172.71, 70.31, 59.91, 46.49. MS (ESI) m/z: 163 (M+H⁺).

Referential Example 156

Tetrahydro-2H-pyrane-4-carboxylic Acid

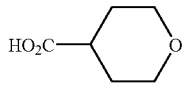

Dimethyl tetrahydro-4H-pyrane-4,4-dicarboxylate (4.04 g) was added to 20% hydrochloric acid (20 ml), and the mixture was heated under reflux for 19 hours. Water was added to the reaction mixture to conduct extraction with diethyl ether. After the resultant organic layer was washed with saturated aqueous solution of sodium chloride and dried over anhydrous sodium sulfate, the solvent was distilled off under reduced pressure. After the resultant residue was solidified with hexane, the resultant solides were collected by filtration and washed to obtain the title compound (2.63 g).
¹H-NMR (CDCl₃) δ: 1.75-1.95 (4H, m), 2.55-2.65 (1H, m), 3.40-3.52 (2H, m), 3.93-4.05 (2H, m).

Referential Example 157

Methyl 3-{[tert-butyl(diphenyl)silyl]oxy}-2,2-dimethylpropionate

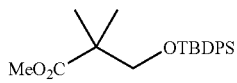

The title compound was obtained from methyl 2,2-dimethyl-3-hydroxypropionate in a similar manner to Referential Example 41.
¹H-NMR (CDCl₃) δ: 1.03 (9H, s), 1.20 (6H, s), 3.64-3.68 (5H, m), 7.38-7.44 (6H, m), 7.63-7.65 (4H, m).

Referential Example 158

3-{[tert-Butyl(diphenyl)silyl]oxy}-2,2-dimethylpropionic Acid

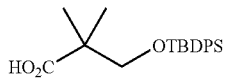

Water (0.24 ml) was added to a suspension composed of potassium tert-butoxide (5.32 g) and diethyl ether (100 ml) under ice cooling, and the mixture was stirred for 5 minutes. The compound (2.22 g) obtained in Referential Example 157 was added thereto, and the resultant mixture was stirred overnight at room temperature. Water was added to the reaction mixture, and the mixture was acidified with 1N hydrochloric acid and extracted 3 times with diethyl ether. After the resultant organic layer was dried over anhydrous sodium sulfate, the solvent was distilled off under reduced pressure, and the resultant residue was purified by column chromatography on silica gel (ethyl acetate:hexane=1:6) to obtain the title compound (735 mg).
¹H-NMR (CDCl₃) δ: 1.04 (9H, d, J=0.7 Hz), 1.22 (6H, s), 3.65 (2H, s), 7.36-7.45 (6H, m), 7.64-7.66 (4H, m).

Referential Example 159

Methyl 3-methoxy-2,2-dimethylpropionate

A solution of methyl 3-hydroxy-2,2-dimethylpropionate (25.0 g) in tetrahydrofuran (300 ml) was added dropwise to a suspension composed of a 60% oil suspension of sodium hydride (8.32 g) and tetrahydrofuran (100 ml) under ice cooling, and the mixture was stirred at 60° C. for 1 hour. Methyl iodide (53.7 g) was added to the reaction mixture, and the resultant mixture was stirred at room temperature for 2 hours. Water was carefully added to conduct extraction twice with methylene chloride. After the resultant organic layer was washed with saturated aqueous solution of sodium chloride and then dried over anhydrous sodium sulfate, the solvent was distilled off under reduced pressure, and the resultant oil was distilled to obtain the title compound (12.8 g).
Boiling point: 140-142° C. (ordinary pressure). ¹H-NMR (CDCl₃) δ: 1.19 (6H, d, J=1.0 Hz), 3.33 (3H, d, J=1.0 Hz), 3.38 (2H, d, J=1.0 Hz), 3.69 (3H, d, J=1.0 Hz).

Referential Example 160

3-Methoxy-2,2-dimethylpropionic Acid

The title compound was obtained from the compound obtained in Referential Example 159 in a similar manner to Referential Example 158.
¹H-NMR (CDCl₃) δ: 1.22 (6H, d, J=0.7 Hz), 3.38 (3H, d, J=0.7 Hz), 3.40 (2H, d, J=0.7 Hz).

Referential Example 161

1-(Methoxycarbonyl)cyclopropanecarboxylic Acid

Dimethyl 1,1-cyclopropanecarboxylate (25 g) was dissloved in methanol (250 ml), and the solution was cooled with ice. A 1N aqueous solution of sodium hydroxide (158 ml) was then added dropwise, and the resultant mixture was warmed to room temperature and stirred overnight. After methanol was distilled off, the residue was washed with chloroform, and a water layer was cooled with ice, adjusted to pH 2 with concentrated hydrochloric acid and extracted with ethyl acetate. The extract was dried over anhydrous sodium sulfate, and the solvent was distilled off under reduced pressure to obtain the title compound (16.8 g).

$^1$H-NMR (CDCl$_3$) δ: 1.76-1.80 (2H, m), 1.82-1.88 (2H, m), 3.79 (3H, s), 12.73 (1H, br).

Referential Example 162

Methyl 1-(hydroxymethyl)cyclopropanecarboxylate

The compound (9.0 g) obtained in Referential Example 161 and triethylamine (9.7 ml) were dissolved in tetrahydrofuran (180 ml), and the solution was cooled to −10° C., to which isobutyl chloroformate (9.1 ml) was added dropwise, and the resultant mixture was stirred for 1 hour. On the other hand, sodium borohydride (7.1 g) was dissolved in tetrahydrofuran (100 ml)-water (25 ml) and cooled with ice. While removing insoluble matter by filtration, the solution prepared previously was added dropwise, and the resultant mixture was stirred at the same temperature for 1 hour. The reaction mixture was poured into a cooled 10% aqueous solution of citric acid to conduct extraction with ethyl acetate. After the extract was washed with saturated aqueous solution of sodium chloride and then dried over anhydrous sodium sulfate, the solvent was distilled off under reduced pressure. The resultant residue was purified by column chromatography on silica gel (ethyl acetate:hexane=1:9-2:1) to obtain the title compound (4.25 g).

$^1$H-NMR (CDCl$_3$) δ: 0.87-0.93 (2H, m), 1.28-1.30 (2H, m), 3.63 (2H, s), 3.70 (3H, s).

Referential Example 163

Methyl 1-(bromomethyl)cyclopropanecarboxylate

Triphenylphosphine (10 g) and carbon tetrabromide (16 g) were added to a solution of the compound (4.20 g) obtained in Referential Example 162 in methylene chloride (168 ml) at room temperature under a nitrogen atmosphere. After 2 minutes, a saturated aqueous solution of sodium hydrogencarbonate was added thereto. After the resultant organic layer was washed with saturated aqueous solution of sodium chloride and dried over anhydrous sodium sulfate, the solvent was distilled off under reduced pressure. The resultant residue was purified by column chromatography on silica gel (ethyl acetate:hexane=1:19) to obtain the title compound (2.15 g).

$^1$H-NMR (CDCl$_3$) δ: 1.00-1.05 (2H, m), 1.52-1.59 (2H, m), 3.61 (2H, s), 3.73 (3H, s).

Referential Example 164 tert-Butyl (4S)-4-[(E)-3-ethoxy-3-oxo-1-propenyl]-2,2-dimethyl-1,3-oxazolidine-3-carboxylate

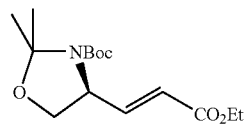

A mixture solution composed of tert-Butyl (4R)-4-formyl-2,2-dimethyl-1,3-oxazolidine-3-carboxylate (11.7 g), (carboethoxymethylene)triphenylphosphorane (20.7 g) and toluene (100 ml) was heated and stirred at 100° C. for 18 hours. The reaction mixture was concentrated, and the resultant residue was purified by column chromatography on silica gel (hexane:ethyl acetate=8:1) to obtain the title compound (17 g).

$^1$H-NMR (CDCl$_3$) δ: 1.29 (3H, t, J=6.6 Hz), 1.43-1.56 (15H, m), 3.80 (1H, dd, J=9.0, 2.4 Hz), 4.09 (1H, dd, J=9.0, 6.6 Hz), 4.11-4.23 (2H, m), 4.30-4.61 (1H, m), 5.83-6.02 (1H, m), 6.74-6.89 (1H, m).

Referential Example 165 tert-Butyl (4S)-4-[1-(benzylamino)-3-ethoxy-3-oxopropyl]-2,2-dimethyl-1,3-oxazolidine-3-carboxylate

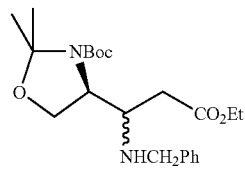

A mixture solution composed of the compound (22.2 g) obtained in Referential Example 164, benzylamine (16 g) and ethanol (100 ml) was heated under reflux for 2 days. The reaction mixture was concentrated, and the resultant residue was purified by column chromatagraphy on silica gel (hexane:ethyl acetate=8:1) to obtain the title compound (26 g).

$^1$H-NMR (CDCl$_3$) δ: 1.25 (3H, t, J=6.6 Hz), 1.42-1.63 (15H, m), 2.24-2.33 (0.5H, m), 2.40-2.50 (1H, m), 2.63-2.74 (0.5H, m), 3.41-3.52 (1H, m), 3.67-3.80 (1H, m), 3.83 (2H, s), 3.89-4.00 (1H, m), 4.03-4.22 (4H, m), 7.23-7.45 (5H, m).

Referential Example 166 tert-Butyl (4S)-4-(1-amino-3-ethoxy-3-oxopropyl)-2,2-dimethyl-1,3-oxazolidine-3-carboxylate

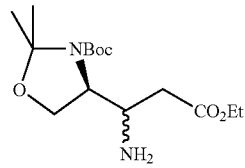

10% Palladium on carbon (10 g) was added to a solution of the compound (13.6 g) obtained in Referential Example 165 in ethanol (200 ml), and the mixture was stirred for 2 days under a hydrogen atmosphere. Insoluble matter was removed through Celite pad, and the filtrate was concentrated under reduced pressure to obtain the title compound (10.5 g).

$^1$H-NMR (DMSO-d$_6$) δ: 1.19 (1.5H, t, J=6.6 Hz), 1.20 (1.5H, t, J=6.6 Hz), 1.32-1.50 (15H, m), 2.63-2.81 (2H, m), 3.22-3.34 (2H, m), 3.93 (1H, dd, J=10.0, 6.8 Hz), 4.08 (2H, q, J=6.6 Hz), 4.20-4.30 (1H, m).

Referential Example 167 tert-Butyl (4S)-4-(1-([[(benzyloxy)carbonyl]amino}-3-ethoxy-3-oxopropyl)-2,2-dimethyl-1,3-oxazolidine-3-carboxylate

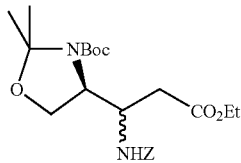

The compound (3.0 g) obtained in Referential Example 166 was suspended in a 9% aqueous solution (56 ml) of sodium hydrogencarbonate, and a solution of N-(benzyloxycarbonyloxy)succinimide (2.3 g) in dioxane (12 ml) was added dropwise to the suspension under ice cooling. The resultant mixture was stirred for 3 hours while the temperature of the system was gradually raised to room temperature. The reaction mixture was diluted with ethyl acetate and washed with water, a 10% aqueous solution of citric acid and saturated aqueous solution of sodium chloride and dried over anhydrous sodium sulfate. The solvent was then distilled off under reduced pressure, and the resultant residue was purified by column chromatography on silica gel (chloroform) to obtain the title compound (3.8 g).

$^1$H-NMR (CDCl$_3$) δ: 1.23 (3H, t, J=6.6 Hz), 1.48 (9H, s), 1.56 (6H, s), 2.40-2.51 (2H, m), 2.63-2.70 (2H, m), 3.92-4.04 (1H, m), 4.06-4.10 (2H, m), 4.14-4.22 (1H, m), 5.09 (2H, s), 7.30-7.43 (5H, m).

Referential Example 168

Ethyl (3S,4S)-3-{[(benzyloxy)carbonyl]amino}-4-[(tert-butoxycarbonyl)amino]-5-hydroxyvalerate (Low-Polar Compound) and ethyl (3R,4S)-3-{[(benzyloxy)carbonyl]amino}-4-[(tert-butoxycarbonyl)amino]-5-hydroxyvalerate (High-Polar Compound)

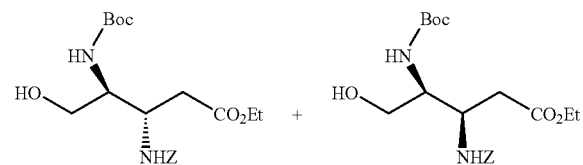

Low-polar Compound   High-polar Compound

Trifluoroacetic acid (100 ml) was added dropwise to a solution of the compound (30 g) obtained in Referential Example 167 in methylene chloride (100 ml) under ice cooling, and the mixture was stirred for 3 hours while the temperature of the system was gradually raised to room temperature. The reaction mixture was concentrated under reduced pressure, and the resultant residue was dissolved in methylene chloride (100 ml). Triethylamine (20 ml) and a solution of di-tert-butyl dicarbonate (19 g) in methylene chloride (100 ml) were successively added dropwise to this solution under ice cooling, and the mixture was stirred for 4 hours while the temperature of the system was gradually raised to room temperature. The reaction mixture was concentrated under reduced pressure, and the resultant residue was purified by column chromatography on silica gel (hexane:ethyl acetate=2:1) to obtain the title low-polar compound (7.6 g) and the title high-polar compound (10 g).

Low-Polar Compound:

$^1$H-NMR (CDCl$_3$) δ: 1.24 (3H, t, J=6.6 Hz), 1.42 (9H, s), 2.63 (2H, d, J=4.4 Hz), 3.30-3.41 (1H, m), 3.50 (1H, t, J=9.7 Hz), 3.65 (1H, t, J=9.7 Hz), 3.75 (1H, d, J=11.7 Hz), 3.90-4.00 (1H, m), 4.03-4.23 (2H, m), 5.12 (2H, s), 5.13-5.25 (1H, m), 5.79-6.02 (1H, m), 7.32-7.41 (5H, m).

High-Polar Compound:

$^1$H-NMR (CDCl$_3$) δ: 1.22 (3H, t, J=6.6 Hz), 1.41 (9H, s), 2.50-2.70 (2H, m), 3.20-3.31 (1H, m), 3.43-3.51 (1H, m), 3.56-3.70 (1H, m), 3.74-3.78 (1H, m), 4.00-4.19 (2H, m), 4.23-4.30 (1H, m), 4.78-4.89 (1H, m), 5.10 (2H, s), 5.56-5.67 (1H, m), 7.31-7.40 (5H, m).

Referential Example 169

(3R,4S)-4-[(Methylsulfonyl)oxy]tetrahydro-3-furanyl methanesulfonate

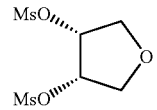

Triethylamine (12.0 ml) and methanesulfonyl chloride (3.6 ml) were successively added dropwise to a solution of 1,4-anhydroerythritol (5.0 g) in methylene chloride (50 ml) under ice cooling, and the mixture was stirred for 10 minutes under ice cooling. The reaction mixture was diluted with methylene chloride and washed with 10% hydrochloric acid, a saturated aqueous solution of sodium hydrogencarbonate and saturated aqueous solution of sodium chloride. After the resultant organic layer was dried over anhydrous sodium sulfate, the solvent was distilled off under reduced pressure to obtain the title compound (9.2 g).

$^1$H-NMR (CDCl$_3$) δ: 3.15 (6H, s), 3.99 (2H, dd, J=11.2, 20.5 Hz), 4.16 (2H, dd, J=11.2, 4.6 Hz), 5.10-5.20 (2H, m).

Referential Example 170

(3R,4S)-3,4-Diazidotetrahydrofuran

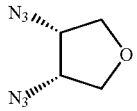

The compound (9.2 g) obtained in Referential Example 169 was dissolved in N,N-dimethylformamide (50 ml), sodium azide (18 g) was added, and the resultant mixture was heated and stirred at 100° C. for 18 hours. The reaction mixture was diluted with ethyl acetate and washed with water and saturated aqueous solution of sodium chloride. After the resultant organic layer was dried over anhydrous sodium sulfate, the solvent was distilled off under reduced pressure to obtain the title compound (3.8 g).

$^1$H-NMR (CDCl$_3$) δ: 3.83 (2H, dd, J=8.6, 2.0 Hz), 3.96-4.12 (4H, m).

Referential Example 171

(3R,4S)-Tetrahydro-3,4-furandiamine Dihydrochloride

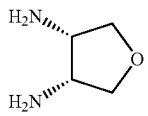

The compound (3.8 g) obtained in Referential Example 170 was dissolved in ethanol (50 ml), 10% palladium on carbon (1.0 g) was added to the solution, and the mixture was stirred for 18 hours under a hydrogen atmosphere. Insoluble matter was removed through Celite pad, and the filtrate was concentrated under reduced pressure. A 1N ethanol solution of hydrochloric acid was added to the resultant residue, giving the hydrochloride salt. The hydrochloride was recrystallized from a mixed solvent of ethanol and diethyl ether to obtain the title compound (2.0 g).

$^1$H-NMR (CDCl$_3$) δ: 3.90 (2H, dd, J=9.0, 3.7 Hz), 4.01-4.13 (4H, m), 8.84 (6H, s).

Referential Example 172

N-[(3R*,4S*)-4-Aminotetrahydro-3-furanyl]-5-chloroindole-2-carboxamide

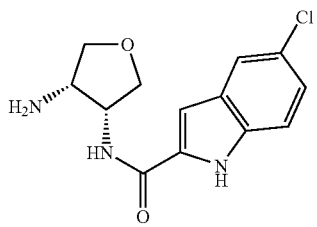

5-Chloroindole-2-carboxylic acid (0.29 g), 1-hydroxybenzotriazole monohydrate (0.2 g) and 1-(3-dimethylaminopropyl)-3-ethylcarbodiimide hydrochloride (0.6 g) were successively added to a solution of the compound (0.5 g) obtained in Referential Example 171 in N,N-dimethylformamide (10 ml), and the mixture was heated and stirred at 50° C. for a day. The reaction mixture was concentrated, and the resultant residue was diluted with a mixed solvent composed of chloroform and methanol (9:1) and washed with a saturated aqueous solution of sodium hydrogencarbonate and saturated aqueous solution of sodium chloride. After the resultant organic layer was dried over anhydrous sodium sulfate, the solvent was distilled off under reduced pressure, and the resultant residue was purified by column chromatography on silica gel (chloroform:methanol=95:5) to obtain the title compound (0.2 g).

$^1$H-NMR (CDCl$_3$) δ: 1.80-1.92 (1H, m), 3.62 (1H, dd, J=9.3, 4.2 Hz), 3.68-3.80 (2H, m), 4.06 (1H, dd, J=9.3, 5.6 Hz), 4.21 (1H, dd, J=9.3, 6.8 Hz), 4.36-4.52 (2H, m), 6.87 (1H, s), 7.24 (1H, dd, J=8.8, 2.0 Hz), 7.36 (1H, d, J=8.8 Hz), 7.44-7.56 (1H, m), 7.62 (1H, d, J=2.0 Hz), 9.41 (1H, s).

Referential Example 173 tert-Butyl (4R)-4-[(E)-3-ethoxy-3-oxo-1-propenyl]-2,2-dimethyl-1,3-oxazolidine-3-carboxylate

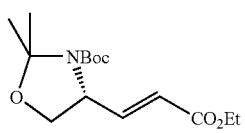

The title compound was obtained from tert-Butyl (4S)-4-formyl-2,2-dimethyl-1,3-oxazolidine-3-carboxylate in a similar manner to Referential Example 164.

$^1$H-NMR (CDCl$_3$) δ: 1.29 (3H, t, J=6.6 Hz), 1.40-1.60 (15H, m), 3.80 (1H, dd, J=9.0, 2.4 Hz), 4.09 (1H, dd, J=9.0, 6.6 Hz), 4.11-4.21 (2H, m), 4.32-4.64 (1H, m), 5.78-6.01 (1H, m), 6.67-6.89 (1H, m).

Referential Example 174 tert-Butyl (4R)-4-[1-(benzylamino)-3-ethoxy-3-oxopropyl]-2,2-dimethyl-1,3-oxazolidine-3-carboxylate

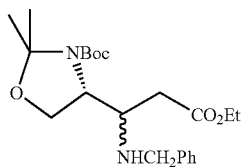

The title compound was obtained from the compound obtained in Referential Example 173 in a similar manner to Referential Example 165.

$^1$H-NMR (CDCl$_3$) δ: 1.25 (3H, t, J=6.6 Hz), 1.40-1.61 (15H, m), 2.21-2.32 (0.5H, m), 2.40-2.51 (1H, m), 2.61-2.72 (0.5H, m), 3.43-3.50 (1H, m), 3.67-3.80 (1H, m), 3.83 (2H, s), 3.90-4.03 (1H, m), 4.04-4.22 (4H, m), 7.20-7.40 (5H, m).

Referential Example 175 tert-Butyl (4R)-4-(1-{[(5-chloroindol-2-yl)carbonyl]amino}-3-ethoxy-3-oxopropyl)-2,2-dimethyl-1,3-oxazolidine-3-carboxylate

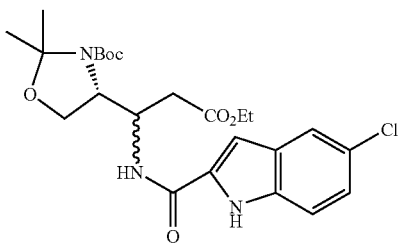

The title compound was obtained by reducing the compound obtained in Referential Example 174 in a similar manner to Referential Example 166 to remove a benzyl group and then condensing it with 5-chloroindole-2-carboxylic acid in a similar manner to Referential Example 172.

$^1$H-NMR (CDCl$_3$) δ: 1.23 (1.5H, t, J=6.6 Hz), 1.25 (1.5H, t, J=6.6 Hz), 1.50 (4.5H, s), 1.54 (4.5H, s), 1.62 (6H, s), 2.50-2.70 (1.5H, m), 2.86 (0.5H, dd, J=16.4, 5.5 Hz), 3.80-3.90 (0.5H, m), 4.00-4.31 (5H, m), 4.41-4.67 (0.5H, m), 6.85 (0.5H, s), 6.87 (0.5H, s), 7.10-7.20 (1H, m), 7.34 (0.5H, d, J=8.8 Hz), 7.38 (0.5H, d, J=8.8 Hz), 7.57 (0.5H, s), 7.63 (0.5H, s), 7.88 (0.5H, d, J=7.6 Hz), 8.54 (0.5H, d, J=7.6 Hz), 9.40 (0.5H, s), 9.54 (0.5H, s).

Referential Example 176 tert-Butyl (3R,4R)-4-{[(5-chloroindol-2-yl)carbonyl]amino}-6-oxotetrahydro-2H-pyran-3-ylcarbamate (Low-Polar Compound) and tert-butyl and (3R,4S)-4-{[(5-chloroindol-2-yl)carbonyl]-amino}-6-oxotetrahydro-2H-pyran-3-ylcarbamate (High-Polar Compound)

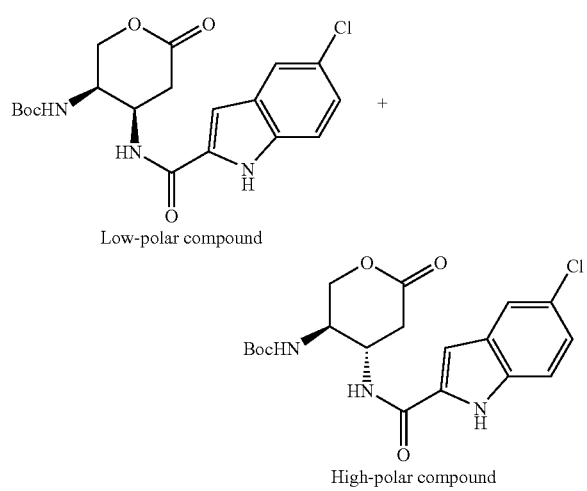

A 1N aqueous solution (4.0 ml) of sodium hydroxide was added to a solution of the compound (1.0 g) obtained in Referential Example 175 in ethanol (20 ml), and the mixture was stirred for 4 hours. Citric acid was added to the reaction mixture to adjust the pH of the reaction mixture to 4.0. The reaction mixture was extracted with ethyl acetate, and the resultant organic layer was washed with saturated aqueous solution of sodium chloride and then dried over anhydrous sodium sulfate. The solvent was distilled off under reduced pressure. The resultant residue was dissolved in methanol (50 ml), and toluenesulfonic acid monohydrate (0.1 g) was added to the solution to stir the resultant mixture for 18 hours. The reaction mixture was diluted with ethyl acetate and washed with a saturated aqueous solution of sodium hydrogencarbonate and saturated aqueous solution of sodium chloride. The resultant organic layer was dried over anhydrous sodium sulfate, and the solvent was distilled off under reduced pressure. The resultant residue was purified by column chromatography on silica gel (chloroform:methanol 99:1) to obtain the title low-polar compound (0.3 g) and the title high-polar compound (0.3 g).

Low-Polar Compound:

$^1$H-NMR (CDCl$_3$) δ: 1.45 (9H, s), 2.70 (1H, dd, J=16.5, 4.9 Hz), 2.85 (1H, dd, J=16.5, 4.6 Hz), 3.50-3.61 (1H, m), 3.71-3.81 (2H, m), 4.30-4.40 (1H, m), 5.30 (1H, d, J=9.5 Hz), 6.89 (1H, s), 7.23 (1H, dd, J=8.8, 2.0 Hz), 7.38 (1H, d, J=8.8 Hz), 7.62 (1H, d, J=2.0 Hz), 7.93 (1H, d, J=9.5 Hz), 9.30 (1H, s).

High-Polar Compound:

$^1$H-NMR (CDCl$_3$) δ: 1.39 (9H, s), 2.75 (1H, dd, J=16.5, 4.9 Hz), 2.82 (1H, dd, J=16.5, 4.6 Hz), 3.41-3.52 (2H, m), 3.71-3.82 (1H, m), 3.85-3.94 (1H, m), 5.03 (1H, d, J=9.3 Hz), 6.99 (1H, s), 7.22-7.31 (1H, m), 7.34 (1H, d, J=8.8 Hz), 7.61 (1H, d, J=2.0 Hz), 7.83 (1H, d, J=9.3 Hz), 9.28 (1H, s).

Referential Example 177 tert-Butyl 1,1,3-trioxohexahydro-1-thiopyran-4-ylcarbamate

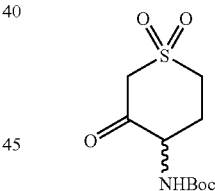

A solution of N-tert-butoxycarbonyl-L-methionine sulfone methyl ester (60.2 g) in tetrahydrofuran (900 ml) was cooled to −78° C., to which 0.5 M potassium bis(trimethylsilyl)amide (toluene solution, 900 ml) was added dropwise, and the mixture was stirred for 2 hours at −78° C. and for 4.5 hours at room temperature. A 1 M aqueous solution of ammonium chloride was added, and the mixture was stirred. The reaction mixture was subjected to liquid separation, and the resultant organic layer was then washed with water and saturated aqueous solution of sodium chloride and dried over anhydrous magnesium sulfate. The solvent was distilled off under reduced pressure, and solids formed were collected by filtration to obtain the title compound (12.4 g). The water layer separated previously was extracted twice with ethyl acetate, and the resultant organic layers were combined, washed with water and saturated aqueous solution of sodium chloride and dried over anhydrous magnesium sulfate. The water layers used in the washing were further combined, and extracted again with ethyl acetate, and the extract was washed with saturated aqueous solution of sodium chloride and dried over anhydrous magnesium sulfate. The ethyl acetate extracts were combined, dried and then concentrated under reduced pressure to obtain the title compound (27.7 g) (total amount of the title compound: 40.1 g).

$^1$H-NMR (CDCl$_3$) δ: 1.45 (9H, s), 1.85-1.96 (1H, m), 2.76-2.78 (1H, m), 3.34-3.46 (2H, m), 4.05 (1H, dd, J=13.5, 3.7 Hz), 4.14 (1H, d, J=13.5 Hz), 4.38-4.44 (1H, m), 5.46 (1H, br). MS (ESI) m/z: 262 (M–H)$^-$.

Referential Example 178 tert-Butyl (3R*,4R*)-3-hydroxy-1,1-dioxohexahydro-1-thiopyran-4-ylcarbamate

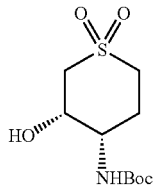

Sodium borohydride (2.17 g) was added to a suspension of the compound (10.1 g) obtained in Referential Example 177 in methanol (200 ml), and the mixture was stirred at room temperature for 2 hours. The reaction mixture was concentrated under reduced pressure. After ethyl acetate and a saturated aqueous solution of sodium hydrogencarbonate were added to the residue to conduct liquid separation, the resultant water layer was extracted twice with ethyl acetate. The resultant organic layers were combined, dried over anhydrous magnesium sulfate and then concentrated under reduced pressure to obtain the title compound (9.96 g).

$^1$H-NMR (CDCl$_3$) δ: 1.44 (9H, s), 2.21-2.36 (2H, m), 3.03-3.17 (2H, m), 3.26-3.28 (2H, m), 3.77-3.80 (2H, m), 4.26-4.28 (1H, m), 5.05-5.07 (1H, m). MS (ESI) m/z: 264 (M–H)$^-$.

Referential Example 179 tert-Butyl (3R*,4R*)-3-amino-1,1-dioxohexahydro-1-thiopyran-4-ylcarbamate (Low-Polar Compound) and tert-Butyl (3R*,4S*)-3-amino-1,1-dioxohexahydro-1-thiopyran-4-ylcarbamate (High-Polar Compound)

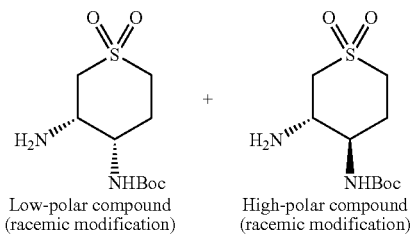

Low-polar compound (racemic modification)     High-polar compound (racemic modification)

Diethyl azodicarboxylate (6.96 g) was added to a solution of the compound (9.66 g) obtained in Referential Example 178 and triphenylphosphine (10.5 g) in tetrahydrofuran (150 ml), and the mixture was stirred at room temperature for 4.5 hours. After the reaction mixture was concentrated under reduced pressure, diethyl ether was added to the residue, and solids formed were collected by filtration. The thus-collected solids were purified by column chromatography on silica gel (hexane:ethyl acetate 7:3) to obtain a mixture (7.25 g) containing tert-butyl 1,1-dioxo-1,2,3,4-tetrahydropyran-4-ylcarbamate as a colorless solid. The mother liquor was concentrated under reduced pressure, and the resultant residue was purified by column chromatagraphy on silica gel (hexane:ethyl acetate=7:3) to obtain a mixture (9.18 g) containing tert-butyl 1,1-dioxo-1,2,3,4-tetrahydropyran-4-ylcarbamate as a colorless solid (total amount: 16.4 g). The thus-obtained mixtures were dissolved in dioxane (60 ml), and 28% aqueous ammonia (60 ml) was added. The resultant mixture was stirred at 60° C. for 4.5 hours in a sealed tube. After allowing to cool, the reaction mixture was concentrated under reduced pressure. After dioxane was distilled off, the residue was extracted 5 times with methylene chloride. The resultant organic layers were combined and concentrated under reduced pressure. The resultant residue was purified by column chromatagraphy on silica gel (methylene chloride:methanol=96:4) to obtain the title low-polar compound (2.31 g) and the title high-polar compound (4.31 g).

Low-Polar Compound:
$^1$H-NMR (CDCl$_3$) δ: 1.44 (9H, s), 2.14-2.28 (2H, m), 3.01-3.08 (3H, m), 3.23 (1H, dd, J=13.8, 3.9 Hz), 3.47-3.49 (1H, m), 3.71-3.76 (1H, m), 5.32 (1H, d, J=7.3 Hz). MS (ESI) m/z: 265 (M+H$^+$).

High-Polar Compound:
$^1$H-NMR (CDCl$_3$) δ: 1.45 (9H, s), 1.94-2.01 (1H, m), 2.37-2.44 (1H, m), 2.91 (1H, dd, J=11.2, 14.1 Hz), 3.04-3.07 (2H, m), 3.12-3.19 (1H, m), 3.26-3.30 (1H, m), 3.39-3.42 (1H, m), 4.62 (1H, br). MS (ESI) m/z: 265 (M+H$^+$).

Referential Example 180

(2S,3S)-2,3-Bis(methoxymethoxy)-1,4-butanediol

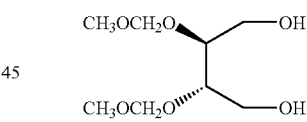

Chloromethyl methyl ether (4.8 ml) was added dropwise to a mixture solution composed of diethyl L-tartrate (8.6 g), diisopropylethylamine (40 ml) and methylene chloride (40 ml) under ice cooling, and the mixture was stirred for 18 hours while the temperature of the system was gradually raised to room temperature. The reaction mixture was concentrated, and the resultant residue was diluted with ethyl acetate and washed with 10% hydrochloric acid, a saturated aqueous solution of sodium hydrogencarbonate and saturated aqueous solution of sodium chloride. After the resultant organic layer was dried over anhydrous sodium sulfate, the solvent was distilled off under reduced pressure, and the resultant residue was dissolved in tetrahydrofuran. The solution was added dropwise to a tetrahydrofuran suspension of lithium aluminum hydride (2.2 g) under ice cooling, and the mixture was stirred for 2 hours under ice cooling. After a 10% aqueous solution of sodium hydrogensulfate was carefully added under ice cooling, and the mixture was stirred for 1 hour, the reaction mixture was diluted with saturated aqueous solution of sodium chloride and extracted with ethyl acetate. After the resultant organic layer was dried over anhydrous sodium sulfate, the solvent was distilled off under reduced pressure to obtain the title compound (3.0 g).

$^1$H-NMR (CDCl$_3$) δ: 1.55-1.64 (2H, m), 3.44 (6H, s), 3.70-3.81 (6H, m), 4.70 (2H, d, J=6.9 Hz), 4.76 (2H, d, J=6.9 Hz).

Referential Example 181

(3S,4S)-3,4-Bis(methoxymethoxy)tetrahydrofuran

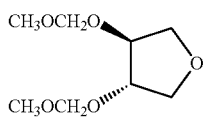

Diethyl azodicarboxylate (2.46 ml) was added dropwise to a mixture solution composed of the compound (3.0 g) obtained in Referential Example 180, triphenylphosphine (4.5 g), tetrahydrofuran (10 ml) and toluene (40 ml), and the mixture was stirred at room temperature for 4 days. The reaction mixture was concentrated under reduced pressure, a mixed solvent (160 ml) of hexane and diethyl ether (1:1) was added to the resultant residue, and the mixture was stirred for 3 hours. Insoluble matter deposited was then collected by filtration. The filtrate was concentrated, and the resultant residue was purified by column chromatography on silica gel (hexane:ethyl acetate 4:1) to obtain the title compound (1.95 g).

$^1$H-NMR (CDCl$_3$) δ: 3.38 (6H, s), 3.80 (2H, dd, J=9.2, 1.7 Hz), 4.00 (2H, dd, J=9.2, 4.4 Hz), 4.23 (2H, dd, J=4.4, 1.7 Hz), 4.67 (2H, d, J=6.9 Hz), 4.71 (2H, d, J=6.9 Hz).

Referential Example 182

(3S,4S)-Tetrahydro-3,4-furandiol

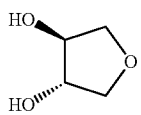

Concentrated hydrochloric acid (2.1 ml) was added to a solution of the compound (1.95 g) obtained in Referential Example 181 in methanol (6.0 ml), and the mixture was stirred for 18 hours. After the reaction mixture was concentrated, and the resultant residue was diluted with chloroform and dried over potassium carbonate, the solvent was distilled off under reduced pressure to obtain the title compound (0.52 g).

$^1$H-NMR (CDCl$_3$) δ: 1.77 (2H, d, J=4.7 Hz), 3.73 (2H, d, J=10.2 Hz), 4.08 (2H, dd, J=10.2, 3.7 Hz), 4.18-4.34 (2H, m).

Referential Example 183

(3S,4S)-Tetrahydro-3,4-furandiamine

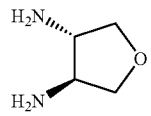

The title compound was obtained from the compound obtained in Referential Example 182 in a siminar manner to the processes described in Referential Examples 169 to 171.

$^1$H-NMR (CDCl$_3$) δ: 1.35-1.46 (4H, m), 3.19 (2H, dd, J=5.6, 4.1 Hz), 3.50 (2H, dd, J=9.0, 4.1 Hz), 4.09 (2H, dd, J=9.0, 5.6 Hz).

Referential Example 184

(2R,3R)-2,3-Bis(methoxymethoxy)-1,4-butanediol

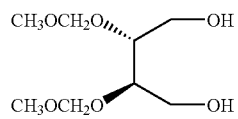

The title compound was obtained from diethyl D-tartrate in a similar manner to Referential Example 180.

$^1$H-NMR: The same as that of the enantiomer in Referential Example 180.

Referential Example 185

(3R,4R)-3,4-Bis(methoxymethoxy)tetrahydrofuran

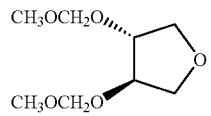

The title compound was obtained from the compound obtained in Referential Example 184 in a similar manner to Referential Example 181.

$^1$H-NMR: The same as that of the enantiomer in Referential Example 181.

Referential Example 186

(3R,4R)-Tetrahydro-3,4-furandiol

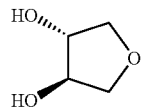

The title compound was obtained from the compound obtained in Referential Example 185 in a similar manner to Referential Example 182.

$^1$H-NMR: The same as that of the enantiomer in Referential Example 182.

Referential Example 187

(3R,4R)-Tetrahydro-3,4-furandiamine

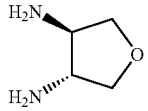

The title compound was obtained from the compound obtained in Referential Example 186 in a similar manner to Referential Example 183.

$^1$H-NMR (CDCl$_3$) δ: The same as that of the enantiomer in Referential Example 183.

Referential Example 188

(3R,4R)-1-Benzyl-3,4-dihydroxy-2,5-pyrrolidinedione

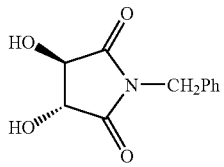

L-Tartaric acid (30 g) and benzylamine (22 ml) were added to xylene (150 ml), and the mixture was heated under reflux at 150° C. for 3 hours using a Dean-Stark trap. After the reaction mixture was allowed to cool overnight, crystals were collected by filtration and washed with acetone. The resultant crude product was recrystallized from ethanol to obtain the title compound (23.2 g).

$^1$H-NMR (DMSO-d$_6$) δ: 4.36-4.40 (2H, m), 4.55 (each 1H, AB type d, J=15 Hz), 6.26-6.30 (2H, m), 7.25-7.35 (5H, m).

Referential Example 189

(3S,4S)-1-Benzyl-3,4-pyrrolidinediol

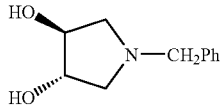

The compound (11 g) obtained in Referential Example 188 was dissolved in tetrahydrofuran (110 ml), and lithium aluminum hydride (5.69 g) was added portionwise to the solution under ice cooling. The mixture was heated to room temperature for 1 hour and heated under reflux and for additional a night. After allowing the reaction mixture to cool, water (5.7 ml), a 15% aqueous solution (5.7 ml) of sodium hydroxide and water (17.1 ml) were added under ice cooling in that order, and the mixture was heated to room temperature and stirred for 1 hour. After deposits were filtered through Celite, and the mother liquor was concentrated under reduced pressure, the resultant residue was recrystallized from ethyl acetate to obtain title compound (6.35 g).

$^1$H-NMR (CDCl$_3$) δ: 2.40-2.44 (2H, m), 2.88-2.92 (2H, m), 3.58 (each 1H, AB type d, J=7.8 Hz), 4.04 (2H, t, J=4.2 Hz), 7.25-7.34 (5H, m).

Referential Example 190

(3S,4S)-1-Benzyl-4-[(methylsulfonyl)oxy]pyrrolidinyl methanesulfonate

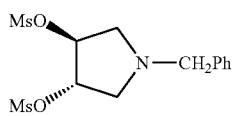

The title compound was obtained from the compound obtained in Referential Example 189 in a similar manner to Referential Example 169.

$^1$H-NMR (CDCl$_3$) δ: 2.76 (2H, dd, J=11, 4.6 Hz), 3.08 (6H, s), 3.64 (2H, d, J=2.5 Hz), 3.68-3.75 (2H, m), 5.12-5.15 (2H, m), 7.27-7.35 (5H, m).

Referential Example 191 tert-Butyl (3S,4S)-3,4-bis[(methylsulfonyl)oxy]-1-pyrrolidinecarboxylate

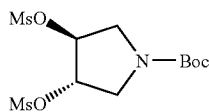

The compound (1.57 g) obtained in Referential Example 190 was dissolved in 1,2-dichloroethane (16 ml), 1-chloroethyl chloroformate (0.73 ml) was added at room temperature, and the resultant mixture was heated under reflux for 4 hours. After the solvent was distilled off under reduced pressure, methanol (16 ml) was added to the resultant residue, and the resultant mixture was heated under reflux for 1 hour, allowed to cool and concentrated. Crystals obtained by recrystallization from ethyl acetate were collected by filtration to obtain (3S,4S)-3,4-bis-[(methylsulfonyl)oxy]pyrrolidine hydrochloride (1.30 g) as colorless crystals. Di-tert-butyl dicarbonate (1.15 ml) was added to a solution of the hydrochloride thus obtained and triethylamine (1.40 ml) in methylene chloride (26 ml), and the mixture was stirred overnight at room temperature. After the reaction mixture was concentrated, the residue was diluted with ethyl acetate, washed with water and saturated aqueous solution of sodium chloride and dried over anhydrous sodium sulfate. The solvent was distilled off under reduced pressure. The resultant residue was purified by column chromatagraphy on silica gel (ethyl acetate:hexane=1:9-1:1) to obtain the title compound (1.40 g).

$^1$H-NMR (CDCl$_3$) δ: 1.47 (9H, s), 3.12 (6H, s), 3.70-3.73 (2H, m), 3.79 (1H, d, J=4.5 Hz), 3.82 (1H, d, J=4.5 Hz), 5.19 (2H, br).

Referential Example 192 tert-Butyl (3R,4R)-3,4-diazido-1-pyrrolidinecarboxylate

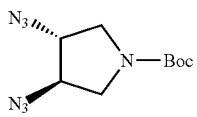

The title compound was obtained from the compound obtained in Referential Example 191 in a similar manner to Referential Example 170.

$^1$H-NMR (CDCl$_3$) δ: 1.47 (9H, s), 3.37-3.46 (2H, m), 3.64-3.71 (2H, m), 3.96 (2H, t, J=3.2 Hz).

Referential Example 193 tert-Butyl (3R,4R)-3-amino-4-{[(5-chloroindol-2-yl)carbonyl]amino}pyrrolidine-1-carboxylate

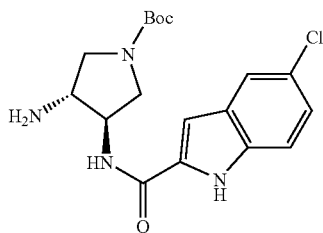

The title compound was obtained from the compound obtained in Referential Example 192 in a similar manner to Referential Examples 171 and 172.

$^1$H-NMR (DMSO-d$_6$) δ: 1.39 (9H, s), 2.95-3.00 (1H, m), 3.09-3.13 (1H, m), 3.52 (1H, dd, J=10, 6.5 Hz), 3.68 (1H, dd, J=10, 7.8 Hz)., 4.04-4.09 (2H, m), 7.16 (1H, s), 7.18 (1H, s), 7.42 (1H, d, J=8.5 Hz), 7.69 (1H, d, J=1.5 Hz), 8.50 (1H, d, J=6.5 Hz), 11.77 (1H, br).

Referential Example 194 tert-Butyl (3S)-5-oxotetrahydro-3-furanylcarbamate

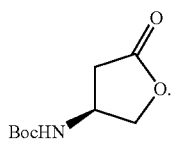

di-tert-Butyl dicarbonate (4.1 g) and 10% palladium on carbon (0.4 g) were added to a solution of benzyl (3S)-(−)-tetrahydro-5-oxo-3-furanylcarbamate (3.3 g) in tetrahydrofuran (20 ml), and the mixture was stirred for a day in a hydrogen atmosphere. After insoluble matter was filtered through Celite pad, the filtrate was concentrated under reduced pressure, and the residue was purified by column chromatography on silica gel (hexane:ethyl acetate=4:1) to obtain the title compound (1.5 g).

$^1$H-NMR (CDCl$_3$) δ: 1.45 (9H, s), 2.45 (1H, dd, J=17.8, 2.7 Hz), 2.86 (1H, dd, J=17.8, 7.3 Hz), 4.12-4.23 (1H, m), 4.54-4.62 (2H, m), 4.85-4.95 (1H, m).

Referential Example 195 tert-Butyl (3S,4S)-4-azido-5-oxotetrahydro-3-furanylcarbamate

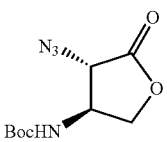

1 M Lithium bis(trimethylsilyl)amide (tetrahydrofuran solution, 8.65 ml) was added dropwise to a solution of the compound (0.87 g) obtained in Referential Example 194 in tetrahydrofuran (20 ml) at −78° C., and the mixture was stirred for 30 minutes. After a solution of p-toluenesulfonylazide (1.02 g) in tetrahydrofuran (10 ml) was then added, and the mixture was stirred for 5 minutes, trimethylchlorosilane (1.7 ml) was added, and the mixture was stirred for 2 hours while the temperature of the system was gradually raised to room temperature. The reaction mixture was diluted with diethyl ether, washed with 10% hydrochloric acid, a 5% saturated aqueous solution of sodium hydrogencarbonate and saturated aqueous solution of sodium chloride, and then dried over anhydrous sodium sulfate. The solvent was distilled off under reduced pressure. The resultant residue was purified by column chromatography on silica gel (hexane:ethyl acetate=4:1) to obtain the title compound (0.62 g).

$^1$H-NMR (CDCl$_3$) δ: 1.46 (9H, s), 4.09 (1H, dt, J=15.3, 7.6 Hz), 4.12-4.23 (1H, m), 4.37-4.50 (1H, m), 4.54 (1H, dd, J=9.0, 7.6 Hz), 4.81-4.90 (1H, m).

Referential Example 196 tert-Butyl (3S,4S)-4-{[(5-chloroindol-2-yl)carbonyl]-amino}-5-oxotetrahydro-3-furanylcarbamate

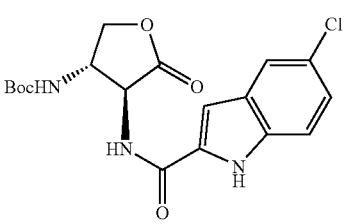

The title compound was obtained from the compound obtained in Referential Example 195 in a similar manner to Referential Examples 90 and 91.

$^1$H-NMR (CDCl$_3$) δ: 1.44 (9H, s), 4.01-4.13 (1H, m), 4.20-4.36 (1H, m), 4.78-4.93 (2H, m), 6.15 (1H, s), 6.93 (1H, s), 7.03-7.11 (1H, m), 7.20-7.28 (1H, m), 7.30 (1H, d, J=8.8 Hz), 7.61 (1H, s), 9.27 (1H, s).

Referential Example 197 tert-Butyl (3S,4S)-4-{[(5-methyl-4,5,6,7-tetrahydrothiazolo[5,4-c]pyridin-2-yl)carbonyl]amino}-5-oxotetrahydro-3-furanylcarbamate

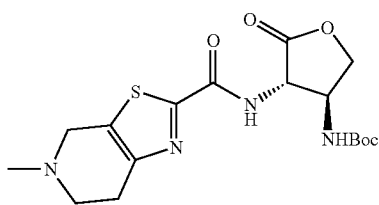

The title compound was obtained by getting tert-butyl (3S,4S)-4-amino-5-oxotetrahydro-3-furanylcarboxylate from the compound obtained in Referential Example 195 in a similar manner to Referential Example 90 and then reacting with the compound obtained in Referential Example 10 in accordance with the reaction conditions of Referential Example 91.

$^1$H-NMR (CDCl$_3$) δ: 1.44 (9H, s), 2.52 (3H, s), 2.83 (2H, t, J=5.9 Hz), 2.79-3.02 (2H, m), 3.74 (2H, s), 4.03-4.12 (1H, m), 4.21-4.36 (1H, m), 4.80-4.95 (2H, m), 6.14-6.24 (1H, m), 7.76-7.85 (1H, m).

Referential Example 198

Ethyl 2-[((3S)-3-[(tert-butoxycarbonyl)amino]-2-{[(5-chloroindol-2-yl)carbonyl]amino}-4-hydroxybutanoyl)amino]-acetate

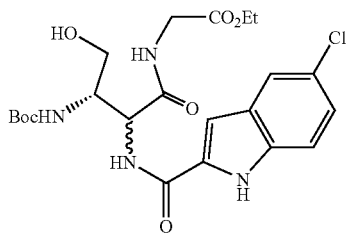

The compound (0.4 g) obtained in Referential Example 196, glycine ethyl ester hydrochloride (1.0 g) and triethylamine (1.0 ml) were added to ethanol (20 ml), and the mixture was heated and stirred at 60° C. for 18 hours. The reaction mixture was diluted with chloroform and washed with a 10% aqueous solution of citric acid and saturated aqueous solution of sodium chloride. The resultant organic layer was dried over anhydrous sodium sulfate, and the solvent was distilled off under reduced pressure. The resultant residue was purified by column chromatography on silica gel (chloroform:methanol=98:2) to obtain title compound (0.31 g).

$^1$H-NMR (DMSO-d$_6$) δ: 1.17 (3H, t, J=7.0 Hz), 1.34 (6H, s), 1.36 (3H, s), 3.51-3.63 (0.6H, m), 3.72-3.80 (2H, m), 4.06 (2H, q, J=7.0 Hz), 4.11-4.23 (1.4H, m), 4.67-4.82 (1H, m), 4.85-4.91 (1H, m), 6.48 (0.4H, d, J=9.5 Hz), 6.80 (0.6H, d, J=9.5 Hz), 7.10-7.22 (2H, m), 7.42 (1H, d, J=8.8 Hz), 7.72 (0.4H, d, J=2.0 Hz), 7.73 (0.6H, d, J=2.0 Hz), 8.23-8.31 (0.6H, m), 8.34-8.41 (0.4H, m), 8.43-8.50 (1H, m), 11.83 (1H, s).

Referential Example 199

Ethyl 2-((4R)-4-amino-3-{[(5-chloroindol-2-yl)carbonyl]-amino}-2-oxopyrrolidin-1-yl)acetate Hydrochloride

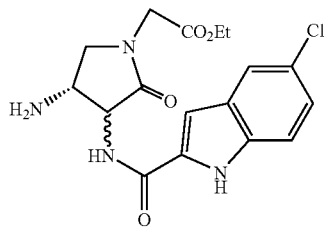

The title compound was obtained by converting the compound obtained in Referential Example 198 into a pyrrolidone derivative using the reaction conditions described in Referential Example 181 and then removing a tert-butoxycarbonyl group in a similar manner to Referential Example 69.

$^1$H-NMR (DMSO-d$_6$) δ: 1.17 (2H, t, J=7.0 Hz), 1.23 (1H, t, J=7.0 Hz), 3.31-3.40 (0.6H, m), 3.57 (0.4H, d, J=11.2 Hz), 3.90-4.23 (4H, m), 4.42 (0.6H, dd, J=12.0, 6.1 Hz), 4.50-4.60 (0.4H, m), 4.62 (0.6H, dd, J=12.0, 3.9 Hz), 5.12-5.23 (0.4H, m), 7.17 (0.4H, s), 7.20 (0.4H, dd, J=8.8, 2.0 Hz), 7.28 (0.6H, dd, J=8.8, 2.0 Hz), 7.30 (0.6H, s), 7.44 (0.4H, d, J=8.8 Hz), 7.50 (0.6H, d, J=8.8 Hz), 7.75 (1H, d, J=2.0 Hz), 8.20-8.33 (1H, m), 8.71-8.94 (3.6H, m), 9.22-9.35 (0.4H, m), 11.97 (0.4H, s), 12.44 (0.6H, s).

Referential Example 200 tert-Butyl (3R,4S)-4-{[(5-chloroindol-2-yl)carbonyl]-amino}-1-methyl-5-oxopyrrolidin-3-ylcarbamate

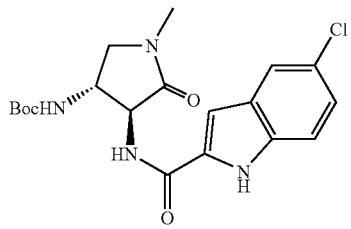

The title compound was obtained by treating a compound obtained by reaction of the compound obtained in Referential Example 196 with methylamine (40% methanol solution) in a similar manner to Referential Example 198 under the same conditions as those in Referential Example 181.

$^1$H-NMR (CDCl$_3$)δ: 1.43 (9H, s), 2.90 (3H, s), 4.26 (1H, br.s), 4.36 (2H, m), 4.51-4.52 (1H, m), 5.35 (1H, br.s), 6.95-6.99 (2H, m), 7.22-7.32 (3H, m), 7.63 (1H, s), 8.95 (1H, br.s).

Referential Example 201

N-[(3S,4R)-4-Amino-1-methyl-2-oxopyrrolidin-3-yl]-5-chloroindole-2-carboxamide

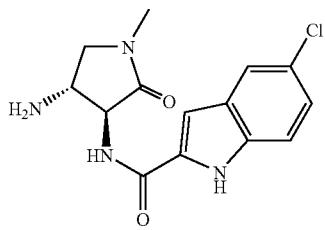

The title compound was obtained by treating the compound obtained in Referential Example 200 in a similar manner to Referential Example 69.

$^1$H-NMR (CDCl$_3$) δ: 2.95 (3H, d, J=5.1 Hz), 3.91-3.93 (1H, m), 4.19 (1H, d, J=3.7 Hz), 4.36 (1H, dd, J=11, 1.7 Hz), 4.48 (1H, dd, J=11, 2.0 Hz), 6.90-6.97 (2H, m), 7.21-7.33 (2H, m), 7.62 (1H, d, J=2.0 Hz), 8.90 (1H, s).

Referential Example 202 tert-Butyl 3,6-dihydro-[(2H)-pyridinecarboxylate

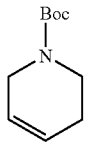

tert-Butyl dicarbonate (6.55 g) was added to a mixture of 1,2,3,6-tetrahydropyridine (2.50 g) and a 10% aqueous solution (3.0 ml) of sodium carbonate, and the mixture was stirred at room temperature for 20 hours. Water was added to the reaction mixture to conduct extraction with ethyl acetate. The resultant organic layer was washed with 0.5N hydrochloric acid, water, a saturated aqueous solution of sodium hydrogencarbonate and saturated aqueous solution of sodium chloride in that order and dried over anhydrous sodium sulfate. The solvent was then distilled off under reduced pressure to obtain the title compound (5.08 g).

$^1$H-NMR (CDCl$_3$) δ: 1.47 (9H, s), 2.12 (2H, br.s), 3.48 (2H, t, J=5.6 Hz), 3.88 (2H, br.s), 5.60 (1H, br.s), 5.78-5.90 (1H, m).

Referential Example 203 tert-Butyl (3R*,4S*)-3,4-dihydroxy-1-piperidinecarboxylate

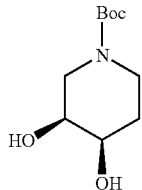

The compound (18.45 g) obtained in Referential Example 202 was dissolved in acetonitrile (200 ml), and water (38 ml), a 0.039 M aqueous solution (82 ml) of osmium tetroxide and N-methylmorpholine N-oxide (23.13 g) were added. The mixture was stirred at room temperature for 17 hours. An excessive oxidizing agent was treated with a saturated aqueous solution of sodium sulfite to conduct extraction with ethyl acetate. The resultant organic layer was washed with water, 0.5N hydrochloric acid, water, a saturated aqueous solution of sodium hydrogencarbonate and saturated aqueous solution of sodium chloride in that order, dried over anhydrous sodium sulfate and then concentrated under reduced pressure. The resultant residue was purified by column chromatagraphy on silica gel (hexane:ethyl acetate=1:3) to obtain the title compound (15.0 g).

$^1$H-NMR (CDCl$_3$) δ: 1.46 (9H, s), 1.60-1.73 (1H, m), 1.77-1.90 (1H, m), 2.68 (1H, br.s), 2.80-3.20 (1H, br), 3.22-3.32 (1H, m), 3.42 (1H, dd, J=14.3, 3.4 Hz), 3.50-3.62 (2H, m), 3.77 (1H, brs), 3.81-3.92 (1H, m).

Referential Example 204 tert-Butyl (3R*,4S*)-3,4-bis[(methylsulfonyl)oxy]-1-piperidinecarboxylate

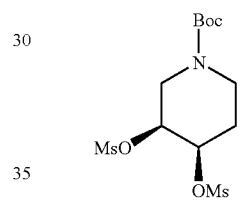

The title compound was obtained from the compound obtained in Referential Example 203 in a similar manner to Referential Example 169.

$^1$H-NMR (CDCl$_3$) δ: 1.47 (9H, s), 1.85-1.97 (1H, m), 2.08-2.20 (1H, m), 3.00-4.20 (4H, m), 3.12 (6H, s), 4.85 (1H, br.s), 4.94 (1H, br.s).

Referential Example 205 tert-Butyl (3R*,4S*)-3,4-diazido-1-piperidinecarboxylate

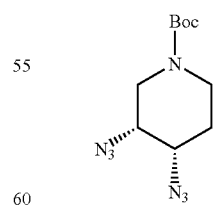

The title compound was obtained from the compound obtained in Referential Example 204 in a similar manner to Referential Example 170.

$^1$H-NMR (CDCl$_3$) δ: 1.47 (9H, s), 1.70-1.80 (1H, m), 1.90-2.00 (1H, m), 3.05-4.00 (6H, m).

Referential Example 206 tert-Butyl (3R*,4S*)-3,4-diamino-1-piperidinecarboxylate

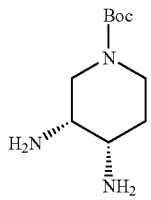

The title compound was obtained from the compound obtained in Referential Example 205 in a similar manner to Referential Example 171.

$^1$H-NMR (CDCl$_3$) δ: 1.46 (9H, s), 1.48-1.60 (2H, m), 1.80-2.10 (4H, br), 2.85-2.91 (2H, m), 2.97 (1H, br.s), 3.09 (1H, dd, J=13.6, 2.7 Hz), 3.74 (1H, dd, J=13.6, 4.2 Hz), 3.81 (1H, s).

Referential Example 207 tert-Butyl (3R*,4S*)-3-amino-4-{[(5-chloroindol-2-yl)carbonyl]amino}-1-piperidinecarboxylate

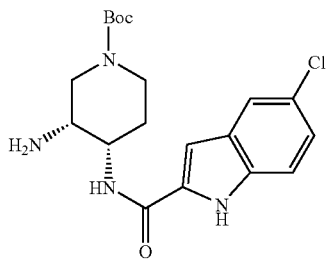

The compound (3.23 g) obtained in Referential Example 206 was dissolved in N,N-dimethylformamide (100 ml), and triethylamine (2.08 ml) and the compound (3.80 g) obtained in Referential Example 52 were added to the solution. The mixture was stirred at room temperature for 3 days. The reaction mixture was concentrated under reduced pressure, and water was added to the residue to conduct extraction with methylene chloride. The resultant organic layer was washed with a saturated aqueous solution of sodium hydrogencarbonate and saturated aqueous solution of sodium chloride, dried over anhydrous sodium sulfate and then concentrated under reduced pressure. The resultant residue was purified by column chromatography on silica gel (methylene chloride:methanol=20:1-10:1) to obtain the title compound (2.70 g).

$^1$H-NMR (DMSO-d$_6$) δ: 1.40-1.58 (3H, m), 1.41 (9H, s), 1.75-1.90 (1H, m), 2.95 (1H, br.s), 2.98-3.05 (1H, m), 3.19-3.28 (1H, m), 3.74 (1H, dd, J=19.5, 15.4 Hz), 3.79 (1H, br.s), 4.04-4.12 (1H, m), 7.17 (1H, dd, J=8.7, 1.9 Hz), 7.21 (1H, s), 7.42 (1H, d, J=8.7 Hz), 7.68 (1H, d, J=1.9 Hz), 8.00 (1H, br.d, J=7.6 Hz), 11.80 (1H, s).

Referential Example 208 tert-Butyl (3R*,4S*)-3-amino-4-{[(5-methyl-4,5,6,7 tetrahydrothiazolo[5,4-c]pyridin-2-yl)carbonyl] amino}-1-piperidinecarboxylate

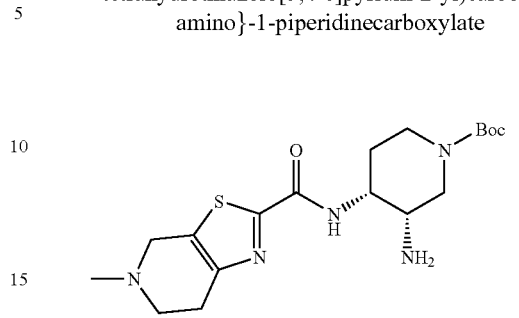

The compound (3.23 g) obtained in Referential Example 206 was dissolved in N,N-dimethylformamide (100 ml), and triethylamine (2.08 ml) was added. The compound (3.83 g) obtained in Referential Example 149 was then added, and the mixture was stirred at room temperature for 3 days. The reaction mixture was concentrated under reduced pressure, and water was added to the residue to conduct extraction with methylene chloride. The resultant organic layer was washed with a saturated aqueous solution of sodium hydrogencarbonate and saturated aqueous solution of sodium chloride and dried over anhydrous sodium sulfate, and the solvent was distilled off under reduced pressure. The resultant residue was purified by column chromatography on silica gel (methylene chloride:methanol=10:1-5:1) to obtain the title compound (2.27 g).

$^1$H-NMR (CDCl$_3$) δ: 1.30-1.62 (3H, m), 1.47 (9H, s), 1.78-1.88 (1H, m), 2.51 (3H, s), 2.81 (2H, t, J=5.9 Hz), 2.85-2.98 (3H, m), 3.00-3.15 (2H, m), 3.71 (2H, s), 3.80-4.15 (3H, m), 7.79 (1H, br.s).

Referential Example 209 tert-Butyl (3R*,4S*)-3-amino-4-{[(5-fluoroindol-2-yl)carbonyl]amino}-1-piperidinecarboxylate

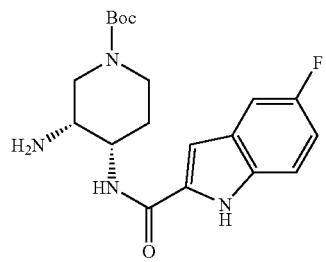

The title compound was obtained from the compound obtained in Referential Example 206 and 5-fluoroindole-2-carboxylic acid in a similar manner to Referential Example 172.

$^1$H-NMR (CDCl$_3$) δ: 1.40-1.70 (3H, m), 1.48 (9H, s), 2.79-2.92 (1H, m), 2.99-3.14 (1H, m), 4.00-4.23 (3H, m), 6.85 (1H, s), 7.04 (1H, td, J=9.0, 2.4 Hz), 7.07-7.20 (1H, br), 7.27 (1H, dd, J=9.0, 2.4 Hz), 7.35 (1H, d, J=9.0, 4.4 Hz), 9.25-9.50 (1H, br). MS (ESI) m/z: 377 (M+H)$^+$.

Referential Example 210

Ethyl (3S,4R)-5-azido-3-{[(benzyloxy)carbonyl]amino}-4-[(tert-butoxycarbonyl)amino]valerate

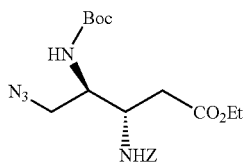

Triethylamine (4.80 ml) and methanesulfonyl chloride (1.55 ml) were successively added dropwise to a solution of the (3S,4S)-compound obtained in Referential Example 168 (low-polar compound) (7.1 g) in methylene chloride (100 ml) under ice cooling, and the mixture was stirred for 30 minutes under ice cooling. The reaction mixture was diluted with chloroform and washed with a 10% aqueous solution of citric acid, a saturated aqueous solution of sodium hydrogencarbonate and saturated aqueous solution of sodium chloride. After the resultant organic layer was dried over anhydrous sodium sulfate, the solvent was distilled off under reduced pressure to obtain a methanesulfonyl derivative (9.20 g). A mixture solution composed of the thus-obtained methanesulfonyl derivative, sodium azide (5.64 g) and N,N-dimethylformamide (100 ml) was stirred at 80° C. for 20 hours. The reaction mixture was diluted with ethyl acetate and washed with water and saturated aqueous solution of sodium chloride. After the resultant organic layer was dried over anhydrous sodium sulfate, the solvent was distilled off under reduced pressure, and the resultant residue was purified by column chromatography on silica gel (chloroform) to obtain the title compound (5.42 g).

$^1$H-NMR (CDCl$_3$) δ: 1.24 (3H, t, J=7.1 Hz), 1.43 (9H, s), 2.56-2.68 (2H, m), 3.48-3.60 (2H, m), 3.88-3.97 (1H, m), 4.04-4.20 (3H, m), 4.88-4.97 (1H, br), 5.10 (2H, s), 5.60-5.75 (1H, br), 7.30-7.40 (5H, m). MS (ESI) m/z: 436 (M+H)$^+$.

Referential Example 211

Benzyl (4S,5R)-5-[(tert-butoxycarbonyl)amino]-2-oxopiperidin-4-ylcarbamate

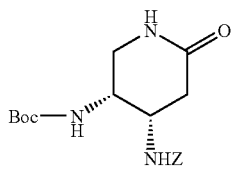

A Lindlar catalyst (2.71 g) was added to a solution of the compound (5.42 g) obtained in Referential Example 210 in a mixed solvent of ethanol (150 ml) and tetrahydrofuran (10.0 ml), and the mixture was stirred for 3 hours under a hydrogen atmosphere and then for 14 hours under nitrogen conditions. After insoluble matter was removed through Celite pad, and the filtrate was concentrated under reduced pressure, the resultant residue was dissolved in tetrahydrofuran (30 ml), and triethylamine (3.0 ml) was added thereto. The mixture was stirred at room temperature for 1.5 hours. The reaction mixture was diluted with ethyl acetate and washed with a 10% aqueous solution of citric acid, a saturated aqueous solution of sodium hydrogencarbonate and saturated aqueous solution of sodium chloride. After the resultant organic layer was dried over anhydrous sodium sulfate, the solvent was distilled off under reduced pressure, and the resultant residue was purified by column chromatography on silica gel (chloroform:methanol=25:1) to obtain the title compound (2.50 g).

$^1$H-NMR (CDCl$_3$) δ: 1.44 (9H, s), 2.30-2.50 (1H, br), 2.65-2.90 (1H, br), 3.15-3.30 (1H, br), 3.35-3.65 (1H, br), 4.00-4.25 (2H, br), 5.11 (2H, s), 5.55-5.60 (1H, br), 5.65-5.90 (1H, br), 6.25-6.55 (1H, br), 7.28-7.40 (5H, m). MS (ESI) m/z: 364 (M+H)$^+$.

Referential Example 212

Benzyl (3R,4S)-3-[(tert-butoxycarbonyl)amino]piperidin-4-ylcarbamate

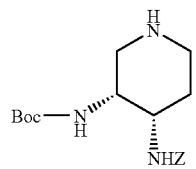

1 M Borane.tetrahydrofuran complex (tetrahydrofuran solution, 34.0 ml) was added dropwise to a tetrahydrofuran solution (70 μl) of the compound (2.49 g) obtained in Referential Example 211 under ice cooling, and the mixture was stirred for 20 hours while the temperature of the system was gradually raised to room temperature. Methanol (100 ml) was added to the reaction mixture, and the solvent was distilled off under reduced pressure. Ethanol (45 ml), water (5 ml) and triethylamine (10 ml) were added to the residue, and the mixture was heated under reflux for 24 hours. The reaction mixture was concentrated, and the resultant residue was purified by column chromatagraphy on silica-gel (chloroform:methanol:water=7:3:1, lower layer) to obtain the title compound (1.61 g).

$^1$H-NMR (CDCl$_3$) δ: 1.44 (9H, s), 1.65-1.72 (2H, m), 2.67 (1H, t, J=12.0 Hz), 2.82 (12H, d, J=12.0 Hz), 2.90-3.10 (1H, br), 3.60-3.80 (2H, m), 3.90-4.00 (1H, m), 5.00-5.20 (2H, m), 5.40-5.60 (2H, br), 7.25-7.74 (5H, m). MS (FAB) m/z: 350 (M+H)$^+$.

Referential Example 213 tert-Buthyl (3R,4S)-1-acetyl-4-{[(benzyloxy)carbonyl]amino}-piperidin-3-ylcarbamate

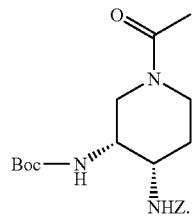

The title compound was obtained by reaction of the compound obtained in Referential Example 212 with acetyl chloride and triethylamine in methylene chloride.

$^1$H-NMR (CDCl$_3$) δ: 1.44 (9H, s), 1.85-2.15 (2H, m), 2.07 (1.5H, s), 2.14 (1.5H, s), 2.75-2.90 (1H, m), 3.10-3.20 (0.5H, m), 3.25-3.35 (0.5H, br.d, J=14.2 Hz), 3.65-4.05 (3H, m), 4.38-4.47 (0.5H, br.d, J=13.0 Hz), 4,5,4-4.63 (0.5H, m), 4.69-4.83 (1H, br), 4.98-5.20 (2.5H, m), 5.90-6.05 (0.5H, br), 7.30-7.40 (5H, m). MS (ESI) m/z: 392 (M+H)$^+$.

Referential Example 214 tert-Butyl (3R,4S)-1-acetyl-4-{[(5-chloroindol-2-yl)carbonyl]amino}piperidin-3-ylcarbamate

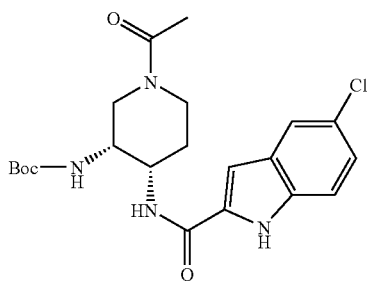

10% Palladium on carbon (532 mg) was added to a solution of the compound (745 mg) obtained in Referential Example 213 in ethanol (50 ml), and the mixture was stirred at room temperature for 16 hours under a hydrogen atmosphere. Insoluble matter was removed by filtration through Celite, and the filtrate was then concentrated under reduced pressure. The resultant residue was treated with 5-chloroindole-2-carboxylic acid (467 mg) in a similar manner to Referential Example 68 to obtain the title compound (650 mg).

$^1$H-NMR (CDCl$_3$) δ: 1.52 (9H, s), 1.60-1.80 (2H, m), 2.12 (1H, s), 2.16 (2H, s), 2.30-2.45 (0.5H, m), 2.67-2.82 (0.3H, m), 2.89 (0.7H, d, J=13.7 Hz), 3.23 (0.7H, t, J=12.9 Hz), 3.37 (0.3H, d, J=13.7 Hz), 3.81-3.95 (1H, m), 4.05-4.33 (2H, m), 4.62-4.72 (0.3H, br), 4.77 (0.7H, d, J=13.7 Hz), 5.10-5.27 (1H, m), 6.81 (0.3H, br.s), 6.85 (0.7H, s), 7.21 (1H, br.d, J=8.8 Hz), 7.34 (1H, d, J=8.8 Hz), 7.57 (0.3H, br.s), 7.61 (0.7H, s), 8.55-8.65 (0.5H, br), 9.43-9.53 (0.7H, br), 9.60-9.70 (0.3H, br). MS (ESI) m/z: 435 (M+H)$^+$.

Referential Example 215

Ethyl (3R,4R)-5-azido-3-{[(benzyloxy)carbonyl]amino}-4-[(tert-butoxycarbonyl)amino]valerate

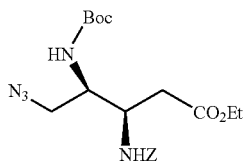

The title compound was obtained from the (3R,4S)-compound (high-polar compound) obtained in Referential Example 168 in a similar manner to Referential Example 210.

$^1$H-NMR (CDCl$_3$) δ: 1.23 (3H, t, J=6.6 Hz), 1.42 (9H, s), 2.51-2.63 (2H, m), 3.43-3.50 (2H, m), 3.84-3.92 (1H, m), 4.03-4.23 (3H, m), 5.10 (2H, s), 5.11-5.24 (1H, m), 5.54-5.60 (1H, m), 7.32-7.44 (5H, m).

Referential Example 216

Benzyl (4R,5R)-5-[(tert-butoxycarbonyl)amino]-2-oxopiperidin-4-ylcarbamate

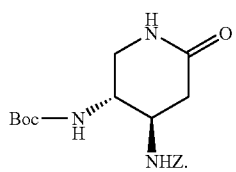

The title compound was obtained by treating the compound obtained in Referential Example 215 in a similar manner to Referential Example 211.

$^1$H-NMR (DMSO-d$_6$) δ: 1.35 (9H, s), 2.19 (1H, dd, J=17.4, 9.1 Hz), 2.41-2.51 (1H, m), 2.97 (1H, t, J=9.1 Hz), 3.00-3.11 (1H, m), 3.51-3.64 (1H, m), 3.67-3.73 (1H, m), 5.00 (2H, s), 6.71-6.80 (1H, m), 7.20-7.30 (5H, m), 7.44-7.52 (1H, m), 8.30 (1H, s).

Referential Example 217

Benzyl (3R,4R)-3-[(tert-butoxycarbonyl)amino]piperidin-4-ylcarbamate

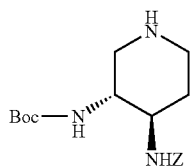

The title compound was obtained by treating the compound obtained in Referential Example 216 in a similar manner to Referential Example 212.

$^1$H-NMR (CDCl$_3$) δ: 1.39 (9H, s), 2.05 (2H, d, J=12.9 Hz), 2.40 (1H, t, J=11.0 Hz), 2.63 (1H, t, J=12.0 Hz), 3.09 (1H, d, J=12.0 Hz), 3.31 (1H, d, J=11.0 Hz), 3.42-3.53 (2H, m), 4.80-4.91 (1H, m), 5.09 (2H, s), 5.23-5.32 (1H, m), 7.34-7.41 (5H, m).

Referential Example 218 tert-Butyl (3R,4R)-1-acetyl-4-{[(benzyloxy)carbonyl]amino}-piperidin-3-ylcarbamate

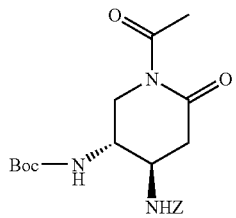

The title compound was obtained by treating the compound obtained in Referential Example 217 in a similar manner to Referential Example 213.

¹H-NMR (CDCl₃) δ: 1.42 (9H, s), 1.53-1.67 (1H, m), 1.89-2.00 (1H, m), 2.09 (1.5H, s), 2.15 (1.5H, s), 2.57 (1H, t, J=12.0 Hz), 2.78 (1H, t, J=12.0 Hz), 3.20-3.30 (1H, m), 3.40-3.56 (2H, m), 2.23-4.31 (1H, m), 4.45-4.56 (1H, m), 5.01-5.08 (1H, m), 5.10 (2H, s), 7.32-7.44 (5H, m).

Referential Example 219 tert-Butyl (3R,4R)-1-acetyl-4-{[(5-chloroindol-2-yl)carbonyl]amino}piperidin-3-ylcarbamate

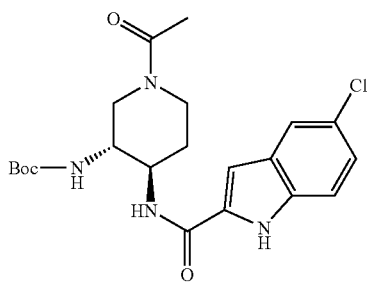

The title compound was obtained by treating the compound obtained in Referential Example 218 in a similar manner to Referential Example 214.

¹H-NMR (CDCl₃) δ: 1.35 (9H, s), 1.42-1.56 (2H, m), 2.00-2.10 (1H, m), 2.12 (1.5H, s), 2.17 (1.5H, s), 2.31-2.43 (1H, m), 2.67-3.00 (1H, m), 3.55-3.63 (1H, m), 3.78-4.00 (1H, m), 4.03-4.21 (1H, m), 4.78-5.24 (2H, m), 6.91 (0.5H, s), 6.92 (0.5H, s), 7.22-7.32 (1H, m), 7.33 (1H, d, J=8.8 Hz), 7.58 (1H, s), 9.45 (0.5H, s), 9.51 (0.5H, s).

Referential Example 220

Benzyl (3R,4S)-3-[(tert-butoxycarbonyl)amino]-1-(2-methoxyacetyl)piperidin-4-ylcarbamate

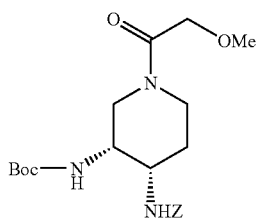

The title compound was obtained from the compound obtained in Referential Example 212 and methoxyacetyl chloride in a similar manner to Referential Example 213.

¹H-NMR (CDCl₃) δ: 1.44 (9H, s), 1.70-2.15 (2H, m), 2.70-2.85 (1H, m), 2.90-3.30 (1H, m), 3.35-3.70 (1H, m), 3.43 (3H, s), 3.75-3.90 (2H, m), 3.90-4.25 (3H, m), 4.40-4.80 (1H, m), 5.05-5.09 (1H, m), 5.10 (2H, br.s), 7.30-7.40 (5H, m). MS (ESI) m/z: 322 (M+H⁺).

Referential Example 221 tert-Butyl (3R,4S)-4-{[(5-chloroindol-2-yl)carbonyl]amino}-1-(2-methoxyacetyl)piperidin-3-ylcarbamate

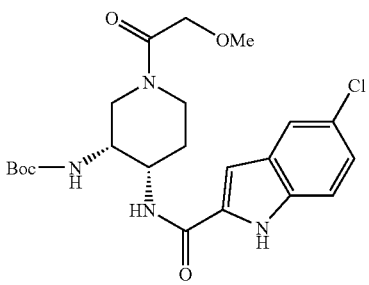

The title compound was obtained from the compound obtained in Referential Example 220 in a similar manner to Referential Example 214.

¹H-NMR (CDCl₃) δ: 1.52 (9H, s), 1.60-1.80 (1H, m), 2.20-2.40 (1H, m), 2.70-2.80 (0.6H, m), 2.90-3.00 (0.4H, m), 3.15-3.30 (0.4H, m), 3.32-3.40 (0.6H, m), 3.46, 3.49 (total 3H, each s), 3.85-4.30 (5H, m), 4.55-4.80 (1H, m), 5.11 (0.4H, br.s), 6.05 (0.6H, br.s), 6.86 (1H, s), 7.20 (1H, dd, J=8.7, 2.0 Hz), 7.33 (1H, d, J=8.7 Hz), 7.61 (1H, s), 8.40-8.60 (1H, m), 9.41 (1H, br.s). MS (FAB) m/z: 465 (M+H)⁺.

Referential Example 222

Benzyl (3R,4R)-3-[(tert-butoxycarbonyl)amino]-1-(2-methoxyacetyl)piperidin-4-ylcarbamate

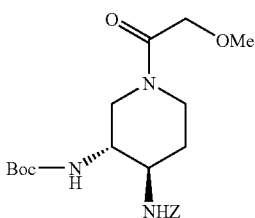

The title compound was obtained from the compound obtained in Referential Example 217 and methoxyacetyl chloride in a similar manner to Referential Example 213.

¹H-NMR (CDCl₃) δ: 1.41 (9H, s), 1.45-1.67 (1H, m), 2.01-2.14 (1H, m), 2.63 (1H, t, J=12.0 Hz), 2.75 (1H, t, J=12.0 Hz), 3.20-3.30 (1H, m), 3.32-3.41 (5H, m), 3.44-3.56 (2H, m), 4.21-4.32 (1H, m), 4.50-4.63 (1H, m), 5.03-5.08 (1H, m), 5.09 (2H, s), 7.32-7.40 (5H, m).

Referential Example 223 tert-Butyl (3R,4R)-4-{[(5-chloroindol-2-yl)carbonyl]-amino}-1-(2-methoxyacetyl)piperidin-3-ylcarbamate

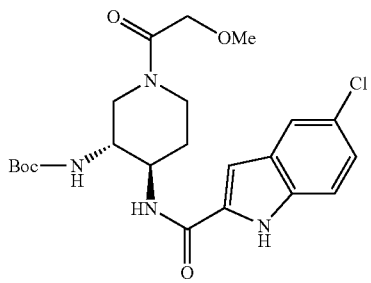

The title compound was obtained from the compound obtained in Referential Example 222 and 5-chloroindole-2-carboxylic acid in a similar manner to Referential Example 214.

$^1$H-NMR (CDCl$_3$) δ: 1.35 (9H, s), 1.41-1.56 (2H, m), 2.11-2.23 (0.5H, m), 2.34-2.50 (0.5H, m), 2.78-2.89 (0.5H, m), 3.01-3.12 (0.5H, m), 3.42 (5H, s), 3.45-3.56 (1H, m), 3.78-3.89 (1H, m), 4.00-4.21 (2H, m), 4.78-5.21 (2H, m), 6.91 (0.5H, s), 6.93 (0.5H, s), 7.23 (1H, dd, J=8.8, 2.0 Hz), 7.33 (1H, d, J=8.8 Hz), 7.59 (1H, s), 9.37 (0.5H, s), 9.54 (0.5H, s).

Referential Example 224

Ethyl (3R,4S)-3-{[(benzyloxy)carbonyl]amino}-4-[(tert-butoxycarbonyl)amino]-5-{[tert-butyl(diphenyl)silyl]oxy}-valerate

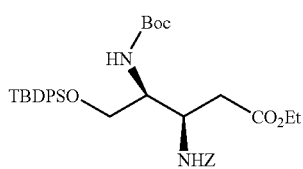

Triethylamine (0.47 ml), imidazole (0.19 g) and tert-butylchlorodiphenylsilane (0.7 ml) were successively added to a solution of the (3R,4S)-compound (high-polar compound) (0.74 g) obtained in Referential Example 168 in N,N-dimethylformamide (30 ml) under ice cooling, and the mixture was stirred for 4 days while the temperature of the system was gradually raised to room temperature. The reaction mixture was diluted with ethyl acetate and washed with a 10% aqueous solution of citric acid and saturated aqueous solution of sodium chloride and then dried over anhydrous sodium sulfate. The solvent was distilled off under reduced pressure, and the resultant residue was purified by column chromatography on silica gel (hexane:ethyl acetate=8:1) to obtain the title compound (0.85 g).

$^1$H-NMR (CDCl$_3$) δ: 1.07 (9H, s), 1.19 (3H, t, J=7.4 Hz), 1.40 (9H, s), 2.40-2.50 (1H, m), 2.60 (1H, dd, J=15.9, 4.5 Hz), 3.56-3.67 (1H, m), 3.74 (1H, dd, J=11.2, 4.5 Hz), 3.78-3.89 (1H, m), 4.08 (2H, q, J=7.4 Hz), 4.21-4.30 (1H, m), 4.99-5.13 (3H, m), 5.41-5.52 (1H, m), 7.40-7.53 (6H, m), 7.60-7.72 (4H, m).

Referential Example 225

Ethyl (3R,4S)-4-[(tert-butoxycarbonyl)amino]-5-{[tert-butyl(diphenyl)silyl]oxy}-3-{[(5-chloroindol-2-yl)carbonyl]amino}valerate

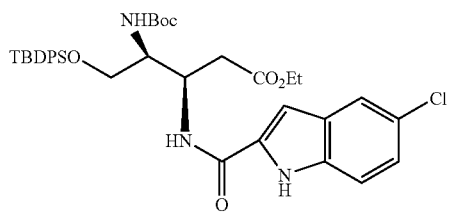

The title compound was obtained by removing the benzyloxycarbonyl group of the compound obtained in Referential Example 224 and condensing with 5-chloroindole-2-carboxylic acid in a similar manner to Referential Example 214.

$^1$H-NMR (CDCl$_3$) δ: 1.10 (9H, s), 1.20 (3H, t, J=7.4 Hz), 1.32 (9H, s), 2.40-2.52 (1H, m), 2.71 (1H, dd, J=15.9, 4.5 Hz), 3.67-3.81 (2H, m), 4.00-4.20 (2H, m), 4.56-4.74 (1H, m), 5.00-5.11 (1H, m), 6.81 (1H, s), 7.21 (1H, dd, J=8.8, 2.0 Hz), 7.32 (1H, d, J=8.8 Hz), 7.40-7.50 (6H, m), 7.58 (1H, d, J=8.5 Hz), 7.63-7.74 (5H, m), 9.01-9.14 (1H, m).

Referential Example 226 tert-Butyl (3R*,4R*)-3-{[(5-methyl-4,5,6,7-tetrahydrothiazolo[5,4-c]pyridin-2-yl)carbonyl]amino}-1,1-dioxohexahydro-1-thiopyran-4-ylcarbamate

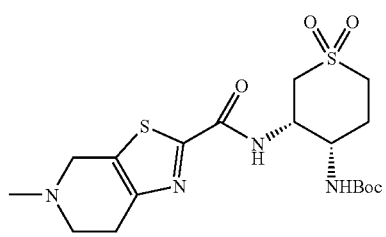

The title compound was obtained from the (3R*,4R*)-compound (low-polar compound) obtained in Referential Example 179 and the compound obtained in Referential Example 10 in a similar manner to Referential Example 68.

$^1$H-NMR (CDCl$_3$) δ: 1.43 (9H, s), 2.30-2.37 (2H, m), 2.51 (3H, s), 2.82-2.85 (2H, m), 2.92-2.95 (2H, m), 3.17-3.20 (4H, m), 3.40-3.43 (1H, m), 3.69-3.77 (2H, m), 3.97-3.98 (1H, m), 4.98 (1H, br), 5.25 (1H, br).

Referential Example 227

N-(3R*,4R*)-4-Amino-1,1-dioxohexahydro-1-thiopyran-3-yl]-5-methyl-4,5,6,7-tetrahydrothiazolo[5,4-c]pyridine-2-carboxamide Hydrochloride

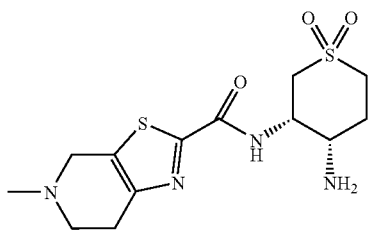

The title compound was obtained by treating the compound obtained in Referential Example 226 in a similar manner to Referential Example 69.

$^1$H-NMR (DMSO-d$_6$) δ: 2.29-2.33 (2H, m), 2.93 (3H, s), 3.16 (2H, br), 3.40 (2H, br), 3.52 (2H, br), 3.69-3.76 (3H, m), 4.48 (1H, br), 4.71-4.82 (2H, m), 8.34 (2H, br), 8.82 (1H, br). MS (ESI) m/z: 345 (M+H)$^+$.

Referential Example 228 tert-Butyl (3R*,4R*)-3-{[(5-chloroindol-2-yl)carbonyl]-amino}-1,1-dioxohexahydro-1-thiopyran-4-ylcarbamate

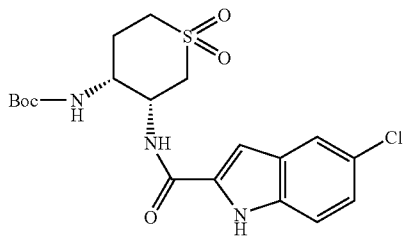

The title compound was obtained from the (3R*,4R*)-compound (low-polar compound) obtained in Referential Example 179 and 5-chloroindole-2-carboxylic acid in a similar manner to Referential Example 68.

$^1$H-NMR (DMSO-d$_6$) δ: 1.34 (9H, s), 2.09 (2H, br), 3.07 (1H, d, J=12.6 Hz), 3.24-3.28 (1H, m), 3.48 (2H, br), 4.12 (1H, br), 4.53 (1H, br), 7.04 (1H, s), 7.16-7.18 (2H, m), 7.44 (1H, d, J=8.7 Hz), 7.67 (1H, s), 8.37 (1H, br), 11.81 (1H, s). MS (ESI) m/z: 442 (M+H)$^+$.

Referential Example 229

N-[(3R*,4R*)-4-Amino-1,1-dioxohexahydro-1-thiopyran-3-yl]-5-chloroindole-2-carboxamide Hydrochloride

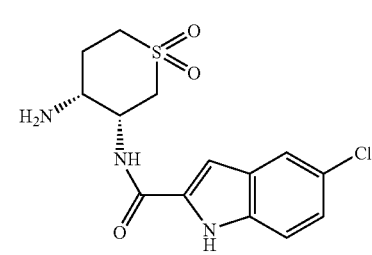

The title compound was obtained by treating the compound obtained in Referential Example 228 in a similar manner to Referential Example 69.

$^1$H-NMR (DMSO-d$_6$) δ: 2.24-2.33 (2H, m), 3.43-3.55 (3H, m), 3.60-3.66 (1H, m), 3.77 (1H, br), 4.75-4.79 (1H, m), 7.18-7.21 (2H, m), 7.46 (1H, d, J=8.8 Hz), 7.72 (1H, d, J=1.7 Hz), 8.39 (2H, br), 8.58 (1H, d, J=6.8 Hz), 11.93 (1H, s). MS (ESI) m/z: 342 (M+H)$^+$.

Referential Example 230 tert-Butyl (3R*,4S*)-3-{[(5-methyl-4,5,6,7-tetrahydrothiazolo[5,4-c]pyridin-2-yl)carbonyl]amino}-1,1-dioxohexahydro-1-thiopyran-4-ylcarbamate

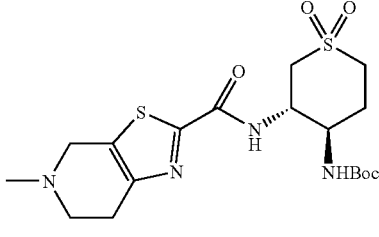

The title compound was obtained from the (3R*,4S*)-compound (high-polar compound) obtained in Referential Example 179 and the compound obtained in Referential Example 10 in a similar manner to Referential Example 98.

$^1$H-NMR (CDCl$_3$) δ: 1.32 (9H, s), 2.14-2.24 (1H, m), 2.33-2.38 (1H, m), 2.50 (3H, s), 2.78-2.83 (2H, m), 2.86-2.95 (2H, m), 3.08-3.14 (3H, m), 3.55 (1H, d, J=13.4 Hz), 3.68 (1H, d, J=15.5 Hz), 3.72 (1H, d, J=15.5 Hz), 3.86-3.88 (1H, m), 4.45-4.53 (1H, m), 4.75 (1H, d, J=8.5 Hz), 7.76 (1H, d, J=8.3 Hz). MS (ESI) m/z: 445 (M+H)$^+$.

Referential Example 231

N-[(3R*,4S*)-4-Amino-1,1-dioxohexahydro-1-thiopyran-3-yl]-5-methyl-4,5,6,7-tetrahydrothiazolo[5,4-c]pyridine-2-carboxamide Hydrochloride

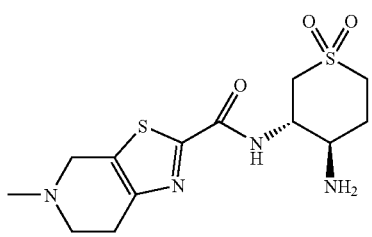

The title compound was obtained by treating the compound obtained in Referential Example 230 in a similar manner to Referential Example 69.

$^1$H-NMR (DMSO-d$_6$) δ: 2.03-2.12 (1H, m), 2.51 (1H, br), 2.93 (3H, s), 3.14 (2H, d, J=12.2 Hz), 3.28 (2H, br), 3.33 (2H, br), 3.48 (3H, br), 3.72 (2H, br), 4.49 (2H, br), 4.71-4.74 (1H, m), 8.38 (2H, br), 9.21-9.24 (1H, m). MS (ESI) m/z: 345 (M+H)$^+$.

Referential Example 232 tert-Butyl (3R*,4R*)-3-{[(5-fluoroindol-2-yl)carbonyl]-amino}-1,1-dioxohexahydro-1-thiopyran-4-ylcarbamate

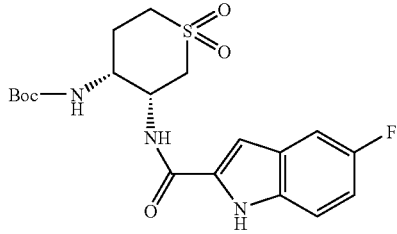

The title compound was obtained from the (3R*,4R*)-compound (low-polar compound) obtained in Referential Example 179 and 5-fluoroindole-2-carboxylic acid in a similar manner to Referential Example 68.

$^1$H-NMR (DMSO-d$_6$) δ: 1.37 (9H, s), 2.10-2.13 (2H, m), 3.06 (1H, br), 3.37-3.49 (3H, m), 4.13 (1H, br), 4.57 (1H, br), 6.95-7.01 (2H, m), 7.14 (1H, br), 7.30 (1H, d, J=8.5 Hz), 7.41 (1H, dd, J=8.8, 4.5 Hz), 8.28 (1H, br), 11.68 (1H, s). MS (ESI) m/z: 426 (M+H)$^+$.

Referential Example 233

N-[(3R*,4R*)-4-Amino-1,1-dioxohexahydro-1-thiopyran-3-yl]-5-fluoroindole-2-carboxamide Hydrochloride

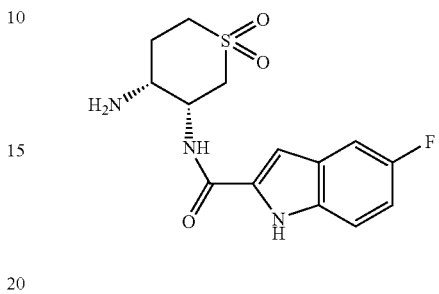

The title compound was obtained by treating the compound obtained in Referential Example 232 in a similar manner to Referential Example 69.

$^1$H-NMR (DMSO-d$_6$) δ: 2.25-2.31 (1H, m), 2.47 (1H, br), 3.30 (1H, br), 3.49-3.53 (2H, m), 3.60-3.66 (1H, m), 3.78 (1H, br), 4.79 (1H, br), 7.01-7.05 (1H, m), 7.21 (1H, s), 7.38 (1H, d, J=9.0 Hz), 7.44 (1H, dd, J=8.8, 4.4 Hz), 8.40 (2H, br), 8.56 (1H, br), 11.81 (1H, s). MS (ESI) m/z: 326 (M+H)$^+$.

Referential Example 234

Ethyl (3R)-3-{[(benzyloxy)carbonyl]amino}-4-[(tert-butoxycarbonyl)amino]-5-oxovalerate

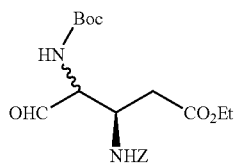

Sulfur trioxide-pyridine complex (1.5 g) was gradually added to a mixed solvent composed of the (3R,4S)-compound (high-polar compound) (0.5 g) obtained in Referential Example 168, dimethyl sulfoxide (6.8 ml) and triethylamine (2.6 ml), and the mixture was stirred for 20 minutes. The reaction mixture was poured into water and extracted with ethyl acetate. The resultant organic layer was washed with a saturated aqueous solution of ammonium chloride, a saturated aqueous solution of sodium hydrogencarbonate and saturated aqueous solution of sodium chloride. The organic layer was dried over anhydrous sodium sulfate, the solvent was distilled off under reduced pressure, and the resultant residue was purified by column chromatography on silica gel (hexane:ethyl acetate=3:1) to obtain the title compound (0.51 g).

$^1$H-NMR (CDCl$_3$) δ: 1.25 (3H, t, J=7.4 Hz), 1.44 (9H, s), 2.51-2.70 (2H, m), 4.01-4.23 (2H, m), 4.45-4.67 (1H, m), 5.00-5.23 (2H, s), 5.24-5.42 (1H, m), 7.23-7.43 (5H, m), 9.63 (0.5H, s), 9.67 (0.5H, s).

Referential Example 235

Benzyl (4R)-5-[(tert-butoxycarbonyl)amino]-1-methyl-2-oxopiperidin-4-ylcarbamate

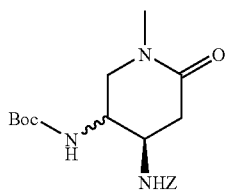

Acetic acid (0.27 ml) and 2 M methylamine (tetrahydrofuran solution, 1.0 ml) were successively added to a solution of the compound (0.51 g) obtained in Referential Example 234 in ethanol (10 ml) under ice cooling, and the mixture was stirred for 1 hour while the temperature of the system was gradually raised to room temperature. Sodium cyanoborohydride (0.15 g) was added to stir the mixture for 18 hours. The reaction mixture was diluted with chloroform and washed with a saturated aqueous solution of sodium hydrogencarbonate and saturated aqueous solution of sodium chloride. The resultant organic layer was dried over anhydrous sodium sulfate, the solvent was distilled off under reduced pressure, and the resultant residue was dissolved in toluene (20 ml). Triethylamine (2 ml) was added to this solution, and the mixture was heated under reflux for 2 hours. The reaction mixture was concentrated under reduced pressure, and the resultant residue was purified by column chromatography on silica gel (chloroform:methanol=98:2) to obtain the title compound (0.28 g).

$^1$H-NMR (DMSO-$d_6$) δ: 1.36 (3.6H, s), 1.38 (5.4H, s), 2.22-2.43 (1H, m), 2.44-2.61 (1H, m), 2.72 (1.2H, s), 2.80 (1.8H, s), 3.10 (0.5H, dd, J=12.5, 8.3 Hz), 3.21-3.30 (0.5H, m), 3.33-3.45 (1H, m), 3.56-3.82 (1H, m), 3.89-4.00 (1H, m), 4.94 (1H, d, J=8.1 Hz), 5.00 (1.2H, s), 5.01 (0.8H, s), 6.89-7.02 (0.5H, m), 7.23-7.44 (5.5H, m).

Referential Example 236 tert-Butyl (4R)-4-{[(5-chloroindol-2-yl)carbonyl]amino}-1-methyl-6-oxopiperidin-3-ylcarbamate

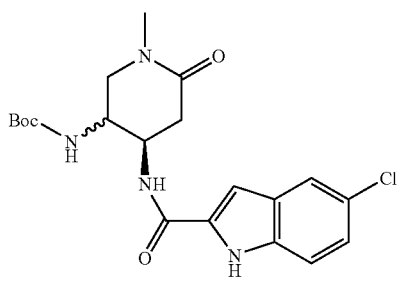

The title compound was obtained from the compound obtained in Referential Example 235 and 5-chloroindole-2-carboxylic acid in a similar manner to Referential Example 214.

$^1$H-NMR (DMSO-$d_6$) δ: 1.24 (5.4H, s), 1.35 (3.6H, s), 2.43-2.56 (2H, m), 2.80 (3H, s), 3.10-3.20 (1H, m), 3.30-3.52 (1H, m), 3.83-3.91 (0.4H, m), 4.02-4.10 (0.6H, m), 4.20-4.31 (0.6H, m), 4.43-4.54 (0.4H, m), 6.94 (0.6H, d, J=8.1 Hz), 7.08 (1H, s), 7.16 (1H, dd, J=8.8, 2.0 Hz), 7.42 (1H, d, J=8.8 Hz), 7.69 (1H, d, J=2.0 Hz), 8.30 (0.4H, s), 8.36 (0.4H, d, J=7.3 Hz), 8.43 (0.6H, d, J=8.3 Hz), 11.75 (0.6H, s), 11.78 (0.4H, s).

Referential Example 237

4-(Pyridin-4-yl)benzoic Acid Hydrochloride

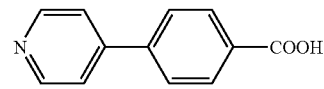

4-Bromopyridine hydrochloride (11.7 g) and 4-carboxyphenylboric acid (10.0 g) were dissolved in a mixed solvent of toluene (250 ml) and water (250 ml), tetrakis(triphenylphosphine)palladium(0) (5.0 g) and anhydrous sodium carbonate (25.4 g) were successively added, and the mixture was heated under reflux at 120° C. for 19 hours. After the reaction mixture was cooled to room temperature, ethyl acetate was added to the reaction mixture to extract it with water. Concentrated hydrochloric acid was added to the water layer to acidify it. The water layer was washed with ethyl acetate and then concentrated, and solids deposited were collected to obtain the title compound (8.37 g).

$^1$H-NMR (DMSO-$d_6$) δ: 8.11 (2H, d, J=8.8 Hz), 8.14 (2H, dJ=8.8 Hz), 8.35 (2H, d, J=6.6 Hz), 8.97 (2H, d, J=6.6 Hz).
MS (FAB) m/z: 200 (M+H)$^+$.

Referential Example 238

Methyl 4-(Pyridin-4-yl)benzoate

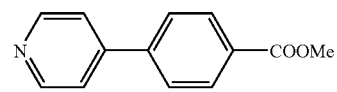

The compound (12.4 g) obtained in Referential Example 237 was dissolved in methanol (200 ml), concentrated sulfuric acid (5 ml) was added at room temperature, and the mixture was heated under reflux for 3 hours. After completion of the reaction, the solvent was distilled off, and a saturated aqueous solution of sodium hydrogencarbonate was added to the residue to extract it with ethyl acetate. The extract was dried over anhydrous sodium sulfate, the solvent was distilled off, and hexane was added to the residue to solidify it, thereby obtaining the title compound (9.86 g).

$^1$H-NMR (CDCl$_3$) δ: 3.96 (3H, s), 7.54 (2H, d, J=5.9 Hz), 7.71 (2H, dJ=8.3 Hz), 8.16 (2H, d, J=8.3 Hz), 8.71 (2H, d, J=5.9 Hz).

Referential Example 239

4-[4-(Methoxycarbonyl)phenyl]pyridine N-oxide

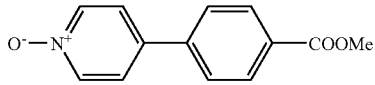

The compound (1.49 g) obtained in Referential Example 238 was dissolved in methylene chloride (30 ml), 70% m-chloroperbenzoic acid (3.46 g) was added, and the mixture was stirred at room temperature for 1 hour. An aqueous solution of sodium sulfite was added to conduct liquid separation. The resultant organic layer was washed with a saturated aqueous solution of sodium hydrogencarbonate and then dried over anhydrous sodium sulfate. The solvent was distilled off to obtain the title compound (1.33 g).

$^1$H-NMR (DMSO) δ: 3.88 (3H, s), 7.86 (2H, d, J=7.2 Hz), 7.94 (2H, d, J=8.3 Hz), 8.05 (2H, d, J=8.3 Hz), 8.30 (2H, d, J=7.2 Hz). MS (FAB) m/z: 230 (M+H)$^+$.

Referential Example 240

4-(4-Carboxyphenyl)pyridine N-oxide

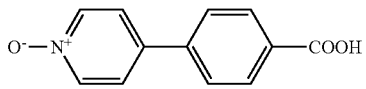

The compound (802 mg) obtained in Referential Example 239 was dissolved in dioxane (20 ml), a 1N aqueous solution (5 ml) of sodium hydroxide was added, and the mixture was refluxed for 1 hour and then stirred at room temperature for 2 hours. 1N Hydrochloric acid (5 ml) was added to neutralize it. Further, water (5 ml) was added, and precipitate formed was collected by filtration to obtain the title compound (627 mg).

$^1$H-NMR (DMSO) δ: 7.85 (2H, d, J=7.2 Hz), 7.91 (2H, d, J=8.3 Hz), 8.03 (2H, d, J=8.3 Hz), 8.30 (2H, d, J=7.2 Hz).

Referential Example 241

2-(4-Carboxyphenyl)-1-pyridine N-oxide

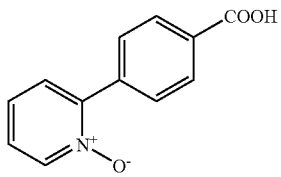

The title compound was obtained from 2-bromopyridine in similar manners to Referential Examples 237, 238, 239 and 240.

$^1$H-NMR (DMSO-d$_6$) δ: 7.41-7.45 (2H, m), 7.65-7.69 (1H, m), 7.94 (2H, d, J=8.3 Hz), 8.02 (2H, d, J=8.3 Hz), 8.34-8.38 (1H, m), 13.09 (1H, s). MS (FAB) m/z: 216 (M+H)$^+$.

Referential Example 242

Ethyl 2-(4-chloroanilino)-2-oxoacetate

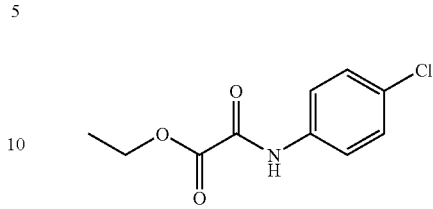

Triethylamine (1.52 ml) and ethyl chlorooxoacetate (1.11 ml) were successively added to a solution of 4-chloroaniline (1.16 g) in methylene chloride (26 ml), and the mixture was stirred at room temperature for 14 hours. After a saturated aqueous solution of sodium hydrogencarbonate was added to the reaction mixture to conduct liquid separation, the resultant organic layer was successively washed with a 10% aqueous solution of citric acid and saturated aqueous solution of sodium chloride and dried over anhydrous sodium sulfate. After the solvent was concentrated under reduced pressure, hexane was added to the residue to deposit crystals, and the crystals were collected by filtration and dried to obtain the title compound (1.89 g).

$^1$H-NMR (CDCl$_3$) δ: 1.43 (3H, t, J=7.1 Hz), 4.42 (2H, q, J=7.1 Hz), 7.34 (2H, d, J=8.8 Hz), 7.60 (2H, d, J=8.8 Hz), 8.86 (1H, br.s). MS (ESI) m/z: 228 (M+H)$^+$.

Referential Example 243

Methyl 2-[(5-chloropyridin-2-yl)amino]-2-oxoacetate

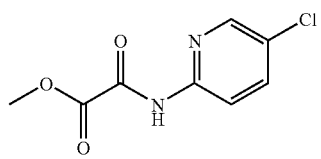

2-Amino-5-chloropyridine (1.16 g) and triethylamine (1.51 ml) were dissolved in methylene chloride (26 ml), ethyl chlorooxoacetate (1.10 ml) was added to the solution under ice cooling, and the mixture was stirred at room temperature for 14 hours. After a saturated aqueous solution of sodium hydrogencarbonate was added to the reaction mixture to conduct liquid separation, the resultant organic layer was dried over anhydrous sodium sulfate, and the solvent was distilled off under reduced pressure. The residue was purified by column chromatography on silica gel (hexane:ethyl acetate=3:1). The thus-obtained pale yellow solids were dissolved in methanol (20 ml), and the solution was stirred at 50° C. for 11 hours. The reaction mixture was concentrated under reduced pressure, and crystals deposited were collected by filtration and dried to obtain the title compound (0.43 g).

$^1$H-NMR (CDCl$_3$) δ: 3.99 (3H, s), 7.73 (1H, dd, J=8.8, 2.2 Hz), 8.24 (1H, d, J=8.8 Hz), 8.31 (1H, d, J=2.2 Hz), 9.39 (1H, br.s). MS (ESI) m/z: 215 (M+H)$^+$.

Referential Example 244

(1S)-3-Cyclohexene-1-carboxylic Acid

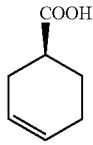

The (R)-(+)-α-methylbenzylamine salt (J. Am. Chem. Soc., Vol. 100, pp. 5199-5203, 1978) (95.0 g) of (1S)-3-cyclohexene-1-carboxylic acid was dissolved in a mixture of ethyl acetate (1.6 l) and 2N hydrochloric acid (1.6 l). After an organic layer was taken out, a water layer was extracted with ethyl acetate (500 ml×2 times). The resultant organic layers were combined and washed with saturated aqueous solution of sodium chloride (300 ml×2 times) to take out an organic layer. After a water layer was extracted with ethyl acetate (200 ml), the resultant organic layer was washed with saturated aqueous solution of sodium chloride (100 ml). All organic layers were combined and dried over anhydrous sodium sulfate and then concentrated under reduced pressure to obtain the title compound (48.3 g).

$[\alpha]^{25}_D = -104°$ (c=1, chloroform). $^1$H-NMR (CDCl$_3$) δ: 1.66-1.77 (1H, m), 2.00-2.20 (3H, m), 2.20-2.38 (2H, m), 2.57-2.65 (1H, m), 5.65-5.75 (2H, m).

Referential Example 245

(1S,4S,5S)-4-Iodo-6-oxabicyclo[3.2.1]octan-7-one

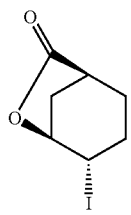

Iodine (125.4 g) was added to a mixture of the compound (48.0 g) obtained in Referential Example 244, methylene chloride (580 ml), potassium iodide (82.1 g), sodium hydrogencarbonate (42.0 g) and water (530 ml) at an internal temperature of 5° C., and the resultant mixture was stirred at room temperature for 3 hours. After a 1N aqueous solution (800 ml) of sodium thiosulfate was added to the reaction mixture, the resultant mixture was extracted with methylene chloride (1 L, 500 ml). The resultant organic layer was washed with an aqueous solution (300 ml) of sodium hydrogencarbonate, water (500 ml) and saturated aqueous solution of sodium chloride (300 ml), dried over anhydrous magnesium sulfate and then concentrated. Crystals deposited were collected by filtration, washed with hexane and then dried to obtain the title compound (89.5 g).

Mp. 130-131° C. $[\alpha]^{25}_D = -41°$ (c=1, chloroform). $^1$H-NMR (CDCl$_3$) δ: 1.78-1.96 (2H, m), 2.12 (1H, dd, J=16.5 Hz,5.2 Hz), 2.35-2.50 (2H, m), 2.65-2.70 (1H, m), 2.80 (1H, d, J=12.2 Hz), 4.45-4.55 (1H, m), 4.77-4.87 (1H, m).

Referential Example 246

Ethyl (1S,3S,6R)-7-oxabicyclo[4.1.0]heptane-3-carboxylate

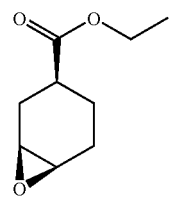

A 2N aqueous solution (213 ml) of sodium hydroxide was added to an ethanol (810 ml) suspension of the compound (89.3 g) obtained in Referential Example 245, and the mixture was stirred at room temperature for 3 hours. The reaction mixture was concentrated under reduced pressure on a hot bath of 35° C., and water (500 ml) was added to the resultant oil to conduct extraction with methylene chloride (500 ml and 300 ml). The extract was washed with water (300 ml) and dried over anhydrous magnesium sulfate and then concentrated under reduced pressure. The resultant oil was purified by column chromatography on silica gel (hexane:ethyl acetate=85:15) to obtain the title compound (41.3 g).

$[\alpha]^{25}_D = -58°$ (c=1, chloroform). $^1$H-NMR (CDCl$_3$) δ: 1.25 (3H, t, J=7.2 Hz), 1.50-1.70 (2H, m), 1.71-1.82 (1H, m), 2.08-2.28 (4H, m), 3.16 (2H, s), 4.12 (2H, q, J=7.2 Hz).

Referential Example 247

Ethyl (1S,3R,4R)-3-azido-4-hydroxycyclohexanecarboxylate

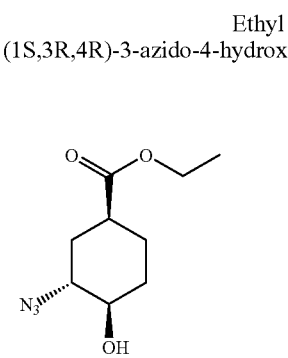

A mixture of the compound (41.0 g) obtained in Referential Example 246, N,N-dimethylformamide (300 ml), ammonium chloride (19.3 g) and sodium azide (23.5 g) was stirred at 76° C. for 13 hours. After insoluble matter was taken out by filtration, the filtrate was concentrated under reduced pressure without solidifying, and the product previously taken out by filtration was added to the residue, and the mixture was dissolved in water (500 ml). The solution was extracted with ethyl acetate (500 ml and 300 ml), and the extract was washed with water and saturated aqueous solution of sodium chloride, dried over anhydrous magnesium sulfate and then concentrated to obtain the title compound (51.5 g).

$[\alpha]^{25}_D = +8°$ (c 1, chloroform). $^1$H-NMR (CDCl$_3$) δ: 1.28 (3H, t, J=7.1 Hz), 1.37-1.64 (3H, m), 1.86-1.95 (1H, m), 2.04-2.16 (1H, m), 2.32-2.41 (1H, m), 2.44 (1H, br.s), 2.68-2.78 (1H, m), 3.45-3.60 (2H, m), 4.17 (2H, q, J=7.1 Hz).

Referential Example 248

Ethyl (1S,3R,4R)-3-[(tert-butoxycarbonyl)amino]-4-hydroxycyclohexanecarboxylate

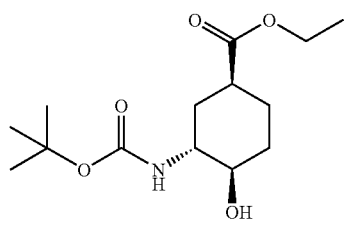

A mixture of the compound (51.2 g) obtained in Referential Example 247, di-tert-butyl dicarbonate (68.1 g), 5% palladium on carbon (5.0 g) and ethyl acetate (1000 ml) was stirred overnight at room temperature under a hydrogen pressure (7 kg/cm$^2$). An oil obtained by filtering the reaction mixture and concentrating the filtrate was purified by column chromatography on silica gel (hexane:ethyl acetate=4:1→3:1). The purified product was crystallized from hexane to obtain the title compound (46.9 g). The mother liquor was additionally purified by column chromatography on silica gel (chloroform:methanol 100:1) to obtain the title compound (6.74 g).

$[\alpha]_D^{25}$=+25° (c=1, chloroform). $^1$H-NMR (CDCl$_3$) δ: 1.28 (3H, t, J=7.1 Hz), 1.38-1.57 (3H, m), 1.45 (9H, s), 1.86-1.95 (1H, m), 2.05-2.17 (1H, m), 2.29-2.39 (1H, m), 2.61-2.68 (1H, m), 3.34 (1H, br.s), 3.39-3.48 (1H, m), 3.53-3.64 (1H, m), 4.10-4.24 (2H, m), 4.54 (1H, br.s).

Referential Example 249

Ethyl (1S,3R,4S)-4-azido-3-[(tert-butoxycarbonyl)amino]-cyclohexanecarboxylate

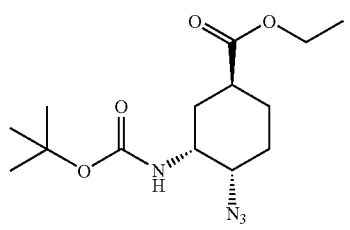

Methanesulfonyl chloride (42 ml) was added dropwise to a solution containing the compound (53.5 g) obtained in Referential Example 248, methylene chloride (500 ml) and triethylamine (130 ml) over 20 minutes at −10° C. to −15° C. The mixture was heated to room temperature over 2 hours and stirred for 2 hours. 0.5N Hydrochloric acid (800 ml) was added dropwise to the reaction mixture at 0° C. to acidify it, and extraction was conducted with methylene chloride (500 ml and 300 ml). The resultant organic layer was washed with a saturated aqueous solution of sodium hydrogencarbonate and saturated aqueous solution of sodium chloride, dried over anhydrous magnesium sulfate and then concentrated under reduced pressure. The crystals thus obtained were dissolved in N,N-dimethylformamide (335 ml), sodium azide (60.5 g) was added, and the mixture was stirred at 67° C. to 75° C. for 16 hours. After the reaction mixture was filtered, the filtrate was concentrated under reduced pressure to distill off 250 ml of the solvent. The residue was combined with the product previously taken out by filtration, and the mixture was dissolved in water (500 ml). The solution was extracted with ethyl acetate (1 L and 300 ml), and the extract was washed with saturated aqueous solution of sodium chloride (400 ml and 200 ml), dried over anhydrous magnesium sulfate and then concentrated. The crystals thus obtained were purified by column chromatography on silica gel (hexane:ethyl acetate=4:1) to obtain the title compounds (18.4 g).

$[\alpha]_D^{25}$=+62° (c=1, chloroform). $^1$H-NMR (CDCl$_3$) δ: 1.26 (3H, t, J=7.1 Hz), 1.35-2.00 (15H, s), 2.60-2.68 (1H, m), 3.80-3.96 (2H, m), 4.15 (2H, q, J=7.1 Hz), 4.61 (1H, br.s).

Referential Example 250

(1S,3R,4S)-4-Azido-3-[(tert-butoxycarbonyl)amino]-cyclohexanecarboxylic Acid

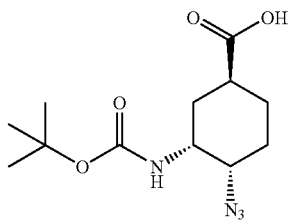

Lithium hydroxide (102 mg) and water (5 ml) were added to a solution of the compound (1.0 g) obtained in Referential Example 249 in tetrahydrofuran (25 ml). After stirring for 17 hours, lithium hydroxide (50 mg) was additionally added to stir the mixture for 4 hours. 1N Hydrochloric acid (6.3 ml) was added to the reaction mixture to conduct extraction with ethyl acetate. After the resultant organic layer was dried, the solvent was distilled off under reduced pressure to obtain the title compound (980 mg).

$^1$H-NMR (CDCl$_3$) δ: 1.30-2.20 (6H, m), 1.45 (9H, s), 2.70-2.80 (1H, m), 3.94 (2H, br.s), 4.73 (1H, br.s).

Referential Example 251 tert-Butyl (1R,2S,5S)-2-azido-5-[(dimethylamino)carbonyl]cyclohexylcarbamate

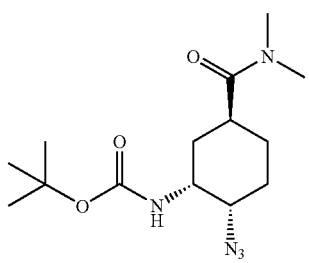

The compound (4.77 g) obtained in Referential Example 250 was dissolved in methylene chloride (150 ml), to which dimethylamine hydrochloride (3.26 g), 1-ethyl-3-(3-dimethylaminopropyl)carbodiimide hydrochloride (4.60 g), 1-hydroxybenzotriazole monohydrate (3.24 g) and N-methylmorpholine (8.09 g) were added, and the mixture was stirred at room temperature for 18 hours. A saturated aqueous solution of sodium hydrogencarbonate was added to the reaction mixture to conduct liquid separation. The resultant organic layer was then dried, and the solvent was distilled off under reduced pressure. The resultant residue was purified by column chromatagraphy on silica gel (methanol:methylene chloride=1:50) to obtain the title compound (4.90 g).

$^{1}$H-NMR (CDCl$_{3}$) δ: 1.30-1.90 (4H, m), 1.45 (9H, s), 1.97-2.18 (2H, m), 2.75-2.85 (1H, m), 2.92 (3H, s), 3.02 (3H, s), 3.68-3.80 (1H, m), 4.05-4.20 (1H, m), 4.55-4.75 (1H, m).

Referential Example 252

N-{(1R,2S,5S)-2-Azido-5-[(dimethylamino)carbonyl]-cyclohexyl}-5-methyl-4,5,6,7-tetrahydrothiazolo[5,4-c]-pyridine-2-carboxamide

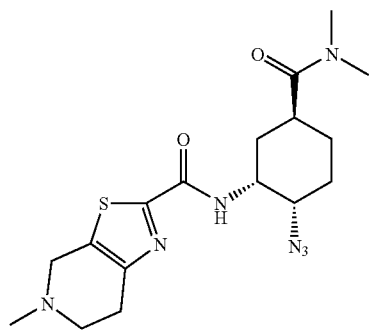

The compound (9.13 g) obtained in Referential Example 251 was dissolved in methylene chloride (100 ml), and an ethanol solution (100 ml) of hydrochloric acid was added to stir the mixture at room temperature for 1 minute. The reaction mixture was concentrated under reduced pressure, and the resultant residue was dissolved in N,N-dimethylformamide (200 ml). To the solution were added the compound (7.75 g) obtained in Referential Example 10, 1-hydroxybenzotriazole monohydrate (4.47 g), 1-(3-dimethylaminopropyl)-3-ethylcarbodiimide hydrochloride (11.2 g) and triethylamine (2.02 ml), and the mixture was stirred overnight at room temperature. The compound (2.38 g) obtained in Referential Example 10 and 1-(3-dimethylaminopropyl)-3-ethylcarbodiimide hydrochloride (5.60 g) were additionally added to stir the mixture for 3 days. The reaction mixture was concentrated under reduced pressure, and methylene chloride and a saturated aqueous solution of sodium hydrogencarbonate were added to the residue to conduct liquid separation. The resultant organic layer was dried over anhydrous sodium sulfate, and the solvent was distilled off under reduced pressure. The resultant residue was then purified by column chromatography on silica gel (methylene chloride:methanol=47:3) to obtain the title compound (7.38 g).

$^{1}$H-NMR (CDCl$_{3}$) δ: 1.72-1.97 (4H, m), 2.10-2.27 (2H, m), 2.51 (3H, s), 2.77-3.05 (11H, m), 3.68 (1H, d, J=15.4 Hz), 3.74 (1H, d, J=15.4 Hz), 3.86-3.93 (1H, m), 4.54-4.60 (1H, m), 7.25 (1H, d, J=7.6 Hz).

Referential Example 253

N-{(1R,2S,5S)-2-Amino-5-[(dimethylamino)carbonyl]-cyclohexyl}-5-methyl-4,5,6,7-tetrahydrothiazolo[5,4-c]-pyridine-2-carboxamide

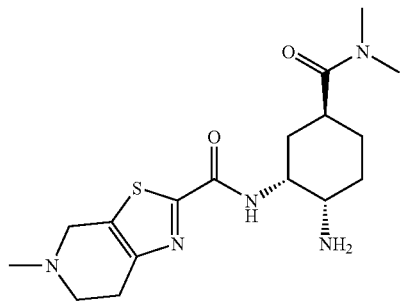

10% Palladium on carbon (6.0 g) was added to a solution of the compound (9.0 g) obtained in Referential Example 252 in methanol (300 ml), and the mixture was vigorously stirred at room temperature for 11 hours under a hydrogen pressure of 4 atm. The catalyst was removed by filtration, and the filtrate was concentrated under reduced pressure to obtain the title compound (7.67 g).

$^{1}$H-NMR (CDCl$_{3}$) δ: 1.42-1.54 (1H, m), 1.66-1.89 (5H, m), 2.30-2.40 (1H, m), 2.51 (3H, s), 2.68-3.05 (6H, m), 2.92 (3H, s), 3.00 (3H, s), 3.10-3.18 (1H, m), 3.65-3.77 (2H, m), 4.21-4.28 (1H, m), 7.52 (1H, d, J=6.1 Hz).

Referential Example 254

Methyl 2-(4-fluoroanilino)-2-oxoacetate

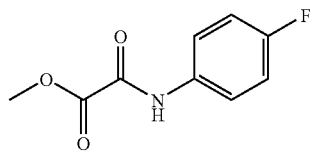

The title compound was obtained from 4-fluoroaniline and methyl chlorooxoacetate in a similar manner to Referential Example 242.

$^{1}$H-NMR (CDCl$_{3}$) δ: 3.98 (3H, s), 7.00-7.14 (2H, m), 7.55-7.68 (2H, m), 8.85 (1H, br.s). MS (ESI) m/z: 198 (M+H)$^{+}$.

Referential Example 255

Methyl 2-(4-bromoanilino)-2-oxoacetate

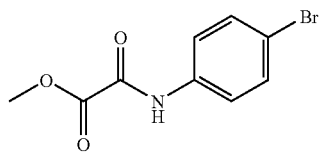

The title compound was obtained from 4-bromoaniline and methyl chlorooxoacetate in a similar manner to Referential Example 242.

$^1$H-NMR (CDCl$_3$) δ: 3.98 (3H, s), 7.49 (2H, d, J=9.0 Hz), 7.55 (2H, d, J=9.0 Hz), 8.85 (1H, br.s). MS (FAB) m/z: 258 M$^+$.

Referential Example 256

Methyl 2-(4-chloro-2-methylanilino)-2-oxoacetate

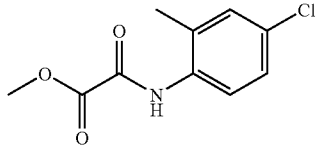

The title compound was obtained from 4-chloro-2-methylaniline and methyl chlorooxoacetate in a similar manner to Referential Example 242.

$^1$H-NMR (CDCl$_3$) δ: 2.31 (3H, s), 3.99 (3H, s), 7.15-7.30 (2H, m), 7.98 (1H, d, J=8.8 Hz), 8.77 (1H, br). MS (FAB) m/z: 228 (M+H)$^+$.

Referential Example 257

Methyl 2-[(4-chloro-3-methylanilino)-2-oxoacetate

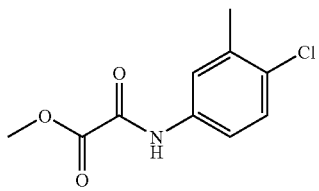

The title compound was obtained from 4-chloro-3-methylaniline and methyl chlorooxoacetate in a similar manner to Reference Example 242.

$^1$H-NMR (CDCl$_3$) δ: 2.39 (3H, s), 3.98 (3H, s) 7.33 (1H, d, J=12.5 Hz), 7.44 (1H, dd, J=12.5, 2.5 Hz), 7.53 (1H, d, J=2.5 Hz), 8.81 (1H, br.s). MS (ESI) m/z: 228 (M+H)$^+$.

Referential Example 258

Methyl 2-(4-chloro-2-fluoroanilino)-2-oxoacetate

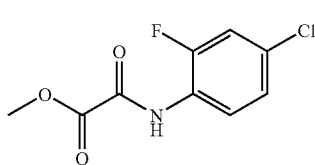

The title compound was obtained from 4-chloro-2-fluoroaniline and methyl chlorooxoacetate in a similar manner to Referential Example 242.

$^1$H-NMR (CDCl$_3$) δ: 3.99 (3H, s), 7.15-7.24 (2H, m), 8.33 (1H, t, J=8.4 Hz), 9.05 (1H, br.s). MS (ESI) m/z: 232 (M+H)$^+$.

Referential Example 259

Methyl 2-(2,4-difluoroanilino)-2-oxoacetate

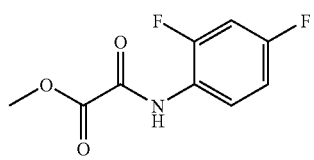

The title compound was obtained from 2,4-difluoroaniline and methyl chlorooxoacetate in a similar manner to the process described in Referential Example 242.

$^1$H-NMR (CDCl$_3$) δ: 3.99 (3H, s), 6.87-7.00 (2H, m), 8.29-8.38 (1H, m), 8.99 (1H, br.s). MS (ESI) m/z: 215 M$^+$.

Referential Example 260

Methyl 2-(3,4-difluoroanilino)-2-oxoacetate

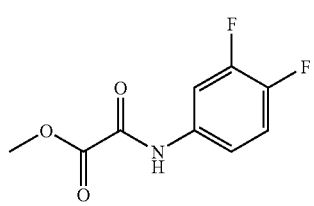

The title compound was obtained from 3,4-difluoroaniline and methyl chlorooxoacetate in a similar manner to the process described in Referential Example 242.

$^1$H-NMR (CDCl$_3$) δ: 3.98 (3H, s), 7.10-7.28 (2H, m), 7.67-7.78 (1H, m), 8.83 (1H, br.s). MS (ESI) m/z: 215 M$^+$.

Referential Example 261

Methyl 2-oxo-2-(pyridin-4-ylamino)acetate

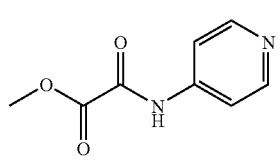

The title compound was obtained from 4-aminopyridine and methyl chlorooxoacetate in a similar manner to the process described in Referential Example 242.

$^1$H-NMR (CDCl$_3$) δ: 3.99 (3H, s), 7.58 (2H, dd, J=4.8, 1.6 Hz), 8.60 (2H, dd, J=4.8, 1.6 Hz), 9.04 (1H, br.s). MS (ESI) m/z: 181 (M+H)$^+$.

Referential Example 262

Methyl 2-[(5-bromopyridin-2-yl)amino]-2-oxoacetate

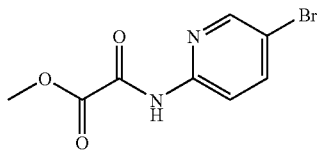

The title compound was obtained from 2-amino-5-bromopyridine and methyl chlorooxoacetate in a similar manner to the process described in Referential Example 242.

$^1$H-NMR (CDCl$_3$) δ: 3.99 (3H, s), 7.87 (1H, dd, J=8.8, 2.4 Hz), 8.19 (1H, d, J=8.8 Hz), 8.41 (1H, d, J=2.4 Hz), 9.38 (1H, br.s). MS (FAB) m/z: 259 M$^+$.

Referential Example 263

Ethyl 2-[(6-chloropyridin-3-yl)amino]-2-oxoacetate

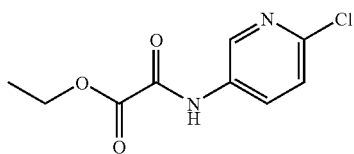

5-Amino-2-chloropyridine (386 mg) was dissolved in N,N-dimethylformamide (8 ml), and potassium 2-ethoxy-2-oxoacetate (469 mg), 1-(3-dimethylaminopropyl)-3-ethylcarbodiimide hydrochloride (863 mg) and 1-hydroxybenzotriazole monohydrate (203 mg) were added to stir the mixture at room temperature for 2 days. After the solvent was distilled off under reduced pressure, methylene chloride and saturated aqueous solution of sodium hydrogencarbonate were added to the residue to conduct liquid separation, the resultant organic layer was dried over anhydrous sodium sulfate. After the solvent was concentrated under reduced pressure, the residue was purified by flash column chromatography on silica gel (hexane:ethyl acetate=2:1) to obtain residue (200 mg) containing the title compound.

$^1$H-NMR (CDCl$_3$) δ: 1.43 (3H, t, J=7.2 Hz), 4.44 (2H, q, J=7.2 Hz), 7.36 (1H, d, J=8.7 Hz), 8.24 (1H, dd, J=8.7, 2.7 Hz), 8.55 (1H, d, J=2.7 Hz), 9.03 (1H, br.s).

Referential Example 264

Methyl 2-[(6-chloropyridazin-3-yl)amino]-2-oxoacetate

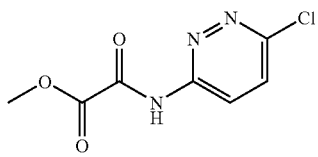

3-Amino-6-chloropyridazine (516 mg) was dissolved in pyridine (26 ml), and triethylamine (665 μl) and methyl chlorooxoacetate (441 μl) were successively added under ice cooling to stir the mixture at room temperature for 14 hours. After water was added to the reaction mixture to conduct liquid separation, the resultant organic layer was dried over anhydrous sodium sulfate. The solvent was distilled off under reduced pressure to obtain the title compound (748 mg).

$^1$H-NMR (CDCl$_3$) δ: 4.03 (3H, s), 7.59 (1H, d, J=9.3 Hz), 8.52 (1H, d, J=9.3 Hz), 9.88 (1H, br.s). MS (FAB) m/z: 215M$^+$.

Referential Example 265

Methyl 2-[(5-chlorothiazol-2-yl)amino]-2-oxoacetate

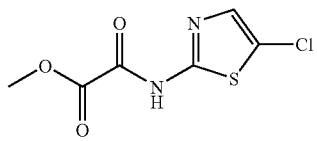

The title compound was obtained from 2-amino-5-chlorothiazole and methyl chlorooxoacetate in a similar manner to the process described in Referential Example 242.

$^1$H-NMR (CDCl$_3$) δ: 4.02 (3H, s), 7.48 (1H, s), 11.03 (1H, br.s). MS (ESI) m/z: 221 (M+H)$^+$.

Referential Example 266

Lithium 2-[(5-chloropyridin-2-yl)amino]-2-oxoacetate

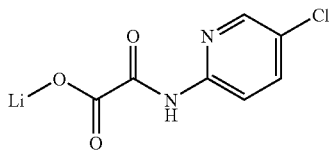

Water (5.0 ml) and lithium hydroxide (128 mg) were added to a solution of the compound (1.12 g) obtained in Referential Example 243 in tetrahydrofuran (20 ml) at room temperature, and the mixture was stirred for 5 hours. The solvent was distilled off under reduced pressure, hexane (30 ml) was added to the resultant white solids, and the mixture was stirred for 30 minutes. The solides were collected by filtration and then dried to obtain the title compound (1.02 g).

$^1$H-NMR (DMSO-d$_6$) δ: 7.90 (1H, dd, J=8.9, 2.6 Hz), 8.12 (1H, d, J=8.9 Hz), 8.34 (1H, d, J=2.6 Hz), 10.18 (1H, s).

Referential Example 267

Ethyl 2-(4-chloroanilino)acetate

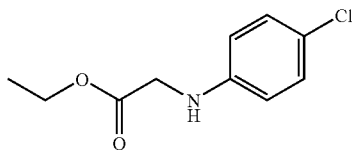

4-Chloroaniline (2.0 g) was dissolved in acetonitrile (20 ml), and ethyl bromoacetate (2.1 g) and potassium carbonate (2.2 g) were added to stir the mixture at 60° C. for 2 days. The reaction mixture was filtered through Celite pad, and the filtrate was concentrated under reduced pressure. The resultant residue was purified by column chromatography on silica gel (hexane:chloroform=2:1) to obtain the title compound (2.3 g).

$^1$H-NMR (CDCl$_3$) δ: 1.30 (3H, t, J=7.3 Hz), 3.86 (2H, s), 4.24 (2H, q, J=7.3 Hz), 4.26-4.35 (1H, m), 6.53 (2H, dd, J=6.6, 2.2 Hz), 7.14 (2H, dd, J=6.6, 2.2 Hz).

Referential Example 268

Ethyl 2-(4-chloro-2-fluoroanilino)acetate

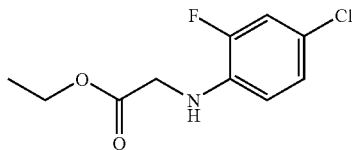

The title compound was obtained from 4-chloro-2-fluoroaniline and ethyl bromoacetate in a similar manner to the process described in Referential Example 267.

$^1$H-NMR (CDCl$_3$) δ: 1.29 (3H, t, J=7.3 Hz), 3.91 (2H, s), 4.22 (2H, q, J=7.3 Hz), 4.42-4.51 (1H, m), 6.49 (1H, t, J=8.8 Hz), 6.98 (1H, dt, J=8.8, 2.5 Hz), 7.01 (1H, dd, J=11.3, 2.5 Hz).

Referential Example 269

Ethyl 2-[(((1S,2R,4S)-4-[(dimethylamino)carbonyl]-2-[[(5-ethyl-4,5,6,7-tetrahydrothiazolo[5,4-c]pyridin-2-yl)carbonyl]amino}cyclohexyl)amino]-2-oxoacetate

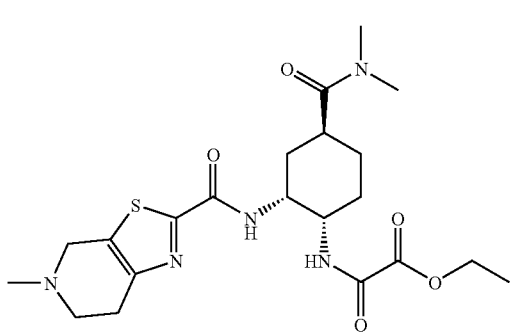

The compound (1.5 g) obtained in Referential Example 253 was dissolved in N,N-dimethylformamide (15 ml), and potassium 2-ethoxy-2-oxoacetate (962 mg), 1-(3-dimethylaminopropyl)-3-ethylcarbodiimide hydrochloride (1.18 g) and 1-hydroxybenzotriazole monohydrate (227 mg) were added to stir the mixture at room temperature for 14 hours. After the solvent was distilled off under reduced pressure, a saturated aqueous solution of sodium hydrogencarbonate and methylene chloride were added to the residue to conduct liquid separation. The resultant organic layer was dried over anhydrous sodium sulfate. After the solvent was distilled off under reduced pressure, the residue was purified by flash column chromatagraphy on silica gel (methylene chloride: methanol=47:3) to obtain the title compound (1.13 g).

$^1$H-NMR (CDCl$_3$) δ: 1.37 (3H, t, J=7.1 Hz), 1.55-2.15 (6H, m), 2.52 (3H, s), 2.77-2.89 (3H, m), 2.94 (5H, br.s), 3.06 (3H, s), 3.71 (1H, d, J=15.5 Hz), 3.73 (1H, d, J=15.5 Hz), 4.06-4.13 (1H, m), 4.32 (2H, q, J=7.1 Hz), 4.60-4.63 (1H, m), 7.39 (1H, d, J=8.3 Hz), 7.83 (1H, d, J=7.6 Hz). MS (ESI) m/z: 466 (M+H)$^+$.

Referential Example 270

Lithium 2-[(((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]-2-oxoacetate

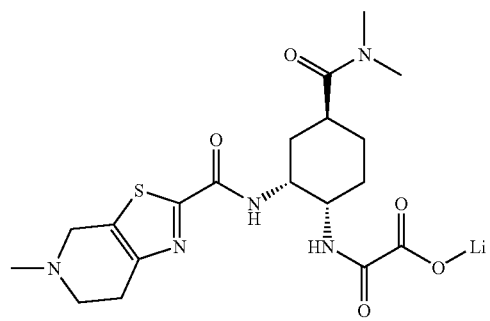

The compound (1.13 g) obtained in Referential Example 269 was dissolved in tetrahydrofuran (20 ml), methanol (10 ml) and water (10 ml), and lithium hydroxide (58 mg) was added to stir the mixture at room temperature for 30 minutes. The solvent was distilled off under reduced pressure to obtain the title compound (1.10 g).

$^1$H-NMR (DMSO-d$_6$) δ: 1.41-1.73 (4H, m), 2.00-2.07 (2H, m), 2.39 (3H, s), 2.74-2.99 (11H, m), 3.67 (2H, s), 3.82-3.88 (1H, m), 4.28-4.30 (1H, m), 8.66-8.70 (2H, m).

Referential Example 271

N-{(1R,2S,5S)-2-Azido-5-[(dimethylamino)carbonyl]-cyclohexyl}-5-methyl-5,6-dihydro-4H-pyrrolo[3,4-d]-thiazole-2-carboxamide

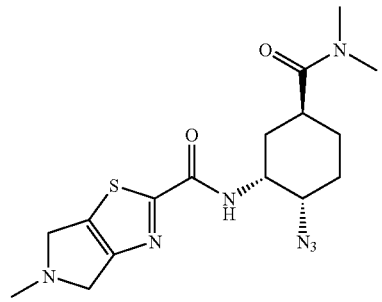

The title compound was obtained from the compound obtained in Referential Example 293 and the compound obtained in Referential Example 251 in a similar manner to the process described in Referential Example 252.

$^1$H-NMR (CDCl$_3$) δ: 1.73-1.87 (4H, m), 2.11-2.20 (2H, m), 2.67 (3H, s), 2.85-2.90 (1H, m), 2.93 (3H, s), 3.00 (3H, s), 3.90-4.10 (5H, m), 4.57-4.62 (1H, m), 7.20-7.22 (1H, m). MS (FAB) m/z: 378 (M+H)$^+$.

Referential Example 272

N-{(1R,2S,5S)-2-Amino-5-[(dimethylamino)carbonyl]-cyclohexyl}-5-methyl-5,6-dihydro-4H-pyrrolo[3,4-d]-thiazole-2-carboxamide

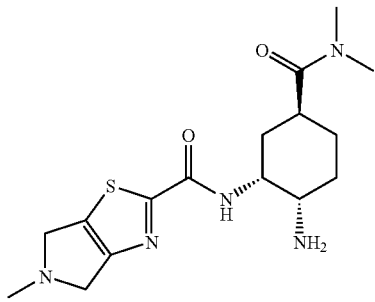

The title compound was obtained from the compound obtained in Referential Example 271 in a similar manner to the process described in Referential Example 253.

$^1$H-NMR (CDCl$_3$) δ: 1.67-1.97 (6H, m), 2.36-2.40 (1H, m), 2.67 (3H, s), 2.92 (3H, s), 3.00 (3H, s), 3.07-3.18 (1H, m), 3.92-3.95 (2H, m), 4.02-4.06 (2H, m), 4.23-4.26 (1H, m), 7.50-7.52 (1H, m).

Referential Example 273

Methyl 5-chloro-4-fluoroindole-2-carboxylate

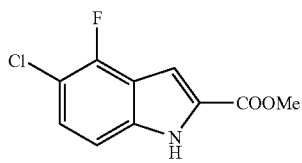

Ethanol (100 ml) was added to sodium hydride (content: 60%, 4.7 g) at 0° C. under an argon atmosphere, and the mixture was stirred for 10 minutes. After 2-nitropropane (11 ml) was added to the reaction mixture to stir the mixture for 10 minutes, 1-(bromomethyl)-3-chloro-2-fluorobenzene (10 g) was added to stir the resultant mixture at room temperature for 3.5 hours. Precipitate was removed by filtration, and the filtrate was concentrated under reduced pressure. The residue was partitioned in diethyl ether and water, and an organic layer was successively washed with a 1N aqueous solution of sodium hydroxide, water and saturated aqueous solution of sodium chloride and dried over anhydrous sodium sulfate. The solvent was distilled off under reduced pressure, and the residue was purified by column chromatography on silica gel (ethyl acetate:hexane=3:7) to obtain crude 3-chloro-2-fluorobenzaldehyde (5.5 g) as a pale yellow oil. Methanol (20 ml) was added to sodium hydride (content: 60%, 1.6 g) at 0° C. under an argon atmosphere, and the mixture was stirred for 10 minutes. The reaction mixture was cooled to −20° C., and the crude 3-chloro-2-fluorobenzaldehyde (5.5 g) and a solution of methyl 2-azidoacetate (5.0 g) in methanol (10 ml) were added within 20 minutes. The temperature of the reaction mixture was raised to 0° C., and after the mixture was stirred for 2.5 hours, water (40 ml) was added thereto. The reaction mixture was concentrated under reduced pressure, the residue was extracted with a mixed solvent of methylene chloride and ethyl acetate. The extract was washed with saturated aqueous solution of sodium chloride and dried over anhydrous sodium sulfate. The solvent was distilled off, and the residue was purified by column chromatography on silica gel (toluene:hexane=3:17) to obtain crude methyl 2-azido-3-[(3-chloro-2-fluoro)phenyl]acrylate (2.6 g). This product was dissolved in xylene (50 ml), and the solution was stirred at 130° C. to 140° C. for 3 hours. The reaction mixture was concentrated, and the resultant residue was purified by column chromatagraphy on silica gel (methylene chloride) and then crystallized from diethyl ether-hexane to obtain the title compound (440 mg).

$^1$H-NMR (DMSO-d$_6$) δ: 4.08 (3H, s), 7.20 (1H, s), 7.31-7.38 (2H, m). MS (FAB) m/z: 228 (M+H)$^+$.

Referential Example 274

5-Chloro-4-fluoroindole-2-carboxylic Acid

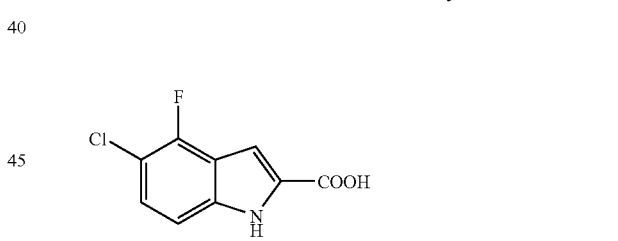

The compound (440 mg) obtained in Referential Example 273 was dissolved in tetrahydrofuran (10 ml), an aqueous solution (5 ml) of lithium hydroxide (160 mg) was added, and the mixture was stirred at room temperature for 3 hours. After an aqueous solution (5 ml) of lithium hydroxide (240 mg) was additionally added to the reaction mixture, and the mixture was stirred for additional 1 hour, the reaction mixture was concentrated under reduced pressure. The residue was neutralized with 1N hydrochloric acid and extracted 3 times with ethyl acetate. The resultant organic layers were combined, washed with saturated aqueous solution of sodium chloride and dried over anhydrous sodium sulfate. The solvent was distilled off under reduced pressure to obtain the title compound (390 mg).

$^1$H-NMR (DMSO-d$_6$) δ: 6.79 (1H, s), 7.16-7.26 (2H, m). MS (FAB) m/z: 214 (M+H)$^+$.

Referential Example 275

Ethyl 1-benzyl-5-chloroindole-2-carboxylate

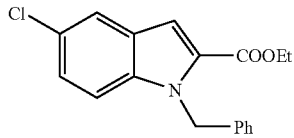

Ethyl 5-chloroindole-2-carboxylate (1.4 g) was dissolved in N,N-dimethylformamide (30 ml), and potassium carbonate (2.9 g) and benzyl chloride (2.4 ml) were added. The mixture was heated and stirred for 1.5 hours on a hot bath controlled to 100° C. The reaction mixture was concentrated under reduced pressure, and the residue was poured into ice water and extracted with ethyl acetate. The resultant organic layer was washed with saturated aqueous solution of sodium chloride and dried over anhydrous sodium sulfate. The solvent was distilled off, and the residue was purified by column chromatagraphy on silica gel (ethyl acetate:hexane=1:19) and crystallized from diethyl ether-hexane to obtain the title compound (1.6 g).

$^1$H-NMR (CDCl$_3$) δ: 1.36 (3H, t, J=7.1 Hz), 4.33 (2H, q, J=7.1 Hz), 5.83 (2H, s), 7.00-7.02 (2H, d), 7.20-7.38 (6H, m), 7.67 (1H, d, J=1.7 Hz).

Referential Example 276

Ethyl 1-benzyl-5-chloro-3-fluoroindole-2-carboxylate

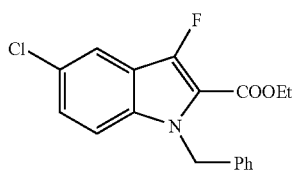

1-Fluoro-2,6-dichloropyridinium triflate (4.4 g) was added to a methylene chloride solution (30 ml) of the compound (2.2 g) obtained in Referential Example 275, and the mixtrue was heated under reflux for 3 days. The reaction mixture was partitioned in ethyl acetate and water, and a water layer was extracted with ethyl acetate. The resultant organic layers were combined, successively washed with 1N hydrochloric acid, water and saturated aqueous solution of sodium chloride and then dried over anhydrous sodium sulfate. The solvent was distilled off, and the residue was purified by column chromatography on silica gel (ethyl acetate:hexane=1:24) to obtain the crude title compound (2.8 g). A part of this product was purified by preparative thin-layer chromatography on silica gel to obtain the title compound.

$^1$H-NMR (DMSO-d$_6$) δ: 1.25 (3H, t, J=7.1 Hz), 4.29 (2H, q, J=7.1 Hz), 5.77 (2H, s), 6.97-6.99 (2H, m), 7.18-7.28 (3H, m), 7.39 (1H, dd, J=9.0, 2.1 Hz), 7.69 (1H, dd, J=9.0, 2.1 Hz), 7.78 (1H, d, J=2.1 Hz).

Referential Example 277

Ethyl 5-chloro-3-fluoroindole-2-carboxylate

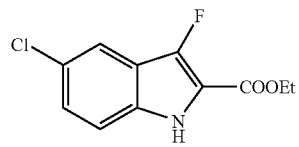

The crude compound (1.4 g) obtained in Referential Example 276 was dissolved in anisole (30 ml), and aluminum chloride (2.9 g) was added portionwise to the solution under ice cooling. The reaction mixture was stirred at room temperature for 30 minutes, and aluminum chloride (2.9 g) was additionally added to stir the mixture for 18 hours. Aluminum chloride (8.0 g) was added to the reaction mixture, and the mixture was stirred for 5 hours, to which water was added. The reaction mixture was extracted with ethyl acetate, the resultant organic layers were combined, successively washed with saturated aqueous solution of sodium hydrogencarbonate and saturated aqueous solution of sodium chloride and then dried over anhydrous sodium sulfate. The solvent was distilled off under reduced pressure, and the residue was purified by column chromatography on silica gel (methylene chloride) to obtain the title compound (470 mg).

$^1$H-NMR (CDCl$_3$) δ: 1.43 (3H, t, J=7.2 Hz), 4.45 (2H, q, J=7.2 Hz), 7.25-7.31 (2H, m), 7.66 (1H, d, J=0.73 Hz), 8.53 (1H, br.s). MS (FAB) m/z: 242 (M+H)$^+$.

Referential Example 278

5-Chloro-3-fluoroindole-2-carboxylic Acid

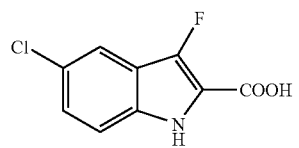

The title compound was obtained from the compound obtained in Referential Example 277 in a similar manner to Referential Example 274.

$^1$H-NMR (DMSO-d$_6$) δ: 7.31 (1H, dd, J=8.8, 1.9 Hz), 7.42 (1H, dd, J=8.8, 1.9 Hz), 7.70 (1H, d, J=1.9 Hz), 11.78 (1H, s). MS (FAB) m/z: 214 (M+H)$^+$.

Referential Example 279 tert-Butyl (1R,2S,5S)-{[(5-chloro-3-fluoroindol-2-yl)carbonyl]amino}-5-[(dimethylamino)carbonyl]cyclohexylcarbamate

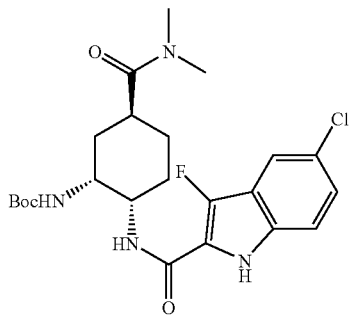

The title compound was obtained from the compound obtained in Referential Example 144 and the compound obtained in Referential Example 278 in a similar manner to Referential Example 97.

$^1$H-NMR (CDCl$_3$) δ: 1.45 (9H, s), 1.73-2.11 (6H, m), 2.65 (1H, br.s), 2.96 (3H, s), 3.07 (3H, s), 4.20 (1H, br.s), 4.28 (1H, br.s), 4.78 (1H, br), 7.23-7.30 (3H, m), 7.58 (1H, s), 9.03 (1H, s). MS (FAB) m/z: 481 (M+H)$^+$.

Referential Example 280

Ethyl 3-bromo-5-chloroindole-2-carboxylate

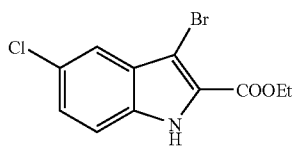

N-Bromosuccinimide (440 mg) was added to a solution of ethyl 5-chloroindole-2-carboxylate (500 mg) in N,N-dimethylformamide (10 ml). The reaction mixture was stirred at room temperature for 18 hours, and the solvent was distilled off under reduced pressure. The residue was partitioned in ethyl acetate and water, and a water layer was extracted with ethyl acetate. The resultant organic layers were combined, washed with saturated aqueous solution of sodium chloride and then dried over anhydrous sodium sulfate. The solvent was distilled off, the residue was purified by column chromatography on silica gel (ethyl acetate:hexane=1:9), and white powder thus obtained was washed with hexane to obtain the title compound (680 mg).

$^1$H-NMR (CDCl$_3$) δ: 1.42-1.48 (3H, m), 4.43-4.49 (2H, m), 7.30-7.32 (2H, m), 7.65 (1H, d, J=0.74 Hz), 9.11 (1H, s). MS (FAB) m/z: 303 (M+H)$^+$.

Referential Example 281

3-Bromo-5-chloroindole-2-carboxylic Acid

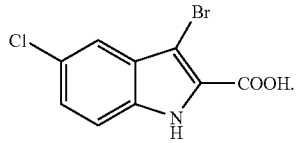

The title compound was obtained from the compound obtained in Referential Example 280 in a similar manner to Referential Example 274.

$^1$H-NMR (DMSO-d$_6$) δ: 7.35 (1H, dd, J=8.8, 2.0 Hz), 7.48-7.53 (2H, m), 12.33 (1H, s). MS (FAB) m/z: 275 (M+H)$^+$.

Referential Example 282 tert-Butyl (1R,2S,5S)-2-{[(3-bromo-5-chloroindol-2-yl)carbonyl]amino}-5-[(dimethylamino)carbonyl]cyclohexylcarbamate

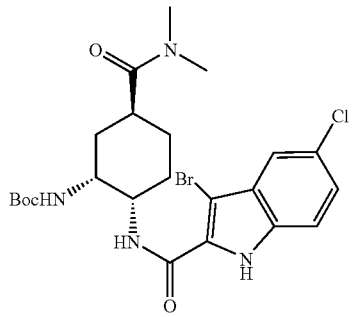

The title compound was obtained from the compound obtained in Referential Example 144 and the compound obtained in Referential Example 281 in a similar manner to Referential Example 97.

$^1$H-NMR (CDCl$_3$) δ: 1.42 (9H, s), 1.58-2.17 (6H, m), 2.70 (1H, br.s), 2.96 (3H, s), 3.07 (3H, s), 4.23-4.28 (2H, m), 4.83 (1H, br), 7.34-7.41 (3H, m), 7.52 (1H, s), 9.76 (1H, s). MS (FAB) m/z: 542 (M+H)$^+$.

Referential Example 283

Ethyl 3-chloro-5-fluoroindole-2-carboxylate

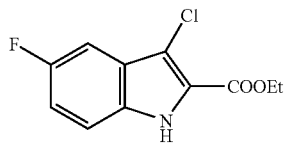

Ethyl 5-fluoroindole-2-carboxylate (2.0 g) was dissolved in N,N-dimethylformamide (20 ml), and a solution of N-chlorosuccinimide (1.4 g) in N,N-dimethylformamide (10 ml) was added dropwise to the solution under ice cooling.

The mixture was stirred at room temperature for 18 hours, and the reaction mixture was diluted with ethyl acetate and successively washed with a saturated aqueous solution of sodium hydrogencarbonate and saturated aqueous solution of sodium chloride. The resultant organic layer was then dried over anhydrous sodium sulfate, the solvent was distilled off under reduced pressure, and the residue was purified by column chromatography on silica gel (hexane:ethyl acetate=5:1) to obtain the title compound (1.9 g).

$^1$H-NMR (CDCl$_3$) δ: 1.45 (3H, t, J=7.4 Hz), 4.46 (2H, q, J=7.4 Hz), 7.14 (1H, dt, J=8.0, 2.7 Hz), 7.32-7.36 (2H, m), 8.91 (1H, br).

Referential Example 284

3-Chloro-5-fluoroindole-2-carboxylic Acid

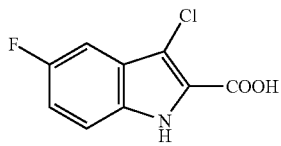

The title compound was obtained from the compound obtained in Referential Example 283 in a similar manner to Referential Example 274.

$^1$H-NMR (DMSO-d$_6$) δ: 7.20 (1H, dt, J=8.8, 2.4 Hz), 7.31 (1H, dd, J=8.8, 2.4 Hz), 7.46 (1H, dd, J=8.8, 4.4 Hz), 12.12 (1H, br).

Referential Example 285

Ethyl 5-chloro-3-formylindole-2-carboxylate

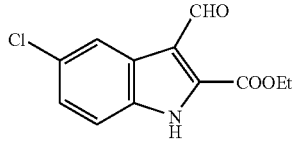

After phosphorus oxychloride (2.0 ml) was added to N-methylformanilide (2.9 g), and the mixture was stirred for 15 minutes, 1,2-dichloroethane (50 ml) and ethyl 5-chloroindole-2-carboxylate (4.0 g) were added, and the resultant mixture was heated under reflux for 1 hour. The reaction mixture was poured into an aqueous solution (28 ml) of sodium acetate (14 g) under ice cooling. After stirring for 18 hours, insoluble matter was collected by filtration. This product was successively washed with water and diethyl ether to obtain the title compound (3.56 g).

$^1$H-NMR (DMSO-d$_6$) δ: 1.38 (3H, t, J=7.1 Hz), 4.44 (2H, q, J=7.1 Hz), 7.38 (1H, dd, J=8.0, 1.4 Hz), 7.56 (1H, d, J=8.0 Hz), 8.19 (1H, d, J=1.4 Hz), 10.53 (1H, s).

Referential Example 286

5-Chloro-3-formylindole-2-carboxylic Acid

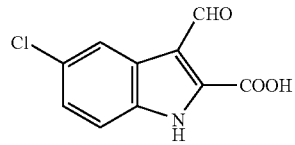

The compound (1.0 g) obtained in Referential Example 285 was dissolved in ethanol (10 ml), and a 1N aqueous solution (10 ml) of sodium hydroxide was added dropwise to stir the mixture at 50° C. for 2 hours. 1N Hydrochloric acid (11 ml) was added to the reaction mixture, the resultant mixture was stirred, and insoluble matter was collected by filtration to obtain the title compound (0.86 g).

$^1$H-NMR (DMSO-d$_6$) δ: 7.39 (1H, d, J=8.0 Hz), 7.55 (1H, d, J=8.0 Hz), 8.20 (1H, s), 10.58 (1H, s), 12.90 (1H, br).

Referential Example 287

5-Chloro-2-ethoxycarbonylindole-3-carboxylic Acid

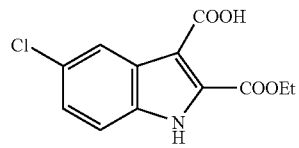

The compound (1.5 g) obtained in Referential Example 286 and sulfamic acid (1.7 g) were dissolved in tert-butanol (30 ml)-water (30 ml), and sodium chlorite (1.6 g) was added to stir the mixture for 8 hours. The reaction mixture was diluted with water and extracted with ethyl acetate, and the extract was successively washed with 1N hydrochloric acid and saturated aqueous solution of sodium chloride and dried over anhydrous sodium sulfate. The solvent was distilled off under reduced pressure, and the residue was recrystallized from a mixed solvent of isopropyl ether and hexane to obtain the title compound (0.7 g).

$^1$H-NMR (DMSO-d$_6$) δ: 1.34 (3H, t, J=7.1 Hz), 4.38 (2H, q, J=7.1 Hz), 7.33 (1H, dd, J=8.0, 1.4 Hz), 7.52 (1H, d, J=8.0 Hz), 7.97 (1H, d, J=1.4 Hz), 12.75 (1H, br).

Referential Example 288

Ethyl 5-chloro-3-[(dimethylamino)carbonyl]indole-2-carboxylate

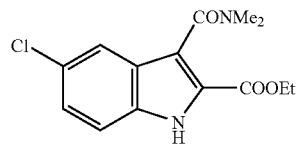

The compound (0.7 g) obtained in Referential Example 87 was dissolved in N,N-dimethylformamide (10 ml), and dimethylamine hydrochloride (0.26 g), 1-hydroxybenzotriazole monohydrate (0.43 g) and 1-(3-dimethylaminopropyl)-3-ethylcarbodiimide hydrochloride (1.0 g) were added to stir the mixture at room temperature for 2 days. After the reaction mixture was diluted with ethyl acetate and washed with 1N hydrochloric acid, a saturated aqueous solution of sodium hydrogencarbonate and saturated aqueous solution of sodium chloride in that order, the resultant organic layer was dried over anhydrous sodium sulfate. The solvent was distilled off under reduced pressure, and the residue was recrystallized from a mixed solvent of isopropyl ether and hexane to obtain the title compound (0.6 g).

$^1$H-NMR (DMSO-$d_6$) δ: 1.29 (3H, t, J=7.1 Hz), 2.78 (3H, s), 3.04 (3H, s), 4.30 (2H, q, J=7.1 Hz), 7.31 (1H, dd, J=8.0, 1.4 Hz), 7.45 (1H, d, J=1.4 Hz), 7.48 (1H, d, J=8.0 Hz), 12.29 (1H, s).

Referential Example 289

5-Chloro-3-[(dimethylamino)carbonyl]indole-2-carboxylic Acid

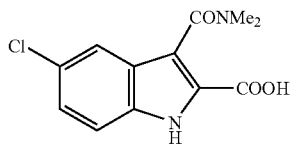

The title compound was obtained from the compound obtained in Referential Example 288 in a similar manner to Referential Example 286.

$^1$H-NMR (DMSO-$d_6$) δ: 2.91 (6H, s), 7.29 (1H, d, J=8.0 Hz), 7.44 (1H, d, J=8.0 Hz), 7.47 (1H, s), 12.16 (1H, s).

Referential Example 290

5-(Phenylsulfonyl)-5,6-dihydro-4H-pyrrolo[3,4-d]thiazole

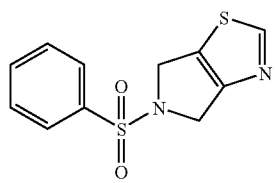

Benzenesulfonamide (638 mg) and 4,5-bis(bromomethyl)thiazole (M. Al. Hariri, O. Galley, F. Pautet, H. Fillion, Eur. J. Org. Chem., 1998, 593-594.) (1.10 g) were dissolved in N,N-dimethylformamide (10 ml), sodium hydride (60% in oil, 357 mg) was added at a time, and the mixture was stirred at room temperature for 3 hours. Water and methylene chloride were added to conduct liquid separation. After the resultant organic layer was dried over anhydrous sodium sulfate, the solvent was distilled off, and the residue was purified by column chromatography on silica gel (methylene chloride:ethyl acetate=9:1) to obtain the title compound (137 mg).

$^1$H-NMR (CDCl$_3$) δ: 4.60-4.63 (2H, m), 4.70-4.73 (2H, m), 7.52-7.64 (3H, m), 7.88-7.92 (2H, m), 8.71 (1H, s). MS (FAB) m/z: 267 (M+H)$^+$.

Referential Example 291

5,6-Dihydro-4H-pyrrolo[3,4-d]thiazole dihydrobromide

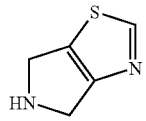

A mixture of the compound (800 mg) obtained in Referential Example 290, phenol (800 μl) and 47% hydrobromic acid (5.00 ml) was heated under reflux for 2 hours. After the reaction mixture was cooled to room temperature, ethyl acetate and water were added to conduct liquid separation. The resultant water layer was concentrated under reduced pressure. Ethyl acetate was added to the residue, precipitate was collected by filtration to obtain the title compound (521 mg).

$^1$H-NMR (DMSO-$d_6$) δ: 4.42 (2H, br.s), 4.56 (2H, br.s), 9.14 (1H, s). MS (FAB) m/z: 127 (M+H)$^+$.

Referential Example 292

5-Methyl-5,6-dihydro-4H-pyrrolo[3,4-d]thiazole

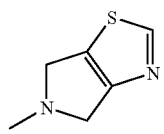

The title compound was obtained from the compound obtained in Referential Example 291 in a similar manner to Referential Example 9.

$^1$H-NMR (CDCl$_3$) δ: 2.67 (3H, s), 3.95-3.99 (2H, m), 4.01-4.05 (2H, m), 8.69 (1H, s). MS (ESI) m/z: 141 (M+H)$^+$.

Referential Example 293

Lithium 5-methyl-5,6-dihydro-4H-pyrrolo[3,4-d]thiazole-2-carboxylate

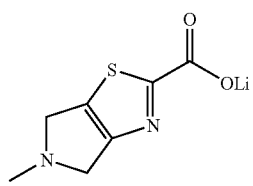

The title compound was obtained from the compound obtained in Referential Example 292 in a similar manner to Referential Example 5.

$^1$H-NMR (DMSO-$d_6$) δ: 2.52 (3H, s), 3.73 (2H, t, J=3.2 Hz), 3.87 (2H, t, J=3.2 Hz).

Referential Example 294 tert-Butyl (1R,2S,5S)-2-[(6-chloro-2-naphthoyl)amino]-5-[(dimethylamino)carbonyl]cyclohexylcarbamate

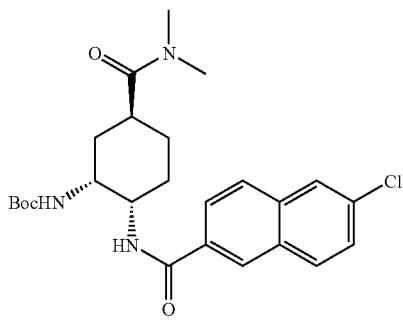

The title compound was obtained from the compound obtained in Referential Example 144 and 6-chloronaphthalene-2-carboxylic acid (Eur. J. Chem-Chim. Ther., 1984, Vol. 19, pp. 205-214) in a similar manner to Referential Example 97.

$^1$H-NMR (CDCl$_3$) δ: 1.30-2.00 (15H, m), 2.60-2.80 (1H, m), 2.96 (3H, s), 3.09 (3H, s), 4.00-4.20 (1H, m), 4.20-4.30 (1H, m), 4.75-4.95 (1H, m), 7.44 (1H, d, J=9.0 Hz), 7.70-7.95 (5H, m), 8.31 (1H, s). MS (FAB) m/z: 474 (M+H)$^+$.

Referential Example 295

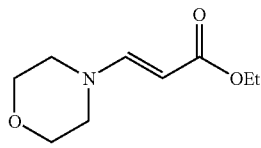

Ethyl (E)-3-(morpholin-4-yl)-2-acrylate

Ethyl propionate (2.0 ml) was dissolved in methylene chloride (20 ml), and morpholine (1.70 ml) was added dropwise under ice cooling. After stirring at room temperature for 1 hour, the reaction mixture was concentrated under reduced pressure, and the residue was purified by column chromatagraphy on silica gel (methylene chloride:methanol=20:1) to obtain the title compound (3.72 g).

$^1$H-NMR (CDCl$_3$) δ: 1.26 (3H, t, J=7.1 Hz), 3.21 (4H, t, J=5.1 Hz), 3.71 (4H, t, J=5.1 Hz), 4.14 (2H, q, J=7.1 Hz), 4.70 (1H, d, J=13.4 Hz), 7.36 (1H, d, J=13.4 Hz). MS (FAB) m/z: 186 (M+H)$^+$.

Referential Example 296

3-Chlorobenzenediazonium Tetrafluoroborate

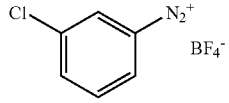

3-Chloroaniline (2.0 g) was dissolved in a mixed solvent of water (30 ml) and concentrated hydrochloric acid (3.5 ml), and sodium nitrite (1.30 g) was added under ice cooling to stir the mixture for 10 minutes. After concentrated hydrochloric acid (5.3 ml) and sodium tetrafluoroborate (6.90 g) were added to the reaction mixture to stir the mixture for 30 minutes under ice cooling, precipitate was collected by filtration and washed with water, methanol and diethyl ether to obtain the title compound (2.63 g). This compound was used in the next reaction as it was.

Referential Example 297

Ethyl 7-chlorocinnoline-3-carboxylate

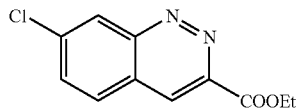

The compound (1.45 g) obtained in Referential Example 295 was dissolved in acetonitrile (100 ml), and the compound (1.73 g) obtained in Referential Example 296 was added. After stirred at room temperature for 1 hour, the mixture was heated under reflux for 7 days. The solvent was distilled off under reduced pressure, and the residue was purified by column chromatagraphy on silica gel (methylene chloride→methylene chloride:ethyl acetate=10:1, then, hexane:ethyl acetate=4:1→1:1) to obtain the title compound (0.25 g).

$^1$H-NMR (CDCl$_3$) δ: 1.53 (3H, t, J=7.1 Hz), 4.62 (2H, q, J=7.1 Hz), 7.80 (1H, dd, J=8.8, 2.0 Hz), 7.95 (1H, d, J=8.8 Hz), 8.64 (1H, s), 8.68 (1H, d, J=2.0 Hz).

Referential Example 298

7-Chlorocinnoline-3-carboxylic Acid

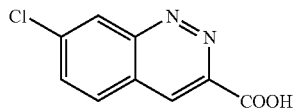

The title compound was obtained from the compound obtained in Referential Example 297 in a similar manner to Referential Example 286.

$^1$H-NMR (DMSO-d$_6$) δ: 8.02 (1H, dd, J=8.8, 2.0 Hz), 8.34 (1H, d, J=8.8 Hz), 8.70 (1H, s), 8.90 (1H, s). MS (FAB) m/z: 209 (M+H)$^+$.

Referential Example 299 tert-Butyl (1R,2S,5S)-2-{[(7-chlorocinnolin-3-yl)carbonyl]-amino}-5-[(dimethylamino)carbonyl]cyclohexylcarbamate

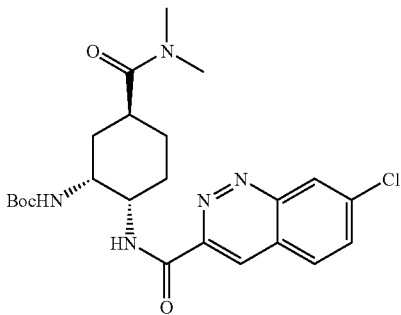

The title compound was obtained from the compound obtained in Referential Example 144 and the compound obtained in Referential Example 298 in a similar manner to Referential Example 97.

$^1$H-NMR (CDCl$_3$) δ: 1.36 (9H, s), 1.80-2.20 (5H, m), 2.72 (1H, m), 2.96 (3H, s), 3.07 (3H, s), 3.49 (1H, d, J=3.7 Hz), 4.30-4.45 (2H, m), 4.87 (1H, br), 7.77 (1H, dd, J=8.8, 2.0 Hz), 7.96 (1H, d, J=8.8 Hz), 8.59 (2H, br), 8.72 (1H, s). MS (FAB) m/z: 476 (M+H)$^+$.

Referential Example 300 tert-Butyl (1R,2S,5S)-2-[([(5-chloro-1H-benzimidazol-2-yl)carbonyl]amino}-5-[(dimethylamino)carbonyl]cyclohexylcarbamate

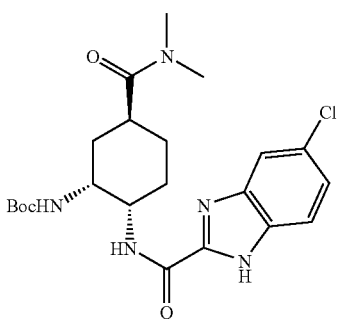

10% Palladium on carbon (50 mg) was added to a solution of the compound (235 mg) obtained in Referential Example 143 in tetrahydrofuran (5.0 ml), and the mixture was stirred overnight at room temperature under a hydrogen atmosphere. To a solution of the product obtained by filtering the reaction mixture and concentrating the filtrate and 5-chlorobenzimidazole-2-carboxylic acid (Bull. Chem. Soc. Jpn., Vol. 62, p. 2668, 1989) (165 mg) in N,N-dimethylformamide (5.0 ml) were added 1-hydroxybenzotriazole monohydrate (100 mg) and 1-(3-dimethylaminopropyl)-3-ethylcarbodiimide hydrochloride (171 mg) at room temperature, and the mixture was stirred for 4 days. After concentrating the reaction mixture, methylene chloride, a saturated aqueous solution of sodium hydrogencarbonate and water were added to conduct liquid separation, and the resultant water layer was extracted with methylene chloride. After the resultant organic layers were combined and dried over anhydrous sodium sulfate, the solvent was distilled off under reduced pressure. The residue was purified by flash column chromatagraphy on silica gel (methylene chloride:methanol=10:1) to obtain the title compound (250 mg).

$^1$H-NMR (DMSO-d$_6$) δ: 1.01-2.00 (6H, m), 1.34 (9H, s), 2.79 (3H, s), 2.80-2.95 (1H, m), 2.98 (3H, s), 3.89-4.06 (2H, m), 7.08 (1H, d, J=6.6 Hz), 7.31 (1H, d, J=8.5 Hz), 7.62 (2H, br.s), 8.47 (1H, d, J=8.5 Hz), 13.46 (1H, br.s). MS (ESI) m/z: 466 (M+H)$^+$.

Referential Example 301

Methyl 3-(4-fluorophenyl)-2-{[(4-methylphenyl)sulfonyl]-amino]propionate

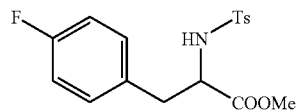

Methyl 2-amino-3-(4-fluorophenyl)propionate (2.01 g), p-toluenesulfonyl chloride (2.25 g) and 4-dimethylaminopyridine (309 mg) were dissolved in chloroform (30 ml), and pyridine (3.0 ml) was added to heat the mixture under reflux for 4.5 hours. P-Toluenesulfonyl chloride (2.20 g) was additionally added, and the mixture was heated under reflux for 3.5 hours. The reaction mixture was poured into ice and 1N hydrochloric acid (17 ml) to conduct liquid separation. The resultant organic layer was successively washed with a saturated aqueous solution of sodium hydrogencarbonate and saturated aqueous solution of sodium chloride and dried over anhydrous sodium sulfate. The solvent was distilled off under reduced pressure, and the residue was purified by column chromatography on silica gel (hexane:ethyl acetate 9:1→2:1) to obtain the title compound (2.89 g).

$^1$H-NMR (CDCl$_3$) δ: 2.41 (3H, s), 2.90-3.10 (2H, m), 3.51 (3H, s), 4.10-4.20 (1H, m), 5.04 (1H, d, J=9.0 Hz), 6.85-6.95 (2H, m), 7.00-7.10 (2H, m), 7.20-7.30 (2H, m), 7.60-7.70 (2H, m). MS (ESI) m/z: 352 (M+H)$^+$.

Referential Example 302

Methyl 7-fluoro-2-[(4-methylphenyl)sulfonyl]-1,2,3,4-tetrahydroisoquinoline-3-carboxylate

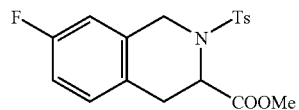

The compound (1.50 g) obtained in Referential Example 301 and paraformaldehyde (207 mg) were dissolved in chloroform (40 ml), and the system was purged with argon. Trifluoroborane-diethyl ether complex (1.20 ml) was then added, and the mixture was stirred at room temperature for 7.5 hours. The reaction mixture was poured into ice and a saturated aqueous solution of sodium hydrogencarbonate to conduct liquid separation. The resultant organic layer was then dried over anhydrous sodium sulfate. The solvent was distilled off under reduced pressure, and the residue was purified by column chromatagraphy on silica gel (hexane:ethyl acetate=3:1) to obtain the title compound (1.45 g).

$^1$H-NMR (CDCl$_3$) δ: 2.42 (3H, s), 3.15 (2H, d, J=3.9 Hz), 3.46 (3H, s), 4.45 (1H, d, J=15.9 Hz), 4.69 (1H, d, J=15.9 Hz), 5.0 (1H, t, J=4.4 Hz), 6.70-6.80 (1H, m), 6.80-6.90 (1H, m), 7.00-7.10 (1H, m), 7.29 (2H, d, J=8.1 Hz), 7.72 (2H, d, J=8.3 Hz). MS (ESI) m/z: 364 (M+H)$^+$.

Referential Example 303

Methyl 7-fluoroisoquinoline-3-carboxylate

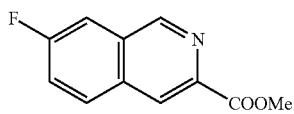

The compound (1.45 g) obtained in Referential Example 302 was dissolved in N,N-dimethylformamide (40 ml). Oxygen was introduced into this solution, and the solution was stirred at 100° C. for 3.5 hours. After the reaction mixture was concentrated under reduced pressure, and a saturated aqueous solution of sodium hydrogencarbonate and methylene chloride were added to the residue to conduct liquid separation, the resultant organic layer was succesively washed with a 10% aqueous solution of citric acid and saturated aqueous solution of sodium chloride and dried over anhydrous sodium sulfate. The solvent was distilled off under reduced pressure, and the residue was purified by column chromatography on silica gel (hexane:ethyl acetate=1:1) to obtain the title compound (0.59 g).

$^1$H-NMR (CDCl$_3$) δ: 4.07 (3H, s), 7.55-7.65 (1H, m), 7.65-7.75 (1H, m), 8.00-8.05 (1H, m), 8.61 (1H, s), 9.30 (1H, s). MS (ESI) m/z: 206 (M+H)$^+$.

Referential Example 304

7-Fluoroisoquinoline-3-carboxylic Hydrochloride

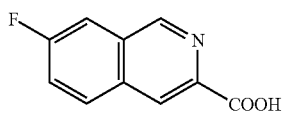

The compound (1.45 g) obtained in Referential Example 303 was dissolved in concentrated hydrochloric acid (18 ml), and the solution was heat under reflux for 2.5 hours. The reaction mixture was cooled, and crystals were collected by filtration, washed with water and then dried to obtain the title compound (0.46 g).

$^1$H-NMR (DMSO-d$_6$) δ: 7.90-8.00 (1H, m), 8.15-8.25 (1H, m), 8.40-8.50 (1H, m), 8.82 (1H, s), 9.55 (1H, s). MS (FAB) m/z: 192 (M+H)$^+$.

Referential Example 305

Ethyl 7-chloro-2H-chromene-3-carboxylate

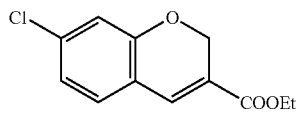

4-Chloro-2-hydroxybenzaldehyde (Acta. Chem. Scand., Vol. 53, p. 258, 1999) (510 mg) was dissolved in tetrahydrofuran (40 ml), sodium hydride (60% in oil, 157 mg) was added, and the mixture was stirred at room temperature for 2 hours. A tetrahydrofuran solution (10 ml) of ethyl 2-diethylphosphonoacrylate (J. Org. Chem., Vol. 43, P. 1256, 1978) (769 mg) was added to the reaction mixture, and the resultant mixture was stirred at room temperature for 2 hours and then heated overnight under reflux. After the reaction mixture was cooled to room temperature, water and diethyl ether were added to conduct liquid separation. After the resultant organic layer was dried over anhydrous sodium sulfate, the solvent was distilled off under reduced pressure, and the residue was purified by column chromatography on silica gel (hexane:ethyl acetate=10:1) to obtain the title compound (247 mg).

$^1$H-NMR (DMSO-d$_6$) δ: 1.33 (3H, t, J=7.1 Hz), 4.27 (2H, q, J=7.1 Hz), 4.99 (2H, d, J=1.2 Hz), 6.85 (1H, d, J=1.2 Hz), 6.89 (1H, dd, J=8.1, 2.0 Hz), 7.04 (1H, d, J=8.1 Hz), 7.38 (1H, d, J=1.0 Hz). MS (EI) m/z: 238 (M$^+$).

Referential Example 306

7-Chloro-2H-chromene-3-carboxylic Acid

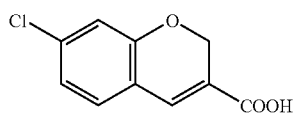

The title compound was obtained from the compound obtained in Referential Example 305 in a similar manner to Referential Example 274.

$^1$H-NMR (DMSO-d$_6$) δ: 4.92 (1H, d, J=2.0 Hz), 6.95 (1H, d, J=2.0 Hz) 7.01 (1H, dd, J=8.1, 2.2 Hz), 7.35 (1H, d, J=8.1 Hz), 7.44 (1H, s). MS (EI) m/z: 210 M$^+$.

Referential Example 307 tert-Butyl (1R,2S,5S)-2-{[(E)-3-(4-chlorophenyl)-2-propenoyl]amino}-5-[(dimethylamino)carbonyl]cyclohexylcarbamate

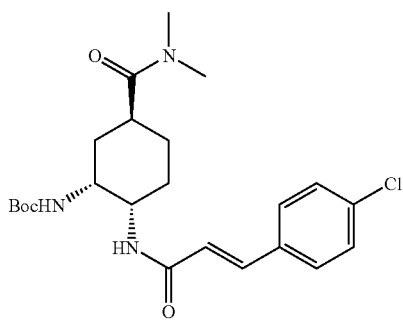

The title compound was obtained from the compound obtained in Referential Example 144 and 4-chlorocinnamic acid in a similar manner to Referential Example 97.

$^1$H-NMR (CDCl$_3$) δ: 1.30-1.55 (3H, m), 1.48 (9H, s), 1.60-2.30 (4H, m), 2.57-2.70 (1H, m), 2.95 (3H, s), 3.06 (3H, s), 4.01 (1H, br s), 4.10-4.20 (1H, m), 4.78 (1H, br.s), 6.30 (1H, d, J=15.6 Hz), 7.02 (1H, s), 7.31 (2H, d, J=8.5 Hz), 7.40 (2H, d, J=8.5 Hz), 7.52 (1H, d, J=15.6 Hz). MS (ESI) m/z: 450 (M+H)$^+$.

Referential Example 308

Methyl 6-chloro-4-oxo-1,4-dihydroquinoline-2-carboxylate

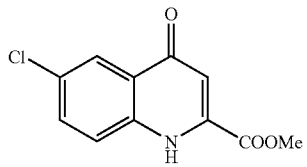

Dimethyl acetylenedicarboxylate (13.5 ml) was added to a solution of 4-chloroaniline (12.76 g) in methanol (150 ml), and the mixture was heated under reflux for 8 hours. The reaction mixture was concentrated under reduced pressure, the residue was dissolved in diphenyl ether (70 ml), and the solution was heated under reflux at 240° C. for 4 hours. After cooling the reaction mixture, a mixed solvent of hexane and diethyl ether was added, and crystals deposited were collected by filtration and washed to obtain the title compound (11.09 g).

$^1$H-NMR (DMSO-d$_6$) δ: 3.97 (3H, s), 7.76 (1H, dd, J=9.0, 2.5 Hz), 7.90-8.05 (2H, m), 12.28 (1H, br.s). MS (ESI) m/z: 238 (M+H)$^+$.

Referential Example 309

6-Chloro-4-oxo-1,4-dihydroquinoline-2-carboxylic Acid

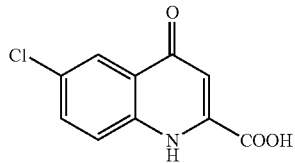

The title compound was obtained from the compound obtained in Referential Example 308 in a similar manner to Referential Example 286.

$^1$H-NMR (DMSO-d$_6$) δ: 6.90-7.05 (1H, m), 7.90-8.05 (2H, m), 10.10-10.30 (1H, m), 12.13 (1H, br.s). MS (ESI) m/z: 224 (M+H)$^+$.

Referential Example 310 tert-Butyl (1R,2S,5S)-2-{[(5-chloroindol-2-yl)carbonyl]-amino}-5-[(dimethylamino)carbonyl]cyclohexylcarbamate

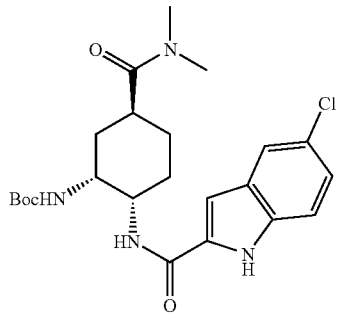

Water (10 ml) and lithium hydroxide (263 mg) were added to a solution of the compound (5.00 g) obtained in Referential Example 97 in tetrahydrofuran (40 ml), and the mixture was stirred overnight at room temperature. The reaction mixture was filtered, the filtrate was concentrated, and 1-hydroxybenzotriazole monohydrate (1.75 g), 1-(3-dimethylaminopropyl)-3-ethylcarbodiimide hydrochloride (3.32 g) and diisopropylethylamine (11.3 ml) were added to a solution of the resultant residue and dimethylamine hydrochloride (1.85 g) in N,N-dimethylformamide (100 ml) at room temperature. The resultant mixture was stirred for 2 days. After concentrating the reaction mixture, methylene chloride, a saturated aqueous solution of sodium hydrogencarbonate and water were added to conduct liquid separation. The resultant water layer was extracted with methylene chloride. The organic layers were combined and dried over anhydrous sodium sulfate, and the solvent was then distilled off under reduced pressure. The residue was purified by column chromatography on silica gel (methylene chloride: acetone=2:1→1:1) to obtain the title compound (4.59 g).

$^1$H-NMR (CDCl$_3$) δ: 1.60-1.76 (2H, m), 1.73 (9H, s), 1.76-1.87 (1H, m), 1.93 (1H, br.s), 2.14 (1H, br.s), 2.28 (1H, br.s), 2.65 (1H, br.s), 2.95 (3H, s), 3.05 (3H, s), 4.01 (1H, br.s), 4.21 (1H, br.s), 4.84 (1H, br.s), 6.81 (1H, br.s), 7.20

Referential Example 311 tert-Butyl (1R,2S,5S)-2-{[(5-fluoroindol-2-yl)carbonyl]amino}-5-[(dimethylamino)carbonyl]cyclohexylcarbamate

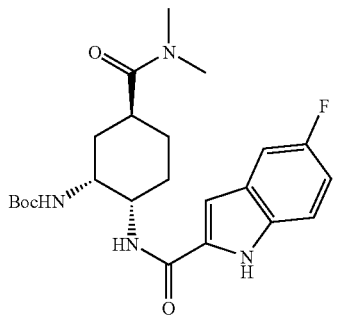

1) Ethyl (1S,3R,4S)-3-[(tert-butoxycarbonyl)amino]-4-{[(5-fluoroindol-2-yl)carbonyl]amino}-cyclohexanecarboxylate was obtained from the compound obtained in Referential Example 96 and 5-fluoroindole-2-carboxylic acid in a similar manner to Referential Example 91.

$^1$H-NMR (CDCl$_3$) δ: 1.26 (3H, t, J=7.1 Hz), 1.52 (9H, s), 1.67-2.41 (7H, m), 3.97 (1H, br.s), 4.15 (2H, q, J=7.1 Hz), 4.08-4.22 (1H, m), 6.83 (1H, s), 7.00-7.05 (1H, m), 7.32-7.36 (1H, m), 8.02 (1H, s), 9.51 (1H, s). MS (FAB) m/z: 448 (M+H)$^+$.

2) The title compound was obtained from the compound obtained above in a similar manner to Referential Example 310.

$^1$H-NMR (CDCl$_3$) δ: 1.52 (9H, s), 1.57-1.79 (2H, m), 1.79-2.00 (2H, m), 2.14 (1H, br.s), 2.31 (1H, br.s), 2.65 (1H, br.s), 2.95 (3H, s), 3.07 (3H, s), 4.02 (1H, br.s), 4.17-4.25 (1H, m), 4.80 (1H, br.s), 6.82 (1H, br.s), 7.02 (1H, dt, J=2.3, 9.0 Hz), 7.24 (1H, br.s), 7.35 (1H, dd, J=9.0, 4.3 Hz), 7.91 (1H, br.s), 9.49 (1H, br.s). MS (FAB) m/z: 447 (M+H)$^+$.

Referential Example 312

Ethyl 2-amino-6,6-dimethyl-6,7-dihydrothiazolo[4,5-c]pyridine-5(4H)-carboxylate

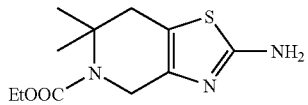

After copper(I) cyanide (918 mg) was suspended in tetrahydrofuran (50 ml) under an argon atmosphere, and the suspension was cooled to −20° C., n-butyllithium (1.56 N hexane solution, 6.41 ml) was added dropwise over 5 minutes, and the mixture was stirred at −20° C. for 30 minutes. After the reaction mixture was cooled to −50° C., diisobutylaluminum hydride (1.00 M hexane solution) was added dropwise over 20 minutes, and the mixture was stirred at −50° C. for 1 hour. A solution of ethyl 2,2-dimethyl-5-oxo-5,6-dihydro-2H-pyridine-1-carboxylate (Helv. Chim. Acta, Vol. 81, p. 303, 1998) (986 mg) in tetrahydrofuran (5 ml) was added dropwise to the reaction mixture over 5 minutes, and the mixture was stirred at −50° C. for 2 hours. After raising the temperature of the reaction mixture to −20°, bromine (4.90 ml) was added at a time, and the mixture was stirred at −20° C. for 30 minutes. Water and ethyl acetate were added to the reaction mixture to conduct liquid separation. The resultant organic layer was washed with a saturated aqueous solution of sodium sulfite and dried over anhydrous sodium sulfate. The solvent was distilled off under reduced pressure, and the residue was dissolved in N,N-dimethylformamide (10 ml), thiourea (760 mg) was added, and the mixture was stirred overnight at 50° C. After the solvent was distilled off, methylene chloride and a saturated aqueous solution of sodium hydrogencarbonate were added to conduct liquid separation. The resultant organic layer was dried over anhydrous sodium sulfate, and the solvent was distilled off. The residue was purified by column chromatography on silica gel (ethyl acetate:hexane=4:1) to obtain the title compound (412 mg).

$^1$H-NMR (CDCl$_3$) δ: 1.25 (3H, t, J=7.1 Hz), 1.54 (6H, s), 2.65-2.67 (2H, m), 4.09 (2H, q, J=7.1 Hz), 4.44-4.46 (2H, m), 4.78 (2H, br.s).

Referential Example 313

Ethyl 2-bromo-6,6-dimethyl-6,7-dihydrothiazolo[4,5-c]-pyridine-5(4H)-carboxylate

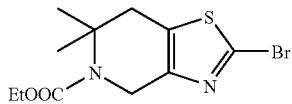

Copper(II) bromide (431 mg) was suspended in acetonitrile (8 ml), and tert-butyl nitrite (249 mg) was added dropwise at room temperature. After an acetonitrile solution (8 ml) of the compound (412 mg) obtained in Referential Example 312 was added to the reaction mixture under ice cooling, the mixture was heated to 50° C. and stirred for 15 minutes. The solvent was distilled off under reduced pressure, and diethyl ether and 10% hydrochloric acid were added to the residue to conduct liquid separation. The resultant organic layer was dried over anhydrous magnesium sulfate and concentrated under reduced pressure. The residue was purified by column chromatography on silica gel (hexane:ethyl acetate=6:1) to obtain the title compound (151 mg).

$^1$H-NMR (CDCl$_3$) δ: 1.26 (3H, t, J=7.1 Hz), 1.55 (6H, s), 2.79-2.81 (2H, m), 4.10 (2H, q, J=7.1 Hz), 4.65-4.67 (2H, m). MS (ESI) m/z: 319 (M+H)$^+$.

Referential Example 314

Ethyl 6,6-dimethyl-6,7-dihydrothiazolo[4,5-c]-pyridine-5(4H)-carboxylate

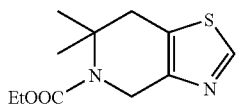

n-Butyllithium (1.56N hexane solution, 1.04 ml) was added to a solution with the compound (432 mg) obtained in Referential Example 313 in diethyl ether (5 ml) at −78° C., and the mixture was stirred at −78° C. for 30 minutes. Water and diethyl ether were added to the reaction mixture to conduct liquid separation. The resultant organic layer was dried over anhydrous magnesium sulfate, and the solvent was distilled off to obtain the title compound (307 mg).

$^1$H-NMR (CDCl$_3$) δ: 1.28 (3H, t, J=7.1 Hz), 1.55 (6H, s), 2.90 (2H, s), 4.12 (2H, q, J=7.1 Hz), 4.75 (2H, m), 8.63 (1H, s).

Referential Example 315

6,6-Dimethyl-4,5,6,7-tetrahydrothiazolo[4,5-c]pyridine

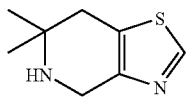

The compound (307 mg) obtained in Referential Example 314 was dissolved in a mixed solvent of water (5 ml), ethanol (5 ml) and dioxane (5 ml), and lithium hydroxide (598 mg) was added to this reaction mixture to heat the mixture under reflux for 7 days. After allowing the reaction mixture to cool to room temperature, water and methylene chloride were added to conduct liquid separation. The resultant water layer was extracted 6 times with methylene chloride. The resultant organic layers were dried over anhydrous sodium sulfate, and the solvent was distilled off to obtain the title compound (207 mg).

$^1$H-NMR (CDCl$_3$) δ: 1.23 (6H, s), 2.71-2.73 (2H, m), 4.09-4.11 (2H, m), 8.61 (1H, s). MS (ESI) m/z: 168 (M$^+$).

Referential Example 316 tert-Butyl 6,6-dimethyl-6,7-dihydrothiazolo[4,5-c]pyridine-5(4H)-carboxylate

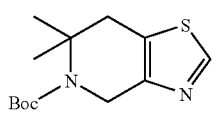

The compound (207 mg) obtained in Referential Example 315 was dissolved in methylene chloride (5 ml), and di-tert-butyl dicarbonate (404 mg) and 4-(N, N-dimethylamino)pyridine (151 mg) were added to stir the mixture at room temperature for 2 hours. Di-tert-butyl dicarbonate (404 mg) was additionally added, and the mixture was stirred overnight at room temperature. Further, di-tert-butyl dicarbonate (1.00 g) was added, and the mixture was stirred for 1 hour. Methylene chloride and 10% hydrochloric acid were added to conduct liquid separation. The resultant organic layer was dried over anhydrous sodium sulfate, and the solvent was distilled off. The residue was purified by column chromatagraphy on silica gel (hexane:ethyl acetate=4:1) to obtain the title compound (95.4 mg).

$^1$H-NMR (CDCl$_3$) δ: 1.47 (9H, s), 1.52 (6H, s), 2.87 (2H, s), 4.69 (2H, s), 8.62 (1H, s). MS (ESI) m/z: 269 (M+H)$^+$.

Referential Example 317

Lithium 4-chloro-5-(1,3-dioxolan-2-yl)thiazole-2-carboxylate

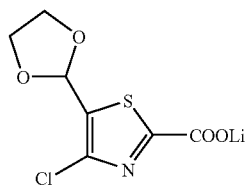

2,4-Dichlorothiazole-5-carbaldehyde ethyleneacetal (J. Chem. Soc. Perkin Trans. 1, 1992, p. 973) (2.26 g) was dissolved in tetrahydrofuran (15 ml), and n-butyllithium (1.5N hexane solution, 6.8 ml) was added under cooling with dry ice-acetone to stir the mixture for 20 minutes. At the same temperature, carbon dioxide was then introduced. The reaction mixture was gradually heated to room temperature over 1.5 hours and then concentrated. Hexane was added to the reaction mixture to powder the product. The product was collected by filtration and suspended in ethyl acetate, and formed powder was collected again by filtration to obtain the title compound (1.65 g).

Referential Example 318

Ethyl 4-chloro-5-(1,3-dioxolan-2-yl)thiazole-2-carboxylate

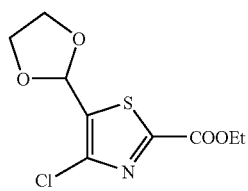

The compound (242 mg) obtained in Referential Example 317 and ethanol (0.2 ml) were dissolved in N, N-dimethylformamide (2 ml), and 1-hydroxybenzotriazole monohydrate (136 mg) and 1-(3-dimethylaminopropyl)-3-ethylcarbodiimide hydrochloride (250 mg) were added to stir the mixture at room temperature for a night. The solvent was distilled off under reduced pressure, and diethyl ether and diluted hydrochloric acid were added to separate an organic layer. The organic layer was washed with water and a saturated aqueous solution of sodium hydrogencarbonate and dried over anhydrous magnesium sulfate. The solvent was distilled off under reduced pressure to obtain the title compound (170 mg).

$^1$H-NMR (CDCl$_3$) δ: 1.43 (3H, t, J=7.3 Hz), 4.00-4.10 (2H, m), 4.10-4.20 (2H, m), 4.48 (2H, q, J=7.3 Hz), 6.15 (1H, s). MS (ESI) m/z: 264 (M+H)$^+$.

Referential Example 319

Ethyl 4-chloro-5-formylthiazole-2-carboxylate

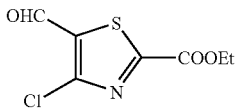

The compound (132 mg) obtained in Referential Example 318 was dissolved in diethyl ether (5 ml), and 20% hydrochloric acid (0.3 ml) was added to stir the mixture at room temperature for 7 hours. A saturated aqueous solution of sodium hydrogencarbonate was added to the reaction mixture to conduct extraction with diethyl ether. The extract was dried over anhydrous magnesium sulfate, and the solvent was distilled off under reduced pressure to obtain the title compound (110 mg).

$^1$H-NMR (CDCl$_3$) δ: 1.46 (3H, t, J=7.1 Hz), 4.52 (2H, q, J=7.1 Hz), 10.12 (1H, s).

Referential Example 320

Ethyl 4-azido-5-formylthiazole-2-carboxylate

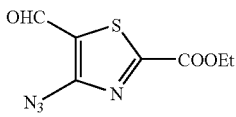

The compound (5.15 g) obtained in Referential Example 319 was dissolved in dimethyl sulfoxide (30 ml), and sodium azide (1.52 g) was added to stir the mixture at room temperature for 2.5 hours. Ice water was added to the reaction mixture to conduct extraction with diethyl ether. The extract was washed twice with water and then dried over anhydrous magnesium sulfate. The solvent was distilled off under reduced pressure, and the residue was purified by column chromatography on silica gel (methylene chloride:methanol=24:1) to obtain the title compound (1.78 g).

$^1$H-NMR (CDCl$_3$) δ: 1.45 (3H, t, J=7.1 Hz), 4.50 (2H, q, J=7.1 Hz), 9.95 (1H, s).

Referential Example 321

Ethyl 6-methyl-6,7-dihydrothiazolo[4,5-d]pyrimidine-2-carboxylate

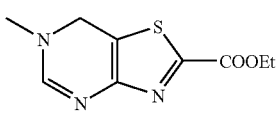

The compound (1.56 g) obtained in Referential Example 320 was dissolved in methylene chloride (20 ml), and acetic acid (2 ml), methylamine (2N tetrahydrofuran solution, 21 ml) and sodium triacetoxyborohydride (2.98 g) were added to stir the mixture. After 1 hour, sodium triacetoxyborohydride (2.98 g) was additionally added, and the stirring was continued for additional 4.5 hours. A 0.5N aqueous solution (100 ml) of sodium hydroxide was added to the reaction mixture to alkalify it. After the reaction mixture was extracted with methylene chloride, the extract was dried over anhydrous magnesium sulfate. The solvent was distilled off under reduced pressure to obtain a brown oil (1.43 g). This oil was dissolved in ethanol (50 ml), 10% palladium on carbon (2.0 g) was added to conduct hydrogenation at normal temperature and pressure. After 2.5 hours, the catalyst was removed by filtration, and the filtrate was concentrated. The residue was dissolved in methylene chloride (30 ml), and trimethyl orthoformate (0.7 ml) and boron trifluoride-diethyl ether complex (0.3 ml) were added to stir the mixture at room temperature for 15 hours. A saturated aqueous solution of sodium hydrogencarbonate was added to the reaction mixture to conduct extraction with methylene chloride. The extract was dried over anhydrous sodium sulfate. The solvent was distilled off under reduced pressure, and the residue was purified by column chromatagraphy on silica gel (methylene chloride:methanol=97:3) to obtain the title compound (100 mg).

$^1$H-NMR (CDCl$_3$) δ: 1.41 (3H, t, J=7.1 Hz), 2.95 (3H, s), 4.44 (2H, q, J=7.1 Hz), 4.87 (2H, s), 7.06 (1H, s). MS (ESI) m/z: 226 (M+H)$^+$.

Referential Example 322

Lithium 6-methyl-6,7-dihydrothiazolo[4,5-d]pyrimidine-2-carboxylate

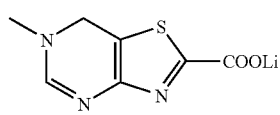

The compound (463 mg) was dissolved in tetrahydrofuran (20 ml), and lithium hydroxide (54.1 mg) and water (4 ml) were added to stir the mixture at room temperature for 4.5 hours. The solvent was distilled off under reduced pressure, and the residue was dried by means of a vacuum pump to obtain the title compound (460 mg).

$^1$H-NMR (DMSO-d$_6$) δ: 2.86 (3H, s), 4.71 (2H, s), 7.03 (1H, s).

Referential Example 323 tert-Butyl (1R,2S,5S)-2-azido-5-{[ethyl(methyl)amino]-carbonyl}cyclohexylcarbamate

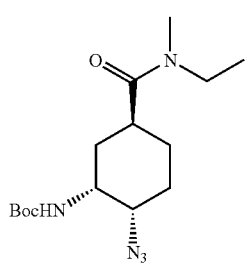

The title compound was obtained by condensing the compound obtained in Referential Example 250 with ethylmethylamine.

$^1$H-NMR (CDCl$_3$) δ: 1.08, 1.18 (total 3H, each t, J=7.1 Hz), 1.46 (9H, s), 1.52-1.80 (4H, m), 2.04-2.08 (2H, m), 2.71-2.77 (1H, m), 2.89, 2.98 (total 3H, each s), 3.32, 3.39 (total 2H, each q, J=7.1 Hz), 3.74-3.76 (1H, m), 4.09-4.11 (1H, m), 4.60 (1H, br.s). MS (EI) m/z: 326 (M+H)$^+$.

Referential Example 324 tert-Butyl (1R,2S,5S)-2-{[(7-chloroisoquinolin-3-yl)carbonyl]amino}-5-{[ethyl(methyl)amino]carbonyl}-cyclohexylcarbamate

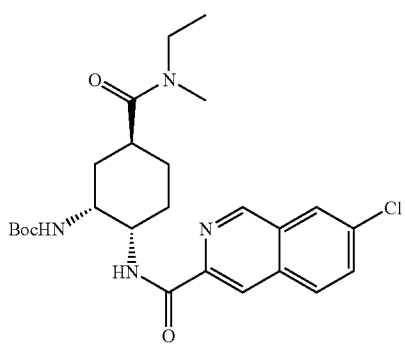

The compound (1.44 g) obtained in Referential Example 323 was dissolved in methanol (20 ml), 10% palladium on carbon (150 mg) was added, and the mixture was stirred under a hydrogen atmosphere. After 24 hours, the catalyst was removed by filtration, and the solvent was then concentrated under reduced pressure to obtain a colorless oil. This oil was used in the next reaction as it is.

The above-obtained oil was dissolved in methylene chloride (30 ml), and the compound (850 mg) obtained in Referential Example 57, 1-ethyl-3-(3-dimethylaminopropyl)carbodiimide hydrochloride (1.27 g), 1-hydroxybenzotriazole monohydrate (900 mg) and N-methylmorpholine (1.34 g) were added to stir the mixture at room temperature. After 17 hours, methylene chloride and a saturated aqueous solution of sodium hydrogencarbonate were added to the reaction mixture to conduct liquid separation, and the resultant organic layer was dried over anhydrous magnesium sulfate. The solvent was disilled off under reduced pressure, and the residue was subjected to column chromatagraphy on silica gel (methanol:methylene chloride=1:50) to obtain the title compound (1.61 g).

$^1$H-NMR (CDCl$_3$) δ: 1.10, 1.22 (total 3H, each t, J=7.1 Hz), 1.43 (9H, s), 1.84-2.17 (6H, m), 2.66 (1H, br.s), 2.92, 3.03 (total 3H, each s), 3.35-3.44 (2H, m), 4.20-4.30 (2H, m), 5.30 (1H, br.s), 7.70 (1H, d, J=8.6 Hz), 7.92 (1H, d, J=8.6 Hz), 8.00 (1H, s), 8.40 (1H, br.s), 8.56 (1H, s), 9.03 (1H, s). MS (FAB) m/z: 489 (M+H)$^+$.

Referential Example 325

N-((1S,2R,4S)-2-Amino-4-[(7-chloroisoquinolin-3-yl)carbonyl]-4-{[ethyl(methyl)amino]carbonyl}cyclohexyl)-7-chloroisoquinoline-3-carboxamide

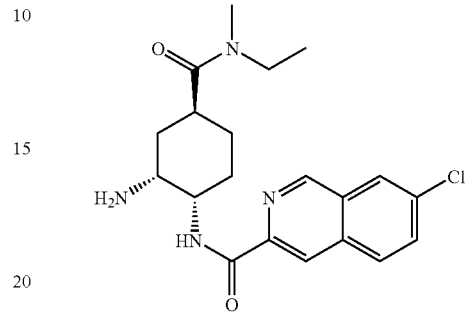

The compound (1.60 g) obtained in Referential Example 324 was dissolved in an ethanol solution (25 ml) of hydrochloric acid, and the solution was stirred at room temperature for 30 minutes. The solvent was distilled off under reduced pressure, and methylene chloride and a 1N aqueous solution of sodium hydroxide were added to the residue to conduct liquid separation. The resultant water layer was extracted with methylene chloride, and organic layers were combined and dried over potassium carbonate. The solvent was distilled off under reduced pressure, hexane was added to the residue, and precipitate was collected by filtration to obtain the title compound (1.22 g).

$^1$H-NMR (DMSO-d$_6$) δ: 1.10, 1.23 (total 3H, each t, J=7.1 Hz), 1.26 (2H, br.s), 1.69-2.11 (6H, m), 2.89 (1H, br.s), 2.93, 3.05 (total 3H, each s), 3.38-3.45 (2H, m), 3.52 (1H, s), 4.18 (1H, br.s), 7.70 (1H, dd, J=8.8, 2.0 Hz), 7.94 (1H, d, J=8.8 Hz), 8.02 (1H, d, J=2.0 Hz), 8.50 (1H, br.s), 8.59 (1H, s), 9.11 (1H, s). MS (FAB) m/z: 389 (M+H)$^+$.

Referential Example 326

Ethyl (1R*,3S*,4S*)-3-[(tert-butoxycarbonyl)amino]-4-{[tert-butyl(diphenyl)silyl]oxy}cyclohexanecarboxylate

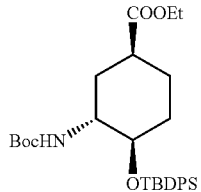

The compound (28.0 g) obtained in Referential Example 88 was dissolved in N,N-dimethylformamide (500 ml), and tert-butyldiphenylsilyl chloride (63.5 ml) and imidazole (19.9 g) were added. After the mixture was stirred at room temperature for 10 hours, ethyl acetate and water were added to the reaction mixture to conduct liquid separation. The resultant water layer was extracted with ethyl acetate, and organic layers were combined, washed twice with water and dried over anhydrous sodium sulfate. After the solvent was distilled off under reduced pressure, the residue was purified by column chromatography on silica gel (methylene chloride:methanol=1:0→47:3) to obtain the title compound (52.5 g) containing 0.4 molecules of N,N-dimethylformamide.

$^1$H-NMR (CDCl$_3$) δ: 1.07 (9H, s), 1.27 (3H, t, J=7.1 Hz), 1.38 (9H, s), 1.43-1.59 (3H, m), 1.63-1.67 (1H, m), 1.92-1.98 (1H, m), 2.25-2.32 (1H, m), 2.37-2.42 (1H, m), 3.66 (1H, br.s), 3.80 (1H, br.s), 4.16 (2H, q, J=7.1 Hz), 4.32 (1H, d, J=8.1 Hz), 7.34-7.46 (6H, m), 7.65-7.73 (4H, m).

Referential Example 327 tert-Butyl (1R*,2R*,5S*)-2-{[tert-butyl(diphenyl)silyl]-oxy}-5-(hydroxymethyl)cyclohexanecarbmate

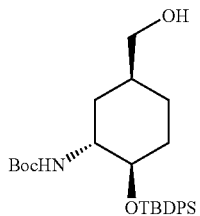

Lithium aluminum hydride (7.11 g) was suspended in absolute diethyl ether (100 ml) at 0° C. while purging with argon, and a diethyl ether solution (500 ml) of the compound (52.5 g) obtained in Referential Example 326 was added dropwise over 30 minutes. After stirring at 0° C. for 30 minutes, methanol (100 ml) was added dropwise to the reaction mixture. The resultant slurry was removed by filtration through Celite, and the filtrate was concentrated. The residue was purified by column chromatagraphy on silica gel (hexane:ethyl acetate=3:1) to obtain the title compound (29.6 g).

$^1$H-NMR (CDCl$_3$) δ: 1.07 (9H, s), 1.32-1.74 (16H, m), 1.87 (1H, t, J=10.4 Hz), 3.35-3.55 (2H, m), 3.71 (1H, br.s), 3.79 (1H, br.s), 4.36 (1H, br.s), 7.34-7.44 (6H, m), 7.65-7.72 (4H, m).

Referential Example 328

((1R*,3S*,4S*)-3-[(tert-Butoxycarbonyl)amino]-4-{[tert-butyl(diphenyl)silyl]oxy}cyclohexyl)methyl methanesulfonate

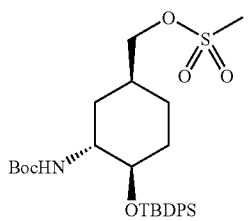

The compound (29.5 g) obtained in Referential Example 327 was dissolved in methylene chloride (200 ml) and pyridine (20 ml), and methanesulfonyl chloride (9.5 ml) was added to stir the mixture at room temperature for 6 hours. The solvent was distilled off under reduced pressure, and ethyl acetate and water were added to the residue to conduct liquid separation. The resultant water layer was extracted with ethyl acetate, and organic layers were combined, washed twice with water and then dried over anhydrous sodium sulfate. The solvent was distilled off under reduced pressure, and the residue was purified by column chromatography on silica gel (hexane:ethyl acetate=2:1) to obtain the title compound (29.8 g).

$^1$H-NMR (CDCl$_3$) δ: 1.08 (9H, s), 1.38 (9H, s), 1.43-1.61 (5H, m), 1.86-1.89 (2H, m), 3.02 (3H, s), 3.77 (1H, br.s), 3.81 (1H, br.s), 4.10 (2H, d, J=5.4 Hz), 4.32 (1H, br.s), 7.35-7.45 (6H, m), 7.64-7.68 (4H, m). MS (ESI) m/z: 562 (M+H)$^+$.

Referential Example 329 tert-Butyl (1R*,2R*,5S*)-2-{[tert-butyl(diphenyl)silyl]-oxy}-5-(cyanomethyl)cyclohexanecarbamate

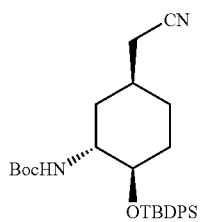

The compound (29.8 g) obtained in Referential Example 328 was dissolved in N,N-dimethylformamide (400 ml), and sodium cyanide (3.64 g) was added to stir the mixture at 80° C. for 11 hours. Ethyl acetate and a saturated aqueous solution of sodium hydrogencarbonate were added to the reaction mixture to conduct liquid separation. The resultant water layer was extracted twice with ethyl acetate, and organic layers were combined, washed with a saturated aqueous solution of sodium hydrogencarbonate and saturated aqueous solution of sodium chloride and then dried over anhydrous sodium sulfate. The solvent was distilled off under reduced pressure, and the residue was purified by column chromatagraphy on silica gel (hexane:ethyl acetate=5:1) to obtain the title compound (20.6 g).

$^1$H-NMR (CDCl$_3$) δ: 1.08 (9H, s), 1.38 (9H, s), 1.43-1.68 (5H, m), 1.79-1.85 (1H, m), 1.88-1.95 (1H, m), 2.32 (2H, d, J=7.1 Hz), 3.77 (1H, br.s), 3.82 (1H, br.s), 4.32 (1H, br.d, J=6.8 Hz), 7.35-7.45 (6H, m), 7.65-7.71 (4H, m).

Referential Example 330 tert-Butyl (1R*,2R*,5S*)-2-{[tert-butyl(diphenyl)silyl]-oxy}-5-(2-oxoethyl)cyclohexanecarbamate

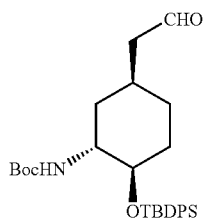

The compound (2.00 g) obtained in Referential Example 329 was dissolved in absolute methylene chloride (20 ml), and the system was purged with argon and then cooled to −78° C. To the solution, was added dropwise diisobutyla-luminum hydride (0.95 M hexane solution, 8.55 ml). The temperature of the mixture was then allowed to raise to room temperature and stirred for 3 hours. The reaction mixture was cooled to 0° C., and methanol (10 ml) was added dropwise. The resultant slurry was removed by filtration through Celite, and the filtrate was concentrated under reduced pressure. The residue was purified by column chromatography on silica gel (methylene chloride:methanol=1:0→49:1) to obtain the title compound (1.45 g).

$^1$H-NMR (CDCl$_3$) δ: 1.07 (9H, s), 1.38 (9H, s), 1.43-1.54 (5H, m), 1.82-1.88 (1H, m), 2.06 (1H, br.s), 2.42-2.43 (2H, m), 3.72 (1H, br.s), 3.77 (1H, br.s), 4.38 (1H, br.s), 7.34-7.44 (6H, m), 7.65-7.68 (4H, m), 9.77 (1H, t, J=1.7 Hz). MS (FAB) m/z: 496 (M+H)$^+$.

Referential Example 331

2-((1R*,3S*,4S*)-3-[(tert-Butoxycarbonyl)amino]-4-{[tert-butyl(diphenyl)silyl]oxy}cyclohexyl)acetic Acid

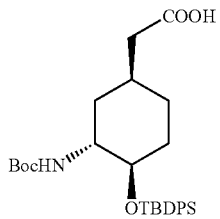

The compound (8.40 g) obtained in Referential Example 330 was dissolved in a mixed solvent of water (33 ml) and tert-butanol (120 ml), and 2-methyl-2-butene (8.08 ml), sodium dihydrogenphosphate dihydrate (2.64 g) and sodium chlorite (3.45 g) were added to stir the mixture at room temperature for 1.5 hours. Methylene chloride and water were added to the reaction mixture to dilute it. The resultant water layer was adjusted to pH of about 4 with 1N hydrochloric acid. Liquid separation was conducted, and the resultant water layer was extracted twice with methylene chloride. Organic layers were combined and dried over anhydrous magnesium sulfate, and the solvent was distilled off under reduced pressure. The residue was purified by column chromatagraphy on silica gel (hexane:ethyl acetate=2:1→1:1) to obtain the title compound (7.62 g).

$^1$H-NMR (CDCl$_3$) δ: 1.07 (9H, s), 1.22-1.63 (15H, m), 1.82 (1H, br.s), 2.17 (1H, br.s), 2.27-2.33 (1H, m), 3.69 (1H, br.s), 3.84 (1H, br.s), 7.00 (1H, br.s), 7.33-7.42 (6H, m), 7.63-7.65 (4H, m). MS (ESI) m/z: 512 (M+H)$^+$.

Referential Example 332 tert-Butyl (1R*,2R*,5S*)-2-{[tert-butyl(diphenyl) silyl]-oxy}-5-[2-(dimethylamino)-2-oxoethyl]cyclo-hexanecarbamate

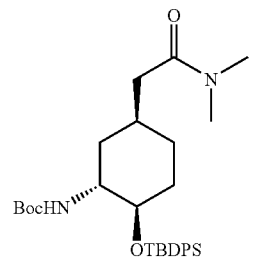

The compound (7.62 g) obtained in Referential Example 331 was dissolved in N,N-dimethylformamide (150 ml), and dimethylamine hydrochloride (6.07 g), 1-(3-dimethylaminopropyl)-3-ethylcarbodiimide hydrochloride (8.56 g), 1-hydroxybenzotriazole monohydrate (1.01 g) and triethylamine (10.3 ml) were added to stir the mixture at room temperature for 4 days. The solvent was distilled off under reduced pressure, and methylene chloride and a saturated aqueous solution of sodium hydrogencarbonate were added to the residue to conduct liquid separation. The resultant organic layer was extracted with methylene chloride, and organic layers were combined and dried over anhydrous sodium sulfate. The solvent was distilled off under reduced pressure, and the residue was purified by column chromatography on silica gel (hexane:ethyl acetate=1:1). The solvent was distilled off, hexane was added to the residue, and formed white precipitate was collected by filtration to obtain the title compound (6.42 g).

$^1$H-NMR (CDCl$_3$) δ: 1.08 (9H, s), 1.38 (9H, br.s), 1.43-1.55 (5H, m), 1.79-1.86 (1H, m), 2.03 (1H, br.s), 2.21-2.32 (2H, s), 2.94 (3H, s), 3.03 (3H, s), 3.74 (1H, br.s), 3.80 (1H, br.s), 4.49 (1H, br.s), 7.33-7.44 (6H, m), 7.64-7.69 (4H, m). MS (ESI) m/z: 539 (M+H)$^+$.

Referential Example 333 tert-Butyl (1R*,2R*,5S*)-5-[2-(dimethylamino)-2-oxoethyl]-2-hydroxycyclohexanecarbamate

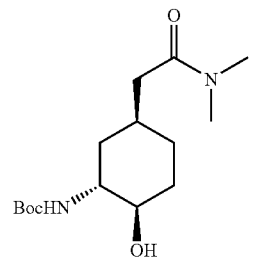

The compound (6.36 g) obtained in Referential Example 332 was dissolved in tetrahydrofuran (50 ml), and tetrabutylammonium fluoride (1N tetrahydrofuran solution, 17.85 ml) was added to stir the mixture at room temperature for 13 hours. The solvent was distilled off under reduced pressure, and the residue was purified by flash column chromatagraphy on silica gel (methylene chloride:methanol=24:1) to obtain the title compound (3.49 g).

$^1$H-NMR (CDCl$_3$) δ: 1.44 (9H, s), 1.46-1.60 (4H, m), 1.79-1.84 (2H, m), 2.28-2.35 (3H, s), 2.82 (1H, br.s), 2.95 (3H, s), 3.01 (3H, s), 3.56 (2H, br.s), 4.67 (1H, br.s). MS (ESI) m/z: 301 (M+H)$^+$.

Referential Example 334

((1R*,2R*,4S*)-2-[(tert-Butoxycarbonyl)amino]-4-[2-(dimethylamino)-2-oxoethyl]cyclohexyl methanesulfonate

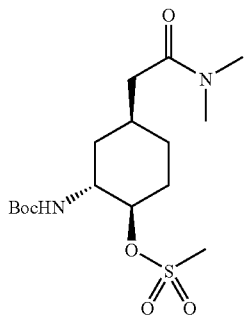

The compound (8.05 mg) obtained in Referential Example 333 was dissolved in methylene chloride (50 ml), and the solution was cooled to −78° C. under an argon atmosphere to add dropwise methanesulfonyl chloride (2.70 ml). After the temperature of the mixture was allowed to raise to 0° C. and stirred for 30 minutes, it was stirred at room temperature for 2 hours. Water was added to the reaction mixture to conduct liquid separation, and the resultant water layer was extracted with methylene chloride. Organic layers were combined, washed with water and dried over anhydrous sodium sulfate. The solvent was distilled off under reduced pressure, and the residue was purified by flash column chromatagraphy on silica gel (hexane:ethyl acetate=1:1→0:1) to obtain the title compound (3.63 g).

$^1$H-NMR (CDCl$_3$) δ: 1.43 (9H, s), 1.59-1.74 (4H, m), 1.85-2.30 (5H, m), 2.95 (3H, s), 3.00 (3H, s), 3.10 (3H, s), 3.79-3.83 (1H, m), 4.72 (1H, br.s), 4.91 (1H, br.s). MS (ESI) m/z: 379 (M+H)$^+$.

Referential Example 335 tert-Butyl (1R*,2S*,5S*)-2-azido-5-[2-(dimethylamino)-2-oxoethyl]cyclohexanecarbamate

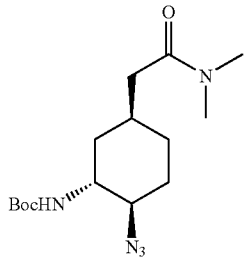

The compound (3.62 g) obtained in Referential Example 334 was dissolved in N,N-dimethylformamide (20 ml), and sodium azide (3.11 g) was added to stir the mixture at 75° C. for 17 hours. The reaction mixture was poured into a mixed solvent of water and ethyl acetate to conduct liquid separation. The resultant water layer was extracted twice with ethyl acetate, and organic layers were combined, washed with water, a saturated aqueous solution of sodium hydrogencarbonate and saturated aqueous solution of sodium chloride and dried over anhydrous sodium sulfate. The solvent was distilled off under reduced pressure, and the residue was purified by flash column chromatography on silica gel (ethyl acetate) to obtain the title compound (1.30 g).

$^1$H-NMR (CDCl$_3$) δ: 1.14-1.21 (1H, m), 1.33-1.40 (1H, m), 1.45 (9H, s), 1.61-1.71 (1H, m), 1.78-1.91 (3H, m), 2.22-2.27 (3H, m), 2.94 (3H, s), 3.00 (3H, s), 3.60-3.62 (1H, m), 3.97 (1H, br.s), 4.76 (1H, br.s). MS (ESI) m/z: 326 (M+H)$^+$.

Referential Example 336

N-{(1R*,2S*,4R*)-2-Amino-4-[2-(dimethylamino)-2-oxoethyl]-cyclohexyl}-5-chloroindole-2-carboxamide hydrochloride

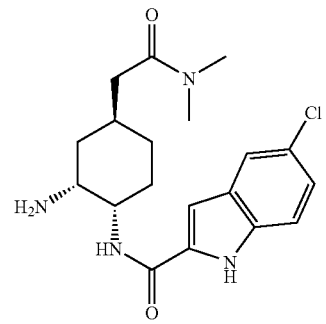

The title compound was obtained by treating, in a similar manner to Referential Example 69, a product obtained by catalytically reducing the compound obtained in Referential Example 335 in a similar manner to Referential Example 324 and then condensing it with 5-chloroindole-2-carboxylic acid.

$^1$H-NMR (DMSO-d$_6$) δ: 1.16-1.19 (1H, m), 1.51-1.56 (1H, m), 1.70-1.73 (1H, m), 1.81-1.91 (2H, m), 1.99-2.03 (1H, m), 2.19-2.30 (3H, m), 2.83 (3H, s), 2.99 (3H, s), 3.63 (1H, br.s), 4.08 (1H, br.s), 7.19 (1H, dd, J=8.7, 1.7 Hz), 7.35 (1H, s), 7.44 (1H, d, J=8.7 Hz), 7.69 (1H, d, J=1.7 Hz), 8.22 (3H, br.s), 8.62 (1H, d, J=7.1 Hz), 11.91 (1H, s). MS (ESI) m/z: 377 (M+H)$^+$.

Referential Example 337 tert-Butyl (1R,2S,5S)-2-{[(5-chloroindol-2-yl)carbonyl]-amino}-5-(hydroxymethyl)cyclohexanecarbamate

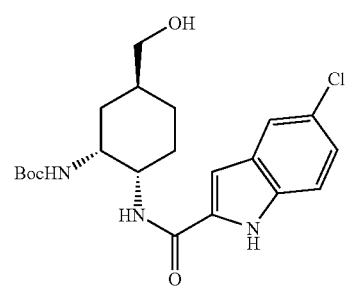

The title compound was obtained from the compound obtained in Referential Example 97 in a similar manner to step 2) of Referential Example 129.

Referential Example 338

((1S,3R,4S)-3-[(tert-butoxycarbonyl)amino]-4-{[(5-chloroindol-2-yl)carbonyl]amino}cyclohexyl)methyl methanesulfonate

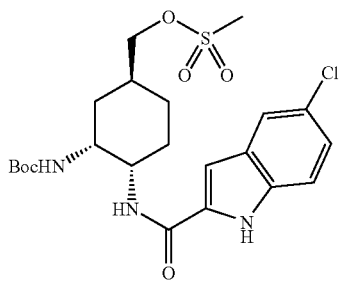

The compound (500 mg) obtained in Referential Example 337 and triethylamine (329 ml) were suspended in tetrahydrofuran (8 ml)-methylene chloride (8 ml), and the suspension was cooled to −78° C. After methanesulfonyl chloride (138 ml) was added dropwise to the suspension, the temperature of the suspension was gradually raised to −5° C., and the suspension was stirred for 15 hours at the same temperature. After the reaction mixture was concentrated, water was added to the residue to conduct extraction 3 times with methylene chloride. The resultant organic layers were washed with saturated aqueous solution of sodium chloride and dried over anhydrous sodium sulfate, and the solvent was then distilled off under reduced pressure to obtain the title compound (654 mg).

$^1$H-NMR (CDCl$_3$) δ: 1.57 (9H, s), 1.84-2.01 (4H, m), 2.28-2.31 (1H, m), 3.04 (3H, s), 3.68 (1H, s), 3.74-3.75 (1H, m), 3.91-3.93 (1H, m), 4.02-4.12 (2H, m), 4.18-4.20 (1H, m), 4.85 (1H, br.s), 6.81 (1H, s), 7.21 (1H, dd, J=2.0, 8.8 Hz), 7.34 (1H, d, J=8.8 Hz), 7.60 (1H, s), 8.02 (1H, br.s), 9.27 (1H, br.s). MS (ESI) m/z: 500 (M+H)$^+$.

Referential Example 339 tert-Butyl (1R,2S,5S)-2-[([(5-chloroindol-2-yl)carbonyl]-amino}-5-[(methylsulfanyl)methyl]cyclohexanecarbamate

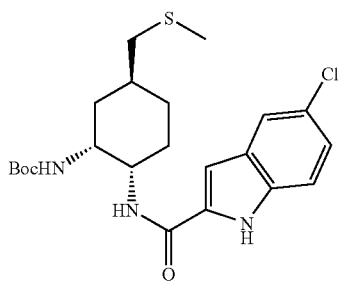

The compound (654 mg) obtained in Referential Example 338 was dissolved in N,N-dimethylformamide (8 ml), and a 15% aqueous solution (1.8 ml) of sodium thiomethoxide was added to stir the mixture at room temperature for 4 hours. The reaction mixture was poured into water and extracted 3 times with ethyl acetate. The resultant organic layers were washed with saturated aqueous solution of sodium chloride, dried over anhydrous sodium sulfate and then concentrated. The residue was purified by column chromatagraphy on silica gel (methylene chloride:methanol=24:1) to obtain the title compound (492 mg).

$^1$H-NMR (CDCl$_3$) δ: 1.52 (9H, s), 1.87-3.04 (13H, m), 3.91-3.94 (1H, m), 4.12-4.15 (1H, m), 4.95 (1H, br.s), 6.81 (1H, s), 7.19 (1H, dd, J=8.8, 1.2 Hz), 7.35 (1H, d, J=8.8 Hz), 7.57 (1H, s), 9.82 (1H, br.s). MS (ESI) m/z: 452 (M+H)$^+$.

Referential Example 340 tert-Butyl (1R,2S,5S)-2-{[(5-chloroindol-2-yl)carbonyl]-amino}-5-[(methylsulfonyl)methyl]cyclohexanecarbamate

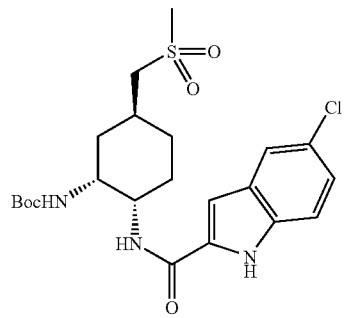

The compound (300 mg) obtained in Referential Example 339 was dissolved in methylene chloride (10 ml), and m-chloroperbenzoic acid (70%, 400 mg) was added at 0° C. under stirring. After stirring was continued for 1 hour as it is, the reaction mixture was poured into water and extracted 3 times with ethyl acetate. The resultant organic layers were washed with saturated aqueous solution of sodium chloride, dried over anhydrous sodium sulfate and then concentrated. After the residue was purified by column chromatagraphy on silica gel (methylene chloride:methanol=24:1), liquid separation was conducted with a saturated aqueous solution of sodium hydrogencarbonate and ethyl acetate, and the resultant organic layer was concentrated to obtain the title compound (254 mg).

$^1$H-NMR (CDCl$_3$) δ: 1.44-2.19 (13H, m), 2.22-2.30 (2H, m), 2.89-3.25 (7H, m), 3.93-4.15 (2H, m), 4.98 (1H, br.s), 6.82 (1H, s), 7.21 (1H, dd, J=8.8, 2.0 Hz), 7.34 (1H, d, J=8.8 Hz), 7.60 (1H, br.s), 9.54 (1H, br.s).

Referential Example 341

(5-Chlorothien-3-yl)methanol

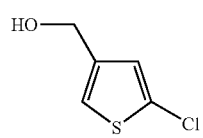

5-Chlorothiophene-3-carboxylic acid (Monatsh. Chem., Vol. 120, p. 53, 1989) (6.93 g) was dissolved in tetrahydrofuran (750 ml), and triethylamine (27.3 ml) and ethyl chloroformate (18.7 ml) were added to stir the mixture at room temperature for 2.5 hours. An aqueous solution (41 ml) of sodium borohydride (19.3 g) was added dropwise over 10 minutes, and the mixture was stirred at room temperature for 18.5 hours. After acetic acid was added to the reaction mixture to acidify it, the solvent was distilled off under reduced pressure. Water and methylene chloride were added to the residue to conduct liquid separation. The resultant organic layer was washed with water and a saturated aqueous solution of sodium hydrogencarbonate. After drying the organic layer, the solvent was distilled off under reduced pressure. The residue was purified by flash column chromatagraphy on silica gel (ethyl acetate:hexane=1:4) to obtain the title compound (5.17 g).

$^1$H-NMR (CDCl$_3$) δ: 1.63 (1H, t, J=5.8 Hz), 4.59 (2H, d, J=5.3 Hz), 6.91 (1H, d, J=1.7 Hz), 6.98-6.99 (1H, m).

Referential Example 342

5-Chlorothiophene-3-carbaldehyde

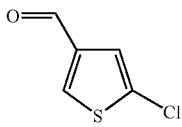

The compound (5.17 g) obtained in Referential Example 341 was dissolved in methylene chloride (400 ml), and manganese dioxide (51.3 g) was added to stir the mixture at room temperature for 15 hours. After the reaction mixture was filtered, the solvent was distilled off under reduced pressure to obtain the title compound (2.84 g).

$^1$H-NMR (CDCl$_3$) δ: 7.35 (1H, d, J=1.7 Hz), 7.88 (1H, d, J=1.7 Hz), 9.75 (1H, s).

Referential Example 343

Ethyl 2-azido-3-(5-chlorothien-3-yl)acrylate

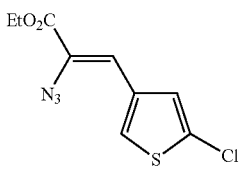

After ethanol (15 ml) was added to a 20% ethanol solution (10.7 ml) of sodium ethoxide, and the mixture was cooled to 0° C., a mixture of the compound (1.01 g) obtained in Referential Example 342 and ethyl azidoacetate (3.55 g) was added dropwise over 30 minutes, and the resultant mixture was stirred at 0° C. for 3 hours. A cooled aqueous solution of ammonium chloride was added to the reaction mixture to conduct extraction 3 times with diethyl ether. Organic layers were combined, and the solvent was distilled off under reduced pressure. The residue was purified by flach column chromatagraphy on silica gel (ethyl acetate:hexane=1:49) to obtain the title compound (1.04 g).

$^1$H-NMR (CDCl$_3$) δ: 1.38 (3H, t, J=7.1 Hz), 4.34 (2H, q, J=7.1 Hz), 6.75 (1H, s), 7.39 (1H, d, J=1.7 Hz), 7.54 (1H, d, J=1.7 Hz).

Referential Example 344

Ethyl 2-chloro-6H-thieno[2,3-b]pyrrole-5-carboxylate

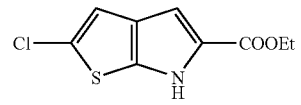

The compound (0.97 g) obtained in Referential Example 343 was dissolved in xylene (20 ml), and the solution was heated under reflux for 30 minutes. After allowing the reaction mixture to cool, the solvent was distilled off under reduced pressure. Hexane was added to the residue, solids formed were collected by filtration to obtain the title compound (0.608 g).

$^1$H-NMR (CDCl$_3$) δ: 1.38 (3H, t, J=7.0 Hz), 4.35 (2H, q, J=7.0 Hz), 6.90 (1H, s), 7.00 (1H, d, J=1.9 Hz), 9.32 (1H, br).

Referential Example 345

2-Chloro-6H-thieno[2,3-b]pyrrole-5-carboxylic Acid

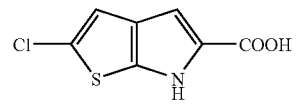

The title compound was obtained from the compound obtained in Referential Example 344 in a similar manner to Referential Example 274.

$^1$H-NMR (CD$_3$OD) δ: 3.35 (1H, s), 6.94 (1H, s), 6.96 (1H, s). MS (ESI) m/z: 200 (M−H)$^-$.

Referential Example 346

1-Chloro-4-(2,2-dibromovinyl)benzene

4-Chlorobenzaldehyde (2.81 g) was dissolved in methylene chloride (300 ml), and carbon tetrabromide (13.3 g) and triphenylphosphine (21.0 g) were added to stir the mixture at room temperature for 90 minutes. After insoluble matter deposited was removed by filtration, the filtrate was concentrated under reduced pressure. The residue was purified by column chromatography on silica gel (hexane:ethyl acetate=20:1) to obtain the title compound (5.54 g).

$^1$H-NMR (CDCl$_3$) δ: 7.33 (2H, d, J=8.5 Hz), 7.43 (1H, s), 7.47 (2H, d, J=8.5 Hz). MS (EI) m/z: 296 (M$^+$).

Referential Example 347

3-(4-Chlorophenyl)-2-propiolic Acid

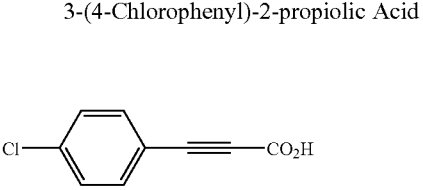

The compound (1.0 g) obtained in Referential Example 346 was dissolved in tetrahydrofuran (30 ml), and n-butyllithium (1.59 N hexane solution, 4.46 ml) was added dropwise at −78° C. under an argon atmosphere. The temperature of the reaction mixture was allowed to raise to room temperature and stirred for 1 hour. The reaction mixture was cooled again to −78° C., stirred for 2 minutes under a carbon dioxide atmosphere and then warmed to room temperature. After the reaction mixture was concentrated under reduced pressure, saturated aqueous solution of sodium chloride and ethyl acetate were added to the residue to conduct liquid separation. 3N Hydrochloric acid was added to the resultant water layer to acidify it, and extraction was conducted with ethyl acetate. The resultant organic layer was dried over anhydrous sodium sulfate and concentrated under reduced pressure to obtain the title compound (453 mg).

$^1$H-NMR (DMSO-d$_6$) δ: 7.55 (2H, d, J=8.5 Hz), 7.66 (2H, d, J=8.5 Hz), 13.90 (1H, br.s). MS (EI) m/z: 180 (M$^+$).

Referential Example 348

Ethyl 6-chloro-4-oxo-1,4-dihydroquinazoline-2-carboxylate

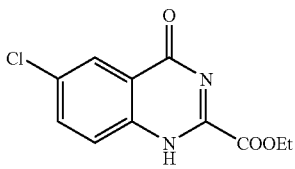

Ethyl chlorooxoacetate (2.0 ml) was added to a solution of 2-amino-5-chlorobenzamide (2.50 g) in pyridine (15 ml), and the mixture was stirred at room temperature for 18 hours. The reaction mixture was concentrated under reduced pressure, and the resultant residue was dissolved in acetic acid (50 ml). Acetic anhydride (5.0 ml) was added to the solution, and the mixture was heated under reflux for 16 hours. The solvent was distilled off under reduced pressure, and ethanol was added to the residue. Crystals deposited were collected by filtration and washed to obtain the title compound (2.71 g).

$^1$H-NMR (DMSO-d$_6$) δ: 1.35 (3H, t, J=7.1 Hz), 4.38 (2H, q, J=7.1 Hz), 7.85 (1H, d, J=8.6 Hz), 7.91 (1H, dd, J=8.6, 2.3 Hz), 8.10 (1H, d, J=2.3 Hz), 12.85 (1H, br.s). MS (ESI) m/z: 253 (M+H)$^+$.

Referential Example 349

6-Chloro-4-oxo-1,4-dihydroquinazoline-2-carboxylic Acid

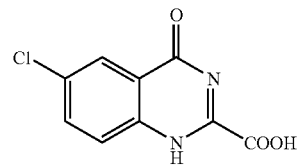

Lithium hydroxide (263 mg) was added to a solution of the compound (1.26 g) obtained in Referential Example 348 in a mixed solvent of water (5 ml) and tetrahydrofuran (15 ml), and the mixture was stirred at room temperature for 18 hours. The reaction mixture was neutralized with 1N hydrochloric acid (11 ml) under ice cooling and stirred for 1 hour. Crystals deposited were collected by filtration and washed with water to obtain the title compound (0.96 g).

$^1$H-NMR (DMSO-d$_6$) δ: 7.50-8.20 (3H, m), 12.44 (1H, br.s). MS (ESI) m/z: 265 (M+H+CH$_3$CN)$^+$.

Referential Example 350

2-Chloro-N-(4-chlorophenyl)acetamide

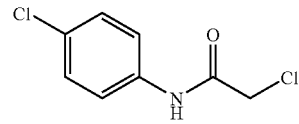

p-Chloroaniline (3.82 g) was dissolved in ethyl acetate (30 ml), and chloroacetyl chloride (2.39 ml) was added at room temperature to stir the mixture for 1 hour. After the reaction mixture was heated and stirred at 60° C. for 3.5 hours, crystals deposited were collected by filtration to obtain the title compound (4.78 g). The filtrate was concentrated to about 1/4, and crystals deposited were collected by filtration to obtain the title compound (1.01 g).

$^1$H-NMR (CDCl$_3$) δ: 4.19 (2H, s), 7.33 (2H, d, J=9.0 Hz), 7.51 (2H, d, J=9.0 Hz), 8.22 (1H, br.s).

Referential Example 351

Sodium S-[2-(4-chloroanilino)-2-oxoethyl]thiosulfate

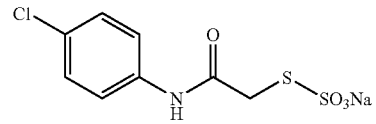

The compound (5.79 g) obtained in Referential Example 350 was dissolved in ethanol (140 ml), and an aqueous solution (140 ml) of sodium thiosulfate pentahydrate (7.04 g) was added at a time at 70° C. to heat the mixture under reflux for 1.5 hours. The reaction mixture was concentrated Referential Example 352

2-Chloro-N-(5-chloropyridin-2-yl)acetamide Hydrochloride

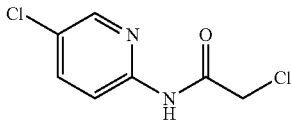

2-Amino-5-chloropyridine (3.85 g) was dissolved in ethyl acetate (60 ml), and chloroacetyl chloride (2.39 ml) was added at room temperature to stir the mixture for 1 hour. After the reaction mixture was heated and stirred at 60° C. for 30 minutes, chloroacetyl chloride (0.5 ml) was additionally added, and the mixture was stirred at 60° C. for additional 1 hour. Powder deposited was collected by filtration to obtain the title compound (6.18 g).

$^1$H-NMR (DMSO-d$_6$) δ: 4.36 (2H, s), 7.94 (1H, dd, J=8.8, 2.7 Hz), 8.09 (1H, d, J=8.8 Hz), 8.40 (1H, d, J=2.7 Hz), 11.03 (1H, s).

Referential Example 353

Sodium S-{2-[(5-chloropyridin-2-yl)amino]-2-oxoethyl}thiosulfate

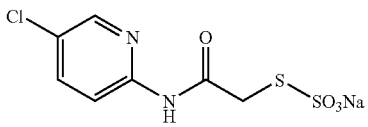

An aqueous solution (130 ml) with sodium thiosulfate pentahydrate (6.35 g) and sodium hydrogencarbonate (2.15 g) dissolved therein was added to a solution with the compound (6.18 g) obtained in Referential Example 352 dissolved in ethanol (130 ml) at a time at 80° C. under stirring, and the mixture was heated under reflux at 110° C. for 2 hours. The reaction mixture was concentrated to solids under reduced pressure, and ethanol (500 ml) was added to the residue. The resultant mixture was heated and extracted twice. The extract was concentrated to about 1/20, and diethyl ether was added. Insoluble matter deposited was collected by filtration to obtain the title compound (6.65 g).

$^1$H-NMR (DMSO-d$_6$) δ: 3.77 (2H, s), 7.89 (1H, dd, J=9.0, 2.7 Hz), 8.09 (1H, d, J=9.0 Hz), 8.34 (1H, d, J=2.7 Hz), 10.57 (1H, s).

to about 1/10, and crystals deposited were collected by filtration to obtain the title compound (8.20 g).

$^1$H-NMR (DMSO-d$_6$) δ: 3.73 (2H, s), 7.35 (2H, d, J=8.8 Hz), 7.57 (2H, d, J=8.8 Hz), 10.30 (1H, s).

Referential Example 354

N-{(1R,2S,5S)-2-[(2-chloroacetyl)amino]-5-[(dimethylamino)carbonyl]cyclohexyl}-5-methyl-4,5,6,7-tetrathiazolo[5,4-c]pyridine-2-carboxamide hydrochloride

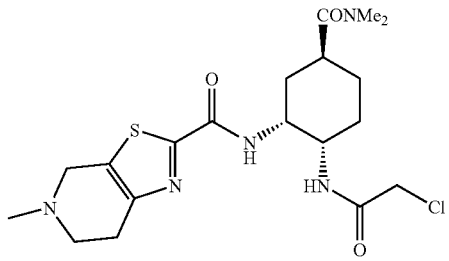

The compound (100 mg) obtained in Referential Example 253 was dissolved in ethyl acetate (10 ml), and chloroacetyl chloride (21.6 µl) was added to heat and stir the mixture at 60° C. for 30 minutes. After allowing the reaction mixture to cool, insoluble matter was collected by filtration and dissolved in methylene chloride-methanol, and the solvent was distilled off under reduced pressure to obtain the crude title compound (112 mg).

$^1$H-NMR (DMSO-d$_6$) δ: 1.35-1.50 (1H, m), 1.55-2.00 (5H, m), 2.78 (3H, s), 2.98 (3H, s), 3.00-3.25 (5H, m), 3.17 (3H, s), 3.80-3.90 (1H, m), 3.96 (1H, d, J=12.9 Hz), 4.00-4.15 (1H, m), 4.02 (1H, d, J=12.9 Hz), 4.45-4,70 (2H, m), 7.85-8.00 (1H, br), 8.12 (1H, d, J=7.3 Hz), 8.35 (1H, d, J=8.3 Hz). MS (ESI) m/z: 442 (M+H)$^+$.

Referential Example 355

Sodium S-{2-[((1S,2R,4S)-4-[(dimethylamino)carbonyl]-2-{[(5-methyl-4,5,6,7-tetrathiazolo[5,4-c]pyridine-2-yl)carbonyl]amino}cyclohexyl)amino]-2-oxoethyl}thiosulfate

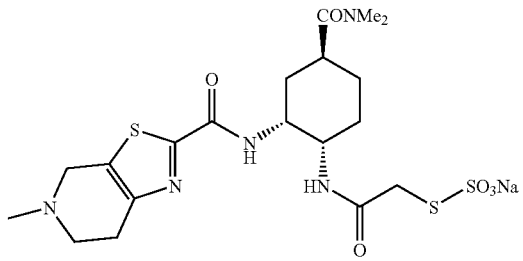

The compound (106 mg) obtained in Referential Example 354 was dissolved in ethanol (1.5 ml), and an aqueous solution (1.5 ml) of sodium thiosulfate pentahydrate (55 mg) and sodium hydrogencarbonate (18.6 mg) dissolved therein was added at a time at 90° C. under stirring. The resultant mixture was heated under reflux for 1 hour. The reaction mixture was concentrated to solids under reduced pressure, and ethanol (10 ml) was added to the residue. The resultant mixture was heated and extracted. The extract was concentrated to about 1/2, and isopropyl ether (10 ml) was added. Insoluble matter deposited was collected by filtration to obtain the title compound (72 mg).

¹H-NMR (DMSO-d₆) δ: 1.35-1.50 (1H, m), 1.55-1.90 (5H, m), 2.40 (3H, s), 2.78 (3H, s), 2.80-3.10 (5H, m), 2.96 (3H, s), 3.44 (1H, d, J=14.2 Hz), 3.50 (1H, d, J=14.2 Hz), 3.68 (2H, s), 3.75-3.90 (1H, m), 4.45-4.50 (1H, m), 8.01 (1H, d, J=7.4 Hz), 8.15 (1H, d, J=8.3 Hz).

Referential Example 356

Methyl 2-[(5-chlorothien-2-yl)amino]-2-oxoacetate

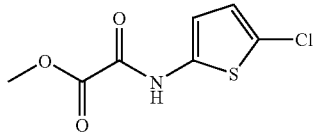

Triethylamine (1.25 ml) and diphenylphosphoryl azide (1.55 ml) were added to a suspension of 5-chlorothiophene-2-carboxylic acid (0.99 g) in toluene (20 ml), and the mixture was stirred at 80° C. for 1 hour. After the reaction mixture was cooled to room temperature, tert-butanol (2 ml) was added, and the mixture was heated under reflux for 19 hours. The reaction mixture was concentrated under reduced pressure, and methylene chloride (200 ml) was added to the resultant residue. The resultant mixture was successively washed with distilled water, a 10% aqueous solution of citric acid, distilled water, a saturated aqueous solution of sodium hydrogencarbonate and saturated aqueous solution of sodium chloride and then dried over anhydrous sodium sulfate. The solvent was distilled off under reduced pressure, and the residue was subjected to column chromatography on silica gel (hexane:ethyl acetate=4:1) to obtain tert-butyl 5-chloro-2-thienylcarbamate (1.05 g).

¹H-NMR (CDCl₃) δ: 1.51 (9H, s), 6.21 (1H, d, J=3.1 Hz), 6.60 (1H, d, J=3.1 Hz), 6.91 (1H, br.s). MS (ESI) m/z: 234 (M+H)⁺.

After the product (1.87 g) obtained above was added to a 4N dioxane solution (40 ml) of hydrochloric acid, and the mixture was stirred at room temperature for 4 hours, the solvent was distilled off under reduced pressure. The residue was suspended in tetrahydrofuran (50 ml), and sodium hydrogencarbonate (2.02 g) and methyl chlorooxoacetate (0.883 ml) were added under ice cooling to stir the mixture at room temperature for 18 hours. After the solvent was distilled off under reduced pressure, and water and methylene chloride were added to the residue to conduct liquid separation, the resultant organic layer was washed with saturated aqueous solution of sodium chloride and dried over anhydrous sodium sulfate and then concentrated under reduced pressure. The residue was purified by column chromatography on silica gel (hexane:ethyl acetate=3:1), and the solvent was distilled off to obtain the title compound-(1.44 g).

¹H-NMR (CDCl₃) δ: 3.98 (3H, s), 6.61 (1H, d, J=4.2 Hz), 6.75 (1H, d, J=4.2 Hz), 9.42 (1H, br.s). MS (FAB) m/z: 220 (M+H)⁺.

Referential Example 357

Methyl 2-[(5-fluoropyridin-2-yl)amino]-2-oxoacetate

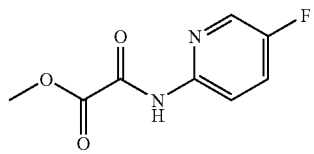

The title compound was obtained from 2-amino-5-fluoropyridine and methyl chlorooxoacetate in a similar manner to the process described in Referential Example 242.

¹H-NMR (CDCl₃) δ: 3.99 (3H, s), 7.48-7.53 (1H, m), 8.21 (1H, d, J=2.9 Hz), 8.27-8.31 (1H, m), 9.41 (1H, br.s). MS (FAB) m/z: 198 (M+H)⁺.

Referential Example 358

Methyl 2-[4-chloro-2-(trifluoromethyl)anilino]-2-oxoacetate

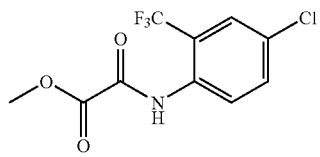

The title compound was obtained from 4-chloro-2-trifluoroaniline and methyl chlorooxoacetate in a similar manner to the process described in Referential Example 242.

¹H-NMR (CDCl₃) δ: 4.01 (3H, s), 7.58 (1H, dd, J=8.8, 2.2 Hz), 7.65 (1H, d, J=2.2 Hz), 8.34 (1H, d, J=8.8 Hz), 9.30 (1H, br.s). MS (EI) m/z: 281 (M+H)⁺.

Referential Example 359

2-[4-Chloro-2-(trifluoromethyl)anilino]-2-oxoacetic acid

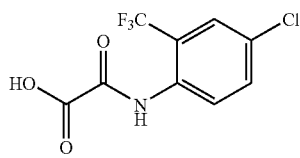

Lithium hydroxide (28 mg) was added to a solution of the compound (297 mg) obtained in Referential Example 358 in a mixed solvent of tetrahydrofuran (7 ml) and water (3 ml), and the mixture was stirred at room temperature for 2 hours. 1N Hydrochloric acid (8 ml) and methylene chloride (20 ml) were added to the reaction mixture to conduct liquid separation. After the resultant organic layer was dried over anhydrous sodium sulfate, the solvent was distilled off under reduced pressure, and the residue was dried to obtain the title compound (291 mg).

¹H-NMR (CDCl₃) δ: 7.61 (1H, dd, J=8.8, 2.5 Hz), 7.68 (1H, d, J=2.5 Hz), 8.26 (1H, d, J=8.8 Hz), 9.36 (1H, br.s). MS (ESI, anion) m/z: 267 (M−H)⁻.

Referential Example 360

5-Chloro-N,N-dimethyl-2-nitrobenzamide

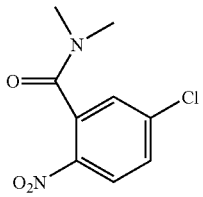

The title compound was obtained by condensing 5-chloro-2-nitrobenzoic acid with dimethylamine in a similar manner to the process described in Referential Example 143.

¹H-NMR (CDCl₃) δ: 2.86 (3H, s), 3.16 (3H, s), 7.38 (1H, d, J=2.2 Hz), 7.51 (1H, dd, J=8.8, 2.2 Hz), 8.15 (1H, d, J=8.8 Hz).

Referential Example 361

2-Amino-5-chloro-N,N-dimethylbenzamide

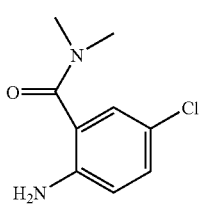

Iron(III) chloride hexahydrate (9.93 g) and zinc powder (8.01 g) were added to a solution of the compound (2.8 g) obtained in Referential Example 360 in a mixed solvent of N,N-dimethylformamide (80 ml) and water (40 ml), and the mixture was heated under reflux for 20 minutes. The reaction mixture was filtered through Celite 545, and ethyl acetate (200 ml) was added to the filtrate to conduct liquid separation. The resultant water layer was washed with ethyl acetate (100 ml×2), and organic layers were combined, washed with distilled water and dried over anhydrous sodium sulfate. The solvent was distilled off under reduced pressure, and the resultant residue was subjected to column chromatography on silica gel (methylene chloride:hexane=1:1→1:0→methanol:methylene chloride 1:100) to obtain the title compound (2.41 g).

¹H-NMR (CDCl₃) δ: 3.13 (6H, s), 4.33 (2H, br), 6.65 (1H, d, J=8.5 Hz), 7.07 (1H, d, J=2.2 Hz), 7.11 (1H, dd, J=8.5, 2.2 Hz). MS (ESI) m/z: 240 (M+MeCN)⁺.

Referential Example 362

Methyl 2-{4-chloro-2-[(dimethylamino)carbonyl]anilino}-2-oxoacetate

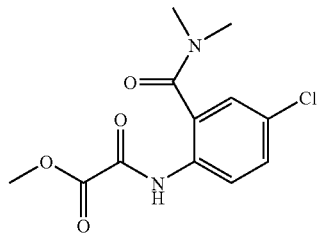

The title compound was obtained from the compound obtained in Referential Example 361 and methyl chlorooxoacetate in a similar manner to the process described in Referential Example 242.

¹H-NMR (CDCl₃) δ: 3.09 (6H, br), 3.96 (3H, s), 7.30 (1H, d, J=2.4 Hz), 7.41 (1H, d, J=8.8, 2.4 Hz), 8.34 (1H, d, J=8.8 Hz), 10.46 (1H, br). MS (ESI) m/z: 285 (M+H)⁺.

Referential Example 363

4-Chloro-2-methoxyaniline

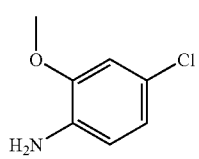

The title compound was obtained from 5-chloro-2-nitroanisole in a similar manner to the process described in Referential Example 361.

¹H-NMR (CDCl₃) δ: 3.65-3.95 (2H, br), 3.87 (3H, s), 6.61 (1H, d, J=8.8 Hz), 6.74-6.78 (2H, m). MS (ESI) m/z: 199 (M+MeCN+H)⁺.

Referential Example 364

Methyl 2-(4-chloro-2-methoxyanilino)-2-oxoacetate

The title compound was obtained from the compound obtained in Referential Example 363 and methyl chlorooxoacetate in a similar manner to the process described in Referential Example 242.

¹H-NMR (CDCl₃) δ: 3.92 (3H, s), 3.97 (3H, s), 6.90 (1H, d, J=2.2 Hz), 6.98 (1H, dd, J=8.8, 2.2 Hz), 8.35 (1H, d, J=8.8 Hz), 9.33-9.44 (1H, br). MS (ESI) m/z: 244 (M+H)⁺.

Referential Example 365

Ethyl 2-(4-chloroanilino)-2-(hydroxyimino)-acetate

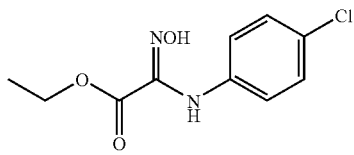

The title compound was obtained from 4-chloroaniline (3.03 g) and ethyl 2-chloro-2-hydroxyiminoacetate in a similar manner to the process described in literature (Gilchrist, T. L.; Peek, M. E.; Rees, C. W.; J. Chem. Soc. Chem. Commun., 1975, 913).

$^1$H-NMR (CDCl$_3$) δ: 1.26 (3H, t, J=7.1 Hz), 1.60-1.80 (1H, br), 4.28 (2H, q, J=7.1 Hz), 6.85 (2H, d, J=8.6 Hz), 7.24 (2H, d, J=8.6 Hz), 8.15-8.45 (1H, br). MS (ESI) m/z: 243 (M+H)$^+$.

Referential Example 366 tert-Butyl (1R,2S,5S)-2-{[2-(4-chloroanilino)-2-(hydroxyimino)acetyl]amino}-5-[(dimethylamino)carbonyl]-cyclohexylcarbamate

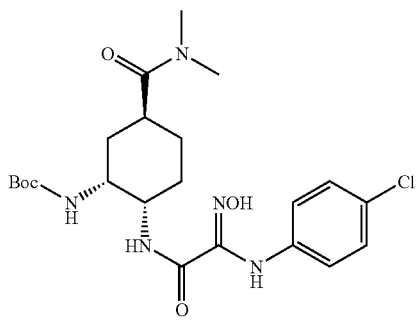

The compound (597 mg) obtained in Referential Example 144 was added to a solution of the compound (350 mg) obtained in Referential Example 365 in ethanol (5.0 ml), and the mixture was stirred at 70° C. for 3 days. After the reaction mixture was concentrated under reduced pressure, the residue was purified by column chromatography on silica gel (methylene chloride:methanol=30:1) to obtain the title compound (180 mg).

$^1$H-NMR (CD$_3$OD) δ: 1.46 (9H, s), 1.47-1.84 (6H, m), 1.88-1.95 (1H, m), 2.90 (3H, s), 3.08 (3H, s), 3.90-3.97 (1H, m), 4.11-4.17 (1H, m), 6.84 (2H, d, J=8.8 Hz), 7.18 (2H, d, J=8.8 Hz). MS (ESI) m/z: 504 (M+Na)$^+$.

Referential Example 367 tert-Butyl (3R,4S)-4-{[2-(4-chloroanilino)-2-oxoacetyl]amino}-1-(2-methoxyacetyl)piperidin-3-ylcarbamate

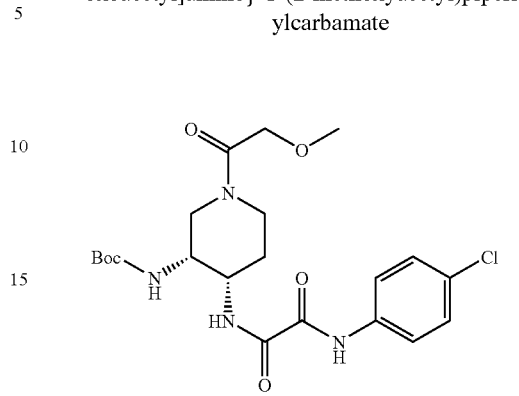

The title compound was obtained from the compound obtained in Referential Example 374 and the compound obtained in Referential Example 220 in a similar manner to the process described in Referential Example 214.

$^1$H-NMR (CDCl$_3$) δ: 1.45 (9H, s), 1.55-1.75 (1H, br), 1.94-2.07 (1H, br), 2.70-3.00 (1H, m), 3.10-3.37 (1H, m), 3.44 (3H, s), 3.88-4.22 (4H, m), 4.55-4.69 (1H, br), 4.80-4.90 (0.5H, br), 5.36-5.48 (0.5H, br), 7.20-7.30 (1H, br), 7.32 (2H, d, J=8.8 Hz), 7.62 (2H, d, J=8.8 Hz), 8.20-8.40 (1H, br), 9.15-9.25 (1H, br). MS (ESI) m/z: 469 (M+H)$^+$.

Referential Example 368 tert-Butyl (3R,4S)-4-({2-[(5-chloropyridin-2-yl)amino]-2-oxoacetyl}amino)-1-(2-methoxyacetyl)piperidin-3-ylcarbamate

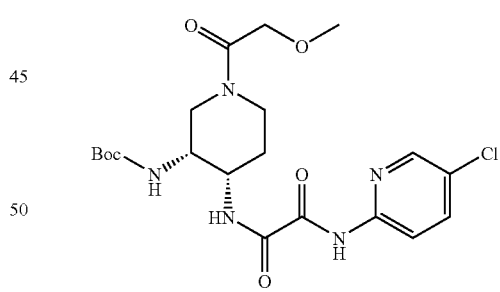

The title compound was obtained from the compound obtained in Referential Example 266 and the compound obtained in Referential Example 220 in a similar manner to the process described in Referential Example 214.

$^1$H-NMR (CDCl$_3$) δ: 1.45 (9H, s), 1.65-2.30 (2H, br), 2.68-3.02 (1H, m), 3.10-3.35 (1H, m), 3.44 (3H, s), 3.80-4.25 (4H, m), 4.45-4.70 (1H, m), 5.05-5.20 (0.5H, m), 5.80-5.93 (0.5H, m), 7.30-7.40 (1H, br), 7.71 (1H, br d, J=8.7 Hz), 7.95-8.05 (0.3H, br), 8.19 (1H, br d, J=8.8 Hz), 8.31 (1H, br.s), 8.38-8.53 (0.7H, br), 9.74-9.84 (1H, br). MS (ESI) m/z: 470 (M+H)$^+$.

Referential Example 369 tert-Butyl (3R,4S)-4-({2-[(5-bromopyridin-2-yl)amino]-2-oxoacetyl]amino)-1-(2-methoxyacetyl)piperidin-3-ylcarbamate

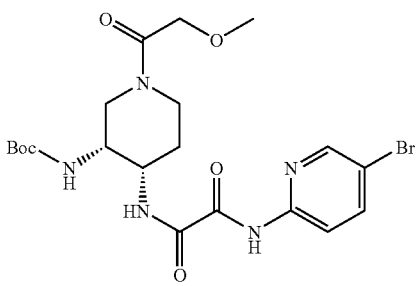

The title compound was obtained from the compound obtained in Referential Example 375 and the compound obtained in Referential Example 220 in a similar manner to the process described in Referential Example 214.

$^1$H-NMR (CDCl$_3$) δ: 1.47 (9H, s), 1.50-1.75 (1H, m), 1.95-2.13 (1H, br), 2.70-2.98 (1H, m), 3.05-3.36 (1H, m), 3.45 (3H, s), 3.80-4.24 (4H, m), 4.57-4.73 (1H, br), 4.85-4.95 (0.25H, br), 5.10-5.15 (0.25H, br), 5.45-5.58 (0.5H, br), 7.30-7.38 (1H, m), 7.84 (1H, dd, J=8.8, 2.2 Hz), 8.16 (1H, d, J=8.8 Hz), 8.30-8.55 (1H, br), 8.40 (1H, d, J=2.2 Hz), 9.68 (1H, br.s).

Referential Example 370

Ethyl 3-(4-chloroanilino)-3-oxopropionate

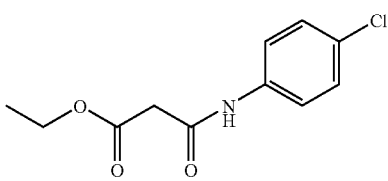

Potassium ethyl malonate (3.2 g), 1-hydroxybenzotriazole (2.1 g) and 1-(3-dimethylaminopropyl)-3-ethylcarbodiimide hydrochloride (4.5 g) were successively added to a solution of 4-chloroaniline (2.0 g) in N,N-dimethylformamide (20 ml) at room temperature, and the mixture was stirred at room temperature for 2 hours. The reaction mixture was diluted with ethyl acetate and washed with a saturated aqueous solution of sodium hydrogencarbonate, a 10% aqueous solution of citric acid and saturated aqueous solution of sodium chloride. After the resultant organic layer was dried over anhydrous sodium sulfate, the solvent was distilled off under reduced pressure to obtain the title compound (4.0 g).

$^1$H-NMR (CDCl$_3$) δ: 1.33 (3H, t, J=7.3 Hz), 3.47 (2H, s), 4.26 (2H, q, J=7.3 Hz), 7.29 (2H, d, J=8.8 Hz), 7.51 (2H, d, J=8.8 Hz), 9.32 (1H, br.s).

Referential Example 371

3-(4-Chloroanilino)-3-oxopropionic Acid

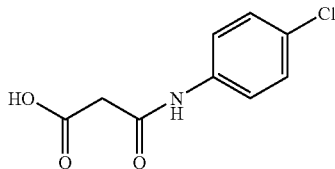

A 1N aqueous solution (10 ml) of sodium hydroxide was added dropwise to a solution of the compound (1.0 g) obtained in Referential Example 370 in ethanol (10 ml) at room temperature, and the mixture was stirred for 2 hours. 1N Hydrochloric acid (10 ml) was added to the reaction mixture, the mixture was stirred, and insoluble matter deposited was then collected by filtration to obtain the title compound (0.5 g).

$^1$H-NMR (DMSO-d$_6$) δ: 3.34 (2H, s), 7.35 (2H, d, J=8.8 Hz), 7.59 (2H, d, J=8.8 Hz), 10.26 (1H, s), 12.66 (1H, br.s).

Referential Example 372

Ethyl 3-(3-chloroanilino)-3-oxopropionate

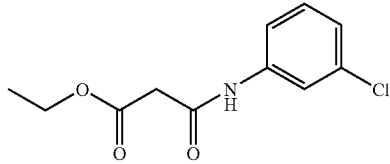

The title compound was obtained by condensing 3-chloroaniline with potassium ethyl malonate in a similar manner to the process described in Referential Example 370.

$^1$H-NMR (CDCl$_3$) δ: 1.33 (3H, t, J=7.3 Hz), 3.47 (2H, s), 4.26 (2H, q, J=7.3 Hz), 7.09 (1H, d, J=8.8 Hz), 7.22-7.26 (1H, m), 7.39 (1H, d, J=8.8 Hz), 7.69 (1H, s), 9.35 (1H, br.s).

Referential Example 373

3-(3-Chloroanilino)-3-oxopropionic Acid

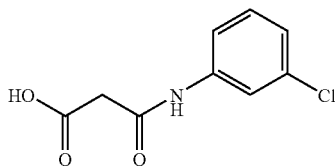

The title compound was obtained from the compound obtained in Referential Example 372 in a similar manner to the process described in Referential Example 371.

$^1$H-NMR (DMSO-d$_6$) δ: 3.35 (2H, s), 7.11 (1H, d, J=8.8 Hz), 7.33 (1H, t, J=8.8 Hz), 7.39 (1H, d, J=8.8 Hz), 7.78 (1H, s), 10.31 (1H, s), 12.67 (1H, br.s).

Referential Example 374

2-(4-Chloroanilino)-2-oxoacetic acid

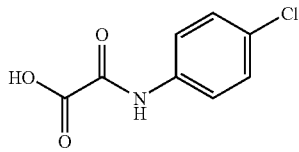

The title compound was obtained from the compound obtained in Referential Example 242 in a similar manner to the process described in Referential Example 359.

$^1$H-NMR (DMSO-$d_6$) δ: 7.37 (2H, d, J=8.8 Hz), 7.79 (2H, d, J=8.8 Hz), 10.66 (1H, s).

Referential Example 375

2-[(5-Bromopyridin-2-yl)amino]-2-oxoacetic acid

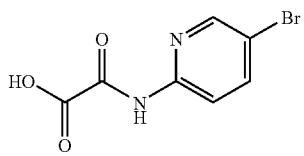

The title compound was obtained from the compound obtained in Referential Example 262 in a similar manner to the process described in Referential Example 359.

$^1$H-NMR (DMSO-$d_6$) δ: 7.95-8.00 (1H, m), 8.08 (1H, dd, J=8.8, 2.0 Hz), 8.50 (1H, d, J=2.0 Hz), 10.74 (1H, s).

Referential Example 376

4-Chloro-3-fluorobenzoic acid

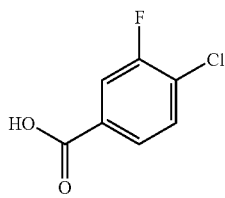

Sodium chlorite (17 g) was added portionwise to a mixture solution composed of 4-chloro-3-fluorobenzaldehyde (10 g), amidosulfuric acid (18 g), tert-butyl alcohol (50 ml) and water (50 ml) under ice cooling, and the mixture was stirred for 4 days while the temperature of the system was gradually raised to room temperature. The reaction mixture was diluted with ethyl acetate and washed with water, 1N hydrochloric acid and saturated aqueous solution of sodium chloride. After the resultant organic layer was dried over anhydrous sodium sulfate, and the solvent was distilled off under reduced pressure, the resultant residue was recrystallized from a mixed solvent of diisopropyl ether and hexane to obtain the title compound (11.2 g).

$^1$H-NMR (DMSO-$d_6$) δ: 7.72 (1H, dt, J=8.3, 1.5 Hz), 7.77 (1H, dt, J=8.3, 1.6 Hz), 7.82 (1H, dt, J=9.7, 1.5 Hz), 13.45 (1H, s).

Referential Example 377

Methyl 2-(4-chloro-3-fluoroanilino)-2-oxoacetate

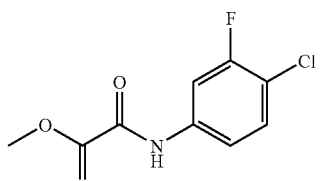

The title compound was obtained by subjecting the compound obtained in Referential Example 376 to Curtius rearrangement reaction and then condensing this product with methyl chlorooxoacetate in a similar manner to the process described in Referential Example 356.

H-NMR (CDCl$_3$) δ: 3.99 (3H, s), 7.25-7.27 (1H, m), 7.39 (1H, t, J=8.5 Hz), 7.72 (1H, dd, J=10.4, 2.4 Hz), 8.90 (1H, br.s).

Referential Example 378

2-(4-Chloro-3-fluoroanilino)-2-oxoacetic acid

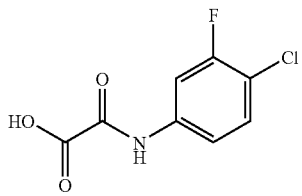

The title compound was obtained from the compound obtained in Referential Example 377 in a similar manner to the process described in Referential Example 359.

$^1$H-NMR (DMSO-$d_6$) δ: 7.52 (1H, t, J=8.8 Hz), 7.63 (1H, dd, J=8.8, 2.2 Hz), 7.88 (1H, dd, J=12.0, 2.2 Hz), 10.83 (1H, br.s).

Referential Example 379

Ethyl 3-(4-chlorophenyl)-3-oxopropionate

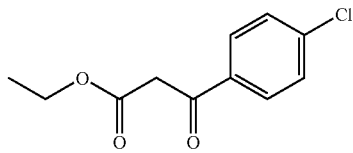

Triethylamine (17 ml) and magnesium chloride (5.5 g) were added to a suspension of potassium ethyl malonate (8.2 g) in ethyl acetate (100 ml) under ice cooling, and the mixture was stirred for 18 hours while the temperature of the system was gradually raised to room temperature. On the other hand, a suspension composed of 4-chlorobenzoic acid (5.0 g), thionyl chloride (12 ml), N,N-dimethylformamide (one drop) and toluene (100 ml) was heated under reflux for 1 hour, and the reaction mixture was then concentrated. The resultant residue was dissolved in ethyl acetate, and the solution was added dropwise to the reaction mixture previously prepared under ice cooling. The resultant mixture was stirred for 18 hours while the temperature of the system was gradually raised to room temperature. A 10% aqueous solution of citric acid was added to the reaction mixture, and the mixture was stirred for 30 minutes to separate the resultant organic layer. The organic layer was washed with saturated aqueous solution of sodium chloride and then dried over anhydrous sodium sulfate, and the solvent was distilled off under reduced pressure. The resultant residue was isolated and purified by column chromatography on silica gel (chloroform) to obtain the title compound (6.4 g).

$^1$H-NMR (CDCl$_3$) δ: 1.26 (3H, t, J=7.3 Hz), 3.96 (2H, s), 4.21 (2H, q, J=7.3 Hz), 7.46 (2H, d, J=8.8 Hz), 7.89 (2H, d, J=8.8 Hz).

Referential Example 380

Ethyl 3-(4-chlorophenyl)-3-hydroxypropionate

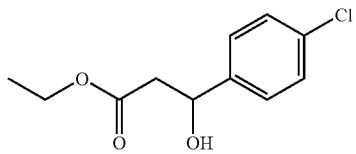

Sodium borohydride (0.2 g) was added portionwise under ice cooling to a solution of the compound (1.0 g) obtained in Referential Example 379 in tetrahydrofuran (10 ml), and the mixture was stirred for 2 hours while the temperature of the system was gradually raised to room temperature. A 10% aqueous solution of citric acid was added to the reaction mixture, and the resultant mixture was extracted with ethyl acetate. The resultant organic layer was washed with saturated aqueous solution of sodium chloride and then dried over anhydrous sodium sulfate, and the solvent was distilled off under reduced pressure. The resultant residue was isolated and purified by column chromatography on silica gel (chloroform) to obtain the title compound (0.56 g).

$^1$H-NMR (CDCl$_3$) δ: 1.27 (3H, t, J=7.3 Hz), 2.70 (1H, d, J=7.8 Hz), 2.71 (1H, d, J=3.4 Hz), 3.37 (1H, d, J=3.4 Hz), 4.18 (2H, q, J=7.3 Hz), 5.09-5.13 (1H, m), 7.30-7.35 (5H, m).

Referential Example 381

3-(4-Chlorophenyl)-3-hydroxypropionic acid

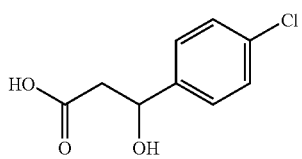

The title compound was obtained from the compound obtained in Referential Example 380 in a similar manner to the process described in Referential Example 359.

$^1$H-NMR (DMSO-d$_6$) δ: 3.25-3.32 (1H, m), 4.89-4.95 (1H, m), 5.45-5.53 (1H, m), 7.35-7.36 (5H, m), 12.11-12.18 (1H, m). MS (ESI, anion) m/z: 198 (M−H)$_-$.

Referential Example 382 tert-Butyl (1R,2S,5S)-2-{[3-(4-chlorophenyl)-3-hydroxypropanoyl]amino}-5-[(dimethylamino)carbonyl]-cyclohexylcarbamate

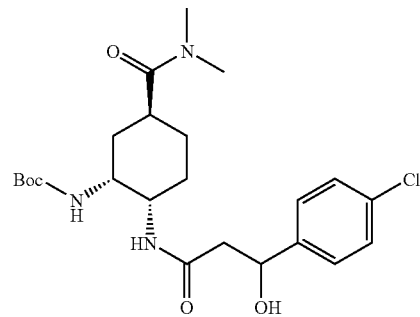

The title compound was obtained by condensing the compound obtained in Referential Example 144 with the compound obtained in Referential Example 381 in a similar manner to the process described in Referential Example 91.

$^1$H-NMR (CDCl$_3$) δ: 1.21-1.44 (2H, m), 1.46 (9H, s), 1.76-1.92 (2H, m), 1.95-2.10 (2H, m), 2.40-2.55 (2H, m), 2.55-2.68 (1H, m), 2.94 (3H, s), 3.05 (3H, s), 3.82-3.96 (1H, m), 4.02-4.17 (1H, m), 4.65-4.80 (2H, m), 5.03-5.13 (1H, m), 7.28-7.33 (5H, m). MS (ESI) m/z: 468 (M+H)$^+$.

Referential Example 383 tert-Butyl (1R,2S,5S)-2-{[3-(4-chlorophenyl)-3-oxopropanoyl]amino}-5-[(dimethylamino)carbonyl]-cyclohexylcarbamate

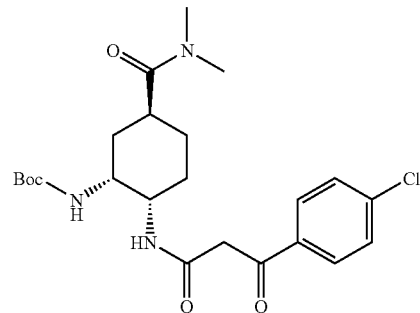

Manganese dioxide (0.47 g) was added to a solution of the compound (0.5 g) obtained in Referential Example 382 in 1,4-dioxane (20 ml) at room temperature, and the mixture was stirred for 4 days. Insoluble matter was removed by filtration through Celite pad, and the resultant filtrate was concentrated under reduced pressure to obtain the title compound (0.46 g).

$^1$H-NMR (DMSO-d$_6$) δ: 1.28-1.39 (1H, m), 1.40 (9H, s), 1.41-1.63 (3H, m), 2.25-2.42 (2H, m), 2.76 (3H, s), 2.90-2.97 (1H, m), 2.98 (3H, s), 3.56 (2H, s), 3.89-3.97 (1H, m), 4.88-4.98 (1H, m), 6.65-6.70 (1H, m), 7.30-7.35 (4H, m), 7.33 (1H, dd, J=2.9, 1.7 Hz). MS (ESI, anion) m/z: 464 (M−H)⁻.

Referential Example 384

Ethyl (1S,3R,4R)-4-azido-3-[(tert-butoxycarbonyl)amino]-cyclohexanecarboxylate

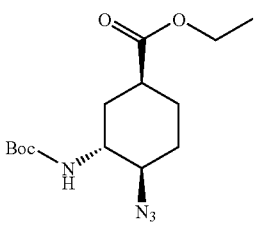

The title compound was obtained from the compound obtained in Referential Example 248 in a similar manner to the process described in Referential Example 249.

$[\alpha]_D^{25}$ +62° (c=1, chloroform). ¹H-NMR (CDCl₃) δ: 1.27 (3H, t, J=7.1 Hz), 1.46 (9H, s), 1.61 (1H, s), 1.61-1.71 (2H, m), 1.81-1.90 (1H, m), 1.97-2.03 (1H, m), 2.22-2.28 (1H, m), 2.56-2.60 (1H, m), 3.54 (1H, br.s), 3.63-3.68 (1H, m), 4.16 (2H, q, J=7.1 Hz), 4.58 (1H, br.s).

Referential Example 385 tert-Butyl (1R,2R,5S)-2-azido-5-[(dimethylamino)carbonyl]cyclohexylcarbamate

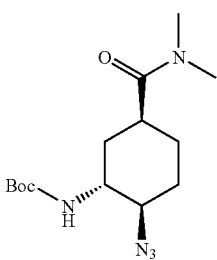

The title compound was obtained from the compound obtained in Referential Example 384 in similar manners to Referential Examples 250 and 251.

¹H-NMR (CDCl₃) δ: 1.46 (9H, s), 1.40-2.20 (6H, m), 2.70-2.80 (1H, m), 2.93 (3H, s), 3.03 (3H, s), 3.60-3.78 (1H, m), 3.83-3.95 (1H, m), 4.65 (1H, d, J=7.2 Hz).

Referential Example 386 tert-Butyl (1R,2R,5S)-2-({2-[(5-chloropyridin-2-yl)amino]-2-oxoacetyl}amino)-5-[(dimethylamino)carbonyl]cyclohexylcarbamate

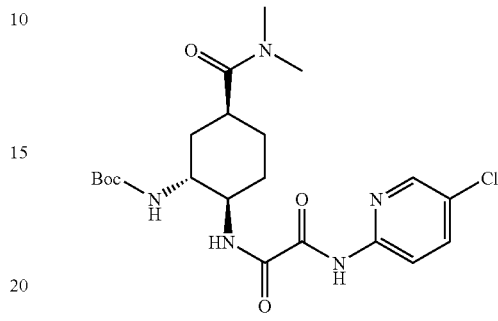

The title compound was obtained by converting the azide group of the compound obtained in Referential Example 385 into an amino group in a similar manner to the process described in Referential Example 90 and then condensing this product with the compound obtained in Referential Example 266 in a similar manner to the process described in Referential Example 91.

¹H-NMR (CDCl₃) δ: 1.13-2.25 (16H, m), 2.94 (3H, s), 3.03 (3H, s), 3.60-3.78 (1H, m), 4.13-4.31 (1H, m), 4.45-4.65 (1H, m), 7.80 (1H, dd, J=8.8, 2.4 Hz), 8.03 (1H, br.s), 8.21 (1H, d, J=8.8 Hz), 8.29 (1H, d, J=2.4 Hz), 9.71 (1H, s). MS (ESI) m/z: 468 (M+H)⁺.

Referential Example 387

N-{(1R,2R,5S)-2-Azido-5-[(dimethylamino)carbonyl]-cyclohexyl}-5-methyl-4,5,6,7-tetrahydrothiazolo[5,4-c]-pyridine-2-carboxamide

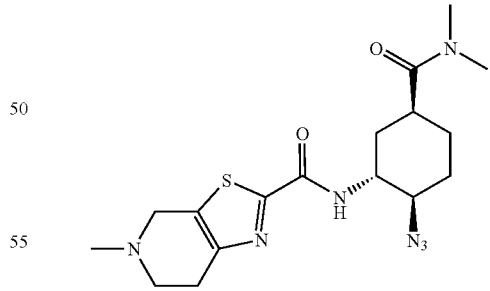

The title compound was obtained from the compound obtained in Referential Example 385 and the compound obtained in Referential Example 10 in a similar manner to the process described in Referential Example 252.

¹H-NMR (CDCl₃) δ: 1.75-2.08 (6H, m), 2.20-2.32 (1H, m), 2.51 (3H, s), 2.75-2.97 (4H, m), 2.95 (3H, s), 3.04 (3H, s), 3.65-3.80 (3H, m), 4.27-4.39 (1H, m), 7.17-7.28 (1H, m). MS (ESI) m/z: 392 (M+H)⁺.

Referential Example 388 tert-Butyl 4-[(2-methoxy-2-oxoacetyl)amino]piperidine-1-carboxylate

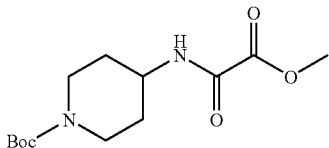

The title compound was obtained from (4-amino-N-tert-butoxycarbonyl)piperidine and methyl chlorooxoacetate in a similar manner to the process described in Referential Example 242.

$^1$H-NMR (DMSO-$d_6$) δ: 1.46 (9H, s), 1.34-1.51 (2H, m), 1.89-1.98 (2H, m), 2.82-2.96 (2H, m), 3.91 (3H, s), 3.88-4.14 (3H, m), 6.96-7.07 (1H, m). MS (FAB) m/z: 287 (M+H)$^+$.

Referential Example 389 tert-Butyl 4-{[2-({(1R,2S,5S)-2-{[(5-chloroindol-2-yl)carbonyl]amino}-5-[(dimethylamino)carboyl]cyclohexyl}-amino)-2-oxoacetyl]amino}piperidine-1-carboxylate

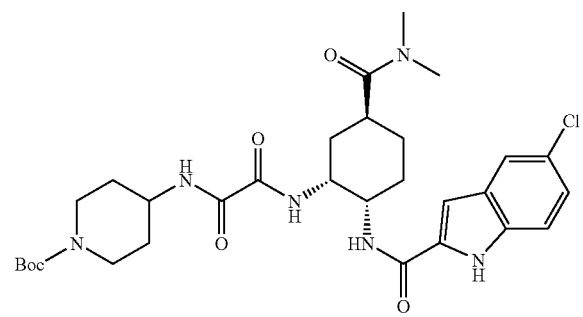

The title compound was obtained from the compound obtained in Referential Example 310 and the compound obtained in Referential Example 388 in a similar manner to the process described in Referential Example 191.

$^1$H-NMR (DMSO-$d_6$) δ: 1.46 (9H, s), 1.35-2.28 (11H, m), 2.70-3.18 (9H, m), 3.80-4.57 (4H, m), 6.78 (1H, s), 7.15-8.12 (6H, m), 9.45 (1H, s). MS (FAB) m/z: 617 (M+H)$^+$.

Referential Example 390

Methyl 2-[(5-chloropyridin-2-yl)(methyl)amino]-2-oxoacetate

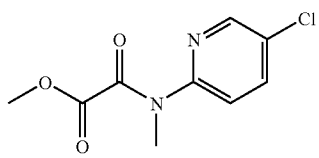

The title compound was obtained from 5-chloro-N-methyl-2-pyridineamine and methyl chlorooxoacetate in a similar manner to the process described in Referential Example 242.

$^1$H-NMR (CDCl$_3$) δ: 3.43 (3H, s), 3.81 (3H, s), 7.08 (1H, br.s), 7.68-7.78 (1H, m), 8.27 (1H, br.s). MS (ESI) m/z: 229 (M+H)$^+$.

Referential Example 391

Methyl 2-[(5-chloropyrimidin-2-yl)amino]-2-oxoacetate

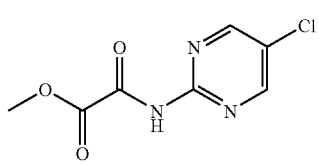

The title compound was obtained from 2-amino-5-chloropyrimidine and methyl chlorooxoacetate in a similar manner to the process described in Referential Example 242.

$^1$H-NMR (CDCl$_3$) δ: 4.00 (3H, s), 8.63 (2H, s), 9.58 (1H, br.s). MS (ESI) m/z: 215 (M+H)$^+$.

Referential Example 392

N-((1R,2S,5S)-2-Azido-5-{[ethyl(methyl)amino]carbonyl}-cyclohexyl)-5-methyl-5,6-dihydro-4H-pyrrolo[3,4-d]-thiazole-2-carboxamide

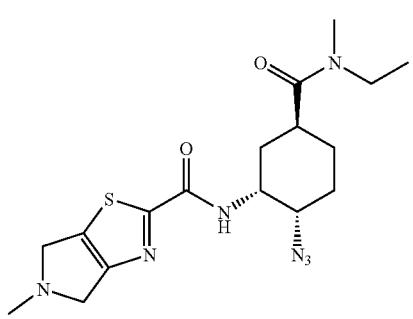

The title compound was obtained from the compound obtained in Referential Example 323 and the compound obtained in Referential Example 293 in a similar manner to the process described in Referential Example 252.

$^1$H-NMR (CDCl$_3$) δ: 1.08, 1.15 (3H, each t, J=7.1 Hz), 1.74-1.88 (4H, m), 2.12-2.22 (2H, m), 2.67 (3H, s), 2.81-2.86 (1H, m), 2.89, 2.96 (3H, each s), 3.28-3.43 (2H, m), 3.91-4.10 (5H, m), 4.60-4.62 (1H, m), 7.21 (1H, d, J=7.6 Hz). MS (ESI) m/z: 392 (M+H)$^+$.

Referential Example 393

Methyl 2-(4-chloro-3-methoxyanilino)-2-oxoacetate

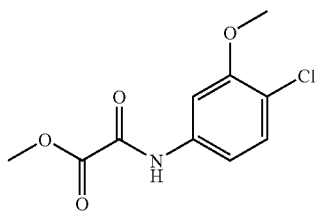

The title compound was obtained by reducing 2-chloro-5-nitroanisole in a similar manner to the process described in Referential Example 361 into an amino derivative and then condensing the amino derivative with methyl chlorooxoacetate in a similar manner to the process described in Referential Example 242.

$^1$H-NMR (CDCl$_3$) δ: 3.93 (3H, s), 3.98 (3H, s), 7.00 (1H, dd, J=8.5, 2.4 Hz), 7.33 (1H, d, J=8.5 Hz), 7.57 (1H, d, J=2.4 Hz), 8.89 (1H, br.s).

Referential Example 394

2-(4-Chloro-3-methoxyanilino)-2-oxoacetic acid

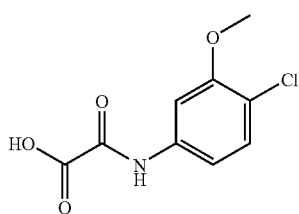

The title compound was obtained by hydrolyzing the compound obtained in Referential Example 393 in a similar manner to the process described in Referential Example 359.

$^1$H-NMR (DMSO-d$_6$) δ: 3.81 (3H, s), 7.36 (1H, d, J=8.7 Hz), 7.43 (1H, d, J=8.7 Hz), 7.65 (1H, d, J=2.2 Hz), 10.79 (1H, s). MS (ESI, anion) m/z: 228 (M−H)$^−$.

Referential Example 395

N$^1$-{(1S,2R,4S)-2-Amino-4-[(dimethylamino)carbonyl]-cyclohexyl}-N$^2$-(4-chloro-3-methoxyphenyl)ethanediamide

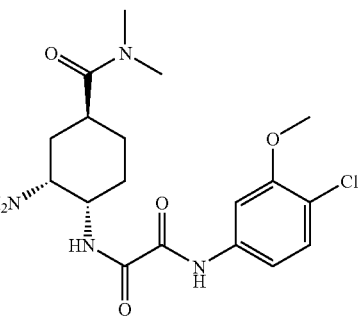

The title compound was obtained by condensing the compound obtained in Referential Example 144 with the compound obtained in Referential Example 394 in a similar manner to the process described in Referential Example 97, treating this product with hydrochloric acid in a similar manner to the process described in Referential Example 69 and then neutralizing it with a 1N aqueous solution of sodium hydroxide.

$^1$H-NMR (CDCl$_3$) δ: 1.48-2.00 (8H, m), 2.84-2.93 (1H, m), 2.95 (3H, s), 3.08 (3H, s), 3.33-3.35 (1H, m), 3.89-3.94 (4H, m), 7.06 (1H, dd, J=8.5, 2.2 Hz), 7.32 (1H, d, J=8.5 Hz), 7.56 (1H, d, J=2.2 Hz), 8.05 (1H, d, J=8.5 Hz), 9.43 (1H, br.s). MS (ESI) m/z: 397 (M$^+$).

Referential Example 396

Methyl 2-(4-ethynylanilino)-2-oxoacetate

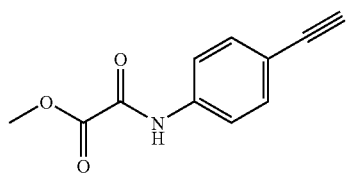

The title compound was obtained from 4-ethynylaniline and methyl chlorooxoacetate in a similar manner to the process described in Referential Example 242.

$^1$H-NMR (CDCl$_3$) δ: 3.09 (1H, s), 3.98 (3H, s), 7.50 (2H, d, J=8.4 Hz), 7.62 (2H, d, J=8.4 Hz), 8.89 (1H, br.s).

Referential Example 397

Sodium 2-(4-ethynylanilino)-2-oxoacetate

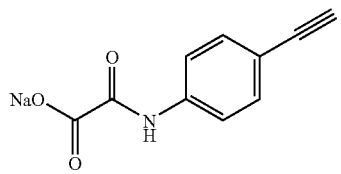

The title compound was obtained by hydrolyzing the compound obtained in Referential Example 396 with sodium hydroxide in a similar manner to the process described in Referential Example 266.

¹H-NMR (DMSO-d₆) δ: 4.06 (1H, s), 7.39 (2H, d, J=8.4 Hz), 7.80 (2H, d, J=8.4 Hz), 10.33 (1H, br.s).

Referential Example 398

Methyl 2-[(5-chloropyrazin-2-yl)amino]-2-oxoacetate

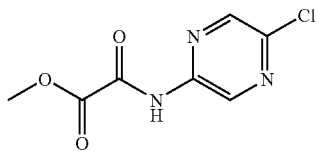

The title compound was obtained from 2-amino-5-chloropyrazine synthesized in accordance with literature (Sato, Nobuhiro et al., J. Heterocycl. Chem., 1982, 19(3), 673-4) and methyl chlorooxoacetate in a similar manner to the process described in Referential Example 242.

¹H-NMR (CDCl₃) δ: 4.02 (3H, s), 8.35 (1H, d, J=1.5 Hz), 9.37 (1H, d, J=1.5 Hz), 9.41 (1H, br.s). MS (FAB) m/z: 216 (M+H)⁺.

Referential Example 399

2-[(5-Chloropyrazin-2-yl)amino]-2-oxoacetic acid

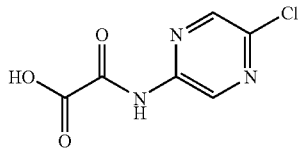

The title compound was obtained from the compound obtained in Referential Example 398 in a similar manner to the process described in Referential Example 359.

¹H-NMR (DMSO-d₆) δ: 8.62 (1H, s), 9.02 (1H, br.s), 11.30 (1H, s). MS (EI) m/z: 201 M⁺.

Referential Example 400

2-(4-Chloro-3-nitroanilino)-2-oxoacetic acid

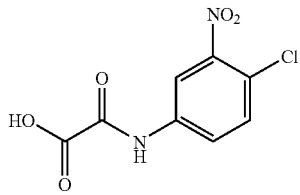

The title compound was obtained by condensing 4-chloro-3-nitroaniline with methyl chlorooxoacetate in a similar manner to the process described in Referential Example 242 and then hydrolyzing this product in a similar manner to the process described in Referential Example 359.

¹H-NMR (DMSO-d₆) δ: 7.76 (1H, dd, J=8.8 Hz), 8.04 (1H, dd, J=8.8, 2.4 Hz), 8.55 (1H, d, J=2.4 Hz), 11.24 (1H, s). No proton attributable to the carboxylic acid was observed. MS (EI) m/z: 244 M+.

Referential Example 401

Sodium 2-(4-chloro-2-nitroanilino)-2-oxoacetate

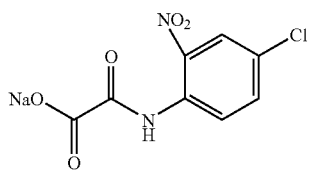

The title compound was obtained by condensing 4-chloro-2-nitroaniline with methyl chlorooxoacetate in a similar manner to the process described in Referential Example 242, hydrolyzing this product in a similar manner to the process described in Referential Example 266, dissolvig the resultant residue in methanol, adding a 1N aqueous solution of sodium hydroxide and collecting precipitate formed by filtration.

¹H-NMR (DMSO-d₆) δ: 7.84 (1H, dd, J=9.0, 2.5 Hz), 8.20 (1H, d, J=2.5 Hz), 8.67 (1H, d, J=9.0 Hz), 11.89 (1H, s).

Referential Example 402

6-Chloro-4-methyl-3-pyridineamine

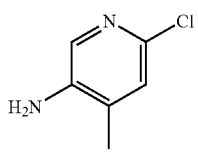

2-Chloro-4-methyl-5-nitropyridine (173 mg) was dissolved in ethanol (5 ml), and a catalytic amount of Raney nickel catalyst was added to stir the mixture at room temperature for 9 hours under a hydrogen atmosphere. The catalyst was removed by filtration, and the solvent was distilled off under reduced pressure. The residue was purified by column chromatography on silica gel (hexane:ethyl acetate=3:2) to obtain the title compound (113 mg).

¹H-NMR (CDCl₃) δ: 2.13 (3H, s), 3.85 (2H, br.s), 6.96 (1H, s), 7.74 (1H, s). MS (EI) m/z: 142 M+.

Referential Example 403

N[1]-(2-Aminophenyl)-N[2]-(4-chlorophenyl)ethanamide

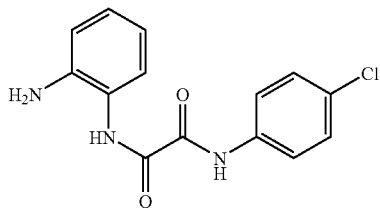

The title compound was obtained by condensing 1,2-benzenediamine with the compound obtained in Referential Example 374 in a similar manner to the process described in Referential Example 59.

$^1$H-NMR (DMSO-$d_6$) δ: 5.00 (2H, s), 6.59-6.63 (1H, m), 6.78 (1H, dd, J=8.1, 1.2 Hz), 6.96-7.01 (1H, m), 7.25 (1H, dd, J=7.8, 1.2 Hz), 7.44 (2H, d, J=8.8 Hz), 7.91 (2H, d, J=8.8 Hz), 10.04 (1H, s), 10.91 (1H, s). MS (FAB): 290 (M+H)+.

Referential Example 404

N-((1R,2S,5S)-2-Azido-5-{[ethyl(methyl)amino]carbonyl}-cyclohexyl)-5-methyl-4,5,6,7-tetrahydrothiazolo[5,4-c]-pyridine-2-carboxamide

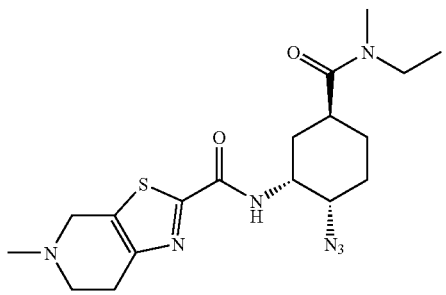

The title compound was obtained by treating the compound obtained in Referential Example 323 with hydrochloric acid, performing deprotection and then condensing this product with the compound obtained in Referential Example 10 in a similar manner to the process described in Referential Example 252.

$^1$H-NMR (CDCl$_3$) δ: 1.08 (1/2 of 3H, t, J=7.2 Hz), 1.14 (1/2 of 3H, t, J=7.2 Hz), 1.70-1.90 (4H, m), 2.10-2.25 (2H, m), 2.52 (3H, s), 2.78-3.00 (8H, m), 3.25-3.45 (2H, m), 3.69 (1H, d, J=13.4 Hz), 3.73 (1H, d, J=13.4 Hz), 3.87-3.95 (1H, m), 4.55-4.62 (1H, m), 7.26 (1H, d, J=7.6 Hz).

Referential Example 405

Phenyl 2-(4-chlorophenyl)-1-hydrazinecarboxylate

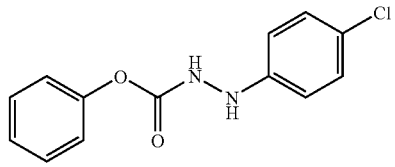

(4-Chlorophenyl)hydrazine hydrochloride (3.00 g) was dissolved in tetrahydrofuran (50 ml), diethyl ether (50 ml) and a saturated aqueous solution of sodium hydrogencarbonate. An organic layer was separated, dried over anhydrous sodium sulfate and then concentrated, giving (4-chlorophenyl)hydrazine as a brown solid. This product was dissolved in benzene (15 ml), and the solution was heated under reflux, to which a solution of diphenyl carbonate (5.22 g) in benzene (8.0 ml) was added dropwise over at least 30 minutes. After refluxing for 19 hours, the reaction mixture was allowed to cool and concentrated. Benzene (15 ml) was then added to the residue. The mixture was subjected to ultrasonic treatment, giving a suspension. After hexane (50 ml) was added to the suspension, and the mixture was stirred for 30 minutes, insoluble matter was collected by filtration and dried to obtain the title compound (1.05 g).

$^1$H-NMR (CDCl$_3$) δ: 5.86 (1H, br.s), 6.83-6.92 (3H, m), 7.17 (1H, br.s), 7.20-7.32 (4H, m), 7.37 (2H, t, J=7.7 Hz). MS (ESI) m/z: 263 (M+H)+.

Referential Example 406

Lithium 5-tert-butoxycarbonyl-5,6-dihydro-4H-pyrrolo[3,4-d]thiazole-2-carboxylate

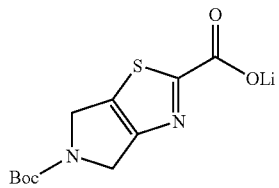

The title compound was obtained from the compound obtained in Referential Example 33 in a similar manner to the process described in Referential Example 10.

$^1$H-NMR (DMSO-$d_6$) δ: 1.46 (9H, s), 4.30-4.70 (4H, m).

Referential Example 407

Benzyl 1-hydroxycyclopropanecarboxylate

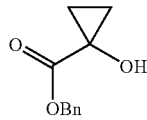

Triethylamine (1.0 ml) and benzyl bromide (650 μl) were added to a solution of 1-hydroxycyclopropanecarboxylic acid (409 mg) in tetrahydrofuran (3.0 ml), and the mixture was stirred at room temperature for 23 hours. Methylene chloride and 1N hydrochloric acid were added to the reaction mixture to separate the mixture into two layers. An organic layer was washed with a saturated aqueous solution of sodium hydrogencarbonate and saturated aqueous solution of sodium chloride and then dried over anhydrous sodium sulfate. A crude product was purified by column chromatography on silica gel (hexane:ethyl acetate=4:1) to obtain the title compound (607 mg).

¹H-NMR (CDCl₃) δ: 1.16 (2H, dd, J=7.9, 4.9 Hz), 1.32 (2H, dd, J=7.9, 4.9 Hz), 3.09 (0.5H, s), 3.11 (0.5H, s), 5.17 (2H, s), 7.30-7.39 (5H, m). MS (FAB) m/z: 192 (M+H)⁺.

Referential Example 408

Benzyl 1-methoxycyclopropanecarboxylate

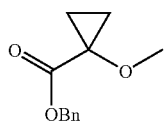

60% Sodium hydride in oil (345 mg) and methyl iodide (900 μl) were added to a solution of the compound (600 mg) obtained in Referential Example 407 in tetrahydrofuran (5.0 ml), and the mixture was heated under reflux for 28 hours. Ethyl acetate and a saturated aqueous solution of ammonium chloride were added to the reaction mixture to separate the mixture into two layers. An organic layer was washed with saturated aqueous solution of sodium chloride and then dried over anhydrous sodium sulfate. A crude product was purified by column chromatography on silica gel (hexane:ethyl acetate=10:1) to obtain the title compound (340 mg).

¹H-NMR (CDCl₃) δ: 1.16 (2H, dd, J=7.9, 4.8 Hz), 1.31 (2H, dd, J=7.9, 4.8 Hz), 3.42 (3H, s), 5.18 (2H, s), 7.30-7.39 (5H, m). MS (FAB) m/z: 207 (M+H)⁺.

Referential Example 409

1-Methoxycyclopropanecarboxylic acid

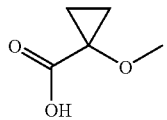

The title compound was obtained from the compound obtained in Referential Example 408 in a similar manner to the process described in Referential Example 152.

¹H-NMR (CDCl₃) δ: 1.23 (2H, dd, J=8.0, 4.9 Hz), 1.38 (2H, dd, J=8.0, 4.9 Hz), 3.45 (3H, s), 8.80-9.00 (1H, br).

Referential Example 410 tert-Butyl (3R,4S)-4-({7-chloroisoquinolin-3-yl}carbonyl)amino}-1-(2-methoxyacetyl)piperidin-3-ylcarbamate

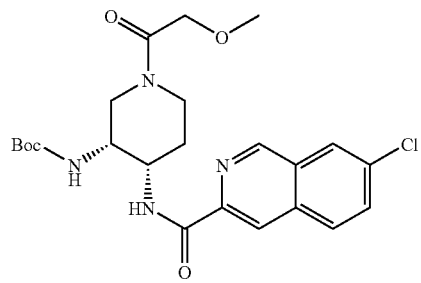

The title compound was obtained from the compound obtained in Referential Example 220 in a similar manner to the process described in Referential Example 214.

¹H-NMR (CDCl₃) δ: 1.46 (9H, br s), 1.62-1.80 (1H, m), 2.04-2.22 (1H, m), 2.95-3.32 (1H, m), 3.38-3.53 (1H, m), 3.46 (3H, s), 3.84-3.95 (1H, m), 4.02-4.27 (3H, m), 4.30-4.65 (2H, m), 4.87-4.98 (0.5H, br), 5.32-5.43 (0.5H, br), 7.71 (1H, dd, J=8.8, 2.0 Hz), 7.94 (1H, d, J=8.8 Hz), 8.02 (1H, s), 8.55-8.66 (0.7H, br), 8.58 (1H, s), 8.73-8.85 (0.3H, br), 9.14 (1H, br s). MS (ESI) m/z: 477 (M+H)⁺.

Referential Example 411 tert-Butyl (3R,4S)-4-{[2-(4-chloro-3-fluoroanilino)-2-oxoacetyl]amino}-1-(2-methoxyacetyl)piperidin-3-ylcarbamate

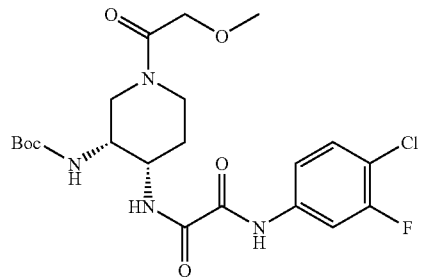

The title compound was obtained by condensing the compound obtained in Referential Example 220 with the compound obtained in Referential Example 337 in a similar manner to the process described in Referential Example 214.

¹H-NMR (CDCl₃) δ: 1.46 (9H, s), 1.60-1.75 (1H, m), 1.92-2.08 (1H, m), 2.68-2.80 (0.5H, m), 2.88-3.03 (0.5H, m), 3.06-3.24 (0.5H, m), 3.27-3.36 (0.5H, m), 3.45 (3H, s), 3.90-4.22 (5H, m), 4.56-4.71 (1H, m), 4.80-4.92 (0.3H, br), 5.44-5.54 (0.7H, br), 7.24 (1H, d, J=12.9 Hz), 7.35 (1H, t, J=8.3 Hz), 7.72 (1H, dd, J=8.3, 2.3 Hz), 8.20-8.42 (1H, br), 9.18-9.28 (1H, br). MS (ESI) m/z: 487 (M+H)⁺.

Referential Example 412 tert-Butyl (3R,4S)-4-({2-[(5-chloro-2-thienyl)amino]-2-oxoacetyl}amino)-1-(2-methoxyacetyl)piperidin-3-ylcarbamate

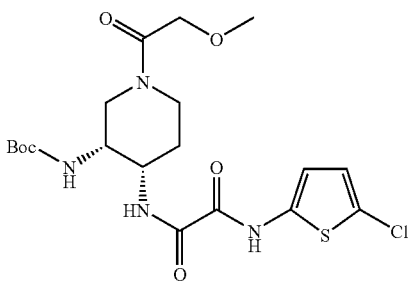

The title compound was obtained from the compound obtained in Referential Example 220 and the lithium salt of a carboxylic acid obtained by hydrolyzing the compound obtained in Referential Example 356 in a similar manner to the process described in Referential Example 214.

¹H-NMR (CDCl₃) δ: 1.45 (9H, s), 1.55-1.75 (1H, br), 1.90-2.10 (1H, br), 2.68-2.80 (0.7H, m), 2.90-3.03 (0.3H, br), 3.07-3.22 (0.3H, br), 3.25-3.35 (0.7H, br), 3.45 (3H, s), 3.83-4.22 (5H, m), 4.55-4.70 (1H, br), 4.80-4.90 (0.2H, br), 5.07-5.14 (0.2H, br), 5.44-5.55 (0.6H, br), 6.58-6.64 (1H, br), 6.73 (1H, d, J=3.9 Hz), 8.05-8.27 (1H, br), 9.65-9.88 (1H, br). MS (FAB) m/z: 475 (M+H)⁺.

Referential Example 413

Ethyl 5-methyl-5H-pyrrolo[3,4-d]thiazolo-2-carboxylate

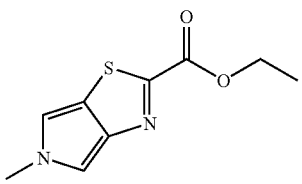

1) Ethyl 2-thioxoacetate (26.75 g) was added to a solution of 3-bromo-2-butanone (26.36 g) in ethanol (250 ml), and the mixture was heated under reflux for 14 hours. After cooling the reaction mixture, it was concentrated, and ethyl acetate and saturated aqueous solution of sodium chloride were added to separate the mixture into two layers. An organic layer was washed with a saturated aqueous solution of sodium hydrogencarbonate and saturated aqueous solution of sodium chloride and then dried over anhydrous sodium sulfate. The solvent was distilled off under reduced pressure, and the residue was purified by column chromatography on silica gel (hexane:ethyl acetate=6:1) to obtain ethyl 4,5-dimethylthiazole-2-carboxylate (19.53 g).

¹H-NMR (CDCl₃) δ: 1.42 (3H, t, J=7.1 Hz), 2.42 (3H, s), 2.44 (3H, s), 4.45 (2H, q, J=7.1 Hz).

2) N-Bromosuccinimide (62.42 g) and 2,2'-azobisisobutyronitrile (227 mg) were added to a solution of the above-described product (19.53 g) in 1,2-dichloroethane (500 ml), and the mixture was refluxed for 42 hours. After cooling the reaction mixture, water and methylene chloride were added to separate the mixture into two layers. An organic layer was washed with saturated aqueous solution of sodium chloride and then concentrated under reduced pressure to obtain a crude product (40.54 g) as a dark brown oil. Triethylamine (8.0 ml) and a 2 M tetrahydrofuran solution (11.0 ml) of methylamine were added to the crude product (8.41 g), and the mixture was stirred at room temperature for 3 days. After the reaction mixture was concentrated under reduced pressure, methylene chloride and saturated aqueous solution of sodium chloride were added to the residue to separate the mixture into two layers. An organic layer was washed with saturated aqueous solution of sodium chloride and then dried over anhydrous sodium sulfate. The solvent was distilled off under reduced pressure, and the residue was purified by column chromatography on silica gel (hexane:ethyl acetate=3:1) to obtain the title compound (270 mg).

¹H-NMR (CDCl₃) δ: 1.45 (3H, t, J=7.1 Hz), 3.91 (3H, s), 4.48 (2H, q, J=7.1 Hz), 6.73 (1H, d, J=1.7 Hz), 7.30 (1H, d, J=1.7 Hz). MS (ESI) m/z: 211 (M+H)⁺.

Referential Example 414

Ethyl 6-chloro-4-oxo-4H-chromene-2-carboxylate

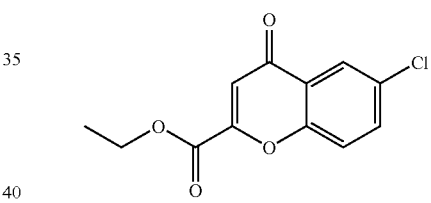

About 60% sodium hydride in oil (1.68 g) was added to ethanol (10 ml) under purging with argon, and the mixture was stirred at room temperature for 10 minutes. After diethyl oxalate (3.36 ml) was added, an ethanol solution (20 ml) of 5'-chloro-2'-hydroxyacetophenone (2.82 g) was added dropwise. Ethanol (40 ml) was additionally added, and the mixture was refluxed for 1.5 hours and stirred at 50° C. for 14 hours. Concentrated sulfuric acid (1.5 ml) and ethanol (10 ml) were added to the reaction mixture, and the resultant mixture was refluxed for 4 hours. After cooling, the solvent was decreased to a half by concentration under reduced pressure. Toluene and a 1N aqueous solution (15 ml) of sodium hydroxide were added to the concentrated the reaction mixture. Extraction was conducted with ethyl acetate, and the resultant organic layer was washed with saturated aqueous solution of sodium chloride and then dried over anhydrous sodium sulfate. After the solvent was distilled off under reduced pressure, and the residue was purified by column chromatography on silica gel (hexane:ethyl acetate=7:1), the resultant solids were washed with hexane to obtain the title compound (1.20 g).

¹H-NMR (CDCl₃) δ: 1.44 (3H, t, J=7.1 Hz), 4.47 (2H, q, J=7.1 Hz), 7.12 (1H, s), 7.58 (1H, d, J=9.0 Hz), 7.69 (1H, dd, J=9.0, 2.7 Hz), 8.16 (1H, d, J=2.7 Hz). MS (ESI) m/z: 293 (M+MeCN+H)⁺.

Referential Example 415

6-Chloro-4-oxo-4H-chromene-2-carboxylic acid

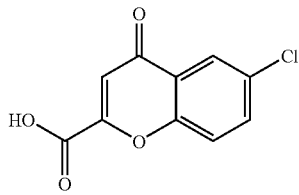

The title compound was obtained from the compound obtained in Referential Example 414 in a similar manner to the process described in Referential Example 359.

$^1$H-NMR (CDCl$_3$) δ: 7.12 (1H, s), 7.60 (1H, d, J=8.8 Hz), 7.69 (1H, dd, J=8.8, 2.7 Hz), 8.15 (1H, d, J=2.7 Hz). MS (FAB) m/z: 225 (M+H)$^+$.

Referential Example 416

Ethyl (1S,3R,4S)-4-amino-3-[(tert-butoxycarbonyl)amino]-cyclohexanecarboxylate

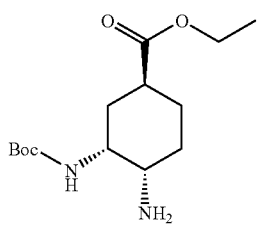

The title compound was obtained from the compound obtained in Referential Example 249 in a similar manner to the process described in Referential Example 90.

$^1$H-NMR (CDCl$_3$) δ: 1.20-1.80 (4H, m), 1.25 (3H, t, J=7.3 Hz), 1.46 (9H, s), 1.85-2.00 (1H, m), 2.10-2.20 (1H, m), 2.30-2.45 (1H, m), 2.90-3.00 (1H, m), 3.84 (1H, br s), 4.12 (2H, q, J=7.3 Hz), 4.75 (1H, br s).

Referential Example 417 tert-Butyl (1R,2S,5S)-2-{[(6-chloro-4-oxo-4H-chromen-2-yl)carbonyl]amino}-5-[(dimethylamino)carbonyl]cyclohexylcarbamate

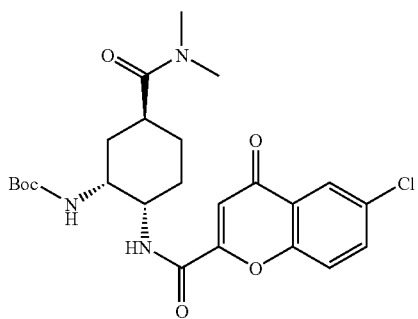

N,N-Dimethylformamide (0.02 ml) was added to a solution of the compound (213 mg) obtained in Referential Example 415 in thionyl chloride (2.0 ml), and the mixture was refluxed for 15 minutes. The reaction mixture was concentrated under reduced pressure, and the residue was dissolved in tetrahydrofuran (4.0 ml). To the solution were added triethylamine (500 μl) and the compound (294 mg) obtained in Referential Example 144, and the mixture was stirred at room temperature for 15 minutes. Ethyl acetate and a 10% aqueous solution of citric acid to separate the reaction mixture into two layers. An organic layer was washed with a saturated aqueous solution of sodium hydrogencarbonate and saturated aqueous solution of sodium chloride, dried over anhydrous sodium sulfate and then concentrated under reduced pressure. The residue was purified by column chromatography on silica gel (methylene chloride:methanol=30:1) to obtain the title compound (230 mg).

$^1$H-NMR (CDCl$_3$) δ: 1.33-1.77 (3H, m), 1.50 (9H, s), 1.81-2.34 (3H, m), 2.63-2.80 (1H, m), 2.95 (3H, s), 3.10 (3H, s), 3.90-4.04 (1H, br), 4.18-4.31 (1H, br), 4.93-5.12 (1H, br), 7.13 (1H, s), 7.55 (1H, d, J=8.8 Hz), 7.66 (1H, dd, J=8.8, 2.4 Hz), 8.14 (1H, d, J=2.4 Hz), 8.77-8.92 (1H, br). MS (ESI) m/z: 492 (M+H)$^+$.

Referential Example 418 tert-Butyl (3R,4S)-4-{[(7-chlorocinnolin-3-yl)carbonyl]amino}-1-(2-methoxyacetyl)piperidin-3-ylcarbamate

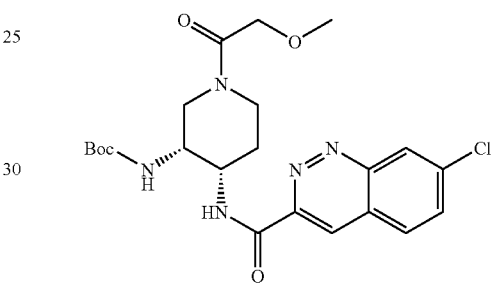

The title compound was obtained from the compound obtained in Referential Example 220 and the lithium salt of a carboxylic acid obtained by hydrolyzing the ester described in Referential Example 297 in a similar manner to the process described in Referential Example 214.

$^1$H-NMR (CDCl$_3$) δ: 1.38 (9H, s), 1.65-1.90 (1H, m), 1.90-2.15 (1H, m), 2.80-3.00 (0.6H, m), 3.00-3.15 (0.4H, m), 3.20-3.50 (1H, m), 3.46 (3H, s), 3.80-4.70 (6H, m), 4.87 (0.4H, br s), 5.30 (0.6H, br s), 7.78 (1H, d, J=8.8 Hz), 7.97 (1H, d, J=8.8 Hz), 8.61 (1H, s), 8.62-8.90 (1H, br), 8.73 (1H, s). MS (ESI) m/z: 478 (M+H)$^+$.

Referential Example 419 tert-Butyl (1R,2S,5S)-2-({2-[(5-chloropyridin-2-yl)amino]-2-oxoacetyl}amino)-5-[(dimethylamino)carbonyl]cyclohexylcarbamate

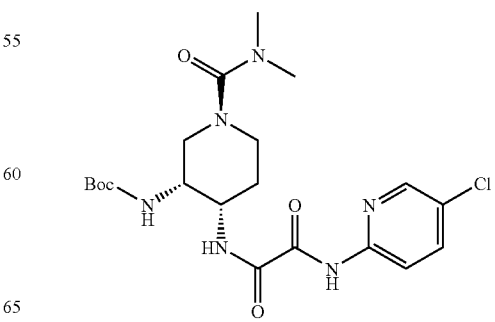

The title compound was obtained by condensing the compound obtained in Referential Example 144 with the compound obtained in Referential Example 266 in a similar manner to the process described in Referential Example 68.

$^1$H-NMR (CDCl$_3$) δ: 1.35-1.65 (1H, m), 1.45 (9H, s), 1.65-1.89 (2H, m), 1.90-2.10 (3H, m), 2.56-2.74 (1H, br), 2.95 (3H, s), 3.06 (3H, s), 3.94-4.01 (1H, m), 4.18-4.27 (1H, m), 4.70-4.90 (0.7H, br), 5.80-6.20 (0.3H, br), 7.68 (1H, dd, J=8.9, 2.6 Hz), 7.83 (1H, br s), 8.14 (1H, br d, J=7.8 Hz), 8.30 (1H, s), 9.72 (1H, s). MS (ESI) m/z: 468 (M+H)$^+$.

Referential Example 420

N$^1$-{(1S,2R,4S)-2-Amino-4-[(dimethylamino)carbonyl]-cyclohexyl}-N$^2$-(5-chloropyridin-2-yl)ethanediamide hydrochloride

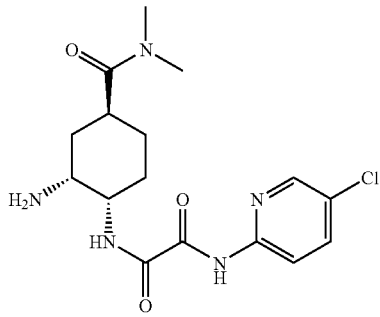

The title compound was obtained from the compound obtained in Referential Example 419 in a similar manner to the process described in Referential Example 69.

$^1$H-NMR (DMSO-d$_6$) δ: 1.38-1.51 (1H, m), 1.65-1.85 (3H, m), 1.96-2.10 (2H, m), 2.81 (3H, s), 3.07 (3H, s), 3.23-3.33 (1H, m), 3.74 (1H, br s), 3.84-3.92 (1H, m), 8.02 (1H, dd, J=9.0, 2.5 Hz), 8.07 (1H, d, J=9.0 Hz), 8.34 (3H, br s), 8.46 (1H, d, J=2.5 Hz), 8.96 (1H, d, J=6.6 Hz), 10.34 (1H, s). MS (ESI) m/z: 368 (M+H)$^+$.

Referential Example 421 tert-Butyl 2-[({(1R,2S,5S)-2-({2-[(5-chloropyridin-2-yl)amino]-2-oxoacetyl}amino)-5-[(dimethylamino)carbonyl]-cyclohexyl}amino)carbonyl]-6,7-dihydrothieno[3,2-c]-pyridine-5(4H)-carboxylate

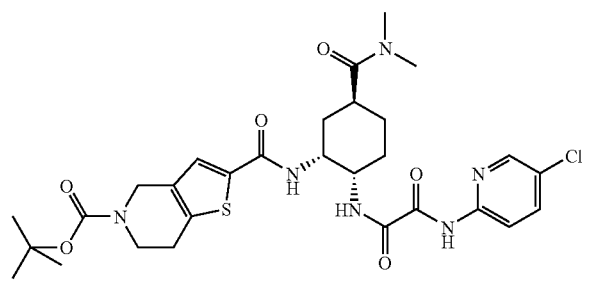

The title compound was obtained by condensing the compound obtained in Referential Example 420 with 5-(tert-butoxycarbonyl)-4,5,6,7-tetrahydrothieno[3,2-c]pyridine-2-carboxylic acid (WO94/21599).

$^1$H-NMR (CDCl$_3$) δ: 1.50 (9H, s), 1.73-1.95 (3H, m), 1.95-2.06 (1H, m), 2.08-2.20 (2H, m), 2.82 (3H, br s), 2.94 (3H, s), 3.03 (3H, s), 3.60-3.80 (2H, m), 3.96-4.08 (1H, m), 4.44 (2H, br s), 4.66 (1H, br s), 6.74 (1H, br s), 7.20-7.32 (1H, m), 7.66 (1H, dd, J=9.0, 2.4 Hz), 8.13 (1H, d, J=9.0 Hz), 8.13-8.25 (1H, m), 8.28 (1H, d, J=2.4 Hz), 9.75 (1H, s). MS (ESI) m/z: 633 (M+H)$^+$.

Referential Example 422

2-Chloro-N-(4-fluorophenyl)acetamide

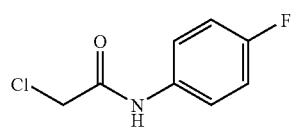

The title compound was obtained from p-fluoroaniline in a similar manner to the process described in Referential Example 350.

$^1$H-NMR (CDCl$_3$) δ: 4.19 (2H, s), 7.05 (2H, t, J=8.6 Hz), 7.51 (2H, dd, J=9.1, 4.7 Hz), 8.19 (1H, br s).

Referential Example 423

Sodium S-[2-(4-fluoroanilino)-2-oxoethyl]thiosulfate

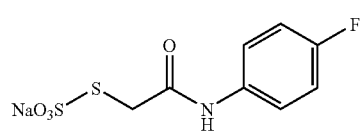

The title compound was obtained from the compound obtained in Referential Example 422 in a similar manner to the process described in Referential Example 351.

$^1$H-NMR (DMSO-d$_6$) δ: 3.72 (2H, s), 7.14 (2H, t, J=9.0 Hz), 7.56 (2H, dd, J=9.0, 5.1 Hz), 10.21 (1H, s).

Referential Example 424 tert-Butyl (1R,2S,5S)-5-[(dimethylamino)carbonyl]-2-{[2-(4-fluoroanilino)-2-oxoethanethioyl]amino}cyclohexylcarbamate

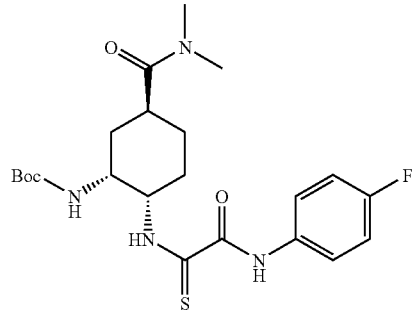

The compound (1.1 g) obtained in Referential Example 144 and the compound (1.2 g) obtained in Referential Example 423 were dissolved in N-methylmorpholine (20 ml), and the temperature of a bath was raised from room temperature to 140° C. over 15 minutes to heat and stir the mixture for 15 minutes at the same temperature. After allowing to cool, ice water was added to the reaction mixture to collect insoluble matter by filtration. This product was purified by column chromatography on silica gel (methylene chloride:methanol=200:1→197:3) to obtain the title compound (1.43 g).

$^1$H-NMR (CDCl$_3$) δ: 1.45 (9H, s), 1.70-2.10 (5H, m), 2.10-2.30 (1H, m), 2.60-2.80 (1H, m), 2.96 (3H, s), 3.07 (3H, s), 4.30-4.50 (2H, m), 4.65-4.85 (1H, m), 7.06 (2H, t, J=8.5 Hz), 7.50-7.70 (2H, m), 9.75-9.95 (1H, m), 10.13 (1H, s). MS (ESI) m/z: 467 (M+H)$^+$.

Referential Example 425

2-Chloro-N-(5-fluoropyridin-2-yl)acetamide

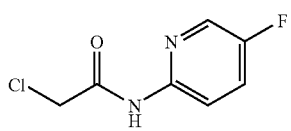

The title compound was obtained from 2-amino-5-fluoropyridine in a similar manner to the process described in Referential Example 352.

$^1$H-NMR (DMSO-d$_6$) δ: 4.35 (2H, s), 7.74-7.82 (1H, m), 8.10 (1H, dd, J=9.0, 4.2 Hz), 8.36 (1H, d, J=2.9 Hz), (1H, br s). MS (ESI) m/z: 188 (M+H)$^+$.

Referential Example 426

Sodium S-{2-[(5-fluoropyridin-2-yl)amino]-2-oxoethyl}thiosulfate

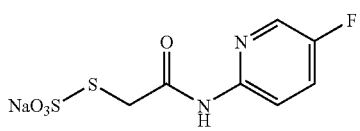

The title compound was obtained from the compound obtained in Referential Example 425 in a similar manner to the process described in Referential Example 353.

$^1$H-NMR (DMSO-d$_6$) δ: 3.75 (2H, s), 7.67-7.77 (1H, m), 8.07 (1H, dd, J=9.2, 4.2 Hz), 8.28 (1H, d, J=2.9 Hz), 10.48 (1H, s).

Referential Example 427 tert-Butyl (1R,2S,5S)-5-[(dimethylamino)carbonyl]-2-({2-[(5-fluoropyridin-2-yl)amino]-2-oxoethanethioyl}amino)cyclohexylcarbamate

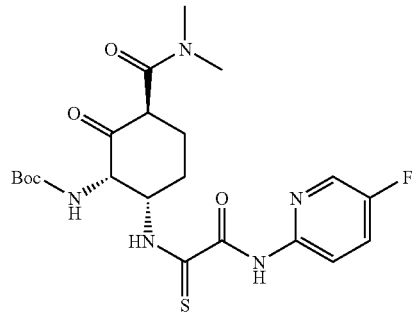

A solution of the compound (1.20 g) obtained in Referential Example 144 in pyridine (70 ml) was heated to 120° C., and the compound (2.42 g) obtained in Referential Example 426 was added. After stirring the mixture for 30 minutes, the reaction mixture was allowed to cool to room temperature, and the solvent was distilled off under reduced pressure. Methylene chloride (100 ml), a saturated aqueous solution (100 ml) of sodium hydrogencarbonate and water (50 ml) were added to the resultant residue to conduct liquid separation. A water layer was then extracted with methylene chloride. Organic layers were combined and dried over anhydrous sodium sulfate, and the solvent was then distilled off under reduced pressure. The resultant residue was purified by column chromatography on silica gel (hexane:tetrahydrofuran=1:1). After the resultant solids were slurried for 1 hour in isopropyl ether (40 ml), they were collected by filtration and dried to obtain the title compound (920 mg).

$^1$H-NMR (CDCl$_3$) δ: 1.47 (9H, s), 1.70-2.10 (5H, m), 2.27 (1H, br s), 2.70 (1H, br s), 2.96 (3H, s), 3.08 (3H, s), 4.34-4.44 (2H, m), 4.77 (1H, br s), 7.44-7.51 (1H, m), 8.18-8.27 (2H, m), 9.90 (1H, br s), 10.57 (1H, s). MS (ESI) m/z: 468 (M+H)$^+$.

Referential Example 428 tert-Butyl (1R,2S,5S)-2-({2-[(5-chloropyridin-2-yl)amino]-2-oxoethanethioyl}amino)-5-[(dimethylamino)carbonyl]-cyclohexylcarbamate

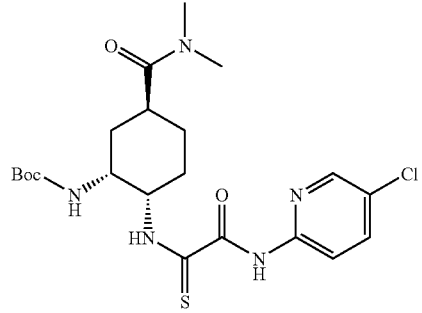

The title compound was obtained from the compound obtained in Referential Example 144 and the compound obtained in Referential Example 353 in a similar manner to the process described in Referential Example 427.

$^1$H-NMR (CDCl$_3$) δ: 1.43 (9H, s), 1.65-2.35 (6H, m), 2.70 (1H, br s), 2.95 (3H, s), 3.09 (3H, s), 4.30-4.60 (2H, m), 4.87 (1/2H, br s), 6.92 (1/2H, br s), 7.69 (1H, dd, J=8.9, 2.6 Hz), 7.95-8.20 (1H, br), 8.29 (1H, s), 9.67 (1/2H, br s), 9.93 (1/2H, br s), 10.54 (1H, br s).

Referential Example 429

2-Chloro-4,5,6,7-tetrahydrobenzothiazol-6-ylformamide

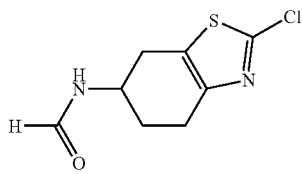

Ammonium acetate (18.58 g) and sodium cyanoborohydride (10.68 g) were added to a solution of 2-chloro-5-oxo-4,5,6,7-tetrahydrobenzo[d]thiazole (Helv. Cim. Acta., 1994, Vol. 77, p. 1256) (4.53 g) in methanol (200 ml), and the mixture was heated under reflux. After 19 hours, hydrochloric acid was added to decompose excessive reagents before the reaction mixture was concentrated under reduced pressure. After the residue was alkalified with a 1N aqueous solution of sodium hydroxide, methylene chloride was added to conduct liquid separation. The resultant organic layer was dried over anhydrous magnesium sulfate, and the solvent was distilled off under reduced pressure. The resultant residue was subjected to column chromatography on silica gel (methylene chloride:methanol=20:1), and the solvent was distilled off to obtain a pale yellow oil (2.42 g). This oil was dissolved in methylene chloride (100 ml), and formic acid (530 µl), 1-(3-dimethylaminopropyl)-3-ethylcarbodiimide hydrochloride (3.68 g), 1-hydroxybenzotriazole (2.60 g) and N-methylmorpholine (3.88 g) were added to stir the mixture at room temperature. After 20 hours, methylene chloride and a saturated aqueous solution of sodium hydrogencarbonate were added to the reaction mixture to conduct liquid separation. The resultant organic layer was dried over anhydrous magnesium sulfate, the solvent was then distilled off under reduced pressure, and the resultant residue was purified by column chromatography on silica gel (methylene chloride:methanol=20:1) to obtain the title compound (2.21 g).

$^1$H-NMR (CDCl$_3$) δ: 1.93-2.11 (2H, m), 2.63-2.69 (1H, m), 2.83-2.89 (2H, m), 3.13 (1H, dd, J=16.2, 4.4 Hz), 4.46-4.48 (1H, m), 5.76 (1H, br s), 8.17 (1H, s).

Referential Example 430 tert-Butyl N-(2-chloro-4,5,6,7-tetrahydrobenzothiazol-6-yl)-N-methylcarbamate

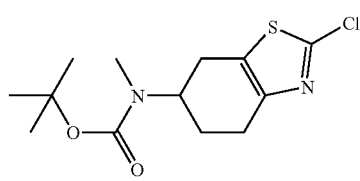

A 1 M tetrahydrofuran solution (14.6 ml) of borane-tetrahydrofuran complex was added to a solution of the compound (2.11 g) obtained in Referential Example 429 in tetrahydrofuran (50 ml), and the mixture was heated under reflux. After 15 hours, a 1 M tetrahydrofuran solution (6.0 ml) of borane-tetrahydrofuran complex was additionally added to heat the mixture under reflux. After 4 hours, ethanol (10 ml) and 1N hydrochloric acid (15 ml) were added to heat the mixture under reflux. After 3 hours, the reaction mixture was concentrated under reduced pressure. A 1N aqueous solution of sodium hydroxide and methylene chloride were added to the residue to conduct liquid separation. The resultant organic layer was dried over anhydrous magnesium sulfate, and the solvent was distilled off under reduced pressure. The resultant residue was dissolved in methylene chloride (50 ml), and triethylamine (1.28 g) and di-tert-butyl dicarbonate (2.21 g) were added to stir the mixture at room temperature. After 30 minutes, methylene chloride and 1N hydrochloric acid were added to conduct liquid separation. The resultant organic layer was dried over anhydrous magnesium sulfate, and the solvent was distilled off under reduced pressure. The resultant residue was purified by column chromatography on silica gel (hexane:ethyl acetate=2:1) to obtain the title compound (2.26 g).

$^1$H-NMR (CDCl$_3$) δ: 1.47 (9H, s), 1.96-1.98 (2H, m), 2.80-2.96 (7H, m), 4.40-4.50 (1H, m). MS (FAB) m/z: 303 (M+H)$^+$.

Referential Example 431 tert-Butyl N-(2-[({(1R,2S,5S)-2-({2-[(5-chloropyridin-2-yl)amino]-2-oxoacetyl}amino)-5-[(dimethylamino)carbonyl]-cyclohexyl}amino)carbonyl]-4,5,6,7-tetrahydrobenzothiazol-6-yl)-N-methylcarbamate

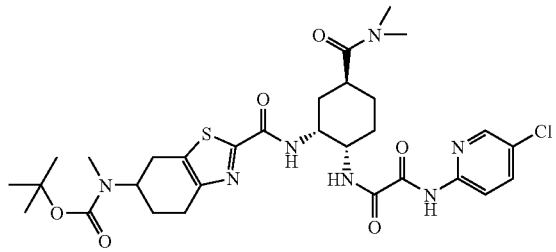

After a solution of the compound (1.0 g) obtained in Referential Example 430 in diethyl ether (10 ml)-tetrahydrofuran (5 ml) was cooled −78° C., a 1.6N pentane solution (3.1 ml) of tert-butyllithium was added, and the mixture was stirred for 20 minutes. Carbon dioxide was then introduced for 20 minutes. The reaction mixture was warmed to room temperature and concentrated under reduced pressure, giving lithium 6-[(tert-butoxycarbonyl)(methyl)amino]-4,5,6,7-tetrahydrobenzothiazole-2-carboxylate.

The lithium salt (350.2 mg) of the carboxylic acid obtained by the above-described reaction, 1-(3-dimethylaminopropyl)-3-ethylcarbodiimide hydrochloride (287.6 mg), 1-hydroxybenzotriazole (202.7 mg) and N-methylmorpholine (0.319 ml) were added to a solution of the compound (490.5 mg) obtained in Referential Example 420 in N,N-dimethylformamide (20 ml), and the mixture was stirred at room temperature for 4 days. The solvent was distilled off under reduced pressure, and water and methylene chloride were added to the residue to conduct liquid separation. The resultant organic layer was then successively washed with a saturated aqueous solution of sodium hydrogencarbonate and saturated aqueous solution of sodium chloride. The organic layer was dried over anhydrous sodium sulfate, concentrated under reduced pressure and purified by column chromatography on silica gel (methylene chloride:methanol=40:1→20:1) to obtain the title compound (323.9 mg).

$^1$H-NMR (CDCl$_3$) δ: 1.48, 1.49 (total 9H, each s), 1.60-1.92 (4H, m), 1.95-2.20 (6H, m), 2.78-3.10 (3H, m), 2.83 (3H, s), 2.95 (3H, s), 3.06, 3.07 (total 3H, each s), 4.05-4.15 (1H, m), 4.20-4.60 (1H, m), 4.63-4.73 (1H, m), 7.39 (1H, d, J=8.6 Hz), 7.68 (1H, dt, J=8.8, 2.6 Hz), 7.95-8.10 (1H, m), 8.13-8.22 (1H, m), 8.30-8.35 (1H, m), 9.72 (1H, brs). MS (ESI) m/z: 662 (M+H)$^+$.

Referential Example 432

N-{(1S,2R,4S)-2-Amino-4-[(dimethylamino)carbonyl]-cyclohexyl}-5-chloroindole-2-carboxamide hydrochloride

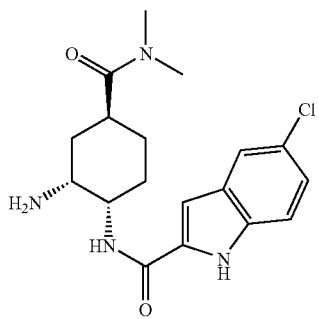

The title compound was obtained by deprotecting the compound obtained in Referential Example 310 in a similar manner to the process described in Referential Example 69.

$^1$H-NMR (DMSO-d$_6$) δ: 1.43-1.56 (0.5H, m), 1.72-1.97 (4.5H, m), 2.82 (3H, s), 3.06 (3H, s), 3.11-3.26 (1H, m), 3.75-3.84 (1H, m), 4.07-4.14 (1H, m), 4.22-4.41 (1H, m), 7.19 (1H, dd, J=2.0, 8.8 Hz), 7.29 (1H, d, J=2.0 Hz), 7.45 (1H, d, J=8.8 Hz), 7.72 (1H, s), 8.07 (3H, br), 8.47 (1H, m), 11.85 (1H, br).

Referential Example 433

Lithium 2-[(5-chloropyridin-2-yl)amino]-2-oxoacetate

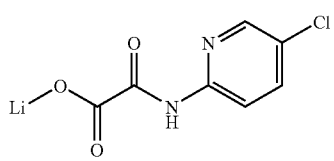

Methyl chlorooxoacetate (78.7 ml) was added dropwise to a suspension of 2-amino-5-chloropyridine (100 g) and sodium hydrogencarbonate (78.4 g) in tetrahydrofuran (2000 ml) at 0° C., and the mixture was stirred at room temperature for 2 hours. After the reaction mixture was added to a mixture of diethyl ether (2000 ml), ammonium chloride (62.4 g) and water (1000 ml), liquid separation was performed. The resultant water layer was extracted with methylene chloride. Organic layers were combined and dried over anhydrous sodium sulfate, and the solvent was distilled off under reduced pressure to obtain methyl 2-[(5-chloropyridin-2-yl)amino]-2-oxoacetate (162 g). Water (450 ml) and lithium hydroxide (18.2 g) were added to a solution of this ester (160 g) in tetrahydrofuran (1800 ml). After the mixture was stirred at room temperature for 2 hours, the solvent was distilled off under reduced pressure, and hexane (3000 ml) was added to the resultant residue to stir the mixture for 3 hours. Solids were collected by filtration and dried. Acetonitrile (1000 ml) was added to the solids (190 g), and the mixture was stirred for 1 hour. Solids formed were collected by filtration, washed with diethyl ether (500 ml) and then dried to obtain the title compound (158 g).

$^1$H-NMR (DMSO-d$_6$) δ: 7.92 (1H, dd, J=9.1, 2.7 Hz), 8.13 (1H, dd, J=9.1, 0.5 Hz), 8.36 (1H, dd, J=2.7, 0.5 Hz), 10.19 (1H, s).

Referential Example 434 tert-Butyl (1R,2S,5S)-2-({2-[(5-chloropyridin-2-yl)amino]-2-oxoacetyl}amino)-5-[(dimethylamino)carbonyl]cyclohexylcarbamate

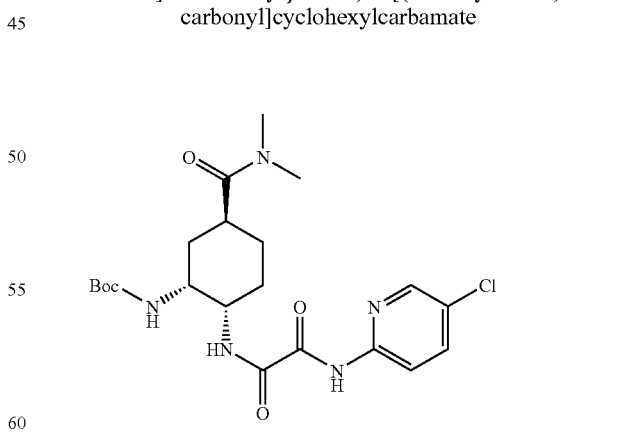

The title compound was obtained from the compound obtained in Referential Example 144 and the compound obtained in Referential Example 433 in a similar manner to Referential Example 91.

$^1$H-NMR (CDCl$_3$) δ: 1.25-1.55 (1H, m), 1.45 (9H, s), 1.60-2.15 (5H, m), 2.56-2.74 (1H, br), 2.95 (3H, s), 3.06

(3H, s), 3.90-4.01 (1H, m), 4.18-4.27 (1H, m), 4.70-4.85 (0.7H, br), 5.70-6.00 (0.3H, br), 7.70 (1H, dd, J=8.8, 2.4 Hz), 7.75-8.00 (1H, br), 8.16 (1H, br d, J=8.8 Hz), 8.30 (1H, d, J=2.4 Hz), 9.73 (1H, s). MS (ESI) m/z: 468 (M+H)$^+$.

Referential Example 435

N$^1$-{(1S,2R,4S)-2-Amino-4-[(dimethylamino)carbonyl]-cyclohexyl}-N$^2$-(5-chloropyridin-2-yl)ethanediamide hydrochloride

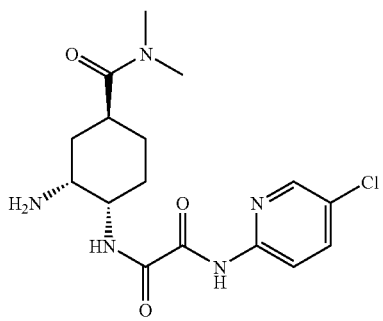

The title compound was obtained from the compound obtained in Referential Example 434 in a similar manner to Referential Example 69.

$^1$H-NMR (DMSO-d$_6$) δ: 1.38-1.51 (1H, m), 1.65-1.85 (3H, m), 1.92-2.09 (2H, m), 2.80 (3H, s), 3.06 (3H, s), 3.20-3.32 (1H, m), 3.55-4.40 (2H, br), 8.02 (1H, dd, J=9.1, 2.5 Hz), 8.07 (1H, d, J=9.1 Hz), 8.15-8.40 (3H, br), 8.45 (1H, d, J=2.5 Hz), 8.96 (1H, d, J=6.6 Hz), 10.33 (1H, s).

Example 1

N-((1R*,2S*)-2-{[(5-Chloroindol-2-yl)carbonyl]amino}cyclopropyl)-5-methyl-4,5,6,7-tetrahydrothiazolo[5,4-c]pyridine-2-carboxamide hydrochloride

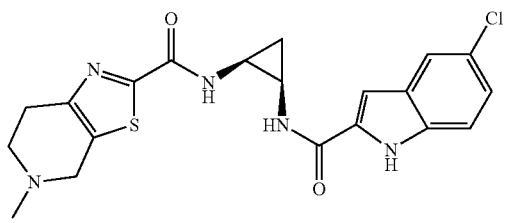

1-Hydroxybenzotriazole monohydrate (71 mg) and 1-(3-dimethylaminopropyl)-3-ethylcarbodiimide hydrochloride (100 mg) were added to a solution with the compound (108 mg) obtained in Referential Example 59 and the compound (124 mg) obtained in Referential Example 10 dissolved in N,N-dimethylformamide (3 ml) at room temperature, and the mixture was stirred for 8 days. After concentrating the reaction mixture under reduced pressure using a vacuum pump, water (50 ml) and a saturated aqueous solution (50 ml) of sodium hydrogencarbonate were added to the residue to conduct extraction with methylene chloride. The resultant organic layers were combined and dried over anhydrous sodium sulfate, the solvent was distilled off under reduced pressure, and the residue was purified by preparative thin-layer chromatography on silica gel (methylene chloride:methanol=10:1). After 1N hydrochloric acid, methylene chloride and methanol were added to the thus-obtained amorphous substance, the mixture was concentrated to obtain the title compound (72 mg).

$^1$H-NMR (DMSO-d$_6$) δ: 1.15-1.35 (2H, m), 2.88 (3H, s), 2.95-3.25 (4H, m), 3.35-3.75 (2H, m), 4.32-4.45 (1H, m), 4.68 (1H, br, J=15.4 Hz), 7.08 (1H, s), 7.17 (1H, dd, J=8.6, 2.1 Hz), 7.41 (1H, d, J=8.6 Hz), 7.70 (1H, s), 8.50 (1H, br, J=11.0 Hz), 8.56 (1H, br.s), 11.56 (1H, br, J=19.3 Hz), 11.86 (1H, s). MS (FAB) m/z: 430 (M+H)$^+$.

Example 2

N-((1R*,2S*)-2-{[(5-Chloroindol-2-yl)carbonyl]amino}-cyclobutyl)-5-methyl-4,5,6,7-tetrahydrothiazolo[5,4-c]-pyridine-2-carboxamide hydrochloride

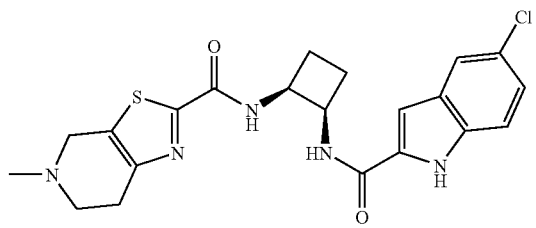

The compound (136 mg) obtained in Referential Example 10, 1-(3-dimethylaminopropyl)-3-ethylcarbodiimide hydrochloride (255 mg) and 1-hydroxybenzotriazole monohydrate (90 mg) were added to a solution with the compound (117 mg) obtained in Referential Example 60 dissolved in N,N-dimethylformamide (5 ml), and the mixture was stirred overnight at room temperature. The solvent was then distilled off under reduced pressure using a vacuum pump, and methylene chloride and a saturated aqueous solution of sodium hydrogencarbonate were added to the residue to conduct liquid separation. The resultant organic layer was washed with saturated aqueous solution of sodium chloride and dried over anhydrous sodium sulfate, the solvent was distilled off under reduced pressure, and the residue was purified by column chromatography on silica gel (methanol:methylene chloride=7:93). After ethyl acetate and a 1N ethanol solution of hydrochloric acid were added to the thus-obtained compound to acidify it, and the solvent was distilled off under reduced pressure. Ethyl acetate was added again, and precipitate formed was collected by filtration and dried to obtain the title compound (56 mg).

$^1$H-NMR (DMSO-d$_6$) δ: 2.00-2.35 (4H, m), 2.88 (3H, m), 3.10 (2H, br.s), 3.20-3.75 (3H, m), 4.20-4.85 (3H, m), 7.09 (1H, s), 7.16 (1H, d, J=8.8 Hz), 7.38 (1H, d, J=8.8 Hz), 7.71 (1H, s), 8.63 (1H, d, J=8.3 Hz), 8.85 (1H, d, J=8.6 Hz), 10.85-11.20 (1H, br), 11.81 (1H, s). MS (FAB) m/z: 444 (M+H)$^+$.

Example 3

N-((1R*,2R*)-2-{[(5-Chloroindol-2-yl)carbonyl]amino}-cyclopentyl)-5-methyl-4,5,6,7-tetrahydrothiazolo[5,4-c]-pyridine-2-carboxamide hydrochloride

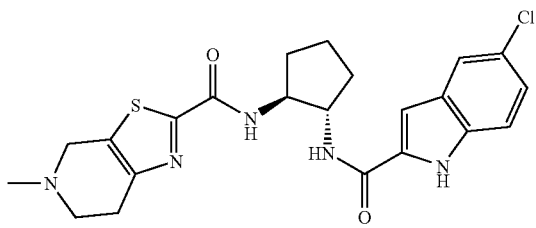

5-Chloroindole-2-carboxylic acid (80 mg), 1-(3-dimethylaminopropyl)-3-ethylcarbodiimide hydrochloride (98 mg), 1-hydroxybenzotriazole monohydrate (23 mg) and triethylamine (141 μl) were added to a solution with the compound (120 mg) obtained in Referential Example 62 dissolved in N,N-dimethylformamide (5 ml), and the mixture was stirred at room temperature for 3 days. The solvent was distilled off under reduced pressure, and methylene chloride and a saturated aqueous solution of sodium hydrogencarbonate were added to the residue to conduct liquid separation. The resultant organic layer was washed with saturated aqueous solution of sodium chloride and dried over anhydrous sodium sulfate, the solvent was distilled off under reduced pressure, and the residue was purified by column chromatography on silica gel (methylene chloride:methanol=93:7). After methylene chloride (5 ml) and a 1N ethanol solution (282 μl) of hydrochloric acid were added to the thus-obtained pale yellow solid, ethyl acetate was added, and precipitate formed was collected by filtration to obtain the title compound (109 mg).

$^1$H-NMR (DMSO-d$_6$) δ: 1.64-1.74 (4H, m), 1.98-2.02 (2H, m), 2.89 (3H, s), 3.14 (2H, br.s), 3.47-3.65 (2H, m), 4.29-4.63 (4H, m), 7.10 (1H, d, J=1.5 Hz), 7.14 (1H, dd, J=8.5, 2.0 Hz), 7.38 (1H, d, J=8.5 Hz), 7.68 (1H, d, J=2.0 Hz), 8.55 (1H, d, J=8.5 Hz), 8.91 (1H, d, J=8.5 Hz), 11.49 (1H, br.s), 11.76 (1H, s). MS (ESI) m/z: 458 (M+H)$^+$.

Example 4

N-((1R*,2S*)-2-{[(5-Chloroindol-2-yl)sulfonyl]amino}-cyclohexyl)-5-methyl-4,5,6,7-tetrahydrothiazolo[5,4-c]-pyridine-2-carboxamide hydrochloride

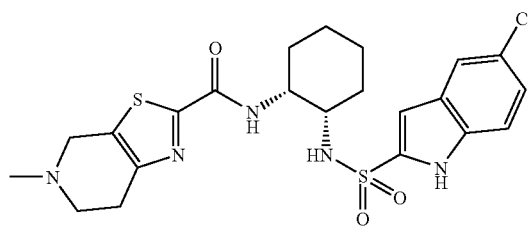

The compound (400 mg) obtained in Referential Example 67 was suspended in methylene chloride (10 ml), triethylamine (0.514 ml) and (5-chloro-1-phenylsulfonylindole-2-sulfonyl chloride (Japanese Patent Application Laid-Open No. 2000-119253) (319 mg) were added, and the mixture was stirred at room temperature for 15 minutes. After water was added to the reaction mixture to conduct liquid separation, the resultant organic layer was dried over anhydrous sodium sulfate. The solvent was distilled off under reduced pressure, and the residue was purified by column chromatography on silica gel (methylene chloride:methanol=100:3) to obtain a pale yellow foamy substance. This substance was dissolved in tetrahydrofuran (3 ml), and methanol (2 ml) and a 1N aqueous solution (1.5 ml) of sodium hydroxide were added to heat the mixture under reflux for 2 hours. The reaction mixture was concentrated under reduced pressure, and methylene chloride and 1N hydrochloric acid were added to the residue to conduct liquid separation. After the resultant organic layer was dried over anhydrous sodium sulfate, the solvent was distilled off under reduced pressure, and the residue was purified by column chromatography on silica gel (methylene chloride:methanol=100:3). 1N Hydrochloric acid (1 ml) was added to the resultant product, and the mixture was concentrated under reduced pressure to obtain the title compound (108 mg).

$^1$H-NMR (DMSO-d$_6$) δ: 1.20-1.78 (8H, m), 2.94 (3H, s), 3.13 (2H, br.s), 3.22-3.40 (1H, m), 3.44-3.70 (3H, m), 3.83-3.95 (1H, m), 4.20-4.70 (1H, m), 6.78 (1H, s), 7.18-7.30 (2H, m), 7.44 (1H, s), 7.69 (1H, br.s), 8.09 (1H, br.s), 11.92 (1H, s). MS (FAB) m/z: 508 (M+H)$^+$.

Example 5

N-((1R*,2R*)-2-{[(5-Chloroindol-2-yl)carbonyl]amino}-cyclohexyl)-5-methyl-4,5,6,7-tetrahydrothiazolo[5,4-c]-pyridine-2-carboxamide hydrochloride

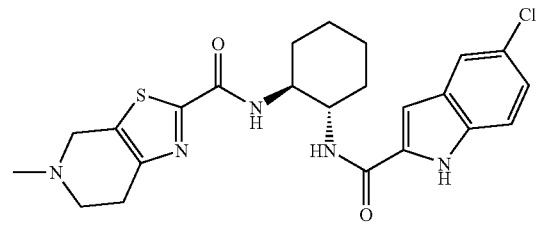

5-Chloroindole-2-carboxylic acid (109 mg), 1-hydroxybenzotriazole monohydrate (9 mg), 1-(3-dimethylaminopropyl)-3-ethylcarbodiimide hydrochloride (321 mg) and triethylamine (0.232 ml) were added to a solution with the compound (300 mg) obtained in Referential Example 65 dissolved in N,N-dimethylformamide (20 ml), and the mixture was stirred overnight at room temperature. The reaction mixture was concentrated under reduced pressure using a vacuum pump, and methylene chloride and water were added to the residue to conduct liquid separation. The resultant organic layer was dried over anhydrous sodium sulfate, the solvent was distilled off under reduced pressure, and the residue was purified by column chromatography on silica gel (methylene chloride:methanol=25:1) to obtain a colorless foamy substance. This substance was suspended in 1N hydrochloric acid (1 ml), and the suspension was concentrated under reduced pressure to obtain the title compound (203 mg).

$^1$H-NMR (DMSO-d$_6$) δ: 1.25-1.40 (2H, m), 1.46-1.81 (4H, m), 1.88-1.98 (2H, m), 2.89 (3H, s), 3.00-3.76 (5H, m), 3.86-3.97 (1H, m), 4.00-4.10 (1H, m), 4.25-4.72 (1H, m), 7.03 (1H, s), 7.12 (1H, dd, J=8.5, 1.2 Hz), 7.38 (1H, d, J=8.5 Hz), 7.64 (1H, s), 8.28 (1H, d, J=8.5 Hz), 8.54 (1H, d, J=8.5 Hz), 11.70 (1H, s). MS (FAB) m/z: 472 (M+H)⁺.

Example 6

N-((1R*,2S*)-2-{[(5-Chloroindol-2-yl)carbonyl]amino}-cyclohexyl)-5-methyl-4,5,6,7-tetrahydrothiazolo[5,4-c]pyridine-2-carboxamide hydrochloride

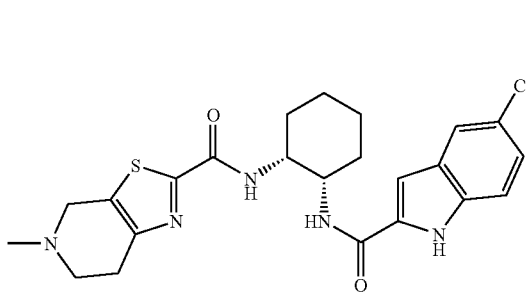

The title compound was obtained from the compound obtained in Referential Example 67 and 5-chloroindole-2-carboxylic acid in a similar manner to Example 5.

¹H-NMR (DMSO-d₆) δ: 1.35-1.70 (6H, m), 1.80-2.06 (2H, m), 2.89 (3H, s), 3.00-3.27 (2H, m), 3.35-3.51 (1H, m), 3.57-3.82 (1H, m), 4.15-4.30 (2H, m), 4.32-4.48 (1H, m), 4.60-4.74 (1H, m), 7.15 (1H, s), 7.17 (1H, dd, J=8.8, 2.0 Hz), 7.41 (1H, d, J=8.6 Hz), 7.70 (1H, d, J=2.0 Hz), 8.14 (1H, br.s), 8.36-8.48 (1H, m), 11.51 (1H, br.s), 11.86 (1H, s). MS (FAB) m/z: 472 (M+H)⁺.

Example 7

N-{(1R*,2S*)-2-[(6-Chloro-2-naphthoyl)amino]cyclohexyl}-5-methyl-4,5,6,7-tetrahydrothiazolo[5,4-c]pyridine-2-carboxamide hydrochloride

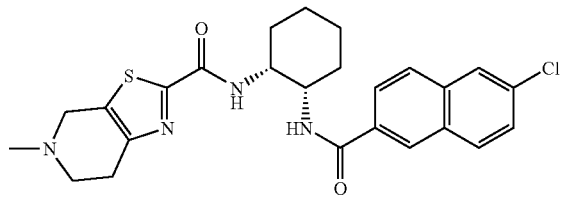

The title compound (186 mg) was obtained by dissolving the compound (275 mg) obtained in Referential Example 67, 6-chloronaphthalene-2-carboxylic acid (Eur. J. Chem. Chim. Ther., 1984, Vol. 19, pp. 205-214) (148 mg), triethylamine (0.298 ml) and 1-hydroxybenzotriazole monohydrate (11 mg) in N,N-dimethylformamide (20 ml) and causing 1-(3-dimethylaminopropyl)-3-ethylcarbodiimide hydrochloride (412 mg) to react in a similar manner to Example 5.

¹H-NMR (DMSO-d₆) δ: 1.40-1.56 (2H, m), 1.57-1.77 (4H, m), 1.90-2.10 (2H, m), 2.90 (3H, s), 3.13 (2H, br.s), 3.28-3.74 (2H, m), 4.26 (2H, br.s), 4.30-4.74 (2H, m), 7.59 (1H, d, J=8.6 Hz), 7.90 (1H, d, J=8.6 Hz), 7.98 (1H, d, J=8.3 Hz), 8.03-8.11 (2H, m), 8.25-8.58 (3H, m), 11.52 (1H, br.s). MS (FAB) m/z: 483 (M+H)⁺.

Example 8

N-((1R*,2R*)-2-{[(6-Chloro-1-benzothiophen-2-yl)carbonyl]amino}cyclohexyl)-5-methyl-4,5,6,7-tetrahydrothiazolo[5,4-c]pyridine-2-carboxamide hydrochloride

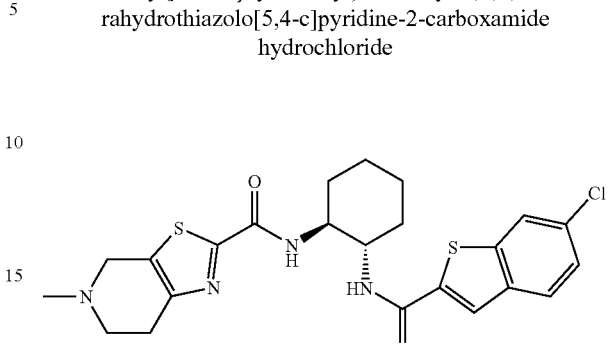

The title compound (239 mg) was obtained by dissolving the compound (255 mg) obtained in Referential Example 65, 6-chlorobenzo[b]thiophene-2-carboxylic acid (Japanese Patent Application Laid-Open No. 2000-119253) (141 mg), triethylamine (0.276 ml) and 1-hydroxybenzotriazole monohydrate (10 mg) in N,N-dimethylformamide (20 ml) and causing 1-(3-dimethylaminopropyl)-3-ethylcarbodiimide hydrochloride (382 mg) to react in a similar manner to Example 5.

¹H-NMR (DMSO-d₆) δ: 1.20-1.98 (8H, m), 2.88 (3H, s), 3.00-3.72 (4H, m), 3.84-4.09 (2H, m), 4.20-4.75 (2H, m), 7.41 (1H, dd, J=8.6, 1.7 Hz), 7.91 (1H, d, J=8.6 Hz), 7.99 (1H, s), 8.12 (1H, s), 8.54-8.67 (2H, m), 11.53 (1H, br.s). MS (FAB) m/z: 489 (M+H)⁺.

Example 9

N-((1R*,2R*)-2-{[(5-Fluoroindol-2-yl)carbonyl]amino}-cyclohexyl)-5-methyl-4,5,6,7-tetrahydrothiazolo[5,4-c]-pyridine-2-carboxamide hydrochloride

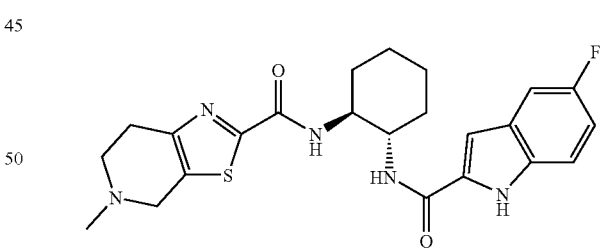

The title compound was obtained from the compound obtained in Referential Example 65 and 5-fluoroindole-2-carboxylic acid in a similar manner to Example 5.

¹H-NMR (DMSO-d₆) δ: 1.20-1.38 (2H, m), 1.40-1.57 (1H, m), 1.54-1.68 (1H, m), 1.71 (2H, d, J=7.3 Hz), 1.88 (2H, d, J=12.0 Hz), 2.86 (3H, s), 2.95-3.24 (2H, m), 3.40 (1H, br.s), 3.63 (1H, br.s), 3.90 (1H, br.s), 3.97-4.10 (1H, m), 4.20-4.44 (1H, m), 4.53-4.70 (1H, m), 6.98 (1H, dd, J=9.2, 2.3 Hz), 7.01 (1H, s), 7.31-7.39 (2H, m), 8.26 (1H, d, J=8.6 Hz), 8.59 (1H, d, J=8.4 Hz), 11.21 (1/2H, br.s), 11.42 (1/2H, br.s), 11.60 (1H, s). MS (ESI) m/z: 456 (M+H)⁺.

Example 10

N-((1R*,2R*)-2-{[(5-Chloro-6-fluoroindol-2-yl)carbonyl]-amino}cyclohexyl)-5-methyl-4,5,6,7-tetrahydrothiazolo-[5,4-c]pyridine-2-carboxamide hydrochloride

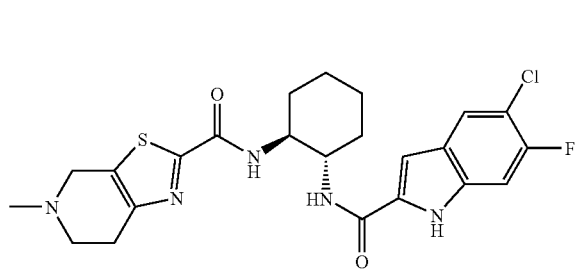

The title compound was obtained from the compound obtained in Referential Example 65 and the compound obtained in Referential Example 23 in a similar manner to Example 5.

$^1$H-NMR (DMSO-d$_6$) δ: 1.20-1.40 (2H, m), 1.40-1.80 (4H, m), 1.80-2.00 (2H, m), 2.87 (3H, s), 3.01 (2H, br.s), 3.30-3.80 (2H, m), 3.81-3.97 (2H, m), 4.20-4.80 (2H, m), 7.06 (1H, s), 7.28 (1H, d, J=10.0 Hz), 7.86 (1H, d, J=7.3 Hz), 8.32 (1H, d, J=8.5 Hz), 8.59 (1H, d, J=8.5 Hz), 11.77 (1H, s). MS (FAB) m/z: 490 (M+H)$^+$.

Example 11

N-((1R*,2S*)-2-{[(5-Bromoindol-2-yl)carbonyl]amino}-cyclohexyl)-5-methyl-4,5,6,7-tetrahydrothiazolo[5,4-c]-pyridine-2-carboxamide hydrochloride

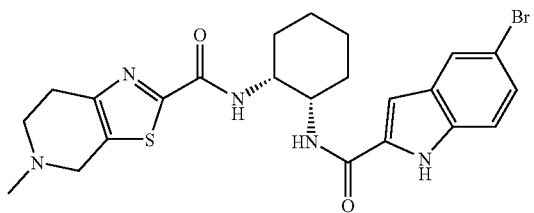

The title compound was obtained from the compound obtained in Referential Example 67 and 5-bromoindole-2-carboxylic acid in a similar manner to Example 5.

$^1$H-NMR (DMSO-d$_6$) δ: 1.43 (2H, br.s), 1.61 (4H, br.s), 1.80-2.10 (2H, m), 2.88 (3H, s), 3.00-3.26 (2H, m), 3.40 (1H, br.s), 3.65 (1H, br.s), 4.22 (1H, br.s), 4.26 (1H, br.s), 4.41 (1H, br.s), 4.67 (1H, d, J=15.6 Hz), 7.14 (1H, s), 7.28 (1H, d, J=8.7 Hz), 7.37 (1H, d, J=8.7 Hz), 7.84 (1H, s), 8.13 (1H, br.s), 8.33-8.52 (1H, m), 11.51 (1H, s), 11.86 (1H, s). MS (ESI) m/z: 515 (M$^+$).

Example 12

N-((1R*,2S*)-2-{[(5-Ethynylindol-2-yl)carbonyl]amino}-cyclohexyl)-5-methyl-4,5,6,7-tetrahydrothiazolo[5,4-c]-pyridine-2-carboxamide hydrochloride

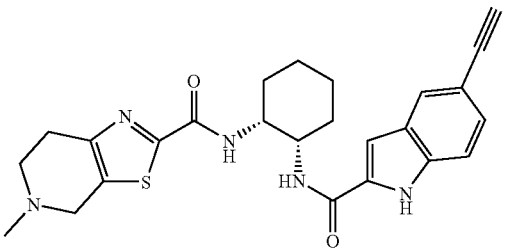

Triethylamine (6 ml), N,N-dimethylformamide (5 ml), trimethylsilylacetylene (0.250 ml) and palladium acetate (20 mg) were added to a tetrahydrofuran solution (2 ml) of the compound (300 mg) obtained in Example 11 and triphenylphosphine (70 mg) at room temperature. After stirring at 90° C. for 2 hours, the reaction mixture was allowed to cool to room temperature, and methylene chloride (20 ml) and a saturated aqueous solution (30 ml) of sodium hydrogencarbonate were added to conduct liquid separation. The resultant water layer was extracted with methylene chloride (3×10 ml), the organic layers were combined and dried over anhydrous sodium sulfate, and the solvent was distilled off under reduced pressure to obtain residue. The resultant residue was purified by preparative thin-layer chromatography on silica gel (methylene chloride:acetone:methanol=10:10:1) to obtain colorless solids. This product was dissolved in methanol (6 ml), potassium carbonate (120 mg) was added, and the mixture was stirred for 1 hour. Methylene chloride (20 ml) and water (20 ml) were added to the reaction mixture to conduct liquid separation. The resultant water layer was extracted with methylene chloride (2×15 ml), the organic layers were combined and dried over anhydrous sodium sulfate, and the solvent was distilled off under reduced pressure. The residue was purified by preparative thin-layer chromatography on silica gel (methylene chloride:acetone:methanol=10:10:1) and dissolved in water-methanol-methylene chloride. The resultant solution was then concentrated to obtain the title compound (72 mg).

$^1$H-NMR (CDCl$_3$) δ: 1.50-2.25 (8H, m), 2.53 (3H, s), 2.85 (2H, br.s), 2.93 (2H, br.s), 3.01 (1H, s), 3.74 (1H, d, J=14.1 Hz), 3.77 (1H, d, J=14.1 Hz), 4.21 (1H, br.s), 4.45 (1H, br.s), 6.91 (1H, s), 7.25-7.42 (2H, m), 7.61 (1H, br.s), 7.80-7.97 (2H, m), 9.72 (1H, s). MS (FAB) m/z: 462 (M+H)$^+$.

Example 13

N-((1R*,2S*)-2-{[(5-Chloroindol-2-yl)carbonyl]amino}-cyclohexyl)-5,6-dimethyl-4,5,6,7-tetrahydrothiazolo[4,5-d]pyridazine-2-carboxamide hydrochloride

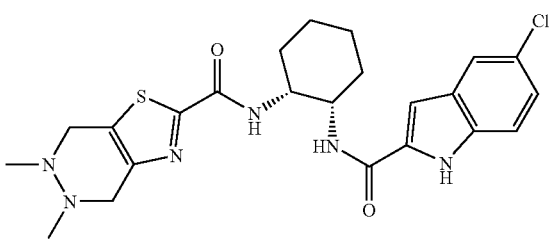

The title compound was obtained from the compound obtained in Referential Example 71 and the compound obtained in Referential Example 51 in a similar manner to Example 2.

¹H-NMR (DMSO-d₆) δ: 1.35-1.50 (2H, m), 1.50-1.75 (4H, m), 1.80-2.10 (2H, m), 2.70 (3H, br.s), 2.79 (3H, br.s), 4.10-4.70 (6H, m), 7.10-7.27 (2H, m), 7.41 (1H, d, J=8.8 Hz), 7.70 (1H, s), 8.12 (1H, d, J=6.8 Hz), 8.47 (1H, d, J=7.6 Hz), 11.85 (1H, s). MS (FAB) m/z: 487 (M+H)⁺.

Example 14

N-((1R*,2S*)-2-{[(5-Chloroindol-2-yl)carbonyl]amino}-cyclohexyl)-6,7-dihydro-4H-pyrano[4,3-d]thiazole-2-carboxamide

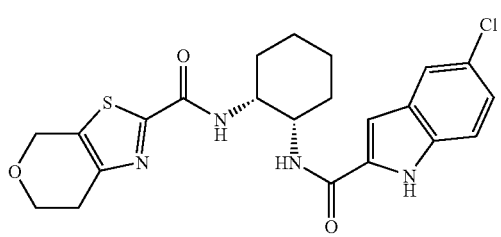

The title compound was obtained from the compound obtained in Referential Example 71 and the compound obtained in Referential Example 26 in a similar manner to Example 2.

¹H-NMR (DMSO-d₆) δ: 1.36-1.72 (6H, m), 1.90-2.10 (2H, m), 2.80-2.87 (2H, m), 3.93 (2H, t, J=5.6 Hz), 4.20-4.32 (2H, m), 4.81 (2H, s), 7.12 (1H, s), 7.15 (1H, dd, J=8.8, 2.0 Hz), 7.41 (1H, d, J=8.8 Hz), 7.67 (1H, d, J=1.7 Hz), 8.11 (1H, d, J=6.6 Hz), 8.36 (1H, d, J=8.3 Hz), 11.78 (1H, s). MS (FAB) m/z: 459 (M+H)⁺.

Example 15

N-((1R*,2S*)-2-{[(5-Chloroindol-2-yl)carbonyl]amino}-cyclohexyl)-5-methyl-4,5,6,7-tetrahydrothiazolo[4,5-c]-pyridine-2-carboxamide hydrochloride

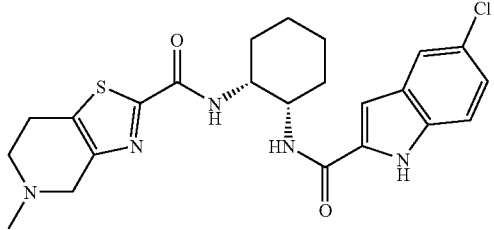

The title compound was obtained from the compound obtained in Referential Example 71 and the compound obtained in Referential Example 29 in a similar manner to Example 2.

¹H-NMR (DMSO-d₆) δ: 1.32-1.74 (6H, m), 1.82-2.10 (2H, m), 2.92 (3H, s), 3.12-3.50 (3H, m), 3.69 (1H, br.s), 4.13-4.39 (3H, m), 4.51 (1H, br.s), 7.10-7.19 (2H, m), 7.41 (1H, d, J=8.6 Hz), 7.68 (1H, s), 8.10 (1H, br.s), 8.40 (1H, br.s), 11.41 (1H, br.s), 11.87 (1H, s). MS (FAB) m/z: 472 (M+H)⁺.

Example 16

N-((1R*,2R*)-2-{[(5-Chloroindol-2-yl)carbonyl]amino}-cyclohexyl)-5-methyl-4,5,6,7-tetrahydrooxazolo[5,4-c]-pyridine-2-carboxamide hydrochloride

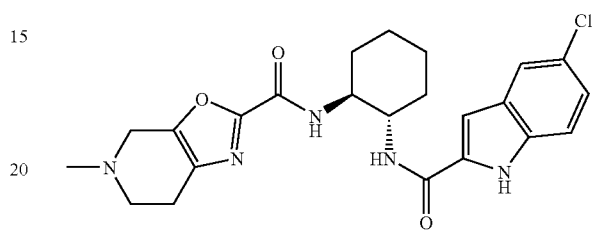

The title compound was obtained from the compound obtained in Referential Example 69 and the compound obtained in Referential Example 21 in a similar manner to Example 2.

¹H-NMR (DMSO-d₆) δ: 1.23-1.39 (2H, m), 1.40-1.81 (4H, m), 1.82-1.98 (2H, m), 2.60-3.00 (5H, m), 3.20-3.70 (2H, m), 3.87-3.96 (1H, m), 3.98-4.10 (1H, m), 4.12-4.70 (2H, m), 7.04 (1H, d, J=1.5 Hz), 7.12 (1H, dd, J=8.8, 2.0 Hz), 7.38 (1H, d, J=8.8 Hz), 7.65 (1H, d, J=2.0 Hz), 8.33 (1H, d, J=8.6 Hz), 8.72 (1H, d, J=8.6 Hz), 11.61 (1H, br.s), 11.72 (1H, s). MS (FAB) m/z: 456 (M+H)⁺.

Example 17

N-((1R*,2S*)-2-{[(5-Chloroindol-2-yl)carbonyl]amino}-cyclohexyl)-4,5,6,7-tetrahydrothieno[3,2-c]pyridine-2-carboxamide hydrochloride

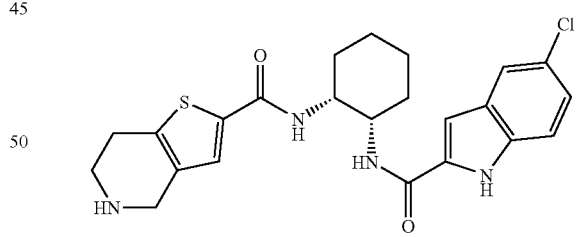

The title compound was obtained by condensing the compound obtained in Referential Example 71 with 5-tert-butoxycarbonyl-4,5,6,7-tetrahydrothieno[3,2-c]-pyridine-2-carboxylic acid (WO94/21599) and treating the formed product with hydrochloric acid to deprotect in a similar manner to Example 2.

¹H-NMR (DMSO-d₆) δ: 1.42 (2H, br.s), 1.56-1.76 (4H, m), 1.98-2.11 (2H, m), 3.04 (2H, br.s), 3.32-3.45 (2H, m), 4.15 (3H, br.s), 4.26 (1H, br.s), 7.14 (1H, dd, J=8.8, 2.0 Hz), 7.23 (1H, s), 7.41 (1H, d, J=8.8 Hz), 7.62 (1H, s), 7.77 (1H, s), 8.18-8.30 (2H, m), 9.42 (2H, br.s), 11.92 (1H, s). MS (FAB) m/z: 457 (M+H)⁺.

Example 18

N-((1R*,2S*)-2-{[(5-Chloroindol-2-yl)carbonyl]amino}-cyclohexyl)-5-methyl-4,5,6,7-tetrahydrothieno[3,2-c]-pyridine-2-carboxamide hydrochloride

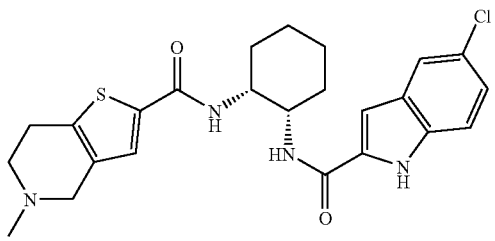

The compound (171 mg) obtained in Example 17 was suspended in methylene chloride (10 ml), and triethylamine (0.104 ml) was added to stir the mixture at room temperature for 10 minutes. After acetic acid (0.059 ml) was added to the reaction mixture, a 35% aqueous formaldehyde solution (0.070 ml) and sodium triacetoxyborohydride (118 mg) were added, and the mixture was stirred at room temperature for 30 minutes. After a 1N aqueous solution (3 ml) of sodium hydroxide was added to the reaction mixture, water was added to conduct liquid separation. After the resultant organic layer was dried over anhydrous sodium sulfate, the solvent was then distilled off under reduced pressure, and the residue was purified by column chromatography on silica gel (methylene chloride:methanol=50:3) to obtain a colorless foamy substance. This substance was suspended in 1N hydrochloric acid, and the suspension was concentrated under reduced pressure to obtain the title compound (85 mg).

$^1$H-NMR (DMSO-$d_6$) δ: 1.40 (2H, br.s), 1.50-1.71 (4H, m), 1.97-2.05 (2H, m), 2.87 (3H, s), 2.98-3.20 (1H, m), 3.30-3.38 (2H, m), 3.54-3.70 (1H, m), 4.05-4.42 (4H, m), 7.14 (1H, d, J=8.6 Hz), 7.23 (1H, s), 7.40 (1H, d, J=8.6 Hz), 7.63 (1H, s), 7.77 (1H, s), 8.17-8.27 (2H, m), 10.83 (1H, br.s), 11.92 (1H, s). MS (FAB) m/z: 471 (M+H)$^+$.

Example 19

N-((1R*,2S*)-2-{[(5-Chloroindol-2-yl)carbonyl]amino}-cyclohexyl)-6-(dimethylamino)-4,5,6,7-tetrahydrobenzothiazole-2-carboxamide hydrochloride

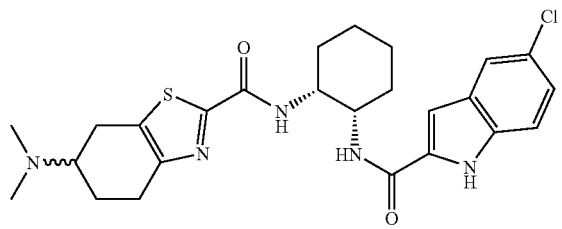

The title compound was obtained from the compound obtained in Referential Example 71 and the compound obtained in Referential Example 31 in a similar manner to Example 2.

$^1$H-NMR (DMSO-$d_6$) δ: 1.44 (2H, br.s), 1.52-1.68 (4H, m), 1.87-2.08 (3H, m), 2.30-2.40 (1H, m), 2.65-2.75 (1H, m), 2.77 (6H, s), 2.95-3.17 (2H, m), 3.30-3.70 (2H, m), 4.15-4.30 (2H, m), 7.10-7.20 (2H, m), 7.41 (1H, d, J=8.6 Hz), 7.69 (1H, s), 8.11 (1H, d, J=5.1 Hz), 8.34 (1H, d, J=8.1 Hz), 10.95 (1H, br.s), 11.83 (1H, s). MS (FAB) m/z: 500 (M+H)$^+$.

Example 20

N-((1R*,2S*)-2-{[(5-Chloroindol-2-yl)carbonyl]amino}-cyclohexyl)-5-(pyridin-4-yl)-4,5,6,7-tetrahydrothiazolo-[5,4-c]pyridine-2-carboxamide hydrochloride

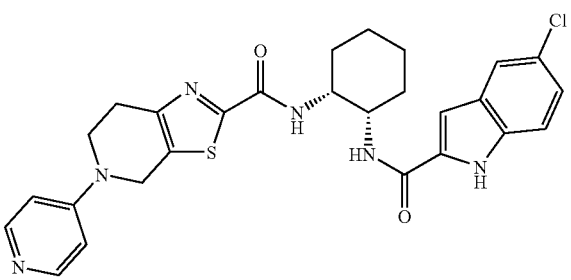

After n-butyllithium (1.60N hexane solution, 0.704 ml) was added dropwise to a solution of the compound (204 mg) obtained in Referential Example 24 in tetrahydrofuran (3 ml) at −78° C., the mixture was stirred at 0° C. for 30 minutes. After the reaction mixture was cooled to −78° C. again, it was warmed to room temperature in 20 minutes while blowing carbon dioxide, and the reaction mixture was concentrated under reduced pressure. The compound (400 mg) obtained in Referential Example 71, 1-hydroxybenzotriazole monohydrate (254 mg), 1-(3-dimethylaminopropyl)-3-ethylcarbodiimide hydrochloride (360 mg) and isopropylamine (0.491 ml) were added to a solution of the resultant residue in N,N-dimethylformamide (6 ml) at room temperature. After stirring for 3 days, the reaction mixture was concentrated under reduced pressure, and methylene chloride (30 ml), a saturated aqueous solution (100 ml) of sodium hydrogencarbonate and water (100 ml) were added to the residue to conduct liquid separation. The resultant water layer was extracted with methylene chloride (4×15 ml), the organic layers were combined and dried over anhydrous sodium sulfate, and the solvent was distilled off under reduced pressure. The resultant residue was purified by column chromatography on silica gel (methylene chloride:methanol=20:1→10:1) and dissolved in 1N hydrochloric acid-methanol-methylene chloride. The resultant solution was then concentrated to obtain the title compound (245 mg).

$^1$H-NMR (DMSO-$d_6$) δ: 1.42 (2H, br.s), 1.60 (4H, br.s), 1.84-1.94 (1H, m), 1.94-2.08 (1H, m), 2.97 (2H, br.s), 3.97-4.13 (2H, m), 4.19 (1H, br.s), 4.27 (1H, br.s), 5.03 (2H, s), 7.13 (1H, br.s), 7.16 (1H, dd, J=8.8, 2.0 Hz), 7.32 (2H, br.s), 7.40 (1H, d, J=8.8 Hz), 7.68 (1H, d, J=2.0 Hz), 8.15 (1H, br, J=7.3 Hz), 8.31 (2H, d, J=5.9 Hz), 8.39 (1H, d, J=8.1 Hz), 11.90 (1H, s), 14.03 (1H, br.s). MS (ESI) m/z: 535 (M+H)$^+$.

Example 21

N-((1R*,2R*)-2-{[(5-Chloroindol-2-yl)carbonyl]amino}-cycloheptyl)-5-methyl-4,5,6,7-tetrahydrothiazolo[5,4-c]-pyridine-2-carboxamide hydrochloride

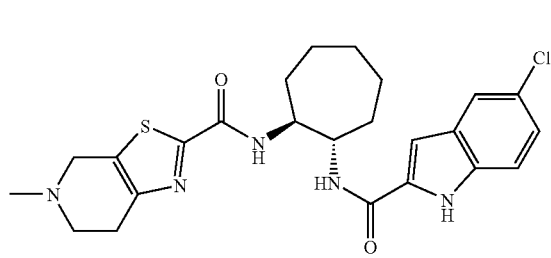

The title compound was obtained from the compound obtained in Referential Example 74 and the compound obtained in Referential Example 10 in a similar manner to Example 2.

¹H-NMR (DMSO-d$_6$): 1.51-1.55 (4H, m), 1.75-1.80 (6H, m), 2.88 (3H, s), 3.12 (1H, br.s), 3.35-3.63 (4H, m), 4.10-4.13 (1H, m), 4.29-4.61 (2H, m), 7.06 (1H, s), 7.14 (1H, dd, J=8.8, 2.0 Hz), 7.39 (1H, d, J=8.8 Hz), 7.67 (1H, d, J=2.0 Hz), 8.46 (1H, d, J=8.3 Hz), 8.77 (1H, d, J=8.3 Hz), 11.21-11.35 (1H, m), 11.71 (1H, s). MS (ESI) m/z: 486 (M+H)⁺.

Example 22

N-((1R*,2S*)-2-{[(5-Chloroindol-2-yl)carbonyl]amino}-cyclooctyl)-5-methyl-4,5,6,7-tetrahydrothiazolo[5,4-c]-pyridine-2-carboxamide hydrochloride

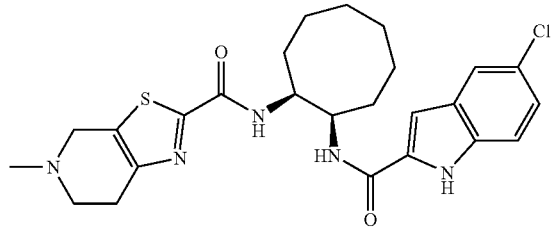

The title compound was obtained from the compound obtained in Referential Example 78 and the compound obtained in Referential Example 10 in a similar manner to Example 2.

¹H-NMR (DMSO-d$_6$) δ: 1.61-2.06 (12H, m), 2.90 (3H, s), 3.08-3.17 (2H, m), 3.43-3.45 (1H, br.s), 3.67 (1H, br.s), 4.43 (3H, br.s), 4.67 (1H, br.s), 7.16-7.18 (2H, m), 7.42 (1H, d, J=8.8 Hz), 7.70 (1H, s), 8.24 (1H, br.s), 8.58 (1H, d, J=8.3 Hz), 11.43, 11.63 (1H, each br.s), 11.80 (1H, s). MS (ESI) m/z: 500 (M+H)⁺.

Example 23

N-((1R*,2R*)-2-{[(5-Chloroindol-2-yl)carbonyl]amino}-cyclopentyl)-4,5,6,7-tetrahydrothiazolo[5,4-c]pyridine-2-carboxamide hydrochloride

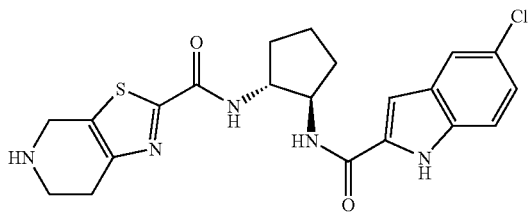

The title compound was obtained by treating a product obtained by the reaction of the compound obtained in Referential Example 63 with the compound obtained in Referential Example 34 with hydrochloric acid in a similar manner to Example 2.

¹H-NMR (DMSO-d$_6$) δ: 1.60-1.82 (4H, m), 1.91-2.15 (2H, m), 3.08 (2H, s), 3.37-3.49 (2H, m), 4.28-4.56 (4H, m), 7.13 (1H, s), 7.15 (1H, d, J=8.8 Hz), 7.40 (1H, d, J=8.8 Hz), 7.69 (1H, s), 8.61 (1H, d, J=8.3 Hz), 8.88 (1H, d, J=8.3 Hz), 10.05 (2H, br.s), 11.82 (1H, s). MS (FAB) m/z: 444 (M+H)⁺.

Example 24

N-((1R*,2R*)-2-{[(5-Chloroindol-2-yl)carbonyl]amino}-cyclopentyl)-5-isopropyl-4,5,6,7-tetrahydrothiazolo-[5,4-c]pyridine-2-carboxamide hydrochloride

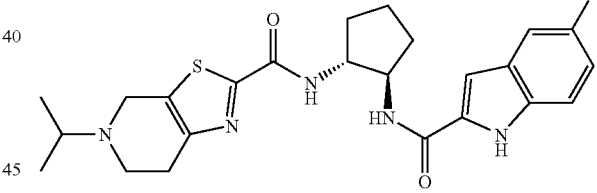

The compound (30 mg) obtained in Example 23 was suspended in methylene chloride (20 ml), and triethylamine (260 µl) was added to stir the mixture at room temperature for 15 minutes. Acetic acid (179 µl) and acetone (920 µl) were added to the reaction mixture, and the resultant mixture was stirred at room temperature for 2 minutes. Sodium triacetoxyborohydride (796 mg) was added to the reaction mixture to stir them at room temperature for 5 hours. A 1N aqueous solution (10 ml) of sodium hydroxide was added to the reaction mixture to conduct liquid separation. The resultant organic layer was dried over anhydrous sodium sulfate, and the solvent was distilled off under reduced pressure. The residue was purified by column chromatography on silica gel (methylene chloride:methanol=100:3) to obtain a colorless foamy substance. This product was dissolved in methylene chloride, and a 1N ethanol solution (1 ml) of hydrochloric acid was added. The solution was concentrated under reduced pressure to obtain the title compound (205 mg).

¹H-NMR (DMSO-d$_6$) δ: 1.27-1.39 (6H, m), 1.58-1.80 (4H, m), 1.95-2.10 (2H, m), 3.00-3.12 (1H, m), 3.25-3.45

(2H, m), 3.59-3.77 (2H, m), 4.25-4.39 (1H, m), 4.40-4.55 (2H, m), 4.57-4.65 (1H, m), 7.10 (1H, s), 7.14 (1H, d, J=8.8 Hz), 7.38 (1H, d, J=8.8 Hz), 7.68 (1H, s), 8.56 (1H, d, J=8.8 Hz), 8.90 (1H, d, J=8.8 Hz), 11.39 (1H, br.s), 11.76 (0.5H, s), 11.80 (0.5H, s). MS (FAB) m/z: 486 (M+H)+.

Example 25

N-((1R*,2R*)-2-{[(5-Chloroindol-2-yl)carbonyl]amino}-cyclopentyl)-5-ethyl-4,5,6,7-tetrahydrothiazolo[5,4-c]-pyridine-2-carboxamide hydrochloride

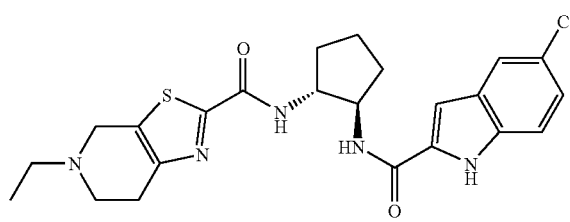

The compound (500 mg) obtained in Example 23 was dissolved in N,N-dimethylformamide (10 ml), and triethylamine (576 μl) and ethyl iodide (329 μl) were added to stir the mixture overnight at room temperature. The reaction mixture was concentrated under reduced pressure, and water was added to the residue to collect insoluble matter by filtration. This product was purified by column chromatography on silica gel (methylene chloride:methanol=100:3) to obtain a pale brown foamy substance. This substance was suspended in 1N hydrochloric acid, and the suspension was concentrated under reduced pressure to obtain the title compound (180 mg).

$^1$H-NMR (DMSO-$d_6$) δ: 1.32 (3H, t, J=7.1 Hz), 1.60-1.80 (4H, m) 1.96-2.10 (2H, m), 3.20-3.39 (5H, m), 3.70-3.80 (1H, m), 4.26-4.58 (3H, m), 4.68-4.79 (1H, m), 7.11 (1H, s), 7.15 (1H, dd, J=8.8, 2.0 Hz), 7.39 (1H, d, J=8.8 Hz), 7.69 (1H, d, J=1.5 Hz), 8.55 (1H, d, J=8.5 Hz), 8.92 (1H, d, J=8.5 Hz), 11.38 (1H, br.s), 11.70-11.80 (1H, m). MS (FAB) m/z: 472 (M+H)+.

Example 26

N-((1R*,2R*)-2-{[(5-Chloroindol-2-yl)carbonyl]amino}-cyclopentyl)-5-(1-methylcyclopropyl)-4,5,6,7-tetrahydrothiazolo[5,4-c]pyridine-2-carboxamide hydrochloride

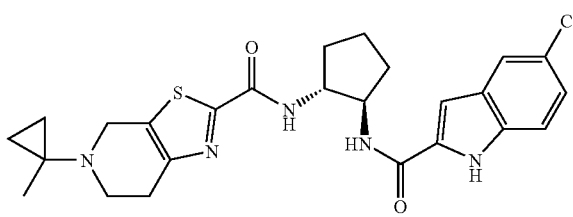

The title compound was obtained from the compound obtained in Referential Example 63 and the compound obtained in Referential Example 39 in a similar manner to Example 2.

$^1$H-NMR (DMSO-$d_6$) δ: 0.81 (2H, br.s), 1.20-1.55 (5H, br), 1.55-1.80 (4H, m), 1.95-2.12 (2H, m), 3.05-3.40 (2H, br), 3.60-3.80 (2H, br), 4.25-4.80 (4H, m), 7.10 (1H, s), 7.16 (1H, d, J=8.8 Hz), 7.39 (1H, d, J=8.8 Hz), 7.69 (1H, s), 8.53 (1H, d, J=8.6 Hz), 8.85-8.95 (1H, m), 10.60-10.90 (1H, br), 11.73 (1H, br.s). MS (FAB) m/z: 498 (M+H)+.

Example 27

N-((1R*,2R*)-2-{[(5-Chloroindol-2-yl)carbonyl]amino}-4-methoxycyclopentyl)-5-methyl-4,5,6,7-tetrahydrothiazolo-[5,4-c]pyridine-2-carboxamide hydrochloride (Stereoisomer A and Stereoisomer B)

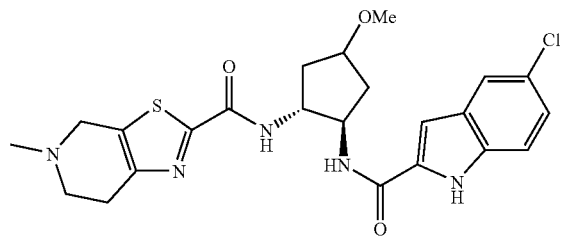

A mixture of the title compounds, i.e., Stereoisomer A and Stereoisomer B was synthesized by condensing the compound (mixture of 4-position stereoisomers) (268 mg) obtained in Referential Example 82 with the compound obtained in Referential Example 10 in a similar manner to Example 2. The isomers were isolated by column chromatography on silica gel and then converted into hydrochlorides to obtain the title compounds [Stereoisomer A (75 mg) and Stereoisomer B (70 mg)].

Stereoisomer A:
$^1$H-NMR (DMSO-$d_6$) δ: 1.70-2.15 (4H, m), 2.90 (3H, s), 3.00-3.90 (8H, m), 4.10-4.80 (4H, m), 7.08 (1H, s), 7.16 (1H, d, J=8.8 Hz), 7.38 (1H, d, J=8.8 Hz), 7.69 (1H, s), 8.56 (1H, d, J=8.8 Hz), 8.88 (1H, d, J=8.3 Hz), 10.96 (1H, br.s), 11.75 (1H, br.s). MS (FAB) m/z: 488 (M+H)+.

Stereoisomer B:
H-NMR (DMSO-$d_6$) δ: 1.60-2.10 (4H, m), 2.89 (3H, s), 3.00-3.70 (7H, m), 3.70-3.90 (1H, m), 4.20-4.80 (4H, m), 7.05-7.20 (2H, m), 7.38 (1H, d, J=8.8 Hz), 7.68 (1H, s), 8.59 (1H, d, J=8.3 Hz), 8.90 (1H, d, J=8.5 Hz), 11.26 (1H, br.s), 11.74 (1H, br.s). MS (FAB) m/z: 488 (M+H)+.

Example 28

N-[(1R*,2R*)-2-{[(5-Chloroindol-2-yl)carbonyl]amino}-4-(hydroxymethyl)cyclopentyl]-5-(1,1-dimethyl-2-hydroxyethyl)-4,5,6,7-tetrahydrothiazolo[5,4-c]pyridine-2-carboxamide hydrochloride (Stereoisomer A)

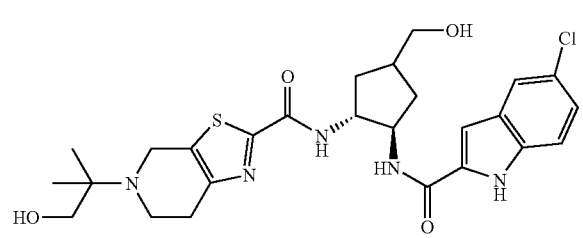

1) Stereoisomers A and B of N-((1R*,2R*)-4-[(benzyloxy)methyl]-2-{(5-chloroindol-2-yl)carbonyl}amino)cyclopentyl)-5-(2-{[tert-butyl(diphenyl)silyl]oxy}-1,1-dimethylethyl)-4,5,6,7-tetrahydrothiazolo[5,4-c]pyridine-2-carboxamide were obtained from the compound obtained in Referential Example 85 and the compound obtained in Referential Example 42 in a similar manner to Example 2.

Stereoisomer A:

¹H-NMR (CDCl₃) δ: 1.05 (9H, s), 1.168, 1.171 (6H, each s), 1.53-1.61 (1H, m), 1.76-1.88 (1H, m), 2.30-2.37 (2H, m), 2.78-2.79 (2H, m), 2.87-2.90 (1H, m), 2.96-3.00 (1H, m), 3.37-3.47 (2H, m), 3.58 (2H, s), 3.96 (1H, q, J=13.1 Hz), 4.41-4.45 (1H, m), 4.51-4.57 (2H, m), 6.88 (1H, d, J=1.5 Hz), 7.17 (1H, dd, J=8.8, 2.0 Hz), 7.23-7.43 (12H, m), 7.52 (1H, d, J=7.6 Hz), 9.37 (1H, br.s).

Stereoisomer B:

¹H-NMR (CDCl₃) δ: 1.05 (9H, s), 1.17 (6H, s), 1.43-1.47 (1H, m), 1.85-1.88 (1H, m), 2.09-2.14 (1H, m), 2.58-2.63 (1H, m), 2.78-2.79 (2H, m), 2.86-2.90 (1H, m), 2.96-3.00 (1H, m), 3.38-3.46 (2H, m), 3.59 (2H, s), 3.95 (1H, q, J=13.3 Hz), 4.15-4.20 (1H, m), 4.45-4.56 (3H, m), 6.74 (1H, d, J=2.0 Hz), 7.16 (1H, dd, J=8.8, 2.0 Hz), 7.27-7.43 (12H, m), 7.57 (1H, d, J=2.0 Hz), 9.48 (1H, br.s).

2) The above Stereoisomer A (288 mg) was suspended in methylene chloride (20 ml), and dimethyl sulfide (1.15 ml) and anhydrous aluminum chloride (350 mg) were added to stir the mixture at room temperature for 1 hour. A 1N aqueous solution (10 ml) of sodium hydroxide was added to the reaction mixture, and the mixture was extracted with methylene chloride. The resultant organic layer was dried over anhydrous sodium sulfate. The solvent was distilled off under reduced pressure, and the residue was purified by column chromatography on silica gel (methylene chloride:methanol=9:1) to obtain 5-(2-{[tert-butyl(diphenyl)silyl]oxy}-1,1-dimethylethyl)-N-[(1R*,2R*)-2-{[(5-Chloroindol-2-yl)carbonyl]amino}-4-(hydroxymethyl)cyclopentyl]-4,5,6,7-tetrahydrothiazolo[5,4-c]pyridine-2-carboxamide (Stereoisomer A) (184 mg).

¹H-NMR (CDCl₃)δ: 1.04 (9H, s), 1.15 (6H, s), 1.54-1.62 (1H, m), 1.73-1.81 (1H, m), 1.99-2.25 (2H, m), 2.34-2.38 (2H, m), 2.67-2.85 (3H, m), 2.92-2.97 (1H, m), 3.48-3.62 (4H, m), 3.93 (1H, q, J=15.6 Hz), 4.20-4.28 (1H, m), 4.47-4.56 (1H, m), 6.89 (1H, s), 7.11-7.18 (1H, m), 7.24-7.27 (1H, m), 7.32-7.43 (6H, m), 7.54 (1H, d, J=1.7 Hz), 7.63 (4H, dd, J=7.8, 1.5 Hz), 7.90-7.92 (2H, m), 10.13 (1H, br.s). MS (FAB) m/z: 784 (M+H)⁺.

3) Stereoisomer A (180 mg) obtained in the step 2) described above was dissolved in a 1N tetrahydrofuran solution (2 ml) of tetrabutylammonium fluoride, and the solution was stirred overnight at room temperature. Methylene chloride, a 1N aqueous solution of sodium hydroxide and sodium chloride were added to the reaction mixture to conduct liquid separation. The resultant organic layer was dried over anhydrous sodium sulfate. The solvent was distilled off under reduced pressure, and the residue was purified by column chromatography on silica gel (methylene chloride:methanol=19:1). The thus-obtained powder was dissolved in methanol, and a 1N ethanol solution (229 μl) of hydrochloric acid was added, to which ethyl acetate was added. The solvent was concentrated under reduced pressure to obtain the title compound (63 mg).

¹H-NMR (DMSO-d₆) δ: 1.33-1.50 (8H, m), 1.70-1.91 (2H, m), 2.07-2.14 (1H, m), 2.23-2.24 (1H, m), 3.04-3.10 (1H, m), 3.27-3.44 (4H, m), 3.57-3.70 (2H, m), 3.92-3.95 (1H, m), 4.29-4.72 (4H, m), 5.81 (1H, br.s), 7.11 (1H, s), 7.15 (1H, dd, J=8.6, 2.0 Hz), 7.39 (1H, d, J=8.6 Hz), 7.68 (1H, d, J=2.0 Hz), 8.53-8.56 (1H, m), 8.83 (1H, d, J=8.3 Hz), 10.36 (1H, br.s), 11.75, 11.77 (1H, each s). MS (ESI) m/z: 546 (M+H)⁺.

Example 29

N-((1R*,2S*)-2-{[(5-Chloroindol-2-yl)carbonyl]amino}-cyclohexyl)-4,7,8,10-tetrahydro-6H-pyrazolo[1,2-a]-thiazolo[4,5-d]pyridazine-2-carboxamide hydrochloride

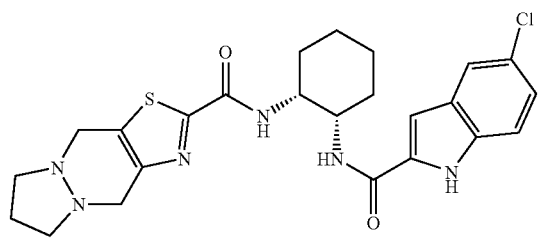

The title compound was obtained from the compound obtained in Referential Example 71 and the compound obtained in Referential Example 44 in a similar manner to Example 2.

¹H-NMR (DMSO-d₆) δ: 1.35-1.50 (2H, m), 1.61 (4H, br.s), 1.80-2.00 (2H, m), 2.27 (2H, br.s), 2.80-4.80 (10H, m), 7.14 (1H, d, J=1.5 Hz), 7.17 (1H, dd, J=8.5, 2.0 Hz), 7.41 (1H, d, J=8.5 Hz), 7.70 (1H, d, J=2.0 Hz), 8.09 (1H, d, J=7.3 Hz), 8.44 (1H, br.s), 11.81 (1H, br.s). MS (FAB) m/z: 499 (M+H)⁺.

Example 30

N-((1R*,2S*)-2-{[(5-Chloroindol-2-yl)carbonyl]amino}-cyclohexyl)-4,6,7,8,9,11-hexahydropyridazino[1,2-a]-thiazolo[4,5-d]pyridazine-2-carboxamide hydrochloride

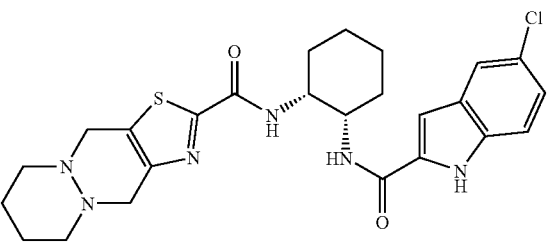

The title compound was obtained from the compound obtained in Referential Example 46 and the compound obtained in Referential Example 71 in a similar manner to Example 2.

¹H-NMR (DMSO-d₆) δ: 1.35-1.55 (2H, m), 1.55-2.10 (10H, m), 2.80-4.80 (10H, m), 7.10-7.25 (2H, m), 7.42 (1H, d, J=8.8 Hz), 7.72 (1H, d, J=1.7 Hz), 8.12 (1H, br.s), 8.41 (1H, br.s), 11.83 (1H, br.s). MS (FAB) m/z: 513 (M+H)⁺.

Example 31

5-Chloro-N-{(1R*,2S*)-2-[(5,6-dihydro-4H-pyrrolo[3,4-d]-thiazol-2-ylcarbonyl)amino]cyclohexyl}indole-2-carboxamide hydrochloride

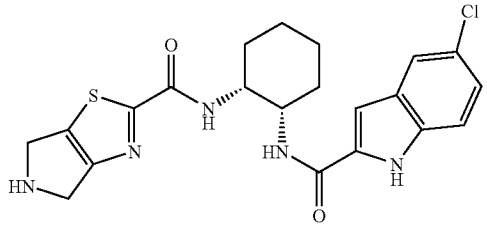

The compound (171 mg) obtained in Referential Example 33 was dissolved in diethyl ether (5 ml) in an argon atmosphere, and the solution was cooled to −78° C., to which n-butyllithium (1.60N hexane solution, 385 μl) was added dropwise. After the reaction mixture was stirred for 10 minutes at −78° C., and carbon dioxide was blown into the reaction mixture for 20 minutes, it was warmed to room temperature. After the reaction mixture was concentrated under reduced pressure, the residue was dissolved in N,N-dimethylformamide (10 ml). To the solution, were added the compound (184 mg) obtained in Referential Example 71, 1-hydroxybenzotriazole monohydrate (76 mg) and 1-(3-dimethylaminopropyl)-3-ethylcarbodiimide hydrochloride (215 mg). The resultant mixture was stirred for 3 days. The reaction mixture was concentrated, and methylene chloride and a saturated aqueous solution of sodium hydrogencarbonate were added to the residue to separate an organic layer. The organic layer was dried over anhydrous sodium sulfate, and the solvent was then distilled off under reduced pressure. The resultant residue was purified by column chromatography on silica gel (methanol:methylene chloride=3:97). After an ethanol solution (5 ml) of hydrochloric acid was added to the thus-obtained product, the mixture was stirred at room temperature for 1 hour, and the reaction mixture was concentrated. Ethyl acetate was added to the residue to solidify it. The resultant powder was collected by filtration to obtain the title compound (31 mg).

$^1$H-NMR (DMSO-$d_6$) δ: 1.35-1.52 (2H, m), 1.55-1.80 (4H, m), 1.82-2.05 (2H, m), 4.22 (1H, br.s), 4.28 (1H, br.s), 4.38 (2H, s), 4.56 (2H, s), 7.14-7.20 (2H, m), 7.42 (1H, d, J=8.6 Hz), 7.71 (1H, d, J=1.7 Hz), 8.10 (1H, d, J=7.1 Hz), 8.45 (1H, d, J=7.8 Hz), 10.10-10.50 (2H, br), 11.83 (1H, br.s). MS (FAB) m/z: 444 (M+H)$^+$.

Example 32 tert-Butyl 2-{[(((1R*,2S*)-2-{[(5-chloroindol-2-yl)carbonyl]amino}cyclohexyl)amino]carbonyl}-5,7-dihydro-6H-pyrrolo[3,4-d]pyrimidine-6-carboxylate

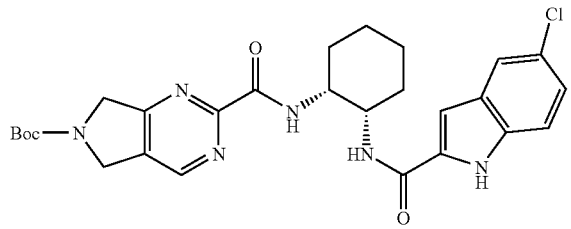

After the compound obtained in Referential Example 50 was hydrolyzed with lithium hydroxide, it was reacted with the compound obtained in Referential Example 71 in a similar manner to Example 2 to obtain the title compound.

$^1$H-NMR (CDCl$_3$) δ: 1.54 (9H, s), 1.55-2.30 (8H, m), 4.23 (1H, br.s), 4.53 (1H, br.s), 4.74-4.83 (4H, m), 6.99 (1H, d, J=1.5 Hz), 7.19 (1H, dd, J=8.8, 2.1 Hz), 7.34 (1H, d, J=8.8 Hz), 7.62 (1H, d, J=2.1 Hz), 8.11 (1H, br.s), 8.48-8.53 (1H, br), 8.70-8.76 (1H, br), 9.60-9.70 (1H, br). MS (ESI) m/z: 539 (M+H)$^+$.

Example 33

N-((1R*,2S*)-2-{[(5-Chloroindol-2-yl)carbonyl]amino}-cyclohexyl)-6-methyl-6,7-dihydro-5H-pyrrolo[3,4-d]-pyrimidine-2-carboxamide hydrochloride

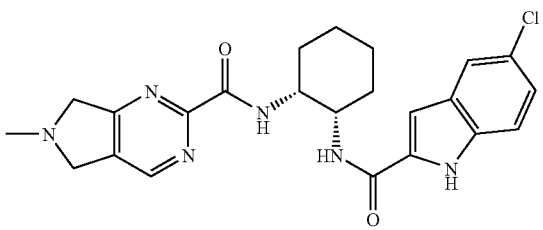

Trifluoroacetic acid (1 ml) was added to a solution of the compound (34.0 mg) obtained in Example 32 dissolved in methylene chloride (1 ml) at room temperature, and the mixture was stirred for 1 hour. The reaction mixture was concentrated under reduced pressure, and the residue was dissolved in methylene chloride (1 ml), to which triethylamine (17.6 μl), acetic acid (7.21 μl), 35% formalin (8.13 μl) and sodium triacetoxyborohydride (20.1 mg) were added at room temperature. The resultant mixture was stirred for 1 hour. Methylene chloride (10 ml) and saturated aqueous solution (10 ml) of sodium hydrogencarbonate were added to the reaction mixture to separate an organic layer. The organic layer was dried over anhydrous sodium sulfate. The solvent was distilled off under reduced pressure, and the residue was purified by column chromatography on silica gel (methanol:methylene chloride=7:93). A 1N ethanol solution of hydrochloric acid and ethyl acetate were added to the product thus obtained to solidify it, and the resultant solids were collected by filtration to obtain the title compound (8.0 mg).

$^1$H-NMR (DMSO-$d_6$) δ: 1.40-1.55 (2H, m), 1.55-1.75 (4H, m), 1.80-2.05 (2H, m), 2.98 (3H, br.s), 4.28 (2H, br.s), 4.65 (4H, br.s), 7.14-7.20 (2H, m), 7.41 (1H, d, J=8.8 Hz), 7.69 (1H, d, J=2.0 Hz), 8.17 (1H, d, J=6.9 Hz), 8.65 (1H, d, J=8.3 Hz), 8.93 (1H, s), 11.73 (1H, br.s), 11.82 (1H, br.s). MS (FAB) m/z: 453 (M+H)$^+$.

Example 34

N-((1R*,2S*)-2-{[(5-Chloroindol-2-yl)carbonyl]amino}-cyclohexyl)-4,5,6,7-tetrahydrothiazolo[5,4-c]pyridine-2-carboxamide hydrochloride

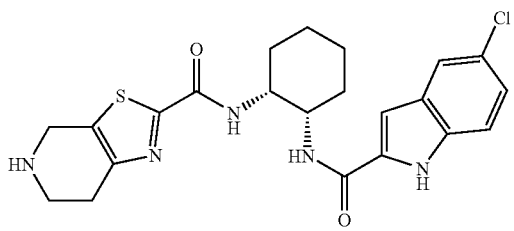

The title compound was obtained by treating a product obtained by the reaction of the compound obtained in Referential Example 71 with the compound obtained in Referential Example 34 with hydrochloric acid in a similar manner to Example 2.

$^1$H-NMR (DMSO-d$_6$) δ: 1.39-1.52 (2H, m), 1.62 (4H, br.s), 1.86-2.09 (2H, m), 3.03 (2H, br.s), 3.40-3.47 (2H, m), 4.17-4.32 (2H, m), 4.44 (2H, s), 7.15 (1H, s), 7.17 (1H, dd, J=8.6, 2.0 Hz), 7.41 (1H, d, J=8.6 Hz), 7.71 (1H, s), 8.10-8.15 (1H, m), 8.40-8.47 (1H, m), 9.69 (2H, br.s), 11.85 (1H, s). MS (FAB) m/z: 458 (M+H)$^+$.

Example 35

N-((1R*,2S*)-2-{[(5-Chloroindol-2-yl)carbonyl]amino}-cyclohexyl)-5-(2-methoxyethyl)-4,5,6,7-tetrahydrothiazolo-[5,4-c]pyridine-2-carboxamide hydrochloride

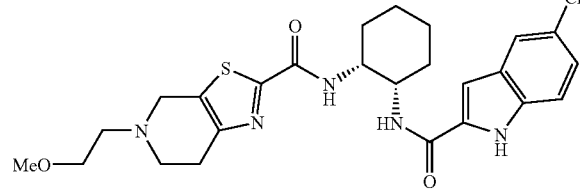

The title compound was obtained from the compound obtained in Example 34 and 2-methoxyethyl bromide in a similar manner to Example 25.

$^1$H-NMR (DMSO-d$_6$) δ: 1.44 (2H, br.s), 1.62 (4H, br.s), 1.85-2.10 (2H, m), 2.76-3.21 (6H, m), 3.28 (3H, s), 3.64 (2H, br.s), 4.00-4.52 (4H, m), 7.14 (1H, s), 7.17 (1H, dd, J=8.8, 2.0 Hz), 7.41 (1H, d, J=8.8 Hz), 7.70 (1H, d, J=2.0 Hz), 8.08-8.20 (1H, m), 8.36-8.48 (1H, m), 11.84 (1H, s). MS (FAB) m/z: 516 (M+H)$^+$.

Example 36

Methyl 2-[2-{[((1R*,2S*)-2-{[(5-chloroindol-2-yl)carbonyl]amino}cyclohexyl)amino]carbonyl}-6,7-dihydrothiazolo[5,4-c]pyridin-5(4H)-yl]acetate hydrochloride

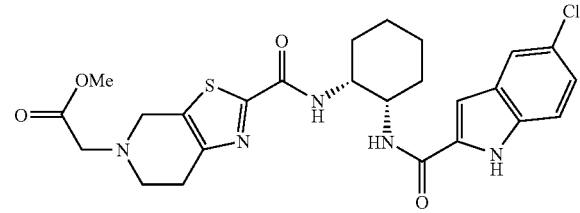

The title compound was obtained from the compound obtained in Example 34 and methyl bromoacetate in a similar manner to Example 25.

$^1$H-NMR (CDCl$_3$) δ: 1.52-1.98 (7H, m), 2.17 (1H, br.s), 2.87-3.10 (4H, m), 3.49 (2H, s), 3.76 (3H, s), 3.93 (1H, d, J=15.4 Hz), 3.99 (1H, d, J=15.4 Hz), 4.22 (1H, br.s), 4.45 (1H, br.s), 6.86 (1H, d, J=1.2 Hz), 7.18 (1H, dd, J=8.8, 2.0 Hz), 7.33 (1H, d, J=8.8 Hz), 7.58-7.63 (2H, m), 7.87 (1H, br.s), 9.88 (1H, br.s). MS (FAB) m/z: 530 (M+H)$^+$.

Example 37

N-((1R*,2S*)-2-{[(5-Chloroindol-2-yl)carbonyl]amino}-cyclohexyl)-5-isopropyl-4,5,6,7-tetrahydrothiazolo[5,4-c]-pyridine-2-carboxamide hydrochloride

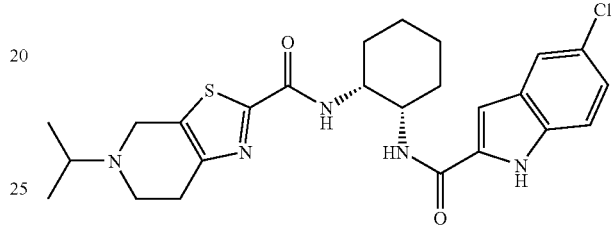

The title compound was obtained from the compound obtained in Example 34 and acetone in a similar manner to Example 24.

$^1$H-NMR (DMSO-d$_6$)δ: 1.18-1.73 (8H, m), 1.81-2.10 (2H, m), 2.97-3.16 (1H, m), 3.20-3.41 (2H, m), 3.52-3.80 (2H, m), 4.19-4.31 (2H, m), 4.34-4.77 (2H, m), 7.17 (1H, s), 7.18 (1H, dd, J=8.8, 2.0 Hz), 7.42 (1H, d, J=8.8 Hz), 7.71 (1H, d, J=2.0 Hz), 8.15 (1H, br.s), 8.28-8.51 (1H, m), 11.31 (1H, br.s), 11.86 (1H, s). MS (FAB) m/z: 500 (M+H)$^+$.

Example 38

N-((1R*,2S*)-2-{[(5-Chloroindol-2-yl)carbonyl]amino}-cyclohexyl)-5-(tetrahydro-2H-pyran-4-yl)-4,5,6,7-tetrahydrothiazolo[5,4-c]pyridine-2-carboxamide hydrochloride

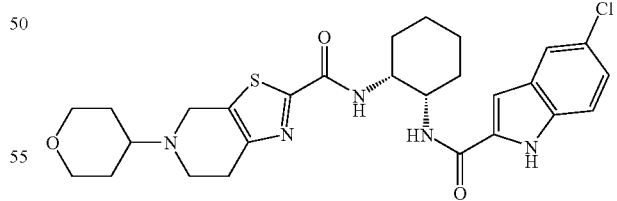

The title compound was obtained from the compound obtained in Example 34 and tetrahydro-4H-pyran-4-one in a similar manner to Example 24.

$^1$H-NMR (DMSO-d$_6$) δ: 1.30-3.56 (19H, m), 3.70-4.01 (3H, m), 4.17-4.30 (2H, m), 4.32-4.80 (1H, m), 7.15 (1H, s), 7.17 (1H, dd, J=8.6, 2.0 Hz), 7.41 (1H, d, J=8.6 Hz), 7.71 (1H, d, J=2.0 Hz), 8.14 (1H, br.s), 8.39 (1H, br.s), 11.84 (1H, s). MS (FAB) m/z: 542 (M+H)$^+$.

Example 39 tert-Butyl 2-[2-{[(1R*,2S*)-2-{[(5-chloroindol-2-yl)carbonyl]amino}cyclohexyl)amino]carbonyl}-6,7-dihydrothiazolo[5,4-c]pyridin-5(4H)-yl]ethylcarbamate

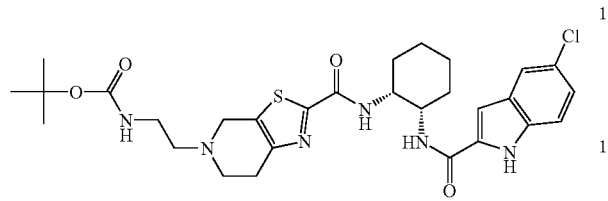

The title compound was obtained from the compound obtained in Example 34 and N-(tert-butoxycarbonyl)aminoacetoaldehyde (J. Org. Chem., 1988, Vol. 53, p. 3457) in a similar manner to Example 24.

$^1$H-NMR (CDCl$_3$) δ: 1.44 (9H, s), 1.54-1.98 (7H, m), 2.10-2.20 (1H, m), 2.74 (2H, br.s), 2.92 (4H, br.s), 3.34 (2H, br.s), 3.84 (2H, br.s), 4.21 (1H, br.s), 4.45 (1H, br.s), 6.86 (1H, s), 7.19 (1H, dd, J=8.8, 2.0 Hz), 7.33 (1H, d, J=8.8 Hz), 7.57-7.63 (2H, m), 7.81 (1H, br.s), 9.66 (1H, br.s). MS (FAB) m/z: 601 (M+H)$^+$.

Example 40

5-(2-Aminoethyl)-N-((1R*,2S*)-2-{[(5-chloroindol-2-yl)carbonyl]amino}cyclohexyl)-4,5,6,7-tetrahydrothiazolo-[5,4-c]pyridine-2-carboxamide hydrochloride

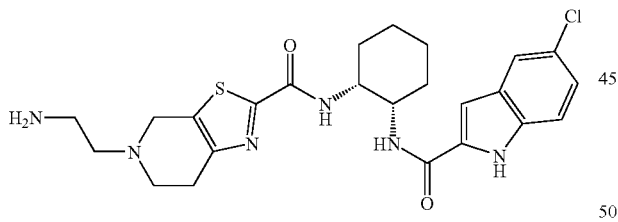

The compound (450 mg) obtained in Example 39 was dissolved in methylene chloride (5 ml), and a saturated ethanol solution (30 ml) of hydrochloric acid was added to stir the mixture at room temperature for 1 minute. The reaction mixture was concentrated under reduced pressure, ethyl acetate was added to the residue, and solids deposited were collected by filtration to obtain the title compound (367 mg).

$^1$H-NMR (DMSO-d$_6$) δ: 1.38-1.50 (2H, m), 1.61 (4H, br.s), 1.85-2.08 (2H, m), 3.00-4.62 (12H, m), 7.14 (1H, s), 7.16 (1H, dd, J=8.8, 2.0 Hz), 7.41 (1H, d, J=8.8 Hz), 7.69 (1H, d, J=2.0 Hz), 8.12 (1H, d, J=6.6 Hz), 8.15-8.68 (4H, m), 11.85 (1H, s). MS (FAB) m/z: 501 (M+H)$^+$.

Example 41

N-((1R*,2S*)-2-{[(5-Chloroindol-2-yl)carbonyl]amino]-cyclohexyl)-5-{2-[(methylsulfonyl)amino]ethyl}-4,5,6,7-tetrahydrothiazolo[5,4-c]pyridine-2-carboxamide hydrochloride

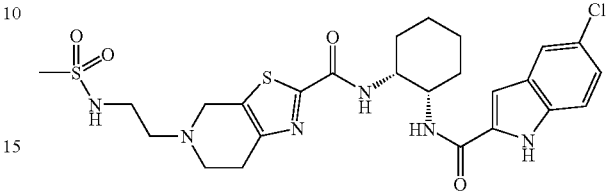

The compound (110 mg) obtained in Example 40 was dissolved in pyridine (3 ml), methanesulfonyl chloride (30 μl) was added, and the mixture was stirred overnight at room temperature. The reaction mixture was concentrated under reduced pressure, and a 85:15 mixed solvent of methylene chloride and methanol, and water were added to conduct liquid separation. The resultant organic layer was dried over anhydrous sodium sulfate. The solvent was distilled off under reduced pressure, and the residue was purified by column chromatography on silica gel (methylene chloride:methanol=100:3) to obtain a pale yellow foamy substance. This product was suspended in 1N hydrochloric acid (0.3 ml), and the suspension was concentrated under reduced pressure to obtain the title compound (63 mg).

$^1$H-NMR (DMSO-d$_6$) δ: 1.38-1.50 (2H, m), 1.55-1.70 (4H, m), 1.86-2.05 (2H, m), 2.97 (3H, s), 3.02-3.25 (2H, m), 3.30-3.60 (5H, m), 3.78 (1H, br.s), 4.18-4.30 (2H, m), 4.45-4.86 (2H, m), 7.14 (1H, s), 7.16 (1H, dd, J=8.8, 2.0 Hz), 7.40 (1H, d, J=8.8 Hz), 7.41 (1H, br.s), 7.69 (1H, d, J=2.0 Hz), 8.09 (1H, br.s), 8.43 (1H, br.s), 11.18 (1H, br.s), 11.82 (1H, s). MS (FAB) m/z: 579 (M+H)$^+$.

Example 42

Methyl 2-[2-{[((1R*,2S*)-2-{[(5-chloroindol-2-yl)carbonyl]amino}cyclohexyl)amino]carbonyl}-6,7-dihydrothiazolo[5,4-c]pyridin-5(4H)-yl]ethylcarbamate hydrochloride

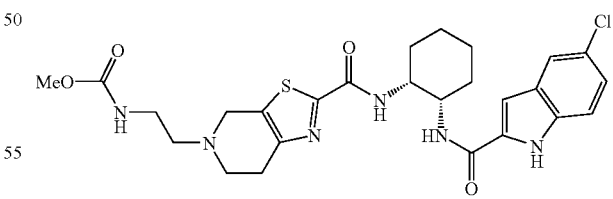

The compound (144 mg) obtained in Example 40 was dissolved in pyridine (3 ml), triethylamine (138 μl) was added, and the mixture was stirred at room temperature for 5 minutes. A solution prepared by adding triphosgene (49 mg) to tetrahydrofuran (1 ml) containing methanol (20 μl) was added dropwise to this solution. After stirring for 1 hour, the reaction mixture was concentrated under reduced pressure, and the residue was dissolved in a 9:1 mixed solvent of methylene chloride and methanol. Water was added to the solution to conduct liquid separation. The resultant organic layer was dried over anhydrous sodium sulfate. The solvent was distilled off under reduced pressure, and the residue was purified by column chromatography on silica gel (methylene chloride:methanol=100:3) to obtain a colorless foamy substance. This product was suspended in 1N hydrochloric acid (0.2 ml), and the suspension was concentrated under reduced pressure to obtain the title compound (60 mg).

$^1$H-NMR (DMSO-$d_6$) δ: 1.38-1.50 (2H, m), 1.61 (4H, br.s), 1.85-2.04 (2H, m), 2.80-3.49 (8H, m), 3.52 (3H, s), 3.62-4.91 (4H, m), 7.14 (1H, s), 7.16 (1H, dd, J=8.8, 2.0 Hz), 7.37 (1H, br.s), 7.40 (1H, d, J=8.8 Hz), 7.70 (1H, s), 8.11 (1H, d, J=6.8 Hz), 8.40 (1H, br.s), 11.05 (1H, br.s), 11.82 (1H, br.s). MS (FAB) m/z: 559 (M+H)$^+$.

Example 43

5-[2-(Acetylamino)ethyl]-N-((1R*,2S*)-2-{[(5-chloroindol-2-yl)carbonyl]amino}cyclohexyl)-4,5,6,7-tetrahydrothiazolo-[5,4-c]pyridine-2-carboxamide hydrochloride

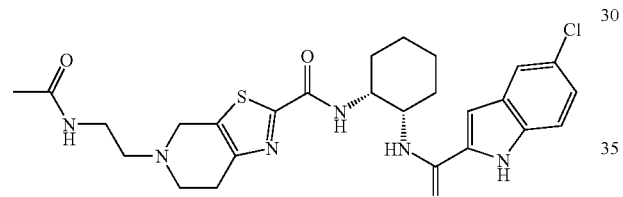

The compound (90 mg) obtained in Example 40 was dissolved in N,N-dimethylformamide (3 ml), triethylamine (65 μl) and acetic anhydride (22 μl) were added, and the mixture was stirred overnight at room temperature. The reaction mixture was concentrated under reduced pressure, and methylene chloride and a 0.3N aqueous solution of sodium hydroxide were added to the residue to conduct liquid separation. The resultant organic layer was dried over anhydrous sodium sulfate. The solvent was distilled off under reduced pressure, and the residue was purified by column chromatography on silica gel (methylene chloride:methanol=100:3) to obtain a colorless foamy substance. This product was suspended in 1N hydrochloric acid (0.3 ml), and the suspension was concentrated under reduced pressure to obtain the title compound (73 mg).

$^1$H-NMR (DMSO-$d_6$) δ: 1.39-1.52 (2H, m), 1.54-1.70 (4H, m), 1.83 (3H, s), 1.84-2.06 (2H, m), 3.02-3.87 (8H, m), 4.16-4.32 (2H, m), 4.40-4.52 (1H, m), 4.78-4.88 (1H, m), 7.14 (1H, s), 7.16 (1H, d, J=8.6 Hz), 7.40 (1H, d, J=8.6 Hz), 7.70 (1H, s), 8.07-8.17 (1H, m), 8.22-8.30 (1H, m), 8.38-8.52 (1H, m), 11.14 (1H, br.s), 11.83 (1H, s). MS (FAB) m/z: 543 (M+H)$^+$.

Example 44

N-((1R*,2S*)-2-{[(5-Chloroindol-2-yl)carbonyl]amino}cyclohexyl)-5-(2-hydroxyethyl)-4,5,6,7-tetrahydrothiazolo[5,4-c]pyridine-2-carboxamide

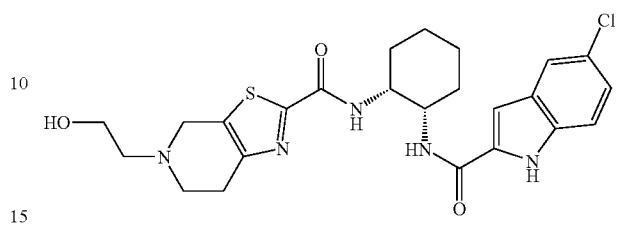

The title compound was obtained from the compound obtained in Example 34 and 2-bromoethanol in a similar manner to Example 25.

$^1$H-NMR (DMSO-$d_6$) δ: 1.37-1.69 (6H, m), 1.86-2.03 (2H, m), 2.54-2.61 (2H, m), 2.75-2.86 (4H, m), 3.52-3.59 (2H, m), 3.75 (2H, s), 4.47 (1H, t, J=5.4 Hz), 7.12 (1H, s), 7.16 (1H, dd, J=8.8, 2.0 Hz), 7.40 (1H, d, J=8.8 Hz), 7.70 (1H, s), 8.05-8.13 (1H, m), 8.28-8.35 (1H, m), 11.78 (1H, s). MS (FAB) m/z: 502 (M+H)$^+$.

Example 45

5-Butyl-N-((1R*,2S*)-2-{[(5-chloroindol-2-yl)carbonyl]-amino}cyclohexyl)-4,5,6,7-tetrahydrothiazolo[5,4-c]-pyridine-2-carboxamide hydrochloride

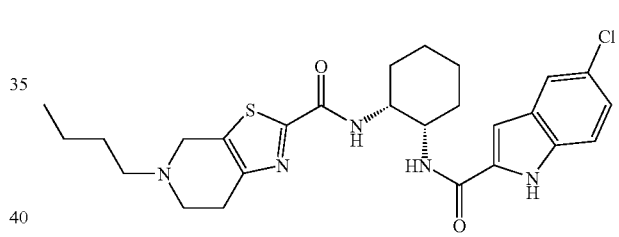

The title compound was obtained from the compound obtained in Example 34 and n-bromobutane in a similar manner to Example 25.

$^1$H-NMR (DMSO-$d_6$) δ: 0.88 (3H, t, J=7.2 Hz), 1.20-1.70 (10H, m), 1.87-2.05 (2H, m), 2.55-3.40 (8H, m), 4.16-4.30 (2H, m), 7.13 (1H, s), 7.16 (1H, d, J=8.8 Hz), 7.40 (1H, d, J=8.8 Hz), 7.69 (1H, s), 8.05-8.14 (1H, m), 8.35 (1H, br.s), 11.81 (1H, s). MS (FAB) m/z: 514 (M+H)$^+$.

Example 46

5-Acetyl-N-((1R*,2S*)-2-{[(5-chloroindol-2-yl)carbonyl]-amino}cyclohexyl)-4,5,6,7-tetrahydrothiazolo[5,4-c]-pyridine-2-carboxamide

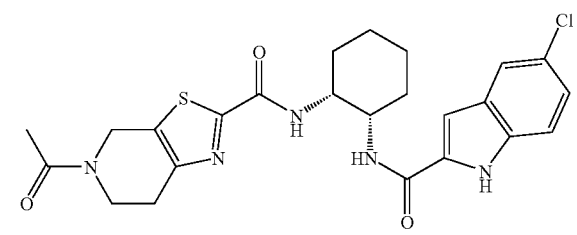

The compound (100 mg) obtained in Example 34 was dissolved in N,N-dimethylformamide (3 ml), triethylamine (84 μl) and acetic anhydride (29 μl) were added, and the mixture was stirred at room temperature for 3 hours. The reaction mixture was concentrated under reduced pressure, and methylene chloride and 1N hydrochloric acid were added to the residue to conduct liquid separation. The resultant organic layer was dried over anhydrous sodium sulfate. The solvent was distilled off under reduced pressure, and the residue was purified by column chromatography on silica gel (methylene chloride:methanol=100:3) to obtain the title compound (86 mg).

$^1$H-NMR (CDCl$_3$) δ: 1.52-1.85 (5H, m), 1.91 (2H, br.s), 2.10-2.28 (4H, m), 2.77-3.00 (2H, m), 3.70-4.00 (2H, m), 4.19-4.38 (1H, m), 4.45 (1H, br.s), 4.68-4.99 (2H, m), 6.85 (1H, s), 7.17-7.22 (1H, m), 7.30-7.39 (1H, m), 7.50-7.84 (3H, m), 9.72-10.05 (1H, m). MS (FAB) m/z: 500 (M+H)$^+$.

Example 47

N-((1R*,2S*)-2-{[(5-Chloroindol-2-yl)carbonyl]amino}-cyclohexyl)-5-(methylsulfonyl)-4,5,6,7-tetrahydrothiazolo[5,4-c]pyridine-2-carboxamide

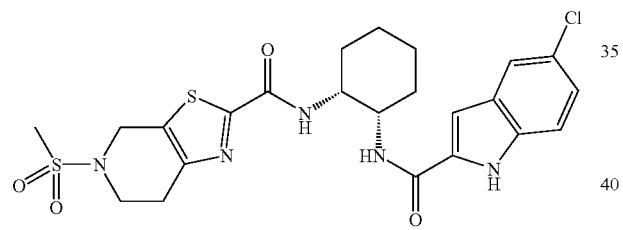

The compound (100 mg) obtained in Example 34 was dissolved in pyridine (3 ml), triethylamine (168 μl) and methanesulfonyl chloride (48 μl) were added, and the mixture was stirred overnight at room temperature. The reaction mixture was concentrated under reduced pressure, and methylene chloride and 1N hydrochloric acid were added to the residue to separate an organic layer. The resultant organic layer was dried over anhydrous sodium sulfate. The solvent was distilled off under reduced pressure, and the residue was purified by column chromatography on silica gel (methylene chloride:methanol=100:1) to obtain the title compound (79 mg).

$^1$H-NMR (CDCl$_3$) δ: 1.50-1.82 (5H, m), 1.90 (2H, br.s), 2.13 (1H, br.s), 2.89 (3H, s), 2.91-2.98 (2H, m), 3.60-3.70 (2H, m), 4.30 (1H, br.s), 4.44 (1H, br.s), 4.58 (2H, s), 6.87 (1H, s), 7.19 (1H, d, J=8.8 Hz), 7.34 (1H, d, J=8.8 Hz), 7.61 (3H, br.s), 9.91 (1H, br.s). MS (FAB) m/z: 536 (M+H)$^+$.

Example 48

5-Methyl-N-((1R*,2S*)-2-{[(5-methylindol-2-yl)carbonyl]-amino}cyclohexyl)-4,5,6,7-tetrahydrothiazolo[5,4-c]-pyridine-2-carboxamide hydrochloride

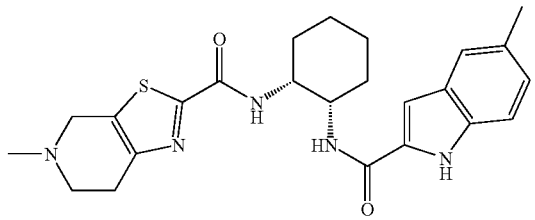

The title compound was obtained from the compound obtained in Referential Example 67 and 5-methylindole-2-carboxylic acid in a similar manner to Example 5.

$^1$H-NMR (DMSO-d$_6$) δ: 1.35-1.50 (2H, m), 1.50-1.80 (4H, m), 1.85-2.07 (2H, m), 2.36 (3H, s), 2.88 (3H, s), 3.12 (2H, br.s), 3.53 (2H, br.s), 4.15-4.30 (2H, m), 4.30-4.80 (2H, br), 7.00 (1H, dd, J=8.4, 1.5 Hz), 7.05 (1H, d, J=1.5 Hz), 7.30 (1H, d, J=8.4 Hz), 7.38 (1H, s), 8.00 (1H, d, J=7.3 Hz), 8.43 (1H, br.s), 11.45 (1H, br.s), 11.49 (1H, br.s). MS (FAB) m/z: 452 (M+H)$^+$.

Example 49

Ethyl (1R*,3S*,4R*)-4-{[(5-chloroindol-2-yl)carbonyl]-amino}-3-{[(5-methyl-4,5,6,7-tetrahydrothiazolo[5,4-c]-pyridin-2-yl)carbonyl]amino}cyclohexanecarboxylate

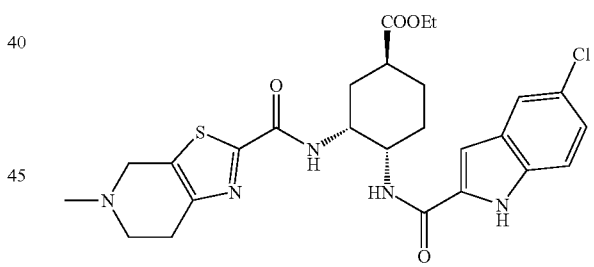

The compound (1.40 g) obtained in Referential Example 91 was suspended in ethanol (8 ml), and a saturated ethanol solution (10 ml) of hydrochloric acid was added at room temperature to stir the mixture for 12 hours. The solvent was distilled off under reduced pressure to obtain ethyl (1R*,3S*,4R*)-3-amino-4-{[(5-chloroindol-2-yl)carbonyl]amino}cyclohexanecarboxylate hydrochloride (1.25 g).

The title compound was obtained from the above-described product and the compound obtained in Referential Example 10 in a similar manner to Example 2.

$^1$H-NMR (CDCl$_3$) δ: 1.29 (3H, t, J=7.1 Hz), 1.52-1.80 (2H, m), 2.03-2.37 (4H, m), 2.53 (3H, s), 2.57-2.71 (1H, m), 3.73 and 3.78 (total 1H, each d, J=14.4 Hz), 4.08-4.17 (1H, m), 4.18 (2H, q, J=7.2 Hz), 4.55-4.65 (1H, m), 6.85 (1H, br.s), 7.21 (1H, dd, J=8.8, 2.0 Hz), 7.33 (1H, d, J=8.8 Hz), 7.48 (1H, d, J=7.6 Hz), 7.63 (1H, d, J=2.0 Hz), 7.98 (1H, d, J=7.6 Hz), 9.30 (1H, s). MS (ESI) m/z: 544 (M+H)$^+$.

Example 50

Ethyl (1S,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylate

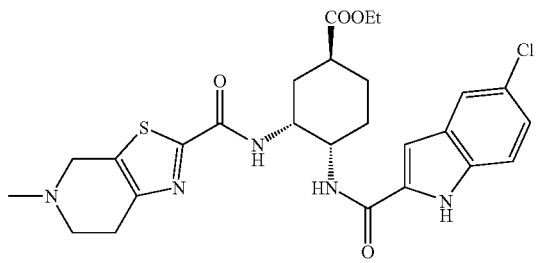

The compound (4.2 g) obtained in Referential Example 97 was suspended in ethanol (25 ml), and a saturated ethanol solution (55 ml) of hydrochloric acid was added at room temperature to stir the mixture for 11 hours. The solvent was distilled off under reduced pressure to obtain colorless solids (4.15 g).

This product (4.15 g) was dissolved in N,N-dimethylformamide (40 ml), and the compound (2.86 g) obtained in Referential Example 10, 1-hydroxybenzotriazole monohydrate (1.72 g) and 1-(3-dimethylaminopropyl)-3-ethylcarbodiimide hydrochloride (2.15 g) were added to this solution at room temperature to stir the mixture for 39 hours. The reaction mixture was concentrated under reduced pressure, and water was added to the residue to conduct extraction with chloroform. The resultant organic layer was washed with saturated aqueous solution of sodium chloride and dried over anhydrous magnesium sulfate. The solvent was distilled off under reduced pressure, and the resultant residue was purified by column chromatography on silica gel (chloroform:methanol=100:1) to obtain the title compound (1.71 g).

$[\alpha]_D$ –94° (C=1.0, chloroform).

Example 51

Methyl (1R*,3R*,4S*)-3-{[(5-chloroindol-2-yl)carbonyl]-amino}-4-{[(5-methyl-4,5,6,7-tetrahydrothiazolo[5,4-c]-pyridin-2-yl)carbonyl]amino}cyclohexanecarboxylate

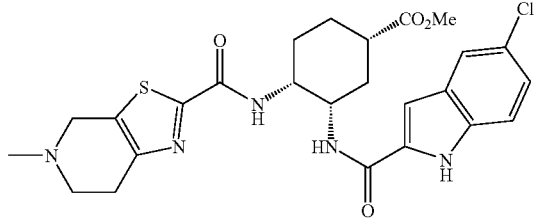

The title compound was obtained by treating the compound obtained in Referential Example 107 with an ethanol solution of hydrochloric acid and then condensing this compound with the compound obtained in Referential Example 10 in a similar manner to Example 49.

$^1$H-NMR (DMSO-d$_6$) δ: 1.55-1.80 (3H, m), 1.80-2.20 (3H, m), 2.60-2.75 (1H, m), 2.92 (3H, s), 3.15-3.30 (1H, m), 3.30-3.50 (4H, m), 3.57 (3H, s), 3.55-3.70 (1H, m), 4.20-4.30 (1H, m), 4.30-4.40 (1H, m), 7.02 (1H, s), 7.17 (1H, dd, J=8.5, 2.0 Hz), 7.41 (1H, d, J=8.5 Hz), 7.71 (1H, s), 8.20-8.35 (1H, m), 8.35-8.45 (1H, m), 11.82 (1H, br). MS (FAB) m/z: 530 (M+H)$^+$.

Example 52

Ethyl (1R*,3S*,4R*)-3-{[(5-chloroindol-2-yl)carbonyl]-amino}-4-{[(5-methyl-4,5,6,7-tetrahydrothiazolo[5,4-c]-pyridin-2-yl)carbonyl]amino}cyclohexanecarboxylate

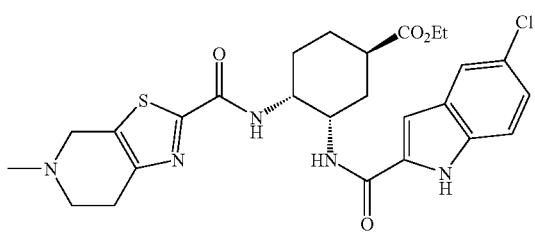

The title compound was obtained by treating the compound obtained in Referential Example 98 with a saturated ethanol solution of hydrochloric acid and then condensing it with 5-chloroindole-2-carboxylic acid in a similar manner to Example 49.

$^1$H-NMR (CDCl$_3$) δ: 1.29 (3H, t, J=7.1 Hz), 1.82-2.30 (6H, m), 2.49 (3H, s), 2.62-2.73 (1H, m), 3.74-3.85 (2H, m), 3.85-3.93 (2H, m), 3.71 (2H, s), 4.12-4.29 (3H, m), 4.49-4.59 (1H, m), 6.89 (1H, br.s), 7.21 (1H, dd, J=8.8, 2.0 Hz), 7.32 (1H, d, J=8.8 Hz), 7.33 (1H, br.s), 7.41 (1H, br.s), 7.62 (1H, br.s), 9.37 (1H, s). MS (ESI) m/z: 544 (M+H)$^+$.

Example 53

Methyl (1R*,3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}cyclohexanecarboxylate

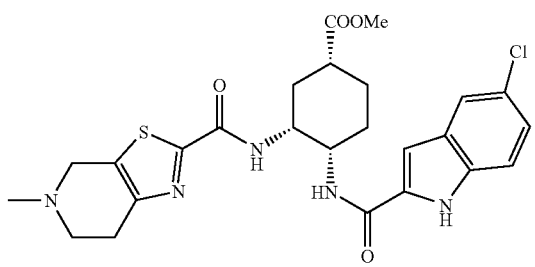

The title compound was obtained by treating the compound obtained in Referential Example 106 with a 4N dioxane solution of hydrochloric acid and then condensing it with 5-chloroindole-2-carboxylic acid in a similar manner to Example 49.

$^1$H-NMR (DMSO-d$_6$) δ: 1.65-1.80 (3H, m), 1.80-2.10 (2H, m), 2.15-2.25 (1H, m), 2.55-2.70 (1H, m), 2.89 (3H, s), 3.05-3.20 (1H, m), 3.30-3.50 (4H, m), 3.55-3.65 (1H, m), 3.62 (3H, s), 4.20-4.30 (1H, m), 4.35-4.45 (1H, m), 7.19 (1H, dd, J=8.8, 1.2 Hz), 7.23 (1H, s), 7.43 (1H, d, J=8.8 Hz), 7.73 (1H, s), 8.03 (1H, d, J=6.8 Hz), 8.73 (1H, d, J=8.5 Hz), 11.15-11.38 (1H, br), 11.85 (1H, s). MS (FAB) m/z: 530 (M+H)+.

Example 54

Methyl (1R,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylate

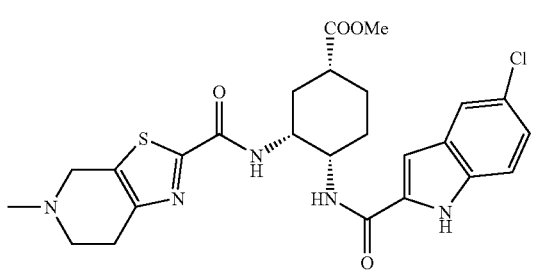

The title compound was obtained by treating the compound obtained in Referential Example 112 a 4N dioxane solution of hydrochloric acid and then condensing it with 5-chloroindole-2-carboxylic acid in a similar manner to Example 49.

1H-NMR (DMSO-d6) δ: 1.67-1.76 (3H, m), 1.88-1.91 (1H, m), 2.01 (1H, br.s), 2.13-2.22 (1H, m), 2.52-2.67 (4H, m), 2.86 (2H, br.s), 3.04 (2H, br.s), 3.33-3.41 (1H, m), 3.61 (3H, s), 4.22-4.36 (3H, m), 7.17-7.22 (2H, m), 7.42 (1H, d, J=8.8 Hz), 7.72 (1H, s), 8.00 (1H, d, J=6.9 Hz), 8.68 (1H, d, J=8.6 Hz), 11.80 (1H, s). MS (FAB) m/z: 530 (M+H)+.

Example 55

N-((1R*,2S*,5S*)-5-(Aminocarbonyl)-2-{[(5-chloroindol-2-yl)carbonyl]amino}cyclohexyl)-5-methyl-4,5,6,7-tetrahydrothiazolo[5,4-c]pyridine-2-carboxamide

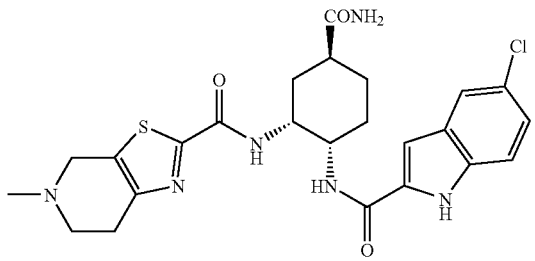

The title compound was obtained by treating the compound obtained in Referential Example 113 with a 4N dioxane solution of hydrochloric acid and then condensing it with the compound obtained in Referential Example 10.

1H-NMR (CDCl3) δ: 0.78-2.40 (7H, m), 2.53 (3H, s), 2.80-2.89 (1H, m), 2.91-3.00 (1H, m), 3.68-3.76 (2H, m), 4.08-4.19 (1H, m), 4.54-4.65 (1H, m), 6.80 (1H, br.s), 7.21 (1H, dd, J=8.4, 1.6 Hz), 7.33 (1H, d, J=8.4 Hz), 7.38-7.43 (1H, m), 7.49-7.55 (1H, m), 7.63 (1H, br.s), 9.14 (1H, br.s). MS (ESI) m/z: 515 (M+H)+.

Example 56

(1R*,3S*,4R*)-4-{[(5-Chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid

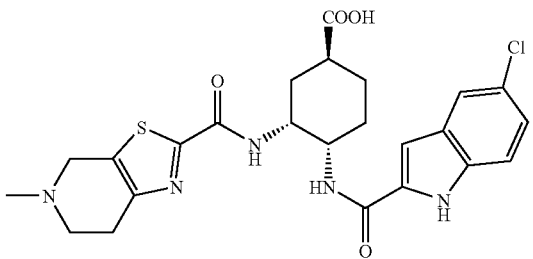

The compound (916 mg) obtained in Example 49 was suspended in a mixed solvent of ethanol (10 ml) and tetrahydrofuran (8 ml), and a 1N aqueous solution (3.3 ml) of sodium hydroxide was added at room temperature to stir the mixture for 12 hours at the same temperature. After adding 1N hydrochloric acid (3.3 ml), the solvent was distilled off under reduced pressure, and the residue was washed with water and diethyl ether to obtain the title compound (712 mg).

Example 57

N-{(1R*,2S*,5S*)-2-{[(5-Chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

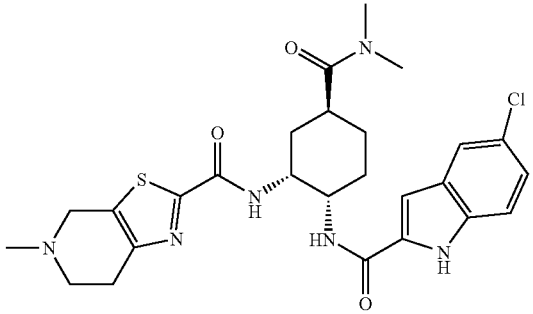

Triethylamine (0.25 ml), dimethylamine hydrochloride (133 mg), 1-hydroxybenzotriazole monohydrate (53 mg) and 1-(3-dimethylaminopropyl)-3-ethylcarbodiimide hydrochloride (75 mg) were added to a chloroform suspension (10 ml) of the compound (168 mg) obtained in Example 56, and the mixture was stirred for 72 hours. The solvent was distilled off under reduced pressure, and water was added to the residue to conduct extraction with chloroform. The resultant organic layer was washed with saturated aqueous solution of sodium chloride and dried over anhydrous magnesium sulfate. The solvent was distilled off under reduced pressure, and the resultant residue was purified by column chromatography on silica gel (methylene chloride:methanol=93:7). The thus-obtained colorless solids (135 mg) were suspended in ethanol (5 ml), to which 1N ethanol solution (0.5 ml) of hydrochloric acid was added. The mixture was stirred for 2 hours, and the solvent was distilled off to obtain the title compound (112 mg).

$^1$H-NMR (DMSO-$d_6$) δ: 1.42-2.07 (6H, m), 2.73-3.70 (10H, m), 2.88 (3H, s), 2.97 (3H, s), 4.03-4.20 (1H, m), 4.51-4.67 (1H, m), 7.04 (1H, br.s), 7.16 (1H, br, J=8.8 Hz), 7.41 (1H, d, J=8.8 Hz), 7.68 (1H, br.s), 8.32-8.47 (2H, m), 10.76 (1H, br.s). MS (ESI) m/z: 543 (M+H)$^+$.

Example 58

(1S,3R,4S)-4-{[(5-Chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid

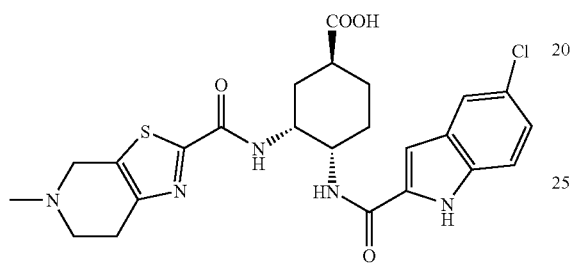

The compound (1.6 g) obtained in Example 50 was suspended in a mixed solvent of ethanol (20 ml) and tetrahydrofuran (15 ml), and a 1N aqueous solution (5.9 ml) of sodium hydroxide was added at room temperature to stir the mixture for 12 hours at the same temperature. After adding 1N hydrochloric acid (5.9 ml), the solvent was distilled off under reduced pressure, and the residue was washed with water and diethyl ether to obtain the title compound (1.19 g).

m.p. 234-236° C. [α]$_D$ −57° (C=1.0, methanol).

Example 59

N-{(1R,2S,5S)-2-{[(5-Chloroindol-2-yl)carbonyl]amino}-5-[(cyclopropylamino)carboyl]cyclohexyl}-5-methyl-4,5,6,7-tetrahydrothiazolo[5,4-c]pyridine-2-carboxamide hydrochloride

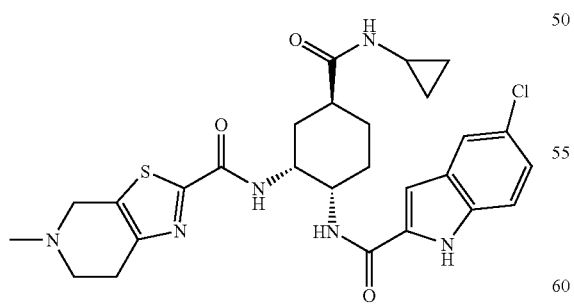

The title compound was obtained from the compound obtained in Example 58 and cyclopropylamine in a similar manner to Example 57.

$^1$H-NMR (DMSO-$d_6$) δ: 0.32-0.40 (2H, m), 0.53-0.63 (2H, m), 1.50-2.10 (6H, m), 2.25-2.40 (1H, m), 2.45-2.70 (2H, m), 2.91 (3H, s), 3.05-3.80 (3H, m), 4.05-4.17 (1H, m), 4.30-4.55 (2H, m), 4.55-4.80 (1H, m), 7.03 (1H, d, J=1.5 Hz), 7.16 (1H, dd, J=8.8, 2.0 Hz), 7.41 (1H, d, J=8.8 Hz), 7.68 (1H, d, J=2.0 Hz), 7.86 (1H, br, J=3.4 Hz), 8.06 (1H, br.s), 8.40 (1H, br, J=7.6 Hz), 11.20-11.60 (1H, br), 11.79 (1H, s). MS (FAB) m/z: 555 (M+H)$^+$.

Example 60

N-[(1R,2S,5S)-2-{[(5-Chloroindol-2-yl)carbonyl]amino}-5-(pyrrolidin-1-ylcarbonyl)cyclohexyl]-5-methyl-4,5,6,7-tetrahydrothiazolo[5,4-c]pyridine-2-carboxamide hydrochloride

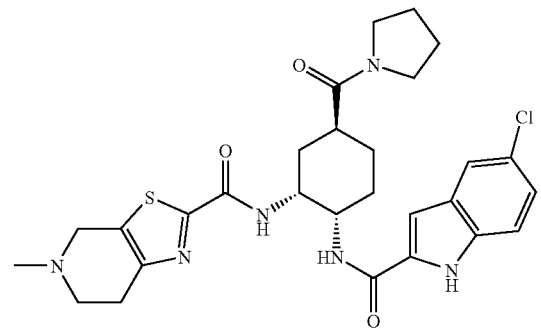

The title compound was obtained from the compound obtained in Example 58 and pyrrolidine in a similar manner to Example 57.

$^1$H-NMR (DMSO-$d_6$) δ: 1.45-2.10 (10H, m), 2.75-2.90 (2H, m), 2.90 (3H, s), 3.10-3.70 (H, m), 4.05-4.20 (1H, m), 4.25-4.80 (3H, m), 7.05 (1H, s), 7.17 (1H, d, J=8.7 Hz), 7.41 (1H, d, J=8.7 Hz), 7.69 (1H, s), 8.32 (1H, br, J=7.6 Hz), 8.38 (1H, br, J=7.1 Hz), 11.22 (1H, br.s), 11.78 (1H, s). MS (FAB) m/z: 569 (M+H)$^+$.

Example 61

N-[(1R*,2S*,5S*)-2-{[(5-Chloroindol-2-yl)carbonyl]amino}-5-(4-morpholinylcarbonyl)cyclohexyl]-5-methyl-4,5,6,7-tetrahydrothiazolo[5,4-c]pyridine-2-carboxamide hydrochloride

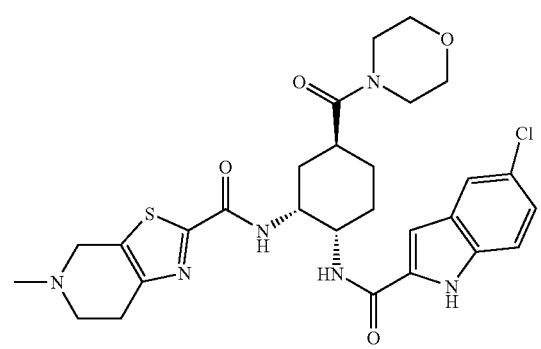

The title compound was obtained from the compound obtained in Example 56 and morpholine in a similar manner to Example 57.

$^1$H-NMR (DMSO-$d_6$) δ: 1.40-2.05 (6H, m), 2.75-3.70 (18H, m), 4.02-4.17 (1H, m), 4.55-4.69 (1H, m), 7.05 (1H, br.s), 7.17 (1H, br, J=8.8 Hz), 7.41 (1H, d, J=8.8 Hz), 7.67 (1H, br.s), 8.35 (1H, d, J=7.6 Hz), 8.40 (1H, d, J=7.6 Hz), 10.79 (1H, br.s). MS (ESI) m/z: 585 (M+H)+.

Example 62

N-((1R,2S,5S)-2-{[(5-Chloroindol-2-yl)carbonyl]amino}-5-[(ethylamino)carbonyl]cyclohexyl}-5-methyl-4,5,6,7-tetrahydrothiazolo[5,4-c]pyridine-2-carboxamide hydrochloride

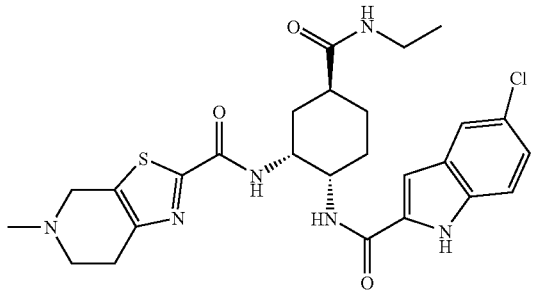

The compound (150 mg) obtained in Example 58 was dissolved in N,N-dimethylformamide (3 ml), to which N-ethylamine hydrochloride (119 mg), 1-hydroxybenzotriazole monohydrate (79 mg), 1-(3-dimethylaminopropyl)-3-ethylcarbodiimide hydrochloride (112 mg) and triethylamine (326 µl) were added, and the mixture was stirred at room temperature for 4 days. The solvent was distilled off under reduced pressure, and a saturated aqueous solution of sodium hydrogencarbonate was added to the residue to conduct extraction with methylene chloride. The resultant organic layer was dried over anhydrous sodium sulfate. The solvent was distilled off under reduced pressure, and the resultant residue was purified by column chromatography on silica gel (methylene chloride:methanol=47:3). The thus-obtained solid was dissolved in methylene chloride, to which 1N ethanol solution (171 µl) of hydrochloric acid was added. The solvent was distilled off under reduced pressure, and methanol and diethyl ether were added to the residue to collect precipitate formed by filtration, thereby obtaining the title compound (74 mg).

$^1$H-NMR (DMSO-$d_6$) δ: 0.99 (3H, t, J=7.2 Hz), 1.57-2.02 (6H, m), 2.33-2.38 (1H, m), 2.92 (3H, s), 3.01-3.08 (2H, m), 3.17-3.20 (2H, s), 3.45-3.70 (2H, m), 4.10-4.17 (1H, m), 4.40-4.69 (3H, m), 7.04 (1H, d, J=2.0 Hz), 7.17 (1H, dd, J=8.8, 2.0 Hz), 7.41 (1H, d, J=8.8 Hz), 7.69 (1H, d, J=2.0 Hz), 7.78-7.81 (1H, m), 8.08-8.12 (1H, m), 8.40 (1H, d, J=8.1 Hz), 11.23 (1H, br.s), 11.79 (1H, br.s). MS (FAB) m/z: 543 (M+H)+.

Example 63

N-{(1R,2S,5S)-2-{[(5-Chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

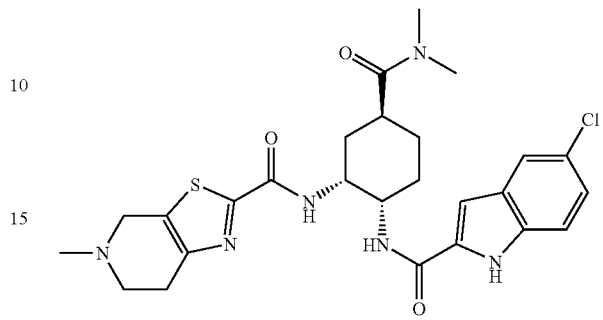

The compound (900 mg) obtained in Example 58 was dissolved in N,N-dimethylformamide (50 ml), to which dimethylamine hydrochloride (304 mg), 1-hydroxybenzotriazole monohydrate (262 mg), 1-(3-dimethylaminopropyl)-3-ethylcarbodiimide hydrochloride (369 mg) and diisopropylethylamine (1.83 ml) were added, and the mixture was stirred at room temperature for 12 hours. The solvent was distilled off under reduced pressure, and a saturated aqueous solution of sodium hydrogencarbonate was added to the residue to conduct extraction with methylene chloride. The resultant organic layer was dried over anhydrous sodium sulfate. The solvent was distilled off under reduced pressure, and the resultant residue was purified by column chromatography on silica gel (methylene chloride:methanol=47:3). The thus-obtained white solids were dissolved in methylene chloride, to which 1N ethanol solution (1.49 ml) of hydrochloric acid was added. The solvent was distilled off under reduced pressure, and methanol and diethyl ether were added to the residue to collect precipitate formed by filtration, thereby obtaining the title compound (777 mg).

[α]$_D$=−53.9° (18° C., c=0.505, methanol). $^1$H-NMR (DMSO-$d_6$) δ: 1.45-1.60 (1H, m), 1.70-1.85 (3H, m), 1.90-2.05 (2H, m), 2.80 (3H, s), 2.91 (3H, s), 2.95-3.10 (1H, m), 2.97 (3H, s), 3.10-3.75 (4H, m), 4.05-4.15 (1H, m), 4.35-4.75 (3H, m), 7.05 (1H, s), 7.16 (1H, dd, J=8.7, 2.1 Hz), 7.41 (1H, d, J=8.6 Hz), 7.67 (1H, s), 8.30-8.45 (2H, m), 11.63 (1H, br), 11.78 (1H, s). MS (FAB) m/z: 543 (M+H)+.

Example 64

N-((1R,2S,5S)-2-{[(5-Chloroindol-2-yl)carbonyl]amino}-5-{[(2-methoxyethyl)(methyl)amino]carbonyl}cyclohexyl)-5-methyl-4,5,6,7-tetrahydrothiazolo[5,4-c]pyridine-2-carboxamide hydrochloride

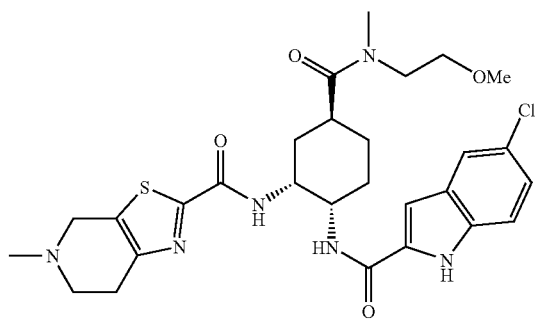

The title compound was obtained from the compound obtained in Example 58 in a similar manner to Example 57.

$^{1}$H-NMR (DMSO-$d_6$) δ: 1.50-1.99 (6H, m), 2.80, 3.01 (3H, each s), 2.91 (3H, s), 3.03 (1H, br.s), 3.16 (2H, s), 3.23 (3H, s), 3.35-3.67 (6H, m), 4.09-4.16 (1H, m), 4.43-4.67 (3H, m), 7.04-7.06 (1H, m), 7.16 (1H, dd, J=8.8, 2.0 Hz), 7.42 (1H, d, J=8.8 Hz), 7.69 (1H, br.s), 8.29-8.41 (2H, m), 11.59 (1H, br.s), 11.80 (1H, br.s). MS (FAB) m/z: 587 (M+H)$^+$.

Example 65

N-((1R,2S,5S)-2-{[(5-Chloroindol-2-yl)carbonyl]amino}-5-{[(2-hydroxyethyl)(methyl)amino]carbonyl}cyclohexyl)-5-methyl-4,5,6,7-tetrahydrothiazolo[5,4-c]pyridine-2-carboxamide hydrochloride

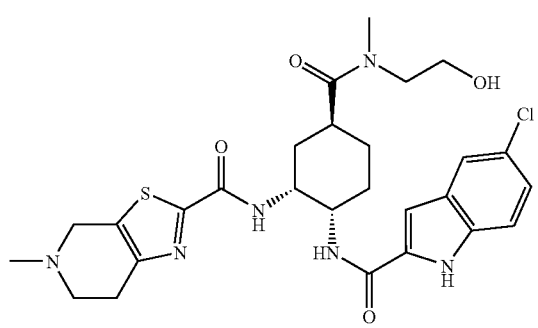

The title compound was obtained from the compound obtained in Example 58 in a similar manner to Example 57.

$^{1}$H-NMR (DMSO-$d_6$) δ: 1.50-1.55 (1H, m), 1.74-1.84 (3H, m), 1.94-1.97 (2H, m), 2.67, 3.02 (3H, each s), 2.91 (3H, s), 3.10-3.68 (9H, m), 4.11-4.13 (1H, m), 4.43-4.66 (4H, m), 7.05 (1H, s), 7.16 (1H, dd, J=8.7, 2.0 Hz), 7.41 (1H, d, J=8.7 Hz), 7.68 (1H, s), 8.34-8.40 (2H, m), 11.47 (1H, br.s), 11.79 (1H, s). MS (FAB) m/z: 573 (M+H)$^+$.

Example 66

N-((1R,2S,5S)-5-(1-Azetidinylcarbonyl)-2-{[(5-chloroindol-2-yl)carbonyl]amino}cyclohexyl)-5-methyl-4,5,6,7-tetrahydrothiazolo[5,4-c]pyridine-2-carboxamide hydrochloride

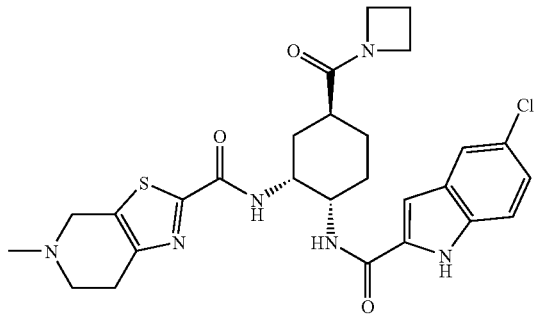

The title compound was obtained from the compound obtained in Example 58 and azetidine hydrochloride in a similar manner to Example 57.

$^{1}$H-NMR (DMSO-$d_6$)δ: 1.47-1.55 (1H, m), 1.65-1.82 (3H, m), 1.88-2.01 (2H, m), 2.16 (2H, quint., J=7.6 Hz), 3.17-3.67 (5H, m), 3.82 (2H, t, J=7.6 Hz), 4.02-4.14 (3H, m), 4.43-4.67 (3H, m), 7.06 (1H, s), 7.17 (1H, dd, J=8.7, 1.7 Hz), 7.41 (1H, d, J=8.7 Hz), 7.69 (1H, br.s), 8.31 (1H, d, J=7.6 Hz), 8.38 (1H, d, J=7.6 Hz), 11.41 (1H, br.s), 11.80 (1H, s). MS (FAB) m/z: 555 (M+H)$^+$.

Example 67

N-((1R,2S,5S)-2-{[(5-Chloroindol-2-yl)carbonyl]amino}-5-{[(3S)-3-fluoropyrrolidinyl]carbonyl}cyclohexyl)-5-methyl-4,5,6,7-tetrahydrothiazolo[5,4-c]pyridinecarboxamide hydrochloride

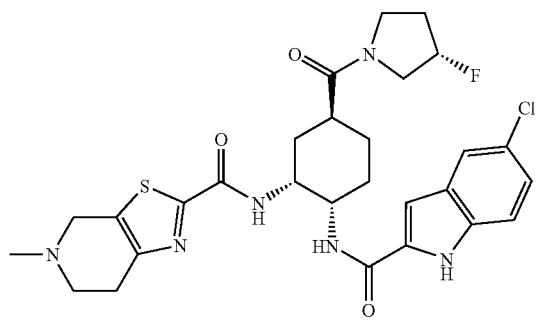

The title compound was obtained from the compound obtained in Example 58 and (S)-3-fluoropyrrolidine (Synlett., 1995, p. 55) in a similar manner to Example 57.

$^{1}$H-NMR (DMSO-$d_6$) δ: 1.23-3.77 (22H, m), 4.11-4.16 (1H, m), 4.58-4.51 (1H, m), 5.23-5.42 (1H, m), 7.05 (1H, s), 7.16 (1H, d, J=8.3 Hz), 7.42 (1H, d, J=8.3 Hz), 7.68 (1H, s), 8.34-8.37 (2H, m), 11.78 (1H, s). MS (FAB) m/z: 587 (M+H)$^+$.

Example 68

Lithium(1R*,3R*,4S*)-3-{[(5-Chloroindol-2-yl)carbonyl]-amino}-4-{[(5-methyl-4,5,6,7-tetrahydrothiazolo[5,4-c]-pyridin-2-yl)carbonyl]amino}cyclohexanecarboxylate

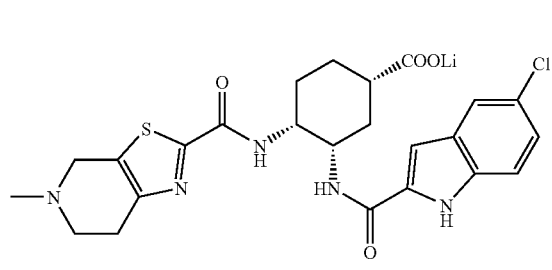

The compound (1.20 g) obtained in Example 51 was dissolved in tetrahydrofuran (32 ml), and lithium hydroxide (60.8 mg) and water (4 ml) were successively added under ice cooling to stir the mixture at room temperature for 14 hours. The solvent was distilled off under reduced pressure to obtain the title compound (1.12 g).

$^1$H-NMR (DMSO-d$_6$) δ: 1.55-1.70 (2H, m), 1.70-2.05 (4H, m), 2.10-2.20 (1H, m), 2.25-2.40 (4H, m), 2.50-2.80 (4H, m), 3.45-3.65 (3H, m), 4.10-4.30 (2H, m), 7.00-7.20 (2H, m), 7.50-7.65 (2H, m).

Example 69

N-{(1R*,2S*,4S*)-2-{[(5-Chloroindol-2-yl)carbonyl]amino}-4-[(dimethylamino)carbonyl]cyclohexyl}-5-methyl-4,5,6,7-tetrahydrothiazolo[5,4-c]pyridine-2-carboxamide hydrochloride

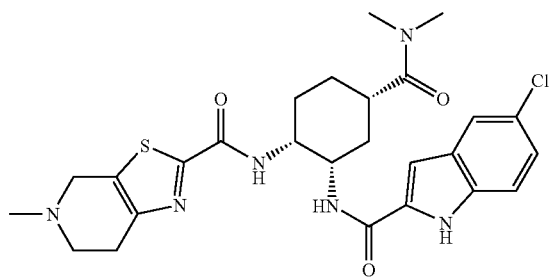

The title compound was obtained from the compound obtained in Example 68 and dimethylamine in a similar manner to Example 57.

$^1$H-NMR (DMSO-d$_6$) δ: 1.40-1.60 (2H, m), 1.65-1.80 (2H, m), 1.95-2.10 (2H, m), 2.84 (3H, s), 2.90-3.05 (1H, m), 2.92 (3H, s), 3.06 (3H, s), 3.15-3.75 (4H, m), 4.25-4.75 (4H, m), 7.02 (1H, d, J=1.5 Hz), 7.15 (1H, dd, J=8.8, 2.1 Hz), 7.41 (1H, d, J=8.8 Hz), 7.69 (1H, d, J=2.1 Hz), 8.05 (1H, d, J=7.7 Hz), 8.63 (1H, d, J=7.7 Hz), 11.20 (1H, br), 11.79 (1H, s). MS (FAB) m/z: 543 (M+H)$^+$.

Example 70

N-((1R,2S,5S)-2-{[(5-Chloroindol-2-yl)carbonyl]amino}-5-{[(3R)-3-hydroxypyrrolidinyl]carbonyl}cyclohexyl-5-methyl-4,5,6,7-tetrahydrothiazolo[5,4-c]pyridine-2-carboxamide hydrochloride

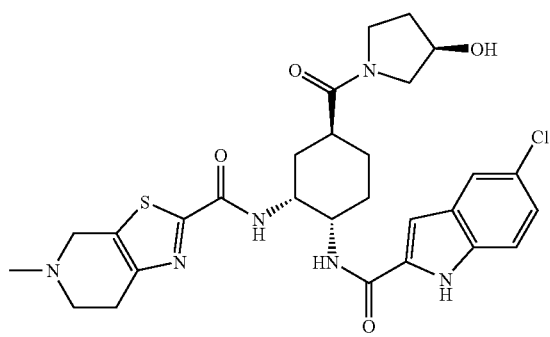

1) The compound (1.18 g) obtained in Referential Example 58 was dissolved in methanol (12 ml), 1N hydrochloric acid (240 μl) and palladium hydroxide (221 mg) were added, and hydrogen was introduced to conduct catalytic reduction under normal pressure at room temperature for 4.5 hours. The catalyst was removed by filtration, and the filtrate was concentrated to solid under reduced pressure to obtain crude (3R)-3-{[tert-butyl(diphenyl)silyl]oxy}pyrrolidine hydrochloride (984 mg).

The thus-obtained product (249 mg), the product (295 mg) obtained in Example 58, 1-(3-dimethylaminopropyl)-3-ethylcarbodiimide hydrochloride (126 mg) and 1-hydroxybenzotriazole monohydrate (87 mg) were dissolved in N,N-dimethylformamide (10 ml). Diisopropylethylamine (450 μl) was added dropwise to the solution under ice cooling, and the mixture was stirred at room temperature for 12 hours. The solvent was distilled off under reduced pressure, methylene chloride and a saturated aqueous solution of sodium hydrogencarbonate were added to the residue to conduct liquid separation. The resultant organic layer was dried over anhydrous sodium sulfate, and the solvent was distilled off under reduced pressure. The residue was subjected to column chromatography on silica gel (methanol:methylene chloride=3:97) to obtain N-((1R,2S,5S)-5-[((3R)-3-{[tert-butyl(diphenyl)silyl]oxy}-pyrrolidinyl)carbonyl]-2-{[(5-chloroindol-2-yl)carbonyl]amino}cyclohexyl)-5-methyl-4,5,6,7-tetrahydrothiazolo-[5,4-c]pyridine-2-carboxamide (248 mg).

$^1$H-NMR (CDCl$_3$) δ: 1.06 (9H, s), 1.50-1.60 (1H, m), 1.75-2.10 (5H, m), 2.20-2.50 (2H, m), 2.54 (3H, d, J=2.8 Hz), 2.60-3.00 (5H, m), 3.30-3.80 (6H, m), 4.10-4.20 (1H, m), 4.40-4.70 (2H, m), 6.85 (1H, s), 7.15-7.25 (1H, m), 7.30-7.50 (8H, m), 7.60-7.70 (5H, m), 7.90-8.00 (1H, m), 9.38 (1H, s). MS (FAB) m/z: 823 (M+H)$^+$.

2) The above product (240 mg) was dissolved in pyridine (10 ml), and hydrogen fluoride-pyridine complex (3.0 ml) was added dropwise under ice cooling to stir the mixture at 0° C. for 4.5 hours. Ethyl acetate (80 ml) was added to the reaction mixture under ice cooling to dilute it. The diluted reaction mixture was poured into ice. After sodium hydrogencarbonate was added to this solution to alkalify it, liquid separation was conducted. The resultant organic layer was dried over anhydrous sodium sulfate. The solvent was distilled under reduced pressure, and the residue was purified by column chromatography on silica gel (methanol:methylene chloride=1:19→1:9). The resultant crude purified product was dissolved in methylene chloride and methanol, to which 1N ethanol solution (225 μl) of hydrochloric acid was added to dry it once. Methanol and diethyl ether were added to the residue to solidify it, thereby obtaining the title compound (114 mg).

$^1$H-NMR (DMSO-d$_6$) δ: 1.50-1.60 (1H, m), 1.70-2.10 (6H, m), 2.75-2.85 (1H, m), 2.92 (3H, s), 3.10-3.80 (8H, m), 4.10-5.10 (6H, m), 7.05 (1H, d, J=1.7 Hz), 7.16 (1H, dd, J=8.8, 1.7 Hz), 7.42 (1H, d, J=8.8 Hz), 7.68 (1H, s), 8.30-8.45 (2H, m), 11.10-11.40 (1H, m), 11.78 (1H, s). MS (FAB) m/z: 585 (M+H)$^+$.

Example 71

N-((1R*,2S*)-2-{[(5-Chloroindol-2-yl)carbonyl]amino)-5,5-dimethoxycyclohexyl)-5-methyl-4,5,6,7-tetrahydrothiazolo-[5,4-c]pyridine-2-carboxamide or N-((1R*,2S*)-2-{[(5-chloroindol-2-yl)carbonyl]amino}-4,4-dimethoxycyclohexyl)-5-methyl-4,5,6,7-tetrahydrothiazolo[5,4-c]pyridine-2-carboxamide The title compound was obtained from the compound obtained in Referential Example 118 and the compound obtained in Referential Example 10 in a similar manner to Example 2.

$^1$H-NMR (CDCl$_3$) δ: 2.11-2.15 (1H, m), 2.21-2.25 (1H, m), 2.41-2.43 (1H, m), 2.46 (3H, s), 2.70-2.75 (1H, m), 2.81-2.88 (1H, m), 3.21 (3H, s), 3.24 (3H, s), 3.49 (1H, s), 3.58 (1H, d, J=15.6 Hz), 3.71 (1H, d, J=15.6 Hz), 3.87-3.93 (1H, m), 4.26-4.29 (1H, m), 6.85 (1H, d, J=2.0 Hz), 7.19 (1H, dd, J=8.5, 2.0 Hz), 7.30 (1H, d, J=8.5 Hz), 7.62 (1H, s), 9.21 (1H, s).

Example 72

N-((1R*,2S*)-2-{[(5-Chloroindol-2-yl)carbonyl]
amino}-5-oxocyclohexyl)-5-methyl-4,5,6,7-tetrahydrothiazolo[5,4-c]-pyridine-2-carboxamide or
N-((1R*,2S*)-2-{[(5-chloroindol-2-yl)carbonyl]
amino}-4-oxocyclohexyl)-5-methyl-4,5,6,7-tetrahydrothiazolo[5,4-c]pyridine-2-carboxamide The compound (100 mg) obtained in Example 71 was dissolved in chloroform (2 ml), and trifluoroacetic acid (0.5 ml) and water (0.5 ml) were added to stir the mixture at room temperature for 3.5 hours. A saturated aqueous solution of sodium hydrogencarbonate was added to the reaction mixture to conduct extraction with ethyl acetate. The resultant organic layer was washed with saturated aqueous solution of sodium chloride and dried over anhydrous sodium sulfate. The solvent was distilled off under reduced pressure, and the resultant residue was purified by preparative thin-layer chromatography on silica gel (methylene chloride:methanol=19:1). The thus-obtained white solids were dissolved in methanol (4 ml), to which a 1N ethanol solution (0.38 ml) of hydrochloric acid was added. The solvent was distilled off under reduced pressure to obtain the title compound (35 mg).

$^1$H-NMR (DMSO-$d_6$) δ: 1.83-1.90 (1H, m), 2.08-2.10 (1H, m), 2.28-2.32 (1H, m), 2.50-2.59 (1H, m), 2.87 (3H, s), 2.96 (1H, t, J=13.0 Hz), 3.06-3.10 (2H, m), 3.33-3.36 (3H, m), 4.02-4.04 (2H, m), 4.55-4.57 (2H, m), 7.03 (1H, s), 7.15 (1H, d, J=8.8 Hz), 7.38 (1H, d, J=8.8 HZ), 7.69 (1H, s), 8.43 (1H, d, J=8.8 Hz), 8.91 (1H, d, J=8.8 Hz), 11.75 (1H, s).

Example 73

N-[(1R*,2S*)-2-{[(5-Chloroindol-2-yl)carbonyl]
amino}-5-(hydroxyimino)cyclohexyl]-5-methyl-4,5,
6,7-tetrahydrothiazolo[5,4-c]pyridine-2-carboxamide
or N-[(1R*,2S*)-2-{[(5-chloroindol-2-yl)carbonyl]
amino}-4-(hydroxyimino)cyclohexyl]-5-methyl-4,5,
6,7-tetrahydrothiazolo[5,4-c]pyridine-2-carboxamide The compound (133 mg) obtained in Example 72 was dissolved in a mixed solvent of pyridine (8 ml) and methanol (8 ml), and hydroxylamine hydrochloride (30 mg) was added to stir the mixture at room temperature for 3 days. The reaction mixture was concentrated, and water was added to the residue to conduct extraction with ethyl acetate. The resultant organic layer was washed with saturated aqueous solution of sodium chloride and dried over anhydrous magnesium sulfate. The solvent was distilled off under reduced pressure, and the resultant residue was purified by column chromatography on silica gel (methylene chloride:methanol=97:3→17:3) to obtain the title compound (131 mg).

$^1$H-NMR (CDCl$_3$) δ: 1.43-1.86 (3H, m), 1.98-2.03 (1H, m), 2.26-2.30 (1H, m), 2.45 (3H, s), 2.47-2.51 (1H, m), 2.67-2.71 (1H, m), 2.78-2.86 (3H, m), 3.86-3.43 (2H, m), 4.16-4.24 (2H, m), 6.85 (1H, s), 7.13-7.16 (1H, m), 7.20-7.24 (1H, m), 7.46, 7.50 (total 1H, s), 7.56-7.64 (2H, m), 9.59, 9.62 (total 1H, s).

Example 74

N-((7R*,8S*)-8-{[(5-Chloroindol-2-yl)carbonyl]
amino}-1,4-dioxaspiro[4.5]dec-7-yl)-5-methyl-4,5,6,
7-tetrahydrothiazolo[5,4-c]pyridine-2-carboxamide
or N-((7R*,8S*)-7-{[(5-chloroindol-2-yl)carbonyl]
amino}-1,4-dioxaspiro-[4.5]dec-8-yl)-5-methyl-4,5,
6,7-tetrahydrothiazolo[5,4-c]pyridine-2-carboxamide The title compound was obtained from the compound obtained in Referential Example 120 and the compound obtained in Referential Example 10 in a similar manner to Example 2.

$^1$H-NMR (CDCl$_3$) δ: 1.69-1.87 (6H, m), 2.14-2.17 (1H, m) 2.30-2.32 (1H, m), 2.47 (3H, s), 2.70-2.75 (1H, m), 2.81-2.89 (2H, m), 3.58 (1H, d, J=15.4 Hz), 3.72 (1H, d, J=15.4 Hz), 3.89-3.91 (1H, m), 3.99 (4H, s), 4.37-4.40 (1H, m), 6.86 (1H, d, J=2.0 Hz), 7.19 (1H, dd, J=8.8, 2.0 Hz), 7.30 (1H, d, J=8.8 Hz), 7.38 (1H, d, J=7.3 Hz), 7.62 (1H, d, J=2.0 Hz), 9.15 (1H, s).

Example 75

N-[(1R*,2S*)-2-{[(5-Chloroindol-2-yl)carbonyl]
amino}-5-(methoxyimino)cyclohexyl]-5-methyl-4,5,
6,7-tetrahydrothiazolo[5,4-c]pyridine-2-carboxamide
or N-[(1R*,2S*)-2-{[(5-chloroindol-2-yl)carbonyl]
amino}-4-(methoxyimino)cyclohexyl]-5-methyl-4,5,
6,7-tetrahydrothiazolo[5,4-c]-pyridine-2-carboxamide 1) The compound (2.21 g) obtained in Referential Example 124 was dissolved in methylene chloride (30 ml), and trifluoroacetic acid (6 ml) was added to stir the mixture at room temperature for 1.5 hours. The reaction mixture was concentrated, dried with a vacuum pump and then dissolved in N,N-dimethylformamide (20 ml), to which 5-chloroindole-2-carboxylic acid (500 mg), 1-(3-dimethylaminopropyl)-3-ethylcarbodiimide hydrochloride (593 mg), 1-hydroxybenzotriazole monohydrate (473 mg) and N-methylmorpholine (2.8 ml) were added. The mixture was stirred at room temperature for 10 hours. Additionally, 5-chloroindole-2-carboxylic acid (242 mg), 1-(3-dimethylaminopropyl)-3-ethylcarbodiimide hydrochloride (237 mg) and 1-hydroxybenzotriazole monohydrate (189 mg) were added to stir the mixture for 4 hours. A saturated aqueous solution of sodium hydrogencarbonate was added to the reaction mixture to conduct extraction with ethyl acetate and with a mixed solvent of ethyl acetate and tetrahydrofuran. The resultant organic layers were washed with saturated aqueous solution of sodium chloride and dried over anhydrous sodium sulfate. The solvent was distilled off under reduced pressure, and the resultant residue was purified by column chromatography on silica gel (methylene chloride:methanol=97:3→4:1) to obtain N-[(1R*,2S*)-2-amino-5-(methoxyimino)cyclohexyl]-5-chloroindole-2-carboxamide (368 mg) and N-[(1R*,2S*)-2-amino-4-(methoxyimino)-cyclohexyl]-5-chloroindole-2-carboxamide (300 mg).

2) The title compound (mixture of syn and anti isomers at the methoxyimino group) from one of the above-obtained N-[(1R*,2S*)-2-amino-5-(methoxyimino)cyclohexyl]-5-chloroindole-2-carboxamide or N-[(1R*,2S*)-2-amino-4-(methoxyimino)cyclohexyl]-5-chloroindole-2-carboxamide and the compound obtained in Referential Example 10 in a similar manner to Example 2.

$^1$H-NMR (CDCl$_3$) δ: 1.84-2.00 (3H, m), 2.26-2.56 (3H, m), 2.46 (3H, s), 2.80-2.83 (4H, m), 3.57 (1H, q, J=15.4 Hz), 3.70 (1H, q, J=15.4 Hz), 3.84, 3.85 (total 3H, s), 4.08-4.14 (1H, m), 4.26-4.30 (1H, m), 6.84 (1H, s), 7.17 (1H, d, J=8.8 Hz), 7.27 (1H, d, J=8.8 Hz), 7.46-7.48 (2H, m), 7.56 (1H, m), 9.42, 9.55 (total 1H, s).

Example 76

N-((1R*,2S*)-2-{[(5-Chloroindol-2-yl)carbonyl] amino}-5-hydroxycyclohexyl)-5-methyl-4,5,6,7-tetrahydrothiazolo-[5,4-c]pyridine-2-carboxamide (Stereoisomer A) or N-((1R*, 2S*)-2-{[(5-chloroindol-2-yl)carbonyl]amino}-4-hydroxycyclohexyl)-5-methyl-4,5,6,7-tetrahydrothiazolo-[5,4-c]pyridine-2-carboxamide (Stereoisomer A)

1) N-((1R*,2S*)-2-amino-4-{[tert-butyl(diphenyl)silyl]oxy}cyclohexyl)-5-chloroindole-2-carboxamide (Stereoisomer A) and N-((1R*,2S*)-2-amino-5-{[tert-butyl(diphenyl)silyl]oxy}cyclohexyl)-5-chloroindole-2-carboxamide (Stereoisomer A) were obtained by subjecting the ((1R*, 2S*)-form obtained in Referential Example 125 to de(tert-butoxycarbonylation) in the same manner as in the step 1) of Example 75 and reacting the formed product with 5-chloroindole-2-carboxylic acid.

2) N-((1R*,2S*)-5-{[tert-Butyl(diphenyl)silyl]oxy}-2-{[(5-chloroindol-2-yl)carbonyl]amino}cyclohexyl)-5-methyl-4,5,6,7-tetrahydrothiazolo[5,4-c]pyridine-2-carboxamide (Stereoisomer A) or N-((1R*,2S*)-4-{[tert-butyl(diphenyl)silyl]oxy}-2-{[(5-chloroindol-2-yl)carbonyl] amino}cyclohexyl-5)-methyl-4,5,6,7-tetrahydrothiazolo[5,4-c]pyridine-2-carboxamide (Stereoisomer A) was obtained from the product obtained by the above reaction and the compound obtained in Referential Example 10 in a similar manner to Example 2.

$^1$H-NMR (CDCl$_3$) δ: 1.06 (9H, s), 1.55-1.61 (1H, m), 1.85-1.90 (1H, m), 2.18-2.25 (1H, m), 2.46 (3H, s), 2.51 (2H, d, J=7.6 Hz), 2.72 (1H, m), 3.56 (1H, s), 3.57 (1H, d, J=15.3 Hz), 3.72 (1H, d, J=15.3 Hz), 3.71-3.81 (1H, m), 3.88-3.95 (1H, m), 6.78 (1H, s), 7.17 (1H, dd, J=2.0, 8.8 Hz), 7.37-7.44 (7H, m), 7.59 (1H, s), 7.65-7.68 (6H, m), 9.30 (1H, s).

3) The title compound was obtained from the compound obtained by the above-described reaction in the same manner as in the step 3) of Example 28.

$^1$H-NMR (DMSO-d$_6$) δ: 1.25-1.30 (2H, m), 1.45-1.64 (2H, m), 1.86 (1H, d, J=9.0 Hz), 1.98-2.03 (1H, m), 2.33 (3H, s), 2.66-2.73 (2H, m), 2.75-2.79 (2H, m), 3.54 (1H, d, J=15.6 Hz), 3.62 (1H, d, J=15.6 Hz), 3.96-4.02 (2H, m), 4.78 (1H, d, J=4.2 Hz), 7.00 (1H, s), 7.14 (1H, dd, J=2.0, 8.8 Hz), 7.38 (1H, d, J=8.8 Hz), 7.66 (1H, s), 8.20 (1H, d, J=7.8 Hz), 8.54 (1H, d, J=7.8 Hz), 11.69 (1H, s).

Example 77

N-((1R*,2S*)-2-{[(5-Chloroindol-2-yl)carbonyl] amino}-5-hydroxy-5-methylcyclohexyl)-5-methyl-4,5,6,7-tetrahydrothiazolo[5,4-c]pyridine-2-carboxamide (Stereoisomer A1) or N-((1R*,2S*)-2-{[(5-chloroindol-2-yl)carbonyl]amino}-4-hydroxy-4-methylcyclohexyl)-5-methyl-4,5,6,7-tetrahydrothiazolo[5,4-c]pyridine-2-carboxamide (Stereoisomer A2)

The title compounds were obtained by reacting the compound obtained in Referential Example 128 with the compound obtained in Referential Example 10 in a similar manner to Example 2.

Stereoisomer A1:
$^1$H-NMR (DMSO-d$_6$) δ: 1.24 (3H, s), 1.33-1.82 (4H, m), 2.34 (3H, s), 2.67-3.64 (8H, m), 4.02-4.10 (2H, m), 4.67 (1H, br.s), 7.02 (1H, s), 7.13 (1H, d, J=8.6 Hz), 7.38 (1H, d, J=8.6 Hz), 7.66 (1H, d, J=2.0 Hz), 8.21-8.26 (1H, br), 8.59 (1H, d, J=8.1 Hz), 11.73 (1H, br.s). MS (FAB) m/z: 502 (M+H)$^+$.

Stereoisomer A2:
$^1$H-NMR (DMSO-d$_6$) δ: 1.25 (3H, s), 1.33-1.79 (4H, m), 2.33 (3H, s), 2.65-3.63 (8H, m), 3.88-3.94 (1H, m), 4.20-4.25 (1H, m), 4.59 (1H, br), 7.01 (1H, s), 7.13 (1H, d, J=7.8 Hz), 7.38 (1H, d, J=8.6 Hz), 7.67 (1H, s), 8.29 (1H, br), 8.43 (1H, d, J=9.3 Hz), 11.67 (1H, br). MS (FAB) m/z: 502 (M+H)$^+$.

Example 78

N-[(1R*,2R*,5S*)-2-{[(5-Chloroindol-2-yl)carbonyl]amino}-5-(hydroxymethyl)cyclohexyl]-5-methyl-4,5,6,7-tetrahydrothiazolo[5,4-c]pyridine-2-carboxamide

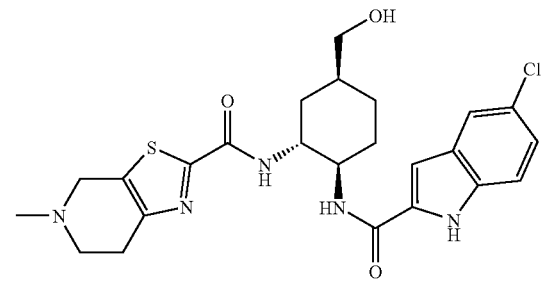

The title compound was obtained by treating the compound obtained in Referential Example 129 with an ethanol solution of hydrochloric acid and then condensing it with the compound obtained in Referential Example 10 in a similar manner to Example 49.

$^1$H-NMR (DMSO-d$_6$) δ: 1.42-1.90 (5H, m), 2.07-2.26 (3H, m), 2.46 (3H, s), 2.67-2.95 (4H, m), 3.55-3.80 (4H, m), 3.80-3.95 (1H, m), 4.13-4.25 (1H, m), 6.84 (1H, br.s), 7.17 (1H, dd, J=8.8, 2.0 Hz), 7.23-7.35 (2H, m), 7.43 (1H, d, J=7.2 Hz), 7.58 (1H, br.s), 9.29 (1H, s). MS (ESI) m/z: 502 (M+H)$^+$.

Example 79

N-[(1R*,2S*,5S*)-2-{[(5-Chloroindol-2-yl)carbonyl]amino}-5-(methoxymethyl)cyclohexyl]-5-methyl-4,5,6,7-tetrahydrothiazolo[5,4-c]pyridine-2-carboxamide

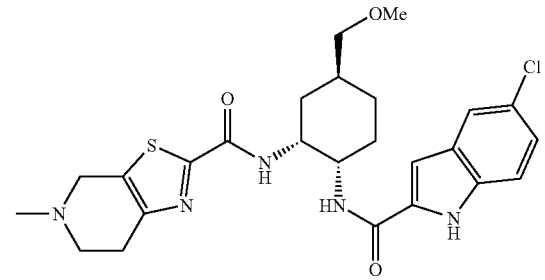

The title compound was obtained by treating the compound obtained in Referential Example 135 with an ethanol solution of hydrochloric acid and then condensing it with the compound obtained in Referential Example 10 in a similar manner to Example 49.

$^1$H-NMR (CDCl$_3$) δ: 1.20-1.38 (1H, m), 1.50-1.67 (2H, m), 1.88-2.03 (2H, m), 2.03-2.14 (1H, m), 2.21-2.32 (1H, m), 2.53 (3H, s), 2.75-2.95 (2H, m), 3.20-3.35 (2H, m), 3.37 (3H, s), 3.73 (1H, d, J=16.0 Hz), 3.76 (1H, d, J=16.0 Hz), 4.04-4.13 (1H, m), 4.53-4.62 (1H, m), 6.85 (1H, d, J=2.0 Hz), 7.19 (1H, dd, J=8.8, 2.0 Hz), 7.33 (1H, d, J=8.8 Hz), 7.54 (1H, d, J=7.2 Hz), 7.63 (1H, d, J=2.0 Hz), 8.07 (1H, d, J=5.6 Hz), 9.49 (1H, br.s).

Example 80

N-((1R*,2S*,5S*)-2-{[(5-Chloroindol-2-yl)carbonyl]amino}-5-{[(methylsulfonyl)amino]methyl}cyclohexyl)-5-methyl-4,5,6,7-tetrahydrothiazolo[5,4-c]pyridine-2-carboxamide

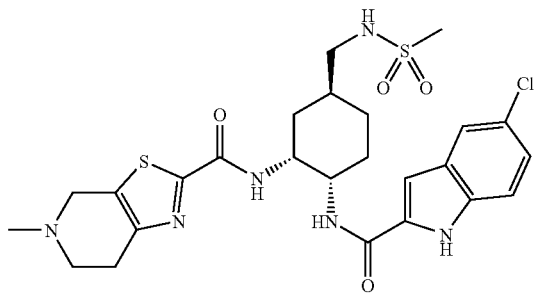

1) The compound (437 mg) obtained in Referential Example 137 was dissolved in ethanol (5 ml), and a 4N dioxane solution (5 ml) of hydrochloric acid was added at room temperature to stir the mixture for 13 hours. The solvent was distilled off, and the residue was dissolved in N,N-dimethylformamide (10 ml), to which triethylamine (0.7 ml), the compound (300 mg) obtained in Referential Example 10, 1-hydroxybenzotriazole monohydrate (162 mg) and 1-(3-dimethylaminopropyl)-3-ethylcarbodiimide hydrochloride (230 mg) were added. The mixture was stirred for 13 hours, and water was added to the reaction mixture to conduct extraction with chloroform. The resultant organic layer was washed with a saturated aqueous solution of sodium hydrogencarbonate and saturated aqueous solution of sodium chloride and dried over anhydrous magnesium sulfate. The solvent was distilled off under reduced pressure, and the resultant residue was purified by column chromatography on silica gel (methylene chloride:methanol=97:3) to obtain N-((1R*,2S*,5S*)-5-(azidomethyl)-2-{[(5-chloroindol-2-yl)carbonyl]amino}cyclohexyl)-5-methyl-4,5,6,7-tetrahydrothiazolo[5,4-c]pyridine-2-carboxamide (330 mg).

$^1$H-NMR (DMSO-d$_6$) δ: 1.15-2.08 (7H, m), 2.33 (3H, s), 2.34-2.95 (6H, m), 3.64 (2H, s), 4.05-4.17 (1H, m), 4.36-4.47 (1H, m), 7.02 (1H, s), 7.15 (1H, dd, J=8.8, 2.0 Hz), 7.40 (1H, d, J=8.8 Hz), 7.67 (1H, d, J=2.0 Hz), 8.02 (1H, d, J=7.6 Hz), 8.44 (1H, d, J=7.6 Hz), 11.8 (1H, s).

2) The compound (300 mg) obtained by the above reaction was dissolved in ethanol (8 ml), and a catalytic amount of 10% palladium on carbon was added to stir the mixture at room temperature for 168 hours in a hydrogen atmosphere. Insoluble matter was filtered, and the solvent was distilled off. The thus-obtained crude N-(1R*,2S*,5S*)-5-(aminomethyl)-2-{(5-chloroindol-2-yl)carbonyl]amino}cyclohexyl)-5-methyl-4,5,6,7-tetrahydrothiazolo[5,4-c]pyridine-2-carboxamide (150 mg) was dissolved in chloroform (6 ml), and triethylamine (0.2 ml) and methanesulfonyl chloride (0.035 ml) were added to stir the mixture for 13 hours. The solvent was distilled off under reduced pressure, and water was added to the residue to conduct extraction with chloroform. The resultant organic layer was washed with a saturated aqueous solution of sodium hydrogencarbonate and saturated aqueous solution of sodium chloride and dried over anhydrous magnesium sulfate. The solvent was distilled off under reduced pressure, and the resultant residue was purified by column chromatography on silica gel (methylene chloride:methanol=24:1) to obtain the title compound (56 mg).

$^1$H-NMR (CDCl$_3$) δ: 1.18-1.34 (2H, m), 1.50-1.75 (4H, m), 1.90-2.30 (4H, m), 2.53 (3H, s), 2.78-2.90 (2H, m), 2.90-3.05 (6H, m), 3.20-3.30 (1H, m), 3.68-3.81 (2H, m), 3.98-4.08 (1H, m), 4.54-4.62 (1H, m)., 6.10-6.19 (1H, m), 6.86 (1H, s), 7.19 (1H, dd, J=8.8, 2.0 Hz), 7.35 (1H, d, J=8.8 Hz), 7.52 (1H, d, J=7.6 Hz), 7.62 (1H, d, J=2.0 Hz), 8.21 (1H, d, J=5.6 Hz), 9.89 (1H, s). MS (ESI) m/z: 579 (M+H)$^+$.

Example 81

N-{(1R*,2S*,5S*)-2-{[(5-Chloroindol-2-yl)carbonyl]amino}-5-[(dimethylamino)methyl]cyclohexyl}-5-methyl-4,5,6,7-tetrahydrothiazolo[5,4-c]pyridine-2-carboxamide Trifluoroacetate

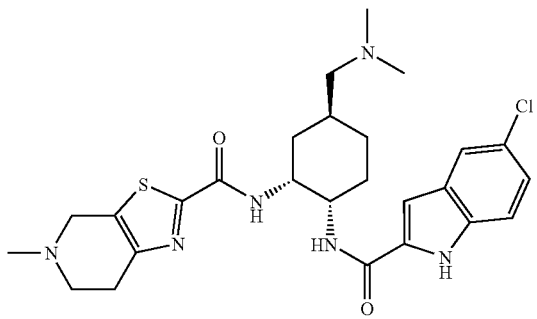

The title compound was obtained from the amine obtained in the step 2) of Example 80 in a similar manner to Example 24.

$^1$H-NMR (DMSO-d$_6$) δ: 1.15-2.22 (7H, m), 2.40-2.65 (2H, m), 2.68-2.85 (6H, m), 2.92-3.08 (5H, m), 3.10-3.18 (2H, m), 4.08-4.20 (1H, m), 4.35-4.51 (2H, m), 7.04 (1H, s), 7.14-7.20 (1H, m), 7.41 (1H, d, J=8.8 Hz), 7.67 (1H, s), 8.25-8.42 (2H, m), 9.11 (1H, br.s), 9.89 (1H, s). MS (ESI) m/z: 529 (M+H)$^+$.

Example 82 tert-Butyl (3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}cyclohexylcarbamate (Isomer B) and tert-butyl (3R*,4S*)-3-{[(5-chloroindol-2-yl)carbonyl]-amino}-4-{[(5-methyl-4,5,6,7-tetrahydrothiazolo[5,4-c]-pyridin-2-yl)carbonyl]amino}cyclohexylcarbamate (Isomer B)

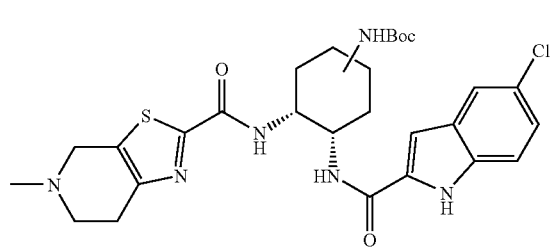

The compound (Stereoisomer B) (1.79 g) obtained in Referential Example 140 was dissolved in tetrahydrofuran (36 ml), and 10% palladium on carbon (0.40 g) was added to stir the mixture at room temperature for 20 hours in a hydrogen atmosphere. After the catalyst was removed by filtration, the filtrate was concentrated under reduced pressure, and the residue was dissolved in N,N-dimethylformamide (36 ml), to which p-nitrophenyl 5-chloroindole-2-carboxylate (2.02 g) was added to stir the mixture for 16 hours. The reaction mixture was concentrated under reduced pressure, and ethyl acetate and water were added to the residue to collect insoluble matter by filtration. The product was washed with ethyl acetate to obtain crude tert-butyl (3R,4S*)-3-amino-4-{[(5-chloroindol-2-yl)carbonyl]amino}cyclohexylcarbamate (or (3R*,4S*)-4-amino-3-{[(5-chloroindol-2-yl)carbonyl]-amino}cyclohexylcarbamate) (Isomer B1) (1.49 g). The organic layer of the filtrate was washed with water and dried over anhydrous sodium sulfate. The solvent was distilled off under reduced pressure, and the residue was purified by column chromatography on silica gel (methylene chloride:methanol=30:1→10:1) to obtain tert-butyl (3R*,4S*)-4-amino-3-{[(5-chloroindol-2-yl)carbonyl]amino}-cyclohexylcarbamate (or tert-butyl (3R*,4S*)-3-amino-4-{[(5-chloroindol-2-yl)carbonyl]amino}cyclohexylcarbamate) (Isomer B2) (0.37 g).

One of the title compounds was obtained from the Isomer B1 and the compound obtained in Referential Example 10 in a similar manner to Example 2.

$^1$H-NMR (DMSO-$d_6$) δ: 1.25-1.50 (1H, m), 1.37 (9H, s), 1.50-1.65 (1H, m), 1.75-2.20 (4H, m), 2.37 (3H, s), 2.70-3.00 (4H, m), 3.60-3.80 (3H, m), 4.13 (1H, br.s), 4.43 (1H, br.s), 6.92 (1H, d, J=7.1 Hz), 7.05 (1H, s), 7.17 (1H, dd, J=8.8, 2.2 Hz), 7.41 (1H, d, J=8.8 Hz), 7.69 (1H, s), 8.15 (1H, d, J=7.8 Hz), 8.37 (1H, d, J=7.1 Hz), 11.78 (1H, s). MS (FAB) m/z: 587 (M+H)$^+$.

The other title compound was obtained from the Isomer B2 in the same manner.

$^1$H-NMR (DMSO-$d_6$) δ: 1.15-1.30 (1H, m), 1.35 (9H, s), 1.45-1.60 (1H, m), 1.65-1.75 (1H, m), 1.85-1.95 (1H, m), 2.05-2.20 (2H, m), 2.34 (3H, s), 2.65-2.85 (4H, m), 3.55-3.70 (3H, m), 4.05-4.14 (1H, m), 4.40 (1H, br.s), 6.80 (1H, d, J=7.3 Hz), 7.15-7.25 (2H, m), 7.43 (1H, d, J=8.8 Hz), 7.73 (1H, d, J=2.0 Hz), 8.05 (1H, d, J=6.6 Hz), 8.51 (1H, d, J=8.8 Hz), 11.82 (1H, s). MS (FAB) m/z: 587 (M+H)$^+$.

Example 83

N-((1R*,2S*)-5-Amino-2-{[(5-chloroindol-2-yl)carbonyl]-amino}cyclohexyl)-5-methyl-4,5,6,7-tetrahydrothiazolo-[5,4-c]pyridine-2-carboxamide (or N-((1R*,2S*)-4-amino-2-{[(5-chloroindol-2-yl)carbonyl]amino}cyclohexyl)-5-methyl-4,5,6,7-tetrahydrothiazolo[5,4-c]pyridine-2-carboxamide) hydrochloride (Stereoisomer B)

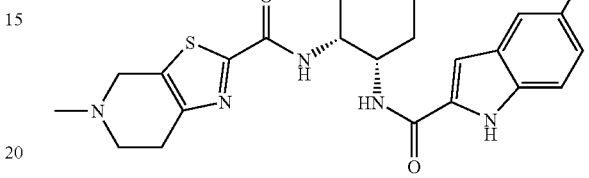

The compound (Stereoisomer B) (1.11 g) synthesized from Isomer B1 in Example 82 was suspended in methylene chloride (20 ml), and an ethanol solution (20 ml) of hydrochloric acid was added to stir the mixture at room temperature for 2 hours. The solvent was distilled off under reduced pressure, and the residue was purified by gel filtration (Sephadex LH-20, methanol) to obtain the title compound (1.05 g).

$^1$H-NMR (DMSO-$d_6$) δ: 1.55-1.65 (1H, m), 1.75-1.90 (2H, m), 1.95-2.20 (2H, m), 2.20-2.40 (1H, m), 2.90 (3H, s), 3.10-3.20 (1H, m), 3.20-3.50 (3H, m), 3.65-3.75 (1H, m), 4.10-4.20 (1H, m), 4.35-4.50 (1H, m), 4.55-4.65 (1H, m), 4.65-4.75 (1H, m), 7.07 (1H, s), 7.17 (1H, dd, J=8.8, 2.0 Hz), 7.42 (1H, d, J=8.8 Hz), 7.69 (1H, s), 8.05-8.30 (3H, br), 8.40-8.50 (2H, m), 11.70-11.90 (2H, m). MS (FAB) m/z: 487 (M+H)$^+$.

Example 84

N-{(1R*,2S*)-2-{[(5-Chloroindol-2-yl)carbonyl]amino}-5-[(methylsulfonyl)amino]cyclohexyl}-5-methyl-4,5,6,7-tetrahydrothiazolo[5,4-c]pyridine-2-carboxamide or N-{(1R*,2S*)-2-{[(5-Chloroindol-2-yl)carbonyl]amino}-4-[(methylsulfonyl)amino]cyclohexyl}-5-methyl-4,5,6,7-tetrahydrothiazolo[5,4-c]pyridine-2-carboxamide (Stereoisomer B)

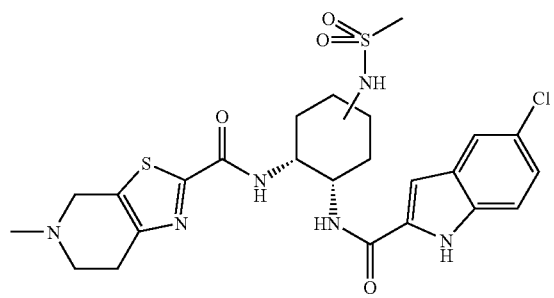

The compound (0.20 g) obtained in Example 83 was suspended in methylene chloride (7 ml), and triethylamine (0.16 ml) and methanesulfonyl chloride (28 μl) were added to stir the mixture at room temperature for 20 hours. After the reaction mixture was diluted with methylene chloride, it was washed with an aqueous solution of sodium hydroxide and dried over anhydrous sodium sulfate. The solvent was distilled off under reduced pressure, and the residue was purified by column chromatography on silica gel (methylene chloride:methanol=30:1→15:1) to obtain the title compound (67.9 mg).

$^1$H-NMR (DMSO-d$_6$) δ: 1.40-1.55 (1H, m), 1.65-1.85 (2H, m), 1.90-2.05 (2H, m), 2.15-2.25 (1H, m), 2.41 (3H, s), 2.75-2.95 (4H, m), 2.92 (3H, s), 3.55-3.80 (3H, m), 4.10-4.20 (1H, m), 4.45-4.55 (1H, m), 7.08 (1H, s), 7.15-7.20 (2H, m), 7.41 (1H, d, J=8.8 Hz), 7.69 (1H, s), 8.27 (1H, d, J=7.3 Hz), 8.33 (1H, d, J=8.1 Hz), 11.77 (1H, s). MS (FAB) m/z: 565 (M+H)$^+$.

Example 85

N-((1R*,2S*)-5-(Acetylamino)-2-{[(5-chloroindol-2-yl)carbonyl]amino}cyclohexyl)-5-methyl-4,5,6,7-tetrahydrothiazolo[5,4-c]pyridine-2-carboxamide or N-((1R*,2S*)-4-(acetylamino)-2-{[(5-chloroindol-2-yl)carbonyl]amino}cyclohexyl)-5-methyl-4,5,6,7-tetrahydrothiazolo[5,4-c]pyridine-2-carboxamide (Stereoisomer B)

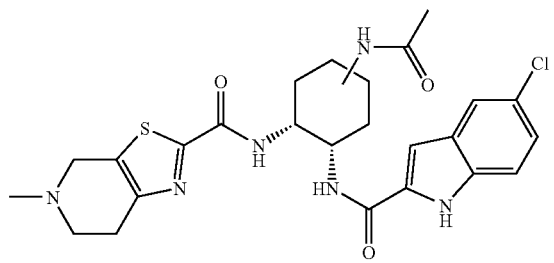

The compound (Stereoisomer B) (0.20 g) obtained in Example 83 was suspended in methylene chloride (7 ml), and triethylamine (0.16 ml) and acetic anhydride (34 μl) were added to stir the mixture at room temperature for 20 hours. Methylene chloride and an aqueous solution of sodium hydroxide were added to the reaction mixture to separate insoluble matter by filtration. The organic layer of the filtrate was separated and dried over anhydrous sodium sulfate, and the solvent was then distilled off under reduced pressure. The residue was purified by column chromatography on silica gel (methylene chloride:methanol=15:1→10:1) to obtain the title compound (0.12 g).

$^1$H-NMR (DMSO-d$_6$) δ: 1.35-1.50 (1H, m), 1.55-1.70 (1H, m), 1.80 (3H, s), 1.80-2.05 (3H, m), 2.05-2.20 (1H, m), 2.47 (3H, s), 2.80-3.00 (4H, m), 3.75-4.00 (3H, m), 4.15-4.30 (1H, m), 4.45-4.55 (1H, m), 7.07 (1H, s), 7.17 (1H, dd, J=8.8, 1.0 Hz), 7.41 (1H, d, J=8.8 Hz), 7.69 (1H, s), 7.89 (1H, d, J=7.3 Hz), 8.24 (1H, d, J=8.1 Hz), 8.31 (1H, d, J=7.3 Hz), 11.77 (1H, s). MS (FAB) m/z: 528 (M+H)$^+$.

Example 86

N-((1R,2S,5S)-2-{[(5-Chloroindol-2-yl)carbonyl]amino}-5-{[methoxy(methyl)amino]carbonyl}cyclohexyl)-5-methyl-4,5,6,7-tetrahydrothiazolo[5,4-c]pyridine-2-carboxamide hydrochloride

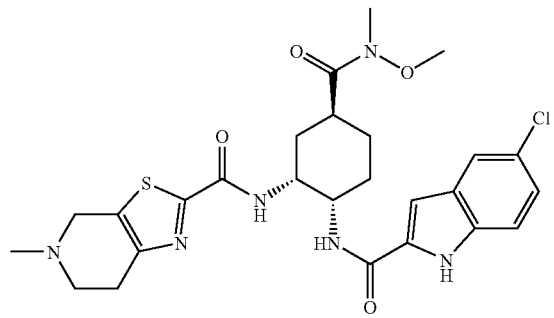

The compound (250 mg) obtained in Example 58 was dissolved in N,N-dimethylformamide (5 ml), and N, O-dimethylhydroxylamine hydrochloride (142 mg), 1-(3-dimethylaminopropyl)-3-ethylcarbodiimide hydrochloride (111 mg), 1-hydroxybenzotriazole monohydrate (89 mg) and N-methylmorpholine (213 ml) were added to stir the mixture at room temperature for 19 hours. After the reaction mixture was concentrated, an aqueous solution of sodium hydrogencarbonate was added to the residue to conduct extraction with ethyl acetate. After the resultant organic layer was washed with saturated aqueous solution of sodium chloride and dried over anhydrous sodium sulfate, the solvent was distilled off under reduced pressure. The residue was purified by column chromatography on silica gel (methylene chloride:methanol=47:3→23:2) to obtain a colorless amorphous solid (179 mg). This prodcut was dissolved in methanol-tetrahydrofuran, and 1N ethanol solution (960 ml) of hydrochloric acid was added to obtain the title compound.

$^1$H-NMR (DMSO-d$_6$) δ: 1.57-1.91 (4H, m), 1.96-2.00 (1H, m), 2.10-2.21 (1H, m), 2.92 (3H, s), 2.93-3.03 (2H, m), 3.08 (3H, s), 3.10-3.28 (2H, m), 4.16-4.19 (1H, m), 4.50-4.52 (1H, m), 4.69 (1H, br.s), 7.06 (1H, s), 7.17 (1H, dd, J=8.8, 1.5 Hz), 7.42 (1H, d, J=8.8 Hz), 7.70 (1H, s), 8.33 (1H, br.s), 8.41 (1H, d, J=7.8 Hz), 11.81 (1H, br.s). MS (ESI) m/z: 559 (M+H)$^+$.

Example 87

N-{(1R,2S,5S)-2-{[(5-Chloroindol-2-yl)carbonyl]amino}-5-[(2,2-dimethylhydrazino)carbonyl]cyclohexyl}-5-methyl-4,5,6,7-tetrahydrothiazolo[5,4-c]pyridine-2-carboxamide hydrochloride

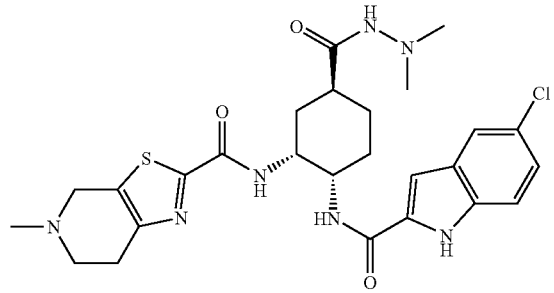

The title compound was obtained from the compound obtained in Example 58 and N,N-dimethylhydrazine in a similar manner to Example 57.

$^1$H-NMR (DMSO-d$_6$) δ: 1.49-1.54 (1H, m), 1.76-1.81 (2H, m), 1.89-1.93 (2H, m), 2.07-2.17 (1H, m), 2.33-3.60 (14H, m), 4.15-4.19 (1H, m), 4.40-4.47 (2H, m), 4.70-4.72 (1H, m), 7.04 (1H, s), 7.17 (1H, dd, J=8.5, 2.0 Hz), 7.42 (1H, d, J=8.5 Hz), 7.70 (1H, s), 8.17-8.22 (1H, m), 8.41-8.43 (1H, m), 11.80 (1H, br.s). MS (ESI) m/z: 558 (M+H)$^+$.

Example 88

6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-2-quinolinecarboxamide hydrochloride

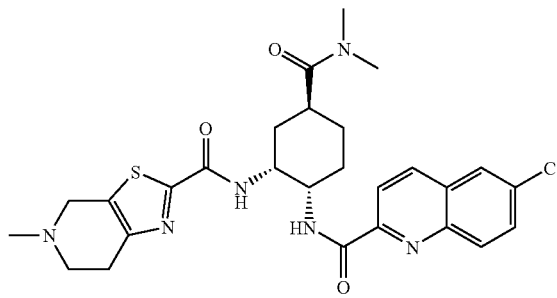

The title compound was obtained by treating the compound obtained in Referential Example 145 with an ethanol solution of hydrochloric acid in a similar manner to Example 49 and then condensing it with the compound obtained in Referential Example 10.

$^1$H-NMR (DMSO-d$_6$) δ: 1.45-1.60 (1H, m), 1.75-1.90 (3H, m), 1.90-2.00 (1H, m), 2.00-2.20 (1H, m), 2.80 (3H, s), 2.90 (3H, s), 2.99 (3H, s), 3.10-3.30 (5H, m), 3.56 (1H, br), 4.10-4.20 (1H, m), 4.40-4.70 (2H, m), 7.88 (2H, s), 8.15 (1H, d, J=8.6 Hz), 8.22 (1H, s), 8.52 (1H, d, J=8.6 Hz), 8.72 (1H, d, J=8.3 Hz), 8.89 (1H, d, J=8.3 Hz). MS (FAB) m/z: 555 (M+H)$^+$.

Example 89

N-{(1R,2S,5S)-2-{[(5-Chloro-4-fluoroindol-2-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

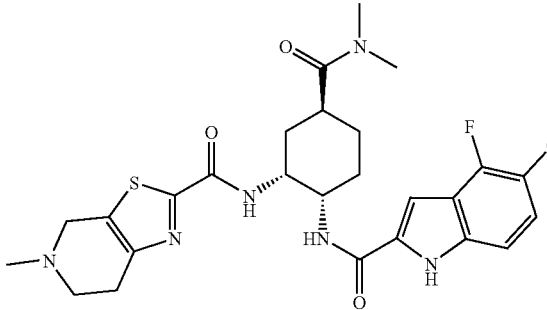

The title compound was obtained by condensing the compound obtained in Referential Example 144 with the compound obtained in Referential Example 274 in a similar manner to Referential Example 91 and treating the resultant compound with a 4N dioxane solution of hydrochloric acid and then with the compound obtained in Referential Example 10.

$^1$H-NMR (DMSO-d$_6$) δ: 1.24-1.98 (6H, m), 2.33-3.33 (6H, m), 2.81 (3H, s), 2.90 (3H, s), 2.99 (3H, s), 4.12 (1H, br.s), 4.30-4.70 (1H, m), 4.60 (1H, br.s), 7.21 (1H, s), 7.27 (2H, br.s), 8.37 (1H, d, J=8.1 Hz), 8.43 (1H, d, J=7.6 Hz), 12.11 (1H, s). MS (FAB) m/z: 561 (M+H)$^+$.

Example 90

7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)isoquinoline-3-carboxamide hydrochloride

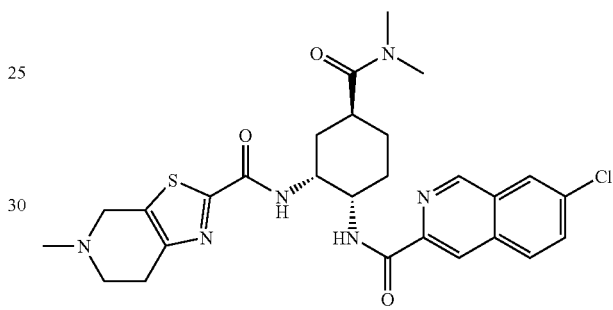

The title compound was obtained by treating the compound obtained in Referential Example 146 with an ethanol solution of hydrochloric acid in a similar manner to Example 49 and then condensing it with the compound obtained in Referential Example 10.

$^1$H-NMR (DMSO-d$_6$) δ: 1.45-1.65 (1H, m), 1.70-1.85 (3H, m), 1.95-2.10 (1H, m), 2.10-2.20 (1H, m), 2.80 (3H, s), 2.92 (3H, s), 2.96 (3H, s), 2.95-3.10 (1H, m), 3.10-3.40 (3H, m), 3.70-3.80 (1H, m), 4.20-4.30 (1H, m), 4.40-4.60 (2H, m), 4.65-4.80 (1H, m), 7.83-7.93 (1H, m), 8.26 (1H, d, J=8.8 Hz), 8.38 (1H, s), 8.60 (1H, s), 8.85-9.00 (2H, m), 9.30-9.40 (1H, m). MS (FAB) m/z: 555 (M+H)$^+$.

Example 91

N-((3R*,4S*)-4-{[(5-Chloroindol-2-yl)carbonyl]amino}-tetrahydrofuran-3-yl)-5-methyl-4,5,6,7-tetrahydrothiazolo-[5,4-c]pyridine-2-carboxamide hydrochloride

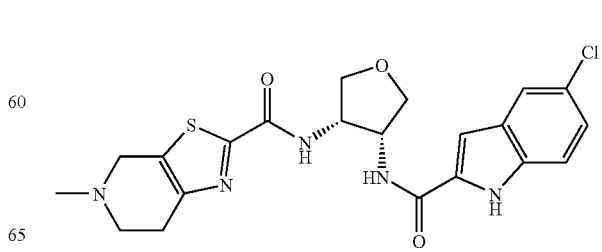

The compound (0.1 g) obtained in Referential Example 10, 1-hydroxybenzotriazole monohydrate (78 mg) and 1-(3-dimethylaminopropyl)-3-ethylcarbodiimide hydrochloride (0.2 g) were successively added to a solution of the compound (0.12 g) obtained in Referential Example 172 in N,N-dimethylformamide (20 ml), and the mixture was stirred at room temperature for 1 day. After the reaction mixture was concentrated, and the resultant residue was diluted with chloroform-methanol (9:1) and washed with a saturated aqueous solution of sodium hydrogencarbonate and saturated aqueous solution of sodium chloride, the resultant organic layer was dried over anhydrous sodium sulfate, and the solvent was distilled off under reduced pressure. The residue was purified by column chromatography on silica gel (chloroform:methanol=95:5) to obtain a free base of the title compound. This product was treated with an ethanol solution of hydrochloric acid to obtain the title compound (0.1 g).

$^1$H-NMR (CDCl$_3$) δ: 2.50 (3H, s), 2.70-2.90 (4H, m), 3.67 (1H, s), 3.70 (1H, s), 3.86 (1H, dd, J=9.2, 6.3 Hz), 3.97 (1H, dd, J=9.7, 4.1 Hz), 4.15 (1H, dd, J=9.7, 5.8 Hz), 4.24 (1H, dd, J=9.2, 7.0 Hz), 4.75-4.89 (1H, m), 4.92-5.03 (1H, m), 6.88 (1H, s), 7.20 (1H, dd, J=8.8, 2.0 Hz), 7.33 (1H, d, J=8.8 Hz), 7.35-7.43 (1H, m), 7.58 (1H, d, J=2.0 Hz), 7.64 (1H, d, J=7.1 Hz), 9.38 (1H, s). MS (FAB) m/z: 460 (M+H$^+$).

Example 92

N-((3S,4S)-4-([(5-Chloroindol-2-yl)carbonyl]amino}-tetrahydrofuran-3-yl)-5-methyl-4,5,6,7-tetrahydrothiazolo-[5,4-c]pyridine-2-carboxamide

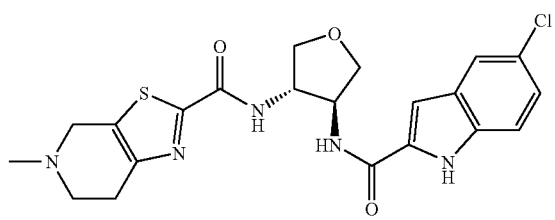

The title compound was obtained from the compound obtained in Referential Example 183 in accordance with the processes of Referential Example 172 and Example 91.

$^1$H-NMR (CDCl$_3$) δ: 2.51 (3H, s), 2.83 (2H, t, J=5.3 Hz), 2.93 (2H, t, J=5.3 Hz), 3.72 (2H, s), 3.78-3.89 (2H, m), 4.31 (1H, dd, J=9.2, 7.3 Hz), 4.41-4.56 (2H, m), 4.63-4.75 (1H, m), 6.88 (1H, s), 7.22 (1H, dd, J=8.8, 2.0 Hz), 7.32 (1H, d, J=8.8 Hz), 7.35-7.46 (1H, m), 7.55 (1H, d, J=7.1 Hz), 7.60 (1H, d, J=2.0 Hz), 9.38 (1H, s). MS (FAB) m/z: 460 (M+H$^+$).

Example 93

N-((3R,4R)-4-{[(5-Chloroindol-2-yl)carbonyl]amino}-tetrahydrofuran-3-yl)-5-methyl-4,5,6,7-tetrahydrothiazolo-[5,4-c]pyridine-2-carboxamide hydrochloride

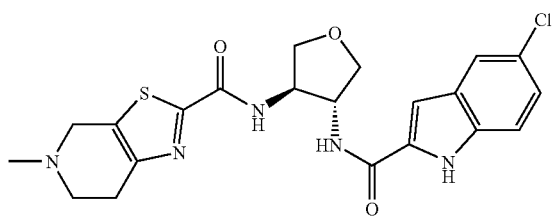

The title compound was obtained from the compound obtained in Referential Example 187 in accordance with the processes of Referential Example 172 and Example 91.

$^1$H-NMR and MS (FAB): The same as those of the enantiomer in Example 92.

Example 94 tert-Butyl (3R,4R)-3-{[(5-chloroindol-2-yl)carbonyl]-amino}-4-{[(5-methyl-4,5,6,7-tetrahydrothiazolo[5,4-c]-pyridin-2-yl)carbonyl]amino}pyrrolidine-1-carboxylate

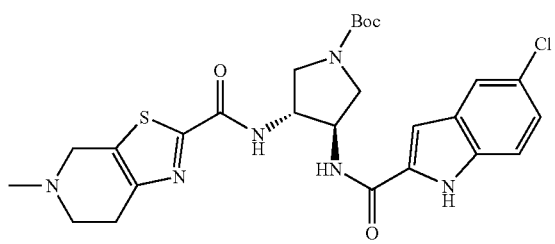

The title compound was obtained from the compound obtained in Referential Example 193 and the compound obtained in Referential Example 10 in accordance with the process of Example 91.

Melting point: 190-192° C.

$^1$H-NMR (CDCl$_3$) δ: 1.45 (9H, s), 2.46 (3H, s), 2.74-2.81 (4H, m), 3.24-3.37 (2H, m), 3.54-3.70 (2H, m), 3.96-4.00 (1H, m), 4.15-4.23 (1H, m), 4.50-4.65 (1H, m), 4.77-4.82 (1H, m), 6.79, 6.87 (total 1H, each s), 7.12-7.95 (5H, m), 9.91, 9.97 (total 1H, each s). MS (FAB) m/z: 559 (M+H$^+$).

Example 95

N-((3R,4R)-4-{[(5-Chloroindol-2-yl)carbonyl]amino}-pyrrolidin-3-yl)-5-methyl-4,5,6,7-tetrahydrothiazolo-[5,4-c]pyridine-2-carboxamide hydrochloride

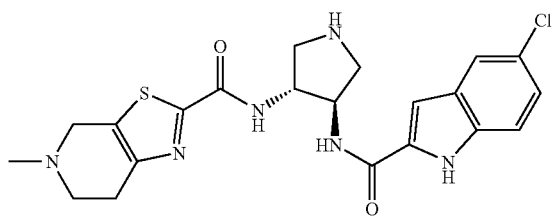

The compound (170 mg) obtained in Example 94 was dissolved in methylene chloride (3 ml), and trifluoroacetic acid (2 ml) was added at room temperature to stir the mixture for 1 hour. After concentrating the reaction mixture, chloroform and a saturated aqueous solution of sodium hydrogencarbonate were added. The resultant organic layer was dried over anhydrous sodium sulfate, and the solvent was distilled off under reduced pressure. The resultant residue was purified by preparative thin-layer chromatography on silica gel (chloroform:methanol:water=7:3:1 under layer). A methanol solution of hydrochloric acid was added to the resultant intended product to obtain the title compound (90 mg) as a hydrochloride (NMR was measured in the form of a free base).

Melting point: 248-250° C. (decomposed).

$^1$H-NMR (CDCl$_3$) δ: 2.44 (3H, s), 2.70-2.80 (4H, m), 2.97-3.05 (2H, m), 3.46-3.68 (4H, m), 4.49-4.52 (1H, m), 4.60-4.65 (1H, m), 6.86 (1H, s), 7.05-7.08 (1H, m), 7.20 (1H, d, J=8.5 Hz), 7.44 (1H, s), 7.89 (2H, br), 10.51 (1H, br). MS (FAB) m/z: 459 (M+H$^+$).

Example 96

N-((3S,4S)-4-{[(5-Chloroindol-2-yl)carbonyl]amino}-5-oxotetrahydrofuran-3-yl)-5-methyl-4,5,6,7-tetrahydrothiazolo[5,4-c]pyridine-2-carboxamide hydrochloride

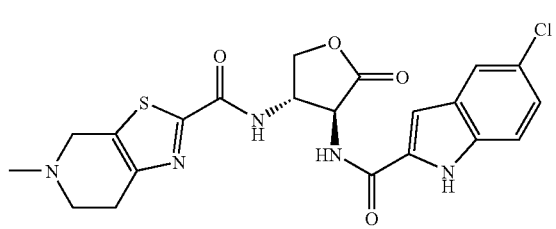

The title compound was obtained by removing the tert-butoxycarbonyl group of the compound obtained in Referential Example 196 in a similar manner to Referential Example 69 and reacting the resultant product with the compound obtained in Referential Example 10 in a similar manner to Example 91.

$^1$H-NMR (DMSO-d$_6$) δ: 2.90 (3H, s), 3.02-3.17 (2H, m), 3.23-3.34 (4H, m), 4.20 (1H, t, J=8.6 Hz), 4.61 (1H, t, J=8.6 Hz), 4.92-5.01 (1H, m), 5.14-5.26 (1H, m), 7.09 (1H, s), 7.19 (1H, dd, J=8.8, 2.0 Hz), 7.41 (1H, d, J=8.8 Hz), 7.73 (1H, d, J=2.0 Hz), 9.27 (1H, d, J=6.8 Hz), 9.35 (1H, d, J=6.8 Hz), 11.22-11.33 (1H, m), 11.89 (1H, s). MS (FAB) m/z: 474 (M+H$^+$).

Example 97

N-((3S,4S)-4-{[(5-Chloroindol-2-yl)carbonyl]amino}-2-oxotetrahydrofuran-3-yl)-5-methyl-4,5,6,7-tetrahydrothiazolo[5,4-c]pyridine-2-carboxamide hydrochloride

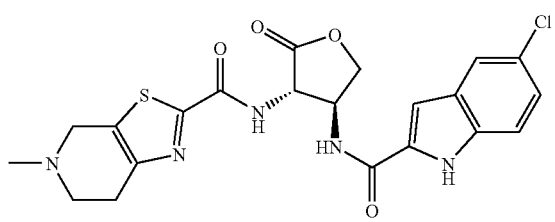

The title compound was obtained by removing the tert-butoxycarbonyl group of the compound obtained in Referential Example 197 in a similar manner to Referential Example 69 and reacting the resultant product with 5-chloroindole-2-carboxylic acid in a similar manner to Example 91.

$^1$H-NMR (DMSO-d$_6$) δ: 2.52 (3H, s), 2.83 (2H, t, J=5.9 Hz), 2.91-3.00 (2H, m), 3.73 (2H, s), 4.23 (1H, t, J=8.6 Hz), 4.40-4.53 (1H, m), 4.96 (1H, dd, J=10.8, 5.2 Hz), 5.16 (1H, dd, J=9.2, 7.3 Hz), 7.01 (1H, s), 7.25 (1H, dd, J=8.8, 2.0 Hz), 7.34 (1H, d, J=8.8 Hz), 7.52 (1H, d, J=2.0 Hz), 8.01 (1H, d, J=5.4 Hz), 8.51-8.63 (1H, m), 9.22 (1H, s). MS (FAB) m/z: 474 (M+H$^+$).

Example 98

Ethyl (3S,4R)-2-(3-{[(5-chloroindol-2-yl)carbonyl]amino}-4-{[(5-methyl-4,5,6,7-tetrahydrothiazolo[5,4-c]-pyridin-2-yl)carbonyl]amino}-2-oxopyrrolidin-1-yl)acetate hydrochloride

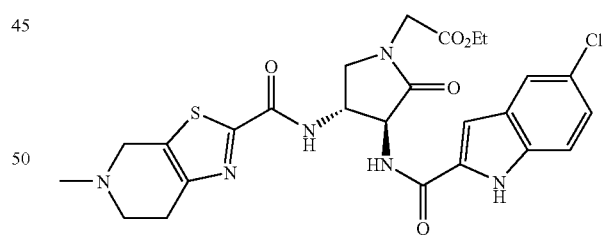

The title compound was obtained from the compound obtained in Referential Example 199 and the compound obtained in Referential Example 10 in a similar manner to Example 91. NMR was measured in the form of a free base.

$^1$H-NMR (DMSO-d$_6$) δ: 1.19 (3H, t, J=7.1 Hz), 2.35 (3H, s), 2.71-2.84 (2H, m), 2.80-2.90 (2H, m), 3.40 (1H, d, J=10.3 Hz), 3.61 (2H, d, J=10.8 Hz), 3.84 (1H, dd, J=10.3, 5.6 Hz), 4.01-4.23 (4H, m), 4.80-4.94 (1H, m), 5.04 (1H, t, J=8.6 Hz), 7.01 (1H, s), 7.16 (1H, dd, J=8.8, 2.0 Hz), 7.40 (1H, d, J=8.8 Hz), 7.69 (1H, d, J=2.0 Hz), 8.73 (1H, d, J=8.6 Hz), 8.90 (1H, d, J=8.8 Hz), 11.86 (1H, s). MS (FAB) m/z: 559 (M+H$^+$).

Example 99

N-((3R,4S)-4-{[(5-Chloroindol-2-yl)carbonyl]amino}-1-methyl-5-oxopyrrolidin-3-yl)-5-methyl-4,5,6,7-tetrahydrothiazolo[5,4-c]pyridine-2-carboxamide

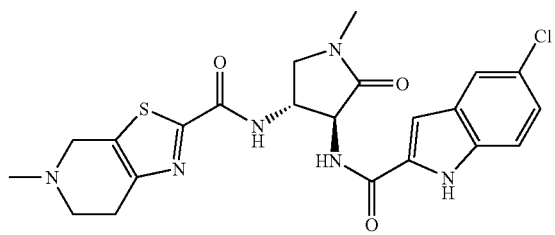

The title compound was obtained from the compound obtained in Referential Example 201 and the compound obtained in Referential Example 10 in a similar manner to Example 91.

$^1$H-NMR (CDCl$_3$) δ: 2.49 (3H, s), 2.77-2.82 (2H, m), 2.86-2.91 (5H, m), 3.69 (2H, d, J=1.2 Hz), 4.39-4.54 (3H, m), 4.93-4.98 (1H, m), 6.98 (1H, d, J=1.2 Hz), 7.05-7.34 (3H, m), 7.63 (1H, d, J=2.0 Hz), 8.11 (1H, d, J=7.8 Hz), 9.00 (1H, s). MS (FAB) m/z: 487 (M+H$^+$).

Example 100

Methyl 2-[((3R,4R)-3-{[(5-chloroindol-2-yl)carbonyl]-amino}-4-{[(5-methyl-4,5,6,7-tetrahydrothiazolo[5,4-c]-pyridin-2-yl)carbonyl]amino}pyrrolidin-1-yl)sulfonyl]acetate

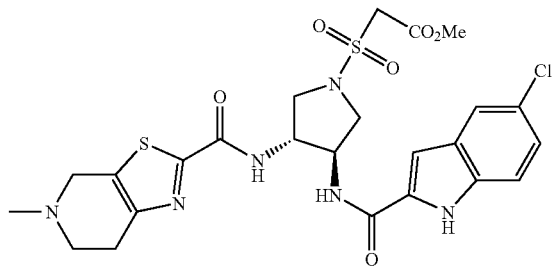

The compound (230 mg) obtained in Example 95 and triethylamine (0.10 ml) were dissolved in methylene chloride (6.9 ml), and the mixture was cooled with ice. Methoxycarbonylmethanesulfonyl chloride (Synthesis, p. 321, 1975) (105 mg) was added, and the resultant mixture was warmed to room temperature and stirred overnight. The reaction mixture was diluted with chloroform, washed with water and saturated aqueous solution of sodium chloride and then dried over anhydrous sodium sulfate, and the solvent was distilled off under reduced pressure. The resultant residue was purified by preparative thin-layer chromatography on silica gel (chloroform:methanol=20:1) and powdered with methanol-water to obtain the title compound (150 mg).

$^1$H-NMR (CDCl$_3$) δ: 2.48 (3H, s), 2.76-2.86 (4H, m), 3.49-3.73 (4H, m), 3.87 (3H, s), 3.94-3.98 (1H, m), 4.08-4.11 (1H, m), 4.13 (2H, s), 4.69-4.72 (1H, m), 4.88-4.91 (1H, m), 6.89 (1H, s), 7.12-7.15 (1H, m), 7.27-7.28 (1H, m), 7.50 (1H, s), 7.81-7.86 (2H, m), 9.92 (1H, s). MS (FAB) m/z: 595 (M+H$^+$).

Example 101

2-[((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)sulfonyl]acetic acid

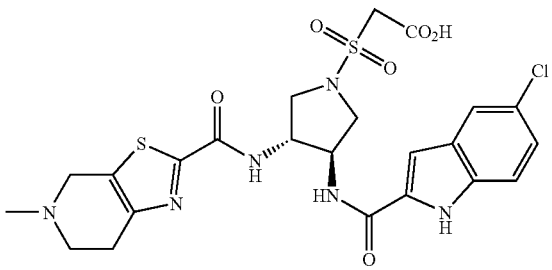

The compound (100 mg) obtained in Example 100 was dissolved in tetrahydrofuran (4 ml)-water (1 ml), and the mixture was cooled with ice. Lithium hydroxide monohydrate (7.8 mg) was added, and the resultant mixture was heated to room temperature and stirred for 4 hours. After the reaction mixture was neutralized with 1N hydrochloric acid, it was concentrated. Deposits were collected by filtration, washed with water and 50% ethanol and dried overnight at 50° C. under reduced pressure to obtain the title compound (87 mg).

$^1$H-NMR (DMSO-d$_6$) δ: 2.50 (3H, s), 2.92 (4H, s), 3.34-3.43 (4H, m), 3.76-3.85 (2H, m), 4.27 (each 1H, AB type d, J=14.5 Hz), 4.65-4.71 (1H, m), 4.78-4.84 (1H, m), 7.14 (1H, s), 7.18 (1H, d, J=8.8 Hz), 7.40 (1H, d, J=8.8 Hz), 7.72 (1H, s), 8.87 (1H, d, J=7.8 Hz), 9.12 (1H, d, J=8.2 Hz), 11.83 (1H, s).

Example 102

Methyl 2-((3R,4R)-3-{[(5-chloroindol-2-yl)carbonyl]-amino}-4-{[(5-methyl-4,5,6,7-tetrahydrothiazolo[5,4-c]-pyridin-2-yl)carbonyl]amino}pyrrolidin-1-yl)acetate

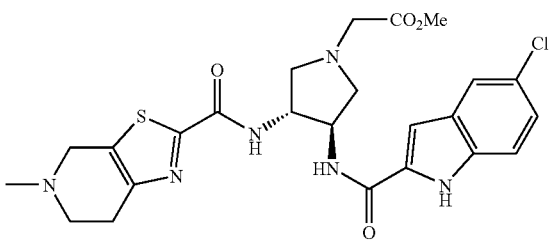

The compound (230 mg) obtained in Example 95 and potassium carbonate (90 mg) were dissolved in N,N-dimethylformamide (4.6 ml), and the mixture was cooled with ice. Methyl bromoacetate (0.062 ml) was added, and the resultant mixture was stirred for 45 minutes. The reaction mixture was diluted with ethyl acetate, washed with water and saturated aqueous solution of sodium chloride and then dried over anhydrous sodium sulfate, and the solvent was distilled off under reduced pressure. The resultant residue was purified by preparative thin-layer chromatography on silica gel (chloroform:methanol=10:1) and solidifier with methanol-water to obtain the title compound (190 mg).

$^1$H-NMR (CDCl$_3$) δ: 2.35 (2H, s), 2.48 (3H, s), 2.73-2.95 (4H, m), 3.34-3.42 (2H, m), 3.46 (2H, q, J=6.5 Hz), 3.67 (2H, q, J=6.5 Hz), 3.75 (3H, s), 4.57-4.71 (2H, m), 6.91 (1H, s), 7.10-7.13 (1H, m), 7.31 (1H, d, J=9.0 Hz), 7.53 (1H, s), 7.77 (1H, d, J=8.0 Hz), 7.87 (1H, d, J=6.8 Hz), 10.22 (1H, s). MS (FAB) m/z: 531 (M+H$^+$).

Example 103

2-((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)acetic acid

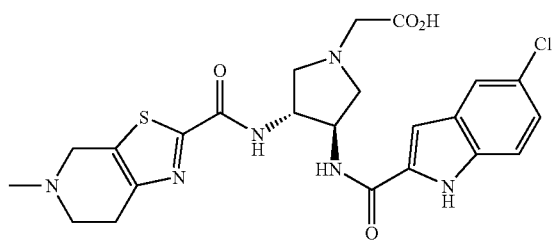

The title compound was obtained from the compound obtained in Example 102 in a similar manner to Example 101.

$^1$H-NMR (DMSO-d$_6$) δ: 2.42 (3H, s), 2.69-2.87 (6H, m), 3.13 (1H, t, J=9.0 Hz), 3.22 (1H, t, J=9.0 Hz), 3.33 (each 1H, AB type d, J=6.8 Hz), 3.72 (2H, s), 4.53-4.60 (1H, m), 4.65-4.72 (1H, m), 7.16-7.20 (2H, m), 7.42 (1H, d, J=8.8 Hz), 7.70 (1H, s), 8.85 (1H, d, J=7.5 Hz), 9.00 (1H, d, J=8.3 Hz), 11.79 (1H, s).

Example 104

Methyl 3-((3R,4R)-3-{[(5-chloroindol-2-yl)carbonyl]-amino}-4-{[(5-methyl-4,5,6,7-tetrahydrothiazolo[5,4-c]-pyridin-2-yl)carbonyl]amino}pyrrolidin-1-yl)propionate

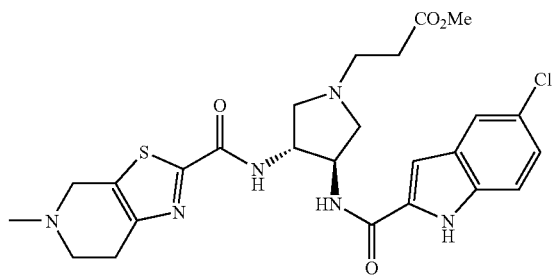

The title compound was obtained from the compound obtained in Example 95 and methyl 3-bromopropionate in a similar manner to Example 102.

$^1$H-NMR (CDCl$_3$) δ: 1.96-2.20 (2H, m), 2.49 (3H, s), 2.61-2.96 (8H, m), 3.17-3.21 (2H, m), 3.62-3.72 (2H, m), 3.69 (3H, s), 4.46-4.49 (1H, m), 4.56-4.61 (1H, m), 6.87 (1H, s), 7.05-7.14 (1H, m), 7.32 (1H, d, J=9.2 Hz), 7.53 (1H, s), 7.65-7.71 (2H, m), 10.02 (1H, s). MS (FAB) m/z: 545 (M+H$^+$).

Example 105

3-((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)propionic acid

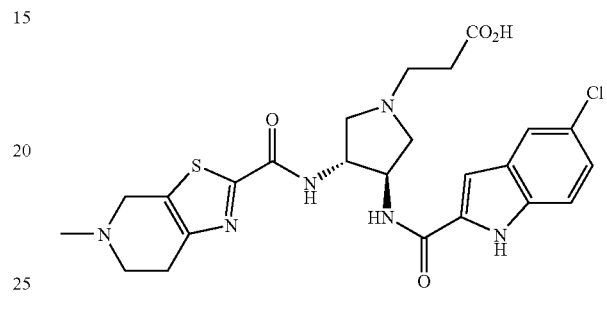

The title compound was obtained from the compound obtained in Example 104 in a similar manner to Example 101.

$^1$H-NMR (DMSO-d$_6$) δ: 2.38 (3H, s), 2.39-2.84 (10H, m), 2.93 (1H, t, J=8.8 Hz), 3.05 (1H, t, J=8.8 Hz), 3.65 (2H, s), 4.51-4.56 (1H, m), 4.63-4.68 (1H, m), 7.16-7.19 (2H, m), 7.41 (1H, d, J=8.8 Hz), 7.69 (1H, s), 8.81 (1H, d, J=7.8 Hz), 8.97 (1H, d, J=8.3 Hz), 11.75 (1H, s).

Example 106

Ethyl 3-((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)-3-oxopropionate

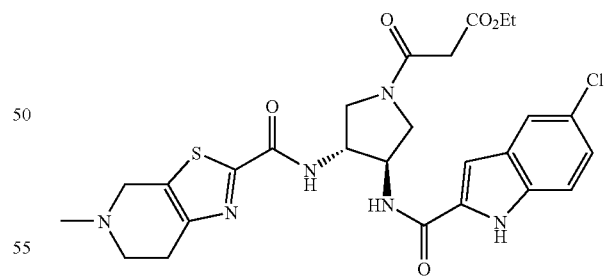

The title compound was obtained from the compound obtained in Example 95 and ethylmalonyl chloride in a similar manner to Example 100.

$^1$H-NMR (DMSO-d$_6$) δ: 1.20 (3H, t, J=7.0 Hz), 2.37 (3H, s), 2.73-2.75 (2H, m), 2.82-2.84 (2H, m), 3.35-3.38 (2H, m), 3.64 (2H, s), 3.68-3.83 (2H, m), 3.91-4.00 (2H, m), 4.10 (2H, q, J=7.0 Hz), 4.61-4.84 (2H, m), 7.13 (1H, s), 7.18 (1H, dd, J=8.5, 2.0 Hz), 7.41 (1H, d, J=8.5 Hz), 7.72 (1H, s), 8.73 (1H, t, J=9.0 Hz), 9.10 (1H, d, J=9.0 Hz), 11.79 (1H, s).

Example 107

3-((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)-3-oxopropionic acid

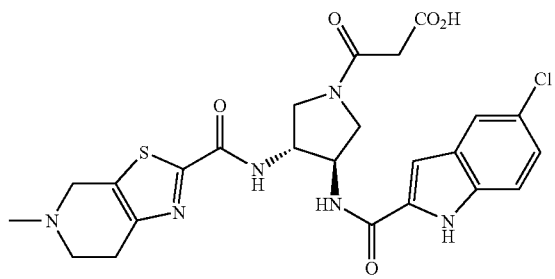

The title compound was obtained from the compound obtained in Example 106 in a similar manner to Example 101.

$^1$H-NMR (DMSO-$d_6$) δ: 2.39 (3H, s), 2.77 (2H, s), 2.85 (2H, s), 3.29-3.55 (4H, m), 3.68 (2H, s), 3.82-4.01 (2H, m), 4.62-4.68 (1H, m), 4.77-4.86 (1H, m), 7.14 (1H, s), 7.18 (1H, d, J=8.8 Hz), 7.41 (1H, d, J=8.8 Hz), 7.72 (1H, s), 8.75 (1H, t, J=8.8 Hz), 9.12 (1H, d, J=7.8 Hz), 11.81 (1H, s).

Example 108

Methyl 1-[((3R,4R)-3-{[(5-chloroindol-2-yl)carbonyl]-amino}-4-{[(5-methyl-4,5,6,7-tetrahydrothiazolo[5,4-c]-pyridin-2-yl)carbonyl]amino}pyrrolidin-1-yl)methyl]-cyclopropanecarboxylate

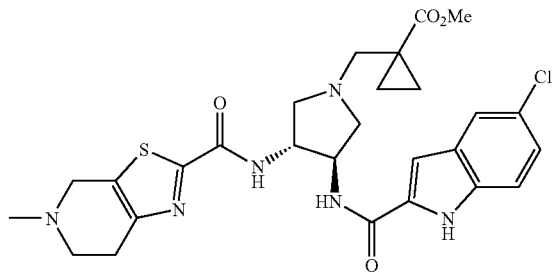

The title compound was obtained from the compound obtained in Example 95 and methyl 1-(bromomethyl)cyclopropanecarboxylate in a similar manner to Example 102.

$^1$H-NMR (CDCl$_3$) δ: 0.78-0.79 (2H, m), 1.24-1.26 (2H, m), 2.49 (3H, s), 2.62-2.88 (6H, m), 3.20-3.28 (2H, m), 3.66 (3H, s), 3.61-3.75 (4H, m), 4.45-4.62 (2H, m), 6.86 (1H, s), 7.12-7.15 (1H, m), 7.24-7.28 (1H, m), 7.52 (1H, d, J=8.5 Hz), 7.54 (1H, s), 7.69 (1H, d, J=8.0 Hz), 10.00 (1H, s). MS (ESI) m/z: 571 (M+H$^+$).

Example 109

1-[((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)methyl]-cyclopropanecarboxylic acid

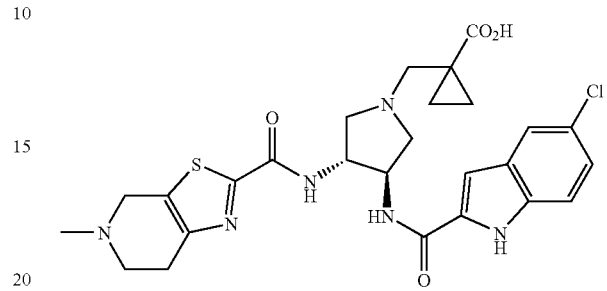

The title compound was obtained from the compound obtained in Example 108 in a similar manner to Example 101.

$^1$H-NMR (DMSO-$d_6$) δ: 0.73-0.78 (2H, m), 1.04-1.07 (2H, m), 2.37 (3H, s), 2.65-2.84 (6H, m), 3.11-3.20 (4H, m), 3.64 (2H, s), 4.59-4.74 (2H, m), 7.16 (1H, s), 7.17 (1H, d, J=8.5 Hz), 7.40 (1H, d, J=8.5 Hz), 7.70 (1H, s), 8.84 (1H, d, J=7.5 Hz), 9.12 (1H, d, J=7.5 Hz), 11.77 (1H, s).

Example 110 tert-Butyl (3R,4R)-3-{[(5-chloroindol-2-yl)carbonyl]-amino}-4-{[(5-isopropyl-4,5,6,7-tetrahydrothiazolo[5,4-c]-pyridin-2-yl)carbonyl]amino}pyrrolidine-1-carboxylate

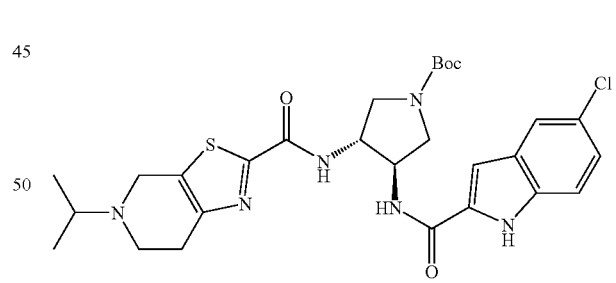

The title compound was obtained from the compound obtained in Referential Example 193 and Referential Example 148 in a similar manner to Example 91.

$^1$H-NMR (CDCl$_3$) δ: 1.12 (6H, d, J=6.6 Hz), 1.47 (9H, s), 2.83-2.88 (4H, m), 2.94-2.99 (1H, m), 3.20-3.29 (1H, m), 3.31-3.42 (1H, m), 3.75-3.81 (2H, m), 3.98 (1H, t, J=8.5 Hz), 4.15-4.35 (2H, m), 4.50-4.65 (1H, m), 6.85, 6.91 (total 1H, each s), 7.15-7.90 (5H, m), 9.41, 9.50 (total 1H, each s).

Example 111

N-((3R,4R)-4-{[(5-chloroindol-2-yl)carbonyl]amino}pyrrolidin-3-yl)-5-isopropyl-4,5,6,7-tetrahydrothiazolo[5,4-c]pyridine-2-carboxamide

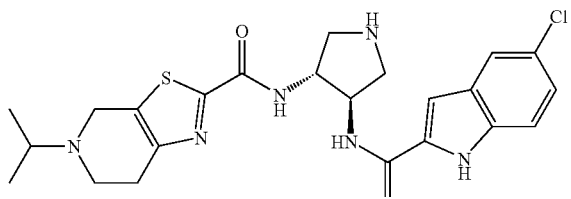

The title compound was obtained from the compound obtained in Example 110 in a similar manner to Example 95.

$^1$H-NMR (CDCl$_3$) δ: 1.13 (6H, d, J=6.3 Hz), 2.85 (4H, br.s), 2.96-3.05 (3H, m), 4.51-4.52 (1H, m), 4.76-4.80 (2H, m), 5.36-5.39 (2H, m), 5.53-5.58 (1H, m), 7.17-7.19 (1H, m), 7.27-7.31 (2H, m), 7.57 (1H, s), 7.64 (2H, br), 9.82 (1H, br).

Example 112

Ethyl 3-((3R,4R)-3-{[(5-chloroindol-2-yl)carbonyl]amino}-4-{[(5-isopropyl-4,5,6,7-tetrahydrothiazolo[5,4-c]pyridin-2-yl)carbonyl]amino}pyrrolidin-1-yl)propionate

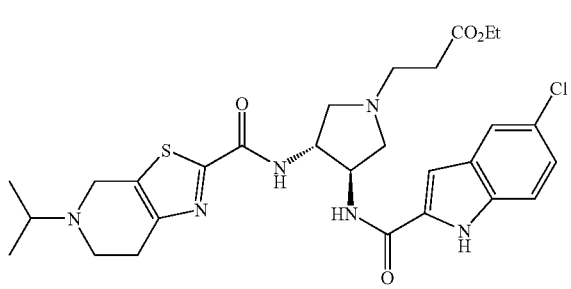

The title compound was obtained from the compound obtained in Example 111 and ethyl 3-bromopropionate in a similar manner to Example 102.

$^1$H-NMR (CDCl$_3$) δ: 1.14 (6H, d, J=6.5 Hz), 1.26 (3H, t, J=7.0 Hz), 2.51 (3H, t, J=7.0 Hz), 2.63 (1H, dd, J=9.5, 6.5 Hz), 2.73-2.91 (6H, m), 2.95-3.02 (1H, m), 3.22 (2H, q, J=7.0 Hz), 3.81 (each 1H, AB type d, J=14.5 Hz), 4.16 (2H, q, J=7.0 Hz), 4.40-4.45 (1H, m), 4.52-4.59 (1H, m), 6.88 (1H, d, J=2.0 Hz), 7.17-7.19 (1H, m)., 7.30-7.32 (2H, m), 7.59 (1H, s), 7.62 (1H, s), 9.56 (1H, s). MS (FAB) m/z: 587 (M+H$^+$).

Example 113

3-((3R,4R)-3-{[(5-Chloroindol-2-yl)carbonyl]amino}-4-{[(5-isopropyl-4,5,6,7-tetrahydrothiazolo[5,4-c]pyridin-2-yl)carbonyl]amino}pyrrolidin-1-yl)propionic acid

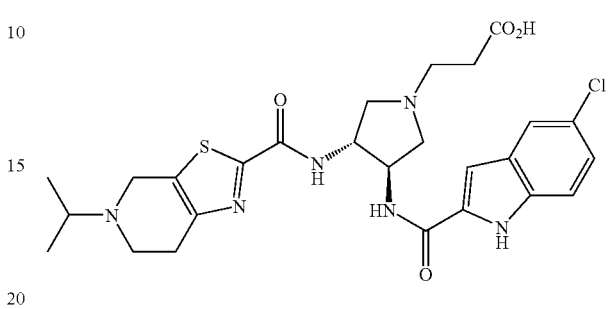

The title compound was obtained from the compound obtained in Example 112 in a similar manner to Example 101.

$^1$H-NMR (DMSO-d$_6$) δ: 1.04 (6H, d, J=6.6 Hz), 2.40 (2H, q, J=7.0 Hz), 2.50 (4H, s), 2.60-2.74 (4H, m), 2.90-2.94 (2H, m), 3.02-3.06 (1H, m), 3.20-3.35 (2H, m), 4.50-4.53 (1H, m), 4.61-4.65 (1H, m), 7.15-7.18 (2H, m), 7.41 (1H, d, J=8.8 Hz), 7.68 (1H, s), 8.78 (1H, d, J=7.5 Hz), 8.90 (1H, d, J=8.0 Hz), 11.73 (1H, s).

Example 114

N-((3R,4R)-1-Acetyl-4-{[(5-chloroindol-2-yl)carbonyl]-amino}pyrrolidin-3-yl)-5-isopropyl-4,5,6,7-tetrahydrothiazolo[5,4-c]pyridine-2-carboxamide hydrochloride

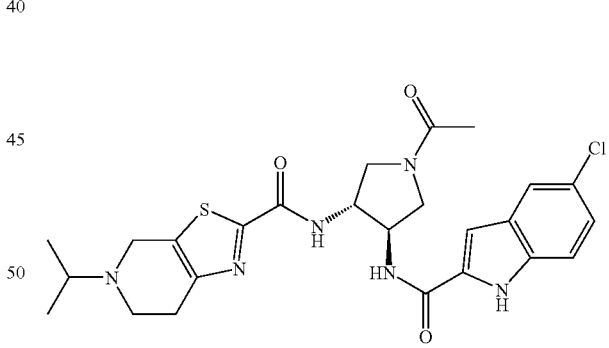

The title compound was obtained from the compound obtained in Example 111 and acetic anhydride in a similar manner to Example 100.

Melting point: 254-258° C. (decomposed).

$^1$H-NMR (DMSO-d$_6$) δ: 1.34-1.37 (6H, m), 1.96 (3H, s), 3.30-3.55 (5H, m), 3.66-3.82 (3H, m), 3.95 (1H, q, J=8.3 Hz), 4.45-4.82 (4H, m), 7.15 (1H, s), 7.18 (1H, d, J=9.0 Hz), 7.41 (1H, d, J=9.0 Hz), 7.71 (1H, s), 8.75-8.81 (1H, m), 9.21 (1H, d, J=8.0 Hz), 11.32 (1H, br), 11.83 (1H, d, J=7.3 Hz). MS (FAB) m/z: 529 (M+H$^+$).

Example 115

N-[(3R,4R)-4-{[(5-Chloroindol-2-yl)carbonyl]amino}-1-(methylsulfonyl)pyrrolidin-3-yl]-5-isopropyl-4,5,6,7-tetrahydrothiazolo[5,4-c]pyridine-2-carboxamide hydrochloride

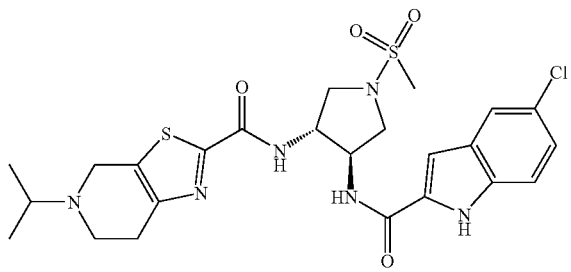

The title compound was obtained from the compound obtained in Example 111 and methanesulfonyl chloride in a similar manner to Example 100.

Melting point: 230-235° C. (decomposed).

¹H-NMR (DMSO-d₆) δ: 1.32-1.36 (6H, m), 3.32 (3H, s), 3.43-3.46 (5H, m), 3.68-3.75 (4H, m), 4.48 (1H, m), 4.62-4.72 (2H, m), 4.83 (1H, t, J=5.5 Hz), 7.14 (1H, s), 7.18 (1H, d, J=8.6 Hz), 7.40 (1H, d, J=8.6 Hz), 7.72 (1H, s), 8.82 (1H, br), 9.20 (1H, d, J=8.3 Hz), 11.30 (1H, br), 11.86 (1H, d, J=7.5 Hz). MS (FAB) m/z: 565 (M+H⁺).

Example 116

Ethyl (3R,4R)-3-{[(5-chloroindol-2-yl)carbonyl]amino}-4-{[(5-isopropyl-4,5,6,7-tetrahydrothiazolo[5,4-c]pyridin-2-yl)carbonyl]amino}pyrrolidine-1-carboxylate hydrochloride

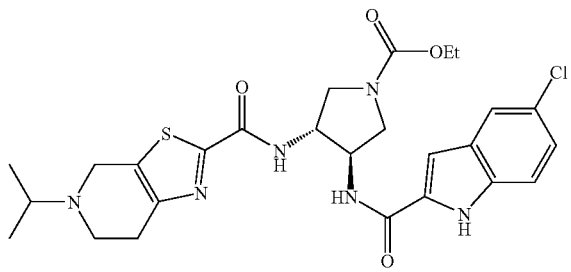

The title compound was obtained from the compound obtained in Example 111 and ethyl chloroformate in a similar manner to Example 100.

Melting point: 225-228° C. (decomposed).

¹H-NMR (DMSO-d₆) δ: 1.20 (3H, t, J=7.0 Hz), 1.31-1.37 (6H, m), 3.33-3.45 (5H, m), 3.66-3.75 (4H, m), 4.05 (2H, q, J=7.0 Hz), 4.45-4.77 (4H, m), 7.15 (1H, s), 7.17 (1H, dd, J=8.8, 2.0 Hz), 7.41 (1H, d, J=8.8 Hz), 7.71 (1H, d, J=2.0 Hz), 8.77 (1H, d, J=7.0 Hz), 9.20 (1H, d, J=8.0 Hz), 11.30 (1H, br), 11.83 (1H, d, J=7.5 Hz). MS (FAB) m/z: 559 (M+H⁺).

Example 117 tert-Butyl (3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}piperidine-1-carboxylate

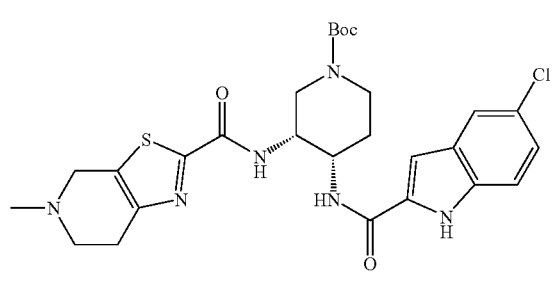

The title compound was obtained from the compound obtained in Referential Example 207 and Referential Example 10 in a similar manner to Example 91.

Melting point: 152-154° C. (decomposed).

¹H-NMR (CDCl₃) δ: 1.53 (9H, s), 1.62-1.80 (1H, m), 2.23-2.30 (1H, m), 2.52 (3H, s), 2.75-3.05 (5H, m), 3.10-3.25 (1H, m), 3.68-3.82 (2H, m), 4.15-4.45 (4H, m), 6.89 (1H, s), 7.19 (1H, dd, J=8.8, 1.8 Hz), 7.32 (1H, d, J=8.8 Hz), 7.92 (1H, d, J=1.8 Hz), 7.75 (1H, br.s), 8.21 (1H, br.s), 9.39 (1H, s). MS (ESI) m/z: 573 (M+H)⁺.

Example 118

N-((3R*,4S*)-4-{[(5-Chloroindol-2-yl)carbonyl]amino}-piperidin-3-yl)-5-methyl-4,5,6,7-tetrahydrothiazolo[5,4-c]pyridine-2-carboxamide Dihydrochloride

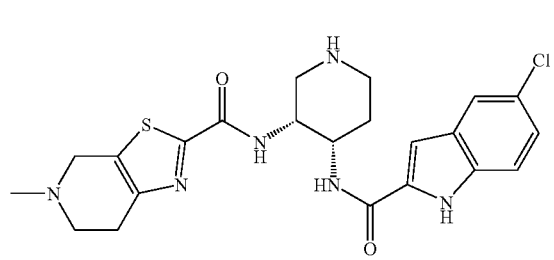

The title compound was obtained from the compound obtained in Example 117 in a similar manner to Example 95.

Melting point: 240-258° C. (decomposed).

¹H-NMR (DMSO-d₆) δ: 1.85-2.00 (1H, m), 2.05-2.20 (2H, m), 2.93 (3H, s), 3.05-3.60 (7H, m), 3.65-3.75 (1H, m), 4.10-4.52 (2H, m), 4.60-4.75 (2H, m), 7.10-7.21 (2H, m), 7.43 (1H, d, J=8.6 Hz), 7.70 (1H, s), 8.50 (1H, br.d, J=7.8 Hz), 8.90-9.05 (2H, m), 9.27 (1H, br.s), 11.9 (1H, br.d, J=13.4 Hz). MS (ESI) m/z: 473 (M+H)⁺.

Example 119 tert-Butyl (3R*,4S*)-3-{[(5-chloroindol-2-yl)carbonyl]-amino}-4-{[(5-methyl-4,5,6,7-tetrahydrothiazolo[5,4-c]-pyridin-2-yl)carbonyl]amino}piperidine-1-carboxylate

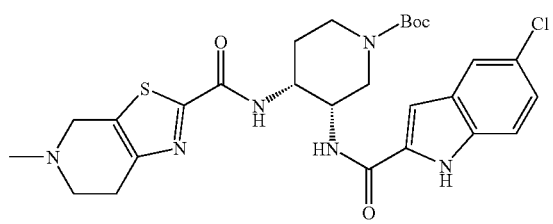

The title compound was obtained from the compound obtained in Referential Example 208 and 5-chloroindole-2-carboxylic acid in a similar manner to Example 91.

Melting point: 187-189° C. (decomposed).

$^1$H-NMR (CDCl$_3$) δ: 1.48 (9H, s), 1.72-1.90 (1H, m), 2.00 (1H, br.s), 2.00-2.10 (1H, m), 2.45 (3H, s), 2.60-2.70 (2H, m), 2.70-2.80 (2H, m), 3.23 (1H, t, J=10.8 Hz), 3.35-3.50 (1H, m), 3.50-3.72 (2H, m), 3.90-4.20 (2H, m), 4.30-4.40 (1H, m), 4.45-4.55 (1H, m), 6.85 (1H, d, J=1.5 Hz), 7.17 (1H, dd, J=8.8, 1.9 Hz), 7.20-7.30 (1H, m), 7.33 (1H, d, J=8.8 Hz), 7.58 (1H, d, J=1.9 Hz), 10.17 (1H, s). MS (ESI) m/z: 573 (M+H$^+$).

Example 120

N-((3R*,4S*)-3-{[(5-Chloroindol-2-yl)carbonyl]amino}-piperidin-4-yl)-5-methyl-4,5,6,7-tetrahydrothiazolo-[5,4-c]pyridine-2-carboxamide dihydrochloride

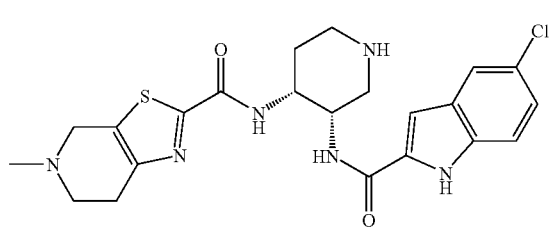

The title compound was obtained from the compound obtained in Example 119 in a similar manner to Example 95.

Melting point: 276-278° C. (decomposed).

$^1$H-NMR (DMSO-d$_6$) δ: 1.77-1.88 (1H, m), 2.40-2.50 (2H, m), 2.89 (3H, s), 2.90-3.20 (4H, m), 3.30-3.50 (2H, m), 3.63 (1H, br.s), 4.33-4.47 (2H, m), 4.62-4.75 (2H, m), 7.18 (1H, dd, J=8.8, 1.9 Hz), 7.42 (1H, d, J=8.8 Hz), 7.48 (1H, br.s), 7.71 (1H, d, J=1.9 Hz), 8.66 (1H, br.s), 8.95 (1H, d, J=8.1 Hz), 9.20-9.30 (1H, m), 9.45-9.70 (1H, m), 11.61 (1H, s), 11.90 (1H, s). MS (ESI) m/z: 473 (M+H)$^+$.

Example 121 tert-Butyl (3R*,4S*)-4-{[(5-fluoroindol-2-yl)carbonyl]-amino}-3-{[(5-methyl-4,5,6,7-tetrahydrothiazolo[5,4-c]-pyridin-2-yl)carbonyl]amino}piperidine-1-carboxylate

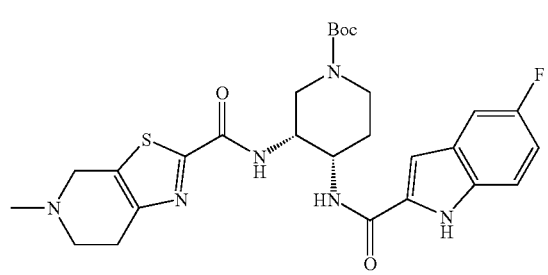

The title compound was obtained from the compound obtained in Referential Example 209 and Referential Example 10 in a similar manner to Example 91.

$^1$H-NMR (CDCl$_3$) δ: 1.53 (9H, s), 1.65-1.78 (1H, m), 2.23-2.32 (1H, br), 2.52 (3H, s), 2.78-3.03 (5H, m), 3.15-3.24 (1H, br), 3.68-3.82 (2H, br), 4.16-4.45 (4H, br), 6.91 (1H, s), 7.02 (1H, td, J=9.0, 2.7 Hz), 7.30 (1H, dd, J=9.0, 2.7 Hz), 7.34 (1H, dd, J=9.0, 4.4 Hz), 7.65-7.90 (1H, br), 8.10-8.40 (1H, br), 9.31-9.41 (1H, br). MS (ESI) m/z: 557 (M+H$^+$).

Example 122

N-((3R*,4S*)-4-{[(5-Fluoroindol-2-yl)carbonyl]amino}-piperidin-3-yl)-5-methyl-4,5,6,7-tetrahydrothiazolo[5,4-c]pyridine-2-carboxamide dihydrochloride

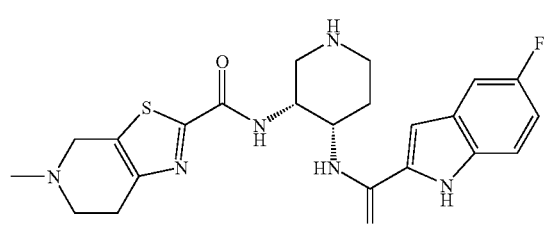

The title compound was obtained from the compound obtained in Example 121 in a similar manner to Example 95.

Melting point: 236-245° C. (decomposed).

$^1$H-NMR (DMSO-d$_6$) δ: 1.85-1.98 (1H, br), 2.06-2.18 (1H, br), 2.89 (3H, s), 3.05-3.75 (8H, s), 4.34-4.54 (2H, br), 4.60-4.75 (2H, br), 7.04 (1H, td, J=9.3, 2.4 Hz), 7.15 (1H, br.s), 7.37-7.44 (2H, m), 8.46 (1H, d, J=7.8 Hz), 8.88-9.00 (1H, br), 9.09-9.27 (2H, br), 11.55-11.75 (1H, br), 11.76-11.84 (1H, br). MS (FAB) m/z: 457 (M+H$^+$).

Example 123

N-((3R*,4S*)-1-Acetyl-4-{[(5-chloroindol-2-yl)carbonyl]-amino}piperidin-3-yl)-5-methyl-4,5,6,7-tetrahydrothiazolo[5,4-c]pyridine-2-carboxamide hydrochloride

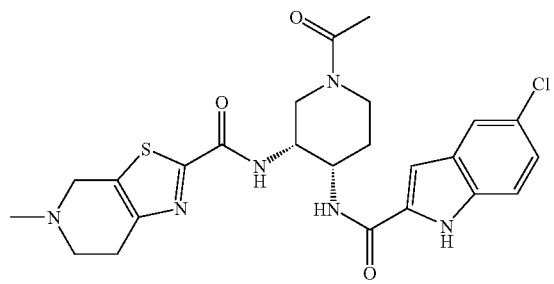

The title compound was obtained from the compound obtained in Example 118 and acetic anhydride in a similar manner to Example 100.

Melting point: 215-225° C. (decomposed). $^1$H-NMR (DMSO-$d_6$) δ: 1.65-1.85 (1H, m), 1.88, 2.06 (total 3H, each s), 1.90-2.10 (1H, m), 2.91 (3H, s), 3.00-3.30 (2H, m), 3.30-3.55 (2H, m), 3.60-3.90 (3H, m), 3.98-4.50 (4H, m), 4.65-4.75 (1H, m), 7.09 (1H, d, J=15.6 Hz), 7.17 (1H, d, J=8.8 Hz), 7.41 (1H, d, J=8.8 Hz), 7.71 (1H, s), 8.23-8.53 (2H, m), 11.20-11.55 (1H, m), 11.85 (1H, br.d, J=5.4 Hz). MS (ESI) m/z: 515 (M+H$^+$).

Example 124

N-((3R*,4S*)-1-Acetyl-3-{[(5-chloroindol-2-yl)carbonyl]-amino}piperidin-4-yl)-5-methyl-4,5,6,7-tetrahydrothiazolo[5,4-c]pyridine-2-carboxamide hydrochloride

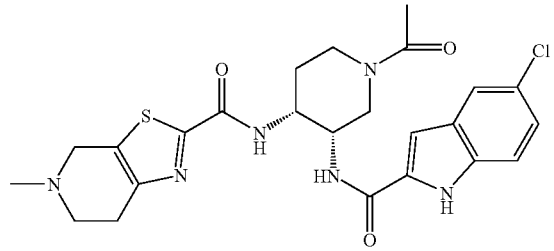

The title compound was obtained from the compound obtained in Example 120 and acetic anhydride in a similar manner to Example 100.

Melting point: 225-250° C. (decomposed). $^1$H-NMR (DMSO-$d_6$) δ: 1.65-1.80 (1H, m), 1.81, 2.05 (total 3H, each s), 2.00-2.20 (1H, m), 2.70-2.85 (1H, m), 2.89 (3H, s), 3.00-3.20 (2H, m), 3.20-3.50 (2H, m), 3.64 (1H, br.s), 3.78-4.30 (2H, m), 4.30-4.50 (2H, m), 4.55-4.75 (1H, m), 7.05-7.23 (2H, m), 7.38-7.48 (1H, m), 7.70-7.80 (1H, m), 7.79, 8.12 (total 1H, each d, J=6.8 Hz), 8.73, 8.83 (total 1H, each d, J=8.3 Hz), 11.20-11.50 (1H, m), 11.89, 11.92 (total 1H, each s). MS (FAB) m/z: 515 (M+H$^+$).

Example 125

N-((3R*,4S*)-1-Acetyl-4-{[(5-fluoroindol-2-yl)carbonyl]-amino}piperidin-3-yl)-5-methyl-4,5,6,7-tetrahydrothiazolo[5,4-c]pyridine-2-carboxamide hydrochloride

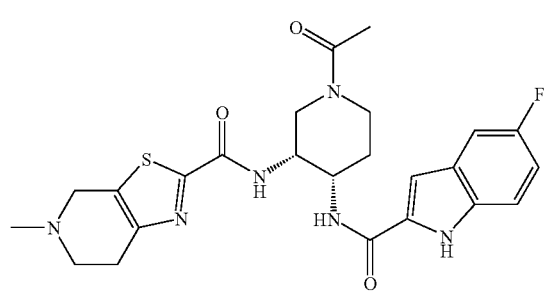

The title compound was obtained from the compound obtained in Example 122 and acetic anhydride in a similar manner to Example 100.

Melting point: 202° C. (decomposed). $^1$H-NMR (DMSO-$d_6$) δ: 1.67-1.85 (1H, m), 1.87 (1.5H, s), 1.87-2.10 (1H, m), 2.06 (1.5H, s), 2.88-2.96 (3H, br.s), 3.05-3.30 (2H, m), 3.32-3.83 (5H, br), 3.97-4.33 (2H, m), 4.35-4.50 (2H, br), 4.67-4.78 (1H, br), 7.01-7.14 (2H, m), 7.38-7.44 (2H, m), 8.25-8.50 (2H, m), 10.85-11.15 (1H, br), 11.72-11.80 (1H, br). MS (FAB) m/z: 499 (M+H$^+$).

Example 126

N-[(3R*,4S*)-4-{[(5-Chloroindol-2-yl)carbonyl]amino}-1-(methylsulfonyl)piperidin-3-yl]-5-methyl-4,5,6,7-tetrahydrothiazolo[5,4-c]pyridine-2-carboxamide hydrochloride

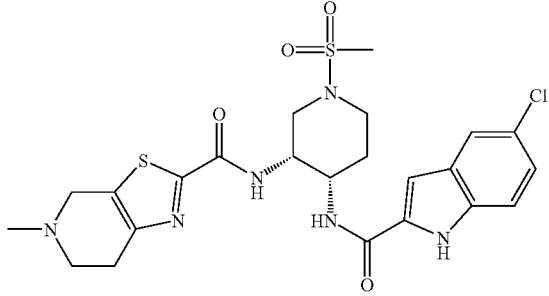

The title compound was obtained from the compound obtained in Example 118 and methanesulfonyl chloride in a similar manner to Example 100.

Melting point: 225-230° C. (decomposed). $^1$H-NMR (DMSO-$d_6$) δ: 1.80-1.90 (1H, m), 2.05-2.15 (1H, m), 2.30-2.80 (5H, m), 2.85-3.80 (9H, m), 4.20-4.90 (4H, m), 7.08 (1H, d, J=1.7 Hz), 7.18 (1H, dd, J=8.7, 1.7 Hz), 7.42 (1H, d, J=8.7 Hz), 7.77 (1H, s), 8.02-8.20 (1H, m), 8.40-8.50 (1H, m), 11.00-11.60 (1H, m), 11.87 (1H, s). MS (ESI) m/z: 551 (M+H$^+$).

Example 127

N-[(3R*,4S*)-3-{[(5-Chloroindol-2-yl)carbonyl]amino}-1-(methylsulfonyl)piperidin-4-yl]-5-methyl-4,5,6,7-tetrahydrothiazolo[5,4-c]pyridine-2-carboxamide hydrochloride

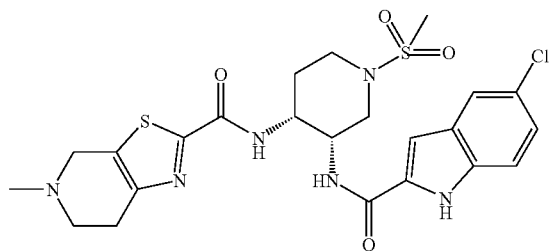

The title compound was obtained from the compound obtained in Example 120 and methanesulfonyl chloride in a similar manner to Example 100.

Melting point: 228-245° C. (decomposed). $^1$H-NMR (DMSO-$d_6$) δ: 1.75-1.85 (1H, m), 2.25-2.40 (1H, m), 2.40-2.60 (2H, m), 2.76 (3H, br.s), 2.90 (3H, s), 2.93-3.05 (3H, m), 3.12 (1H, d, J=10.6 Hz), 3.55-3.80 (2H, m), 4.25-4.40 (4H, m), 7.17 (1H, d, J=1.7 Hz), 7.19 (1H, dd, J=8.7, 2.0 Hz), 7.43 (1H, d, J=8.7 Hz), 7.74 (1H, d, J=2.0 Hz), 8.03 (1H, d, J=6.6 Hz), 8.78 (1H, d, J=7.4 Hz), 10.90-11.20 (1H, br.s), 11.89 (1H, s). MS (ESI) m/z: 551 (M+H$^+$).

Example 128

N-[(3R*,4S*)-4-{[(5-Fluoroindol-2-yl)carbonyl]amino}-1-(methylsulfonyl)piperazin-3-yl]-5-methyl-4,5,6,7-tetrahydrothiazolo[5,4-c]pyridine-2-carboxamide hydrochloride

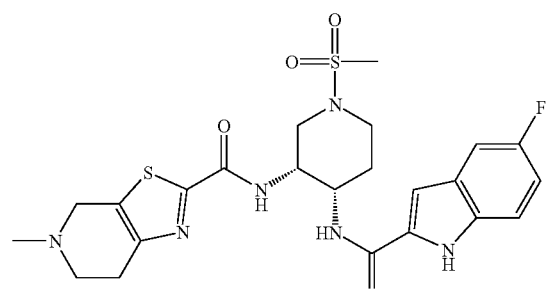

The title compound was obtained from the compound obtained in Example 122 and methanesulfonyl chloride in a similar manner to Example 100.

Melting point: 216-250° C. (decomposed). $^1$H-NMR (DMSO-$d_6$) δ: 1.80-1.90 (1H, m), 2.01-2.12 (1H, m), 2.92 (3H, s), 2.94 (3H, s), 3.00-3.80 (8H, m), 4.28-4.53 (3H, m), 4.60-4.80 (1H, br), 7.01-7.12 (2H, m), 7.37-7.44 (2H, m), 8.00-8.18 (1H, br), 8.39-8.50 (1H, br), 11.00-11.60 (1H, br), 11.72-11.80 (1H, br). MS (FAB) m/z: 535 (M+H$^+$).

Example 129

Methyl (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylate hydrochloride

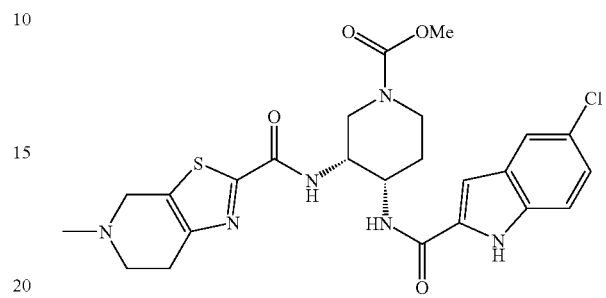

The title compound was obtained from the compound obtained in Example 118 and methyl chloroformate in a similar manner to Example 100.

Melting point: 248-253° C. (decomposed). $^1$H-NMR (DMSO-$d_6$) δ: 1.65-1.78 (1H, m), 1.88-2.03 (1H, m), 2.90 (3H, s), 3.00-3.80 (9H, m), 3.80-3.90 (1H, m), 3.95-4.08 (1H, m), 4.20-4.70 (4H, m), 7.10 (1H, s), 7.17 (1H, dd, J=8.8, 1.8 Hz), 7.42 (1H, d, J=8.8 Hz), 7.71 (1H, d, J=1.8 Hz), 8.29 (1H, br.s), 8.41 (1H, d, J=8.1 Hz), 11.29 (1H, br.s), 11.85 (1H, s). MS (ESI) m/z: 531 (M+H$^+$).

Example 130

Ethyl (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylate hydrochloride

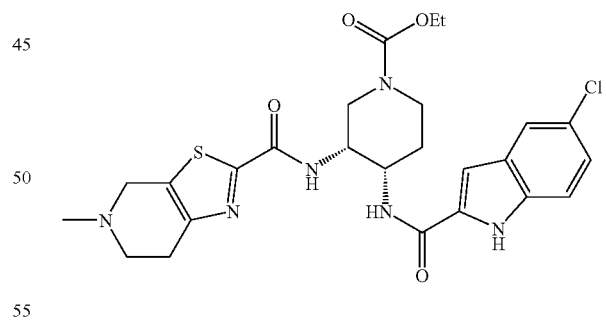

The title compound was obtained from the compound obtained in Example 118 and ethyl chloroformate in a similar manner to Example 100.

Melting point: 215-225° C. (decomposed). $^1$H-NMR (DMSO-$d_6$) δ: 0.85-1.30 (3H, m), 1.65-1.78 (1H, m), 1.90-2.03 (1H, m), 2.90 (3H, s), 3.10-3.40 (4H, m), 3.48 (1H, br.s), 3.65 (1H, br.s), 3.75-4.15 (4H, m), 4.25 (1H, br.s), 4.32-4.50 (2H, m), 4.66 (1H, br.s), 7.09 (1H, s), 7.18 (1H, dd, J=8.8, 2.0 Hz), 7.41 (1H, d, J=8.8 Hz), 7.71 (1H, d, J=2.0 Hz), 8.23 (1H, br.s), 8.45 (1H, br.d, J=8.1 Hz), 11.50 (1H, br.s), 11.86 (1H, s). MS (ESI) m/z: 545 (M+H$^+$).

Example 131

2-Methoxyethyl (3R*,4S*)-4-{[(5-chloroindol-2-yl)carbonyl]amino}-3-{[(5-methyl-4,5,6,7-tetrahydrothiazolo-[5,4-c]pyridin-2-yl)carbonyl]amino}piperidine-1-carboxylate hydrochloride

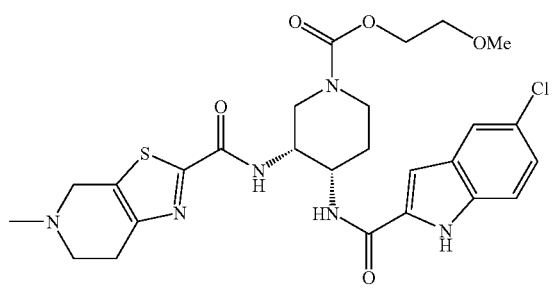

The title compound was obtained from the compound obtained in Example 118 and 2-methoxyethyl chloroformate in a similar manner to Example 100.

Melting point: 224-226° C. (decomposed). $^1$H-NMR (DMSO-$d_6$) δ: 1.68-1.78 (1H, m), 1.90-2.03 (1H, m), 2.89 (3H, s), 3.00-3.75 (11H, m), 3.80-3.90 (1H, m), 3.95-4.18 (3H, m), 4.20-4.70 (4H, m), 7.10 (1H, s), 7.17 (1H, dd, J=8.8, 2.0 Hz), 7.41 (1H, d, J=8.8 Hz), 7.71 (1H, d, J=2.0 Hz), 8.26 (1H, br.s), 8.42 (1H, d, J=7.8 Hz), 11.30 (1H, br.s), 11.86 (1H, s). MS (ESI) m/z: 575 (M+H$^+$).

Example 132

Ethyl (3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}piperidine-1-carboxylate hydrochloride

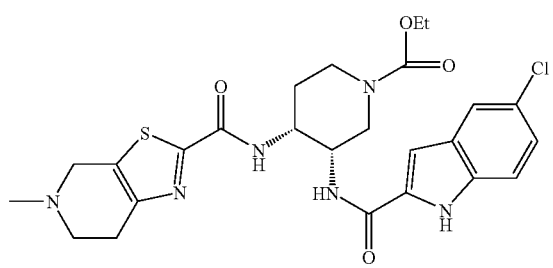

The title compound was obtained from the compound obtained in Example 120 and ethyl chloroformate in a similar manner to Example 100.

Melting point: 213-225° C. (decomposed). $^1$H-NMR (DMSO-$d_6$) δ: 0.75-1.30 (3H, m), 1.60-1.72 (1H, m), 2.12-2.25 (1H, m), 2.89 (3H, s), 2.95-3.20 (4H, m), 3.40-3.88 (4H, m), 3.90-4.10 (2H, m), 4.10-4.30 (2H, m), 4.30-4.40 (1H, m), 4.40-4.80 (1H, m), 7.10 (1H, s), 7.18 (1H, dd, J=8.8, 2.0 Hz), 7.43 (1H, d, J=8.8 Hz), 7.74 (1H, s), 8.03 (1H, d, J=5.6 Hz), 8.79 (1H, s), 11.37 (1H, s), 11.88 (1H, s). MS (ESI) m/z: 545 (M+H$^+$).

Example 133

N-((3R*,4S*)-4-{[(5-Chloroindol-2-yl)carbonyl]amino}-1-propionylpiperidin-3-yl)-5-methyl-4,5,6,7-tetrahydrothiazolo[5,4-c]pyridine-2-carboxamide hydrochloride

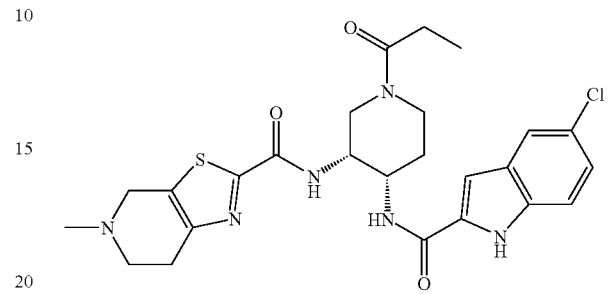

The title compound was obtained from the compound obtained in Example 118 and propionyl chloride in a similar manner to Example 100.

Melting point: 214-228° C. (decomposed). $^1$H-NMR (DMSO-$d_6$) δ: 0.88-1.10 (3H, m), 1.70-2.05 (2H, m), 2.06-2.60 (2H, m), 2.91 (3H, s), 3.14 (2H, br.s), 3.20-3.90 (5H, m), 3.95-4.80 (5H, m), 7.09 (1H, d, J=11.0 Hz), 7.17 (1H, dd, J=8.8, 1.2 Hz), 7.41 (1H, d, J=8.8 Hz), 7.71 (1H, s), 8.20-8.50 (2H, m), 11.00-11.40 (1H, m), 11.86 (1H, s). MS (ESI) m/z: 529 (M+H$^+$).

Example 134

N-((3R*,4S*)-4-{[(5-Chloroindol-2-yl)carbonyl]amino}-1-isobutyrylpiperidin-3-yl)-5-methyl-4,5,6,7-tetrahydrothiazolo[5,4-c]pyridine-2-carboxamide hydrochloride

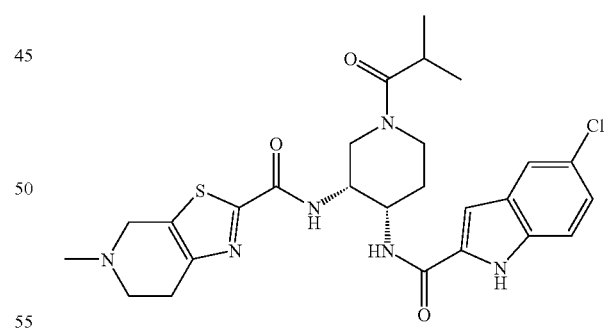

The title compound was obtained from the compound obtained in Example 118 and isobutyryl chloride in a similar manner to Example 100.

Melting point: 266-272° C. (decomposed). $^1$H-NMR (DMSO-$d_6$) δ: 0.80-1.15 (6H, m), 1.70-2.05 (2H, m), 2.65-2.80 (1H, m), 2.90 (3H, s), 2.90-4.80 (12H, m), 7.09 (1H, d, J=11.0 Hz), 7.17 (1H, dd, J=8.8, 2.0 Hz), 7.41 (1H, d, J=8.8 Hz), 7.71 (1H, s), 8.00-8.30 (1H, m), 8.30-8.50 (1H, m), 10.95-11.50 (1H, m), 11.86 (1H, s). MS (ESI) m/z: 543 (M+H$^+$).

Example 135

N-[(3R*,4S*)-4-{[(5-Chloroindol-2-yl)carbonyl]amino}-1-(2,2-dimethylpropanoyl)piperidin-3-yl]-5-methyl-4,5,6,7-tetrahydrothiazolo[5,4-c]pyridine-2-carboxamide hydrochloride

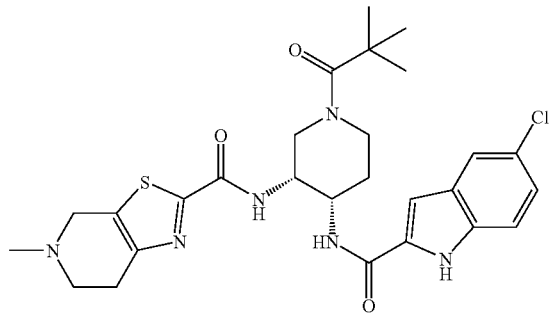

The title compound was obtained from the compound obtained in Example 118 and pivaloyl chloride in a similar manner to Example 100.

Melting point: 250-255° C. (decomposed). $^1$H-NMR (DMSO-d$_6$) δ: 1.20 (9H, s), 1.70-1.81 (1H, m), 1.90-2.00 (1H, m), 2.88 (3H, s), 3.10 (2H, br.s), 3.20-3.70 (4H, m), 3.95-4.08 (1H, m), 4.10-4.20 (1H, m), 4.25-4.35 (1H, m), 4.35-4.80 (3H, m), 7.10 (1H, s), 7.16 (1H, dd, J=8.8, 1.9 Hz), 7.41 (1H, d, J=8.8 Hz), 7.69 (1H, d, J=1.9 Hz), 8.06 (1H, br.s), 8.38 (1H, d, J=7.8 Hz), 11.31 (1H, br.s), 11.84 (1H, s). MS (ESI) m/z: 557 (M+H$^+$).

Example 136

N-[(3R*,4S*)-4-{[(5-Chloroindol-2-yl)carbonyl]amino}-1-(3,3-dimethylbutanoyl)piperidin-3-yl]-5-methyl-4,5,6,7-tetrahydrothiazolo[5,4-c]pyridine-2-carboxamide hydrochloride

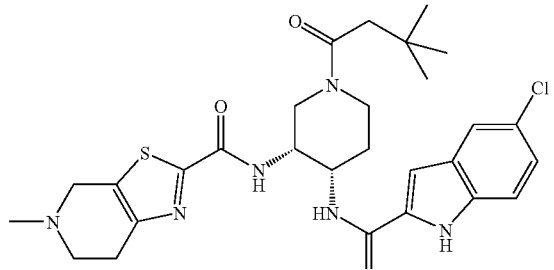

The title compound was obtained from the compound obtained in Example 118 and tert-butylacetyl chloride in a similar manner to Example 100.

Melting point: 260-265° C. (decomposed). $^1$H-NMR (DMSO-d$_6$) δ: 0.91, 1.04 (total 9H, each s), 1.68-1.82 (1H, m), 1.93-2.40 (3H, m), 2.91 (3H, s), 3.00-3.20 (2H, m), 3.20-4.80 (10H, m), 7.08 (1H, s), 7.17 (1H, dd, J=8.7, 1.2 Hz), 7.41 (1H, d, J=8.7 Hz), 7.69 (1H, d, J=7.6 Hz), 7.93-8.18 (1H, m), 8.38-8.45 (1H, m), 10.95-11.30 (1H, m), 11.80-11.90 (1H, m). MS (ESI) m/z: 571 (M+H$^+$).

Example 137

N-[(3R*,4S*)-4-{[(5-Chloroindol-2-yl)carbonyl]amino}-1-(2,2,2-trifluoroacetyl)piperidin-3-yl]-5-methyl-4,5,6,7-tetrahydrothiazolo[5,4-c]pyridine-2-carboxamide hydrochloride

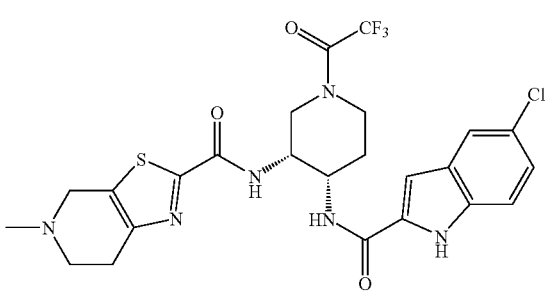

The title compound was obtained from the compound obtained in Example 118 and trifluoroacetic anhydride in a similar manner to Example 100.

Melting point: 262-267° C. (decomposed). $^1$H-NMR (DMSO-d$_6$) δ: 1.82-1.98 (1H, m), 2.05-2.21 (1H, m), 2.89 (3H, s), 3.05-3.20 (2H, m), 3.40-3.75 (4H, m), 3.85-3.95 (1H, m), 4.00-4.07 (1H, m), 4.20-4.70 (4H, m), 7.10 (1H, s), 7.18 (1H, dd, J=8.6, 1.9 Hz), 7.41 (1H, d, J=8.6 Hz), 7.72 (1H, s), 8.47 (1H, dd, J=22.4, 7.9 Hz), 8.60 (1H, br), 11.08 (1H, br.s), 11.87 (1H, s). MS (ESI) m/z: 569 (M+H$^+$).

Example 138

N-[(3R*,4S*)-4-{[(5-Chloroindol-2-yl)carbonyl]amino}-1-(cyclopropylcarbonyl)piperidin-3-yl]-5-methyl-4,5,6,7-tetrahydrothiazolo[5,4-c]pyridine-2-carboxamide hydrochloride

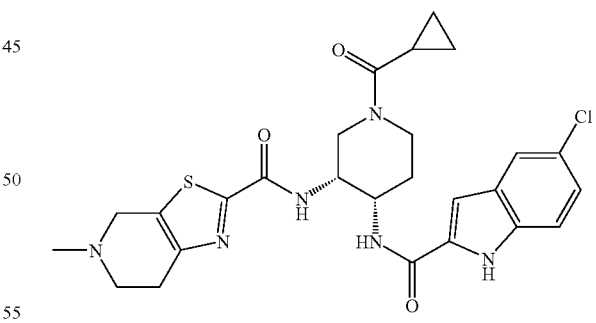

The title compound was obtained from the compound obtained in Example 118 and cyclopropanecarbonyl chloride in a similar manner to Example 100.

Melting point: 280-286° C. (decomposed). $^1$H-NMR (DMSO-d$_6$) δ: 0.25-0.80 (4H, m), 1.65-2.15 (4H, m), 2.91 (3H, s), 2.90-3.20 (3H, m), 3.35-3.70 (2H, m), 4.00-4.80 (6H, m), 7.06 (1H, s), 7.18 (1H, d, J=8.8 Hz), 7.42 (1H, d, J=8.7 Hz), 7.71 (1H, s), 8.18 (1H, br.s), 8.40, 8.48 (total 1H, each br.s), 11.11 (1H, br.s), 11.85 (1H, s). MS (ESI) m/z: 542 (M+H$^+$).

Example 139

N-[(3R*,4S*)-4-{[(5-Chloroindol-2-yl)carbonyl]amino}-1-(cyclobutylcarbonyl)piperidin-3-yl]-5-methyl-4,5,6,7-tetrahydrothiazolo[5,4-c]pyridine-2-carboxamide hydrochloride

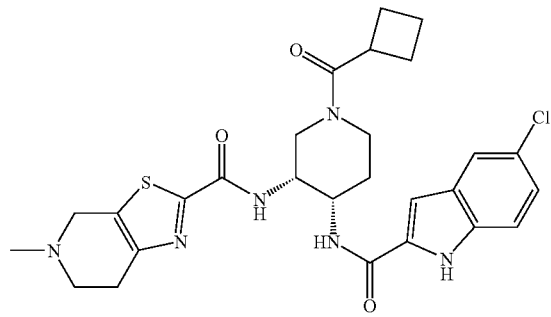

The title compound was obtained from the compound obtained in Example 118 and cyclobutanecarbonyl chloride in a similar manner to Example 100.

Melting point: 271-275° C. (decomposed). $^1$H-NMR (DMSO-$d_6$) δ: 1.60-2.30 (8H, m), 2.89 (3H, s), 3.12 (2H, br.s), 3.20-3.75 (6H, m), 3.75-3.90 (1H, m), 4.05-4.80 (4H, m), 7.08 (1H, s), 7.15 (1H, dd, J=9.0, 2.0 Hz), 7.39 (1H, d, J=9.0 Hz), 7.68 (1H, d, J=2.0 Hz), 8.15 (1H, br.s), 8.39 (1H, br), 11.19 (1H, br.s), 11.84 (1H, s). MS (ESI) m/z: 555 (M+H$^+$).

Example 140

N-[(3R*,4S*)-4-{[(5-Chloroindol-2-yl)carbonyl]amino}-1-(cyclopentylcarbonyl)piperidin-3-yl]-5-methyl-4,5,6,7-tetrahydrothiazolo[5,4-c]pyridine-2-carboxamide hydrochloride

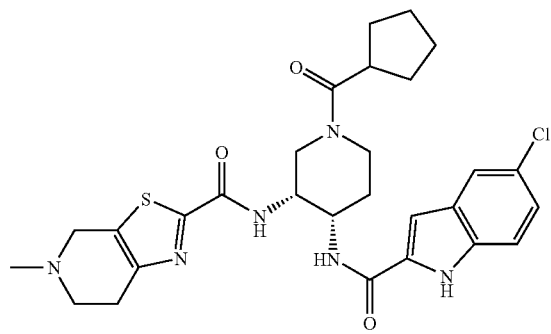

The title compound was obtained from the compound obtained in Example 118 and cyclopentanecarbonyl chloride in a similar manner to Example 100.

Melting point: 254-260° C. (decomposed). $^1$H-NMR (DMSO-$d_6$) δ: 1.30-2.10 (10H, m), 2.90 (3H, s), 3.00-3.20 (2H, m), 3.20-3.75 (5H, m), 3.80-4.80 (6H, m), 7.09 (1H, s), 7.17 (1H, dd, J=8.7, 2.0 Hz), 7.42 (1H, d, J=8.7 Hz), 7.71 (1H, s), 7.95-8.30 (1H, m), 8.35-8.50 (1H, m), 11.23 (1H, br.s), 11.85 (1H, s). MS (ESI) m/z: 569 (M+H$^+$).

Example 141

2-((3R*,4S*)-4-{[(5-Chloroindol-2-yl)carbonyl]amino}-3-{[(5-methyl-4,5,6,7-tetrahydrothiazolo[5,4-c]pyridin-2-yl)carbonyl]amino}piperidin-1-yl)-2-oxoethyl acetate

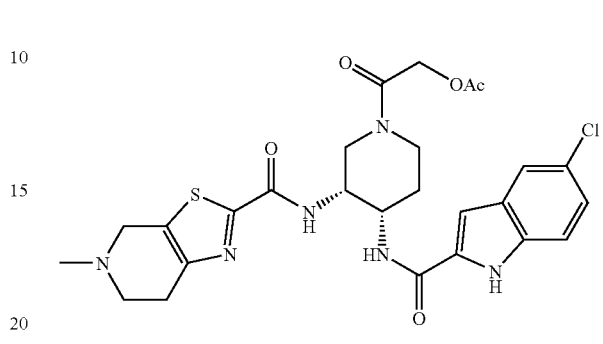

The title compound was obtained from the compound obtained in Example 118 and acetoxyacetyl chloride in a similar manner to Example 100.

$^1$H-NMR (CDCl$_3$) δ: 1.70-2.00 (1H, m), 2.05-2.48 (3H, m), 2.51 (3H, s), 2.70-3.05 (4H, m), 3.05-4.10 (5H, m), 4.20-4.48 (1H, m), 4.50-5.10 (4H, m), 6.87 (1H, br.s), 7.10-7.82 (4H, m), 7.32 (1H, d, J=8.8 Hz), 8.35 (1H, br.s), 9.34, 9.45 (total 1H, each br.s). MS (ESI) m/z: 573 (M+H$^+$).

Example 142

N-((3R*,4S*)-4-{[(5-Chloroindol-2-yl)carbonyl]amino}-1-glycoloylpiperidin-3-yl)-5-methyl-4,5,6,7-tetrahydrothiazolo[5,4-c]pyridine-2-carboxamide hydrochloride

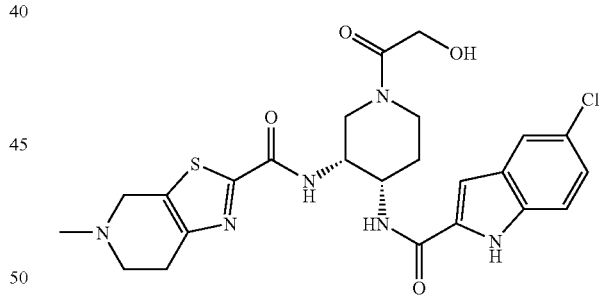

The compound (301.8 mg) obtained in Example 141 was dissolved in tetrahydrofuran (10 ml), and a 1N aqueous solution (0.53 ml) of sodium hydroxide was added to stir the mixture at room temperature for 18 hours. Water was added to the reaction mixture to conduct extraction with methylene chloride. The resultant organic layer was successively washed with water and saturated aqueous solution of sodium chloride and dried over anhydrous sodium sulfate. The solvent was distilled off under reduced pressure, the residue was purified by column chromatography on silica gel (methylene chloride:methanol=20:1-10:1), and the solvent was distilled off under reduced pressure. The thus-obtained purified product was dissolved in ethanol (3 ml) and methylene chloride (2 ml), and a 1N ethanol solution of hydrochloric acid to stir the mixture for 30 minutes. The solvent was distilled off under reduced pressure, and the residue was solidified with diethyl ether to obtain the title compound (195 mg).

Melting point: 216-230° C. (decomposed). $^1$H-NMR (DMSO-$d_6$) δ: 1.70-1.80 (1H, m), 1.88-2.10 (2H, m), 2.68 (3H, s), 3.18 (2H, s), 3.08-3.70 (5H, m), 3.80-3.95 (1H, m), 4.00-4.25 (3H, m), 4.25-4.50 (2H, m), 4.50-4.65 (1H, m), 7.09 (1H, d, J=11.0 Hz), 7.17 (1H, dd, J=8.8, 2.0 Hz), 7.42 (1H, d, J=8.8 Hz), 7.71 (1H, s), 8.33 (1H, br.s), 8.35-8.50 (1H, m), 10.80-11.30 (1H, br.s), 11.84 (1H, br.s).

Example 143

N-[(3R*,4S*)-4-{[(5-Chloroindol-2-yl)carbonyl]amino}-1-(2-methoxyacetyl)piperidin-3-yl]-5-methyl-4,5,6,7-tetrahydrothiazolo[5,4-c]pyridine-2-carboxamide hydrochloride

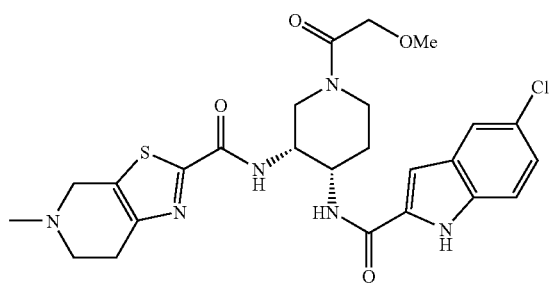

The title compound was obtained from the compound obtained in Example 118 in a similar manner to Example 100.

Melting point: 214-228° C. (decomposed). $^1$H-NMR (DMSO-$d_6$) δ: 1.70-1.80 (1H, m), 1.85-2.05 (1H, m), 2.90 (3H, s), 3.00-3.20 (2H, m), 3.16 (3H, s), 3.22-3.82 (7H, m), 3.88-4.80 (5H, m), 7.09 (1H, d, J=9.0 Hz), 7.17 (1H, dd, J=8.8, 1.9 Hz), 7.42 (1H, d, J=8.8 Hz), 7.70 (1H, d, J=1.9 Hz), 8.29 (1H, br.s), 8.40-8.50 (1H, m), 11.34 (1H, br.s), 11.86 (1H, s). MS (ESI) m/z: 545 (M+H)$^+$.

Example 144

N-[(3R*,4S*)-4-{[(5-Fluoroindol-2-yl)carbonyl]amino}-1-(2-methoxyacetyl)piperidin-3-yl]-5-methyl-4,5,6,7-tetrahydrothiazolo[5,4-c]pyridine-2-carboxamide hydrochloride

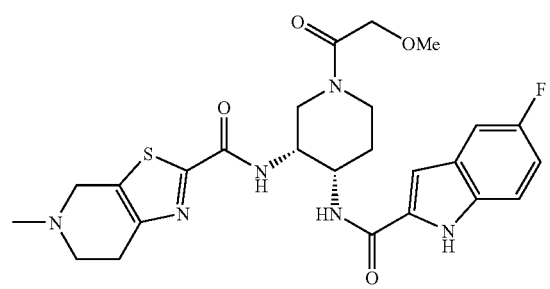

The title compound was obtained from the compound obtained in Example 122 and methoxyacetyl chloride in a similar manner to Example 100.

Melting point: 190-208° C. (decomposed). $^1$H-NMR (DMSO-$d_6$) δ: 1.70-1.83 (1H, br), 1.85-2.10 (1H, m), 2.91 (3H, s), 3.00-3.55 (10H, m), 3.62-3.85 (1H, m), 3.90-4.50 (6H, m), 4.63-4.78 (1H, br), 7.04 (1H, td, J=9.4, 2.4 Hz), 7.07-7.13 (1H, br), 7.37-7.44 (1H, m), 8.16-8.49 (2H, m), 11.30-11.70 (1H, br), 11.72-11.80 (1H, br). MS (FAB) m/z: 529 (M+H$^+$).

Example 145

N-((3R*,4S*)-1-(3-[(tert-butyl(diphenyl)silyl]oxy)-2,2-dimethylpropanoyl)-4-{[(5-chloroindol-2-yl)carbonyl]-amino}piperidin-3-yl)-5-methyl-4,5,6,7-tetrahydrothiazolo[5,4-c]pyridine-2-carboxamide

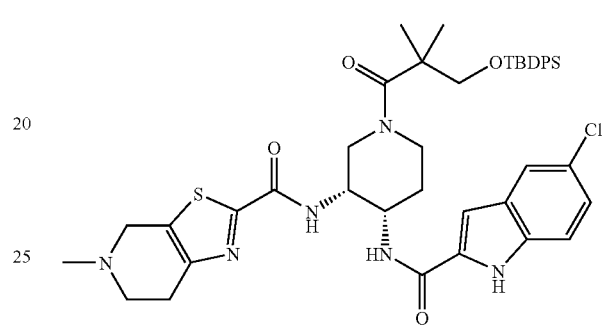

Thionyl chloride (3.0 ml) and a catalytic amount of dimethylformamide were added to a solution of the compound (261 mg) obtained in Referential Example 158 in chloroform (10 ml), and the mixture was stirred overnight at 60° C. The reaction mixture was concentrated under reduced pressure, giving a pale yellow oil. The title compound was obtained from this product and the compound (200 mg) obtained in Example 118 in a similar manner to Example 100.

Melting point: 153° C. $^1$H-NMR (CDCl$_3$) δ: 1.07 (9H, s), 1.39 (6H, d, J=3.9 Hz), 1.57 (1H, br.s), 2.26 (1H, d, J=10.7 Hz), 2.57 (3H, s), 2.86 (4H, s), 2.97-3.01 (2H, m), 3.78 (4H, s), 4.20 (1H, br.s), 4.33 (1H, d, J=13 Hz), 4.42 (1H, br.s), 4.67 (1H, d, J=13 Hz), 6.88 (1H, s), 7.20-7.23 (1H, m), 7.32-7.46 (7H, m), 7.64-7.65 (6H, m), 7.86 (1H, d, J=6.8 Hz), 8.23 (1H, s), 9.10 (1H, s).

Example 146

N-[(3R*,4S*)-4-{[(5-chloroindol-2-yl)carbonyl]amino}-1-(3-hydroxy-2,2-dimethylpropanoyl)piperidin-3-yl)-5-methyl-4,5,6,7-tetrahydrothiazolo[5,4-c]pyridine-2-carboxamide

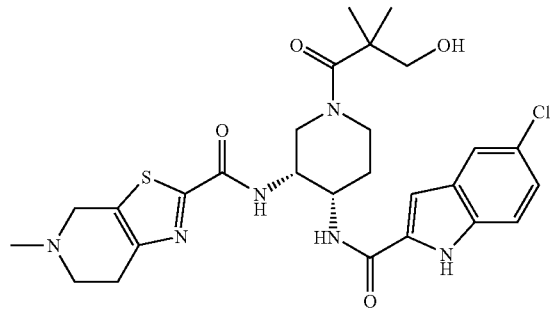

Tetrabutylammonium fluoride (1 M tetrahydrofuran solution, 0.594 ml) was added to a solution of the compound (241 mg) obtained in Example 145 in tetrahydrofuran (30 ml) under ice cooling, and the mixture was stirred overnight at room temperature. The reaction mixture was concentrated under reduced pressure, and the resultant residue was dissolved in methylene chloride. The solution was washed with water and saturated aqueous solution of sodium chloride and then dried over anhydrous sodium sulfate, and the solvent was distilled off under reduced pressure. The resultant residue was purified by preparative thin-layer chromatography on silica gel (methylene chloride:methanol=9:1) to obtain the title compound (116 mg).

Melting point: 220° C. (decomposed). $^1$H-NMR (DMSO-$d_6$) δ: 1.17 (6H, d, J=8.3 Hz), 1.79 (1H, br.s), 1.91-1.97 (1H, m), 2.49 (3H, s), 2.87 (4H, s), 3.35-3.50 (4H, m), 3.81 (1H, br.s), 3.97 (1H, m), 4.10-4.15 (1H, m), 4.32 (1H, br.s), 4.42 (1H, br.s), 4.52 (1H, t, J=5.7 Hz), 7.10 (1H, s), 7.16-7.19 (1H, m), 7.42 (1H, d, J=8.8 Hz), 7.69 (1H, s), 8.11 (1H, d, J=8.8 Hz), 8.37 (1H, d, J=7.3 Hz), 11.8 (1H, s). MS (FAB) m/z: 573 (M+H$^+$).

Example 147

N-[(3R*,4S*)-4-{[(5-chloroindol-2-yl)carbonyl]amino}-1-(3-methoxy-2,2-dimethylpropanoyl)piperidin-3-yl]-5-methyl-4,5,6,7-tetrahydrothiazolo[5,4-c]pyridine-2-carboxamide

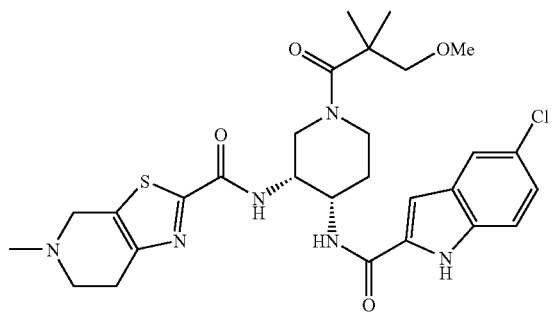

The title compound was obtained from the compound obtained in Example 118 and the compound obtained in Referential Example 160 in a similar manner to Example 145.

Melting point: 240° C. (decomposed). $^1$H-NMR (CDCl$_3$) δ: 1.34 (3H, s), 1.37 (3H, s), 1.65-1.77 (1H, m), 2.33-2.37 (1H, m), 2.53 (3H, s), 2.82-3.29 (6H, m), 3.34 (3H, s), 3.41 (1H, d, J=9.3 Hz), 3.56 (1H, d, J=9.3 Hz), 3.76 (2H, d, J=5.9 Hz), 4.26 (1H, m), 4.44-4.53 (2H, m), 4.82 (1H, d, J=13.7 Hz), 6.88 (1H, d, J=1.5 Hz), 7.20-7.23 (1H, m), 7.33 (1H, d, J=8.8 Hz), 7.64 (1H, d, J=1.5 Hz), 7.90 (1H, d, J=7.1 Hz), 8.22 (1H, d, J=5.1 Hz), 9.18 (1H, s). MS (FAB) m/z: 587 (M+H$^+$).

Example 148

2-((3R*,4S*)-4-{[(5-Chloroindol-2-yl)carbonyl]amino}-3-{[(5-methyl-4,5,6,7-tetrahydrothiazolo[5,4-c]pyridin-2-yl)carbonyl]amino}piperidin-1-yl)-1,1-dimethyl-2-oxoethyl acetate

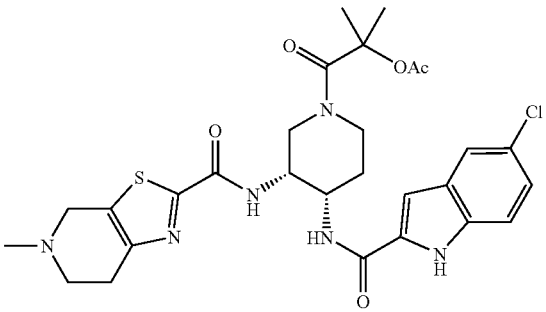

The title compound was obtained from the compound obtained in Example 118 and 2-acetoxyisobutyryl chloride in a similar manner to Example 100.

Melting point: 190° C. (decomposed). $^1$H-NMR (CDCl$_3$) δ: 1.56-1.67 (8H, m), 2.08 (3H, s), 2.35 (1H, d, J=10.5 Hz), 2.52 (3H, s), 2.82-2.84 (2H, m), 2.90-2.96 (2H, m), 3.14 (1H, br.s), 3.75 (2H, s), 4.25 (1H, br.s), 4.40-4.47 (1H, m), 4.54 (1H, br.s), 4.80 (1H, br.s), 6.86 (1H, s), 7.20-7.33 (3H, m), 7.64 (1H, d, J=1.7 Hz), 7.76 (1H, d, J=7.3 Hz), 9.11 (1H, s). MS (FAB) m/z: 601 (M+H$^+$).

Example 149

N-[(3R*,4S*)-4-{[(5-Chloroindol-2-yl)carbonyl]amino}-1-(2-hydroxy-2-methylpropanoyl)piperidin-3-yl]-5-methyl-4,5,6,7-tetrahydrothiazolo[5,4-c]pyridine-2-carboxamide

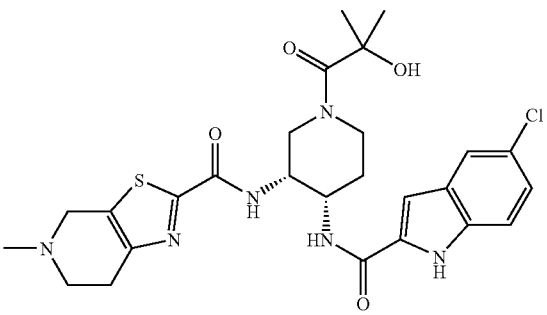

Sodium methoxide (76.8 mg) was added to a solution of the compound (190 mg) obtained in Example 148 in methanol (50 ml), and the mixture was stirred overnight at room temperature. After the reaction mixture was concentrated under reduced pressure, the resultant residue was purified by preparative thin-layer chromatography on silica gel (methylene chloride:methanol=9:1) to obtain the title compound (130 mg).

Melting point: 190° C. (decomposed). $^1$H-NMR (CDCl$_3$) δ: 1.53 (3H, s), 1.56-1.78 (5H, m), 2.34 (1H, d, J=10.5 Hz), 2.53 (3H, s), 2.83-2.86 (2H, m), 2.91-2.93 (2H, m), 3.30 (1H, d, J=12.5 Hz), 3.75 (2H, s), 4.28 (1H, d, J=5.6 Hz), 4.43

(1H, s), 4.65 (1H, d, J=13.5 Hz), 4.95 (1H, d, J=13.5 Hz), 6.92 (1H, d, J=1.5 Hz), 7.20-7.23 (1H, m), 7.33 (1H, d, J=8.6 Hz), 7.65 (1H, d, J=2.0 Hz), 8.43 (1H, d, J=5.6 Hz), 9.14 (1H, s). MS (FAB) m/z: 559 (M+H$^+$).

Example 150

N-{(3R*,4S*)-4-{[(5-Chloroindol-2-yl)carbonyl]amino}-1-[(3-hydroxycyclobutyl)carbonyl]piperidin-3-yl}-5-methyl-4,5,6,7-tetrahydrothiazolo[5,4-c]pyridine-2-carboxamide hydrochloride

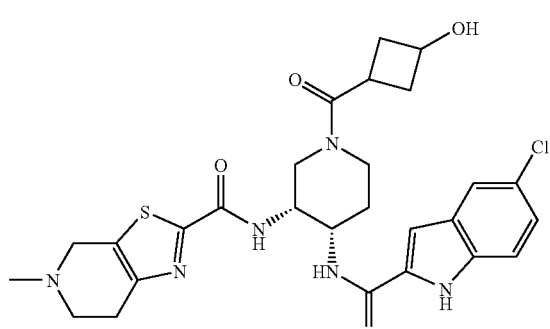

The compound (306 mg) obtained in Example 118, n-methylmorpholine (200 µl), 1-hydroxybenzotriazole monohydrate (87 mg) and 1-(3-dimethylaminopropyl)-3-ethylcarbodiimide hydrochloride (197 mg) were added to a solution of the compound (117 mg) obtained Referential Example 152 in a mixed solvent of tetrahydrofuran (20 ml), methylene chloride (3.0 ml) and N,N-dimethylformamide (2.0 ml), and the mixture was stirred at room temperature for 3 days. The reaction mixture was diluted with methylene chloride, and a saturated aqueous solution of sodium hydrogencarbonate was added to separate the mixture into two layers. The resultant organic layer was washed with saturated aqueous solution of sodium chloride, dried over anhydrous sodium sulfate and then concentrated under reduced pressure. The resultant residue was purified by column chromatography on silica gel (methylene chloride:methanol=10:1) to obtain a free base (207 mg) of the title compound. The free base was treated with a 1N ethanol solution of hydrochloric acid to obtain the title compound.

Melting point: 200° C. (decomposed). $^1$H-NMR (DMSO-d$_6$) δ: 1.78-2.10 (4H, m), 2.24-2.68 (3H, m), 2.75-5.20 (14H, m), 2.91 (3H, s), 7.08 (0.5H, s), 7.09 (0.5H, s), 7.18 (1H, dd, J=8.8, 2.0 Hz), 7.42 (1H, d, J=8.8 Hz), 7.70 (1H, d, J=2.0 Hz), 8.05-8.28 (1H, br), 8.38 (0.5H, br.d, J=7.3 Hz), 8.43 (0.5H, br.d, J=8.3 Hz), 10.80-11.25 (1H, br), 11.84 (1H, br.s). MS (ESI) m/z: 571 (M+H$^+$).

Example 151

N-{(3R*,4S*)-4-{[(5-Chloroindol-2-yl)carbonyl]amino}-1-[(methoxycyclobutyl)carbonyl]piperidin-3-yl]-5-methyl-4,5,6,7-tetrahydrothiazolo[5,4-c]pyridine-2-carboxamide hydrochloride

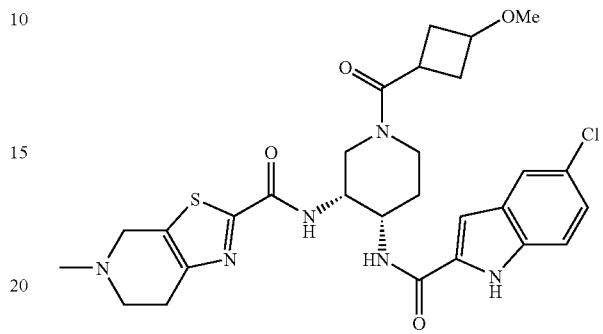

The title compound was obtained from the compound obtained in Example 118 and the compound obtained in Referential Example 154 in a similar manner to Example 150.

Melting point: 191° C. (decomposed). $^1$H-NMR (DMSO-d$_6$) δ: 1.69-2.23 (4H, m), 2.25-2.40 (1H, m), 2.71-2.84 (0.5H, m), 2.89-3.93 (9.5H, m), 2.91 (3H, s), 3.01 (1H, s), 3.14 (2H, s), 4.05-4.80 (5H, m), 7.09 (1H, s), 7.18 (1H, d, J=8.4 Hz), 7.42 (1H, d, J=8.4 Hz), 7.70 (1H, s), 8.00-8.30 (1H, br), 8.36-8.53 (1H, m), 11.25-11.75 (1H, br), 11.85 (1H, br.s). MS (ESI) m/z: 585 (M+H$^+$).

Example 152

N-{(3R*,4S*)-4-{[(5-Chloroindol-2-yl)carbonyl]amino}-1-[3-methoxy-2-(methoxymethyl)propanoyl]piperidin-3-yl}-5-methyl-4,5,6,7-tetrahydrothiazolo[5,4-c]pyridine-2-carboxamide hydrochloride

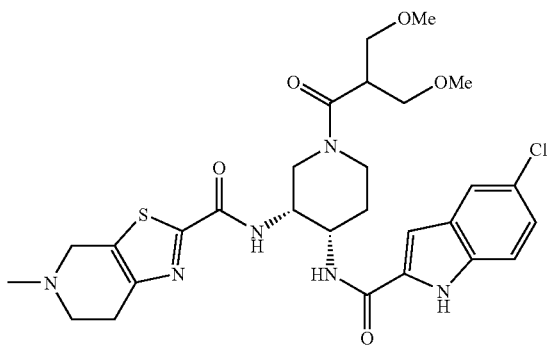

The title compound was obtained by condensing a carboxylic acid obtained by hydrolysis of the compound obtained in Referential Example 155 with the compound obtained in Example 118 in a similar manner to Example 150.

Melting point: 178-184° C. (decomposed). $^1$H-NMR (DMSO-d$_6$) δ: 1.69-1.82 (1H, m), 1.84-2.04 (1H, m), 2.91 (3H, s), 3.00-3.75 (17H, m), 3.95-4.55 (5H, m), 4.60-4.80

(1H, m), 7.10 (1H, br.s), 7.18 (1H, dd, J=8.8, 2.0 Hz), 7.42 (1H, d, J=8.8 Hz), 7.69 (0.5H, br.s), 7.71 (1H, br.s), 8.18-8.28 (1H, br), 8.35-8.50 (1H, br), 11.83 (1H, br.s). MS (ESI) m/z: 603 (M+H⁺).

Example 153

N-[(3R*,4S*)-4-{[(5-Chloroindol-2-yl)carbonyl]amino}-(tetrahydro-2H-pyran-4-ylcarbonyl)piperidin-3-yl]-5-methyl-4,5,6,7-tetrahydrothiazolo[5,4-c]pyridine-2-carboxamide hydrochloride

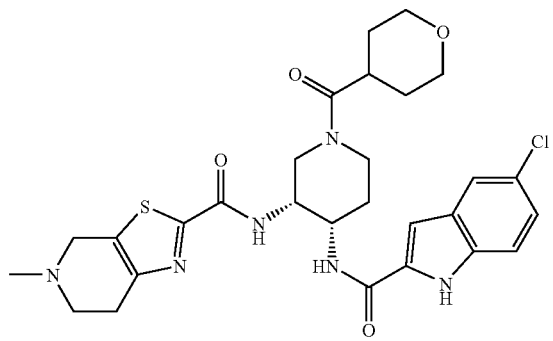

The title compound was obtained from the compound obtained in Example 118 and the compound obtained in Referential Example 156 in a similar manner to Example 150.

Melting point: 225-248° C. (decomposed). ¹H-NMR (DMSO-d₆) δ: 1.55-1.68 (4H, m), 1.70-1.85 (1H, m), 1.85-2.05 (1H, m), 2.60-2.95 (1H, m), 2.89 (3H, s), 2.95-3.20 (3H, m), 3.20-4.00 (9H, m), 4.00-4.80 (4H, m), 7.08 (1H, s), 7.17 (1H, dd, J=8.8, 2.0 Hz), 7.42 (1H, d, J=8.8 Hz), 7.71 (1H, s), 8.00-8.30 (1H, m), 8.35-8.50 (1H, m), 11.16 (1H, br.s), 11.85 (1H, s). MS (ESI) m/z: 585 (M+H⁺).

Example 154

N-((3R*,4S*)-1-benzoyl-4-{[(5-Chloroindol-2-yl)carbonyl]amino}piperidin-3-yl)-5-methyl-4,5,6,7-tetrahydrothiazolo[5,4-c]pyridine-2-carboxamide hydrochloride

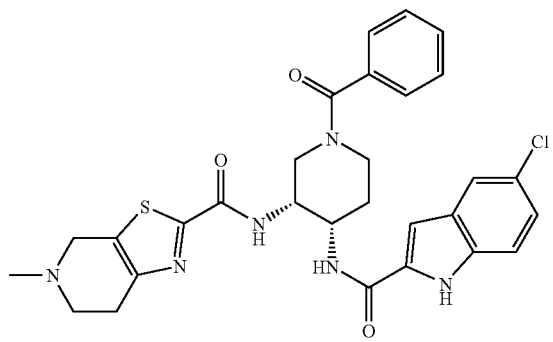

The title compound was obtained from the compound obtained in Example 118 and benzoyl chloride in a similar manner to Example 100.

Melting point: 215-225° C. (decomposed). ¹H-NMR (DMSO-d₆) δ: 1.75-1.90 (1H, m), 1.90-2.20 (1H, m), 2.93 (3H, s), 3.10-4.00 (8H, m), 4.05-4.80 (4H, m), 7.00-7.60 (5H, m), 7.08 (1H, s), 7.16 (1H, dd, J=8.8, 1.6 Hz), 7.40 (1H, d, J=8.8 Hz), 7.71 (1H, d, J=1.6 Hz), 8.31 (1H, br.s), 8.46 (1H, br.s), 11.39 (1H, br.s), 11.86 (1H, s). MS (FAB) m/z: 577 (M+H⁺).

Example 155 tert-Butyl (3R*,4S*)-3-({[5-(2-{[tert-butyl(diphenyl)silyl]oxy}-1,1-dimethylethyl)-4,5,6,7-tetrahydrothiazolo-[5,4-c]pyridin-2-yl]carbonyl}amino)-4-{[(5-chloroindol-2-yl)carbonyl]amino}piperidine-1-carboxylate

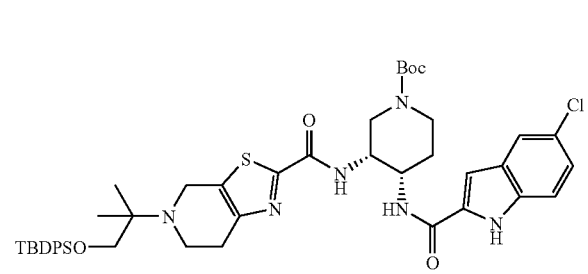

The title compound was obtained from the compound obtained in Referential Example 207 and the compound obtained in Referential Example 42 in a similar manner to Example 91.

¹H-NMR (DMSO-d₆) δ: 1.00 (9H, s), 1.12 (6H, s), 1.15-1.50 (9H, m), 1.63-1.75 (1H, m), 1.82-2.00 (1H, m), 2.60-2.80 (3H, m), 2.83-2.95 (2H, m), 3.12-3.30 (1H, m), 3.30 (2H, s), 3.58 (2H, s), 3.85-4.10 (2H, m), 4.19 (1H, br.s), 4.37 (1H, br.s), 7.04 (1H, s), 7.16 (1H, d, J=9.0 Hz), 7.30-7.50 (7H, m), 7.50-7.65 (4H, m), 7.70 (1H, s), 7.99 (1H, d, J=6.8 Hz), 8.45 (1H, br.s), 11.82 (1H, s). MS (ESI) m/z: 869 (M+H⁺).

Example 156

5-(2-{[tert-Butyl(diphenyl)silyl]oxy}-1,1-dimethylethyl)-N-((3R*,4S*)-4-{[(5-chloroindol-2-yl)carbonyl]amino}-piperidin-3-yl)-4,5,6,7-tetrahydrothiazolo[5,4-c]pyridine-2-carboxamide dihydrochloride

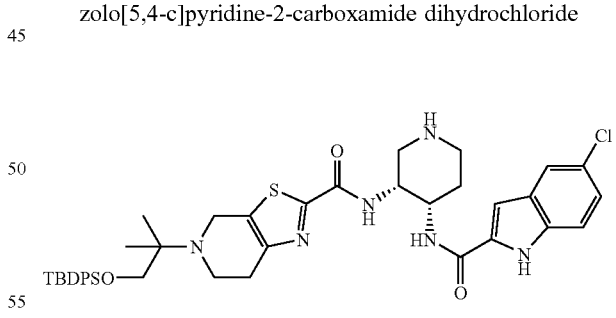

The title compound was obtained by treating the compound obtained in Example 155 in a similar manner to Example 95.

¹H-NMR (DMSO-d₆) δ: 1.04 (9H, s), 1.43, 1.48 (total 6H, each s), 1.85-2.00 (1H, m), 2.05-2.20 (1H, m), 2.95-3.20 (2H, m), 3.25-3.60 (6H, m), 3.80-3.90 (1H, m), 3.95-4.05 (1H, m), 4.45-4.55 (1H, m), 4.60-4.85 (3H, m), 7.10-7.20 (2H, m), 7.35-7.55 (7H, m), 7.55-7.75 (5H, m), 8.52 (1H, dd, J=14.4, 7.8 Hz), 8.93 (1H, br), 9.20-9.40 (2H, m), 11.30-11.50 (1H, m), 11.87, 11.92 (total 1H, each s). MS (ESI) m/z: 769 (M+H⁺).

Example 157

5-(2-([tert-Butyl(diphenyl)silyl]oxy}-1,1-dimethyl-ethyl)-N-[(3R*,4S*)-4-{[(5-chloroindol-2-yl)carbonyl]amino}-1-(2-methoxyacetyl)piperidin-3-yl]-4,5,6,7-tetrahydrothiazolo-[5,4-c]pyridine-2-carboxamide

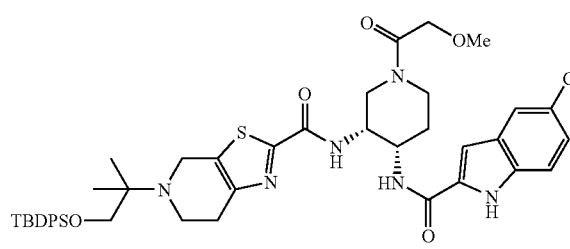

The title compound was obtained from the compound obtained in Example 156 and methoxyacetyl chloride in a similar manner to Example 100.

$^1$H-NMR (CDCl$_3$) δ: 1.07 (9H, s), 1.20 (6H, s), 1.60-1.85 (1H, m), 2.25-2.40 (1H, m), 2.36 (2H, s), 2.70-3.20 (4H, m), 3.20-3.55 (4H, m), 3.55-3.70 (2H, m), 3.95-4.10 (3H, m), 4.10-4.90 (4H, m), 6.90 (1H, d, J=1.5 Hz), 7.15-7.30 (2H, m), 7.30-7.50 (6H, m), 7.60-7.70 (5H, m), 8.15-8.22 (1H, m), 8.46 (1H, d, J=5.1 Hz), 9.28 (1H, s). MS (ESI) m/z: 842 (M+H$^+$).

Example 158

N-[(3R*,4S*)-4-{[(5-Chloroindol-2-yl)carbonyl]amino}-1-(2-methoxyacetyl)piperidin-3-yl]-5-(2-hydroxy-1,1-dimethylethyl)-4,5,6,7-tetrahydrothiazolo[5,4-c]pyridine-2-carboxamide hydrochloride

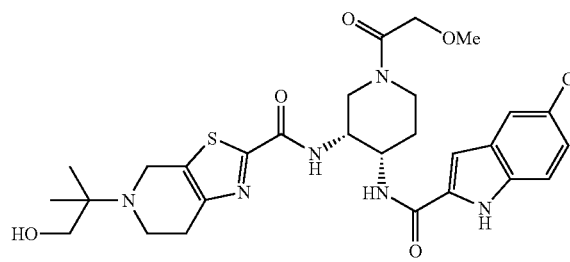

The title compound was obtained from the compound obtained in Example 157 in a similar manner to Example 146.

Melting point: 221-232° C. (decomposed). $^1$H-NMR (DMSO-d$_6$) δ: 1.32 (3H, s), 1.40 (3H, s), 1.70-1.85 (1H, m), 1.85-2.10 (1H, m), 2.60-3.35 (8H, m), 3.40-3.82 (3H, m), 3.85-4.05 (3H, m), 4.05-4.35 (2H, m), 4.50-4.60 (1H, m), 4.55-4.80 (2H, m), 5.75-5.85 (1H, m), 7.08 (1H, br.s), 7.17 (1H, d, J=8.8 Hz), 7.41 (1H, d, J=8.8 Hz), 7.71 (1H, s), 8.20-8.35 (1H, m), 8.40-8.55 (1H, m), 10.00-10.35 (1H, m), 11.87 (1H, s). MS (ESI) m/z: 603 (M+H$^+$).

Example 159 tert-Butyl (3R*,4S*)-4-{[(5-fluoroindol-2-yl)carbonyl]-amino}-3-{[(5-isopropyl-4,5,6,7-tetrahydrothiazolo[5,4-c]-pyridin-2-yl)carbonyl]amino}piperidine-1-carboxylate

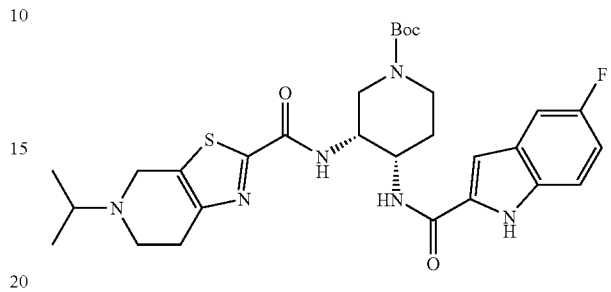

The title compound was obtained from the compound obtained in Referential Example 209 and the compound obtained in Referential Example 148 in a similar manner to Example 91.

$^1$H-NMR (CDCl$_3$) δ: 1.16 (6H, d, J=6.6 Hz), 1.53 (9H, s), 1.65-1.80 (1H, m), 2.23-2.32 (1H, m), 2.80-3.10 (6H, m), 3.10-3.25 (1H, m), 3.80-3.90 (2H, m), 4.00-4.50 (4H, m), 6.91 (1H, s), 6.95-7.05 (1H, m), 7.25-7.40 (2H, m), 7.74 (1H, br.s), 8.21 (1H, br.s), 9.30 (1H, s). MS (ESI) m/z: 585 (M+H$^+$).

Example 160

N-((3R*,4S*)-4-{[(5-Fluoroindol-2-yl)carbonyl]amino}-piperidin-3-yl)-5-isopropyl-4,5,6,7-tetrahydrothiazolo-[5,4-c]pyridine-2-carboxamide dihydrochloride

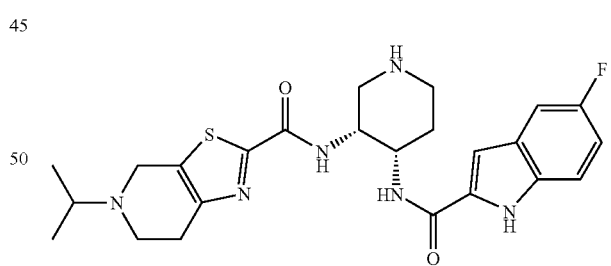

The title compound was obtained by treating the compound obtained in Example 159 in a similar manner to Example 95.

$^1$H-NMR (DMSO-d$_6$) δ: 1.28-1.40 (6H, m), 1.85-2.00 (1H, m), 2.05-2.20 (1H, m), 2.40-2.60 (1H, m), 2.95-3.90 (8H, m), 4.40-4.55 (2H, m), 4.60-4.75 (2H, m), 7.00-7.20 (2H, m), 7.30-7.50 (2H, m), 8.45-8.60 (1H, m), 8.85-9.05 (1H, m), 9.05-9.50 (2H, m), 11.60-11.90 (2H, m). MS (ESI) m/z: 485 (M+H$^+$).

Example 161

N-[(3R*,4S*)-4-{[(5-Fluoroindol-2-yl)carbonyl]amino}-1-(2-methoxyacetyl)piperidin-3-yl]-5-isopropyl-4,5,6,7-tetrahydrothiazolo[5,4-c]pyridine-2-carboxamide hydrochloride

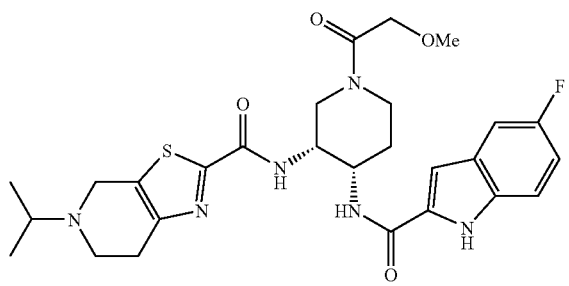

The title compound was obtained from the compound obtained in Example 160 and methoxyacetyl chloride in a similar manner to Example 100.

Melting point: 214-228° C. (decomposed). $^1$H-NMR (DMSO-$d_6$) δ: 1.25-1.40 (6H, m), 1.68-1.82 (1H, m), 1.85-2.10 (1H, m), 2.90-3.60 (8H, m), 3.60-3.85 (2H, m), 3.85-4.40 (5H, m), 4.40-4.55 (2H, m), 4.60-4.75 (1H, m), 7.00-7.15 (2H, m), 7.35-7.50 (2H, m), 8.15-8.50 (2H, m), 10.80-11.30 (1H, m), 11.73 (1H, d, J=6.6 Hz). MS (ESI) m/z: 557 (M+H$^+$).

Example 162

N-{(3R*,4S*)-4-{[(5-Chloroindol-2-yl)carbonyl]amino}-1-[(dimethylamino)carbonyl]piperidin-3-yl}-5-methyl-4,5,6,7-tetrahydrothiazolo[5,4-c]pyridine-2-carboxamide hydrochloride

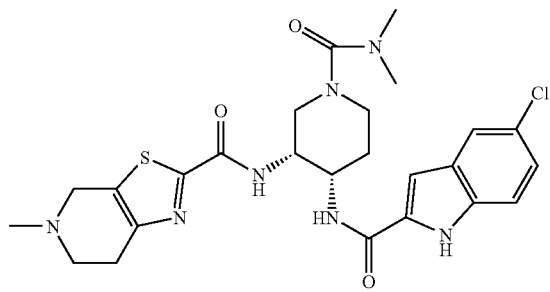

The title compound was obtained from the compound obtained in Example 118 and N,N-dimethylcarbamoyl chloride in a similar manner to Example 100.

Melting point: 267-270° C. (decomposed). $^1$H-NMR (DMSO-$d_6$) δ: 1.65-1.78 (1H, m), 1.97-2.10 (1H, m), 2.70 (6H, s), 2.90 (3H, s), 2.95-3.80 (8H, m), 4.25-4.80 (4H, m), 7.08 (1H, s), 7.16 (1H, dd, J=8.8, 1.8 Hz), 7.41 (1H, d, J=8.8 Hz), 7.70 (1H, s), 8.31 (1H, br.s), 8.40 (1H, d, J=7.3 Hz), 11.15-11.60 (1H, m), 11.82 (1H, s). MS (ESI) m/z: 544 (M+H$^+$).

Example 163

N-{(3R*,4S*)-4-{[(5-Chloroindol-2-yl)carbonyl]amino}-1-[(ethylamino)carbonyl]piperidin-3-yl}-5-methyl-4,5,6,7-tetrahydrothiazolo[5,4-c]pyridine-2-carboxamide hydrochloride

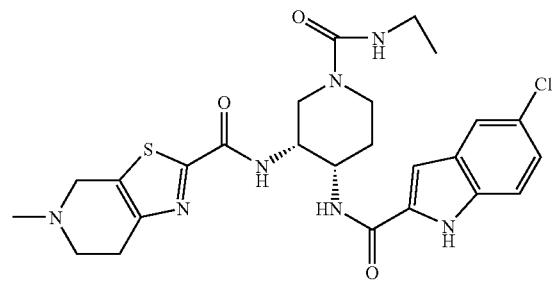

The title compound was obtained from the compound obtained in Example 118 and ethyl isocyanate in a similar manner to Example 100.

Melting point: 221-235° C. (decomposed). $^1$H-NMR (DMSO-$d_6$) δ: 0.98 (3H, t, J=7.1 Hz), 1.60-1.70 (1H, m), 1.80-1.95 (1H, m), 2.90 (3H, s), 2.95-3.40 (6H, m), 3.40-4.00 (4H, m), 4.25-4.80 (4H, m), 6.60-6.80 (1H, m), 7.09 (1H, s), 7.16 (1H, dd, J=8.8, 1.9 Hz), 7.41 (1H, d, J=8.8 Hz), 7.68 (1H, d, J=1.9 Hz), 8.02 (1H, br.s), 8.35 (1H, d, J=7.1 Hz), 11.20-11.70 (1H, m), 11.82 (1H, s). MS (FAB) m/z: 544 (M+H$^+$).

Example 164

N-((3R*,4S*)-1-[(tert-Butylamino)carbonyl]-4-{[(5-chloroindol-2-yl)carbonyl]amino}piperidin-3-yl)-5-methyl-4,5,6,7-tetrahydrothiazolo[5,4-c]pyridine-2-carboxamide hydrochloride

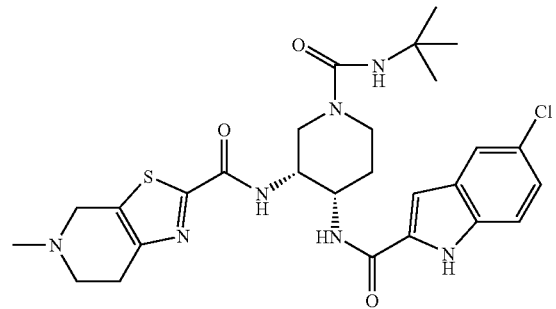

The title compound was obtained from the compound obtained in Example 118 and tert-butyl isocyanate in a similar manner to Example 100.

Melting point: 236-238° C. (decomposed). $^1$H-NMR (DMSO-$d_6$) δ: 1.21 (9H, s), 1.60-1.70 (1H, m), 1.80-1.90 (1H, m), 2.87 (3H, s), 3.00-3.40 (6H, m), 3.49 (1H, br.s), 3.80-3.90 (1H, m), 3.90-4.00 (1H, m), 4.20-4.35 (2H, m), 4.47 (1H, br.s), 5.90 (1H, s), 7.06 (1H, s), 7.16 (1H, dd, J=8.8, 1.9 Hz), 7.41 (1H, d, J=8.8 Hz), 7.67 (1H, d, J=1.9 Hz), 8.04 (1H, d, J=6.8 Hz), 8.34 (1H, d, J=7.3 Hz), 11.22 (1H, br.s), 11.79 (1H, s). MS (FAB) m/z: 572 (M+H$^+$).

Example 165

Methyl 2-((3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}piperidin-3-yl)acetate dihydrochloride

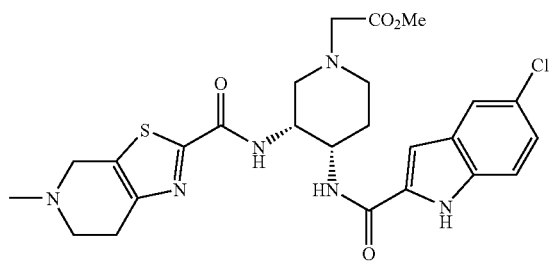

The title compound was obtained from the compound obtained in Example 118 and methyl bromoacetate in a similar manner to Example 102.

Melting point: 253-255° C. (decomposed). $^1$H-NMR (DMSO-$d_6$, 80° C.) δ: 1.95-2.10 (1H, m), 2.10-2.25 (1H, m), 2.88 (3H, s), 3.00-3.73 (8H, m), 3.75 (3H, s), 3.97-4.15 (2H, m), 4.30-4.80 (4H, m), 7.08-7.20 (2H, m), 7.44 (1H, d, J=8.6 Hz), 7.63 (1H, d, J=2.0 Hz), 8.42 (1H, d, J=7.3 Hz), 8.62 (1H, br.s), 11.82 (1H, br.s). MS (ESI) m/z: 545 (M+H$^+$).

Example 166

2-((3R*,4S*)-4-{[(5-Chloroindol-2-yl)carbonyl]amino}-3-{[(5-methyl-4,5,6,7-tetrahydrothiazolo[5,4-c]-pyridin-2-yl)carbonyl]amino}piperidin-3-yl)acetic acid hydrochloride

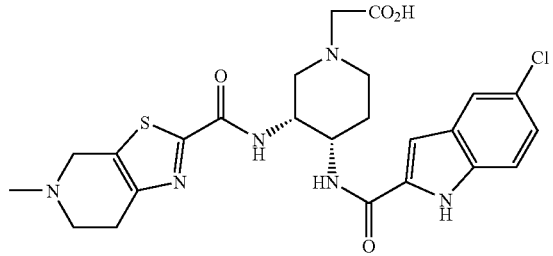

The title compound was obtained by treating the compound obtained in Example 165 in a similar manner to Example 101.

Melting point: 234-240° C. (decomposed). $^1$H-NMR (DMSO-$d_6$) δ: 1.75-1.95 (1H, m), 2.05-2.20 (1H, m), 2.88 (3H, s), 2.95-3.90 (10H, m), 4.20-4.70 (4H, m), 7.11 (1H, s), 7.16 (1H, dd, J=8.8, 2.0 Hz), 7.41 (1H, d, J=8.8 Hz), 7.66 (1H, d, J=2.0 Hz), 8.46 (1H, br.d, J=7.8 Hz), 8.65 (1H, br.s), 11.60-12.70 (2H, br.s), 11.91 (1H, br.s).

Example 167

N-[(3R*,4S*)-4-{[(5-Chloroindol-2-yl)carbonyl]amino}-1-(2-methoxyethyl)piperidin-3-yl]-5-methyl-4,5,6,7-tetrahydrothiazolo[5,4-c]pyridine-2-carboxamide dihydrochloride

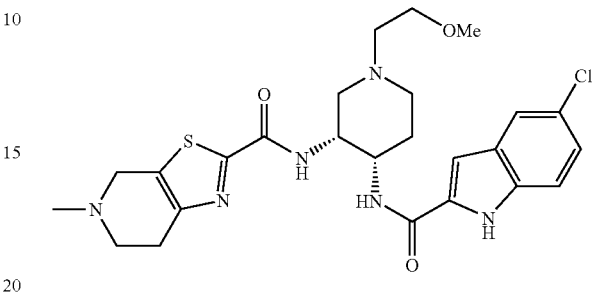

The title compound was obtained from the compound obtained in Example 118 and 2-bromoethyl methyl ether in a similar manner to Example 102 (NMR was measured in the form of a free base).

Melting point: 238-242° C. (decomposed). $^1$H-NMR (CDCl$_3$) δ: 1.75-1.83 (2H, m), 2.27-2.39 (2H, m), 2.52 (3H, s), 2.60-2.66 (1H, m), 2.69-2.75 (1H, m), 2.81-2.90 (2H, m), 2.96-3.07 (2H, m), 3.41 (3H, s), 3.53-3.60 (2H, m), 3.75 (each 1H, AB type d, J=15.5 Hz), 4.02-4.05 (1H, m), 4.40 (1H, br), 6.88 (1H, d, J=1.5 Hz), 7.18-7.21 (1H, m), 7.31-7.33 (1H, m), 7.63 (1H, d, J=1.5 Hz), 8.17 (1H, d, J=5.0 Hz), 8.26 (1H, d, J=7.0 Hz), 9.30 (1H, br.s). MS (FAB) m/z: 531 (M+H$^+$).

Example 168

N-[(3R*,4S*)-4-{[(5-Chloroindol-2-yl)carbonyl]amino}-1-(2-fluoroethyl)piperidin-3-yl]-5-methyl-4,5,6,7-tetrahydrothiazolo[5,4-c]pyridine-2-carboxamide dihydrochloride

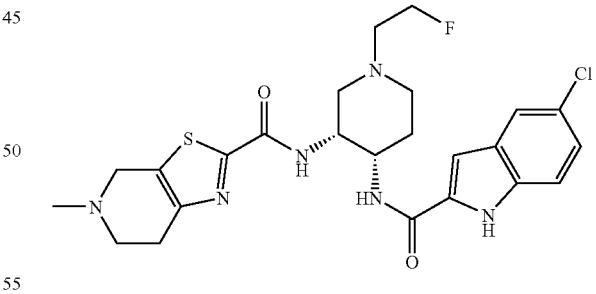

The title compound was obtained from the compound obtained in Example 118 and 2-fluoroethyl bromide in a similar manner to Example 102 (NMR was measured in the form of a free base).

Melting point: 228-233° C. (decomposed). $^1$H-NMR (CDCl$_3$) δ: 1.77 (2H, dq, J=12.5, 4.0 Hz), 2.28-2.32 (1H, m), 2.41 (1H, t, J=12.5 Hz), 2.52 (3H, s), 2.65 (1H, d, J=10.5 Hz), 2.76-2.81 (1H, m), 2.83-2.86 (3H, m), 2.98-3.05 (3H, m), 3.75 (each 1H, AB type d, J=15.5 Hz), 4.02-4.08 (1H, m), 4.45 (1H, br), 4.54-4.59 (1H, m), 4.64-4.70 (1H, m), 6.87 (1H, d, J=1.5 Hz), 7.19-7.22 (1H, m), 7.32 (1H, d, J=8.5

Hz), 7.64 (1H, d, J=2.0 Hz), 8.11 (1H, d, J=5.5 Hz), 8.20 (1H, d, J=7.3 Hz), 9.30 (1H, br). MS (FAB) m/z: 519 (M+H⁺).

Example 169

N-((3R,4S)-1-Acetyl-4-{[(5-chloroindol-2-yl)carbonyl]-amino}piperidin-3-yl)-5-methyl-4,5,6,7-tetrahydrothiazolo[5,4-c]pyridine-2-carboxamide hydrochloride

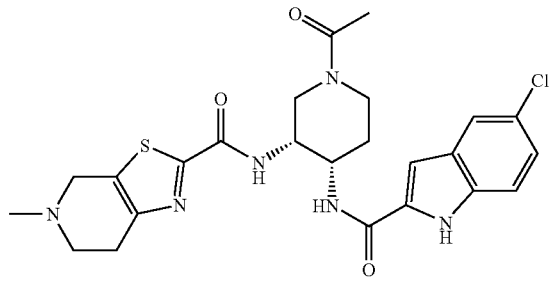

A 4N dioxane solution (7.0 ml) of hydrochloric acid was added to a dioxane solution (15 ml) of the compound (630 mg) obtained in Referential Example 214, and the mixture was stirred at room temperature for 1 hour. The reaction mixture was concentrated under reduced pressure. The thus-obtained yellow solids (590 mg) and the compound (379 mg) obtained in Referential Example 10 were used to obtain a free base (330 mg) of the title compound in a similar manner to Example 91. This free base was treated with an ethanol solution of hydrochloric acid to obtain the title compound (NMR was measured in the form of a free base).

Melting point: 202-222° C. (decomposed). ¹H-NMR (DMSO-d₆) δ: 1.65-1.85 (1H, m), 1.87, 2.06 (total 3H, each s), 1.88-2.10 (1H, m), 2.37 (3H, s), 2.65-2.77 (2H, m), 2.79-2.89 (2H, m), 2.99-3.09 (0.5H, m), 3.30-3.52 (2H, m), 3.64 (2H, s), 3.70-3.80 (0.5H, m), 3.96-4.21 (2H, m), 4.27 (1H, br.s), 4.35-4.48 (1H, m), 7.07, 7.11 (total 1H, each s), 7.18 (1H, d, J=8.8 Hz), 7.42 (1H, d, J=8.8 Hz), 7.71 (1H, s), 8.16-8.22 (1H, m), 8.37, 8.46 (total 1H, each d, J=7.8 Hz), 11.81, 11.83 (total 1H, each s). MS (ESI) m/z: 515 (M+H⁺). [α]²⁵_D=−56.0° (c=0.50, methanol).

Example 170

N-((3R,4R)-1-Acetyl-4-{[(5-chloroindol-2-yl)carbonyl]-amino}piperidin-3-yl)-5-methyl-4,5,6,7-tetrahydrothiazolo[5,4-c]pyridine-2-carboxamide hydrochloride

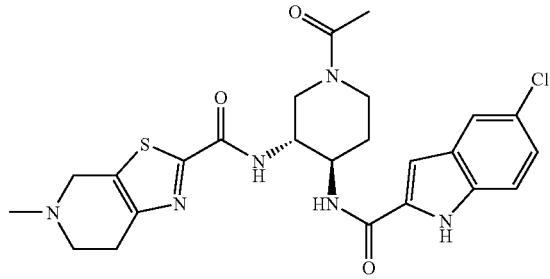

The title compound was obtained from the compound obtained in Referential Example 219 and Referential Example 10 in a similar manner to Example 169.

Melting point: 221-238° C. ¹H-NMR (DMSO-d₆) δ: 1.45-1.56 (0.5H, m), 1.60-1.70 (0.5H, m), 1.89-2.01 (1H, m), 2.05 (3H, s), 2.51-2.67 (1H, m), 2.88 (3H, s), 3.00-3.22 (3H, m), 3.31-3.40 (3H, m), 3.56-3.67 (0.5H, m), 3.78-4.02 (1.5H, m), 4.22-4.44 (2H, m), 4.56-4.72 (1H, m), 7.02 (1H, s), 7.15 (1H, dd, J=8.8, 2.0 Hz), 7.37 (1H, d, J=8.8 Hz), 7.67 (1H, d, J=2.0 Hz), 8.42 (1H, d, J=9.8 Hz), 8.67-8.78 (1H, m), 11.02-11.14 (1H, m), 11.72 (0.5H, s), 11.74 (0.5H, s). MS (FAB) m/z: 515 (M+H⁺). [α]²⁵_D=−105.4° (c=0.58, methanol).

Example 171

N-[(3R,4S)-4-{[(5-Chloroindol-2-yl)carbonyl]-amino}-1-(2-methoxyacetyl)piperidin-3-yl]-5-methyl-4,5,6,7-tetrahydrothiazolo[5,4-c]pyridine-2-carboxamide hydrochloride

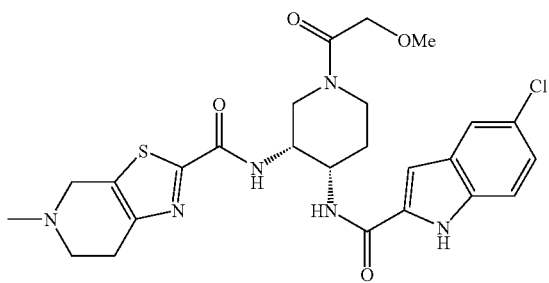

The title compound was obtained from the compound obtained in Referential Example 221 in a similar manner to Example 169.

Melting point: 207-220° C. (decomposed). ¹H-NMR (DMSO-d₆) δ: 1.70-1.80 (1H, m), 1.85-2.05 (1H, m), 2.90 (3H, s), 3.00-3.20 (2H, m), 3.16 (3H, s), 3.22-3.82 (7H, m), 3.88-4.80 (5H, m), 7.09 (1H, d, J=9.0 Hz), 7.17 (1H, dd, J=8.8, 1.9 Hz), 7.42 (1H, d, J=8.8 Hz), 7.70 (1H, d, J=1.9 Hz), 8.29 (1H, br.s), 8.40-8.50 (1H, m), 11.20-11.50 (1H, m), 11.85 (1H, s). MS (ESI) m/z: 545 (M+H⁺). [α]²⁵_D=−53.4° (c=0.52, methanol).

Example 172

N-[(3R,4R)-4-{[(5-Chloroindol-2-yl)carbonyl]-amino}-1-(2-methoxyacetyl)piperidin-3-yl]-5-methyl-4,5,6,7-tetrahydrothiazolo[5,4-c]pyridine-2-carboxamide hydrochloride

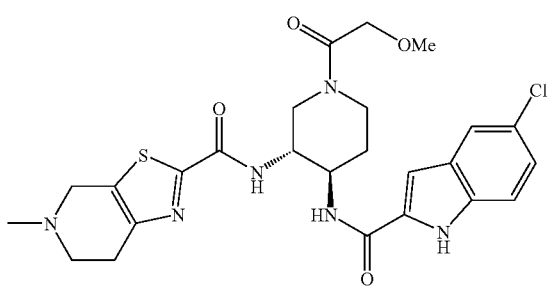

The title compound was obtained from the compound obtained in Referential Example 223 in a similar manner to Example 169.

Melting point: 213-230° C. ¹H-NMR (DMSO-d₆) δ: 1.45-1.56 (0.5H, m), 1.61-1.70 (0.5H, m), 1.89-2.00 (1H, m), 2.05 (3H, s), 2.45-2.67 (1H, m), 2.88 (3H, s), 3.00-3.21 (4H, m), 3.32-3.56 (7H, m), 3.78-3.89 (2H, m), 4.00-4.24 (2H, m), 4.26-4.43 (2H, m), 7.02 (1H, s), 7.13 (1H, dd, J=8.8, 2.0 Hz), 7.37 (1H, d, J=8.8 Hz), 7.67 (1H, d, J=2.0 Hz), 8.41 (1H, d, J=9.8 Hz), 8.74 (1H, d, J=9.8 Hz), 10.80-10.90 (1H, m), 11.72 (1H, s). MS (FAB) m/z: 545 (M+H$^+$). [α]$^{25}_D$=−100.3° (c=0.51, methanol).

Example 173

N-((3R,4R)-4-{[(5-Chloroindol-2-yl)carbonyl] amino}-6-oxotetrahydro-2H-pyran-3-yl)-5-methyl-4,5,6,7-tetrahydrothiazolo[5,4-c]pyridine-2-carboxamide hydrochloride

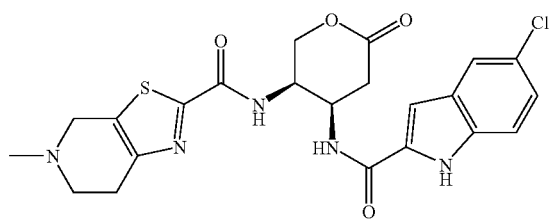

The title compound was obtained from the low-polar compound obtained in Referential Example 176 and the compound obtained in Referential Example 10 in a similar manner to Example 169.

$^1$H-NMR (DMSO-d$_6$) δ: 2.41-2.56 (2H, m), 2.91 (3H, s), 3.01-3.23 (1H, m), 3.24-3.56 (5H, m), 3.62-3.67 (1H, m), 4.21-4.44 (1H, m), 4.56-4.78 (2H, m), 7.11 (1H, s), 7.16 (1H, dd, J=8.8, 2.0 Hz), 7.22 (1H, d, J=8.5 Hz), 7.41 (1H, d, J=8.8 Hz), 7.69 (1H, d, J=2.0 Hz), 8.40-8.50 (1H, m), 11.34-11.56 (1H, m), 11.82 (1H, s). MS (FAB) m/z: 488 (M+H$^+$).

Example 174

N-((3R,4S)-4-{[(5-Chloroindol-2-yl)carbonyl] amino}-6-oxotetrahydro-2H-pyran-3-yl)-5-methyl-4,5,6,7-tetrahydrothiazolo[5,4-c]pyridine-2-carboxamide hydrochloride

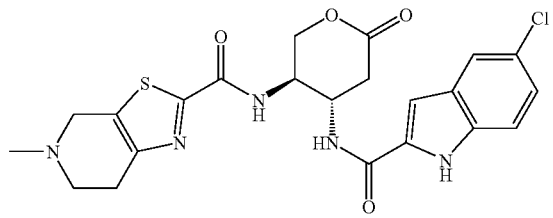

The title compound was obtained from the high-polar compound obtained in Referential Example 176 and the compound obtained in Referential Example 10 in a similar manner to Example 169.

$^1$H-NMR (DMSO-d$_6$) δ: 2.41-2.56 (2H, m), 2.91 (3H, s), 3.23-3.41 (2H, m), 3.43-3.50 (2H, m), 3.56-3.67 (2H, m), 4.37 (1H, dd, J=13.9, 7.1 Hz), 4.40-4.50 (1H, m), 4.56-4.78 (2H, m), 7.12 (1H, s), 7.17 (1H, dd, J=8.8, 2.0 Hz), 7.41 (1H, d, J=8.8 Hz), 7.71 (1H, d, J=2.0 Hz), 8.44 (1H, d, J=8.5 Hz), 8.15 (1H, d, J=8.5 Hz), 11.42-11.53 (1H, m), 11.79 (1H, s). MS (FAB) m/z: 488 (M+H$^+$).

Example 175

Ethyl (3R,4S)-5-{[tert-butyl(diphenyl)silyl]oxy}-3-{[(5-chloroindol-2-yl)carbonyl]amino}-4-{[(5-methyl-4,5,6,7-tetrahydrothiazolo[5,4-c]pyridin-2-yl)carbonyl]amino}-valerate

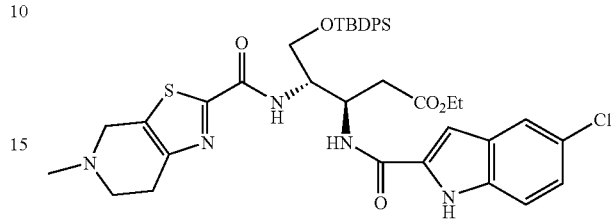

The title compound was obtained from the compound obtained in Referential Example 225 in a similar manner to Example 169.

$^1$H-NMR (CDCl$_3$) δ: 1.09 (9H, s), 1.21 (3H, t, J=7.4 Hz), 2.49 (3H, s), 2.65 (1H, dd, J=15.9, 5.4 Hz), 2.67-2.90 (5H, m), 3.60 (1H, d, J=14.9 Hz), 3.72 (1H, d, J=14.9 Hz), 3.78-3.91 (2H, m), 4.00-4.21 (2H, m), 4.43-4.50 (1H, m), 4.78-4.89 (1H, m), 6.81 (1H, s), 7.20 (1H, dd, J=8.8, 2.0 Hz), 7.32-7.52 (m, 7H), 7.63-7.74 (6H, m), 7.89-8.01 (1H, m), 9.18 (1H, s).

Example 176

Ethyl (3R,4S)-3-{[(5-chloroindol-2-yl)carbonyl] amino}-5-hydroxy-4-{[(5-methyl-4,5,6,7-tetrahydrothiazolo[5,4-c]-pyridin-2-yl)carbonyl] amino}valerate

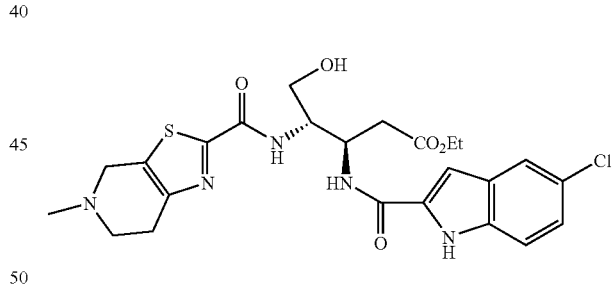

After hydrogen fluoride.pyridine (0.4 ml) was added dropwise to a mixture sulution composed of the compound (0.54 g) obtained in Example 175, pyridine (4.0 ml) and tetrahydrofuran (10 ml) under ice cooling, the reaction mixture was stirred for 18 hours while the temperature thereof was gradually raised to room temperature. The reaction mixture was concentrated, and the resultant residue was purified by column chromatography on silica gel (chloroform:methanol=9:1) to obtain the title compound (0.31 g).

$^1$H-NMR (CDCl$_3$) δ: 1.20 (3H, t, J=7.4 Hz), 2.49 (3H, s), 2.67-2.90 (6H, m), 3.62-3.74 (3H, m), 3.78-3.94 (1H, m), 4.00-4.20 (2H, m), 4.30-4.40 (1H, m), 4.80-4.89 (1H, m), 6.93 (1H, s), 7.23 (1H, dd, J=8.8, 2.0 Hz), 7.33 (1H, d, J=8.8 Hz), 7.56 (1H, d, J=8.5 Hz), 7.61 (1H, d, J=2.0 Hz), 7.88 (1H, d, J=8.5 Hz), 9.29 (1H, s).

Example 177

N-((3S,4R)-4-{[(5-Chloroindol-2-yl)carbonyl]amino}-6-oxotetrahydro-2H-pyran-3-yl]-5-methyl-4,5,6,7-tetrahydrothiazolo[5,4-c]pyridine-2-carboxamide hydrochloride

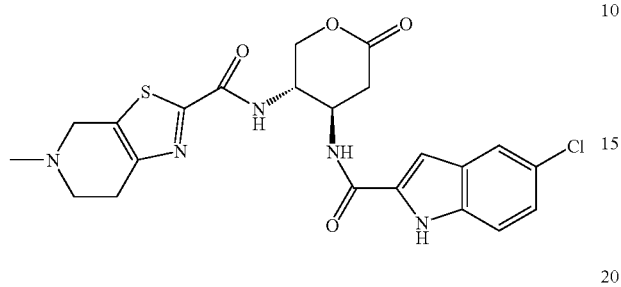

A 4N dioxane solution (20 ml) of hydrochloric acid was added to the compound. (0.31 g) obtained in Example 176, and the mixture was heated under reflux for 4 hours. The reaction mixture was concentrated, and the resultant residue was recrystallized from diethyl ether to obtain the title compound (0.23 g).

Melting point: 221-238° C. (decomposed). $^1$H-NMR and MS (FAB): The same as those of the enantiomer in Example 174.

Example 178

N-((3R*,4R*)-4-{[(5-Chloroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

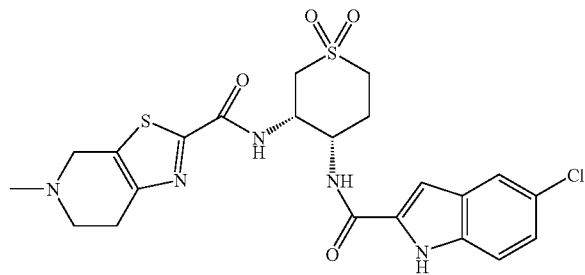

A free base of the title compound was obtained from the compound obtained in Referential Example 227 and 5-chloroindole-2-carboxylic acid in a similar manner to Example 91. This free base was treated with an ethanol solution of hydrochloric acid to obtain the title compound.

Melting point: 241-244° C. $^1$H-NMR (DMSO-$d_6$) δ: 2.14 (1H, br), 2.30-2.34 (1H, m), 2.92 (3H, s), 3.10-3.18 (2H, m), 3.41 (4H, br), 3.68 (2H, br), 4.44 (1H, br), 4.63-4.78 (3H, m), 7.16-7.18 (1H, m), 7.21 (1H, s), 7.43 (1H, d, J=8.5 Hz), 7.67 (1H, d, J=4.6 Hz), 8.39 (1H, br), 8.94 (1H, br), 11.82 (1H, br). MS (ESI) m/z: 522 (M+H$^+$).

Example 179

N-((3R*,4R*)-4-{[(5-Fluoroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

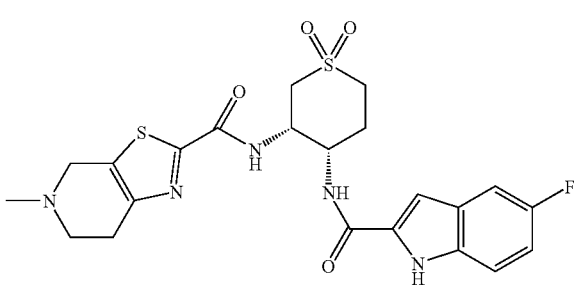

A free base of the title compound was obtained from the compound obtained in Referential Example 227 and 5-fluoroindole-2-carboxylic acid in a similar manner to Example 91. This free base was treated with an ethanol solution of hydrochloric acid to obtain the title compound.

Melting point: 243-245° C. $^1$H-NMR (DMSO-$d_6$) δ: 2.14 (1H, br), 2.30-2.33 (1H, m), 2.92 (3H, s), 3.13 (2H, br), 3.51 (4H, br), 3.63 (2H, br), 4.63 (3H, br), 4.78 (1H, br), 7.01-7.05 (1H, m), 7.21 (1H, s), 7.37-7.44 (2H, m), 8.36 (1H, br), 8.93 (1H, d, J=6.8 Hz), 11.72 (1H, br). MS (ESI) m/z: 506 (M+H$^+$).

Example 180

N-((3R*,4R*)-3-{[(5-Chloroindol-2-yl)carbonyl]amino}-1,1-dioxohexahydro-1-thiopyran-4-yl)-5-methyl-4,5,6,7-tetrahydrothiazolo[5,4-c]pyridine-2-carboxamide hydrochloride

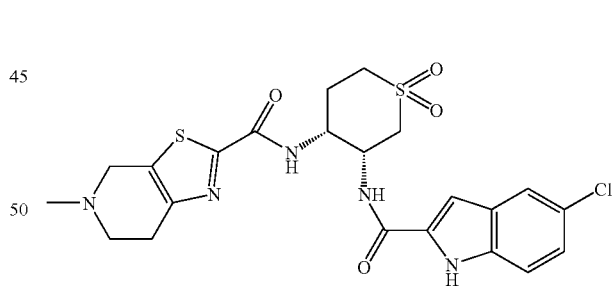

A free base of the title compound was obtained from the compound obtained in Referential Example 229 and the compound obtained in Referential Example 10 in a similar manner to Example 91. This free base was treated with an ethanol solution of hydrochloric acid to obtain the title compound.

Melting point: 242-247° C. $^1$H-NMR (DMSO-$d_6$) δ: 2.16 (1H, br), 2.45 (1H, br), 2.93 (3H, s), 3.13 (2H, br), 3.26 (4H, br), 3.69 (2H, br), 4.45 (1H, br), 4.65-4.77 (3H, m), 7.01 (1H, s), 7.17 (1H, dd, J=8.7, 1.4 Hz), 7.43 (1H, d, J=8.5 Hz), 7.69 (1H, s), 8.35-8.40 (1H, m), 9.04 (1H, br), 11.86 (1H, s). MS (ESI) m/z: 522 (M+H$^+$).

Example 181

N-((3R*,4S*)-4-{[(5-Chloroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

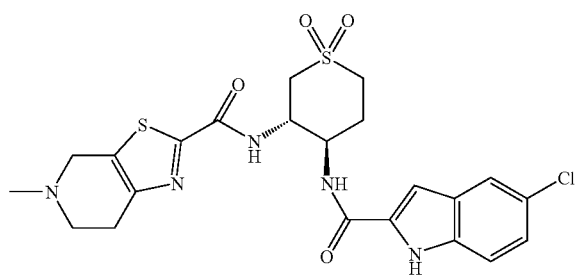

A free base of the title compound was obtained from the compound obtained in Referential Example 231 and 5-chloroindole-2-carboxylic acid in a similar manner to Example 91. This free base was treated with an ethanol solution of hydrochloric acid to obtain the title compound.

Melting point: 244-249° C. $^1$H-NMR (DMSO-$d_6$) δ: 2.17-2.27 (2H, m), 2.90 (3H, s), 3.09 (1H, br), 3.18-3.21 (2H, m), 3.31-3.34 (2H, m), 3.60-3.67 (3H, m), 4.41-4.49 (2H, m), 4.54-4.59 (2H, m), 7.04 (1H, s), 7.09-7.13 (1H, m), 7.39 (1H, d, J=8.5 Hz), 7.61 (1H, d, J=9.9 Hz), 8.52-8.56 (1H, m), 8.83-8.85 (1H, m), 11.65 (1H, d, J=11.9 Hz). MS (ESI) m/z: 522 (M+H$^+$).

Example 182

N-((3R*,4S*)-4-{[(5-Fluoroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

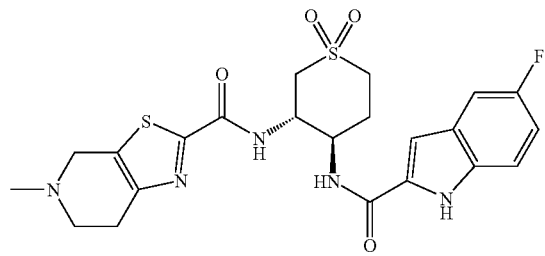

A free base of the title compound was obtained from the compound obtained in Referential Example 231 and 5-fluoroindole-2-carboxylic acid in a similar manner to Example 91. This free base was treated with an ethanol solution of hydrochloric acid to obtain the title compound.

Melting point: 236-241° C. $^1$H-NMR (DMSO-$d_6$) δ: 2.20-2.24 (2H, m), 2.89 (3H, s), 3.07 (1H, br), 3.19-3.22 (2H, m), 3.60-3.66 (4H, m), 4.43-4.58 (5H, m), 6.95-7.00 (1H, m), 7.04 (1H, s), 7.32-7.38 (2H, m), 8.50 (1H, d, J=8.5 Hz), 8.83 (1H, d, J=8.5 Hz), 11.59 (1H, s). MS (ESI) m/z: 506 (M+H$^+$).

Example 183

N-((3R*,4R*)-3-{[(5-Fluoroindol-2-yl)carbonyl]amino}-1,1-dioxohexahydro-1-thiopyran-4-yl)-5-methyl-4,5,6,7-tetrahydrothiazolo[5,4-c]pyridine-2-carboxamide hydrochloride

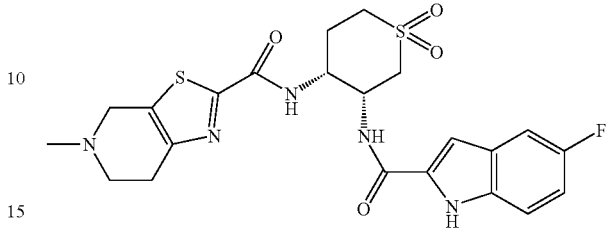

A free base of the title compound was obtained from the compound obtained in Referential Example 233 and the compound obtained in Referential Example 10 in a similar manner to Example 91. This free base was treated with an ethanol solution of hydrochloric acid to obtain the title compound.

Melting point: 244-249° C. $^1$H-NMR (DMSO-$d_6$) δ: 2.12-2.18 (1H, m), 2.50 (1H, br), 2.92 (3H, s), 3.17 (3H, br), 3.50-3.61 (5H, m), 4.45 (1H, br), 4.62-4.78 (3H, m), 6.98-7.03 (2H, m), 7.36-7.42 (2H, m), 8.30 (1H, br), 9.00 (1H, d, J=8.0 Hz), 11.74 (1H, s). MS (ESI) m/z: 506 (M+H$^+$).

Example 184

N-((3S,4R)-4-{[(5-chloroindol-2-yl)carbonyl]amino}-1-methyl-6-oxopiperidin-3-yl)-5-methyl-4,5,6,7-tetrahydrothiazolo[5,4-c]pyridine-2-carboxamide (Low-polar Compound) and N-((3R,4R)-4-{[(5-chloroindol-2-yl)carbonyl]amino}-1-methyl-6-oxopiperidin-3-yl)-5-methyl-4,5,6,7-tetrahydrothiazolo[5,4-c]pyridine-2-carboxamide (High-polar Compound)

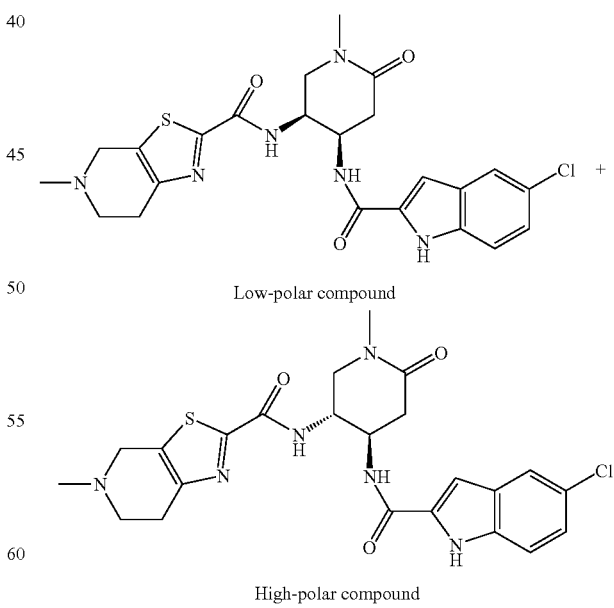

The title compound was obtained from the compound obtained in Referential Example 236 and the compound obtained in Referential Example 10 in a similar manner to Example 169.

Low-polar Compound:

Melting poing: 189-203° C. (decomposed). $^1$H-NMR (CDCl$_3$) δ: 2.52 (3H, s), 2.59 (1H, q, J=8.8 Hz), 2.71-2.78 (2H, m), 2.89-3.00 (2H, m), 3.03 (3H, s), 3.12 (1H, dd, J=17.6, 5.4 Hz), 3.43 (1H, dd, J=12.7, 5.1 Hz), 3.70 (1H, d, J=15.2 Hz), 3.77 (1H, d, J=15.2 Hz), 3.83 (1H, dd, J=12.7, 3.9 Hz), 4.55-4.67 (2H, m), 6.99 (1H, s), 7.23 (1H, dd, J=8.8, 2.0 Hz), 7.33 (1H, d, J=8.8 Hz), 7.65 (1H, d, J=2.0 Hz), 8.07 (1H, d, J=5.1 Hz), 8.16 (1H, d, J=5.4 Hz), 9.43 (1H, s). MS (FAB) m/z: 501 (M+H$^+$).

High-polar Compound:

Melting point: 183-195° C. (decomposed). $^1$H-NMR (DMSO-d$_6$) δ: 2.33 (3H, s), 2.41-2.50 (1H, m), 2.62-2.73 (3H, m), 2.75-2.81 (1H, m), 2.82 (3H, s), 3.21-3.32 (2H, m), 3.34-3.50 (2H, m), 3.55 (1H, d, J=15.4 Hz), 3.63 (1H, d, J=15.4 Hz), 4.30-4.40 (0.5H, m), 4.50-4.60 (0.5H, m), 7.04 (1H, s), 7.15 (1H, dd, J=8.8, 2.0 Hz), 7.38 (1H, d, J=8.8 Hz), 7.67 (1H, d, J=2.0 Hz), 8.49 (1H, d, J=8.5 Hz), 8.71 (1H, d, J=8.5 Hz), 11.74 (1H, s). MS (FAB) m/z: 501 (M+H$^+$).

Example 185

5-Chloro-N-((1R*,2S*)-2-{[4-(pyridin-4-yl)benzoyl]-amino}cyclohexyl)indole-2-carboxamide hydrochloride

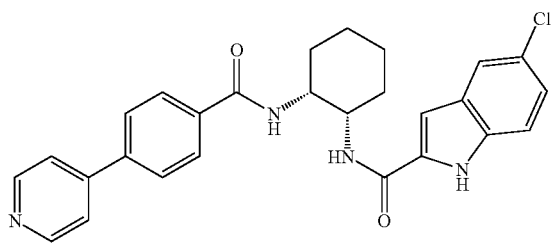

The title compound was obtained from the compound obtained in Referential Example 71 and the compound obtained in Referential Example 237 in a similar manner to the process described in Example 2.

$^1$H-NMR (DMSO-d$_6$) δ: 1.40-1.52 (2H, m), 1.60-1.80 (4H, m), 1.96-2.10 (2H, m), 4.24-4.39 (2H, m), 7.15 (1H, dd, J=8.8, 2.0 Hz), 7.21 (1H, s), 7.40 (1H, d, J=8.8 Hz), 7.64 (1H, d, J=2.0 Hz), 8.06 (4H, s), 8.18 (1H, J=7.3 Hz), 8.34-8.42 (3H, m), 8.94 (2H, d, J=6.9 Hz), 11.91 (1H, s). MS (FAB) m/z: 473 (M+H$^+$).

Example 186

4-(4-{[((1R*,2S*)-2-[([(5-Chloroindol-2-yl)carbonyl]amino}-cyclohexyl)amino]carbonyl}phenyl) pyridine N-oxide

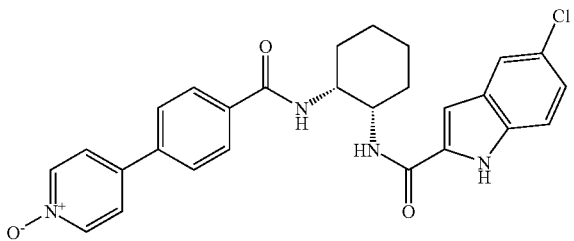

The title compound was obtained from the compound obtained in Referential Example 71 and the compound obtained in Referential Example 240 in a similar manner to the process described in Example 2.

$^1$H-NMR (DMSO-d$_6$) δ: 1.40-1.52 (2H, m), 1.60-1.80 (4H, m), 1.88-2.00 (2H, m), 4.21-4.36 (2H, m), 7.12-7.18 (2H, m), 7.41 (1H, d, J=8.6 Hz), 7.66 (1H, s), 7.80-7.87 (4H, m), 7.91 (2H, d, J=8.3 Hz), 8.01 (1H, d, J=7.6 Hz), 8.09 (1H, d, J=7.3 Hz), 8.27 (2H, d, J=6.6 Hz), 11.79 (1H, s). MS (FAB) m/z: 489 (M+H$^+$).

Example 187

5-Chloro-N-((1R*,2S*)-2-{[4-(pyridin-2-yl)benzoyl]-amino}cyclohexyl)indole-2-carboxamide hydrochloride

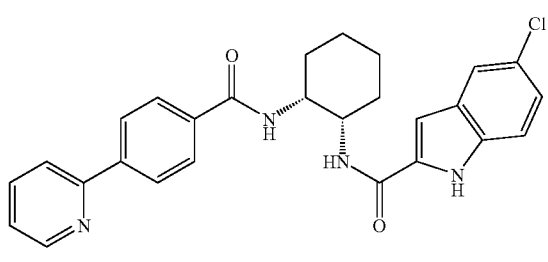

The title compound was obtained from the compound obtained in Referential Example 71 and 4-(2-pyridyl)benzoic acid (Japanese Patent Application Laid-Open No. 2000-119253) in a similar manner to the process described in Example 2.

$^1$H-NMR (DMSO-d$_6$) δ: 1.39-1.51 (2H, m), 1.60-1.80 (4H, m), 1.89-2.00 (2H, m), 4.24-4.38 (2H, m), 7.12-7.16 (2H, m), 7.36-7.39 (1H, m), 7.42 (1H, d, J=8.8 Hz), 7.66 (1H, d, J=2.0 Hz), 7.87-7.90 (1H, m), 7.92 (2H, d, J=8.3 Hz), 7.98-8.11 (3H, m), 8.15 (2H, d, J=8.3 Hz), 8.69 (1H, d, J=4.6 Hz), 11.80 (1H, s). MS (FAB) m/z: 473 (M+H$^+$).

Example 188

2-(4-{[((1R*,2S*)-2-{[(5-Chloroindol-2-yl)carbonyl]amino}-cyclohexyl)amino]carbonyl}phenyl) pyridine N-oxide

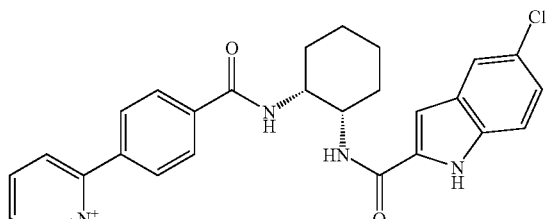

The title compound was obtained from the compound obtained in Referential Example 71 and the compound obtained in Referential Example 241 in a similar manner to the process described in Example 2.

$^1$H-NMR (DMSO-d$_6$) δ: 1.39-1.51 (2H, m), 1.60-1.79 (4H, m), 1.89-2.00 (2H, m), 4.23-4.37 (2H, m), 7.12-7.17 (2H, m), 7.39-7.43 (3H, m), 7.61-7.64 (1H, m), 7.67 (1H, d, J=2.0 Hz), 7.89 (4H, s), 8.00-8.06 (1H.m), 8.08-8.02 (1H, m), 8.32-8.35 (1H, m), 11.79 (1H, s). MS (FAB) m/z: 489 (M+H$^+$).

Example 189

5-Chloro-N-[(1R*,2R*)-2-({[5-(4-pyridin-2-yl)thiazol-2-yl]carbonyl}amino)cyclohexyl]indole-2-carboxamide hydrochloride

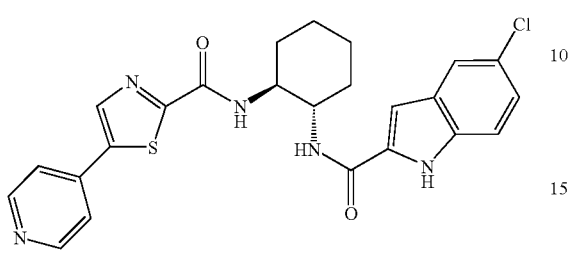

The title compound was obtained from the compound obtained in Referential Example 69 and lithium 5-(4-pyridyl)thiazole-2-carboxylate (Japanese Patent Application Laid-Open No. 2000-143623) in a similar manner to the process described in Example 2.

$^1$H-NMR (DMSO-$d_6$) δ: 1.44 (2H, br.s), 1.65 (4H, br.s), 1.85-2.06 (2H, m), 4.23 (1H, br.s), 4.30 (1H, br.s), 7.14-7.23 (2H, m), 7.41 (1H, d, J=8.8 Hz), 7.69 (1H, s), 8.04-8.13 (2H, m), 8.13 (1H, d, J=8.8 Hz), 8.59 (1H, d, J=8.0 Hz), 8.75-8.87 (3H, m), 11.83 (1H, s). MS (ESI) m/z: 480 (M+H)$^+$.

Example 190

5-Chloro-N-[(1R*,2S*)-2-({[1-(pyridin-4-yl)piperidin-4-yl]carbonyl}amino)cyclohexyl]indole-2-carboxamide hydrochloride

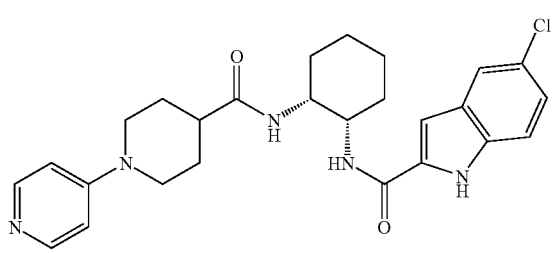

1-(4-Pyridyl)piperidine-4-carboxylic acid (Tetrahedron, 1998, Vol. 44, p. 7095) (206 mg) was suspended in methylene chloride (50 ml), and thionyl chloride (144 μl) was added under ice cooling to stir the mixture for 30 minutes. After triethylamine (969 μl) was added to the reaction mixture, the compound (328 mg) obtained in Referential Example 71 was added to stir the mixture at room temperature for 30 minutes. The reaction mixture was concentrated under reduced pressure, water was added to the residue, the mixture was concentrated under reduced pressure, and precipitate deposited was collected by filtration to obtain the title compound (310 mg).

$^1$H-NMR (DMSO-$d_6$) δ: 1.30-2.00 (10H, m), 2.74 (1H, br.s), 3.18 (2H, q, J=12.3 Hz), 4.03 (1H, br.s), 4.10-4.25 (3H, m), 7.15-7.55 (4H, m), 7.42 (1H, d, J=8.8 Hz), 7.65 (1H, s), 7.91 (1H, d, J=8.8 Hz), 8.20-8.35 (3H, m), 11.91 (1H, s), 13.47 (1H, br.s). MS (FAB) m/z: 480 (M+H)$^+$.

Example 191

N$^1$-(4-Chlorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

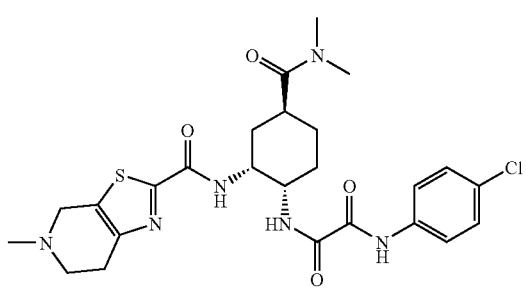

The compound (288 mg) obtained in Referential Example 242 was dissolved in tetrahydrofuran (8.0 ml), lithium hydroxide (46 mg) and water (1.0 ml) were successively added, and the mixture was stirred at room temperature for 2 hours. The reaction mixture was concentrated under reduced pressure to obtain a crude product (292 mg) of lithium 2-(4-chloroanilino)-2-oxoacetate as a colorless solid. This crude product and the compound obtained in Referential Example 253 were dissolved in N,N-dimethylformamide (15 ml), and 1-hydroxybenzotriazole monohydrate (164 mg) and 1-(3-dimethylaminopropyl)-3-ethylcarbodiimide hydrochloride (251 mg) were added to stir the mixture at room temperature for 64.5 hours. The solvent was distilled off under reduced pressure, a saturated aqueous solution of sodium hydrogencarbonate and methylene chloride were added to the residue to conduct liquid separation, and the resultant organic layer was dried over anhydrous sodium sulfate. After the solvent was distilled off under reduced pressure, the residue was purified by column chromatography on silica gel (methylene chloride:methanol=47:3). The thus-obtained pale yellow solids were dissolved in methylene chloride, a 1N ethanol solution (0.52 ml) of hydrochloric acid was added, and the solvent was distilled off under reduced pressure. Methanol and diethyl ether were added to the residue, and precipitate formed was collected by filtration to obtain the title compound (245 mg).

$^1$H-NMR (DMSO-$d_6$) δ: 1.45-1.55 (1H, m), 1.60-1.80 (3H, m), 1.95-2.10 (2H, m), 2.79 (3H, s), 2.80-3.00 (1H, m), 2.92 (3H, s), 2.94 (3H, s), 3.10-3.40 (2H, m), 3.40-3.80 (2H, m), 3.95-4.05 (1H, m), 4.40-4.80 (3H, m), 7.40 (2H, d, J=8.8 Hz), 7.83 (2H, d, J=8.8 Hz), 8.75 (1H, d, J=7.1 Hz), 9.00-9.10 (1H, br), 10.81 (1H, s), 11.45-11.75 (1H, m). MS (FAB) m/z: 547 (M+H)$^+$.

Example 192

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

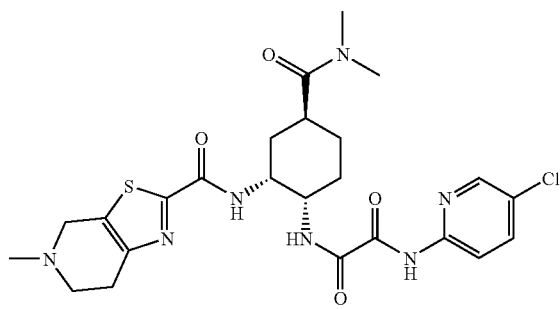

The compound (240 mg) obtained in Referential Example 243 was dissolved in tetrahydrofuran (8.0 ml), lithium hydroxide (41 mg) and water (1.0 ml) were successively added to the solution, and the mixture was stirred at room temperature for 2.5 hours. The reaction mixture was concentrated under reduced pressure to obtain lithium 2-[(5-chloropyridin-2-yl)amino]-2-oxoacetate (249 mg).

On the other hand, 10% palladium on carbon (200 mg) was added to a solution of the compound (293 mg) obtained in Referential Example 252 in methanol (10 ml), and the mixture was stirred at room temperature for 18 hours under a hydrogen atmosphere. After removing palladium on carbon by filtration, the filtrate was concentrated under reduced pressure to obtain a crude product (259 mg) of N-{(1R,2S,5S)-2-amino-5-[(dimethylamino)carbonyl]-cyclohexyl}-5-methyl-4,5,6,7-tetrahydrothiazolo[5,4-c]-pyridine-2-carboxamide.

This crude product (259 mg) and the lithium salt (249 mg) prepared above were added to N,N-dimethylformamide (15 ml), and 1-hydroxybenzotriazole monohydrate (166 mg) and 1-(3-dimethylaminopropyl)-3-ethylcarbodiimide hydrochloride (235 mg) were added to stir the mixture at room temperature for 63.5 hours. The solvent was distilled off under reduced pressure, a saturated aqueous solution of sodium hydrogencarbonate and methylene chloride were added to the residue to conduct liquid separation, and the resultant organic layer was dried over anhydrous sodium sulfate. After the solvent was distilled off under reduced pressure, the residue was purified by column chromatography on silica gel (methylene chloride:methanol=93:7). The thus-obtained pale yellow solids were dissolved in methylene chloride, a 1N ethanol solution (0.855 ml) of hydrochloric acid was added to the solution, and the solvent was distilled off under reduced pressure. Methanol and diethyl ether were added to the residue, and precipitate formed was collected by filtration to obtain the title compound (209 mg).

¹H-NMR (DMSO-$d_6$) δ: 1.40-1.57 (1H, m), 1.60-1.80 (3H, m), 1.95-2.13 (2H, m), 2.79 (3H, s), 2.80-3.00 (1H, m), 2.92 (3H, s), 2.94 (3H, s), 3.10-3.40 (2H, m), 3.40-3.80 (2H, m), 3.95-4.05 (1H, m), 4.37-4.80 (3H, m), 7.90-8.10 (2H, m), 8.45 (1H, d, J=2.2 Hz), 8.71 (1H, d, J=7.6 Hz), 9.10-9.30 (1H, br), 10.26 (1H, s), 11.30-11.60 (1H, br). MS (FAB) m/z: 548 (M+H)⁺.

Example 193

N¹-(3-Chlorophenyl)-N²-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

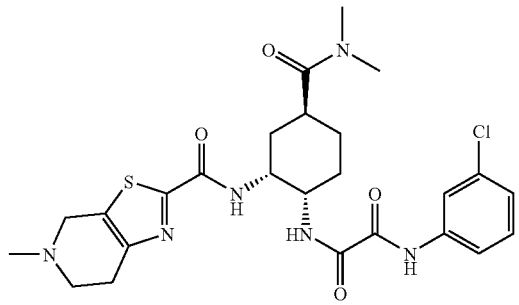

The compound (222 mg) obtained in Referential Example 270 and 3-chloroaniline (63 µl) were dissolved in N,N-dimethylformamide (10 ml), and 1-hydroxybenzotriazole monohydrate (68 mg) and 1-(3-dimethylaminopropyl)-3-ethylcarbodiimide hydrochloride (144 mg) were added to stir the mixture at room temperature for 40 hours. The solvent was distilled off under reduced pressure, a saturated aqueous solution of sodium hydrogencarbonate and methylene chloride were added to the residue to conduct liquid separation, and the resultant organic layer was dried over anhydrous sodium sulfate. After the solvent was distilled off under reduced pressure, the residue was purified by column chromatography on silica gel (methylene chloride:methanol=30:1). The thus-obtained pale yellow solids were dissolved in methylene chloride, a 1N ethanol solution (0.50 ml) of hydrochloric acid was added, and the solvent was distilled off under reduced pressure. Diethyl ether was added to the residue, and precipitate formed was collected by filtration to obtain the title compound (174 mg).

¹H-NMR (DMSO-$d_6$) δ: 1.45-1.62 (1H, m), 1.65-1.90 (3H, m), 1.98-2.20 (2H, m), 2.79 (3H, s), 2.88-3.10 (1H, m), 2.93 (3H, s), 2.94 (3H, s), 3.15-3.40 (2H, m), 3.40-3.90 (2H, m), 3.95-4.10 (1H, m), 4.40-4.80 (3H, m), 7.19 (1H, dd, J=9.3, 2.0 Hz), 7.37 (1H, d, J=8.2 Hz), 7.77 (1H, d, J=8.3 Hz), 7.92-8.05 (1H, m), 8.75 (1H, d, J=7.3 Hz), 8.95-9.20 (1H, br), 10.87 (1H, s), 11.25-11.45 (1H, br).

Example 194

N¹-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-N²-(4-fluorophenyl)ethanediamide hydrochloride

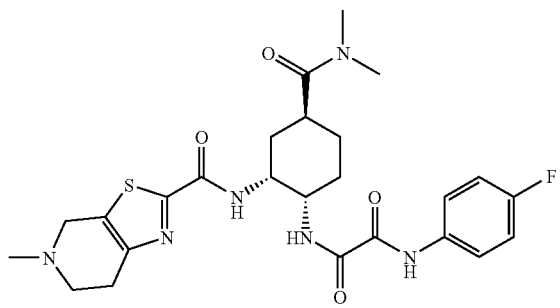

The title compound was obtained by hydrolyzing the compound obtained in Referential Example 254, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.40-2.13 (6H, m), 2.77 (3H, s), 2.93 (3H, s), 2.97 (3H, s), 3.12-3.82 (7H, m), 3.93-4.04 (1H, m), 4.38-4.46 (1H, m), 4.35-4.75 (1H, m), 7.11-7.21 (2H, m), 7.72-7.84 (2H, m), 8.73 (1H, d, J=7.6 Hz), 8.93-9.02 (1H, m), 10.70 (1H, s). MS (FAB) m/z: 531 (M+H)$^+$.

Example 195

N$^1$-(4-Bromophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

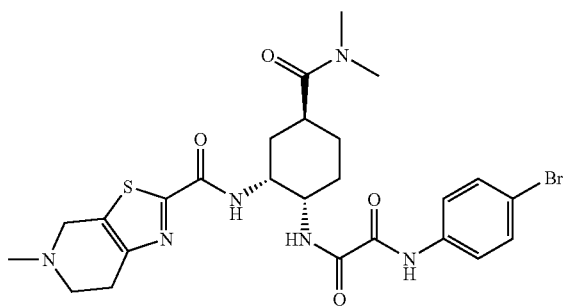

The compound (152 mg) obtained in Referential Example 255 was dissolved in tetrahydrofuran (5.0 ml), a 1N aqueous solution (1.20 ml) of sodium hydroxide and methanol (5.0 ml) were successively added, and the mixture was stirred at room temperature for 2.5 hours. The reaction mixture was concentrated under reduced pressure, and methylene chloride (10 ml) and 1N hydrochloric acid (2.0 ml) were added to the residue to conduct liquid separation. The resultant organic layer was dried over anhydrous sodium sulfate, and the solvent was distilled off under reduced pressure to obtain a crude product (280 mg) of 2-(4-bromoanilino)-2-oxoacetic acid as a colorless solid. This crude product and the compound (280 mg) obtained in Referential Example 253 were dissolved in N,N-dimethylformamide (30 ml), and 1-hydroxybenzotriazole monohydrate (90 mg) and 1-(3-dimethylaminopropyl)-3-ethylcarbodiimide hydrochloride (226 mg) were added to stir the mixture at room temperature for a night. The solvent was distilled off under reduced pressure, a saturated aqueous solution of sodium hydrogencarbonate and methylene chloride were added to the residue to conduct liquid separation, and the resultant organic layer was dried over anhydrous sodium sulfate. After the solvent was distilled off under reduced pressure, the residue was purified by column chromatography on silica gel (methylene chloride:methanol=97:3). The thus-obtained pale yellow solids were dissolved in methylene chloride, a 1N ethanol solution (191 μl) of hydrochloric acid was added, and the solvent was distilled off under reduced pressure. Methanol and diethyl ether were added to the residue, and precipitate formed was collected by filtration to obtain the title compound (103 mg).

$^1$H-NMR (DMSO-d$_6$) δ: 1.43-1.57 (1H, m), 1.59-1.80 (3H, m), 1.97-2.10 (2H, m), 2.79 (3H, s), 2.84-2.98 (7H, m), 3.18 (2H, br.s), 3.39-3.72 (2H, m), 3.95-4.05 (1H, m), 4.20-4.80 (3H, m), 7.53 (2H, d, J=8.8 Hz), 7.77 (2H, d, J=8.8 Hz), 8.75 (1H, d, J=7.3 Hz), 8.97-9.09 (1H, m), 10.82 (1H, s), 11.11 (1H, br.s). MS (FAB) m/z: 591 (M+H)$^+$.

Example 196

N$^1$-(4-Chloro-2-methylphenyl)-N$^2$-((1S,2R,4S)-4-((dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride

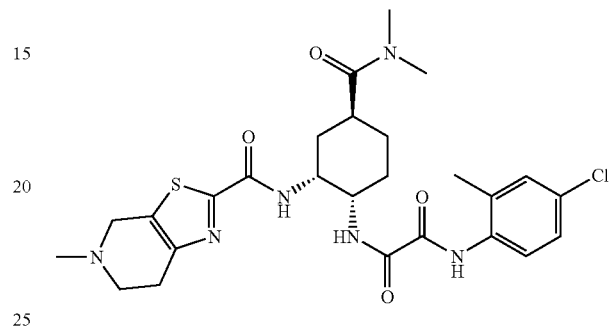

The title compound was obtained by hydrolyzing the compound obtained in Referential Example 256, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.45-1.55 (1H, m), 1.60-1.80 (3H, m), 2.00-2.10 (2H, m), 2.19 (3H, s), 2.79 (3H, s), 2.80-3.00 (7H, m), 3.31 (2H, br.s), 3.40-3.70 (2H, br), 3.95-4.05 (1H, m), 4.35-4.70 (3H, m), 7.20-7.30 (1H, m), 7.35 (1H, d, J=2.5 Hz), 7.43 (1H, d, J=8.6 Hz), 8.76 (1H, d, J=6.6 Hz), 9.00-9.15 (1H, br), 10.19 (1H, s). MS (FAB) m/z: 561 (M+H)$^+$.

Example 197

N$^1$-(4-Chloro-3-methylphenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

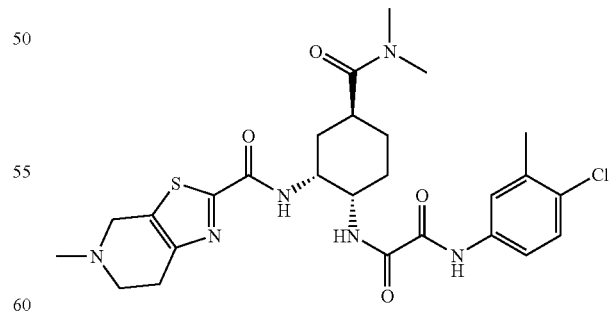

The title compound was obtained by hydrolyzing the compound obtained in Referential Example 257, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.47-1.53 (1H, m), 1.68-1.80 (3H, m), 1.98-2.09 (2H, m), 2.29 (3H, s), 2.79 (3H, s), 2.80-3.00 (1H, m), 2.95 (6H, s), 3.17-3.19 (3H, m), 3.40-3.80 (1H, m), 3.93-4.02 (1H, m), 4.44-4.56 (3H, m), 7.38 (1H, d, J=8.8 Hz), 7.65 (1H, d, J=8.8 Hz), 7.74 (1H, s), 8.75 (1H, d, J=7.8 Hz), 8.96 (1H, d, J=8.0 Hz), 10.69 (1H, s). MS (FAB) m/z: 561 (M+H)$^+$.

Example 198

N$^1$-(4-Chloro-2-fluorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]-amino}cyclohexyl)ethanediamide hydrochloride

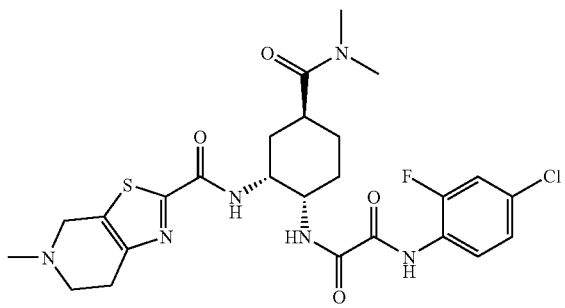

The title compound was obtained by hydrolyzing the compound obtained in Referential Example 258, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.40-1.55 (1H, m), 1.58-1.80 (3H, m), 1.95-2.12 (2H, m), 2.77 (3H, s), 2.80-3.00 (1H, m), 2.91 (3H, s), 2.92 (3H, s), 3.10-3.40 (2H, m), 3.40-3.80 (2H, m), 3.95-4.05 (1H, m), 4.30-4.80 (3H, m), 7.29 (1H, d, J=8.5 Hz), 7.52 (1H, dd, J=10.3, 2.0 Hz), 7.61 (1H, t, J=8.4 Hz), 8.72 (1H, d, J=6.8 Hz), 9.00-9.20 (1H, br), 10.38 (1H, s), 11.20-11.45 (1H, br). MS (FAB) m/z: 565 (M+H)$^+$.

Example 199

N$^1$-(2,4-Dichlorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl] amino}cyclohexyl)ethanediamide hydrochloride

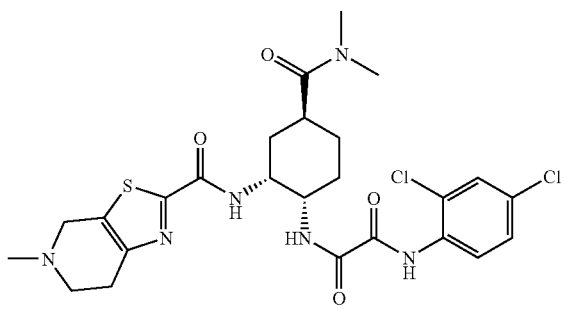

The compound (300 mg) obtained in Referential Example 270 was dissolved in N,N-dimethylformamide (5 ml), and 2,4-dichloroaniline (165 mg), 1-(dimethylaminopropyl)-3-ethylcarbodiimide hydrochloride (260 mg) and 1-hydroxybenzotriazole monohydrate (91 mg) were added to stir the mixture at room temperature for 2 days. The solvent was distilled off under reduced pressure, a saturated aqueous solution of sodium hydrogencarbonate and methylene chloride were added to the residue to conduct liquid separation, and the resultant organic layer was dried over anhydrous sodium sulfate. After the solvent was distilled off under reduced pressure, the residue was purified by column chromatography on silica gel (methylene chloride:methanol=47:3) to obtain a free base of the title compound. This product was dissolved in methylene chloride, a 1N ethanol solution (108 μl) of hydrochloric acid was added, and the solvent was distilled off under reduced pressure. A small amount of methanol was added to the residue, and diethyl ether was added dropwise while irradiating with ultrasonic waves to collect precipitate formed by filtration. This product was washed with diethyl ether to obtain the title compound (60 mg).

$^1$H-NMR (DMSO-d$_6$) δ: 1.45-1.77 (4H, m), 2.03-2.12 (2H, m), 2.79 (3H, s), 2.92-2.96 (7H, m), 3.25 (2H, br.s), 3.49 (1H, br.s), 3.69 (1H, br.s), 3.98-4.04 (1H, m), 4.40-4.43 (1H, m), 4.45 (1H, br.s), 4.69 (1H, br.s), 7.48 (1H, dd, J=8.5, 2.4 Hz), 7.75 (1H, d, J=2.4 Hz), 7.89 (1H, d, J=8.5 Hz), 8.75 (1H, d, J=6.8 Hz), 9.21 (1H, br.s), 10.25 (1H, s), 11.55 (1H, br.s). MS (FAB) m/z: 581 (M+H)$^+$.

Example 200

N$^1$-(3,4-Dichlorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl] amino}cyclohexyl)ethanediamide

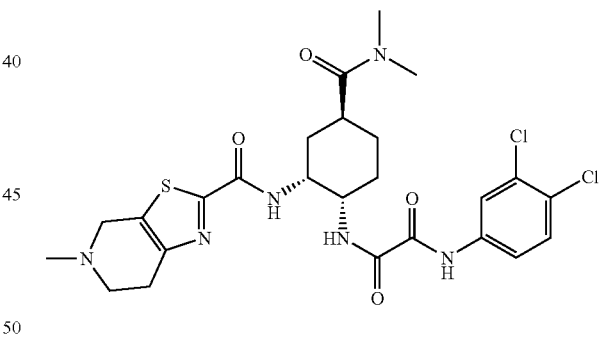

3,4-Dichloroaniline (1.62 g) was dissolved in methylene chloride (20 ml), and triethylamine (1.67 ml) and methyl chlorooxoacetate (1.01 ml) were successively added under ice cooling, and the mixture was stirred at room temperature for 21 hours. Water and methylene chloride were added to the reaction mixture to conduct liquid separation. The resultant water layer was extracted with methylene chloride. Organic layers were combined and dried over anhydrous magnesium sulfate, and the solvent was distilled off under reduced pressure. The resultant residue was dissolved in ethanol (50 ml), and water (25 ml) and lithium hydroxide monohydrate (629 mg) were successively added to stir the mixture at room temperature for 12.5 hours. Lithium hydroxide monohydrate (629 mg) was additionally added to stir the mixture at room temperature for 5.5 hours. The reaction mixture was concentrated under reduced pressure to solidity. Water and diethyl ether were added to the residue to conduct liquid separation. Hydrochloric acid was added to the resultant water layer to acidify it. Solid formed were collected by filtration to obtain a crude product (1.62 g) of 2-(3,4-dichloroanilino)-2-oxoacetic acid as a colorless solid. This crude product (191 mg) and the compound obtained in Referential Example 253 were dissolved in N,N-dimethylformamide (10 ml), and 1-hydroxybenzotriazole monohydrate (110 mg) and 1-(3-dimethylaminopropyl)-3-ethylcarbodiimide hydrochloride (157 mg) were added to stir the mixture at room temperature for 67 hours. The solvent was distilled off under reduced pressure, a saturated aqueous solution of sodium hydrogencarbonate and ethyl acetate were added to the residue to conduct liquid separation, and the resultant water layer was extracted 3 times with methylene chloride. Organic layers were combined and dried over anhydrous sodium sulfate. After the solvent was distilled off under reduced pressure, the residue was purified by column chromatography on silica gel (methylene chloride:methanol=95:5) to obtain the title compound (154 mg).

$^1$H-NMR (CDCl$_3$) δ: 1.77-1.88 (1H, m), 1.91-1.95 (1H, m), 2.05-2.10 (3H, m), 2.51 (3H, s), 2.77-2.99 (6H, m), 2.95 (3H, s), 3.05 (3H, s), 3.68 (1H, d, J=15.5 Hz), 3.74 (1H, d, J=15.5 Hz), 4.08-4.13 (1H, m), 4.69-4.72 (1H, m), 7.40 (2H, s), 7.41 (1H, d, J=7.7 Hz), 7.90 (1H, s), 8.01 (1H, d, J=7.7 Hz), 9.27 (1H, s). MS (ESI) m/z: 581 (M+H)$^+$.

Example 201

$N^1$-(2,4-Difluorophenyl)-$N^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide Hydrochrolide

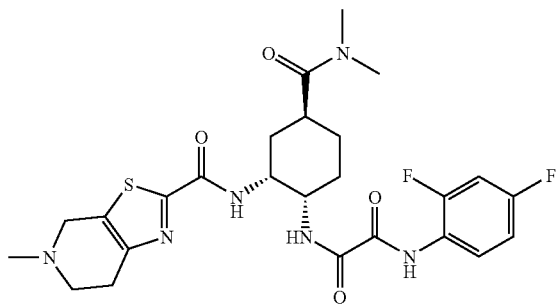

The title compound was obtained by hydrolyzing the compound obtained in Referential Example 259 and condensing the hydrolyzate with the compound obtained in Referential Example 253 in a similar manner to the process described in Example 191.

$^1$H-NMR (CDCl$_3$) δ: 1.55-1.62 (1H, m), 1.67-1.98 (2H, m), 2.01-2.18 (4H, m), 2.52 (3H, s), 2.77-3.00 (4H, m), 2.95 (3H, s), 2.99 (3H, s), 3.65-3.78 (2H, m), 4.06-4.15 (1H, m), 4.66-4.73 (1H, m), 6.85-6.94 (2H, m), 7.38 (1H, d, J=8.5 Hz), 7.96 (1H, d, J=7.3 Hz), 8.22-8.29 (1H, m), 9.36 (1H, br).

Example 202

$N^1$-(3,4-Difluorophenyl)-$N^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide

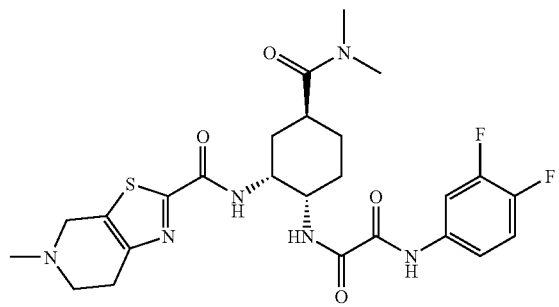

The title compound was obtained by hydrolyzing the compound obtained in Referential Example 260 and condensing the hydrolyzate with the compound obtained in Referential Example 253 in a similar manner to the process described in Example 191.

$^1$H-NMR (CDCl$_3$) δ: 1.56-1.73 (1H, m), 1.77-1.99 (2H, m), 2.00-2.18 (4H, m), 2.52 (3H, s), 2.75-3.00 (4H, m), 2.95 (3H, s), 3.06 (3H, s), 3.64-3.79 (2H, m), 4.05-4.14 (1H, m), 4.68-4.75 (1H, m), 7.09-7.21 (2H, m), 7.38 (1H, d, J=8.8 Hz), 7.72 (1H, ddd, J=12.0, 7.1, 2.6 Hz), 7.95 (1H, d, J=7.8 Hz), 9.22 (1H, br).

Example 203

$N^1$-((1S,2R,4S)-4-[(Dimethylamino)carbonyl]-2-{[(5-methyl-4,5,6,7-tetrahydrothiazolo[5,4-c]pyridin-2-yl)carbonyl]-amino}cyclohexyl)-$N^2$-(pyridin-4-yl)ethanediamide hydrochloride

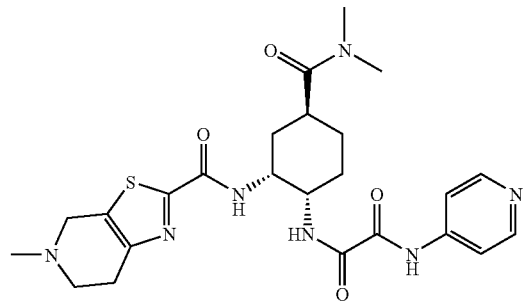

The title compound was obtained by hydrolyzing the compound obtained in Referential Example 261, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.40-2.10 (6H, m), 2.77 (3H, s), 2.927 (3H, s), 2.933 (3H, s), 3.05-4.20 (8H, m), 4.40-4.55 (1H, m), 8.27 (2H, d, J=6.8 Hz), 8.67 (1H, d, J=8.0 Hz), 8.71 (2H, d, J=6.8 Hz), 9.10-9.30 (1H, br), 11.81 (1H, s). MS (FAB) m/z: 514 (M+H)$^+$.

Example 204

N¹-(5-Bromopyridin-2-yl)-N²-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

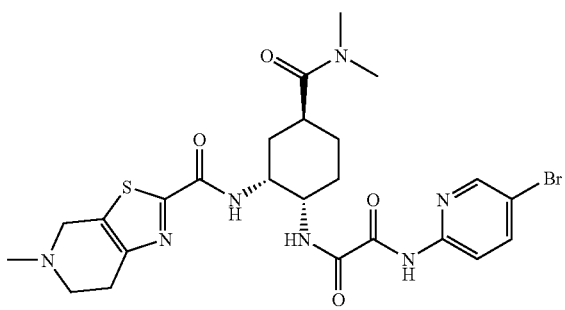

The title compound was obtained by hydrolyzing the compound obtained in Referential Example 262, condensing the hydrolyzate with the compound obtained in Referential Example 253 and then treating the condensation product with hydrochloric acid in a similar manner to the process described in Example 195.

¹H-NMR (DMSO-$d_6$) δ: 1.43-1.57 (1H, m), 1.61-1.81 (3H, m), 1.98-2.15 (2H, m), 2.79 (3H, s), 2.86 (3H, s), 2.89-3.01 (4H, m), 3.18 (2H, br.s), 3.50 (2H, br.s), 3.95-4.05 (1H, m), 4.35-4.62 (3H, m), 7.97 (1H, d, J=9.0 Hz), 8.12 (1H, dd, J=9.0, 2.4 Hz), 8.52 (1H, d, J=2.4 Hz), 8.70 (1H, d, J=7.5 Hz), 9.18 (1H, d, J=7.5 Hz), 10.25 (1H, br.s). MS (FAB) m/z: 592 (M+H)⁺.

Example 205

N¹-(6-Chloropyridin-3-yl)-N 2-((1S,2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

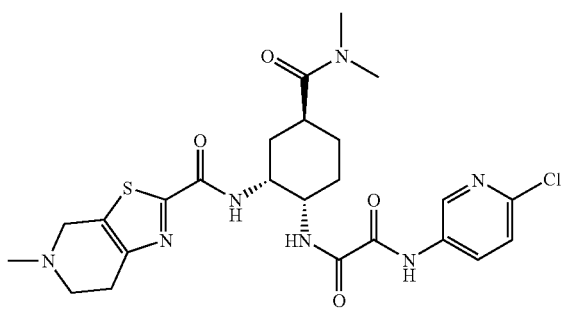

The compound (200 mg) obtained in Referential Example 263, which was a crude product, was dissolved in methanol (10 ml) to heat the solution to 50° C., and a 1N aqueous solution (3 ml) of sodium hydroxide to stir the mixture for 5 minutes. To this mixture was added 1N hydrochloric acid to adjust the pH to a weak acidity. The solvent was distilled off under reduced pressure to obtain residue containing 2-[(2-chloropyridin-5-yl)amino]-2-oxoacetic acid. This residue and the compound (250 mg) obtained in Referential Example 253 were dissolved in N,N-dimethylformamide (5 ml), and 1-(3-dimethylaminopropyl)-3-ethylcarbodiimide hydrochloride (328 mg) and 1-hydroxybenzotriazole monohydrate (46 mg) were added to stir the mixture at room temperature for 3 days. The solvent was distilled off under reduced pressure, and a saturated aqueous solution of sodium hydrogencarbonate and methylene chloride were added to the residue to conduct liquid separation. The resultant organic layer was dried over anhydrous sodium sulfate, the solvent was distilled off under reduced pressure, and the residue was purified by column chromatography on silica gel (methylene chloride:methanol=47:3) to obtain a free base of the title compound as a pale yellow solid. This product was dissolved in methylene chloride, a 1N ethanol solution (862 µl) of hydrochloric acid was added, and the solvent was distilled off under reduced pressure. A small amount of methanol was added to the residue, and ethyl acetate and diethyl ether were added dropwise while irradiating with ultrasonic waves to collect precipitate formed by filtration. This product was washed with diethyl ether to obtain the title compound (229 mg).

¹H-NMR (DMSO-$d_6$) δ: 1.46-1.75 (4H, m), 1.99-2.09 (2H, m), 2.79 (3H, s), 2.92-2.95 (7H, m), 3.12-3.53 (3H, m), 3.70 (1H, br.s), 3.99-4.06 (1H, m), 4.44 (2H, br.s), 4.69, 4.73 (1H, each s), 7.53 (1H, d, J=8.5 Hz), 8.23-8.25 (1H, m), 8.72-8.77 (1H, m), 8.85 (1H, s), 9.07, 9.16 (1H, each d, J=8.1 Hz), 11.09 (1H, d, J=8.1 Hz), 11.78 (1H, br.s). MS (FAB) m/z: 548 (M+H)⁺.

Example 206

N¹-(6-Chloropyridazin-3-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride

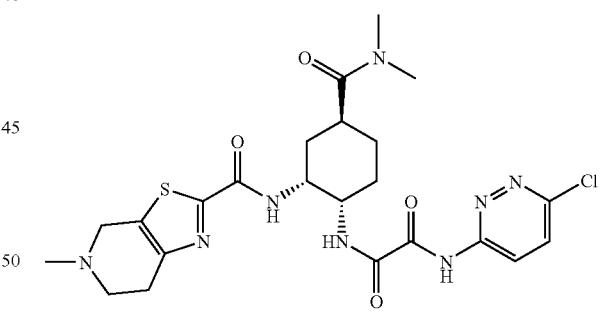

The title compound was obtained by hydrolyzing the compound obtained in Referential Example 264, condensing the hydrolyzate with the compound obtained in Referential Example 253 and then treating the condensation product with hydrochloric acid in a similar manner to the process described in Example 191.

¹H-NMR (DMSO-$d_6$) δ: 1.44-1.57 (1H, m), 1.62-1.80 (3H, m), 2.00-2.10 (2H, m), 2.79 (3H, s), 2.86 (3H, br.s), 2.94 (3H, s), 2.95-3.01 (1H, m), 3.14-3.23 (2H, m), 3.45-3.63 (2H, m), 3.96-4.08 (1H, m), 4.40-4.60 (3H, m), 7.97 (1H, d, J=9.3 Hz), 8.26 (1H, d, J=9.3 Hz), 8.69 (1H, d, J=7.6 Hz), 9.20 (1H, d, J=7.6 Hz), 11.06 (1H, s). MS (FAB) m/z: 549 (M+H)⁺.

Example 207

N¹-(5-Chlorothiazol-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

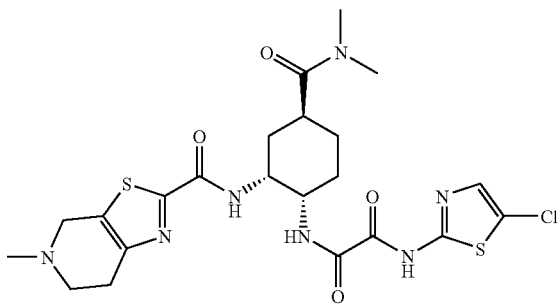

The title compound was obtained by hydrolyzing the compound obtained in Referential Example 265, condensing the hydrolyzate with the compound obtained in Referential Example 253 and then treating the condensation product with hydrochloric acid in a similar manner to the process described in Example 191.

¹H-NMR (DMSO-$d_6$) δ: 1.35-2.10 (6H, m), 2.77 (3H, s), 2.92 (3H, s), 2.93 (3H, s), 3.05-4.23 (8H, m), 4.32-4.80 (2H, m), 7.59 (1H, s), 8.63 (1H, d, J=7.6 Hz), 9.14 (1H, d, J=7.6 Hz). MS (FAB) m/z: 554 (M+H)⁺.

Example 208

N¹-(5-Chloropyridin-2-yl)-N²-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)ethanediamide hydrochloride

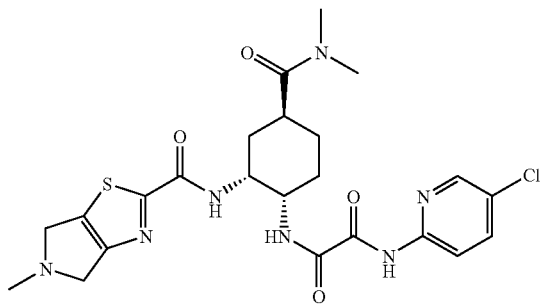

The compound (210 mg) obtained in Referential Example 266 and the compound (350 mg) obtained in Referential Example 272 were dissolved in N,N-dimethylformamide (15 ml), and 1-hydroxybenzotriazole monohydrate (205 mg) and 1-(3-dimethylaminopropyl)-3-ethylcarbodiimide hydrochloride (290 mg) were added to stir the mixture at room temperature for 20 hours. The solvent was distilled off under reduced pressure, and a saturated aqueous solution of sodium hydrogencarbonate and methylene chloride were added to the residue to conduct liquid separation. The resultant organic layer was dried over anhydrous sodium sulfate, the solvent was distilled off under reduced pressure, and the residue was purified by column chromatography on silica gel (methylene chloride:methanol=20:1). The thus-obtained pale yellow solids were dissolved in methylene chloride, a 1N ethanol solution (0.46 ml) of hydrochloric acid was added, and the solvent was distilled off under reduced pressure. Methanol and diethyl ether were added to the residue, and precipitate formed was collected by filtration to obtain the title compound (248 mg).

¹H-NMR (DMSO-$d_6$) δ: 1.47-1.50 (1H, m), 1.69-1.76 (3H, m), 1.98-2.06 (2H, m), 2.79 (3H, s), 2.95 (3H, s), 2.98-3.05 (1H, m), 3.10 (3H, s), 3.49-4.62 (6H, m), 7.98-8.03 (2H, m), 8.45 (1H, s), 8.73 (1H, d, J=7.6 Hz), 9.10 (1H, d, J=8.0 Hz), 10.30 (1H, s). MS (FAB) m/z: 534 (M+H)⁺.

Example 209

N-{(1R,2S,5S)-2-{[2-(4-Chloroanilino)acetyl]amino}-5-[(dimethylamino)carbonyl]cyclohexyl}-5-methyl-4,5,6,7-tetrahydrothiazolo[5,4-c]pyridine-2-carboxamide hydrochloride

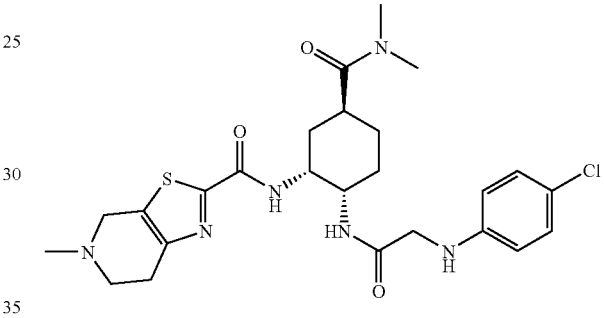

The compound (2.3 g) obtained in Referential Example 267 was dissolved in ethanol (10 ml), and a 1N aqueous solution (20 ml) of sodium hydroxide was added to stir the mixture at room temperature for 2 hours. After 1N hydrochloric acid (20 ml) was added to the reaction mixture, the mixture was diluted with water and stirred for 30 minutes. Insoluble matter deposited was collected by filtration to obtain 2-(4-chloroanilino)acetic acid (1.05 g) as a colorless solid. This solid and the compound (0.25 g) obtained in Referential Example 253 were dissolved in N,N-dimethylformamide (10 ml), and 1-hydroxybenzotriazole monohydrate (0.11 g) and 1-(3-dimethylaminopropyl)-3-ethylcarbodiimide hydrochloride (0.23 g) were added to stir the mixture at room temperature for 4 days. After the reaction mixture was diluted with chloroform and washed with a saturated aqueous solution of sodium hydrogencarbonate and saturated aqueous solution of sodium chloride, the resultant organic layer was dried over anhydrous sodium sulfate. The solvent was distilled off under reduced pressure, and the residue was purified by column chromatography on silica gel (chloroform:methanol=97:3). The thus-obtained pale yellow solid was dissolved in ethanol, a 1N ethanol solution of hydrochloric acid was added, and the solvent was distilled off under reduced pressure. Methanol and diethyl ether were added to the residue, and precipitate formed was collected by filtration to obtain the title compound (0.15 g).

¹H-NMR (DMSO-$d_6$) δ: 1.35-1.41 (1H, m), 1.59-1.80 (3H, m), 1.82-1.95 (2H, m), 2.76 (3H, s), 2.93 (3H, s), 2.94 (3H, s), 2.99-3.10 (1H, m), 3.10-3.22 (2H, m), 3.42-3.60 (2H, m), 3.60-3.77 (2H, m), 3.80-3.90 (1H, m), 4.35-4.48 (2H, m), 4.68-4.80 (1H, m), 6.40 (1H, d, J=6.7 Hz), 6.44

(1H, d, J=6.7 Hz), 6.90 (1H, d, J=6.7 Hz), 7.00 (1H, d, J=6.7 Hz), 7.70-7.89 (1H, m), 8.35-8.42 (1H, m), 11.05-11.38 (1H, m).

Example 210

N-{(1R,2S,5S)-2-{[2-(4-Chloro-2-fluoroanilino)acetyl]amino}-5-[(dimethylamino)carbonyl]cyclohexyl}-5-methyl-4,5,6,7-tetrahydrothiazolo[5,4-c]pyridine-2-carboxamide hydrochloride

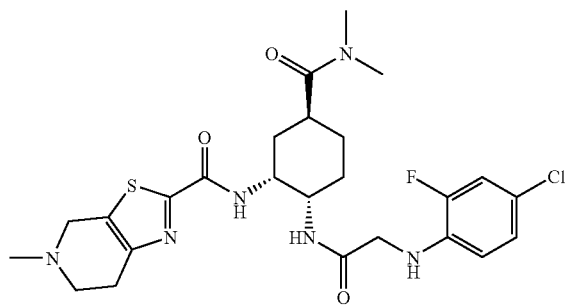

The title compound was obtained by hydrolyzing the compound obtained in Referential Example 268, condensing the hydrolyzate with the compound obtained in Referential Example 253 and then treating the condensation product with hydrochloric acid in a similar manner to the process described in Example 209.

$^1$H-NMR (DMSO-d$_6$) δ: 1.35-1.42 (1H, m), 1.55-1.78 (3H, m), 1.80-2.00 (2H, m), 2.76 (3H, s), 2.92 (3H, s), 2.94 (3H, s), 2.99-3.10 (1H, m), 3.10-3.22 (2H, m), 3.42-3.60 (2H, m), 3.60-3.77 (2H, m), 3.85-4.00 (1H, m), 4.33-4.48 (2H, m), 4.65-4.80 (1H, m), 6.41 (1H, t, J=8.8 Hz), 6.73 (1H, dt, J=8.8, 1.2 Hz), 7.08 (1H, dd, J=11.7, 1.2 Hz), 7.78-7.92 (1H, m), 8.35-8.42 (1H, m), 11.18-11.50 (1H, m).

Example 211

N-{(1R,2S,5S)-2-{[(5-Chloroindol-2-yl)carbonyl]amino}-5-[(dimethylamino)carbonyl]cyclohexyl}-4,5,6,7-tetrahydrothiazolo[5,4-c]pyridine-2-carboxamide hydrochloride

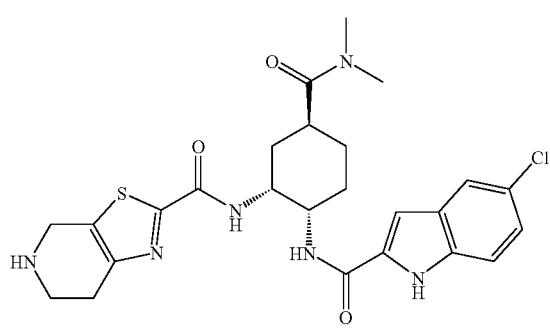

The title compound was obtained by condensing the compound obtained in Referential Example 432 with the compound obtained in Referential Example 34 and then treating the condensation product with hydrochloric acid in a similar manner to the process described in Example 2.

$^1$H-NMR (DMSO-d$_6$) δ: 1.45-1.60 (1H, m), 1.70-2.15 (6H, m), 2.80 (3H, s), 2.97 (3H, s), 2.95-3.15 (2H, m), 3.35-3.55 (2H, m), 4.05-4.20 (1H, m), 4.46 (2H, s), 4.50-4.65 (1H, m), 7.05 (1H, s), 7.16 (1H, dd, J=8.8, 2.2 Hz), 7.41 (1H, d, J=8.8 Hz), 7.68 (1H, s), 8.30-8.45 (1H, br), 9.30-9.50 (1H, br), 11.78 (1H, s). MS (ESI) m/z: 529 (M+H)$^+$.

Example 212

N-{(1R,2S,5S)-2-{[(5-Chloroindol-2-yl)carbonyl]amino}-5-[(dimethylamino)carbonyl]cyclohexyl}-5-(4,5-dihydrooxazol-2-yl)-4,5,6,7-tetrahydrothiazolo[5,4-c]pyridine-2-carboxamide

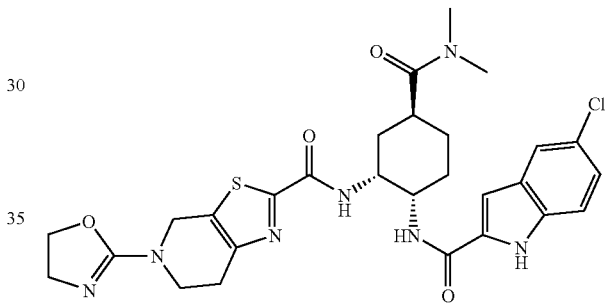

The compound (250 mg) obtained in Example 211 was suspended in methylene chloride, and a saturated aqueous solution of sodium hydrogencarbonate was added to fully stir the mixture. The resultant organic layer was separated and dried over anhydrous magnesium sulfate. Triethylamine (0.5 ml) and bromoethyl isocyanate (43 µl) were then added to stir the mixture at room temperature for 20 hours. A saturated aqueous solution of sodium hydrogencarbonate was added to the reaction mixture to separate an organic layer. The organic layer was dried over anhydrous magnesium sulfate. The solvent was distilled off under reduced pressure, and the residue was purified by column chromatography on silica gel (methylene chloride:methanol=22:3) to obtain the title compound (227 mg).

$^1$H-NMR (CDCl$_3$) δ: 1.50-2.15 (4H, m), 2.15-2.40 (2H, m), 2.80-3.00 (1H, m), 2.97 (3H, s), 3.11 (3H, s), 3.70-3.95 (4H, m), 4.10-4.30 (1H, m), 4.30-4.50 (2H, m), 4.60-4.70 (1H, m), 4.74 (2H, s), 6.85 (1H, s), 7.21 (1H, dd, J=8.8, 2.2 Hz), 7.34 (1H, d, J=8.8 Hz), 7.50 (1H, br.s), 7.62 (1H, s), 7.87 (1H, br.s), 9.48 (1H, br.s). MS (ESI) m/z: 598 (M+H)$^+$.

Example 213

N-{(1R,2S,5S)-2-{[(5-Chloro-4-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

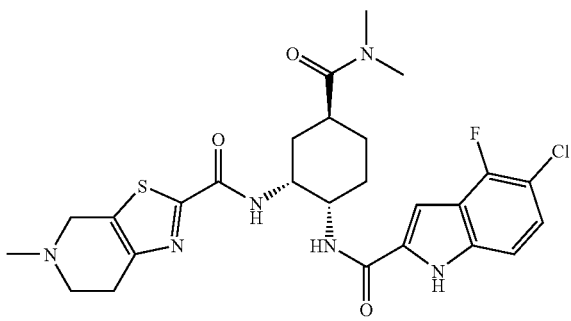

The compound (140 mg) obtained in Referential Example 144 was dissolved in N,N-dimethylformamide (10 ml), and the compound (100 mg) obtained in Referential Example 274, 1-(3-dimethylaminopropyl)-3-ethylcarbodiimide hydrochloride (140 mg) and 1-hydroxybenzotriazole monohydrate (110 mg) were added to stir the mixture at room temperature for 18 hours. The solvent was distilled off under reduced pressure, and the residue was partitioned in water-ethyl acetate, and a water layer was extracted with ethyl acetate. The resultant organic layers were combined, washed with saturated aqueous solution of sodium chloride and then dried over anhydrous sodium sulfate. The solvent was distilled off under reduced pressure, and the residue was purified by column chromatography on silica gel (methanol: methylene chloride=1:19), giving tert-butyl (1R,2S,5S)-2-{[(5-chloro-4-fluoroindol-2-yl)carbonyl]amino}-5-[(dimethylamino)carbonyl]cyclohexylcarbamate (260 mg).

The thus-obtained powder was dissolved in methylene chloride (5 ml), and a 4N dioxane solution (1.2 ml) of hydrochloric acid was added. After the reaction mixture was stirred at room temperature for 3.5 hours, the solvent was distilled off under reduced pressure. Methylene chloride (10 ml) was added to the residue, and the mixture was concentrated. After this process was repeated 3 times, the residue was dried under reduced pressure to obtain crude N-{(1S,2R,4S)-2-amino-4-[(dimethylamino)carbonyl]-cyclohexyl}-5-chloro-4-fluoroindole-2-carboxamide. This product was dissolved in N,N-dimethylformamide (50 ml), and the compound (150 mg) obtained in Referential Example 10, 1-(3-dimethylaminopropyl)-3-ethylcarbodiimide hydrochloride (140 mg) and 1-hydroxybenzotriazole monohydrate (110 mg) were added to stir the mixture at room temperature for 18 hours. The solvent was distilled off under reduced pressure, and the residue was partitioned in a mixed solvent of water-ethyl acetate-tetrahydrofuran, and a water layer was extracted with ethyl acetate. The resultant organic layers were combined, washed with saturated aqueous solution of sodium chloride and then dried over anhydrous sodium sulfate. The solvent was distilled off under reduced pressure, and the residue was purified by column chromatography on silica gel (methanol:methylene chloride 1:19) to obtain a free base of the title compound (270 mg). This product was dissolved in methylene chloride (10 ml), and a 1N ethanol solution (0.72 ml) of hydrochloric acid was added to stir the mixture at room temperature for 30 minutes. Crystals deposited were collected by filtration to obtain the title compound (200 mg).

$^1$H-NMR (DMSO-$d_6$) δ: 1.24-1.98 (6H, m), 2.33-3.33 (6H, m), 2.81 (3H, s), 2.90 (3H, s), 2.99 (3H, s), 4.12 (1H, br.s), 4.30-4.70 (1H, m), 4.60 (1H, br.s), 7.21 (1H, s), 7.27 (2H, br.s), 8.37 (1H, d, J=8.1 Hz), 8.43 (1H, d, J=7.6 Hz), 12.11 (1H, s). MS (FAB) m/z: 561 (M+H)$^+$.

Example 214

N-{(1R,2S,5S)-2-{[(5-Chloro-3-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

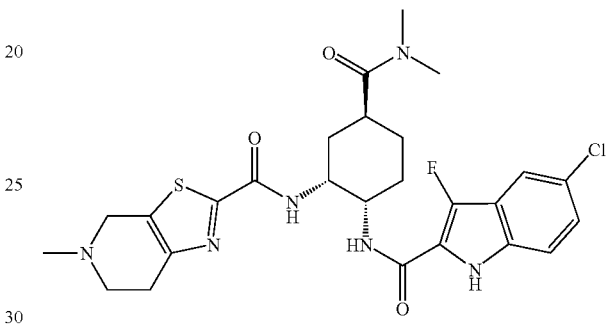

The compound (250 mg) obtained in Referential Example 279 was dissolved in methylene chloride (60 ml), and a 4N dioxane solution (1.3 ml) of hydrochloric acid was added. After the reaction mixture was stirred at room temperature for 5.5 hours, a 4N dioxane solution (0.65 ml) of hydrochloric acid was additionally added, and the mixture was stirred at room temperature for 1 hour. The solvent was distilled off under reduced pressure, methylene chloride (10 ml) was added to the residue, and the mixture was concentrated. This process was repeated 3 times. The residue was dried under reduced pressure, and the thus-obtained crude product was dissolved in N,N-dimethylformamide (50 ml), and the compound (160 mg) obtained in Referential Example 10, 1-(3-dimethylaminopropyl)-3-ethylcarbodiimide hydrochloride (150 mg) and 1-hydroxybenzotriazole monohydrate (120 mg) were added to stir the mixture at room temperature for 18 hours. The solvent was distilled off under reduced pressure, and the residue was partitioned in a mixed solvent of water-ethyl acetate, and a water layer was extracted with ethyl acetate. The resultant organic layers were combined, washed with saturated aqueous solution of sodium chloride and then dried over anhydrous sodium sulfate. The solvent was distilled off under reduced pressure, and the residue was purified twice by column chromatography on silica gel (methanol:methylene chloride=2:23→1:9) to obtain a free base (260 mg) of the title compound. This product was dissolved in methylene chloride, and a 1N ethanol solution (0.69 ml) of hydrochloric acid was added to stir the mixture at room temperature for 30 minutes. The solvent was distilled off. The residue was dissolved in methanol, and diethyl ether and hexane were added. The thus-obtained crystals were collected by filtration to obtain the title compound (230 mg).

$^1$H-NMR (DMSO-$d_6$) δ: 1.50-1.56 (1H, m), 1.73-1.78 (3H, m), 1.94-2.02 (2H, m), 2.33-3.55 (6H, m), 2.80 (3H, s), 2.92 (3H, s), 2.98 (3H, s), 4.17 (1H, br.s), 4.30-4.80 (1H, br), 4.62 (1H, br.s), 7.25 (1H, d, J=8.8, 1.7 Hz), 7.40 (1H, d, J=8.8, 1.7 Hz), 7.65 (1H, d, J=1.7 Hz), 7.72 (1H, d, J=5.9 Hz), 8.74 (1H, d, J=8.0 Hz), 11.12 (1H, br), 11.71 (1H, s). MS (FAB) m/z: 561 (M+H)$^+$.

Example 215

N-{(1R,2S,5S)-2-{[(3-Bromo-5-chloroindol-2-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

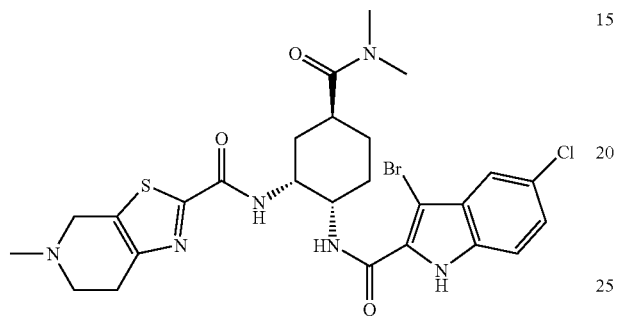

The title compound was obtained by treating the compound obtained in Referential Example 282 with a 4N dioxane solution of hydrochloric acid and condensing the-thus treated compound with the compound obtained in Referential Example 10 in a similar manner to the process described in Example 214.

$^1$H-NMR (DMSO-d$_6$) δ: 1.51-2.01 (6H, m), 2.33-3.29 (7H, m), 2.81 (3H, s), 2.88 (3H, s), 3.01 (3H, s), 4.20 (1H, br.s), 4.48 (1H, br), 4.70-4.73 (1H, m), 7.29 (1H, dd, J=8.9, 1.8 Hz), 7.45-7.49 (2H, m), 7.80 (1H, d, J=7.6 Hz), 8.76 (1H, d, J=8.8 Hz), 12.31 (1H, s). MS (FAB) m/z: 622 (M+H)$^+$.

Example 216

N-{(1R,2S,5S)-2-{[(3-Chloro-5-fluoroindol-2-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

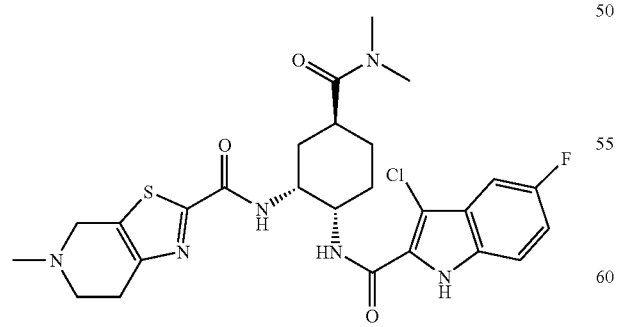

The title compound was obtained from the compound obtained in Referential Example 253 and the compound obtained in Referential Example 284 in a similar manner to the process described in Example 5.

$^1$H-NMR (DMSO-d$_6$) δ: 1.40-1.51 (1H, m), 1.75-2.00 (5H, m), 2.79 (3H, s), 2.92 (3H, s), 2.99 (3H, s), 3.10-3.21 (3H, m), 3.29-3.41 (4H, m), 4.11-4.21 (1H, m), 4.62-4.75 (1H, m), 7.14 (1H, dt, J=8.8, 2.4 Hz), 7.24 (1H, dd, J=8.8, 2.4 Hz), 7.45 (1H, dd, J=8.8, 4.4 Hz), 7.69 (1H, d, J=2.5 Hz), 8.79 (1H, d, J=2.5 Hz), 12.10 (1H, s). MS (FAB) m/z: 561 (M+H)$^+$.

Example 217

N-{(1R,2S,5S)-2-{[(5-Chloro-3-formylindol-2-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

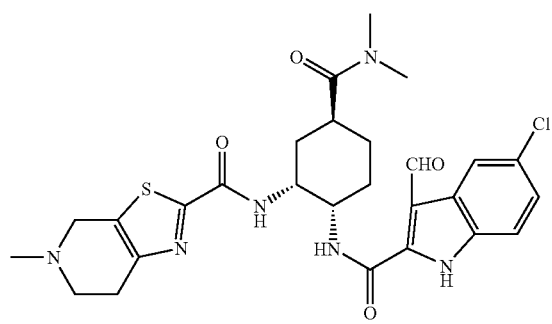

The title compound was obtained from the compound obtained in Referential Example 253 and the compound obtained in Referential Example 286 in a similar manner to the process described in Example 5.

$^1$H-NMR (DMSO-d$_6$) δ: 1.40-1.51 (1H, m), 1.75-1.89 (4H, m), 1.90-2.01 (1H, m), 2.80 (3H, s), 2.91 (3H, s), 3.03 (3H, s), 3.05-3.33 (3H, m), 3.60-3.71 (1H, m), 4.11-4.21 (1H, m), 4.32-4.44 (1H, m), 4.62-4.75 (2H, m), 7.35 (1H, dd, J=8.0, 1.4 Hz), 7.56 (1H, d, J=8.0 Hz), 8.21 (1H, d, J=1.4 Hz), 8.65 (1H, t, J=7.4 Hz), 9.92 (1H, d, J=6.8 Hz), 10.15 (1H, t, J=9.1 Hz), 13.00 (1H, dt, J=6.4). MS (FAB) m/z: 571 (M+H)$^+$.

Example 218

5-Chloro-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl-N$^3$,N$^3$-dimethylindole-2,3-dicarboxamide hydrochloride

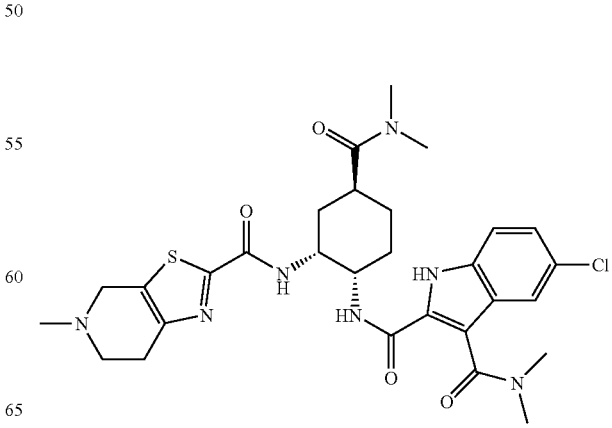

The title compound was obtained from the compound obtained in Referential Example 253 and the compound obtained in Referential Example 289 in a similar manner to the process described in Example 5.

$^1$H-NMR (DMSO-d$_6$) δ: 1.40-1.51 (1H, m), 1.75-2.01 (5H, m), 2.78 (9H, s), 2.93 (3H, s), 3.01 (3H, s), 3.10-3.33 (3H, m), 3.40-3.50 (1H, m), 3.65-3.75 (1H, m), 4.01-4.09 (1H, m), 4.32-4.44 (1H, m), 4.62-4.75 (2H, m), 7.25 (1H, d, J=8.0 Hz), 7.40-7.50 (2H, m), 8.62 (1H, br), 9.08 (1H, br), 12.28 (1H, br). MS (FAB) m/z: 614 (M+H)$^+$.

Example 219

N-{(1R,2S,5S)-2-[(6-Chloro-2-naphthoyl)amino]-5-[(dimethylamino)carbonyl]cyclohexyl}-5-methyl-4,5,6,7-tetrahydrothiazolo[5,4-c]pyridine-2-carboxamide hydrochloride

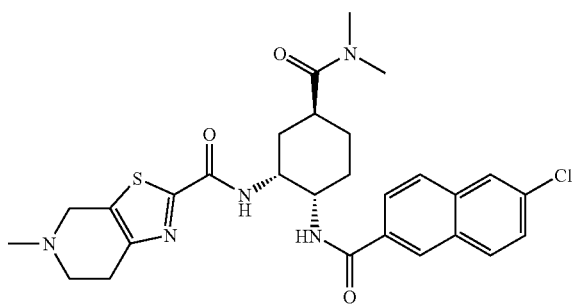

The compound (270 mg) obtained in Referential Example 294 was dissolved in methylene chloride (10 ml), and a 1N ethanol solution (10 ml) of hydrochloric acid was added to stir the mixture for 90 minutes. The solvent was distilled off under reduced pressure, and the resultant residue was dissolved in N,N-dimethylformamide (7 ml). The compound (110 mg) obtained in Referential Example 10, 1-(3-dimethylaminopropyl)-3-ethylcarbodiimide hydrochloride (100 mg) and 1-hydroxybenzotriazole monohydrate (70 mg) were added to stir the mixture at room temperature for 23 hours. The reaction mixture was concentrated under reduced pressure, and water was added to conduct extraction with ethyl acetate. The resultant organic layer was dried over anhydrous sodium sulfate. The solvent was distilled off under reduced pressure, and the residue was purified twice by column chromatography on silica gel (methylene chloride:methanol=20:1→10:1). The thus-obtained free base was dissolved in methanol, and a 1N ethanol solution (0.30 ml) of hydrochloric acid was added. The residue was washed with ethyl acetate to obtain the title compound (130 mg).

$^1$H-NMR (DMSO-d$_6$) δ: 1.45-1.60 (1H, m), 1.70-1.90 (3H, m), 1.90-2.10 (2H, m), 2.81 (3H, s), 2.91 (3H, s), 3.00 (3H, s), 3.00-3.22 (3H, m), 3.53 (2H, br), 4.10-4.20 (1H, m), 4.30-4.70 (3H, m), 7.59 (1H, dd, J=8.8, 2.2 Hz), 7.87 (1H, d, J=8.5 Hz), 7.96 (1H, d, J=8.5 Hz), 8.02 (1H, d, J=8.8 Hz), 8.10 (1H, d, J=2.2 Hz), 8.33 (1H, s), 8.43 (1H, d, J=8.1 Hz), 8.52 (1H, d, J=7.3 Hz). MS (FAB) m/z: 554 (M+H)$^+$.

Example 220

7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)cinnoline-3-carboxamide hydrochloride

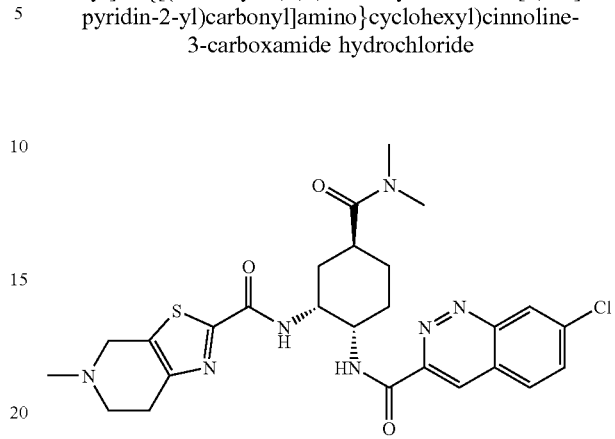

The title compound was obtained by treating the compound obtained in Referential Example 299 with an ethanol solution of hydrochloric acid and then condensing it with the compound obtained in Referential Example 10 in a similar manner to the process described in Example 219.

$^1$H-NMR (CDCl$_3$) δ: 1.50-1.65 (1H, m), 1.70-1.90 (3H, m), 2.05-2.15 (1H, m), 2.15-2.30 (1H, m), 2.81 (3H, s), 2.85-3.05 (8H, m), 3.15-3.25 (2H, m), 3.40-3.80 (1H, m), 4.25-4.80 (4H, m), 8.02 (1H, dd, J=8.8, 2.0 Hz), 8.38 (1H, d, J=8.8 Hz), 8.66 (1H, s), 8.91 (1H, s), 8.96 (1H, d, J=7.3 Hz), 9.53 (1H, br). MS (FAB) m/z: 556 (M+H)$^+$.

Example 221

N-{(1R,2S,5S)-2-{[(5-Chlorobenzimidazol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

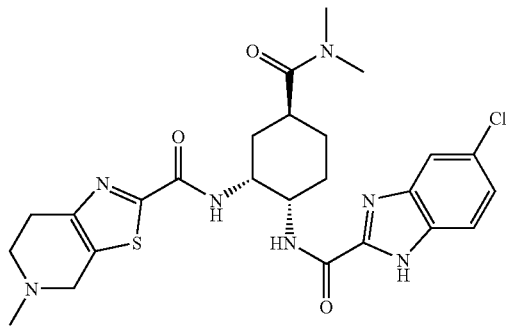

The title compound was obtained by treating the compound obtained in Referential Example 300 with an ethanol solution of hydrochloric acid and then condensing it with the compound obtained in Referential Example 10 in a similar manner to the process described in Example 219.

$^1$H-NMR (DMSO-d$_6$) δ: 1.45-1.60 (1H, m), 1.60-1.83 (3H, m), 2.00-2.20 (2H, m), 2.78 (3H, s), 2.92 (6H, s), 3.00-3.30 (3H, m), 3.47 (2H, br.s), 4.10-4.75 (4H, m), 7.30 (1H, d, J=8.8 Hz), 7.62 (1H, d, J=12.5 Hz), 7.63 (1H, s), 8.75-8.87 (1H, m), 9.09 (1H, dd, J=12.5, 8.8 Hz), 11.2-11.4 (1H, m). MS (FAB) m/z: 546 (M+H)⁺.

Example 222

N-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-7-fluoroisoquinoline-3-carboxamide hydrochloride

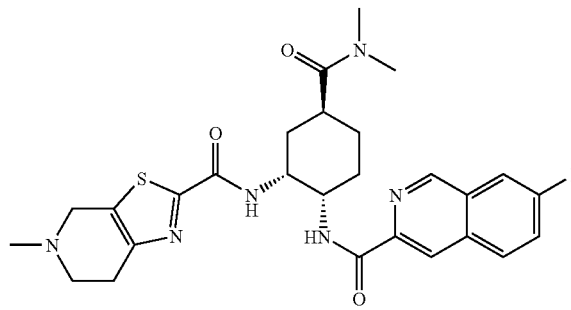

The title compound was obtained from the compound obtained in Referential Example 253 and the compound obtained in Referential Example 304 in a similar manner to the process described in Example 5.

¹H-NMR (DMSO-d₆) δ: 1.50-1.60 (1H, m), 1.70-1.85 (3H, m), 1.95-2.05 (1H, m), 2.10-2.20 (1H, m), 2.80 (3H, s), 2.90-3.90 (5H, m), 2.93 (3H, s), 2.96 (3H, s), 4.10-4.75 (4H, m), 7.75-7.85 (1H, m), 8.00-8.05 (1H, m), 8.30-8.35 (1H, m), 8.61 (1H, s), 8.93 (2H, d, J=7.3 Hz), 9.31 (1H, s). MS (FAB) m/z: 539 (M+H)⁺.

Example 223

N-{(1R,2S,5S)-2-{[(7-Chloro-2H-chromen-3-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

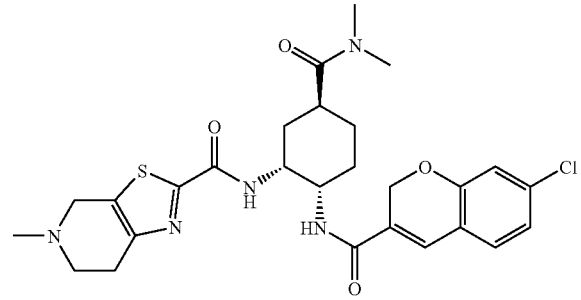

The compound (220 mg) obtained in Referential Example 252 was dissolved in methanol (10 ml), and 10% palladium on carbon (180 mg) was added to stir the mixture at room temperature for 4 hours in a hydrogen atmosphere. After the reaction mixture was filtered, the filtrate was concentrated under reduced pressure, and the residue was dissolved in N,N-dimethylformamide (30 ml). The compound (108 mg) obtained in Referential Example 306, 1-hydroxybenzotriazole monohydrate (78 mg) and 1-(3-dimethylaminopropyl)-3-ethylcarbodiimide hydrochloride (196 mg) were added to stir the mixture at room temperature for a night. The reaction mixture was concentrated under reduced pressure, and methylene chloride and a saturated aqueous solution of sodium hydrogencarbonate were added to the residue to conduct liquid separation. The resultant organic layer was dried over anhydrous sodium sulfate. The solvent was distilled off under reduced pressure, and the residue was purified by column chromatography on silica gel (methylene chloride: methanol=100:3) to obtain a pale yellow foamy substance. This foamy substance was dissolved in methylene chloride (2 ml), a 1N ethanol solution (363 μl) of hydrochloric acid was added, and the solvent was distilled off under reduced pressure. Diethyl ether was added to the residue. Precipitate formed was collected by filtration to obtain the title compound (175 mg).

¹H-NMR (DMSO-d₆) δ: 1.40-1.52 (1H, m), 1.55-1.96 (5H, m), 2.78 (3H, s), 2.90 (3H, s), 2.98 (3H, s), 3.01-3.12 (1H, m), 3.13-3.28 (2H, m), 3.40-3.85 (2H, m), 3.92-4.00 (1H, m), 4.35-4.80 (3H, m), 4.84 (1H, d, J=14.5 Hz), 4.89 (1H, d, J=14.5 Hz), 6.92 (1H, s), 6.98 (1H, dd, J=8.1, 1.7 Hz), 7.08 (1H, s), 7.17 (1H, d, J=8.3 Hz), 8.12 (1H, d, J=8.1 Hz), 8.34 (1H, d, J=8.1 Hz). MS (FAB) m/z: 558 (M+H)⁺.

Example 224

N-{(1R,2S,5S)-2-{[(E)-3-(4-Chlorophenyl)-2-propenoyl]-amino}-5-[(dimethylamino)carbonyl]cyclohexyl}-5-methyl-4,5,6,7-tetrahydrothiazolo[5,4-c]pyridine-2-carboxamide hydrochloride

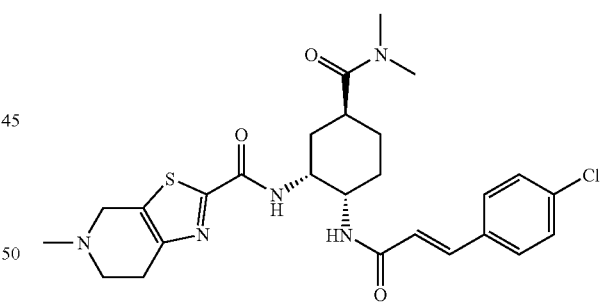

The title compound was obtained by treating the compound obtained in Referential Example 307 with an ethanol solution of hydrochloric acid and then condensing it with the compound obtained in Referential Example 10 in a similar manner to the process described in Example 219.

¹H-NMR (DMSO-d₆) δ: 1.35-1.55 (1H, m), 1.55-1.90 (4H, m), 2.79 (3H, s), 2.92 (3H, s), 2.99 (3H, s), 3.05-3.30 (3H, m), 3.40-3.55 (1H, m), 3.60-3.75 (1H, m), 3.93-4.03 (2H, m), 4.35-4.50 (1H, m), 4.50-4.60 (1H, m), 4.60-4.75 (1H, m), 6.65 (1H, d, J=15.7 Hz), 7.35 (1H, d, J=15.7 Hz), 7.44 (1H, d, J=8.6 Hz), 7.55 (1H, d, J=8.6 Hz), 8.03 (1H, d, J=8.1 Hz), 8.34 (1H, br.s), 11.25-11.70 (1H, br). MS (ESI) m/z: 530 (M+H)⁺.

Example 225

6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinoline-2-carboxamide hydrochloride

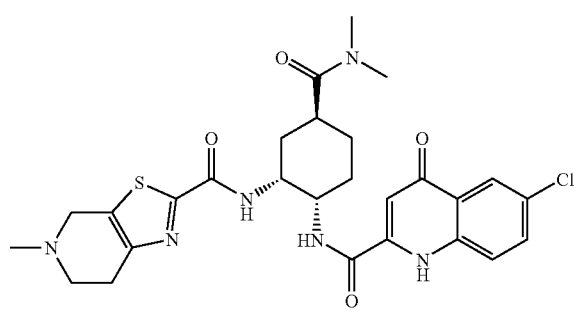

The title compound was obtained from the compound obtained in Referential Example 253 and the compound obtained in Referential Example 309 in a similar manner to the process described in Example 5.

$^1$H-NMR (DMSO-$d_6$) δ: 1.43-1.60 (1H, m), 1.65-2.10 (3H, m), 2.79 (3H, s), 2.92 (3H, s), 2.99 (3H, s), 3.05-3.20 (2H, m), 3.20-3.80 (5H, m), 4.08-4.20 (1H, m), 4.35-4.50 (1H, m), 4.60-4.70 (1H, m), 4.70 (1H, d, J=15.6 Hz), 6.77 (1H, br.s), 7.73 (1H, d, J=8.9 Hz), 7.94 (1H, d, J=8.9 Hz), 7.97 (1H, d, J=2.2 Hz), 8.54 (1H, br.s), 8.80-9.00 (1H, m), 11.20 (1H, br.d), 12.06 (1H, br.s). MS (ESI) m/z: 571 (M+H)$^+$.

Example 226 tert-Butyl 2-[({(1R,2S,5S)-2-{[(5-chloroindol-2-yl)carbonyl]amino}-5-[(dimethylamino)carbonyl]cyclohexyl}-amino)carbonyl]-4,6-dihydro-5H-pyrrolo[3,4-d]thiazole-5-carboxylate

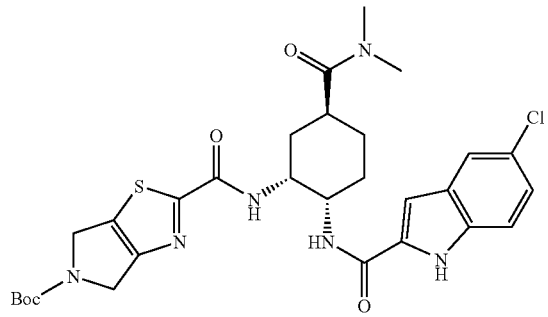

1) The compound (1.46 g) obtained in Referential Example 310 was dissolved in methylene chloride (10 ml), and an ethanol solution (10 ml) of hydrochloric acid was added at room temperature to stir the mixture for 1 hour. After completion of the reaction, the solvent was distilled off, ethanol was added, the mixture was concentrated, and diisopropyl ether was added to the residue to solidify it. The resultant solids were collected by filtration to obtain N-{(1S,2R,4S)-2-amino-4-[(dimethylamino)carbonyl]cyclohexyl}-5-chloroindole-2-carboxamide hydrochloride.

2) This product was dissolved in N,N-dimethylformamide (5 ml), and the compound (1.31 g) obtained in Referential Example 406, 1-hydroxybenzotriazole monohydrate (640 mg) and 1-(3-dimethylaminopropyl)-3-ethylcarbodiimide hydrochloride (1.36 g) were added to stir the mixture at room temperature for 3 days. The reaction mixture was concentrated, and methylene chloride and a saturated aqueous solution of sodium hydrogencarbonate were added to the residue to conduct liquid separation. The resultant organic layer was dried over anhydrous sodium sulfate. After the solvent was distilled off under reduced pressure, the residue was purified by column chromatography on silica gel (methanol:methylene chloride=1:19) to obtain the title compound (1.22 g).

$^1$H-NMR (CDCl$_3$) δ: 1.53 (9H, s), 1.70-2.40 (6H, m), 2.80-3.20 (7H, m), 4.15-4.25 (1H, m), 4.55-4.80 (5H, m), 6.83 (1H, d, J=1.5 Hz), 7.20 (1H, dd, J=8.8, 2.0 Hz), 7.33 (1H, d, J=8.8 Hz), 7.40-7.50 (1H, m), 7.61 (1H, br.s), 7.72-7.80 (1H, m), 9.41 (1H, br.s). MS (ESI) m/z: 615 (M+H)$^+$.

Example 227

5-Chloro-N-{(1S,2R,4S)-2-[[(5,6-dihydro-4H-pyrrolo[3,4-d]-thiazol-2-yl)carbonyl]amino]-4-[(dimethylamino)carbonyl]-cyclohexyl}indole-2-carboxamide hydrochloride

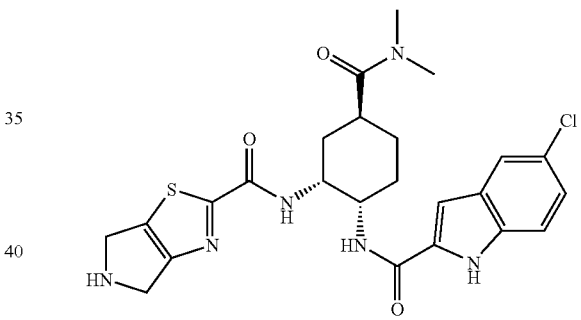

The compound (1.22 g) obtained in Referential Example 226 was dissolved in methylene chloride (5 ml), and an ethanol solution (10 ml) of hydrochloric acid was added to stir the mixture for 1 hour. After the reaction mixture was concentrated, a saturated aqueous solution of sodium hydrogencarbonate and methylene chloride were added to conduct liquid separation, and the resultant organic layer was dried over anhydrous sodium sulfate. The solvent was distilled off, and the residue was purified by column chromatography on silica gel (methanol:methylene chloride=1:9) to obtain a free base (636 mg) of the title compound as a colorless glassy solid. The free base (200 mg) was dissolved in a 1N ethanol solution (1 ml) of hydrochloric acid. After the solution was concentrated, ethyl acetate was added to solidify the residue. The thus-obtained colorless powder was collected by filtration and dried to obtain the title compound (195 mg).

$^1$H-NMR (DMSO-$d_6$) δ: 1.45-1.60 (1H, m), 1.70-1.90 (3H, m), 1.90-2.05 (2H, m), 2.80 (3H, s), 2.98 (3H, s), 2.98-3.15 (1H, m), 4.05-4.20 (1H, m), 4.44 (2H, br.s), 4.58 (3H, br.s), 7.05 (1H, d, J=1.5 Hz), 7.16 (1H, dd, J=8.7, 1.8 Hz), 7.42 (1H, d, J=8.7 Hz), 7.68 (1H, d, J=1.8 Hz), 8.38 (1H, d, J=7.8 Hz), 8.42 (1H, d, J=7.8 Hz), 10.45-10.65 (2H, br), 11.78 (1H, br.s). MS (FAB) m/z: 515 (M+H)$^+$.

Example 228

5-Chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)indole-2-carboxamide hydrochloride

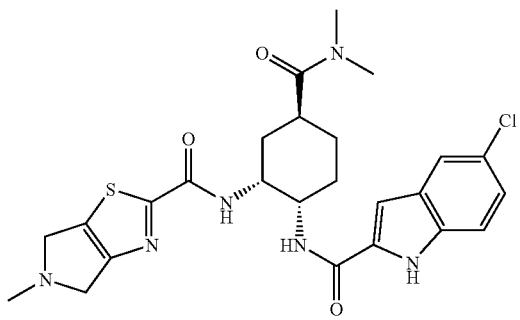

The title compound was obtained from the compound obtained in Example 227 and formalin in a similar manner to the process described in Example 18.

$^1$H-NMR (DMSO-d$_6$) δ: 1.45-1.60 (1H, m), 1.65-1.90 (3H, m), 1.90-2.05 (2H, m), 2.80 (3H, s), 2.98 (3H, s), 2.98-3.06 (1H, m), 3.06 (3H, s), 4.05-4.20 (1H, m), 4.30-5.00 (5H, br.s), 7.04 (1H, d, J=1.7 Hz), 7.17 (1H, dd, J=8.8, 2.1 Hz), 7.41 (1H, d, J=8.8 Hz) 7.68 (1H, d, J=2.1 Hz) 8.36 (1H, d, J=7.8 Hz), 8.42 (1H, d, J=8.1 Hz), 11.78 (1H, br.s), 12.14 (1H, br.s). MS (FAB) m/z: 529 (M+H)$^+$.

Example 229 tert-Butyl 2-{[((1R,2S,5S)-5-[(dimethylamino)carbonyl]-2-{[(5-fluoroindol-2-yl)carbonyl]amino}cyclohexyl)amino]-carbonyl}-4,6-dihydro-5H-pyrrolo[3,4-d]thiazole-5-carboxylate

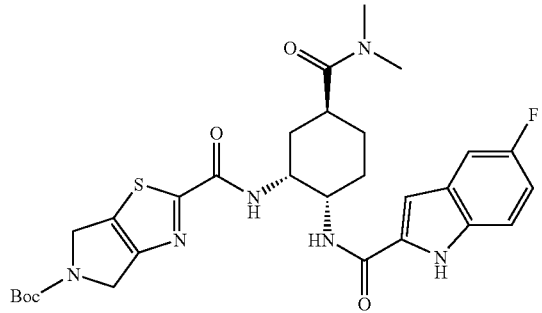

The title compound was obtained from the compound obtained in Referential Example 311 and the compound obtained in Referential Example 406 in a similar manner to the process described in Example 226.

$^1$H-NMR (CDCl$_3$) δ: 1.53 (9H, s), 1.60-2.40 (6H, m), 2.80-3.20 (7H, m), 4.15-4.25 (1H, m), 4.55-4.80 (5H, m), 6.84-6.87 (1H, m), 7.01 (1H, dt, J=2.4, 9.1 Hz), 7.25-7.30 (1H, m), 7.34 (1H, dd, J=9.1, 4.3 Hz), 7.42-7.49 (1H, m), 7.70-7.80 (1H, m), 9.37-9.45 (1H, m). MS (ESI) m/z: 599 (M+H)$^+$.

Example 230

N-{(1S,2R,4S)-2-[[(5,6-Dihydro-4H-pyrrolo[3,4-d]thiazol-2-yl)carbonyl]amino]-4-[(dimethylamino)carbonyl]-5-fluoroindole-2-carboxamide hydrochloride

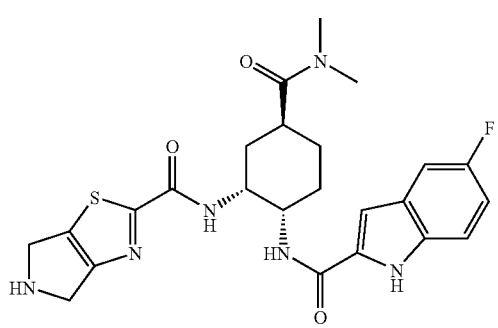

The title compound was obtained from the compound obtained in Example 229 in a similar manner to the process described in Example 227.

$^1$H-NMR (DMSO-d$_6$) δ: 1.45-1.60 (1H, m), 1.65-1.90 (3H, m), 1.90-2.10 (2H, m), 2.80 (3H, s), 2.97 (3H, s), 2.98-3.15 (1H, m), 4.05-4.20 (1H, m), 4.35-4.50 (2H, m), 4.58 (3H, br.s), 6.97-7.10 (2H, m), 7.35-7.47 (2H, m), 8.34 (1H, d, J=7.8 Hz), 8.41 (1H, d, J=8.1 Hz), 10.53 (2H, br.s), 11.68 (1H, br.s). MS (FAB) m/z: 499 (M+H)$^+$.

Example 231

N-((1S,2R,4S)-4-[(Dimethylamino)carbonyl]-2-{[(5-methyl-5,6-dihydro-4H-pyrrolo[3,4-d]thiazol-2-yl)carbonyl]amino}-cyclohexyl)-5-fluoroindole-2-carboxamide hydrochloride

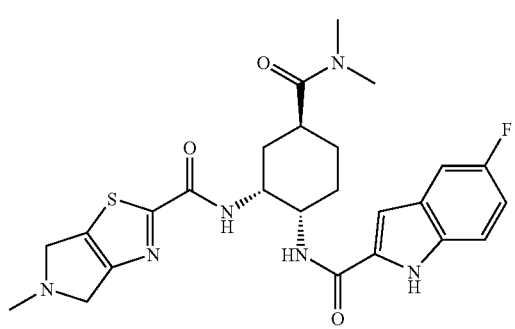

The title compound was obtained from the compound obtained in Example 230 and formalin in a similar manner to the process described in Example 18.

$^1$H-NMR (DMSO-d$_6$) δ: 1.45-1.60 (1H, m), 1.65-1.90 (3H, m), 1.90-2.10 (2H, m), 2.80 (3H, s), 2.90-3.20 (7H, m), 4.05-4.20 (1H, m), 4.30-5.00 (5H, br.s), 6.95-7.10 (2H, m), 7.35-7.50 (2H, m), 8.33 (1H, d, J=7.6 Hz), 8.41 (1H, d, J=8.1 Hz), 11.67 (1H, br.s), 12.37 (1H, br.s). MS (FAB) m/z: 513 (M+H)$^+$.

Example 232

N-{(1R,2S,5S)-2-[(6-Chloro-2-naphthoyl)amino]-5-[(dimethylamino)carbonyl]cyclohexyl}-5-methyl-5,6-dihydro-4H-pyrrolo[3,4-d]thiazole-2-carboxamide hydrochloride

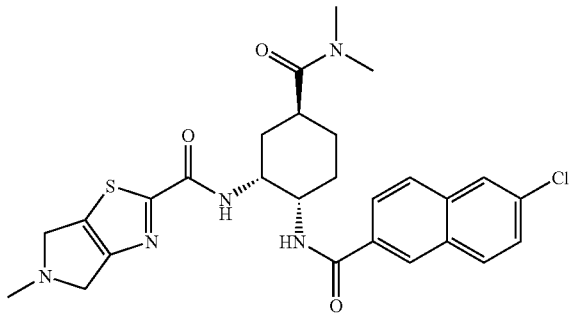

The title compound was obtained from the compound obtained in Referential Example 294 and the compound obtained in Referential Example 293 in a similar manner to the process described in Example 226.

$^1$H-NMR (DMSO-d$_6$) δ: 1.48-1.56 (1H, m), 1.71-1.84 (3H, m), 1.95-2.04 (2H, m), 2.81 (3H, s), 3.00 (3H, s), 3.02 (3H, s), 3.06-3.15 (2H, m), 4.13-4.14 (1H, m), 4.52-4.63 (4H, m), 7.60 (1H, d, J=8.5 Hz), 7.87 (1H, d, J=8.8 Hz), 7.96 (1H, d, J=8.5 Hz), 8.01 (1H, d, J=8.8 Hz), 8.10 (1H, s), 8.32 (1H, s), 8.45 (1H, d, J=8.1 Hz), 8.51 (1H, d, J=7.3 Hz). MS (FAB) m/z: 540 (M+H)$^+$.

Example 233

7-Chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)cinnoline-3-carboxamide hydrochloride and 7-chloro-N-((1S,2R,4S)-4-[(dimethylamino)carbonyl]-2-{[(5-methyl-5H-pyrrolo[3,4-d]thiazol-2-yl)carbonyl]amino}cyclohexyl)cinnoline-3-carboxamide

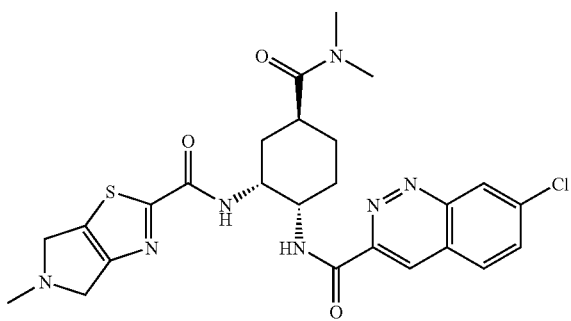

-continued

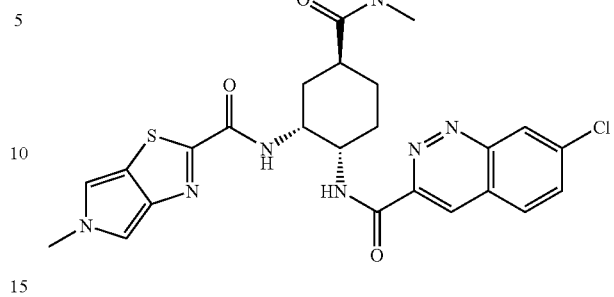

A 4N dioxane solution (3.0 ml) of hydrochloric acid was added to a suspension of the compound (330 mg) obtained in Referential Example 299 in a mixed solvent of dioxane (3.0 ml) and methylene chloride (3.0 ml), and the mixture was stirred at room temperature for 30 minutes. The solvent was distilled off under reduced pressure, and the thus-obtained white powder was dissolved in N,N-dimethylformamide (5.0 ml), and the compound (172 mg) obtained in Referential Example 293, 1-hydroxybenzotriazole monohydrate (130 mg) and 1-(3-dimethylaminopropyl)-3-ethylcarbodiimide hydrochloride (192 mg) were added to stir the mixture at room temperature for 15 hours. The solvent was distilled off under reduced pressure, methylene chloride and a saturated aqueous solution of sodium hydrogencarbonate were added to the residue. The resultant organic layer was washed with saturated saline and then dried over anhydrous sodium sulfate. The solvent was distilled off under reduced pressure, and the residue was purified by column chromatography on silica gel (methylene chloride:methanol=20:1). A 1N ethanol solution (0.35 ml) of hydrochloric acid was added to a solution of the thus-obtained high-polar compound mainly formed in ethanol (4.0 ml), and the solvent was distilled off under reduced pressure. Ethanol and diethyl ether were added to the residue, and precipitate formed was collected by filtration to obtain 7-chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)cinnoline-3-carboxamide hydrochloride (184 mg) a main product.

$^1$H-NMR (DMSO-d$_6$) δ: 1.50-1.65 (1H, m), 1.70-1.90 (3H, m), 2.03-2.12 (1H, m), 2.15-2.30 (1H, m), 2.81 (3H, s), 2.90-3.05 (1H, m), 2.96 (3H, s), 3.07 (3H, s), 4.28-4.37 (1H, m), 4.40-4.95 (5H, br), 8.02 (1H, d, J=8.8 Hz), 8.38 (1H, d, J=8.8 Hz), 8.66 (1H, s), 8.91 (1H, s), 8.97 (1H, d, J=7.1 Hz), 9.43-9.57 (1H, br), 11.75-11.95 (0.5H, br), 12.35-11.55 (0.5H, br). MS (FAB) m/z: 542 (M+H)$^+$.

In the purification by the column chromatography on silica gel, low-polar 7-chloro-N-((1S,2R,4S)-4-[(dimethylamino)carbonyl]-2-{[(5-methyl-5H-pyrrolo[3,4-d]thiazol-2-yl)carbonyl]amino}cyclohexyl)cinnoline-3-carboxamide (98 mg) was also obtained as a by-product.

$^1$H-NMR (CDCl$_3$) δ: 1.90-2.25 (6H, m), 2.85-3.00 (1H, m), 2.95 (3H, s), 3.05 (3H, s), 3.91 (3H, s), 4.43-4.54 (1H, m), 4.86-4.95 (1H, m), 6.70 (1H, d, J=1.5 Hz), 7.19 (1H, d, J=1.5 Hz), 7.59 (1H, d, J=8.8 Hz), 7.76 (1H, d, J=8.8 Hz), 7.95 (1H, d, J=8.8 Hz), 8.53 (1H, s), 8.64 (1H, d, J=8.0 Hz), 8.73 (1H, s). MS (FAB) m/z: 540 (M+H)$^+$.

Example 234

7-Chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)isoquinoline-3-carboxamide hydrochloride

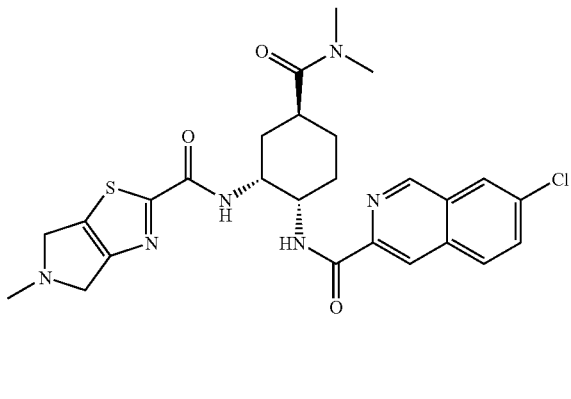

The compound (500 mg) obtained in Referential Example 146 was dissolved in an ethanol solution (5 ml) of hydrochloric acid, and the mixture was stirred at room temperature for 30 minutes. The solvent was distilled off under reduced pressure, and the residue was dissolved in N,N-dimethylformamide (7 ml), and the compound (299 mg) obtained in Referential Example 293, 1-hydroxybenzotriazole monohydrate (71 mg) and 1-(3-dimethylaminopropyl)-3-ethylcarbodiimide hydrochloride (403 mg) were added to the solution to stir the mixture at room temperature for a night. The solvent was distilled off under reduced pressure, a saturated aqueous solution of sodium hydrogencarbonate and methylene chloride were added to the residue to conduct liquid separation. The resultant water layer was extracted with methylene chloride. Organic layers were combined and dried over anhydrous sodium sulfate. The solvent was distilled off under reduced pressure, and the residue was purified by column chromatography on silica gel (methylene chloride:methanol=93:7) to obtain a free base (260 mg) of the title compound as a pale yellow solid. This product was dissolved in methylene chloride, a 1N ethanol solution (961 μl) of hydrochloric acid was added, and the solvent was distilled off under reduced pressure. A small amount of methanol was added to the residue, and diethyl ether was added dropwise to collect precipitate formed by filtration. This product was washed with diethyl ether to obtain the title compound (260 mg).

$^1$H-NMR (DMSO-d$_6$) δ: 1.47-1.56 (1H, m), 1.71-1.75 (3H, m), 1.95-1.99 (1H, m), 2.12-2.15 (1H, m), 2.78 (3H, s), 2.95 (3H, s), 2.98 (1H, br.s), 3.05 (3H, s), 4.19-4.22 (1H, m), 4.44-4.52 (3H, m), 4.74-4.88 (2H, m), 7.87 (1H, dd, J=8.8, 1.7 Hz), 8.24 (1H, d, J=8.8 Hz), 8.36 (1H, d, J=1.7 Hz), 8.58 (1H, s), 8.90-8.92 (2H, m), 9.30 (1H, s), 12.65-12.75 (1H, m). MS (FAB) m/z: 541 (M+H)$^+$.

Example 235 tert-Butyl 2-[({(1R,2S,5S)-2-{[(5-chloroindol-2-yl)carbonyl]amino}-5-[(dimethylamino)carbonyl]cyclohexyl}-amino)carbonyl]-6,6-dimethyl-6,7-dihydrothiazolo[4,5-c]pyridine-5(4H)-carboxylate The compound (95.4 mg) obtained in Referential Example 316 was dissolved in diethyl ether (1 ml) in an argon atmosphere, and tert-butyllithium (1.60N pentane solution, 244 μl) was added dropwise at −78° C. After the mixture was stirred for 1 hour at −78° C., carbon dioxide was blown into the reaction mixture for 10 minutes. The reaction mixture was heated to room temperature. After the reaction mixture was concentrated under reduced pressure, the residue was dissolved in N,N-dimethylformamide (5 ml). To the solution, were successively added the compound (178 mg) obtained in Referential Example 432, 1-hydroxybenzotriazole monohydrate (48.0 mg) and 1-(3-dimethylaminopropyl)-3-ethylcarbodiimide hydrochloride (136 mg). The resultant mixture was stirred overnight at room temperature. The reaction mixture was concentrated, and methylene chloride and a saturated aqueous solution of sodium hydrogencarbonate were added to the residue to separate an organic layer. The organic layer was dried over anhydrous sodium sulfate, and the solvent was then distilled off under reduced pressure. The resultant residue was purified by column chromatography on silica gel (methanol:methylene chloride=1:19) to obtain the title compound (140 mg).

$^1$H-NMR (CDCl$_3$) δ: 1.50 (9H, s), 1.52 (3H, s), 1.54 (3H, s), 1.70-2.10 (4H, m), 2.15-2.45 (2H, m), 2.80-3.20 (9H, m), 4.10-4.25 (1H, br), 4.60-4.75 (3H, m), 6.85 (1H, br.s), 7.21 (1H, dd, J=8.8, 1.8 Hz), 7.34 (1H, d, J=8.8 Hz), 7.48 (1H, d, J=7.3 Hz), 7.61-7.63 (1H, m), 7.89 (1H, br.s), 9.27 (1H, br.s). MS (ESI) m/z: 657 (M+H)$^+$.

Example 236

N-{(1R,2S,5S)-2-{[(5-Chloroindol-2-yl)carbonyl]amino}-5-[(dimethylamino)carbonyl]cyclohexyl}-6,6-dimethyl-4,5,6,7-tetrahydrothiazolo[4,5-c]pyridine-2-carboxamide hydrochloride

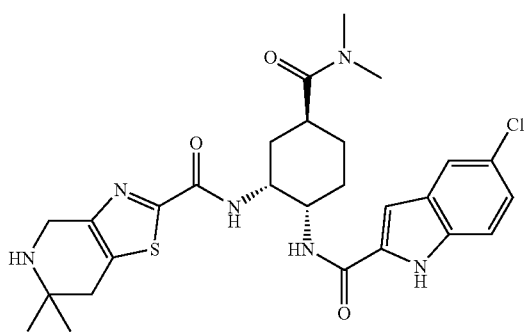

The title compound was obtained from the compound obtained in Example 235 in a similar manner to the process described in Example 227.

$^1$H-NMR (DMSO-$d_6$) δ: 1.40 (6H, s), 1.45-1.60 (1H, m), 1.70-2.05 (5H, m), 2.81 (3H, s), 2.95-3.15 (6H, m), 4.05-4.20 (1H, br), 4.25-4.45 (2H, m), 4.55-4.65 (1H, m), 7.06 (1H, d, J=1.7 Hz), 7.17 (1H, dd, J=8.8, 2.0 Hz), 7.42 (1H, d, J=8.8 Hz), 7.68 (1H, d, J=2.0 Hz), 8.34-8.39 (2H, m), 9.77 (1H, br.s), 9.84 (1H, br.s), 11.79 (1H, br.s). MS (ESI) m/z: 557 (M+H)$^+$.

Example 237 tert-Butyl 2-[({(1R,2S,5S)-2-{[(5-chloroindol-2-yl)carbonyl]amino}-5-[(dimethylamino)carbonyl]cyclohexyl}-amino)carbonyl]-5,7-dihydro-6H-pyrrolo[3,4-d]pyrimidine-6-carboxylate

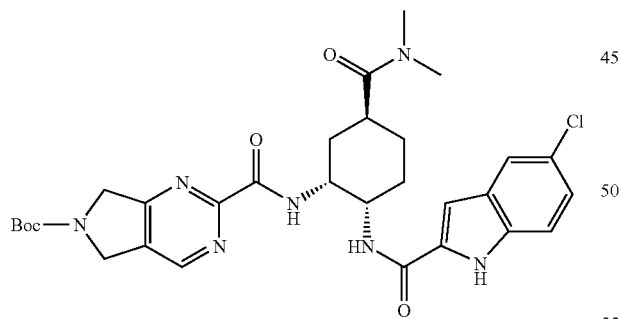

The compound (1.27 g) obtained in Referential Example 50 was dissolved in tetrahydrofuran (48 ml), and lithium hydroxide (117 mg) and water (6.0 ml) were added to stir the mixture at room temperature for 4.5 hours. The reaction mixture was dried to solid under reduced pressure to obtain a crude carboxylic acid lithim salt (1.24 g). This product was condensed with the compound obtained in Referential Example 432 in a similar manner to the process described in the step 2) of Example 226 to obtain the title compound.

$^1$H-NMR (CDCl$_3$) δ: 1.50-1.70 (1H, m), 1.54 (9H, s), 1.80-2.10 (3H, m), 2.25-2.50 (2H, m), 2.85-2.95 (1H, m), 2.99 (3H, s), 3.14 (3H, s), 4.15-4.25 (1H, m), 4.65-4.75 (1H, m), 4.80-4.90 (4H, m), 6.97 (1H, s), 7.15-7.25 (1H, m), 7.30-7.40 (1H, m), 7.60-7.65 (1H, m), 8.15-8.25 (1H, m), 8.40-8.45 (1H, m), 8.75-8.85 (1H, m), 9.40-9.45 (1H, m). MS (ESI) m/z: 611 (M+H)$^+$.

Example 238

N-{(1R,2S,5S)-2-{[(5-Chloroindol-2-yl)carbonyl]amino}-5-[(dimethylamino)carbonyl]cyclohexyl}-6-methyl-6,7-dihydro-5H-pyrrolo[3,4-d]pyrimidine-2-carboxamide hydrochloride

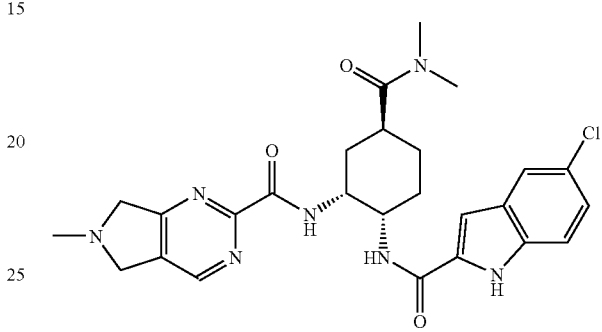

The compound (367 mg) obtained in Example 237 was dissolved in methylene chloride (10 ml), and trifluoroacetic acid (10 ml) was added to stir the mixture at room temperature for 2 hours. The reaction mixture was dried to solid under reduced pressure. The title compound was obtained from the thus-obtained crude product and formalin in a similar manner to the process described in Example 18.

$^1$H-NMR (DMSO-$d_6$) δ: 1.50-1.60 (1H, m), 1.65-2.10 (5H, m), 2.81 (3H, s), 2.90-3.00 (1H, m), 2.96 (3H, s), 3.05 (3H, s), 4.10-4.20 (1H, m), 4.55-4.65 (1H, m), 4.65-4.90 (4H, br), 7.06 (1H, s), 7.15 (1H, dd, J=8.7, 2.1 Hz), 7.41 (1H, d, J=8.8 Hz), 7.66 (1H, d, J=1.7 Hz), 8.35-8.45 (1H, m), 8.57 (1H, d, J=8.1 Hz), 9.00 (1H, s), 11.80 (1H, s), 11.90-12.20 (1H, m). MS (FAB) m/z: 524 (M+H)$^+$.

Example 239

7-Chloro-N-((1S,2R,4S)-4-[(dimethylamino)carbonyl]-2-{[(6-methyl-6,7-dihydrothiazolo[4,5-d]pyrimidin-2-yl)carbonyl]amino}cyclohexyl)isoquinoline-3-carboxamide hydrochloride

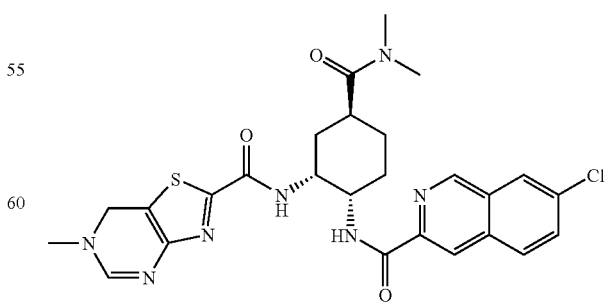

The title compound was obtained by treating the compound obtained in Referential Example 146 with an ethanol solution of hydrochloric acid and then condensing it with the compound obtained in Referential Example 322 in a similar manner to the process described in Example 49.

$^1$H-NMR (DMSO-$d_6$) δ: 1.50-1.60 (1H, m), 1.70-1.90 (3H, m), 1.90-2.15 (2H, m), 2.81 (3H, s), 2.95 (3H, s), 2.90-3.05 (1H, m), 3.26 (3H, s), 4.20-4.55 (2H, m), 5.00 (2H, s), 7.91 (1H, d, J=8.8 Hz), 8.27 (1H, d, J=8.8 Hz), 8.37 (1H, s), 8.54 (1H, s), 8.62 (1H, s), 8.79 (1H, d, J=8.3 Hz), 8.94 (1H, d, J=8.1 Hz), 9.32 (1H, s). MS (ESI) m/z: 554 (M+H)$^+$.

Example 240

7-Chloro-N-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)isoquinoline-3-carboxamide hydrochloride

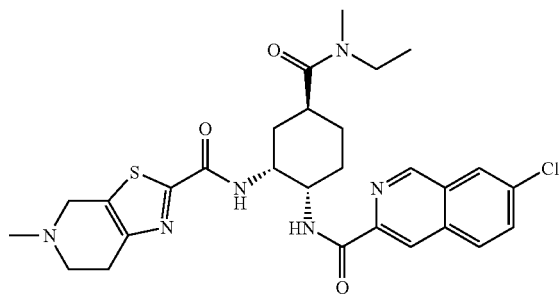

The title compound was obtained from the compound obtained in Referential Example 325 and the compound obtained in Referential Example 10 in a similar manner to the process described in Example 2.

$^1$H-NMR (DMSO-$d_6$) δ: 0.98, 1.04 (3H, each t, J=7.1 Hz), 1.52-1.60 (1H, m), 1.74-1.77 (3H, m), 1.96-2.05 (1H, m), 2.15-2.18 (1H, m), 2.77-2.93 (8H, m), 3.17-3.32 (3H, m), 3.49 (1H, br.s), 4.22 (1H, br.s), 4.41-4.45 (1H, m), 4.51 (1H, br.s), 4.69-4.72 (1H, m), 7.89 (1H, d, J=8.7 Hz), 8.26 (1H, d, J=8.7 Hz), 8.37 (1H, s), 8.60 (1H, s)., 8.91-8.98 (2H, m), 9.32 (1H, d, J=6.6 Hz), 11.39, 11.53 (1H, each m). MS (FAB) m/z: 569 (M+H)$^+$.

Example 241

N-{(1R*,2S*,5S*)-2-{[(5-Chloroindol-2-yl)carbonyl]amino}-5-[2-(dimethylamino)-2-oxoethyl]cyclohexyl}-5-methyl-4,5,6,7-tetrahydrothiazolo[5,4-c]pyridine-2-carboxamide hydrochloride

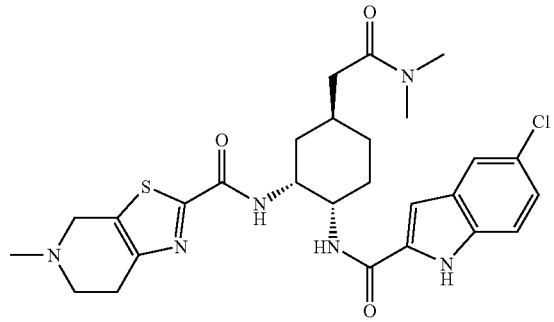

The title compound was obtained from the compound obtained in Referential Example 336 and the compound obtained in Referential Example 10 in a similar manner to the process described in Example 2.

$^1$H-NMR (DMSO-$d_6$) δ: 1.13-1.22 (1H, m), 1.40-1.46 (1H, m), 1.68-1.99 (5H, m), 2.18-2.29 (2H, m), 2.80 (3H, s), 2.92 (3H, s), 2.96 (3H, s), 3.22 (2H, br.s), 3.49 (1H, br.s), 3.70 (1H, br.s), 4.09-4.16 (1H, m), 4.42-4.46 (2H, m), 4.67 (1H, br.s), 7.03 (1H, s), 7.16 (1H, dd, J=8.5, 1.5 Hz), 7.42 (1H, d, J=8.5 Hz), 7.67 (1H, s), 8.01 (1H, d, J=8.5 Hz), 8.40 (1H, d, J=7.8 Hz), 11.35-11.58 (1H, m), 11.76 (1H, br.s). MS (FAB) m/z: 557 (M+H)$^+$.

Example 242

N-{(1R,2S,5S)-2-{[(5-Chloroindol-2-yl)carbonyl]amino}-5-[(methylsulfonyl)methyl]cyclohexyl}-5-methyl-4,5,6,7-tetrahydrothiazolo[5,4-c]pyridine-2-carboxamide hydrochloride

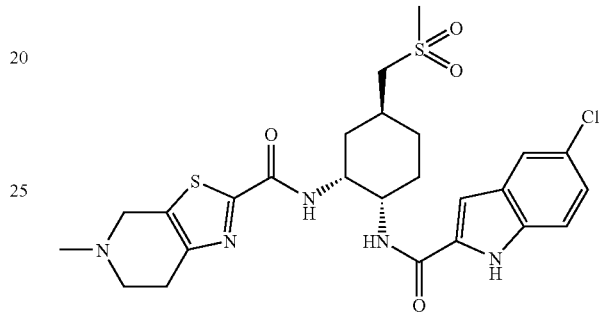

The title compound was obtained by treating the compound obtained in Referential Example 340 with an ethanol solution of hydrochloric acid and then condensing it with the compound obtained in Referential Example 10 in a similar manner to the process described in Example 219.

$^1$H-NMR (DMSO-$d_6$) δ: 1.35-1.40 (1H, m), 1.55-1.62 (1H, m), 1.70-1.76 (1H, m), 1.88-1.94 (1H, m), 2.03-2.07 (1H, m), 2.13-2.17 (1H, m), 2.30-2.33 (1H, m), 2.43-3.48 (10H, m), 3.60-3.73 (2H, m), 4.11-4.16 (1H, m), 4.40-4.42 (2H, m), 4.68-4.73 (1H, m), 7.05 (1H, s), 7.16 (1H, dd, J=2.0, 8.8 Hz), 7.41 (1H, d, J=8.8 Hz), 7.68 (1H, s), 8.26 (1H, d, J=7.8 Hz), 8.39 (1H, d, J=7.8 Hz), 11.78 (1H, br.s). MS (ESI) m/z: 564 (M+H)$^+$.

Example 243

N-{(1R,2S,5S)-2-{[(2-Chloro-6H-thieno[2,3-b]pyrrol-5-yl)carbonyl]amino}-5-[(dimethylamino)carbonyl]cyclohexyl}-5-methyl-4,5,6,7-tetrahydrothiazolo[5,4-c]pyridine-2-carboxamide

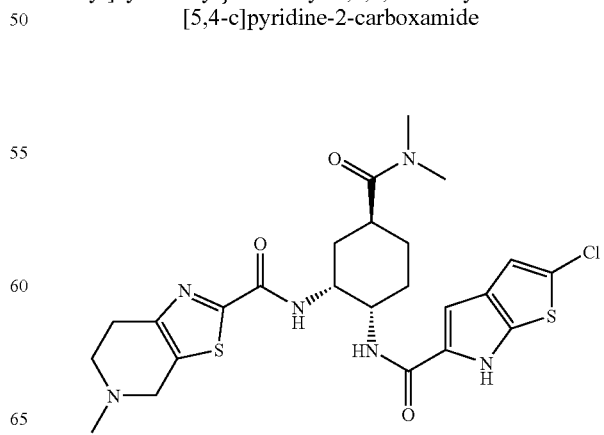

The title compound was obtained by hydrogenation of the compound obtained in Referential Example 252 and then condensing it with the compound obtained in Referential Example 345 in a similar manner to the process described in Example 223.

$^1$H-NMR (CDCl$_3$) δ: 1.56-1.66 (1H, m), 1.76-1.93 (2H, m), 2.02-2.06 (1H, m), 2.19-2.26 (1H, m), 2.30-2.34 (1H, m), 2.52 (3H, s), 2.79-2.88 (3H, m), 2.91-2.94 (2H, m), 2.96 (3H, s), 3.09 (3H, s), 3.69-3.77 (2H, m), 4.13-4.19 (1H, m), 4.58-4.61 (1H, m), 6.72 (1H, s), 6.84 (1H, s), 7.50 (1H, d, J=7.3 Hz), 7.60 (1H, d, J=5.8 Hz), 10.54 (1H, br). MS (ESI) m/z: 549 (M+H)$^+$.

Example 244

N-{(1R,2S,5S)-2-{[3-(4-Chlorophenyl)-2-propynoyl]amino}-5-[(dimethylamino)carbonyl]cyclohexyl}-5-methyl-4,5,6,7-tetrahydrothiazolo[5,4-c]pyridine-2-carboxamide hydrochloride

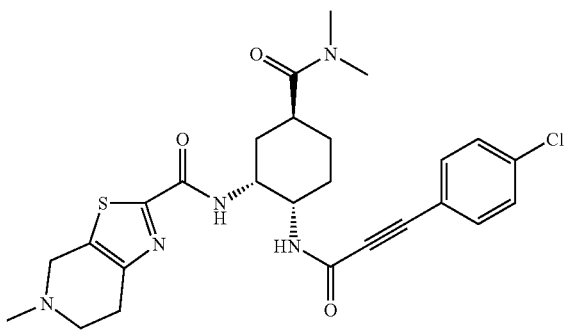

The title compound was obtained by hydrogenation of the compound obtained in Referential Example 252 and then condensing it with the compound obtained in Referential Example 347 in a similar manner to the process described in Example 223.

$^1$H-NMR (DMSO-d$_6$) δ: 1.38-1.50 (1H, m), 1.58-1.92 (4H, m), 2.78 (3H, s), 2.90 (3H, s), 2.97 (3H, s), 3.01-3.24 (3H, m), 3.26-3.80 (2H, m), 3.90-3.98 (1H, m), 4.30-4.78 (3H, m), 7.51 (1H, d, J=8.8 Hz), 7.57 (1H, d, J=8.8 Hz), 8.34 (1H, d, J=8.8 Hz), 8.83 (1H, d, J=7.8 Hz). MS (FAB) m/z: 528 (M+H)$^+$.

Example 245

6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinazoline-2-carboxamide hydrochloride

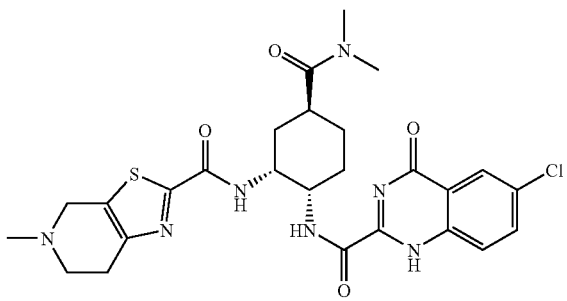

The title compound was obtained by hydrogenation of the compound obtained in Referential Example 252 and then condensing it with the compound obtained in Referential Example 349 in a similar manner to the process described in Example 223.

$^1$H-NMR (DMSO-d$_6$) δ: 1.45-1.60 (1H, m), 1.70-1.90 (3H, m), 1.90-2.20 (3H, m), 2.80 (3H, s), 2.93 (3H, s), 2.97 (3H, s), 2.98-3.80 (4H, m), 4.05-4.20 (2H, m), 4.35-4.80 (3H, m), 7.63 (1H, d, J=8.3 Hz), 7.90 (1H, d, J=7.3 Hz), 8.75-9.00 (2H, m), 11.00-11.50 (1H, br), 12.53 (1H, br.s). MS (ESI) m/z: 573 (M+H)$^+$.

Example 246

N-{(1R,2S,5S)-2-{[2-(4-Chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide

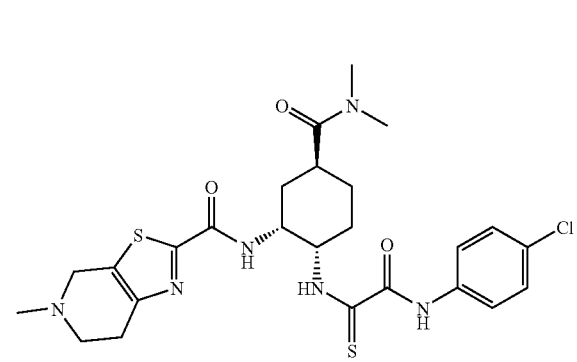

The compound (184 mg) obtained in Referential Example 253 and the compound (150 mg) obtained in Referential Example 351 were dissolved in a mixed solvent of methanol (1 ml)-methylene chloride (4 ml), the solution was heated and stirred at 150° C., and the heating was continued for 5 minutes after distilling off the solvent. After the reaction mixture was allowed to cool, the formed product was purified by column chromatography on silica gel (methylene chloride:methanol=24:1) to obtain the title compound (59 mg).

$^1$H-NMR (CDCl$_3$) δ: 1.65-1.90 (2H, m), 1.90-2.00 (1H, m), 2.00-2.15 (2H, m), 2.20-2.30 (1H, m), 2.52 (3H, s), 2.75-2.95 (5H, m), 2.96 (3H, s), 3.07 (3H, s), 3.68 (1H, d, J=15.2 Hz), 3.75 (1H, d, J=15.7 Hz), 4.45-4, 60 (1H, m), 4.80-4.85 (1H, m), 7.31 (2H, d, J=8.8 Hz), 7.44 (1H, d, J=8.6 Hz), 7.60 (2H, d, J=8.8 Hz), 9.99 (1H, d, J=7.6 Hz), 10.15 (1H, s). MS (ESI) m/z: 563 (M+H)$^+$.

Example 247

N-{(1R,2S,5S)-2-({2-[(5-Chloropyridin-2-yl)amino]-2-oxoethanethioyl}amino)-5-[(dimethylamino)carbonyl]-cyclohexyl}-5-methyl-4,5,6,7-tetrahydrothiazolo[5,4-c]-pyridine-2-carboxamide

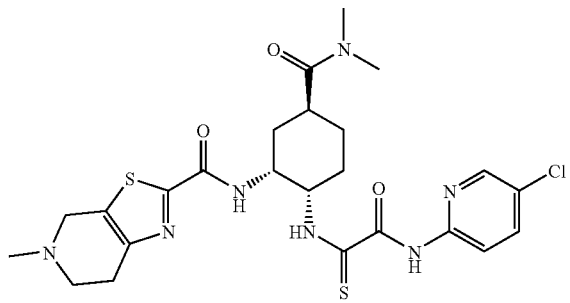

The compound (184 mg) obtained in Referential Example 253 and the compound (150 mg) obtained in Referential Example 353 were dissolved in a mixed solvent of methanol (0.3 ml)-methylene chloride (0.3 ml), the solution was heated and stirred at 150° C., and the heating was continued for 5 minutes after distilling off the solvent. reaction mixture was allowed to cool, the formed product was purified by column chromatography on silica gel (methylene chloride:methanol=24:1) to obtain the title compound (52 mg).

$^1$H-NMR (CDCl$_3$) δ: 1.60-2.00 (3H, m), 2.00-2.20 (2H, m), 2.25-2.40 (1H, m), 2.53 (3H, s), 2.80-2.95 (5H, m), 2.96 (3H, s), 3.08 (3H, s), 3.70 (1H, d, J=15.4 Hz), 3.75 (1H, d, J=15.4 Hz), 4.45-4,60 (1H, m), 4.75-4.85 (1H, m), 7.45 (1H, d, J=8.3 Hz), 7.67 (1H, dd, J=8.8, 2.5 Hz), 8.18 (1H, d, J=8.8 Hz), 8.31 (1H, d, J=2.0 Hz), 10.06 (1H, d, J=6.3 Hz), 10.56 (1H, s). MS (ESI) m/z: 564 (M+H)$^+$.

Example 248

N-{(1R,2S,5S)-2-({2-[(5-Chloropyridin-2-yl)amino]-2-thioxoacetyl}amino)-5-[(dimethylamino)carbonyl]-cyclohexyl}-5-methyl-4,5,6,7-tetrahydrothiazolo[5,4-c]-pyridine-2-carboxamide

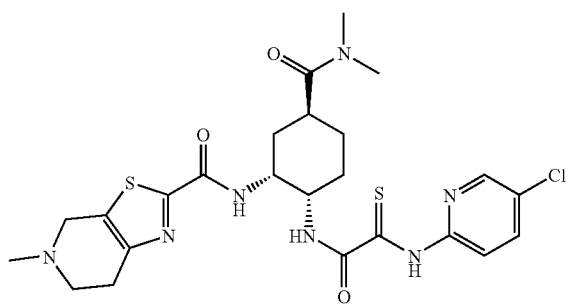

The compound (72 mg) obtained in Referential Example 355 and 2-amino-5-chloropyridine (100 mg) were dissolved in a mixed solvent of methanol (0.2 ml)-methylene chloride (0.2 ml), the solution was heated and stirred at 150° C., and the heating was continued for 8 minutes after distilling off the solvent. After the reaction mixture was allowed to cool, the formed product was purified by preparative thin-layer chromatography on silica gel (methylene chloride:methanol=23:2) to obtain the title compound (4 mg).

$^1$H-NMR (CDCl$_3$) δ: 1.60-2.00 (3H, m), 2.00-2.20 (3H, m), 2.53 (3H, s), 2.75-3.00 (5H, m), 2.95 (3H, s), 3.05 (3H, s), 3.65-3.80 (2H, m), 4.05-4.15 (1H, m), 4.70-4.80 (1H, m), 7.28 (1H, d), 7.43 (1H, d, J=9.3 Hz), 7.75 (1H, dd, J=8.8, 2.7 Hz), 8.41 (1H, d, J=2.7 Hz), 9.05 (1H, d, J=8.8 Hz), 1.56 (1H, s). MS (ESI) m/z: 564 (M+H)$^+$.

Example 249

N$^1$-(5-Chloro-2-thienyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]-amino}cyclohexyl)ethanediamide hydrochloride

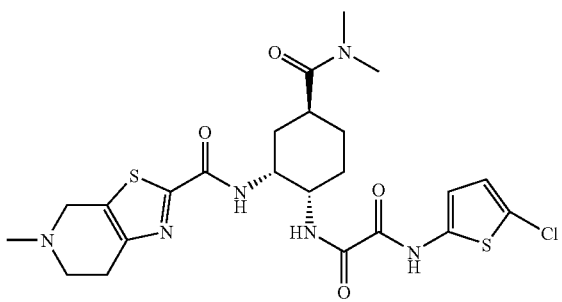

The title compound was obtained by hydrolyzing the compound obtained in Referential Example 356, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.40-1.55 (1H, m), 1.60-1.85 (3H, m), 1.90-2.15 (2H, m), 2.79 (3H, s), 2.90-3.15 (1H, m), 2.92 (3H, s), 2.94 (3H, s), 3.15-3.30 (2H, m), 3.50-3.80 (2H, m), 3.95-4.05 (1H, m), 4.35-4.90 (3H, m), 6.90 (1H, d, J=4.2 Hz), 6.94 (1H, d, J=4.2 Hz), 8.72 (1H, d, J=7.3 Hz), 9.13 (1H, br.s), 11.21 (1H, br.s), 12.32 (1H, br.s). MS (ESI) m/z: 553 (M+H)$^+$.

Example 250

N-{(1R,2S,5S)-2-{[(4-Chloroanilino)carbonyl]amino}-5-[(dimethylamino)carbonyl]cyclohexyl}-5-methyl-4,5,6,7-tetrahydrothiazolo[5,4-c]pyridine-2-carboxamide hydrochloride

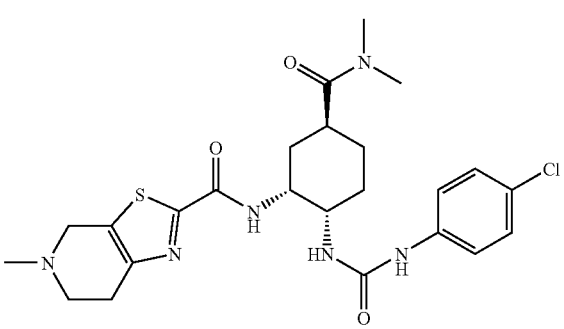

4-Chlorophenyl isocyanate (76.8 mg) was added to a solution of the compound (183 mg) obtained in Referential Example 253 in methylene chloride (20 ml), and the mixture was stirred at room temperature for 24 hours. The solvent was distilled off under reduced pressure, and the residue was purified by column chromatography on silica gel (methylene chloride:methanol=20:1→10:1) to distil off the solvent. The residue was dissolved in ethanol (2 ml) and methylene chloride (2 ml), a 1N ethanol solution (0.4 ml) of hydrochloric acid was added to stir the mixture at room temperature for 30 minutes. The reaction mixture was concentrated under reduced pressure, and the residue was solidified with diethyl ether to obtain the title compound (160 mg).

$^1$H-NMR (DMSO-d$_6$) δ: 1.35-1.50 (1H, m), 1.60-1.90 (5H, m), 2.79 (3H, s), 2.92 (3H, s), 3.00 (3H, s), 3.10-3.60 (4H, m), 3.60-3.90 (2H, m), 4.35-4.80 (3H, m), 6.26 (1H, br.s), 7.23 (2H, d, J=9.0 Hz), 7.37 (2H, d, J=9.0 Hz), 8.53 (1H, br.s), 8.72 (1H, br.s), 11.35, 11.67 (total 1H, each s). MS (ESI) m/z: 519 (M+H)$^+$.

Example 251

N'-((1S,2R,4S)-4-[(Dimethylamino)carbonyl]-2-{[(5-methyl-4,5,6,7-tetrahydrothiazolo[5,4-c]-pyridin-2-yl)carbonyl]-amino}cyclohexyl)-N$^2$-(5-fluoropyridin-2-yl)ethanediamide hydrochloride The title compound was obtained by hydrolyzing the compound obtained in Referential Example 357, condensing the hydrolyzate with the compound obtained in Referential Example 253 and then treating the condensation product with hydrochloric acid in a similar manner to the process described in Example 191.

$^1$H-NMR (DMSO-d$_6$) δ: 1.47-1.53 (1H, m), 1.68-1.75 (3H, m), 1.99-2.10 (2H, m), 2.80 (3H, s), 2.80-3.00 (1H, m), 2.95 (6H, s), 3.18-3.21 (2H, m), 3.40-3.80 (2H, m), 3.87-4.82 (4H, m), 7.82-7.85 (1H, m), 8.01-8.05 (1H, m), 8.40 (1H, d, J=2.9 Hz), 8.71 (1H, d, J=7.7 Hz), 9.13 (1H, d, J=7.3 Hz), 10.27 (1H, s). MS (FAB) m/z: 532 (M+H)$^+$.

Example 252

N$^1$-(4-Chlorophenyl)-N$^2$-((1S,2R,4S)-4-[(dimethylamino)carbonyl]-2-{[(5-methyl-5,6-dihydro-4H-pyrrolo[3,4-d]-thiazol-2-yl)carbonyl]amino}cyclohexyl)ethanediamide hydrochloride The title compound was obtained from the compound obtained in Referential Example 242 and the compound obtained in Referential Example 272 in a similar manner to the process described in Example 191.

$^1$H-NMR (DMSO-d$_6$) δ: 1.47-1.51 (1H, m), 1.69-1.75 (3H, m), 1.98-2.05 (2H, m), 2.80 (3H, s), 2.95 (3H, s), 2.98-3.04 (1H, m), 3.10 (3H, s), 3.40-4.61 (6H, m), 7.41 (2H, d, J=8.8 Hz), 7.81 (2H, d, J=8.8 Hz), 8.76 (1H, d, J=7.6 Hz), 8.95 (1H, d, J=8.3 Hz), 10.79 (1H, s). MS (FAB) m/z: 533 (M+H)$^+$.

Example 253

N$^1$-[4-Chloro-2-(trifluoromethyl)phenyl]-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

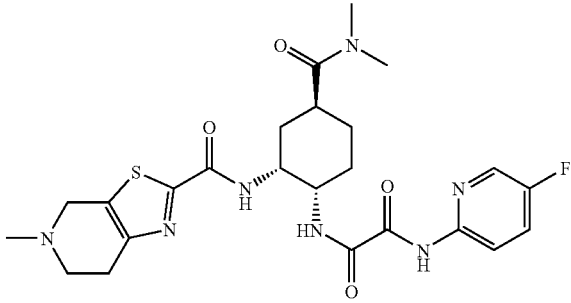

Thionyl chloride (1 ml) was added to a chloroform solution (10 ml) of the compound (269 mg) obtained in Referential Example 359, and the mixture was stirred at 75° C. for 30 minutes. The solvent was distilled off under reduced pressure, and the residue was dried. To the residue were added a methylene chloride solution (7 ml) of the compound (286 mg) obtained in Referential Example 253 and pyridine (3 ml) under ice cooling. The mixture was stirred for 2 hours while the temperature of the system was raised to room temperature. A saturated aqueous solution (10 ml) of sodium hydrogencarbonate was added to the reaction mixture to conduct liquid separation. The resultant organic layer was dried over anhydrous sodium sulfate. The solvent was distilled off under reduced pressure, and the resultant residue was subjected to column chromatography on silica gel (methylene chloride:methanol=20:1) and column chromatography on LH-20 (molecular sieve, methanol) to obtain a free base (90 mg) of the title compound as a pale yellow amorphous solid. Methylene chloride (5 ml), ethanol (5 ml) and a 1N ethanol solution (1 ml) of hydrochloric acid were added to thie product, and distilling-off and drying were conducted under reduced pressure to obtain the title compound.

$^1$H-NMR (DMSO-$d_6$) δ: 1.41-1.55 (1H, m), 1.59-1.80 (3H, m), 1.98-2.13 (2H, m), 2.77 (3H, s), 2.91 (6H, s), 3.12-3.26 (2H, m), 3.30-3.58 (2H, m), 3.60-3.78 (1H, m), 3.94-4.04 (1H, m), 4.35-4.63 (2H, m), 4.64-4.80 (1H, m), 7.73-7.82 (2H, m), 7.85 (1H, s), 8.68-8.73 (1H, m), 9.18 (1H, br.s), 10.31 (1H, s). MS (ESI) m/z: 615 (M+H).

Example 254

$N^1$-{4-Chloro-2-[(dimethylamino)carbonyl]phenyl}-$N^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

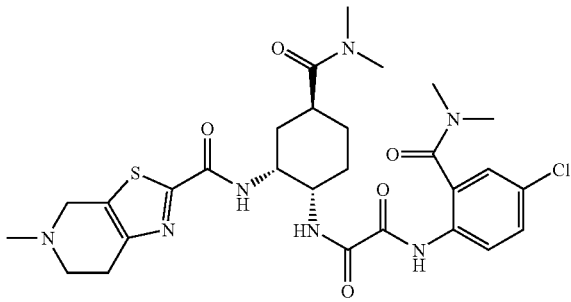

The title compound was obtained by hydrolyzing the compound obtained in Referential Example 362, condensing the hydrolyzate with the compound obtained in Referential Example 253 and then treating the condensation product with hydrochloric acid in a similar manner to the process described in Example 191.

$^1$H-NMR (DMSO-$d_6$) δ: 1.42-1.56 (1H, m), 1.59-1.82 (3H, m), 1.98-2.14 (2H, m), 2.79 (3H, s), 2.91 (3H, s), 2.93 (3H, s), 2.95 (3H, s), 2.98 (3H, s), 3.10-3.30 (4H, m), 3.62-3.79 (1H, m), 3.92-4.01 (1H, m), 4.34-4.50 (2H, m), 4.66-4.79 (1H, m), 7.52 (1H, d, J=2.4 Hz), 7.55 (1H, dd, J=2.4, 8.5 Hz), 8.05 (1H, d, J=8.5 Hz), 8.75 (1H, br), 9.10-9.24 (1H, m), 10.52 (1H, s). MS (ESI) m/z: 618 (M+H)$^+$.

Example 255

$N^1$-[4-Chloro-2-(hydroxymethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

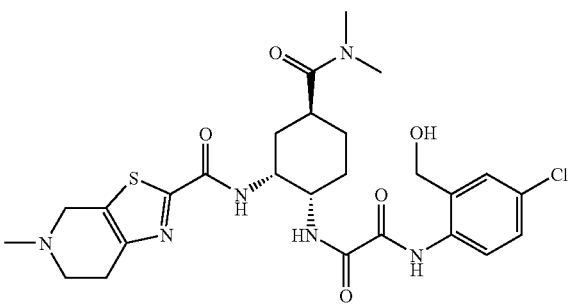

The title compound was obtained by condensing the compound obtained in Referential Example 270 with 4-chloro-2-hydroxymethylaniline and then treating the condensation product with hydrochloric acid in a similar manner to the process described in Example 199.

$^1$H-NMR (DMSO-$d_6$) δ: 1.42-1.57 (1H, m), 1.58-1.81 (3H, m), 1.98-2.14 (2H, m), 2.79 (3H, s), 2.93 (6H, s), 3.12-3.58 (4H, m), 3.67-3.80 (1H, m), 3.94-4.04 (1H, m), 4.37-4.50 (1.5H, m), 4.55 (2H, s), 4.67-4.80 (1H, m), 5.77-5.92 (0.5H, m), 7.37 (1H, dd, J=2.4, 8.6 Hz), 7.42 (1H, d, J=2.4 Hz), 7.91 (1H, d, J=8.6 Hz), 8.74-8.81 (1H, m), 9.03-9.19 (1H, m), 10.79 (1H, s). MS (ESI) m/z: 577 (M+H)$^+$.

Example 256

$N^1$-(4-Chloro-2-methoxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

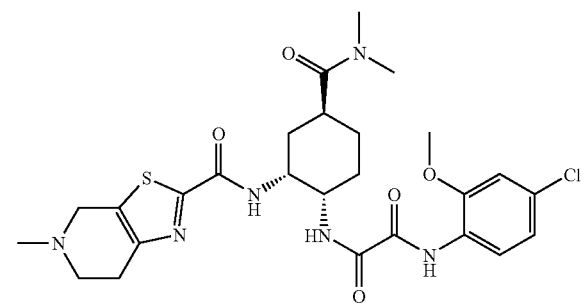

The title compound was obtained by hydrolyzing the compound obtained in Referential Example 364, condensing the hydrolyzate with the compound obtained in Referential Example 253 and then treating the condensation product with hydrochloric acid in a similar manner to the process described in Example 191.

$^1$H-NMR (DMSO-$d_6$) δ: 1.40-1.55 (1H, m), 1.58-1.79 (3H, m), 1.94-2.11 (2H, m), 2.77 (3H, s), 2.92 (6H, s), 3.05-3.55 (4H, m), 3.65-3.75 (1H, br), 3.90 (3H, s), 3.91-4.00 (1H, m), 4.36-4.47 (2H, br), 4.65-4.77 (1H, br), 7.04 (1H, dd, J=8.5, 2.0 Hz), 7.20 (1H, d, J=2.0 Hz), 8.06 (1H, d, J=8.5 Hz), 8.65-8.80 (1H, br), 9.10-9.25 (1H, br), 9.74 (1H, s), 11.10-11.35 (1H, br). MS (ESI) m/z: 577 (M+H)$^+$.

Example 257

N-{(1R,2S,5S)-2-{[2-(4-Chloroanilino)-2-(hydroxyimino)acetyl]amino}-5-[(dimethylamino)carbonyl]-cyclohexyl}-5-methyl-4,5,6,7-tetrahydrothiazolo[5,4-c]-pyridine-2-carboxamide hydrochloride

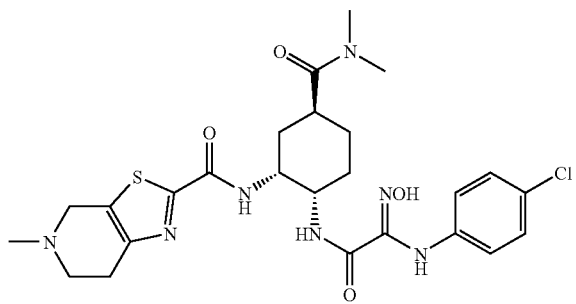

The title compound was obtained by deprotecting the compound obtained in Referential Example 366 by hydrochloric acid treatment, condensing the deprotected compound with the compound obtained in Referential Example 10 and then treating the condensation product with hydrochloric acid in a similar manner to the process described in Example 214.

$^1$H-NMR (DMSO-d$_6$) δ: 1.41-1.53 (1H, m), 1.57-1.77 (3H, m), 1.88-2.04 (2H, m), 2.77 (3H, s), 2.91 (6H, s), 3.00-3.60 (4H, m), 3.65-3.74 (1H, br), 3.87-3.96 (1H, m), 4.37-4.48 (2H, m), 4.66-4.76 (1H, m), 6.70 (2H, d, J=8.8 Hz), 7.04 (1H, d, J=8.8 Hz), 7.10 (1H, d, J=8.8 Hz), 8.40-8.53 (2H, m), 8.57-8.66 (1H, m), 10.66-10.76 (1H, br), 10.30-10.47 (1H, br). MS (ESI) m/z: 562 (M+H)$^+$.

Example 258

N$^1$-(4-Chlorophenyl)-N$^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

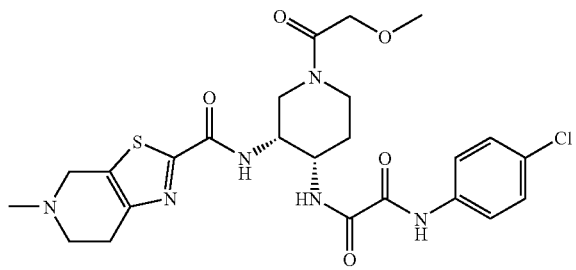

The title compound was obtained by deprotecting the compound obtained in Referential Example 367 by hydrochloric acid treatment, condensing the deprotected compound with the compound obtained in Referential Example 10 and then treating the condensation product with hydrochloric acid in a similar manner to the process described in Example 214.

$^1$H-NMR (DMSO-d$_6$) δ: 1.60-1.72 (1H, m), 1.99-2.22 (1H, m), 2.90 (3H, s), 3.03-4.80 (17H, m), 7.40 (2H, d, J=8.8 Hz), 7.83 (2H, d, J=8.8 Hz), 8.56-8.73 (1H, br), 9.14-9.33 (1H, br), 10.83 (1H, s), 11.20-11.55 (1H, br). MS (ESI) m/z: 549 (M+H)$^+$.

Example 259

N$^1$-(5-Chloropyridin-2-yl)-N$^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

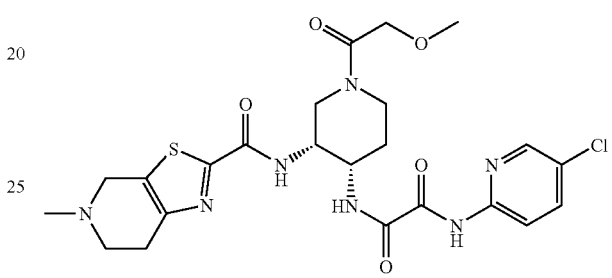

The title compound was obtained by deprotecting the compound obtained in Referential Example 368 by hydrochloric acid treatment, condensing the deprotected compound with the compound obtained in Referential Example 10 and then treating the condensation product with hydrochloric acid in a similar manner to the process described in Example 214.

$^1$H-NMR (DMSO-d$_6$) δ: 1.60-1.72 (1H, m), 1.98-2.20 (1H, m), 2.90 (3H, s), 3.00-4.77 (17H, m), 7.20-7.35 (0.8H, br), 7.48-7.56 (0.2H, br), 7.94-8.07 (1H, br), 8.40-8.70 (1H, br), 8.48-8.70 (1H, br), 9.23-9.45 (1H, br), 10.21-10.35 (1H, br), 11.30-11.70 (1H, br). MS (ESI) m/z: 550 (M+H)$^+$.

Example 260

N$^1$-(5-Bromopyridin-2-yl)-N$^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

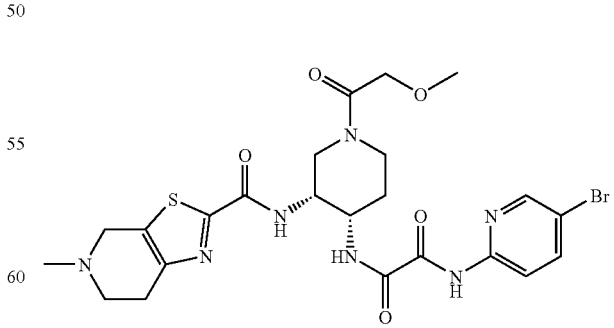

The title compound was obtained by deprotecting the compound obtained in Referential Example 369 by hydrochloric acid treatment, condensing the deprotected compound with the compound obtained in Referential Example 10 and then treating the condensation product with hydrochloric acid in a similar manner to the process described in Example 214.

$^1$H-NMR (DMSO-d$_6$) δ: 1.60-1.73 (1H, m), 1.97-2.20 (1H, m), 2.90 (3H, s), 3.03-3.52 (7H, m), 3.64-4.07 (5H, m), 4.10-4.50 (4H, m), 4.65-4.78 (1H, m), 7.28-7.35 (0.2H, m), 7.97 (1H, d, J=8.8 Hz), 8.11 (1H, dd, J=8.8, 2.2 Hz), 8.51 (1H, d, J=2.2 Hz), 8.55-8.67 (1H, m), 9.22-9.41 (1H, m), 10.20-10.31 (0.8H, m), 11.25-11.70 (1H, br). MS (ESI) m/z: 594 (M+H)$^+$.

Example 261

N$^1$-(4-Chlorophenyl)-N$^3$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)malonamide hydrochloride

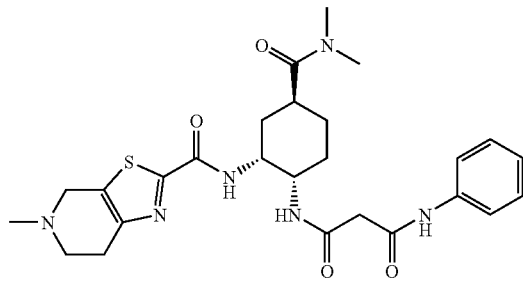

The title compound was obtained by condensing the compound obtained in Referential Example 371 with the compound obtained in Referential Example 253 and then treating the condensation product with hydrochloric acid in a similar manner to the process described in Example 5.

$^1$H-NMR (DMSO-d$_6$) δ: 1.32-1.50 (1H, m), 1.55-1.87 (5H, m), 2.78 (3H, m), 2.92 (3H, s), 2.98 (3H, s), 2.99-3.00 (1H, m), 3.05-3.50 (5H, m), 3.65-3.75 (1H, m), 3.80-3.92 (1H, m), 4.35-4.45 (1H, m), 4.45-4.55 (1H, m), 4.65-4.80 (1H, m), 7.34 (2H, d, J=8.8 Hz), 7.58 (2H, d, J=8.8 Hz), 8.00-8.10 (1H, m), 8.30-8.40 (1H, m), 10.29 (1H, d, J=12.5 Hz), 12.40 (1H, br.s). MS (FAB) m/z: 561 (M+H)$^+$.

Example 262

N$^1$-(3-Chlorophenyl)-N$^3$-(((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)malonamide hydrochloride

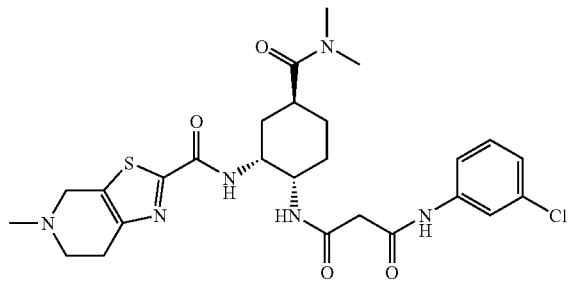

The title compound was obtained by condensing the compound obtained in Referential Example 373 with the compound obtained in Referential Example 253 and then treating the condensation product with hydrochloric acid in a similar manner to the process described in Example 5.

$^1$H-NMR (DMSO-d$_6$) δ: 1.32-1.50 (1H, m), 1.55-1.90 (5H, m), 2.77 (3H, s), 2.91 (3H, s), 2.98 (3H, s), 2.99-3.00 (1H, m), 3.05-3.50 (5H, m), 3.65-3.80 (1H, m), 3.80-3.90 (1H, m), 4.35-4.50 (1H, m), 4.50-4.60 (1H, m), 4.65-4.80 (1H, m), 7.09 (1H, d, J=8.8 Hz), 7.31 (1H, d, J=8.8 Hz), 7.38 (1H, t, J=8.8 Hz), 7.79 (1H, s), 8.00-8.10 (1H, m), 8.30-8.40 (1H, m), 10.28 (1H, d, J=12.5 Hz), 11.67 (1H, br.s). MS (FAB) m/z: 561 (M+H)$^+$.

Example 263

N$^1$-(5-Chloropyridin-2-yl)-N$^2$-((1S,2R,4S)-4-([ethyl(methyl)amino]carbonyl}-2-{[(5-methyl-4,5,6,7-tetrahydrothiazolo[5,4-c]pyridin-2-yl)carbonyl]-amino}cyclohexyl)ethanediamide hydrochloride

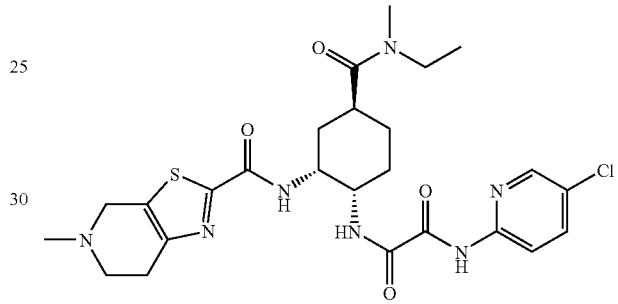

10% Palladium on carbon (0.3 g) was added to a solution of the compound (0.33 g) obtained in Referential Example 404 in ethanol (20 ml), and the mixture was stirred at room temperature for 24 hours under a hydrogen atmosphere. After removing insoluble matter by filtration through Celite pad, the filtrate was concentrated under reduced pressure. The resultant residue (0.37 g) was dissolved in N,N-dimethylformamide (20 ml), and the compound (0.3 g) obtained in Referential Example 266, 1-hydroxybenzotriazole monohydrate (0.2 g) and 1-(3-dimethylaminopropyl)-3-ethylcarbodiimide hydrochloride (0.37 g) were successively added to stir the mixture at room temperature for 18 hours. The reaction mixture was concentrated under reduced pressure, and the resultant residue was diluted with a mixed solvent of chloroform-methanol (9:1) and washed with a saturated aqueous solution of sodium hydrogencarbonate and saturated aqueous solution of sodium chloride. After the resultant organic layer was dried over anhydrous sodium sulfate, and the solvent was distilled off under reduced pressure, the resultant residue was purified by column chromatography on silica gel (chloroform:methanol=95:5) to concentrate the intended fraction. A 1N ethanol solution of hydrochloric acid was added to form a hydrochloride. This salt was recrystallized from a mixed solvent of methanol and diethyl ether to obtain the title compound (0.28 g).

$^1$H-NMR (DMSO-d$_6$) δ: 0.95 (1.5H, t, J=6.9 Hz), 1.42 (1.5H, t, J=6.9 Hz), 1.40-1.52 (1H, m), 1.60-1.78 (3H, m), 1.92-2.11 (2H, m), 2.74 (3H, s), 2.90 (3H, s), 3.10-3.38 (5H, m), 3.40-3.52 (1H, m), 3.68-3.70 (1H, m), 3.96-4.05 (1H, m), 4.41 (2H, s), 4.70 (1H, d, J=15.9 Hz), 8.00-8.01 (2H, m), 8.44 (1H, s), 8.71 (1H, dd, J=10.1, 2.2 Hz), 9.14 (0.5H, d,

J=7.8 Hz), 9.22 (0.5H, d, J=8.3 Hz), 10.24 (0.5H, s), 10.28 (0.5H, s), 11.48 (1H, br.s), 11.61 (1H, br.s). MS (FAB) m/z: 562 (M+H)⁺.

Example 264

N¹-(4-Chlorophenyl)-N²-((1S,2R,4S)-4-{[ethyl(methyl)amino]-carbonyl}-2-{[(5-methyl-4,5,6,7-tetrahydrothiazolo[5,4-c]-pyridin-2-yl)carbonyl]amino}cyclohexyl)ethanediamide hydrochloride

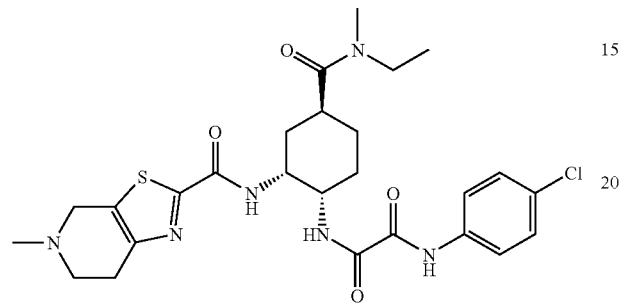

The title compound was obtained by converting the compound obtained in Referential Example 404 into an amine, condensing the amine with the compound obtained in Referential Example 374 and then treating the condensation product with hydrochloric acid in a similar manner to the process described in Example 263.

¹H-NMR (DMSO-d₆) δ: 0.97 (1.5H, t, J=6.9 Hz), 1.04 (1.5H, t, J=6.9 Hz), 1.40-1.60 (1H, m), 1.60-1.80 (3H, m), 1.92-2.11 (2H, m), 2.74 (3H, s), 2.89 (3H, s), 3.10-3.32 (5H, m), 3.40-3.52 (1H, m), 3.65-3.80 (1H, m), 3.90-4.05 (1H, m), 4.40 (2H, s), 4.70 (1H, d, J=15.9 Hz), 7.39 (2H, d, J=8.8 Hz), 7.82 (2H, d, J=8.8 Hz), 8.75 (1H, dd, J=10.1, 2.2 Hz), 9.00 (0.5H, d, J=7.8 Hz), 9.08 (0.5H, d, J=8.3 Hz), 10.81 (1H, d, J=4.9 Hz), 11.45 (1H, br.s). MS (FAB) m/z: 561 (M+H)⁺.

Example 265

N¹-(5-Bromopyridin-2-yl)-N²-((1S,2R,4S)-4-{[ethyl(methyl)amino]carbonyl}-2-{[(5-methyl-4,5,6,7-tetrahydrothiazolo[5,4-c]pyridin-2-yl)carbonyl]-amino}cyclohexyl)ethanediamide hydrochloride

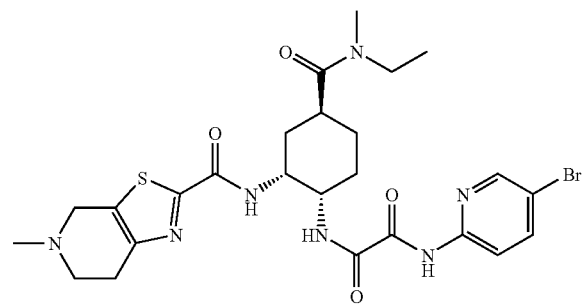

The title compound was obtained by converting the compound obtained in Referential Example 404 into an amine, condensing the amine with the compound obtained in Referential Example 375 and then treating the condensation product with hydrochloric acid in a similar manner to the process described in Example 263.

¹H-NMR (DMSO-d₆) δ: 1.02 (1.5H, t, J=6.9 Hz), 1.08 (1.5H, t, J=6.9 Hz), 1.49-1.60 (1H, m), 1.60-1.86 (3H, m), 2.00-2.20 (2H, m), 2.81 (3H, s), 2.97 (3H, s), 3.15-3.42 (6H, m), 3.50-3.60 (1H, m), 3.70-3.82 (1H, m), 4.48 (2H, s), 4.77 (1H, d, J=15.9 Hz), 8.04 (1H, d, J=8.8 Hz), 8.17 (1H, d, J=8.8 Hz), 8.58 (1H, s), 8.78 (1H, dd, J=10.1, 2.2 Hz), 9.21 (0.5H, d, J=7.8 Hz), 9.29 (0.5H, d, J=8.3 Hz), 10.29 (0.5H, s), 10.33 (0.5H, s), 11.53 (0.5H, br.s), 11.65 (0.5H, br.s). MS (FAB) m/z: 607 (M+H)⁺.

Example 266

N¹-(4-Chlroro-3-fluorophenyl)-N²-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

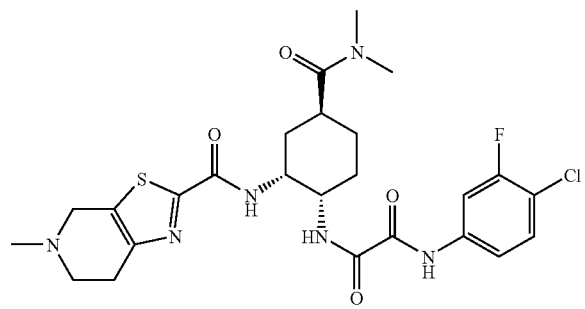

The title compound was obtained by converting the compound obtained in Referential Example 252 into an amine, condensing the amine with the compound obtained in Referential Example 378 and then treating the condensation product with hydrochloric acid in a similar manner to the process described in Example 263.

¹H-NMR (DMSO-d₆) δ: 1.44-1.52 (1H, m), 1.65-1.76 (3H, m), 2.01-2.07 (2H, m), 2.77 (3H, s), 2.93 (6H, s), 2.94-3.00 (1H, m), 3.10-3.38 (3H, m), 3.68-3.70 (1H, m), 3.96-4.05 (1H, m), 4.42 (2H, s), 4.70 (1H, d, J=15.9 Hz), 7.56 (1H, t, J=8.8 Hz), 7.68 (1H, d, J=8.8 Hz), 7.90 (1H, dd, J=11.7, 1.5 Hz), 8.73 (1H, dd, J=12.5, 7.3 Hz), 9.06 (1H, dd, J=12.5, 8.1 Hz), 11.01 (1H, d, J=5.8 Hz), 11.30-11.42 (1H, m). MS (FAB) m/z: 565 (M+H)⁺.

Example 267

N-{(1R,2S,5S)-2-{[3-(4-Chlorophenyl)-3-oxopropanoyl]amino}-5-[(dimethylamino)carbonyl]-cyclohexyl}-5-methyl-4,5,6,7-tetrahydrothiazolo[5,4-c]-pyridine-2-carboxamide

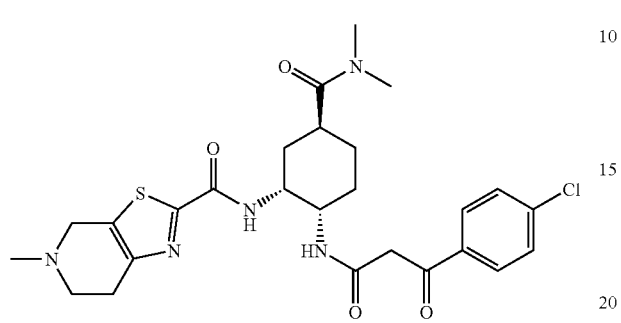

The title compound was obtained by deprotecting the compound obtained in Referential Example 383 by hydrochloric acid treatment, condensing the deprotected compound with the compound obtained in Referential Example 10 and then treating the condensation product with hydrochloric acid in a similar manner to the process described in Example 214.

$^1$H-NMR (CDCl$_3$) (free base) δ: 1.22-1.32 (1H, m), 1.49-1.92 (3H, m), 1.95-2.10 (2H, m), 2.53 (3H, s), 2.70-2.79 (1H, m), 2.80-2.90 (2H, m), 2.93 (6H, s), 2.95-3.09 (2H, m), 3.72 (2H, s), 3.87 (2H, s), 4.05-4.19 (1H, m), 4.60-4.70 (1H, m), 7.20-7.40 (2H, m), 7.42 (2H, d, J=8.3 Hz), 7.87 (2H, d, J=8.3 Hz). MS (FAB) m/z: 546 (M+H)$^+$.

Example 268

N$^1$-(5-Chlroropyridin-2-yl)-N$^2$-((1R,2R,4S)-4-[(dimethylamino)carbonyl]-2-{[(5-methyl-5H-pyrrolo[3,4-d]-thiazol-2-yl)carbonyl]amino}cyclohexyl)ethanediamide

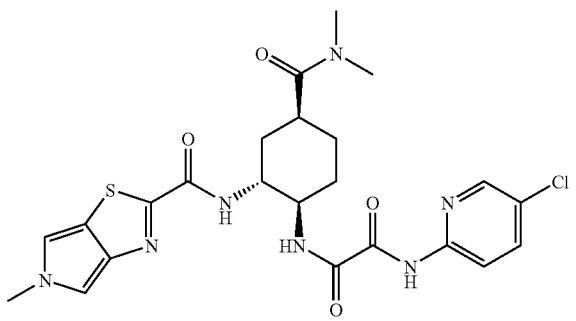

The title compound was obtained by deprotecting the compound obtained in Referential Example 386 by hydrochloric acid treatment, and condensing the deprotected compound with the compound obtained in Referential Example 293 in a similar manner to the process described in Example 214.

$^1$H-NMR (DMSO-d$_6$) δ: 1.00-2.35 (7H, m), 2.96 (3H, s), 3.04 (3H, s), 3.85-3.95 (1H, m), 3.88 (3H, s), 4.60-4.75 (1H, m), 6.68 (1H, d, J=2.0 Hz), 7.17 (1H, d, J=2.0 Hz), 7.20-7.32 (1H, m), 7.67 (1H, dd, J=8.8, 2.8 Hz), 7.99 (1H, d, J=8.4 Hz), 8.21 (1H, d, J=8.8 Hz), 8.25 (1H, d, J=2.8 Hz), 9.64 (1H, s).

HRMS (FAB) m/z: 532.1520 (M+H)$^+$.

(Calculated; C$_{23}$H$_{27}$ClN$_7$O$_4$S: 532.1534).

Example 269

N$^1$-[(5-Chlroropyridin-2-yl)amino]-N$^2$-((1R,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

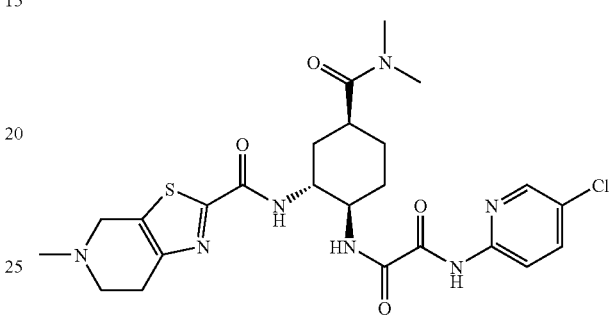

The title compound was obtained by reducing the compound obtained in Referential Example 387 in a similar manner to the process described in Referential Example 253, and condensing the reduction product with the compound obtained in Referential Example 266 and treating the condensation product with hydrochloric acid in a similar manner to the process described in Example 208.

$^1$H-NMR (DMSO-d$_6$) δ: 1.50-1.98 (6H, m), 2.82 (3H, s), 2.91 (3H, s), 2.95 (3H, s), 2.86-3.92 (7H, m), 4.30-4.81 (2H, m), 7.92-8.09 (2H, m), 8.39-8.47 (1H, m), 8.56-8.72 (2H, m), 10.17 (1H, s). MS (ESI) m/z: 548 (M+H)$^+$.

Example 270

N$^1$-(4-Chlorophenyl)-N 2-((1R,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide

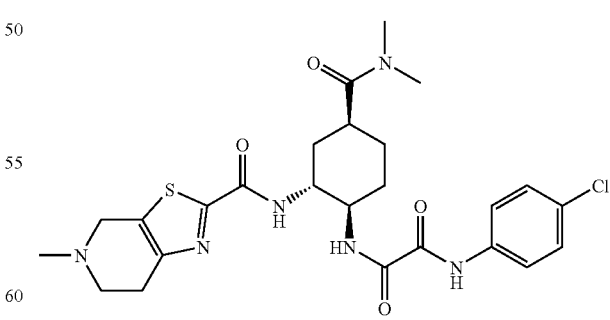

The title compound was obtained by reducing the compound obtained in Referential Example 387 in a similar manner to the process described in Referential Example 253, and condensing the reduction product with the lithium salt obtained by hydrolyzing the compound obtained in Referential Example 242 and treating the condensation product with hydrochloric acid in a similar manner to the process described in Example 191.

$^1$H-NMR (DMSO-d$_6$) δ: 1.50-1.97 (6H, m), 2.82 (3H, s), 2.91 (3H, s), 2.98 (3H, s), 2.83-3.88 (7H, m), 4.30-4.79 (2H, m), 7.37 (2H, d, J=8.8 Hz), 7.89 (2H, d, J=8.8 Hz), 8.34 (1H, d, J=8.4 Hz), 8.63 (1H, d, J=8.8 Hz), 10.72 (1H, s). MS (ESI) m/z: 547 (M+H)$^+$.

Example 271

N$^1$-{(1R,2S,5S)-2-{[(5-Chloroindol-2-yl)carbonyl]amino}-5-[(dimethylamino)carbonyl]cyclohexyl}-N$^2$-(pyridin-4-yl)ethanediamide hydrochloride

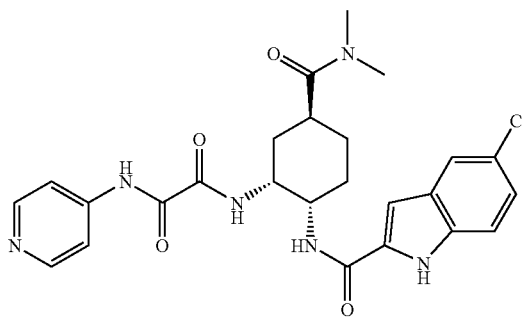

The title compound was obtained by deprotecting the compound obtained in Referential Example 310 by hydrochloric acid treatment, and condensing the deprotected compound with lithium 2-[(pyridin-4-yl)amino]-2-oxoacetate obtained by hydrolyzing the compound obtained in Referential Example 261 and then treating the condensation product with hydrochloric acid in a similar manner to the process described in Example 191.

$^1$H-NMR (DMSO-d$_6$) δ: 1.40-2.01 (6H, m), 2.79 (3H, s), 3.01 (3H, s), 3.00-3.18 (1H, m), 4.02-4.19 (1H, m), 4.45-4.55 (1H, m), 7.09 (1H, s), 7.13-7.22 (1H, m), 7.41 (1H, d, J=8.4 Hz), 7.64 (1H, br.s), 8.28 (2H, d, J=6.8 Hz), 8.36 (1H, d, J=8.0 Hz), 8.62 (1H, d, J=8.8 Hz), 8.72 (2H, d, J=6.8 Hz), 11.74 (1H, s), 11.83 (1H, s). MS (FAB) m/z: 511 (M+H)$^+$.

Example 272

N$^1$-{(1R,2S,5S)-2-{[(5-Chloroindol-2-yl)carbonyl]amino}-5-[(dimethylamino)carbonyl]cyclohexyl}-N$^2$-(pyridin-3-yl)ethanediamide hydrochloride

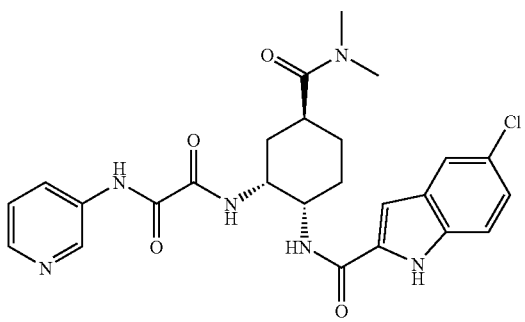

The title compound was obtained by using methyl 2-[(pyridin-3-yl)amino]-2-oxoacetate obtained by condensing 3-aminopyridine with methyl 2-chloro-2-oxoacetate in a similar manner to the process described in Referential Example 242, and the compound obtained in Referential Example 310 as raw materials in a similar manner to the process described in Example 271.

$^1$H-NMR (DMSO-d$_6$) δ: 1.40-2.05 (6H, m), 2.80 (3H, s), 3.02 (3H, s), 2.92-3.15 (1H, m), 4.02-4.17 (1H, m), 4.42-4.58 (1H, m), 7.10 (1H, s), 7.12-7.19 (1H, m), 7.40 (1H, d, J=8.4 Hz), 7.62-7.87 (2H, m), 8.36-8.64 (4H, m), 9.18 (1H, s), 11.39 (1H, s), 11.79 (1H, s). MS (FAB) m/z: 511 (M+H)$^+$.

Example 273

N$^1$-{(1R,2S,5S)-2-{[(5-Chloroindol-2-yl)carbonyl]amino}-5-[(dimethylamino)carbonyl]cyclohexyl}-N$^2$-(piperidin-4-yl)ethanediamide hydrochloride

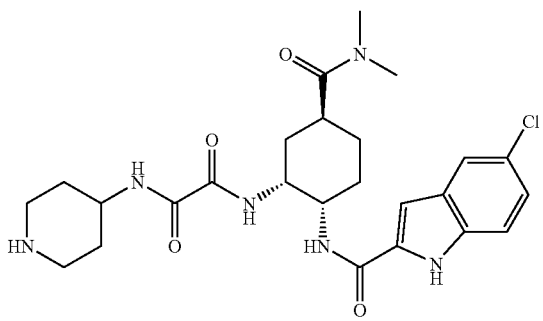

A 4N dioxane solution (8.0 ml) of hydrochloric acid was added to a solution of the compound (400 mg) obtained in Referential Example 389 in ethanol (5.0 ml) at room temperature and the mixture was stirred the same temperature for 5 hours. The solvent was distilled off under reduced pressure, the residue was washed with methylene chloride, and insoluble matter was filterred and washed to obtain the title compound (320 mg).

$^1$H-NMR (DMSO-d$_6$) δ: 1.38-1.92 (10H, m), 2.77 (3H, s), 2.96 (3H, s), 2.82-3.35 (6H, m), 3.88-4.10 (2H, m), 4.34-4.43 (1H, m), 7.05 (1H, s), 7.11-7.17 (1H, m), 7.38 (1H, d, J=8.8 Hz), 7.65 (1H, s), 8.25 (1H, d, J=8.0 Hz), 8.34 (1H, d, J=7.6 Hz), 8.89 (1H, d, J=8.4 Hz), 11.75 (1H, s). MS (ESI) m/z: 517 (M+H)$^+$.

Example 274

N$^1$-{(1R,2S,5S)-2-{[(5-Chloroindol-2-yl)carbonyl]amino}-5-[(dimethylamino)carbonyl]cyclohexyl}-N$^2$-(1-methylpiperidin-4-yl)ethanediamide hydrochloride

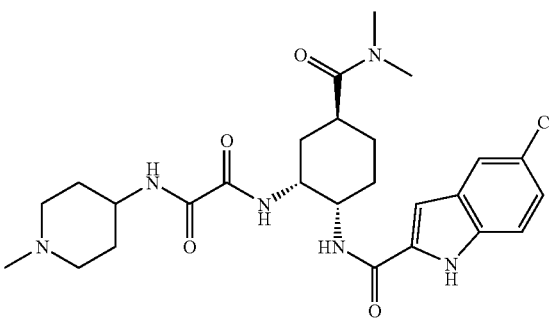

The title compound was obtained by methylating the compound obtained in Example 273 in a similar manner to the process described in Referential Example 9 and treating it with hydrochloric acid.

¹H-NMR (DMSO-d₆) δ: 1.40-2.01 (11H, m), 2.67 (3H, s), 2.79 (3H, s), 2.98 (3H, s), 2.85-4.48 (7H, m), 7.07 (1H, s), 7.16 (1H, dd, J=8.8, 2.0 Hz), 7.40 (1H, d, J=8.8 Hz), 7.68 (1H, d, J=2.0 Hz), 8.25-8.35 (1H, m), 8.37 (1H, d, J=7.6 Hz), 8.90-9.02 (1H, m), 9.82 (1H, br.s), 11.78 (1H, s). MS (ESI) m/z: 531 (M+H)⁺.

Example 275

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl))-N¹-methylethanediamide hydrochloride

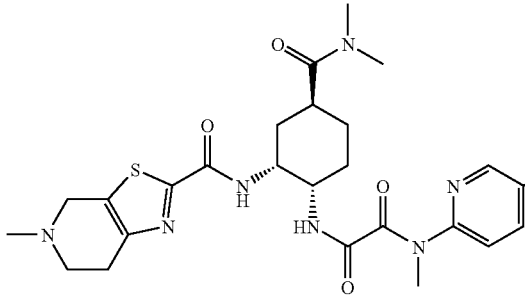

The title compound was obtained by hydrolyzing the compound obtained in Referential Example 390, condensing the hydrolyzate with the compound obtained in Referential Example 253 and then treating the condensation product with hydrochloric acid in a similar manner to the process described in Example 191.

¹H-NMR (DMSO-d₆) δ: 1.32-1.97 (6H, m), 2.42-2.51 (1H, m), 2.76 (3H, s), 2.91 (3H, s), 2.93 (3H, s), 3.27 (3H, s), 3.00-4.80 (8H, m), 7.45 (1H, br.s), 7.88-7.97 (1H, m), 8.25-8.41 (2H, m), 8.78-8.91 (1H, m). MS (FAB) m/z: 562 (M+H)⁺.

Example 276

N¹-(5-Chloropyrimidin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

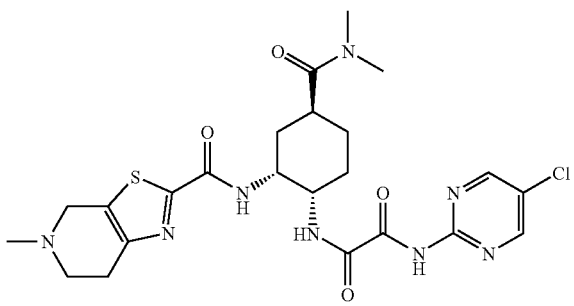

The title compound was obtained by hydrolyzing the compound obtained in Referential Example 391, condensing the hydrolyzate with the compound obtained in Referential Example 253 and then treating the condensation product with hydrochloric acid in a similar manner to the process described in Example 191.

¹H-NMR (DMSO-d₆) δ: 1.38-2.10 (7H, m), 2.77 (3H, s), 2.90 (3H, s), 2.93 (3H, s), 3.04-4.80 (8H, m), 8.60-8.70 (2H, m), 8.82 (2H, s), 9.08 (1H, br.s), 10.64 (1H, s), 11.57 (1H, br.s). MS (FAB) m/z: 549 (M+H)⁺.

Example 277

N¹-(4-Chlorophenyl)-N²-((1S,2R,4S)-4-{[ethyl(methyl)amino]-carbonyl}-2-{[(5-methyl-5,6-dihydro-4H-pyrrolo[3,4-d]-thiazol-2-yl)carbonyl]amino}cyclohexyl)ethanediamide hydrochloride

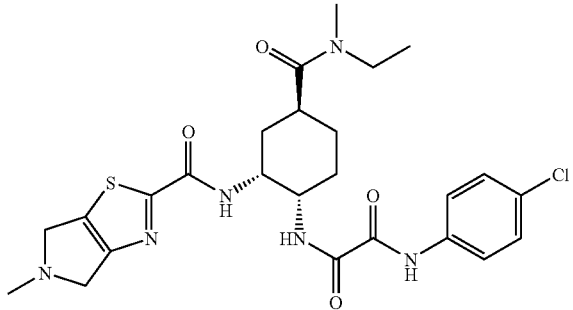

The title compound was obtained by reducing the compound obtained in Referential Example 392 in a similar manner to the process described in Referential Example 253, and condensing the reduction product with the carboxylic acid obtained by hydrolyzing the compound obtained in Referential Example 242 and treating the condensation product with hydrochloric acid in a similar manner to the process described in Example 195.

¹H-NMR (DMSO-d₆) δ: 0.96, 1.02 (3H, each t, J=7.0 Hz), 1.47-1.58 (1H, m), 1.65-1.77 (3H, m), 1.98-2.08 (2H, m), 2.76-2.91 (4H, m), 3.07 (3H, s), 3.19-3.41 (2H, m), 3.98-4.04 (1H, m), 4.42 (1H, br.s), 4.46-4.94 (4H, m), 7.41 (2H, d, J=8.8 Hz), 7.83 (2H, d, J=8.8 Hz), 8.74-8.80 (1H, m), 9.02 (1H, d, J=7.3 Hz), 10.82 (1H, s), 12.41 (1H, br.s). MS (FAB) m/z: 547 (M+H)⁺.

Example 278

N¹-(5-Bromopyridin-2-yl)-N²-((1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride

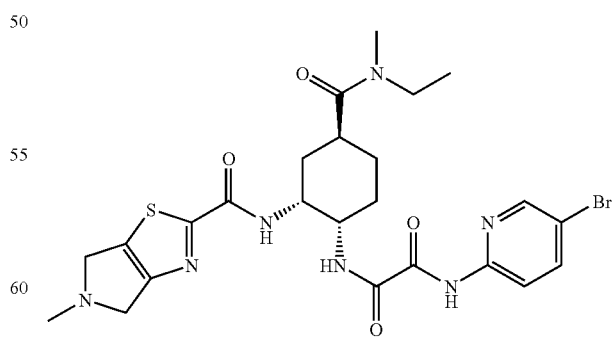

The title compound was obtained from the compound obtained in Referential Example 392 and the compound obtained in Referential Example 262 in a similar manner to the process described in Example 277.

¹H-NMR (DMSO-d₆) δ: 0.90-1.08 (3H, m), 1.40-2.13 (6H, m), 2.70-3.53 (13H, m), 3.92-4.08 (1H, m), 4.35-4.47 (1H, m), 7.95 (1H, d, J=8.8 Hz), 8.10 (1H, dd, J=8.8, 2.4 Hz), 8.50-8.55 (1H, m), 8.68-8.78 (1H, m), 9.12-9.18 (1H, m), 10.26 (1H, s). MS (FAB) m/z: 592 (M+H)⁺.

Example 279

N¹-(5-Chloropyridin-2-yl)-N 2-((1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride

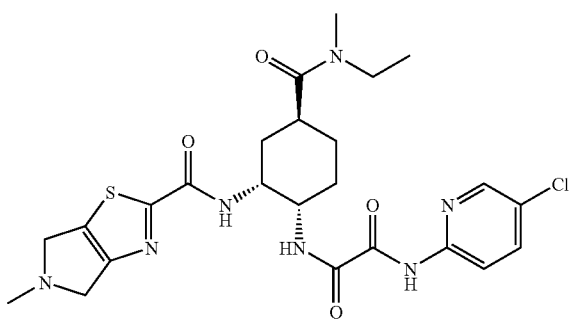

The title compound was obtained from the compound obtained in Referential Example 392 and the compound obtained in Referential Example 243 in a similar manner to the process described in Example 277.

¹H-NMR (DMSO-d₆) δ: [0.95 (t, J=7.0 Hz), 1.01 (t, J=6.8 Hz), 3H], 1.45-1.72 (4H, m), 1.96-2.07 (2H, m), 2.74-2.90 (4H, m), 3.06 (3H, s), 3.18-3.40 (2H, m), 3.95-4.02 (1H, m), 4.41 (1H, br.s), 4.54-4.90 (4H, m), 8.00 (2H, br.s), 8.45 (1H, s), 8.70-8.75 (1H, m), 9.15 (1H, br.s), 10.27 (1H, br.s), 12.29 (1H, br.s). MS (ESI) m/z: 548 (M+H)⁺.

Example 280

N¹-(4-Chloro-3-methoxyphenyl)-N²-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

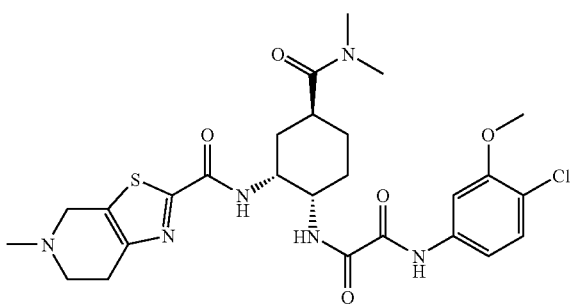

The title compound was obtained by condensing the compound obtained in Referential Example 395 with the compound obtained in Referential Example 10 and treating the condensation product with hydrochloric acid in a similar manner to the process described in Example 2.

¹H-NMR (DMSO-d₆) δ: 1.46-1.54 (1H, m), 1.67-1.77 (3H, m), 2.01-2.10 (2H, m), 2.79 (3H, s), 2.92-2.98 (7H, m), 3.21 (2H, br.s), 3.49 (1H, br.s), 3.69 (1H, br.s), 3.80 (3H, s), 3.98-4.03 (1H, m), 4.42-4.50 (2H, m), 4.69 (1H, br.s), 7.37 (1H, d, J=8.7 Hz), 7.48 (1H, dd, J=8.7, 2.2 Hz), 7.72 (1H, d, J=2.2 Hz), 8.75 (1H, d, J=7.3 Hz), 9.06 (1H, br.s), 10.77 (1H, s), 11.44 (1H, br.s). MS (FAB) m/z: 577 (M+H)⁺.

Example 281

N¹-(4-Chlorophenyl)-N²-((1R*,2R*)-2-{[(5-methyl-4,5,6,7-tetrahydrothiazolo[5,4-c]pyridin-2-yl)carbonyl]-amino}cyclopentyl)ethanediamide hydrochloride

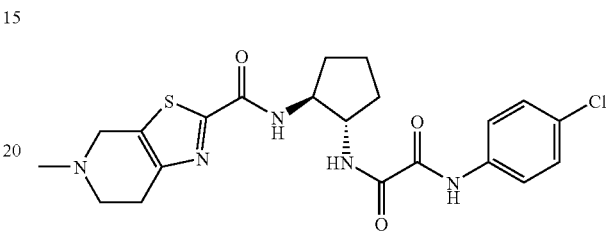

The title compound was obtained by hydrolyzing the compound obtained in Referential Example 242, condensing the hydrolyzate with the compound obtained in Referential Example 62 and then treating the condensation product with hydrochloric acid in a similar manner to the process described in Example 195.

¹H-NMR (DMSO-d₆) δ: 1.65-1.73 (4H, m), 1.91-1.96 (2H, m), 2.91 (3H, s), 3.15 (2H, br.s), 3.49 (1H, br.s), 3.66 (1H, br.s), 4.32-4.42 (3H, m), 4.66 (1H, br.s), 7.40 (2H, d, J=8.9 Hz), 7.84 (2H, d, J=8.9 Hz), 8.92 (1H, d, J=8.5 Hz), 9.03 (1H, d, J=8.3 Hz), 10.76 (1H, s), 11.32 (1H, br.s). MS (FAB) m/z: 462 (M+H)⁺.

Example 282

N¹-(5-Chloropyridin-2-yl)-N²-((1R*,2R*)-2-{[(5-methyl-4,5,6,7-tetrahydrothiazolo[5,4-c]pyridin-2-yl)carbonyl]-amino}cyclopentyl)ethanediamide hydrochloride

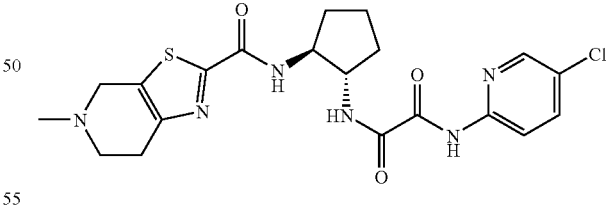

The title compound was obtained by condensing the compound obtained in Referential Example 62 with the compound obtained in Referential Example 266 and then treating the condensation product with hydrochloric acid in a similar manner to the process described in Example 208.

¹H-NMR (DMSO-d₆) δ: 1.71 (4H, br.s), 1.96 (2H, br.s), 2.90 (3H, s), 3.14 (1H, br.s), 3.21 (1H, br.s), 3.47 (1H, br.s), 3.68 (1H, br.s), 4.34-4.45 (3H, m), 4.66 (1H, br.s), 7.99-8.06 (2H, m), 8.43-8.44 (1H, m), 8.94 (1H, d, J=8.3 Hz), 9.20 (1H, d, J=8.5 Hz), 10.20 (1H, br.s), 11.78 (1.1H, br.s). MS (FAB) m/z: 463 (M+H)⁺.

Example 283

N$^1$-((1S,2R,4S)-4-[(Dimethylamino)carbonyl]-2-{[(5-methyl-4,5,6,7-tetrahydrothiazolo[5,4-c]pyridin-2-yl)carbonyl]-amino}cyclohexyl)-N$^2$-(4-ethynylphenyl)ethanediamide

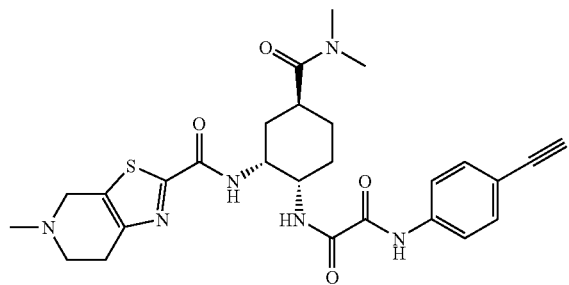

The title compound was obtained by condensing the compound obtained in Referential Example 252 with the compound obtained in Referential Example 397 in a similar manner to the process described in Example 263.

$^1$H-NMR (CDCl$_3$) δ: 1.67-2.16 (6H, m), 2.51 (3H, s), 2.76-2.91 (5H, m), 2.94 (3H, s), 3.04 (3H, s), 3.07 (1H, s), [3.65 (1H, d, J=15.5 Hz), 3.73 (1H, d, J=15.5 Hz)AB pattern], 4.09-4.16 (1H, m), 4.72-4.75 (1H, m), 7.42-7.46 (3H, m), 7.58 (2H, d, J=8.5 Hz), 8.02 (1H, d, J=8.1 Hz), 9.36 (1H, s). MS (FAB) m/z: 537 (M+H)$^+$.

Example 284

N$^1$-(5-Chloropyrazin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino)cyclohexyl)ethanediamide hydrochloride

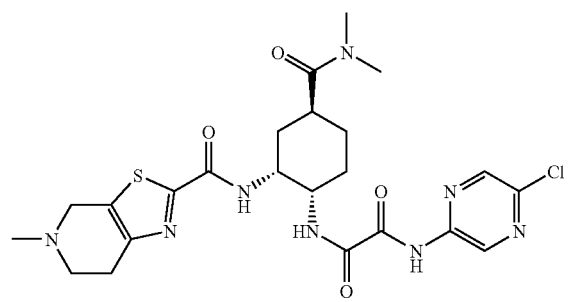

The title compound was obtained by condensing the compound obtained in Referential Example 253 with the compound obtained in Referential Example 399 in a similar manner to the process described in Referential Example 97 and then treating the condensation product with hydrochloric acid.

$^1$H-NMR (DMSO-d$_6$) δ: 1.44-1.52 (1H, m), 1.65-1.77 (3H, m), 2.00-2.10 (2H, m), 2.77 (3H, s), 2.91-2.97 (7H, m), 3.20 (2H, br.s), 3.48 (1H, br.s), 3.68 (1H, br.s), 3.97-4.02 (1H, m), 4.40-4.46 (2H, m), 4.68 (1H, br.s), 8.64 (1H, d, J=1.2 Hz), 8.70 (1H, d, J=7.3 Hz), 9.02 (1H, s), 9.21 (1H, br.s), 10.91 (1H, s), 11.50 (1H, br.s). MS (FAB) m/z: 549 (M+H)$^+$.

Example 285

N$^1$-(4-Chloro-3-nitrophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

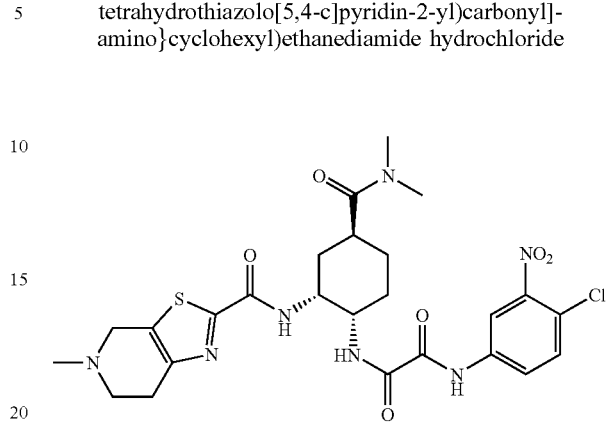

The title compound was obtained by condensing the compound obtained in Referential Example 253 with the compound obtained in Referential Example 400 in a similar manner to the process described in Referential Example 97 and then treating the condensation product with hydrochloric acid.

$^1$H-NMR (DMSO-d$_6$) δ: 1.44-1.53 (1H, m), 1.66-1.73 (3H, m), 197-2.07 (2H, m), 2.77 (3H, s), 2.89-3.05 (7H, m), 3.20 (2H, br.s), 3.55 (2H, br.s), 4.00 (1H, br.s), 4.44 (1H, br.s), 4.52 (2H, br.s), 7.75 (1H, d, J=8.8 Hz), 8.08 (1H, d, J=8.8 Hz), 8.59 (1H, s), 8.71 (1H, d, J=7.3 Hz), 9.07 (1H, d, J=8.0 Hz), 11.24 (1H, s), 11.58 (1H, br.s). MS (FAB) m/z: 592 (M+H)$^+$.

Example 286

N$^1$-(4-Chloro-2-nitrophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

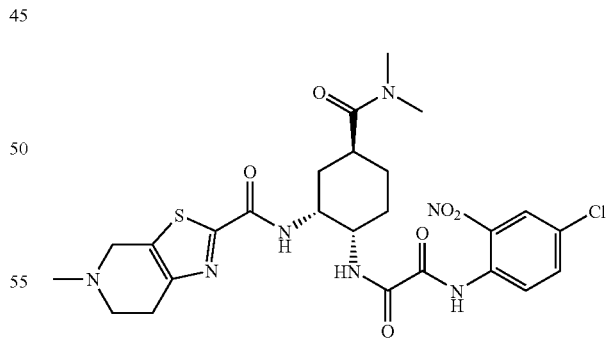

The title compound was obtained by condensing the compound obtained in Referential Example 253 with the compound obtained in Referential Example 401 and then treating the condensation product with hydrochloric acid in a similar manner to the process described in Example 208.

$^1$H-NMR (DMSO-d$_6$) δ: 1.46-1.54 (1H, m), 1.66-1.77 (3H, m), 2.03-2.10 (2H, m), 2.79 (3H, s), 2.90-2.93 (7H, m), 3.17-3.28 (2H, m), 3.49 (1H, br.s), 3.68 (1H, br.s), 3.99-4.04

(1H, m), 4.41 (1H, br.s), 4.46 (1H, br.s), 4.68 (1H, br.s), 7.89 (1H, d, J=9.0 Hz), 8.20-8.21 (2H, m), 8.73 (1H, d, J=6.4 Hz), 9.28 (1H, br.s), 11.49 (1H, br.s), 11.56 (1H, s). MS (FAB) m/z: 592 (M+H)+.

Example 287

N$^1$-(3-Amino-4-chlorophenyl)-N$^2$-((1S,2R,4S)-4-[(dimethylamino)carbonyl]-2-([(5-methyl-4,5,6,7-tetrahydrothiazolo[5,4-c]pyridin-2-yl)carbonyl]-amino}cyclohexyl)ethanediamide hydrochloride

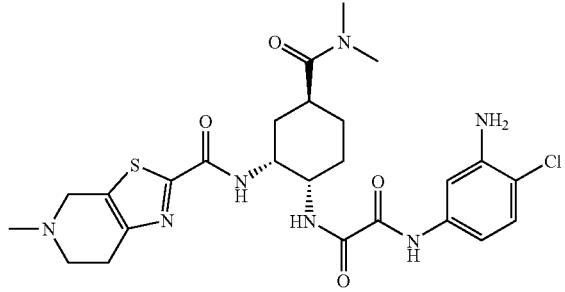

The compound (236 mg) obtained in Example 285 was dissolved in ethanol (25 ml), and a catalytic amount of Raney nickel was added to stir the mixture at room temperature for 17 hours under a hydrogen atmosphere. Thereafter, a catalytic amount of Raney nickel was additionally added to stir the mixture for additional 7 hours. The catalyst was removed by filtration, and the solvent was distilled off under reduced pressure. The residue was purified by column chromatography on silica gel (methylene chloride:methanol=23:2) to obtain a pale yellow solid (101 mg). This product was dissolved in methylene chloride, and a 1N ethanol solution (360 μl) of hydrochloric acid. The solvent was distilled off under reduced pressure, a small amount of methanol was added to the residue, and diethyl ether was added dropwise while irradiating with ultrasonic waves to collect precipitate formed. This product was washed with diethyl ether to obtain the title compound (95 mg).

$^1$H—NMR (DMSO-d$_6$) δ: 1.45-1.53 (1H, m), 1.66-1.73 (3H, m), 1.97-2.10 (2H, m), 2.78 (3H, s), 2.91-2.94 (7H, br.s), 3.11-3.19 (1H, m), 3.29 (1H, br.s), 3.48 (1H, br.s), 3.69 (1H, br.s), 3.95-4.02 (1H, m), 4.44 (2H, br.s), 4.68, 4.72 (1H, each br.s), 4.86 (2.5H, br.s), 6.98 (1H, dd, J=8.5, 1.9 Hz), 7.14 (1H, d, J=8.5 Hz), 7.35, 7.38 (1H, each br.s), 8.72-8.77 (1H, m), [8.91 (d, J=7.8 Hz), 8.99 (d, J=8.5 Hz), 1H], 10.45, 10.47 (1H, each br.s), 11.74 (1H, br.s). MS (FAB) m/z: 562 (M+H)+.

Example 288

N$^1$-(2-Amino-4-chlorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

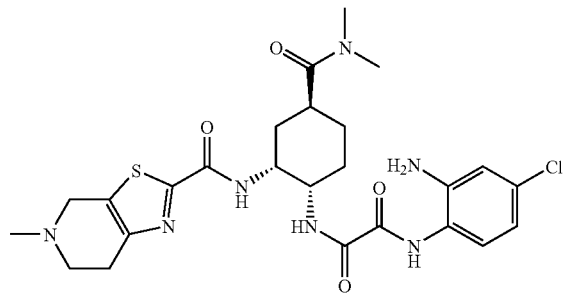

The title compound was obtained from the compound obtained in Example 286 in a similar manner to the process described in Example 287.

$^1$H-NMR (DMSO-d$_6$) δ: 1.45-1.77 (4H, m), 2.06-2.09 (2H, m), 2.78 (3H, s), 2.92 (7H, br.s), 3.12-3.19 (1H, m), 3.26-3.28 (1H, m), 3.48 (1H, br.s), 3.70 (1H, br.s), 4.00-4.44 (5.7H, m), 4.70, 4.74 (1H, each br.s), 6.63-6.66 (1H, m), 6.85 (1H, br.s), 7.18-7.21 (1H, m), 8.77-8.81 (1H, m), [8.97 (d, J=7.8 Hz), 9.06 (d, J=8.1 Hz), 1H], 9.98 (1H, s), 11.60 (1H, br.s). MS (FAB) m/z: 562 (M+H)+.

Example 289

N$^1$-(6-Chloro-4-methylpyridin-3-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride The title compound was obtained by condensing the compound obtained in Referential Example 270 with the compound obtained in Referential Example 402 and then treating the condensation product with hydrochloric acid in a similar manner to the process described Example 199.

$^1$H-NMR (DMSO-d$_6$) δ: 1.45-1.54 (1H, m), 1.65-1.77 (3H, m), 2.02-2.08 (2H, m), 2.22 (3H, s), 2.79 (3H, s)., 2.89-2.93 (7H, m), 3.19 (2H, br.s), 3.54 (2H, br.s), 3.99-4.04 (1H, m), 4.40-4.42 (1H, m), 4.50 (2H, br.s), 7.49 (1H, s), 8.32 (1H, s), 8.75 (1H, d, J=7.1 Hz), 9.09 (1H, d, J=7.3 Hz), 10.48 (1H, s), 11.40 (0.9H, br.s). MS (FAB) m/z: 562 (M+H)+.

Example 290

N-{(1R,2S,5S)-2-({[(E)-2-(4-Chlorophenyl)diazenyl]-carbonyl}amino)-5-[(dimethylamino)carbonyl]cyclohexyl}-5-methyl-4,5,6,7-tetrahydrothiazolo[5,4-c]pyridine-2-carboxamide hydrochloride

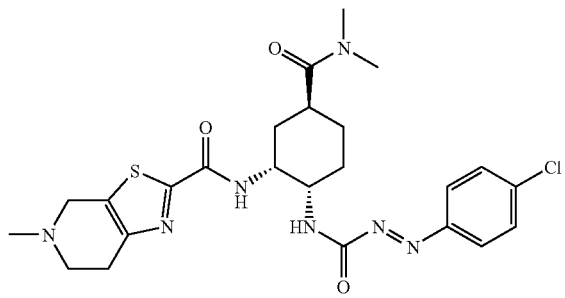

After 10% Palladium on carbon (200 mg) was added to a solution of the compound (700 mg) obtained in Referential Example 252 in tetrahydrofuran (10 ml), and the mixture was stirred at room temperature for 2 days under a hydrogen atmosphere, the reaction mixture was filtered, and the compound obtained in Referential Example 405 (470 mg) was added to a solution of an amine obtained by concentrating the filtrate in formamide (5.0 ml) to stir the mixture at 95° C. for 18 hours. After the reaction mixture was concentrated, and a saturated aqueous solution (50 ml) of sodium hydrogencarbonate, water (50 ml) and methylene chloride (30 ml) were added to conduct liquid separation, the resultant water layer was extracted with methylene chloride (2×20 ml). Organic layere were combined, dried over anhydrous sodium sulfate, concentrated and purified by column chromatography on silica gel (methylene chloride:methanol=12:1). This purified product was treated with a 1N ethanol solution of hydrochloric acid to obtain the title compound (100 mg).

$^1$H-NMR (DMSO-d$_6$) δ: 1.40-1.60 (1H, m), 1.65-2.05 (5H, m), 2.80 (3H, s), 2.91 (3H, s), 2.99 (3H, s), 3.00-3.20 (2H, m), 3.20-3.32 (1H, m), 3.43 (1H, br.s), 3.69 (1H, br.s), 3.95 (1H, br.s), 4.45 (1H, br.s), 4.60-4.80 (2H, m), 7.68 (2H, d, J=8.7 Hz), 7.83 (2H, d, J=8.7 Hz), 8.41 (1H, br.s), 8.68 (1H, d, J=7.6 Hz), 11.40-11.80 (1H, br). MS (ESI) m/z: 532 (M+H)$^+$.

Example 291

N-{(1R,2S,5S)-2-({[2-(4-Chlorophenyl)hydrazino]-carbonyl}amino)-5-[(dimethylamino)carbonyl]cyclohexyl}-5-methyl-4,5,6,7-tetrahydrothiazolo[5,4-c]pyridine-2-carboxamide hydrochloride

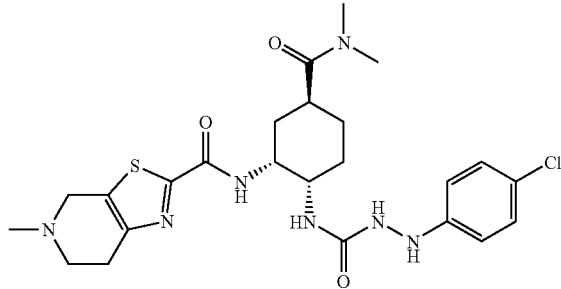

The title compound was obtained by changing the reaction conditions in the reaction described in Example 290 to conditions that stirring was conducted at 40° C. for 3 days.

$^1$H-NMR (DMSO-d$_6$) δ: 1.30-1.50 (1H, m), 1.50-1.80 (3H, m), 1.80-1.97 (2H, m), 2.76 (3H, s), 2.80-3.05 (2H, m), 2.91 (6H, s), 3.05-3.30 (2H, m), 3.47 (2H, br.s), 4.30-4.50 (2H, m), 4.72 (1H, t, J=12.8 Hz), 6.40-6.60 (2H, m), 6.55-6.70 (2H, m), 6.95-7.20 (2H, m), 7.88 (1H, d, J=11.3 Hz), 8.48-8.65 (1H, m), 11.48-11.80 (1H, br). MS (ESI) m/z: 534 (M+H)$^+$.

Example 292

N$^1$-(5-Chloropyridin-2-yl)-N$^2$-((1S,2R,4S)-4-[(dimethylamino)carbonyl]-2-{[(4,5,6,7-tetrahydrothiazolo[5,4-c]pyridin-2-yl)carbonyl]-amino}cyclohexyl)ethanediamide hydrochloride

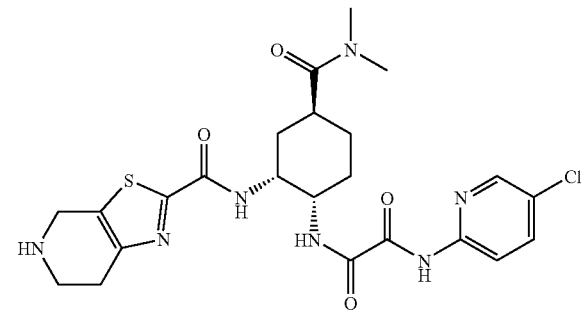

The title compound was obtained by condensing the compound obtained in Referential Example 34 with the compound obtained in Referential Example 420 and then treating the condensation product with hydrochloric acid in a similar manner to the process described Example 17.

$^1$H-NMR (DMSO-d$_6$) δ: 1.45-1.55 (1H, m), 1.60-1.80 (3H, m), 1.95-2.10 (2H, m), 2.78 (3H, s), 2.85-3.00 (4H, m), 3.11 (2H, br s), 3.40-3.55 (2H, m), 3.95-4.07 (1H, m), 4.37-4.45 (1H, m), 4.48 (2H, br s), 8.00-8.01 (2H, m), 8.43-8.47 (1H, m), 8.10 (1H, d, J=7.1 Hz), 9.16 (1H, d, J=7.8 Hz), 9.43 (2H, br s), 10.27 (1H, s). MS (FAB) m/z: 534 (M+H)$^+$.

Example 293

N-((3R*,4S*)-4-{[(5-Chloroindol-2-yl)carbonyl]amino}-1-[(1-hydroxycyclopropyl)carbonyl]piperidin-3-yl)-5-methyl-4,5,6,7-tetrahydrothiazolo[5,4-c]pyridine-2-carboxamide hydrochloride

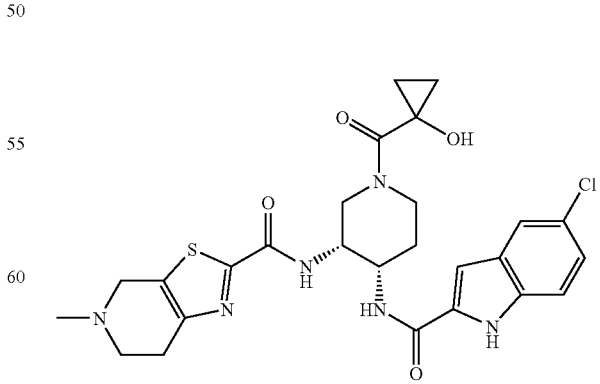

The title compound was obtained by condensing the compound obtained in Example 118 with 1-hydroxy-1- cyclopropanecarboxylic acid and then treating the condensation product with hydrochloric acid in a similar manner to the process described Example 150.

$^1$H-NMR (DMSO-$d_6$) δ: 0.60-0.90 (3H, br), 0.92-1.03 (1H, m), 1.71-1.84 (1H, m), 1.85-2.03 (1H, m), 2.91 (3H, s), 3.00-3.80 (7H, m), 4.05-4.80 (5H, m), 6.28-6.42 (1H, br), 7.09 (1H, s), 7.18 (1H, dd, J=8.8, 1.5 Hz), 7.42 (1H, d, J=8.8 Hz), 7.70 (1H, d, J=1.5 Hz), 8.14-8.29 (1H, br), 8.41 (1H, br d, J=7.6 Hz), 11.83 (1H, s). MS (ESI) m/z: 557 (M+H)$^+$.

Example 294

N-((3R*,4S*)-4-{[(5-Chloroindol-2-yl)carbonyl]amino}-1-[(1-methoxycyclopropyl)carbonyl]piperidin-3-yl)-5-methyl-4,5,6,7-tetrahydrothiazolo[5,4-c]pyridine-2-carboxamide hydrochloride

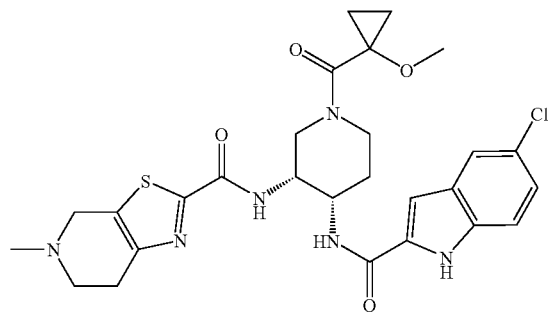

The title compound was obtained by condensing the compound obtained in Example 118 with the compound obtained in Referential Example 409 and then treating the condensation product with hydrochloric acid in a similar manner to the process described Example 150.

$^1$H-NMR (DMSO-$d_6$) δ: 0.65-1.05 (4H, m), 1.74-1.88 (1H, m), 1.92-2.10 (1H, m), 2.91 (3H, s), 3.00-3.80 (10H, m), 4.05-4.83 (6H, m), 7.08 (1H, s), 7.18 (1H, dd, J=8.6, 2.0 Hz), 7.42 (1H, d, J=8.6 Hz), 7.71 (1H, d, J=2.0 Hz), 8.08-8.30 (1H, br), 8.41 (1H, br d, J=7.8 Hz), 10.60-10.80 (0.5H, br), 10.85-11.05 (0.5H, br), 11.84 (1H, s).

Example 295

7-Chloro-N-((3R,4S)-1-(2-methoxyacetyl)-3-{[(5-methyl-4,5,6,7-tetrahydrothiazolo[5,4-c]pyridin-2-yl)carbonyl]-amino}piperidin-4-yl)-3-isoquinolinecarboxamide hydrochloride

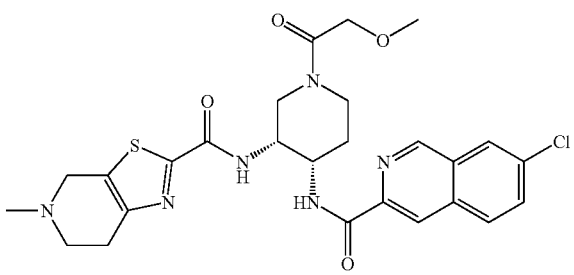

The title compound was obtained by treating the compound obtained in Referential Example 410 with a 4N dioxane solution of hydrochloric acid to deprotect it, condensing the deprotected compound with the compound obtained in Referential Example 10 and then subjecting the condensation product to a hydrochloric acid treatment again in a similar manner to the process described in Example 219.

$^1$H-NMR (DMSO-$d_6$) δ: 1.60-1.80 (1H, m), 2.13-2.38 (1H, m), 2.90 (3H, s), 3.00-3.87 (10H, m), 3.89-4.10 (2H, m), 4.15-4.58 (4H, m), 4.60-4.78 (1H, m), 7.89 (1H, d, J=8.8 Hz), 8.25 (1H, d, J=8.8 Hz), 8.37 (1H, s), 8.61 (1H, s), 8.70-8.95 (1H, m), 9.05-9.29 (1H, m), 9.36 (1H, s), 11.20-11.40 (0.5H, br), 11.45-11.65 (0.5H, br). MS (ESI) m/z: 557 (M+H)$^+$.

Example 296

N$^1$-(4-chloro-3-fluorophenyl)-N$^2$-((3R,4S)-1-(2-methoxyacetyl)-3-{[(5-methyl-4,5,6,7-tetrahydrothiazolo[5,4-c]pyridin-2-yl)carbonyl]-amino}piperidin-4-yl)ethanediamide hydrochloride

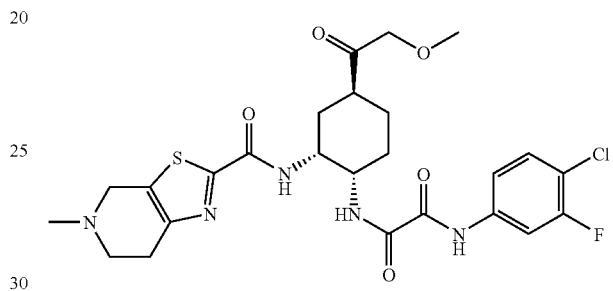

The title compound was obtained by treating the compound obtained in Referential Example 411 with a 4N dioxane solution of hydrochloric acid to deprotect it, condensing the deprotected compound with the compound obtained in Referential Example 10 and then subjecting the condensation product to a hydrochloric acid treatment again in a similar manner to the process described in Example 219.

$^1$H-NMR (DMSO-$d_6$) δ: 1.60-1.72 (1H, m), 1.98-2.21 (1H, m), 2.91 (3H, s), 3.00-3.52 (9H, m), 3.56-4.05 (3H, m), 4.08-4.50 (4H, m), 4.60-4.78 (1H, br), 7.56 (1H, t, J=8.8 Hz), 7.70 (1H, d, J=9.0 Hz), 7.91 (1H, dd, J=8.8, 2.3 Hz), 8.50-8.72 (1H, m), 9.15-9.35 (1H, m), 11.02 (1H, s), 11.15-11.33 (0.5H, br), 11.35-11.50 (0.5H, br). MS (FAB) m/z: 567 (M+H)$^+$.

Example 297

N$^1$-(5-chloro-2-thienyl)-N$^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

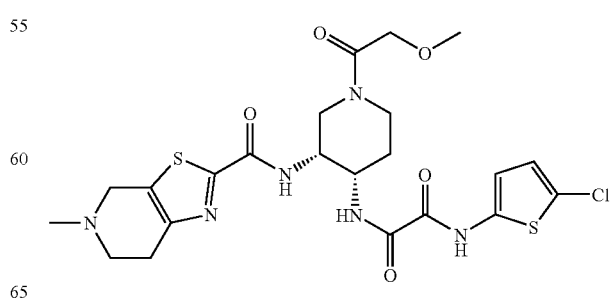

The title compound was obtained by treating the compound obtained in Referential Example 412 with a 4N dioxane solution of hydrochloric acid to deprotect it, condensing the deprotected compound with the compound obtained in Referential Example 10 and then subjecting the condensation product to a hydrochloric acid treatment again in a similar manner to the process described in Example 219.

$^1$H-NMR (DMSO-$d_6$) δ: 1.60-1.73 (1H, m), 1.96-2.19 (1H, m), 2.91 (3H, s), 3.04-3.54 (9H, m), 3.60-4.05 (3H, m), 4.07-4.34 (3H, m), 4.35-4.54 (1H, br), 4.60-4.80 (1H, br), 6.89 (1H, d, J=4.2 Hz), 6.93 (1H, d, J=4.2 Hz), 8.48-8.70 (1H, m), 9.18-9.40 (1H, m), 12.31 (1H, s). MS (ESI) m/z: 555 (M+H)$^+$.

Example 298

N-{(1R,2S,5S)-2-{[2-(4-Chlorophenoxy)acetyl]amino}-5-[(dimethylamino)carbonyl]cyclohexyl}-5-methyl-4,5,6,7-tetrahydrothiazolo[5,4-c]pyridine-2-carboxamide hydrochloride

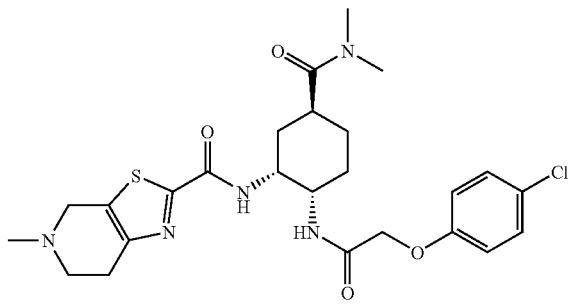

The title compound was obtained by reducing the compound obtained in Referential Example 252, condensing the reduction product with p-chlorophenoxyacetic acid and treating the condensation product with hydrochloric acid in a similar manner to the process described in Example 223.

$^1$H-NMR (DMSO-$d_6$) δ: 1.35-1.47 (1H, m), 1.55-1.90 (5H, m), 2.77 (3H, s), 2.92 (3H, s), 2.96 (3H, s), 2.98-3.10 (1H, m), 3.10-3.80 (3H, m), 3.85-3.95 (1H, m), 4.35-4.50 (4H, m), 4.50-4.80 (1H, br), 6.85 (2H, d, J=8.5 Hz), 7.15-7.35 (1H, br), 7.88-8.03 (1H, br), 8.46 (1H, d, J=8.8 Hz), 11.30-11.65 (1H, br). MS (FAB) m/z: 534 (M+H)$^+$.

Example 299

7-Chloro-N-((1S,2R,4S)-4-[(dimethylamino)carbonyl]-2-{[(5-methyl-5H-pyrrolo[3,4-d]thiazol-2-yl)carbonyl]amino}-cyclohexyl)-3-isoquinolinecarboxamide hydrochloride

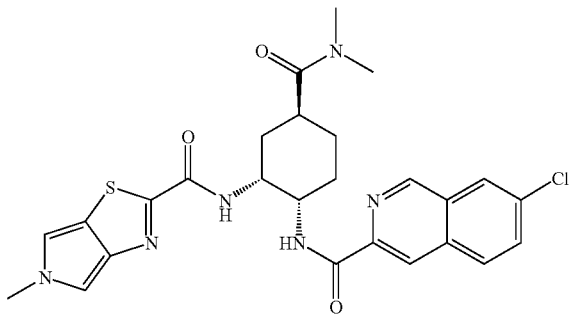

The title compound was obtained by condensing the lithium salt of the carboxylic acid obtained by hydrolyzing the compound obtained in Referential Example 413 with a compound obtained by deprotecting the the compound obtained in Referential Example 146 by an acid treatment and treating the condensation product with hydrochloric acid.

$^1$H-NMR (DMSO-$d_6$) δ: 1.00-1.11 (2H, m), 1.45-1.60 (1H, m), 1.65-1.85 (1H, m), 1.95-2.06 (1H, m), 2.10-2.24 (1H, m), 2.78 (3H, s), 2.87-3.02 (1H, m), 2.94 (3H, s), 3.88 (3H, s), 4.16-4.27 (1H, m), 4.45-4.56 (1H, m), 7.03 (1H, s), 7.55 (1H, s), 7.87 (1H, br d, J=8.3 Hz), 8.24 (1H, br d, J=8.8 Hz), 8.33 (1H, s), 8.59 (1H, s), 8.85 (1H, br d, J=7.6 Hz), 9.01 (1H, br d, J=7.8 Hz), 9.28 (1H, s). MS (ESI) m/z: 539 (M+H)$^+$.

Example 300

N-{(1R,2S,5S)-2-{[(6-Chloro-4-oxo-4H-chromen-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

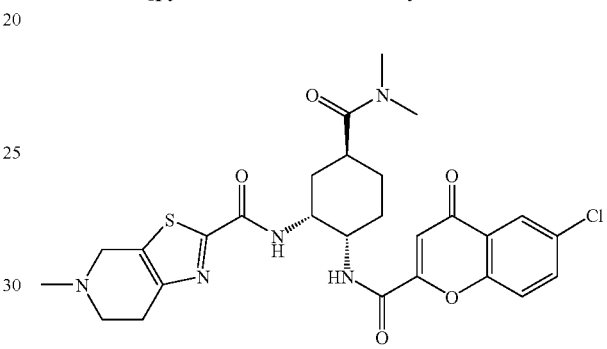

The title compound was obtained by condensing a compound obtained by treating the compound in Referential Example 417 with a 4N dioxane solution of hydrochloric acid with the compound obtained in Referential Example 10 and then treating the condensation product with hydrochloric acid in a similar manner to the process described in Example 219.

$^1$H-NMR (DMSO-$d_6$) δ: 1.40-1.53 (1H, m), 1.67-2.04 (5H, m), 2.40-2.53 (1H, m), 2.80 (3H, s), 2.92 (3H, s), 3.01 (3H, s), 3.09-3.22 (3H, m), 3.66-3.77 (1H, m), 4.01-4.10 (1H, m), 4.34-4.49 (1H, m), 4.58-4.76 (2H, m), 6.80 (1H, d, J=4.9 Hz), 7.59-7.70 (1H, m), 7.90-8.00 (1H, m), 7.96 (1H, s), 8.52-8.60 (1H, m), 8.80-8.90 (1H, m), 11.10-11.25 (0.5H, br), 11.40-11.55 (0.5H, br). MS (ESI) m/z: 572 (M+H)$^+$.

Example 301

7-Chloro-N-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)-3-cinnolinecarboxamide hydrochloride

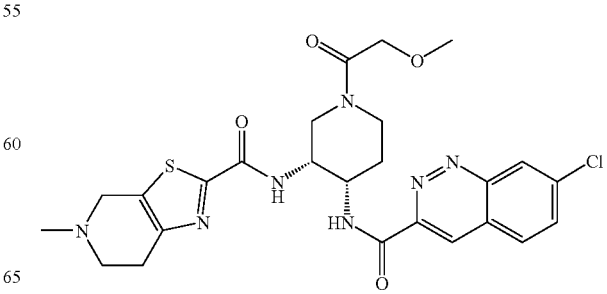

The title compound was obtained by condensing a compound obtained by treating the compound obtained in Referential Example 418 with a 4N dioxane solution of hydrochloric acid with the compound obtained in Referential Example 10 and then treating the condensation product with hydrochloric acid in a similar manner to the process described in Example 219.

$^1$H-NMR (DMSO-$d_6$) δ: 1.70-1.80 (1H, m), 1.85-2.05 (1H, m), 2.90 (3H, s), 3.00-3.20 (2H, m), 3.16 (3H, s), 3.22-3.82 (7H, m), 3.88-4.80 (5H, m), 7.09 (1H, d, J=9.0 Hz), 7.17 (1H, dd, J=8.8, 1.9 Hz), 7.42 (1H, d, J=8.8 Hz), 7.70 (1H, d, J=1.9 Hz), 8.29 (1H, br s), 8.40-8.50 (1H, m), 11.20-11.50 (1H, br m), 11.85 (1H, s). MS (ESI) m/z: 558 (M+H)$^+$.

Example 302

N$^1$-(5-Chloropyridin-2-yl)-N$^2$-((1S,2R,4S)-4-[(dimethylamino)carbonyl]-2-{[(5-methyl-4,5,6,7-tetrahydrothieno[3,2-c]pyridin-2-yl)carbonyl]amino}-cyclohexyl)ethanediamide hydrochloride

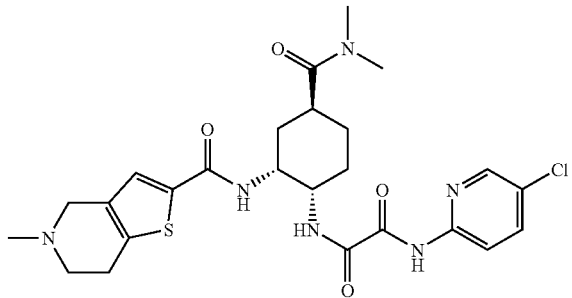

The title compound was obtained by deprotecting the compound obtained in Referential Example 421 with hydrochloric acid, methylating the deprotected compound in a similar manner to the process described in Example 18 and treating it with hydrochloric acid.

$^1$H-NMR (DMSO-$d_6$) δ: 1.42-1.58 (1H, m), 1.59-1.80 (3H, m), 1.83-1.95 (1H, m), 1.97-2.10 (1H, m), 2.78 (3H, s), 2.89 (3H, s), 2.96 (3H, s), 3.00-3.10 (1H, m), 3.10-3.20 (2H, m), 3.45-3.80 (1H, m), 3.90-4.00 (2H, m), 4.00-4.50 (3H, m), 7.77 (1H, s), 7.95-8.05 (3H, m), 8.44 (1H, t, J=1.6 Hz), 8.90 (1H, d, J=8.6 Hz), 10.25 (1H, s), 11.12 (1H, br s). MS (ESI) m/z: 547 (M+H)$^+$.

Example 303

N$^1$-(5-Chloropyridin-2-yl)-N$^2$-((1S,2R,4S)-4-[(dimethylamino)carbonyl]-2-{[(5-isopropyl-4,5,6,7-tetrahydrothiazolo[5,4-c]pyridin-2-yl)carbonyl]aminocyclohexyl)ethanediamide hydrochloride

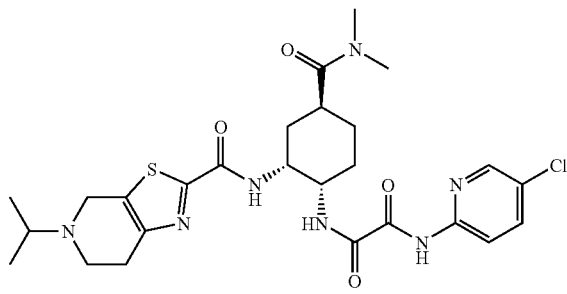

The title compound was obtained by condensing the compound obtained in Referential Example 418 with the compound obtained in Referential Example 420 and then treating the condensation product with hydrochloric acid in a similar manner to the process described in Example 2.

$^1$H-NMR (DMSO-$d_6$) δ: 1.30-1.40 (6H, m), 1.38-1.58 (1H, m), 1.59-1.82 (3H, m), 1.95-2.13 (2H, m), 2.40-2.65 (1H, m), 2.49 (3H, s), 2.87-3.55 (4H, m), 2.49 (3H, s), 3.60-3.82 (2H, m), 3.93-4.04 (1H, m), 4.37-4.55 (2H, m), 4.55-4.72 (1H, m), 7.94-8.10 (2H, m), 8.43 (1H, s), 8.64-8.77 (1H, m), 9.12 (1/2H, d, J=7.8 Hz), 9.24 (1/2H, d, J=7.8 Hz), 10.22 (1/2H, s), 10.26 (1/2H, s), 11.25 (1/2H, br s), 11.44 (1/2H, br s). MS (FAB) m/z: 578 (M+H)$^+$.

Example 304

N-((1R,2S,5S)-5-[(Dimethylamino)carbonyl]-2-{[2-(4-fluoroanilino)-2-oxoethanethioyl]amino}cyclohexyl)-5-methyl-4,5,6,7-tetrahydrothiazolo[5,4-c]pyridine-2-carboxamide hydrochloride

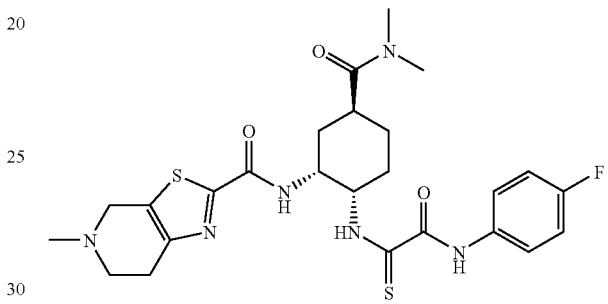

The title compound was obtained by treating the compound obtained in Referential Example 424 with hydrochloric acid to deprotect it, condensing the deprotected compound with the compound obtained in Referential Example 10 and then subjecting the condensation product to a hydrochloric acid treatment again in a similar manner to the process described in Example 219.

$^1$H-NMR (DMSO-$d_6$) δ: 1.45-1.60 (1H, m), 1.60-1.80 (3H, m), 2.00-2.10 (1H, m), 2.20-2.35 (1H, m), 2.79 (3H, s), 2.93 (3H, s), 2.95 (3H, s), 2.95-3.10 (1H, m), 3.10-3.30 (2H, m), 3.40-3.60 (1H, m), 3.60-3.80 (1H, m), 4.35-4.50 (1H, m), 4.50-4.60 (1H, m), 4.60-4.80 (2H, m), 7.20 (2H, t, J=8.8 Hz), 7.77 (2H, dd, J=9.0, 5.1 Hz), 8.80 (1H, br), 10.42 (1H, s), 10.93 (1H, br), 11.28 (1H, br). MS (ESI) m/z: 547 (M+H)$^+$.

Example 305

N-[(1R,2S,5S)-5-[(Dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]-pyridine-2-carboxamide hydrochloride

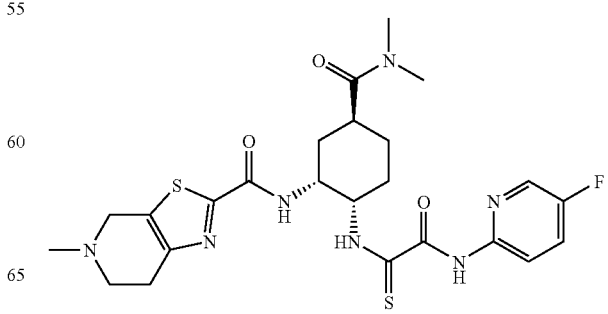

The title compound was obtained by treating the compound obtained in Referential Example 427 with hydrochloric acid to deprotect it, condensing the deprotected compound with the compound obtained in Referential Example 10 and then subjecting the condensation product to a hydrochloric acid treatment again in a similar manner to the process described in Example 219.

$^1$H-NMR (DMSO-$d_6$) δ: 1.43-1.57 (1H, m), 1.64-1.87 (3H, m), 2.00 (1H, br s), 2.17-2.34 (1H, m), 2.78 (3H, s), 2.90 (3H, s), 2.95 (3H, s), 2.95-3.10 (1H, m), 3.10-3.30 (2H, m), 3.40-3.60 (1H, m), 3.68 (1H, br s), 4.44 (1H, br s), 4.45-4.56 (1H, m), 4.60-4.73 (2H, m), 7.80-7.90 (1H, m), 8.08 (1H, dd, J=9.1, 3.9 Hz), 8.41 (1H, d, J=2.9 Hz), 8.79 (1H, d, J=6.6 Hz), 10.49 (1H, s), 11.07 (1H, br s), 11.69 (1H, br). MS (ESI) m/z: 548 (M+H)$^+$.

Example 306

N-{(1R,2S,5S)-2-({2-[(5-Chloropyridin-2-yl)amino]-2-oxoethanethioyl}amino)-5-[(dimethylamino)carbonyl]-cyclohexyl}-5-methyl-5H-pyrrolo[3,4-d]thiazole-2-carboxamide

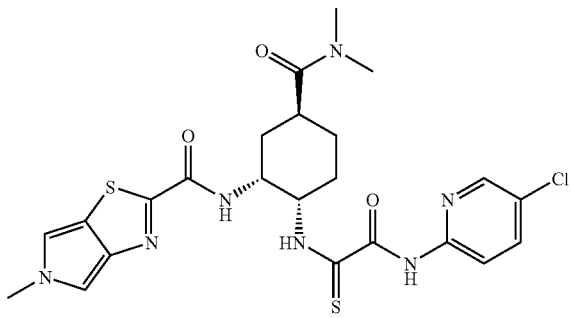

The title compound was obtained by treating the compound obtained in Referential Example 428 with hydrochloric acid to deprotect it and then condensing the deprotected compound with the compound obtained in Referential Example 293 in a similar manner to the process described in Example 219.

$^1$H-NMR (DMSO-$d_6$) δ: 1.45-1.58 (1H, m), 1.63-1.73 (2H, m), 1.73-1.87 (2H, m), 2.00-2.10 (1H, m), 2.20-2.35 (1H, m), 2.79 (3H, s), 2.95 (3H, s), 2.96-3.10 (1H, m), 3.89 (3H, s), 4.48-4.58 (1H, m), 4.60-4.70 (1H, m), 7.05 (1H, d, J=1.7 Hz), 7.55 (1H, d, J=1.7 Hz), 8.00 (1H, dd, J=8.9, 2.4 Hz), 8.05 (1H, d, J=8.9 Hz), 8.44 (1H, d, J=2.4 Hz), 8.71 (1H, d, J=7.3 Hz), 10.57 (1H, s), 11.13 (1H, d, J=7.8 Hz). MS (FAB) m/z: 548 (M+H)$^+$.

Example 307

N-{(1R,2S,5S)-2-({2-[(5-Chloropyridin-2-yl)amino]-2-oxoethanethioyl}amino)-5-[(dimethylamino)carbonyl]-cyclohexyl}-5-methyl-5,6-dihydro-4H-pyrrolo[3,4-d]-thiazole-2-carboxamide hydrochloride

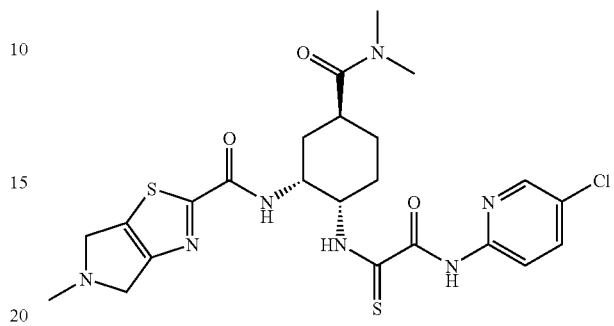

The title compound was obtained by treating the compound obtained in Referential Example 428 with hydrochloric acid to deprotect it, condensing the deprotected compound with the compound obtained in Referential Example 293 under an argon atmosphere and then subjecting the condensation product to a hydrochloric acid treatment again in a similar manner to the process described in Example 219.

$^1$H-NMR (DMSO-$d_6$) δ: 1.42-1.58 (1H, m), 1.65-1.87 (3H, m), 1.97-2.10 (1H, m), 2.17-2.30 (1H, m), 2.80 (3H, s), 2.96 (3H, s), 2.98-3.10 (1H, m), 3.07 (3H, s), 4.30-5.00 (6H, m), 8.00-8.10 (1H, m), 8.46 (1H, d, J=2.4 Hz), 8.79 (1H, t, J=7.3 Hz), 10.54 (1H, s), 11.04 (1H, d, J=7.8 Hz), 12.24 (1H, br s). MS (ESI) m/z: 550 (M+H)$^+$.

Example 308

N$^1$-(5-Chloropyridin-2-yl)-N$^2$-[(1S,2R,4S)-4-[(dimethylamino)carbonyl]-2-({[6-(dimethylamino)-4,5,6,7-tetrahydrobenzothiazol-2-yl]carbonyl}amino)cyclohexyl]-ethanediamide

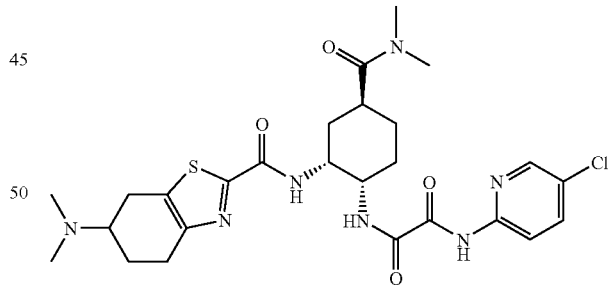

The title compound was obtained by deprotecting the compound obtained in Referential Example 431 with hydrochloric acid, methylating the deprotected compound in a similar manner to the process described in Example 18 and treating it with hydrochloric acid.

$^1$H-NMR (DMSO-$d_6$) δ: 1.42-1.58 (1H, m), 1.59-1.80 (3H, m), 1.90-2.12 (3H, m), 2.30-2.45 (1H, m), 2.70-3.00 (11H, m), 2.92 (3H, s), 3.00-3.20 (2H, m), 3.25-3.45 (1H, m), 3.63-3.80 (1H, m), 3.88-4.02 (1H, m), 4.35-4.47 (1H, m), 8.02 (1H, s), 8.42-8.55 (1H, m), 8.60-8.68 (1H, m), 8.93 (1H, dd, J=14.5, 8.2 Hz), 9.19 (1H, dd, J=17.7, 8.2 Hz), 10.28 (1H, s), 10.91 (1H, br s). MS (ESI) m/z: 576 (M+H)$^+$.

Example 309

N-{(1R[12]S,5S)-2-[({[(4-Chlorophenyl)sulfonyl]amino}-carbonyl)amino]-5[(dimethylamino)carbonyl]cyclohexyl}-5-methyl-4,5,6,7-tetrahydrothiazolo[5,4-c]-pyridine-2-carboxamide hydrochloride

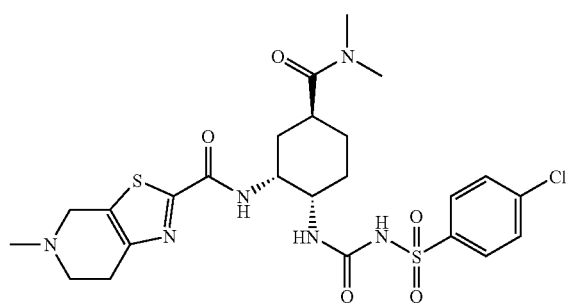

4-Chlorophenylsulfonyl isocyanate (148 μl) was added to a solution of the compound (328.0 mg) obtained in Referential Example 253 in methylene chloride (10 ml), and the mixture was stirred at room temperature for 24 hours. The solvent was distilled off under reduced pressure, and residue was purified by preparative thin-layer column chromatography on silica gel (methylene chloride:methanol=9:1). The thus-obtained product was dissolved in ethanol (2 ml) and methylene chloride (2 ml), and a 1N ethanol solution (0.25 ml) of hydrochloric acid was added to stir the mixture at room temperature for 30 minutes. The reaction mixture was concentrated under reduced pressure, and the residue was solidified with diethyl ether to obtain the title compound (104.3 mg).

$^1$H-NMR (DMSO-$d_6$) δ: 1.25-1.45 (1H, m), 1.45-1.80 (5H, m), 2.76 (3H, s), 2.94 (3H, s), 2.97 (3H, s), 3.00-3.80 (6H, m), 4.35-4.85 (3H, m), 6.53 (1H, brs), 7.66 (2H, d, J=8.5 Hz), 7.86 (2H, d, J=8.5 Hz), 8.50-8.82 (1H, m), 10.64 (1H, br s), 11.10-11.80 (1H, br). MS (ESI) m/z: 583 (M+H)$^+$.

Example 310

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide

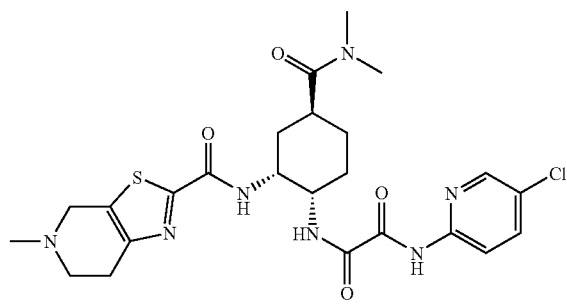

The title compound was obtained from the compound obtained in Referential Example 435 and the compound obtained in Referential Example 10 in a similar manner to Example 2.

$^1$H-NMR (CDCl$_3$) δ: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, d, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s). MS (ESI) m/z: 548 (M+H)$^+$.

Example 311

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate Monohydrate

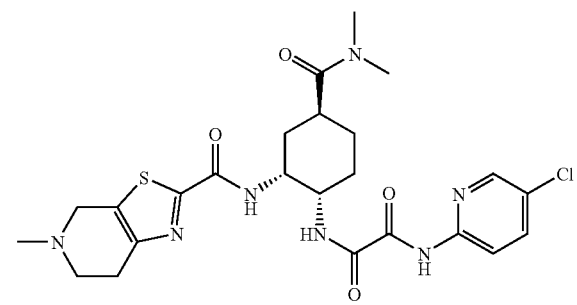

The compound (6.2 g) obtained in Example 310 is dissolved in methylene chloride (120 ml), a 1 mol/L ethanol solution (11.28 ml) of p-toluenesulfonic acid was added to the solution, and the solvent was distilled off. Ethanol (95 ml) containing 15% water was added to the residue, and the mixture was stirred at 60° C. to dissolve it. The solution was then cooled to room temperature and stirred for a day. Crystals deposited were collected by filtration, washed with ethanol and dried at room temperature for 2 hours under reduced pressure to obtain the title compound (7.4 g).

$^1$H-NMR (DMSO-$d_6$) δ: 1.45-1.54 (1H, m), 1.66-1.78 (3H, m), 2.03-2.10 (2H, m), 2.28 (3H, s), 2.79 (3H, s), 2.91-3.02 (1H, m), 2.93 (3H, s), 2.99 (3H, s), 3.13-3.24 (2H, m), 3.46-3.82 (2H, m), 3.98-4.04 (1H, m), 4.43-4.80 (3H, m), 7.11 (2H, d, J=7.8 Hz), 7.46 (2H, d, J=8.2 Hz), 8.01 (2H, d, J=1.8 Hz), 8.46 (1H, t, J=1.8 Hz), 8.75 (1H, d, J=6.9 Hz), 9.10-9.28 (1H, br), 10.18 (1H, br), 10.29 (1H, s). MS (ESI) m/z: 548 (M+H)$^+$. Elemental analysis: $C_{24}H_{30}ClN_7O_4S.C_7H_8O_3S.H_2O$. Calculated: C; 50.43, H; 5.46, N; 13.28, Cl; 4.80, S; 8.69. Found: C; 50.25, H; 5.36, N; 13.32, Cl; 4.93, S; 8.79. mp (decomposed): 245~248° C.

Test Example 1

Determination of Human FXa-inhibiting Effect (IC$_{50}$ Value)

5% DMSO solutions (10 μl) of each test compound, the concentrations of which were suitably set stepwise, Tris buffer (100 mM Tris, 200 mM potassium chloride, 0.2% BSA, pH 7.4) (40 μl) and 0.0625 U/ml human FXa (Enzyme Research Labolatories, Inc., dissolved and diluted with Tris buffer) (10 μl) were respectively put in wells of a 96-well microplate, and a 750 μM aqueous solution (40 μl) of S-2222 (Chromogenix Co.) was added. Absorbance at 405 nm was measured for 10 minutes at room temperature to determine an increase in absorbance (ΔOD/min). As a control, Tris buffer was used in place of the test compound.

The percent inhibition (%) calculated using the following equation at the final concentration of the test compound and the final concentration of the test compound were plotted on the axis of ordinate and the axis of abscissa of logarithmic normal probability paper, respectively, to determine the 50% inhibition concentration (IC$_{50}$ value).

Percent inhibition (%)=[1−(ΔOD/min of test compound)÷(ΔOD/min of control)]×100

(Result)

In Table 1, it is demonstrated that the compounds according to the present invention have a potent FXa-inhibiting effect.

TABLE 1

| Compound | Human FXa-inhibiting effect (IC$_{50}$): nM |
|---|---|
| Ex. 3 | 86 |
| Ex. 7 | 83 |
| Ex. 11 | 92 |
| Ex. 54 | 4.2 |
| Ex. 62 | 3.5 |
| Ex. 63 | 2.5 |
| Ex. 74 | 1.4 |
| Ex. 101 | 26 |
| Ex. 130 | 4.5 |
| Ex. 138 | 4.4 |
| Ex. 143 | 5.8 |
| Ex. 164 | 4.8 |
| Ex. 191 | 1.2 |
| Ex. 192 | 2.0 |
| Ex. 194 | 5.0 |
| Ex. 204 | 1.5 |
| Ex. 246 | 3.1 |
| Ex. 247 | 1.9 |
| Ex. 248 | 5.4 |

Test Example 2

Determination of Anti-FXa Activity in Rat Plasma After Oral Administration:

(A) Administration and Blood Collection:

A drug solution (1 mg/ml) obtained by dissolving or suspending a test compound (10 mg) in 0.5% methyl cellulose (MC) was orally administered to rats (10 ml/kg). After 0.5, 1, 2 and 4 hours from the drug administration, the blood (0.5 ml) was collected through the jugular vein using a syringe which is containing a 3.13% (w/v) aqueous solution (50 µl) of trisodium citrate dihydrate (amount of blood collected: 0.45 ml). For rats of a control group, the same blood collection was conducted after a 0.5% MC solution was administered. Each blood sample was centrifuged at 1500×g for 10 minutes at 4° C. to separate plasma, and the plasma was preserved at −40° C. until it was used in the following determination of anti-FXa activity in plasma.

(B) Determination of FXa-inhibiting Activity in Plasma:

In the determination of anti-FXa activity in plasma, S-2222 was used as a substrate. Tris buffer (100 mM Tris, 200 mM potassium chloride, 0.2% BSA, pH 7.4) (5456 µl), human FXa (2.5 U/ml, 44 µl) and water (0.550 µl) were mixed. The resultant human FXa solution was used in the following test.

Rat plasma (5 µl) obtained in accordance with the procedure (A) described above was put in wells of a 96-well microplate, and the above-described human FXa solution (55 µl) and a 750 µM aqueous solution (40 µl) of S-2222 were sequentially added. Immediately after that, absorbance at 405 nm was measured at room temperature by means of a spectrophotometer SPECTRAmax 340 or 190 (Molecular Devices Co., U.S.A.), thereby determining a rate of reaction (ΔOD/min).

The anti-FXa activity, i.e., percent inhibition (%) was calculated in accordance with the following equation:

Percent inhibition (%)=[1−(ΔOD/min of sample)÷(average value of ΔOD/min of the control group)]×100

(Result)

The compounds described in Examples 63, 191, 192, 194 and 204 exhibited a potent FXa-inhibiting activity of 62 to 96% at an oral dose of 10 mg/kg.

INDUSTRIAL APPLICABILITY

The cyclicdiamine derivatives according to the present invention exhibit a potent inhibitory effect on activated blood coagulation factor X and are useful as medicines, activated blood coagulation factor X inhibitors, anticoagulants, agents for preventing and/or treating thrombosis or embolism, agents for preventing and/or treating thrombotic disease and agents for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood drawing.

The invention claimed is:

1. N$^1$-(5-chloropyridin-2-yl)-N$^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide, a salt thereof,

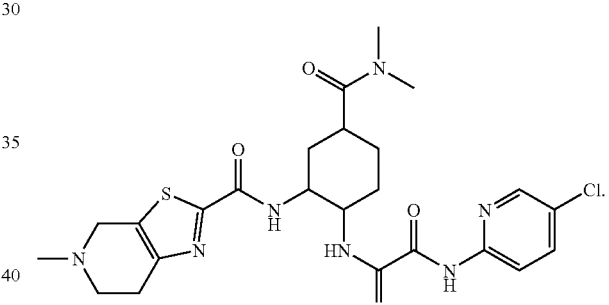

2. N$^1$-(5-chloropyridin-2-yl)-N$^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate

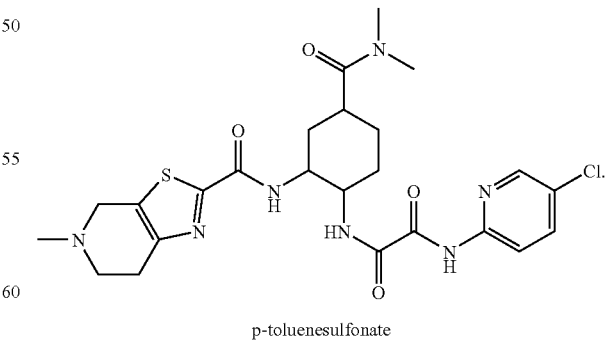

p-toluenesulfonate

3. N$^1$-(5-chloropyridin-2-yl)-N$^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate

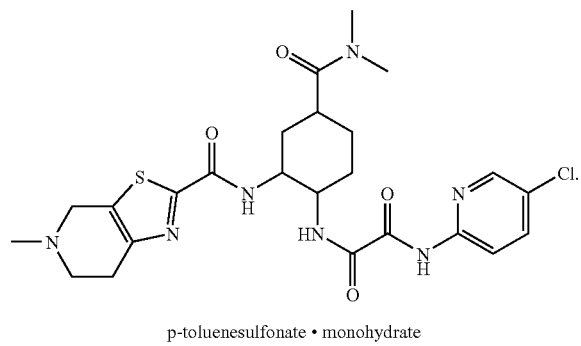

p-toluenesulfonate · monohydrate

4. $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, a salt thereof,

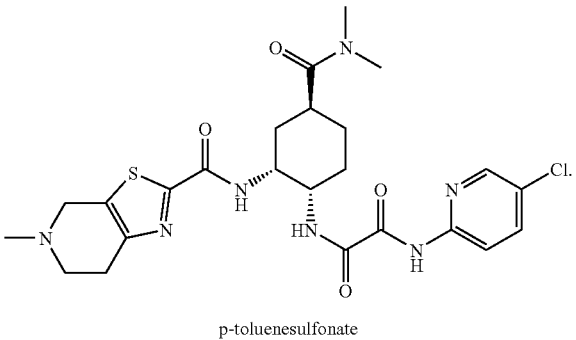

p-toluenesulfonate

6. $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate

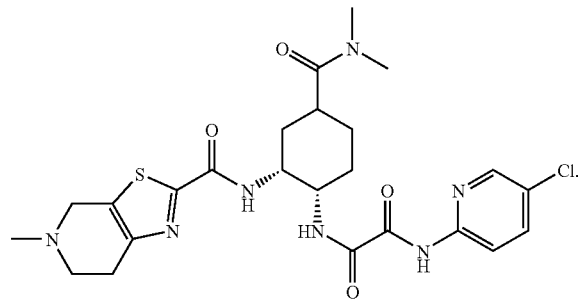

5. $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate.

p-toluenesulfonate·monohydrate

\* \* \* \* \*

UNITED STATES PATENT AND TRADEMARK OFFICE
CERTIFICATE OF CORRECTION

PATENT NO. : 7,365,205 B2
APPLICATION NO. : 10/481262
DATED : April 29, 2008
INVENTOR(S) : Ohta et al.

It is certified that error appears in the above-identified patent and that said Letters Patent is hereby corrected as shown below:

Column 456, claim 1, lines 25-42, the formula reading:

1. $N^1$-(5-chloropyridin-2-yl)-$N^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide, a salt thereof,

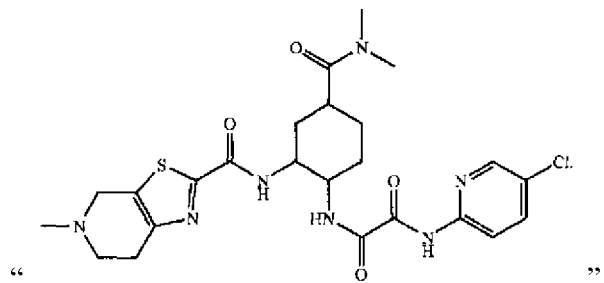

" "

should read:

1. $N^1$-(5-chloropyridin-2-yl)-$N^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide, or a salt thereof,

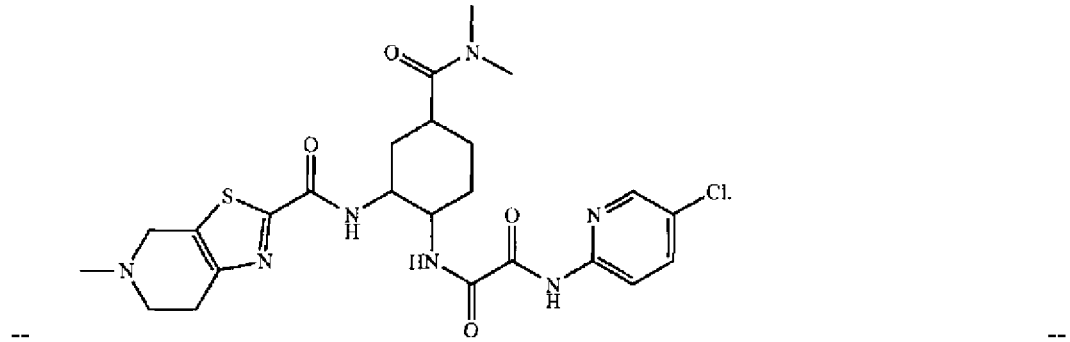

-- --

Signed and Sealed this
Fourteenth Day of February, 2012

David J. Kappos
*Director of the United States Patent and Trademark Office*

CERTIFICATE OF CORRECTION (continued)
U.S. Pat. No. 7,365,205 B2

Column 457, claim 4, lines 18-35, the formula reading:

4. N¹-(5-chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide, a salt thereof,

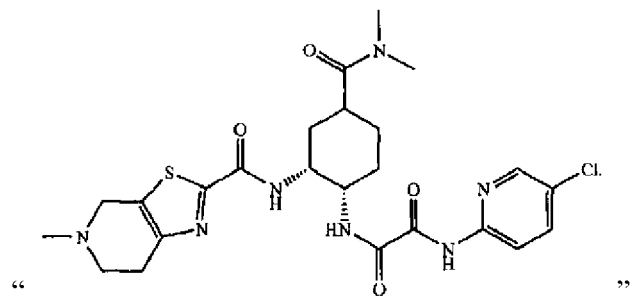

" "

should read:

4. N$^1$-(5-chloropyridin-2-yl)-N$^2$-((1S, 2R, 4S)-4-[(dimethylamino)carbonyl]-2-{[(5- methyl-4,5,6,7-tetrahydrothiazolo[5,4-c]pyridin-2-yl) carbonyl]amino}cyclohexyl)ethanediamide, or a salt thereof,

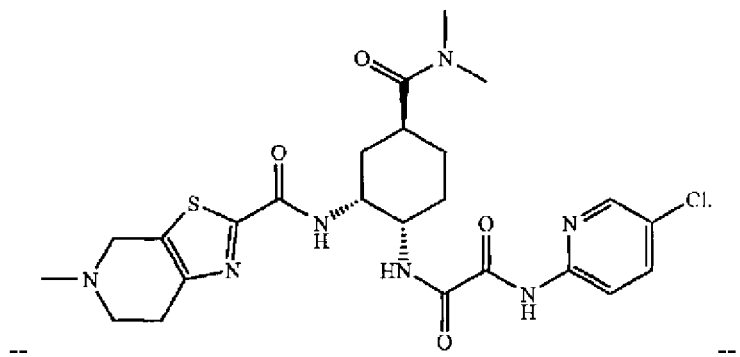

-- --